(12) United States Patent
Nishi et al.

(10) Patent No.: US 6,448,247 B1
(45) Date of Patent: Sep. 10, 2002

(54) METHOD FOR TREATING AN INFLAMMATORY DISEASE

(75) Inventors: Takahide Nishi; Koki Ishibashi; Katsuyoshi Nakajima, all of Tokyo; Tetsuya Fukazawa, Nagareyama; Hitoshi Kurata, Tokyo; Takeshi Yamaguchi, Ibaraki-ken; Kazuhiro Ito, Urawa, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/533,061

(22) Filed: Mar. 22, 2000

Related U.S. Application Data

(62) Division of application No. 08/758,421, filed on Dec. 2, 1996, now Pat. No. 6,159,967.

(30) Foreign Application Priority Data

| Dec. 1, 1995 | (JP) | 07-313828 |
| Dec. 25, 1995 | (JP) | 07-336369 |
| Nov. 8, 1996 | (JP) | 08-296869 |

(51) Int. Cl.$^7$ ............... A61K 31/5375; A61K 31/5386; C07D 265/30; C07D 413/14

(52) U.S. Cl. ............... 514/233.5; 514/233.5; 514/231.2; 514/233.8; 514/234.2; 544/106; 544/107; 544/111; 544/124

(58) Field of Search ............... 514/233.5, 231.2, 514/233.8, 234.2; 544/106, 107, 111, 124

(56) References Cited

U.S. PATENT DOCUMENTS

| 5,236,921 A | 8/1993 | Emonds-Alt et al. ....... 514/252 |
| 5,317,020 A | 5/1994 | Emonds-Alt et al. ....... 514/255 |
| 5,340,822 A | 8/1994 | Emonds-Alt et al. ....... 544/316 |
| 5,350,852 A | 9/1994 | Emonds-Alt et al. ....... 544/332 |
| 5,411,971 A | 5/1995 | Emonds-Alt et al. ....... 514/318 |
| 5,641,777 A | 6/1997 | Emonds-Alt et al. ....... 514/235.5 |

FOREIGN PATENT DOCUMENTS

| EP | 0 630 887 | | 12/1994 |
| EP | 0 673 928 | | 9/1995 |
| EP | 673928 | * | 9/1995 |
| EP | 776893 | * | 2/1999 |
| FR | 2 729 951 | | 8/1996 |
| FR | 2 729 952 | | 8/1996 |
| FR | 2 729 953 | | 8/1996 |
| FR | 2 729 954 | | 8/1996 |
| JP | 11043435 | * | 2/1999 |
| WO | WO 93/1115 | | 6/1993 |
| WO | WO 94/17045 | | 8/1994 |
| WO | WO 94/26735 | | 11/1994 |
| WO | 9426735 | * | 11/1994 |
| WO | WO 94/29309 | | 12/1994 |
| WO | WO 95/28389 | | 10/1995 |
| WO | WO 96/23787 | | 8/1996 |

OTHER PUBLICATIONS

Yamaguchi et al., "Evidence that PGF2.alpha.."J.Appl.Physio. 79/5, 1411–18 (Sep. 1995).*

Ito et al.;"Role of tachykinin and bradykini receptor. ."; Eur.J.Pharmaco. 307/3,291–98(1996), Sep. 1995.*

Database WPI, Derwent Abstract, AN 950382750 of WO 95/28389 of Oct. 1996.

Timothy P. Burkholder et al, "Identification and Chemical Synthesis of MDL 105,212, A Non–Petide Tachykinin Antagonist with High Affinity for NK$_1$ and NK$_2$ Receptors", *Bioorg. Med. Chem. Lett.*, 6, No. 8, 1996, pp. 951–956.

* cited by examiner

*Primary Examiner*—Mukund J. Shah
*Assistant Examiner*—Sudhaker B. Patel
(74) *Attorney, Agent, or Firm*—Frishauf, Holtz, Goodman & Chick, P.C.

(57) ABSTRACT

Compounds of the formula

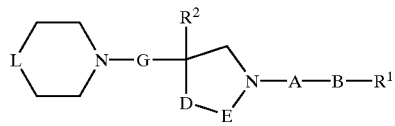

and quaternary ammonium ions thereof, wherein $R^1$ and $R^2$ are the same or different and are carbocyclic aryl or aromatic heterocyclic; A is methylene, carbonyl or sulfonyl; B is a single bond, $C_1$–$C_4$ alkylene or $C_2$–$C_4$ alkenylene; D is oxygen or sulfur; E is $C_2$–$C_6$ alkylene, $C_1$–$C_6$ haloalkylene, $C_3$–$C_6$ cycloalkane-1,1-diyl or $C_3$–$C_6$-cycloalkane-1,1-diylmethyl; G is $C_1$–$C_4$ alkylene or $C_2$–$C_4$ alkenylene; and L is —$NR^3$ or —$C(R^4)(R^5)$, wherein $R^3$ is a carbocyclic aryl or an aromatic heterocyclic; $R^4$ is hydrogen, carbocyclic aryl or aromatic heterocyclic; $R^5$ is —$COR^6$, $C_1$–$C_6$ alkyl, $C_1$–$C_6$ alkoxy, amino, or acylamino, wherein $R^6$ is $C_1$–$C_6$ alkyl or $C_1$–$C_6$ alkoxy, or $R^4$ and $R^5$ together with the carbon atom to which they are attached represent a $C_5$–$C_{10}$ cycloalkyl or a $C_5$–$C_{10}$ heterocyclic. The compounds have tachykinin receptor antagonist activity and exhibit an activity against both the NK$_1$ and NK$_2$ receptors.

51 Claims, No Drawings

METHOD FOR TREATING AN INFLAMMATORY DISEASE

This is a division of application Ser. No. 08/758,421 filed Dec. 2, 1996 (U.S. Pat. No. 6,159,967).

BACKGROUND TO THE INVENTION

The present invention relates to a series of new heterocyclic compounds having tachykinin receptor antagonist activity. It also provides methods and compositions using them for therapeutic and prophylactic purposes, as well as processes for their preparation and intermediates used in their preparation.

The presence in the mammalian body of the various forms of tachykinin is associated with a variety of diseases and disorders, including respiratory diseases, such as asthma, bronchitis, rhinitis and coughs; allergies; ophthalmic inflammatory diseases, such as conjunctivitis and spring catarrh; dermal diseases, such as contact dermatitis, atopic dermatosis and urticaria; inflammatory diseases, such as rheumatism and arthrosis deformans; pain, such as migraine, headache and toothache; central nervous system diseases, such as anxiety and Alzheimer's disease; and gastrointestinal diseases, such as colitis; and cystitis; and many others. Inhibition of the activity of these forms of tachykinin will, therefore, result in a new therapy and/or prophylaxis for these diseases and disorders.

The compounds of the present invention exhibit antagonism generally to tachykinin receptors, but especially to the receptors for substance P (which receptors are generally referred to as "neurokinin 1 receptors" —$NK_1$) and the receptors for neurokinin A (which receptors are generally referred to as "neurokinin 2 receptors" —$NK_2$). It is a particular advantage of the compounds of the present invention that they exhibit antagonism to both of these receptors, a so-called "dual effect".

Compounds which are structurally close to those of the present invention are disclosed in FR 2729952, FR 2729953 and FR 2729954. However, these are selective for the $NK_1$ receptors and none of these compounds exhibits the dual effects of the compounds of the present invention.

A few low molecular weight non-peptide compounds are known to exhibit antagonism to both of these receptors, for example some of the compounds disclosed in WO 9429309 (1994), WO 9417045 (1994), WO 9426735 (1994) and WO 9528389 (1995) exhibit such an effect. Typical examples of compounds which are disclosed in these documents are:

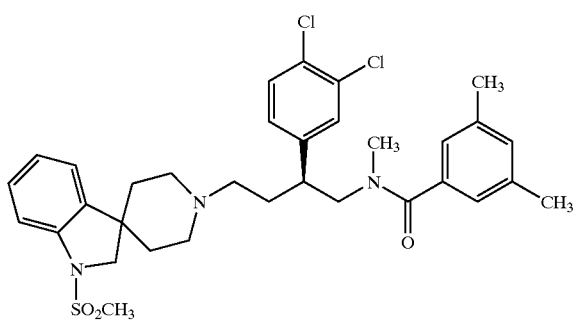

Compound A
WO 9429309

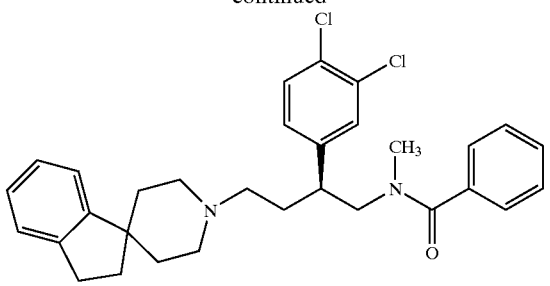

Compound B
WO 9417045

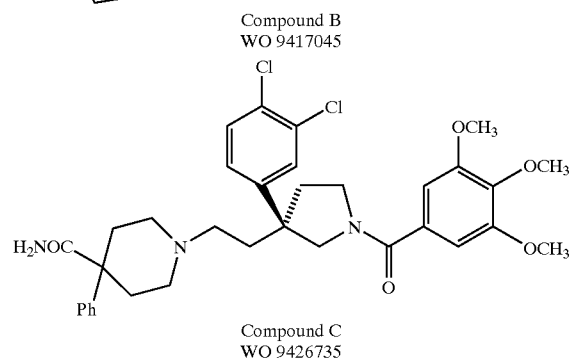

Compound C
WO 9426735

However, oral absorption of these compounds is poor. As a result, these prior art compounds cannot be administered by mouth and must be administered parenterally, for example by injection. It is well known in the medical field that administration of any drug by injection is undesirable, as either the patient must be trained (and some patients are inherently untrainable) or the drug must be administered by experienced staff, which is expensive and inconvenient both for the patient and the staff.

There is, therefore, a need for a new tachykinin receptor antagonist which exhibits the aforementioned dual effects, and which has good oral absorption and a low toxicity.

We have now discovered a series of new compounds which exhibit an activity against the $NK_1$ receptors which is at least equal to that of the prior art compounds showing a dual effect and which unexpectedly exhibit a much stronger activity against the $NK_2$ receptors.

BRIEF SUMMARY OF INVENTION

It is, therefore, an object of the present invention to provide a series of new heterocyclic compounds.

It is a further, and more specific, object of the present invention to provide such compounds which exhibit antagonism to tachykinin receptors.

It is a still further, and more specific, object of the present invention to provide such compounds which exhibit antagonism to those tachykinin receptors known as $NK_1$ and $NK_2$.

It is a still further, and more specific, object of the present invention to provide certain of such compounds which exhibit greatly improved activity.

Other objects and advantages of the present invention will become apparent as the description proceeds.

The compounds of the present invention are those compounds of formula (I):

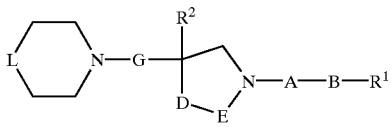

and the quaternary ammonium derivative thereof of formula (Ia):

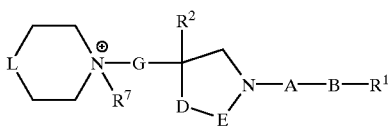

wherein:
- $R^1$ and $R^2$ are the same as or different from each other, and each represents a carbocyclic aryl group or an aromatic heterocyclic group, said aryl group and said heterocyclic group being unsubstituted or being substituted by at least one substituent preferably selected from the group consisting of substituents α, defined below;
- A represents a methylene group, a carbonyl group or a sulfonyl group;
- B represents a single bond between the groups represented by A and $R^1$, an alkylene group having from 1 to 4 carbon atoms or an alkenylene group having from 2 to 4 carbon atoms;
- D represents an oxygen or sulfur atom;
- E represents an alkylene group having from 1 to 6 carbon atoms, a haloalkylene group having from 1 to 6 carbon atoms, a cycloalkane-1,1-diyl group having from 3 to 6 carbon atoms, a cycloalkane-1,1-diylmethyl group having from 3 to 6 carbon atoms in the cycloalkane part, or a cycloalkane-1,1-di(ylmethyl) group having from 3 to 6 carbon atoms in the cycloalkane part;
- G represents an alkylene group having from 1 to 4 carbon atoms or an alkenylene group having from 2 to 4 carbon atoms;
- L represents a group of formula —N($R^3$)— or a group of formula —C($R^4$)($R^5$)—
  - wherein $R^3$ represents a carbocyclic aryl group or an aromatic heterocyclic group, said aryl group and said aromatic heterocyclic group being unsubstituted or being substituted by at least one substituent preferably selected from the group consisting of substituents α, defined below,
  - $R^4$ represents a hydrogen atom, a carbocyclic aryl group or an aromatic heterocyclic group, said aryl group and said aromatic heterocyclic group being unsubstituted or being substituted by at least one substituent preferably selected from the group consisting of substituents α, defined below, and
  - $R^5$ represents a group of formula —CO—$R^6$, an alkyl group having from 1 to 6 carbon atoms, an alkoxy group having from 1 to 6 carbon atoms, an amino group, an acylamino group, an alkyl group which has from 1 to 6 carbon atoms and which is substituted by an acylamino group, an acylamino group whose nitrogen atom is substituted with an alkyl group having from 1 to 6 carbon atoms, a hydroxy group, a hydroxyalkyl group having from 1 to 6 carbon atoms, an alkoxyalkyl group in which the alkoxy and alkyl parts each has from 1 to 6 carbon atoms, or an aralkyloxyalkyl group having from 1 to 6 carbon atoms in the oxyalkyl part, and in which the aralkyl part is an alkyl group which has from 1 to 4 carbon atoms and which is substituted by from 1 to 3 carbocyclic aryl groups which are unsubstituted or which are substituted by at least one substituent preferably selected from the group consisting of substituents α, defined below,
  - wherein $R^6$ represents an alkyl group having from 1 to 6 carbon atoms, an alkoxy group having from 1 to 6 carbon atoms, a group of formula —$NR^aR^b$, a carbocyclic aryl group or a heterocyclic group, said aryl group and said heterocyclic group being unsubstituted or being substituted by at least one substituent preferably selected from the group consisting of substituents α, defined below
    - wherein $R^a$ represents a hydrogen atom, an alkyl group having from 1 to 6 carbon atoms, an alkoxy group having from 1 to 6 carbon atoms, an aliphatic carboxylic acyl group having from 1 to 6 carbon atoms, an alkanesulfonyl group having from 1 to 6 carbon atoms, a haloalkanesulfonyl group having from 1 to 6 carbon atoms, a cycloalkyl group having from 3 to 8 carbon atoms, a carbocyclic aryl group which is unsubstituted or which is substituted by at least one substituent preferably selected from the group consisting of substituents α, defined below, or an aralkyl group in which an alkyl group having from 1 to 4 carbon atoms is substituted by from 1 to 3 carbocyclic aryl groups as defined above, and
    - $R^b$ represents a hydrogen atom, an alkyl group having from 1 to 6 carbon atoms, an alkoxy group having from 1 to 6 carbon atoms, an aliphatic carboxylic acyl group having from 1 to 6 carbon atoms, an alkanesulfonyl group having from 1 to 6 carbon atoms, a haloalkanesulfonyl group having from 1 to 6 carbon atoms, a cycloalkyl group having from 3 to 8 carbon atoms, a carbocyclic aryl group or an aromatic heterocyclic group, said aryl group and said aromatic heterocyclic group being unsubstituted or being substituted by at least one substituent preferably selected from the group consisting of substituents α, defined below, or an aralkyl group in which an alkyl group having from 1 to 4 carbon atoms is substituted by from 1 to 3 carbocyclic aryl groups as defined above,
    - or
    - $R^a$ and $R^b$ together with the nitrogen atom to which they are attached represent a nitrogen-containing heterocyclic group,
    - or
  - $R^4$ and $R^5$ together with the carbon atom to which they are attached represent a cycloalkyl or heterocyclic group having from 5 to 10 ring atoms, said group being unsubstituted or being substituted by at least one substituent selected from the group consisting of substituents β, defined below, and said heterocyclic group having a single hetero-atom selected from the group consisting of nitrogen, oxygen and sulfur atoms, or $R^4$ and $R^5$ together with the carbon atom to which they are attached represent a cycloalkyl or heterocyclic group as defined above which is fused to a carbocyclic aryl group or an aromatic heterocyclic group, said aryl group and said aromatic heterocyclic group being unsubstituted or being substituted by at least one substituent preferably selected from the group consisting of substituents α, defined below;

R⁷ represents an alkyl group having from 1 to 6 carbon atoms; and said substituents α are selected from the group consisting of halogen atoms, alkyl groups having from 1 to 6 carbon atoms, haloalkyl groups having from 1 to 6 carbon atoms, alkoxy groups having from 1 to 6 carbon atoms, aliphatic carboxylic acyl groups having from 1 to 6 carbon atoms, alkanesulfonyl groups having from 1 to 6 carbon atoms, haloalkanesulfonyl groups having from 1 to 6 carbon atoms, hydroxy groups, carboxy groups, alkoxycarbonyl groups having from 1 to 6 carbon atoms in the alkoxy part, acylamino groups having from 1 to 6 carbon atoms, alkanesulfonylamino groups having from 1 to 6 carbon atoms, haloalkanesulfonylamino groups having from 1 to 6 carbon atoms, amino groups, cyano groups, and alkylene groups having from 1 to 8 carbon atoms (to form a cycloalkyl group fused with the aryl or heterocyclic ring);

said substituents β are:

when substituting a carbon atom, oxo groups, when substituting a nitrogen atom, selected from the group consisting of aliphatic acyl groups, alkanesulfonyl groups having from 1 to 6 carbon atoms, alkyl groups having from 1 to 6 carbon atoms which are unsubstituted or are substituted by at least one substituent preferably selected from the group consisting of substituents γ, defined below, carbocyclic aryl groups which are unsubstituted or are substituted by at least one substituent preferably selected from the group consisting of substituents α, defined above, and aralkyl groups in which an alkyl group having from 1 to 4 carbon atoms is substituted by from 1 to 3 carbocyclic aryl groups as defined above, and, when substituting a sulfur atom, one or two oxygen atoms to form a sulfoxide or sulfone group; and said substituents γ are selected from the group consisting of halogen atoms, alkoxy groups having from 1 to 6 carbon atoms, aliphatic carboxylic acyl groups having from 1 to 6 carbon atoms, alkanesulfonyl groups having from 1 to 6 carbon atoms, haloalkanesulfonyl groups having from 1 to 6 carbon atoms, hydroxy groups, carboxy groups, alkoxycarbonyl groups having from 1 to 6 carbon atoms in the alkoxy part, acylamino groups having from 1 to 6 carbon atoms, amino groups, and cyano groups;

and pharmaceutically acceptable salts and esters thereof.

The invention also provides a composition for the treatment or prophylaxis of central nervous system diseases, neurodegenerative diseases, respiratory diseases, inflammatory diseases, allergies, hypersensitivity diseases, ophthalmological diseases, skin diseases, addictions, somatic diseases caused by stress, sympathetic reflex dystrophy, dysthymia, undesirable immune reactions, diseases relating to immunopotentiation, digestive diseases, emesis, urinary bladder functional diseases, eosinophilia, diseases caused by abnormal blood flow, and pain, which comprises an effective amount of a compound of formula (I) or (Ia), or a pharmaceutically acceptable salt or ester thereof, in admixture with a pharmaceutically acceptable carrier or diluent.

The invention still further provides a method for the treatment or prophylaxis of a disease or disorder selected from the group consisting of central nervous system diseases, neurodegenerative diseases, respiratory diseases, inflammatory diseases, allergies, hypersensitivity diseases, ophthalmological diseases, skin diseases, addictions, somatic diseases caused by stress, sympathetic reflex dystrophy, dysthymia, undesirable immune reactions, diseases relating to immunopotentiation, digestive diseases, emesis, urinary bladder functional diseases, eosinophilia, diseases caused by abnormal blood flow, and pain, which comprises administering to an animal (which may be human) suffering from or susceptible to said disease or disorder an effective amount of a compound of formula (I) or (Ia), or a pharmaceutically acceptable salt or ester thereof.

The invention also provides a compound of formula (Iz):

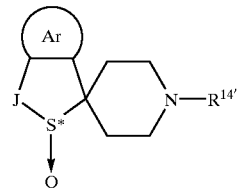

(Iz)

wherein:

J represents an alkylene group having from 1 to 6 carbon atoms;

Ar represents a carbocyclic aryl group or aromatic heterocyclic group fused to the ring containing J and S, said aryl group and said aromatic heterocyclic group being unsubstituted or being substituted by at least one substituent preferably selected from the group consisting of substituents α, defined above;

$R^{14'}$ represents a hydrogen atom or an amino-protecting group; and $S^* \to O$ represents a sulfoxide group in which the sulfur atom is in the S-configuration.

DETAILED DESCRIPTION OF INVENTION

Where $R^1$, $R^2$, $R^3$, $R^4$, $R^6$, $R^a$, $R^b$, Ar or substituent β represents a carbocyclic aryl group, this has from 5 to 14, preferably from 6 to 14, more preferably from 6 to 10, and most preferably 6 or 10, ring carbon atoms. The group may have a single aromatic ring or it may have two or more fused aromatic rings. The group may be unsubstituted or it may be substituted by one or more substituents selected from the group consisting of substituents α, defined above and exemplified below. There is no particular restriction on the number of substituents, except such as may be imposed by the number of substitutable positions, and sometimes by steric constraints. However, in general, where the group is substituted, we prefer from 1 to 3 substituents. Examples of the unsubstituted groups include the phenyl, 1-naphthyl, 2-naphthyl, indenyl, phenanthrenyl and anthracenyl groups, of which the phenyl and naphthyl groups are preferred, the phenyl group being most preferred.

Examples of substituted groups include the 2-methoxyphenyl, 3-methoxyphenyl, 4-methoxyphenyl, 2,4-dimethoxyphenyl, 2,3-dimethoxyphenyl, 2,5-dimethoxyphenyl, 3,4-dimethoxyphenyl, 3,5-dimethoxyphenyl, 2,6-dimethoxyphenyl, 3,4,5-trimethoxyphenyl, 2,4,5-trimethoxyphenyl, 2,3,4-trimethoxyphenyl, 2,3,5-trimethoxyphenyl, 2,3,6-trimethoxyphenyl, 2,4,6-trimethoxyphenyl, 2-ethoxyphenyl, 3-ethoxyphenyl, 4-ethoxyphenyl, 2-isopropoxyphenyl, 3-isopropoxyphenyl, 4-isopropoxyphenyl, 2-methylphenyl, 3-methylphenyl, 4-methylphenyl, 2,4-dimethylphenyl, 2,3-dimethylphenyl, 2,5-dimethylphenyl, 3,4-dimethylphenyl, 3,5-dimethylphenyl, 2,6-dimethylphenyl, 3,4,5-trimethylphenyl, 2,4,5-trimethylphenyl, 2,3,4-trimethylphenyl, 2,3,5-trimethylphenyl, 2,3,6-trimethylphenyl, 2,4,6-trimethylphenyl, 2-chlorophenyl, 3-chlorophenyl, 4-chlorophenyl, 2,4-dichlorophenyl, 2,3-dichlorophenyl, 2,5-dichlorophenyl, 3,4-dichlorophenyl, 3,5-dichlorophenyl, 2,6-dichlorophenyl, 3,4,5-trichlorophenyl, 2,4,5-trichlorophenyl, 2,3,4-trichlorophenyl, 2,3,5-trichlorophenyl, 2,3,6-trichlorophenyl, 2,4,6-trichlorophenyl, 2-fluorophenyl, 3-fluorophenyl, 4-fluorophenyl, 2,4-difluorophenyl, 2,3-difluorophenyl, 3,4-difluorophenyl, 3,5-difluorophenyl, 2,6-difluorophenyl, 3,4,5-trifluorophenyl, 2,4,5-trifluorophenyl, 2-trifluoromethylphenyl, 3-trifluoromethylphenyl, 4-trifluoromethylphenyl, 2,4-bis(trifluoromethyl)phenyl, 2,3-bis(trifluoromethyl)phenyl, 3,4-bis(trifluoromethyl)phenyl, 3,5-bis(trifluoromethyl)phenyl, 2,6-bis(trifluoromethyl)phenyl, 3,4,5-tris(trifluoromethyl)phenyl, 2,4,5-tris(trifluoromethyl)phenyl, 2-acetamidophenyl, 3-acetamidophenyl, 4-acetamidophenyl, 2-methoxycarbonylphenyl, 3-methoxycarbonylphenyl, and 4-methoxycarbonylphenyl groups.

Where substituent a is an alkylene group having from 1 to 8 carbon atoms, this forms, together with the two carbon atoms of the aryl group to which it is attached, a cycloalkyl group fused to the aryl group. An example of such a fused ring group is the indanyl group.

Where $R^1$, $R^2$, $R^3$, $R^4$, $R^6$, $R^b$, or Ar represents an aromatic heterocyclic group, this is a single ring which has from 5 to 7 ring atoms, of which from 1 to 3 atoms are hetero-atoms selected from the group consisting of nitrogen, oxygen and sulfur atoms, or is a fused ring system in which at least one of the rings is an aromatic heterocyclic group as defined above and the or each other ring is such an aromatic heterocyclic group or a carbocyclic aryl group as defined above. Where there are 3 hetero atoms in the aromatic heterocyclic group, these are preferably all nitrogen atoms or one or two are nitrogen atoms and, correspondingly, two or one are oxygen and/or sulfur atoms.

Examples of such aromatic heterocyclic groups include the furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl and pyrazinyl groups. Preferred groups are 5- to 7-membered aromatic heterocyclic groups which have at least one nitrogen atom and optionally one additional nitrogen, oxygen or sulfur atom. Examples of such groups include the pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl and pyrazinyl groups. Of these, the pyridyl, imidazolyl, oxazolyl, pyrazinyl and thiazolyl groups are more preferred.

Such an aromatic heterocyclic group may form a fused ring with another cyclic group, and examples of such fused ring systems include the indolyl, benzofuryl, benzothienyl, benzoxazolyl, benzoimidazolyl, isoquinolyl, quinolyl and quinoxalyl groups.

These aromatic heterocyclic groups may be unsubstituted or they may be substituted by one or more substituents selected from the group consisting of substituents α, defined above and exemplified below. There is no particular restriction on the number of substituents, except such as may be imposed by the number of substitutable positions, and sometimes by steric constraints. However, in general, where the group is substituted, we prefer from 1 to 3 substituents.

Alternatively, $R^6$ may represent a non-aromatic (preferably saturated) heterocyclic group, this may have from 5 to 7 ring atoms, of which from 1 to 3 may be hetero-atoms selected from the group consisting of nitrogen, oxygen and sulfur atoms, at least one preferably being nitrogen. Examples of such groups include the pyrrolidinyl, piperidinyl, piperazinyl, N-methylpiperazinyl, morpholinyl, thiomorpholinyl, oxazolidinyl, thiazolidinyl, diazolidinyl, oxolanyl, thiolanyl and perhydropyridyl groups.

Where B or G represents an alkylene group having from 1 to 4 carbon atoms, this may be a straight or branched chain group having from 1 to 4 carbon atoms, and examples include the methylene, methylmethylene, ethylene, propylene, trimethylene, tetramethylene, 1-methyltrimethylene, 2-methyltrimethylene and 3-methyltrimethylene groups, of which we prefer the straight or branched chain alkylene groups having from 1 to 3 carbon atoms, more preferably the straight or branched chain alkylene groups having 2 or 3 carbon atoms, and most preferably the ethylene or trimethylene group.

Where B or G represents an alkenylene group having from 2 to 4 carbon atoms, this may be a straight or branched chain group having from 2 to 4 carbon atoms, and examples include the ethenylene, 2-propenylene, 1-methyl-2-propenylene, 2-methyl-2-propenylene, 2-ethyl-2-propenylene and 2-butenylene groups, of which we prefer the ethenylene, 2-propenylene and 3-butenylene groups, more preferably the ethenylene or 2-propynylene group.

Where E or J represents an alkylene group having from 1 to 6 carbon atoms, this may be a straight or branched chain group having from 1 to 6 carbon atoms, and examples include the methylene, methylmethylene, ethylene, propylene, trimethylene, tetramethylene, 1-methyltrimethylene, 2-methyltrimethylene, 3-methyltrimethylene, pentamethylene, hexamethylene, 1,1-dimethyltrimethylene, 2,2-dimethyltrimethylene, 1,1-dimethyltetramethylene and 2,2-dimethyltetramethylene groups, of which we prefer the straight or branched chain alkylene groups having from 1 to 4 carbon atoms, more preferably the methylene or ethylene group.

E may also represent a haloalkylene group having from 1 to 6 carbon atoms and substituted by from 1 to 3 halogen atoms, preferably selected from the group consisting of fluorine, chlorine, bromine and iodine atoms, in which the alkylene group may be any of the unsubstituted alkylene groups exemplified above.

Where E represents a cycloalkane-1,1-diyl group having from 3 to 6 carbon atoms, this is a group of formula

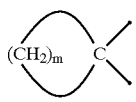

where m is an integer from 2 to 5. Where E represents a cycloalkane-1,1-diylmethyl group having from 3 to 6 carbon atoms in the cycloalkane part, this is a group of formula

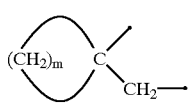

wherein m is as defined above. Where E represents a cycloalkane-1,1-di(ylmethyl) group having from 3 to 6 carbon atoms in the cycloalkane part, this is a group of formula

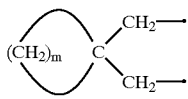

wherein m is as defined above.

Examples of these groups include the cyclopropane-1,1-diyl, cyclobutane-1,1-diyl, cyclopentane-1,1-diyl, cyclohexane-1,1-diyl, cyclopropane-1,1-diylmethyl, cyclobutane-1,1-diylmethyl, cyclopentane-1,1-diylmethyl, cyclohexane-1,1-diylmethyl, cyclopropane-1,1-di(ylmethyl), cyclobutane-1,1-di(ylmethyl), cyclopentane-1,1-di(ylmethyl) and cyclohexane-1,1-di(ylmethyl) groups, of which we prefer the cyclopropane-1,1-diyl, cyclobutane-1,1-diyl, cyclopropane-1,1-diylmethyl and cyclobutane-1,1-diylmethyl groups.

Where $R^5$, $R^6$, $R^7$, $R^a$, $R^b$, substituent α or substituent β represents an alkyl group having from 1 to 6 carbon atoms, this may be a straight or branched chain alkyl group having from 1 to 6, carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, preferably straight or branched chain alkyl groups having from 1 to 4 carbon atoms, such as the methyl, ethyl, propyl, isopropyl, butyl, isobutyl, sec-butyl and t-butyl groups, of which the methyl and ethyl groups are preferred.

Where $R^5$, $R^6$, $R^a$, $R^b$, substituent γ or substituent α represents an alkoxy group having from 1 to 6 carbon atoms, this may be a straight or branched chain alkoxy group having from 1 to 6 carbon atoms, and examples include the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, isohexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutyl and 2-ethylbutyl groups, preferably straight or branched chain alkoxy groups having from 1 to 4 carbon atoms, such as the methoxy, ethoxy, propoxy, isopropoxy, butoxy, isobutoxy, sec-butoxy and t-butoxy groups, of which the methoxy and ethoxy groups are preferred.

Where $R^5$ represents an acylamino group, the acyl part of this group may be selected from a variety of acyl groups well known in the art. For example, it may be:

an aliphatic acyl group, such as an alkanoyl group, preferably having from 1 to 21 carbon atoms, more preferably from 1 to 6 carbon atoms and most preferably from 2 to 6 carbon atoms, for example a formyl, acetyl, propionyl, butyryl, isobutyryl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl or henicosanoyl group;

a haloalkanoyl group, in which the alkanoyl part may be any of the alkanoyl groups exemplified above other than the formyl group, but is preferably a group having from 2 to 6 carbon atoms, and which preferably has from 1 to 3 halogen atoms, for example a chloroacetyl, dichloroacetyl, trichloroacetyl or trifluoroacetyl group;

an alkoxyalkanoyl group in which the alkoxy part has from 1 to 6 carbon atoms and may be any of the alkoxy groups exemplified above in relation to $R^5$ etc., and the alkanoyl part may be any of the alkanoyl groups exemplified above other than the formyl group, but is preferably a group having from 2 to 6 carbon atoms, for example a methoxyacetyl group;

an alkenoyl or alkynoyl group, preferably having from 3 to 6 carbon atoms, for example an acryloyl, propioloyl, methacryloyl, crotonoyl, isocrotonoyl or (E)-2-methyl-2-butenoyl group;

an aromatic acyl group, in which the aryl part may be as defined and exemplified above in relation to $R^1$ etc., for example an unsubstituted arylcarbonyl group, such as a benzoyl, 1-naphthoyl or 2-naphthoyl group;

a halogen-substituted arylcarbonyl group, in which the aryl part may be as defined and exemplified above in relation to $R^1$ etc., for example a 2-bromobenzoyl or 4-chlorobenzoyl group;

an alkyl-substituted arylcarbonyl group, in which the aryl part may be as defined and exemplified above in relation to $R^1$ etc. and the alkyl part may be as defined and exemplified above in relation to $R^5$ etc., for example a 2,4,6-trimethylbenzoyl or 4-toluoyl group;

an alkoxy-substituted arylcarbonyl group, in which the aryl part may be as defined and exemplified above in relation to $R^1$ etc. and the alkoxy part may be as defined and exemplified above in relation to $R^5$ etc., for example a 4-anisoyl group;

a nitro-substituted arylcarbonyl group, in which the aryl part may be as defined and exemplified above in relation to $R^1$ etc., for example a 4-nitrobenzoyl or 2-nitrobenzoyl group;

an alkoxycarbonyl-substituted arylcarbonyl group, in which the aryl part may be as defined and exemplified above in relation to $R^1$ etc. and the alkoxy part of the alkoxycarbonyl group may be as defined and exemplified above in relation to $R^5$ etc., for example a 2-(methoxycarbonyl)benzoyl group;

an aryl-substituted arylcarbonyl group, in which each aryl part may be as defined and exemplified above in relation to $R^1$ etc., for example a 4-phenylbenzoyl group;

an alkoxycarbonyl group having from 1 to 6, preferably from 1 to 4, carbon atoms in the alkoxy part (i.e. a total of from 2 to 7, preferably from 2 to 5, carbon atoms), for example a methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, 2-methylbutoxycarbonyl, neopentyloxycarbonyl, 1-ethylpropoxycarbonyl, hexyloxycarbonyl, isohexyloxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl and 2-ethylbutoxycarbonyl groups, preferably the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups, of which the methoxycarbonyl, ethoxycarbonyl, t-butoxycarbonyl and isobutoxycarbonyl groups are preferred;

an alkoxycarbonyl group substituted with a halogen atom or a trialkylsilyl group having from 1 to 6 carbon atoms in each alkyl part, such as the 2,2,2-trichloroethoxycarbonyl or 2-trimethylsilylethoxycarbonyl groups;

an alkenylcarbonyl group having from 2 to 6 carbon atoms in the alkenyl part, such as the vinylcarbonyl and allylcarbonyl groups;

an aralkylcarbonyl group whose aryl ring may be substituted with 1 or 2 alkoxy groups having from 1 to 6 carbon atoms or nitro groups, such as the benzylcarbonyl, phenacyl, 4-methoxybenzylcarbonyl, 3,4-dimethoxybenzylcarbonyl, 2-nitrobenzylcarbonyl and 4-nitrobenzylcarbonyl groups;

an alkanesulfonyl group having from 1 to 6 carbon atoms, such as the methanesulfonyl, ethanesulfonyl and 1-propanesulfonyl groups;

a fluorinated alkanesulfonyl group having from 1 to 6 carbon atoms, such as the trifluoromethanesulfonyl and pentafluoroethanesulfonyl groups;

an arylsulfonyl group in which the aryl part may be as defined and exemplified above in relation to $R^1$ etc., such as the benzenesulfonyl and p-toluenesulfonyl groups.

Of these, we prefer the aliphatic acyl groups, the aromatic acyl groups and the alkanesulfonyl groups.

Where $R^5$ represents an alkyl group which has from 1 to 6 carbon atoms and which is substituted by an acylamino group, the alkyl part may be any of the alkyl groups defined and exemplified above in relation to $R^5$, and the acyl substituent may also be any of the acyl groups defined and exemplified above in relation to $R^5$.

Where $R^5$ represents an acylamino group whose nitrogen atom is substituted with an alkyl group having from 1 to 6 carbon atoms, the acyl substituent may be any of the acyl groups defined and exemplified above in relation to $R^5$, and the alkyl part may also be any of the alkyl groups defined and exemplified above in relation to $R^5$.

Where $R^5$ represents a hydroxyalkyl group having from 1 to 6 carbon atoms, this may be any one of the above alkyl groups which is substituted by at least one hydroxy group, for example the hydroxymethyl, hydroxyethyl, hydroxypropyl, hydroxybutyl, hydroxypentyl, or hydroxyhexyl group.

Where $R^5$ represents an alkoxyalkyl group, the alkoxy and alkyl parts may be independently selected from the corresponding groups defined and exemplified above in relation to $R^5$. Examples of such alkoxyalkyl groups include the methoxymethyl, ethoxymethyl, propoxymethyl, isopropoxymethyl, butoxymethyl, isobutoxymethyl, sec-butoxymethyl, t-butoxymethyl, pentyloxymethyl, isopentyloxymethyl, neopentyloxymethyl, hexyloxymethyl, isohexyloxymethyl, methoxyethyl, ethoxyethyl, propoxyethyl, isopropoxyethyl, butoxyethyl, isobutoxyethyl, sec-butoxyethyl, t-butoxyethyl, pentyloxyethyl, isopentyloxyethyl, neopentyloxyethyl, hexyloxyethyl, isohexyloxyethyl, methoxypropyl, ethoxypropyl, propoxypropyl, isopropoxypropyl, butoxypropyl, isobutoxypropyl, sec-butoxypropyl, t-butoxypropyl, pentyloxypropyl, isopentyloxypropyl, neopentyloxypropyl, hexyloxypropyl, isohexyloxypropyl, methoxybutyl, ethoxybutyl, propoxybutyl, isopropoxybutyl, butoxybutyl, isobutoxybutyl, sec-butoxybutyl, t-butoxybutyl, pentyloxybutyl, isopentyloxybutyl, neopentyloxybutyl, hexyloxybutyl, isohexyloxybutyl, methoxypentyl, ethoxypentyl, propoxypentyl, isopropoxypentyl, butoxypentyl, isobutoxypentyl, sec-butoxypentyl, t-butoxypentyl, pentyloxypentyl, isopentyloxypentyl, neopentyloxypentyl, hexyloxypentyl, isohexyloxypentyl, methoxyhexyl, ethoxyhexyl, propoxyhexyl, isopropoxyhexyl, butoxyhexyl, isobutoxyhexyl, sec-butoxyhexyl, t-butoxyhexyl, pentyloxyhexyl, isopentyloxyhexyl, neopentyloxyhexyl, hexyloxyhexyl and isohexyloxyhexyl groups.

Where $R^5$ represents an aralkyloxyalkyl group, the aralkyl part is an alkyl group which has from 1 to 4 carbon atoms and which is substituted by from 1 to 3 carbocyclic aryl groups which are unsubstituted or which are substituted by at least one substituent preferably selected from the group consisting of substituents α, defined above and exemplified below, and the alkyl part of the oxyalkyl group has from 1 to 6 carbon atoms. The alkyl parts may be any of the alkyl groups exemplified above in relation to $R^5$. The aralkyl part of the group may be any of the aralkyl groups defined and exemplified below in relation to substituents β. Specific examples of such groups include the benzyloxymethyl, α-naphthylmethoxymethyl, β-naphthylmethoxymethyl, phenethyloxymethyl, 2-benzyloxyethyl, 2-α-naphthylmethoxyethyl, 2-β-naphthylmethoxyethyl, 2-phenethyloxyethyl, 3-benzyloxypropyl, 3-α-naphthylmethoxypropyl, 3-β-naphthylmethoxypropyl, 3-phenethyloxypropyl, 4-benzyloxybutyl, 4-α-naphthylmethoxybutyl, 4-β-naphthylmethoxybutyl, 4-phenethyloxybutyl, 5-benzyloxypentyl, 5-α-naphthylmethoxypentyl, 5-β-naphthylmethoxypentyl, 5-phenethyloxypentyl, 6-benzyloxyhexyl, 6-α-naphthylmethoxyhexyl, 6-β-naphthylmethoxyhexyl and 6-phenethyloxyhexyl groups. The aryl parts of these groups may be substituted or unsubstituted, and, if substituted, the substituents are selected from the group consisting of substituents α, defined above.

Where $R^a$ or $R^b$, substituent α or substituent γ represents an aliphatic carboxylic acyl group, this may be any of the aliphatic acyl groups, haloalkanoyl groups, alkoxyalkanoyl groups, alkenoyl groups, alkynoyl groups, alkoxycarbonyl groups, alkoxycarbonyl groups substituted with a halogen atom, and alkenylcarbonyl groups, defined and exemplified above in relation to $R^5$, particularly the formyl, acetyl, propionyl, butyryl, isobutyryl, pentanoyl, pivaloyl, valeryl and isovaleryl groups, preferably the acetyl and propionyl groups.

Where $R^a$ or $R^b$, substituent α or substituent γ represents an alkanesulfonyl group, or a haloalkanesulfonyl group, this may be any of those groups defined and exemplified above in relation to $R^5$ or substituent β.

Where $R^a$ or $R^b$ represents a cycloalkyl group, this has from 3 to 8 ring carbon atoms, and examples include the cyclopropyl, cyclobutyl, cyclopentyl, cyclohexyl, cycloheptyl and cyclooctyl groups, of which the cyclopentyl and cyclohexyl groups are preferred.

Where $R^a$ and $R^b$, together with the nitrogen atom to which they are attached, represent a nitrogen-containing heterocyclic group, this may have from 5 to 7 ring atoms, of which from 1 to 3 may be hetero-atoms selected from the group consisting of nitrogen, oxygen and sulfur atoms, at least one being nitrogen. The heterocyclic group is preferably a saturated (non-aromatic) group. Examples of such groups include the pyrrolidino, piperidino, piperazino, N-methylpiperazino, morpholino and thiomorpholino groups.

Where $R^4$ and $R^5$ together with the carbon atom to which they are attached represent a cycloalkyl or heterocyclic group having from 5 to 10 ring atoms, this group is unsubstituted or is substituted by at least one substituent selected from the group consisting of substituents β, defined above. The heterocyclic group has a single hetero-atom selected from the group consisting of nitrogen, oxygen and sulfur atoms. Alternatively, $R^4$ and $R^5$ together with the carbon atom to which they are attached may represent a cycloalkyl or heterocyclic group as defined above which is fused to a carbocyclic aryl group or an aromatic heterocyclic group, said aryl group and said aromatic heterocyclic group being unsubstituted or being substituted by at least one substituent preferably selected from the group consisting of substituents α, defined above. Examples of such groups include the aromatic and saturated heterocyclic groups exemplified above in relation to $R^a$ and $R^b$, $R^1$ etc. and $R^6$, respectively, and the cycloalkyl groups exemplified above in relation to $R^a$ and $R^b$.

A particularly preferred group which may be represented by $R^4$ and $R^5$ together is the group of formula:

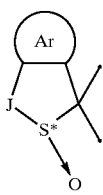

in which Ar, J and S*→O are as defined above.

Where substituent α or substituent γ represents a halogen atom, this may be a fluorine, chlorine, bromine or iodine atom, preferably a fluorine or chlorine atom.

Where substituent a represents a haloalkyl group, the alkyl part may be a straight or branched chain group having from 1 to 6, preferably from 1 to 3, carbon atoms. There is no restriction on the number of halogen atoms, except that imposed by the number of substitutable positions; however, in general, from 1 to 3 halogen atoms are preferred. Examples of such groups include the trifluoromethyl, trichloromethyl, difluoromethyl, dichloromethyl, dibromomethyl, fluoromethyl, chloromethyl, bromomethyl, iodomethyl, 2,2,2-trichloroethyl, 2,2,2-trifluoroethyl, 2-bromoethyl, 2-chloroethyl, 2-fluoroethyl, 2-iodoethyl, 2,2-dibromoethyl, 3-bromopropyl, 3-chloropropyl, 3-fluoropropyl, 3-iodopropyl, 4-bromobutyl, 4-chlorobutyl, 4-fluorobutyl, 4-iodobutyl, 5-bromopentyl, 5-chloropentyl, 5-fluoropentyl, 5-iodopentyl, 6-bromohexyl, 6-chlorohexyl, 6-fluorohexyl and 6-iodohexyl, of which we prefer the trifluoromethyl, 2-bromoethyl, 2-chloroethyl and 2-fluoroethyl groups.

Where substituent α or substituent γ represents an alkoxycarbonyl group having from 1 to 6 carbon atoms in the alkoxy part, this may be any of the groups defined and exemplified above in relation to $R^5$.

Where substituent α or substituent γ represents an acylamino group, the acyl part of this may be any of the groups exemplified above for $R^5$, etc. Specific preferred examples of such groups include aliphatic carboxylic acylamino groups, such as the formamido, acetamido, propionamido, butyramido, isobutyramido, pentanoylamino, pivaloylamino, valerylamino and isovalerylamino groups, preferably the acetamido and propionamido groups.

Where substituent β represents an alkanesulfonyl group having from 1 to 6 carbon atoms, this may be a straight or branched chain group having from 1 to 6, preferably from 1 to 4, carbon atoms, and examples include the methanesulfonyl, ethanesulfonyl, propanesulfonyl, isopropanesulfonyl, butanesulfonyl, isobutanesulfonyl, sec-butanesulfonyl, t-butanesulfonyl, pentanesulfonyl, isopentanesulfonyl, neopentanesulfonyl, 2-methylbutanesulfonyl, 1-ethylpropanesulfonyl, 4-methylpentanesulfonyl, 3-methylpentanesulfonyl, 2-methylpentanesulfonyl, 1-methylpentanesulfonyl, 3,3-dimethylbutanesulfonyl, 2,2-dimethylbutanesulfonyl, 1,1-dimethylbutanesulfonyl, 1,2-dimethylbutanesulfonyl, 1,3-dimethylbutanesulfonyl, 2,3-dimethylbutanesulfonyl, 2-ethylbutanesulfonyl, hexanesulfonyl and isohexanesulfonyl groups. Of these, we prefer those alkanesulfonyl groups having from 1 to 4 carbon atoms, preferably the methanesulfonyl, ethanesulfonyl, propanesulfonyl, isopropanesulfonyl, butanesulfonyl and isobutanesulfonyl groups, and most preferably the methanesulfonyl group.

Where $R^a$ or $R^b$ or substituent , represents an aralkyl group in which an alkyl group having from 1 to 4 carbon atoms is substituted by from 1 to 3 carbocyclic aryl groups, this is as defined above, and examples include the benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-α-naphthylethyl, 2-α-naphthylethyl, 1-β-naphthylethyl, 2-β-naphthylethyl, 1-phenylpropyl, 2-phenylpropyl, 3-phenylpropyl, 1-α-naphthylpropyl, 2-α-naphthylpropyl, 3-α-naphthylpropyl, 1-β-naphthylpropyl, 2-β-naphthylpropyl, 3-β-naphthylpropyl, 1-phenylbutyl, 2-phenylbutyl, 3-phenylbutyl, 4-phenylbutyl, 1-α-naphthylbutyl, 2-α-naphthylbutyl, 3-α-naphthylbutyl, 4-α-naphthylbutyl, 1-β-naphthylbutyl, 2-β-naphthylbutyl, 3-β-naphthylbutyl, 4-β-naphthylbutyl, 1-phenylpentyl, 2-phenylpentyl, 3-phenylpentyl, 4-phenylpentyl, 5-phenylpentyl, 1-α-naphthylpentyl, 2-α-naphthylpentyl, 3-α-naphthylpentyl, 4-α-naphthylpentyl, 5-α-naphthylpentyl, 1-β-naphthylpentyl, 2-β-naphthylpentyl, 3-β-naphthylpentyl, 4-β-naphthylpentyl, 5-β-naphthylpentyl, 1-phenylhexyl, 2-phenylhexyl, 3-phenylhexyl, 4-phenylhexyl, 5-phenylhexyl, 6-phenylhexyl, 1-α-naphthylhexyl, 2-α-naphthylhexyl, 3-α-naphthylhexyl, 4-α-naphthylhexyl, 5-α-naphthylhexyl, 6-α-naphthylhexyl, 1-β-naphthylhexyl, 2-β-naphthylhexyl, 3-β-naphthylhexyl, 4-β-naphthylhexyl, 5-β-naphthylhexyl and 6-β-naphthylhexyl groups, of which we prefer those aralkyl groups in which the aryl group moiety is benzene and the alkyl group has from 1 to 4 carbon atoms, more preferably the benzyl group or the phenethyl group.

Where substituent α represents an alkanesulfonylamino group, or a haloalkanesulfonylamino group, the alkanesulfonyl or haloalkanesulfonyl part of this may be any of those groups defined and exemplified above in relation to $R^5$ or substituent β.

Where $R^{14'}$ represents an amino-protecting group, this may be any of the aliphatic acyl groups, the aromatic acyl groups and the alkoxycarbonyl groups defined and exemplified above in relation to $R^5$ etc., or the alkenyloxycarbonyl groups, the aralkyloxycarbonyl groups and the silyl groups as defined and exemplified below in relation to ester groups, preferably an alkoxycarbonyl group. Of these, we particularly prefer the t-butoxycarbonyl group.

Each compound of the present invention contains a basic group in its molecule and can thus form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glycine, arginine, ornithine, lysine, glutamic acid or aspartic acid.

Since the compounds of formula (I) of the present invention can be converted into a quaternary amine by modifying the nitrogen atom of the piperidino or piperazino group in the molecule with a group $R^7$, and thus salts of the compounds of formula (I) having a cation and an anion (which may be any atom or group which can form an anion, and examples thereof include halogen ion such as chlorine ion, and iodine ion) are also included in the present invention.

The compounds of formula (I) of the present invention can sometimes be converted into a hydrate by absorption of water or adhesion of absorbed water when they are allowed to stand in the atmosphere, and such hydrates are also included in the present invention.

The compounds of formula (I) of the present invention can form esters, which also form part of the present invention. Where the compound is intended for therapeutic use, the ester should be pharmaceutically acceptable, which, as is well known, means that it should not be more toxic (or unacceptably more toxic) than the parent compound, nor should it be less active (or unacceptably less active) than the parent compound. Such esters can be regarded as either "general" esters or "biologically cleavable" esters, either of which may act as protecting groups.

The "general" esters are esters which can be cleaved by a chemical process such as hydrogenolysis, hydrolysis, electrolysis, photolysis and the like. Examples of groups which can form esters with a hydroxy group include:

the above aliphatic acyl groups;

the above aromatic acyl groups;

tetrahydropyranyl or tetrahydrothiopyranyl groups, such as the tetrahydropyran-2-yl, 3-bromotetrahydropyran-2-yl, 4-methoxytetrahydropyran-4-yl, tetrathiopyran-2-yl and 4-methoxytetrahydrothiopyran-4-yl groups;

tetrahydrofuranyl or tetrahydrothiofuranyl groups, such as the tetrahydrofuran-2-yl and tetrahydrothiofuran-2-yl groups;

silyl groups, such as the trialkylsilyl groups having from 1 to 6 carbon atoms in each alkyl part (e.g. trimethylsilyl, triethylsilyl, isopropyldimethylsilyl, t-butyldimethylsilyl, methyldiisopropylsilyl, methyldi-t-butylsilyl and triisopropylsilyl groups), trialkylsilyl groups having from 1 to 6 carbon atoms in each alkyl part and in which one or two of the alkyl groups are replaced by aryl groups as defined and exemplified above in relation to $R^1$ etc. (e.g. diphenylmethylsilyl, diphenylbutylsilyl, diphenylisopropylsilyl and phenyldiusopropylsilyl groups);

optionally substituted alkoxymethyl groups having from 1 to 6 carbon atoms in the alkoxy part, such as the alkoxymethyl groups (e.g. the methoxymethyl, 1,1-dimethyl-1-methoxymethyl, ethoxymethyl, propoxyrnethyl, isopropoxymethyl, butoxymethyl and t-butoxymethyl groups), alkoxylated alkoxymethyl groups having from 1 to 6 carbon atoms in each alkoxy part (e.g. the 2-methoxyethoxymethyl group), haloalkoxymethyl groups having from 1 to 6 carbon atoms in the alkoxy part [e.g. the 2,2,2-trichloroethoxymethyl and bis(2-chloroethoxy)methyl groups];

substituted ethyl groups, such as alkoxylated ethyl groups having from 1 to 6 carbon atoms in the alkoxy part (e.g. the 1-ethoxyethyl and 1-isopropoxyethyl groups), haloethyl groups (e.g. the 2,2,2-trichloroethyl group);

aralkyl groups as defined above in relation to substituents β, preferably alkyl groups substituted with from 1 to 3 aryl groups (e.g. the benzyl, α-naphthylmethyl, β-naphthylmethyl, diphenylmethyl, triphenylmethyl, α-naphthyldiphenylmethyl and 9-anthrylmethyl groups), lower alkyl groups substituted with from 1 to 3 aryl groups, whose aryl ring is substituted with a lower alkyl, lower alkoxy, nitro, halogen or cyano group (e.g. the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups);

the above alkoxycarbonyl groups;

alkenyloxycarbonyl groups, such as the vinyloxycarbonyl and allyloxycarbonyl groups;

aralkyloxycarbonyl groups whose aryl ring may be substituted with 1 or 2 lower alkoxy or nitro groups, such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

Biologically cleavable esters contain groups which can be cleaved by a biological process, such as biodegradation, to form a free acid or a salt thereof. It can be determined whether an ester is biologically cleavable by administering it to an experimental animal (e.g. a rat or mouse) due to phlebclysis, examining the body fluid of the animal after administration and detecting an original compound or a pharmaceutical acceptable salt thereof.

Examples of biologically cleavable esters include:

1-(acyloxy) lower alkyl groups, such as the 1-(aliphatic acyloxy) lower alkyl groups (e.g. the formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivalolyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups);

1-(cycloalkyl carbonyloxy) lower alkyl groups (e.g. the cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl,
1-cyclohexylcarbonyloxypropyl,
1-cylopentylcarbonyloxybutyl and
1-cyclohexylcarbonyloxybutyl groups);

1-(aromatic acyloxy) lower alkyl groups (e.g. the benzoyloxymethyl group);

carbonyloxyalkyl groups, such as the (alkoxycarbonyloxy)alkyl groups and (cycloalkoxycarbonyloxy)alkyl groups (e.g. the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentylcarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 2-(methoxycarbonyloxy)ethyl, 2-(ethoxycarbonyloxy)ethyl, 2-(propoxycarbonyloxy)ethyl, 2-(isopropoxycarbonyloxy)ethyl, 2-(butoxycarbonyloxy)ethyl, 2-(isobutoxycarbonyloxy)ethyl, 2-(pentyloxycarbonyloxy)ethyl, 2-(hexyloxycarbonyloxy)ethyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl groups);

oxodioxolenylmethyl groups (e.g. the (5-phenyl-2-oxo-1,3-dioxolen-4-yl)-methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups);

phthalidyl groups, such as the phthalidyl, dimethylphthalidyl and dimethoxyphthalidyl groups;

the above aliphatic acyl groups;

the above aromatic acyl groups;

half ester salt residues of succinic acid;

phosphate salt residues;

ester forming residues such as with amino acids;

1-(acyloxy)alkyloxycarbonyl groups, such as the pivaloyloxymethoxycarbonyl group.

Of these, we prefer the carbonyloxyalkyl groups.

The compounds of formula (I) of the present invention have an asymmetric carbon atom in the molecule, and stereoisomers whose asymmetric carbon atom has the R or S configurations are present. The stereoisomers whose asymmetric carbon atom has the R or S configurations and a mixture thereof having any proportion are also included in the present invention.

Preferred classes of compounds of the present invention are those compounds of formula (I) and salts and esters thereof in which E represents a methylene group and (A1) $R^1$ and $R^2$ are the same or different and each represents a carbocyclic aryl group, an aromatic heterocyclic group or a carbocyclic aryl group substituted with from 1 to 3 groups selected from the group consisting of substituents α;

(B1) $R^2$ represents a carbocyclic aryl group or a carbocyclic aryl group substituted with from 1 to 3 groups selected from the group consisting of substituents α;

(C1) A represents a carbonyl group;

(D1) B is a single bond;

(E1) D is an oxygen atom;

(F1) G is an alkylene group having from 1 to 4 carbon atoms;

(G1) G is an alkylene group having 2 or 3 carbon atoms;

(H1) $R^3$ represents an aromatic heterocyclic group or a carbocyclic aryl group substituted with from 1 to 3 groups selected from the group consisting of substituents α;

(I1) L represents a group of formula —C($R^4$)($R^5$)—;

(J1) $R^4$ represents a carbocyclic aryl group or an aromatic heterocyclic group;

(K1) $R^5$ represents a group of formula —CO—$R^6$ (where $R^6$ represents an alkyl group having from 1 to 6 carbon atoms or a group of formula —NR$^a$R$^b$);

(L1) $R^5$ represents an amino group, an acylamino group or a hydroxy group;

(M1) $R^4$ and $R^5$ together with the carbon atom to which they are attached represent a cycloalkyl or heterocyclic group having from 5 to 10 ring atoms, said group being unsubstituted or being substituted by at least one substituent selected from the group consisting of substituents β, and said heterocyclic group having a single hetero-atom selected from the group consisting of nitrogen, oxygen and sulfur atoms, or $R^4$ and $R^5$ together with the carbon atom to which they are attached represent a cycloalkyl or heterocyclic group as defined above which is fused to a carbocyclic aryl group or an aromatic heterocyclic group, said aryl group and said aromatic heterocyclic group being unsubstituted or being substituted by at least one substituent preferably selected from the group consisting of substituents α.

Further preferred classes of compounds of the present invention are those compounds of formula (I) and salts and esters thereof in which E represents a group of formula —(CH$_2$)$_n$— in which n is an integer from 2 to 4, and (A2) R$^1$ and R$^2$ are the same or different and each represents a carbocyclic aryl group, an aromatic heterocyclic group or a carbocyclic aryl group substituted with from 1 to 3 groups selected from the group consisting of substituents a;

(B2) R$^2$ represents a carbocyclic aryl group or a carbocyclic aryl group substituted with from 1 to 3 groups selected from the group consisting of substituents c;

(C2) A represents a carbonyl group;

(D2) B represents a single bond;

(E2) D represents an oxygen atom;

(F2) G represents an alkylene group having 1 to 4 carbon atoms;

(G2) G represents an alkylene group having 2 to 3 carbon atoms;

(H2) R$^3$ represents an aromatic heterocyclic group or a carbocyclic aryl group substituted with from 1 to 3 groups selected from the group consisting of substituents α;

(I2) L represents a group of the general formula —C(R$^4$)(R$^5$)—;

(J2) R$^4$ represents a carbocyclic aryl group or an aromatic heterocyclic group;

(K2) R$^5$ represents a group of formula —CO—R$^6$ (wherein R$^6$ represents an alkyl group having from 1 to 6 carbon atoms or a group of formula —NR$^a$R$^b$);

(L2) R$^5$ represents an amino group, an acylamino group or a hydroxy group;

(M2) n is 2 or 3;

(N2) n is 2;

(O2) R$^4$ and R$^5$ together with the carbon atom to which they are attached represent a cycloalkyl or heterocyclic group having from 5 to 10 ring atoms, said group being unsubstituted or being substituted by at least one substituent selected from the group consisting of substituents β, and said heterocyclic group having a single hetero-atom selected from the group consisting of nitrogen, oxygen and sulfur atoms, or R$^4$ and R$^5$ together with the carbon atom to which they are attached represent a cycloalkyl or heterocyclic group as defined above which is fused to a carbocyclic aryl group or an aromatic heterocyclic group, said aryl group and said aromatic heterocyclic group being unsubstituted or being substituted by at least one substituent preferably selected from the group consisting of substituents α.

Still further preferred classes of compounds of the present invention are those compounds of formula (I) and salts and esters thereof in which R$^4$ and R$^5$ together with the carbon atom to which they are attached represent a group of formula:

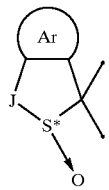

and (A3) R$^1$ represents a carbocyclic aryl group, an aromatic heterocyclic group, or a carbocyclic aryl group substituted with from 1 to 3 groups selected from the group consisting of substituents α;

(B3) R$^1$ represents a carbocyclic aryl group or a carbocyclic aryl group substituted with from 1 to 3 groups selected from the group consisting of substituents α$^1$; substituents α$^1$ are selected from the group consisting of alkyl groups having from 1 to 6 carbon atoms, haloalkyl groups having from 1 to 6 carbon atoms, and alkoxy groups having from 1 to 6 carbon atoms;

(C3) R$^2$ represents a carbocyclic aryl group or a carbocyclic aryl group substituted with from 1 to 3 groups selected from the group consisting of substituents α;

(D3) R$^2$ represents a carbocyclic aryl group or a carbocyclic aryl group substituted with from 1 to 3 halogen atoms;

(E3) A represents a carbonyl group;

(F3) B represents a single bond;

(G3) D represents an oxygen atom;

(H3) E represents a C$_{1-4}$ alkylene group or a C$_{3-8}$ alkylene group which contains a C$_{3-6}$ cycloalkane-1,1-diyl group;

(I3) E represents a methylene, ethylene, dimethylmethylene, 1,1-dimethylethylene, 2,2-dimethylethylene, cyclopropane-1,1-diyl, cyclobutane-1,1-diyl, cyclopentane-1,1-diyl, cyclohexane-1,1-diyl, cyclopropane-1,1-diylmethyl, cyclobutane-1,1-diylmethyl, cyclopentane-1,1-diylmethyl or cyclohexane-1,1-diylmethyl group;

(J3) G represents a C$_{1-4}$ alkylene group;

(K3) G represents a C$_{2-3}$ alkylene group;

(L3) J represents a C$_{1-4}$ alkylene group;

(M3) J represents a methylene or ethylene group;

(N3) the ring Ar represents a carbocyclic aryl group, a carbocyclic aryl group substituted with from 1 to 3 groups selected from the group consisting of substituents α or an aromatic heterocyclic group;

(O3) the ring Ar represents a carbocyclic aryl group or a carbocyclic aryl group substituted with from 1 to 3 groups selected from the group consisting of substituents α.

Examples of certain of the compounds of the present invention, which can be prepared as described hereinafter in the Examples, are shown in the following formulae (I-1), (I-2) and (I-3). The substituent groups are as defined in the corresponding one of Tables 1, 2 and 3, i.e. Table 1 relates to formula (I-1), etc.

Each of the compound numbers shown in these Tables covers 2 compounds, one in which G represents a dimethylene group (which may be referred to by the number assigned to it in the Table and the suffix "a") and one in which G represents a trimethylene group (which may be referred to by the number assigned to it in the Table and the suffix "b").

Moreover, each of Compounds No. 2-1537 to 2-3072 also covers compounds in which B can represent a single bond or a CH$_2$ group. These may be identified by a further suffix, α or β, respectively, so that, for example, Compound No. 2-1537 where G represents a dimethylene group and B represents a single bond may be known as Compound No. 2-1537aα, Compound No. 2-1537 where G represents a dimethylene group and B represents a CH$_2$ group may be known as Compound No. 2-1537aβ, Compound No. 2-1537 where G represents a trimethylene group and B represents a single bond may be known as Compound No. 2-1537bα, and Compound No. 2-1537 where G represents a trimethylene group and B represents a CH$_2$ group may be known as Compound No. 2-1537bβ.

Certain of the names of substituent groups are abbreviated in the Tables, as follows:

| | |
|---|---|
| cBu | cyclobutane-1,1-diyl |
| cHx | cyclohexane-1,1-diyl |
| Me | methyl |
| Ph | phenyl |
| cPn | cyclopentane-1,1-diyl |
| cPr | cyclopropane-1,1-diyl |

Also, the groups having the following formulae are referred to by the associated reference Sub-xx as shown below:

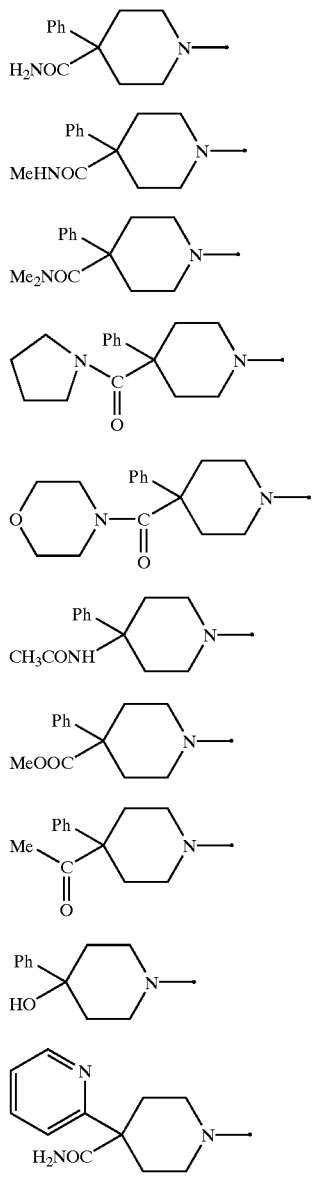

Sub-1
Sub-2
Sub-3
Sub-4
Sub-5
Sub-6
Sub-7
Sub-8
Sub-9
Sub-10

-continued

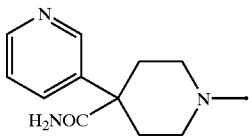
Sub-11

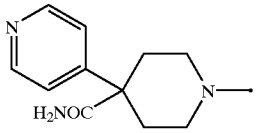
Sub-12

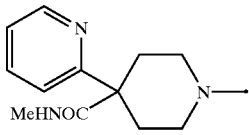
Sub-13

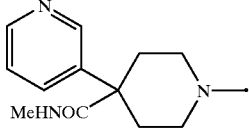
Sub-14

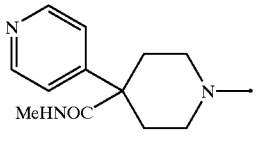
Sub-15

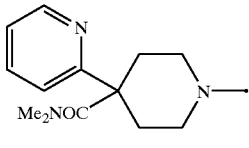
Sub-16

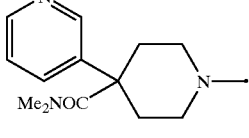
Sub-17

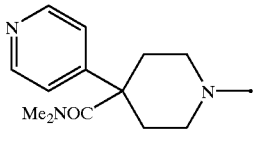
Sub-18

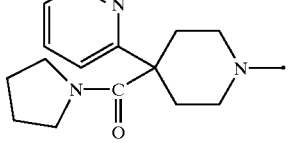
Sub-19

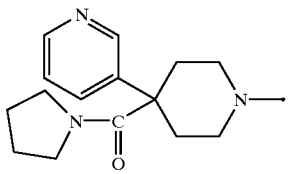
Sub-20

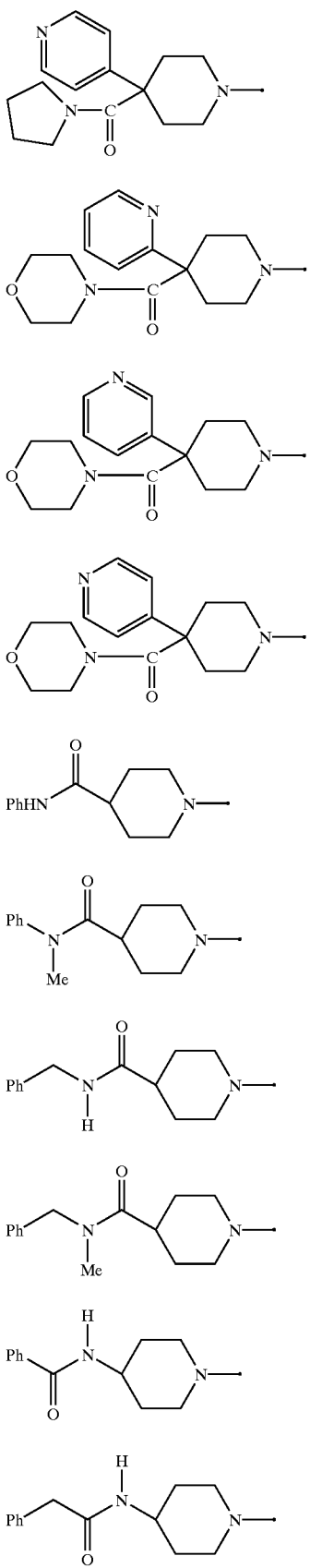
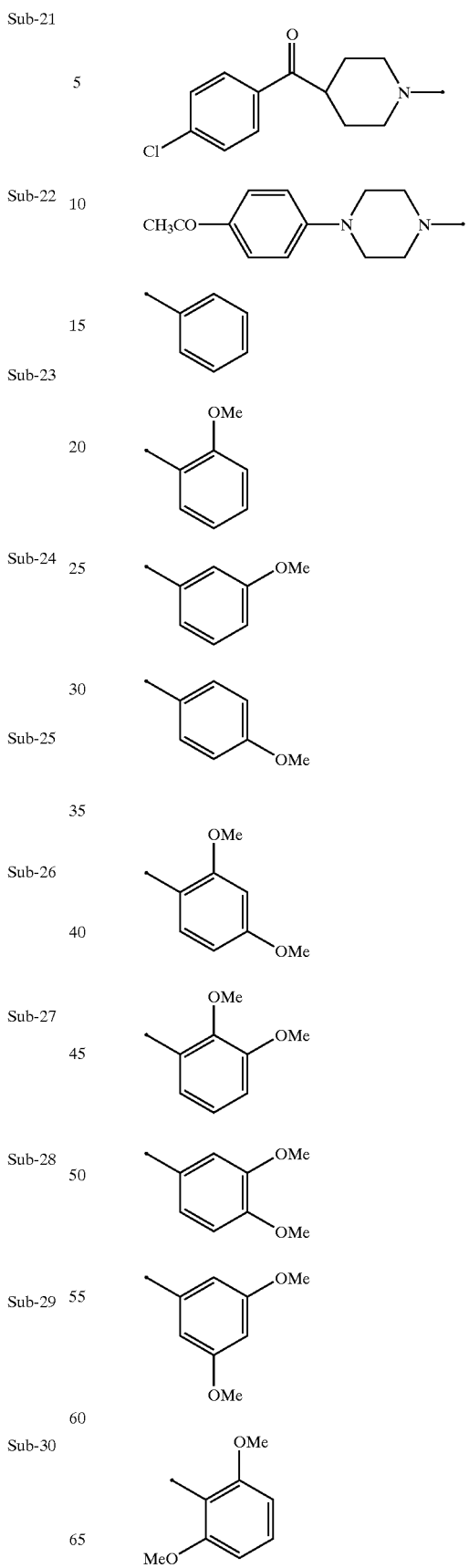

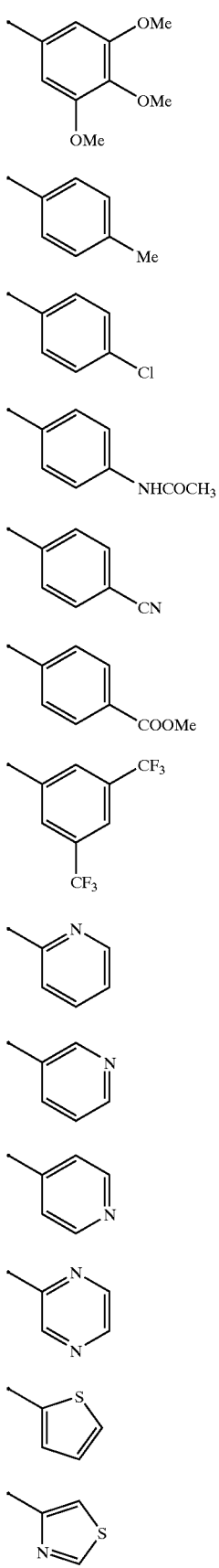
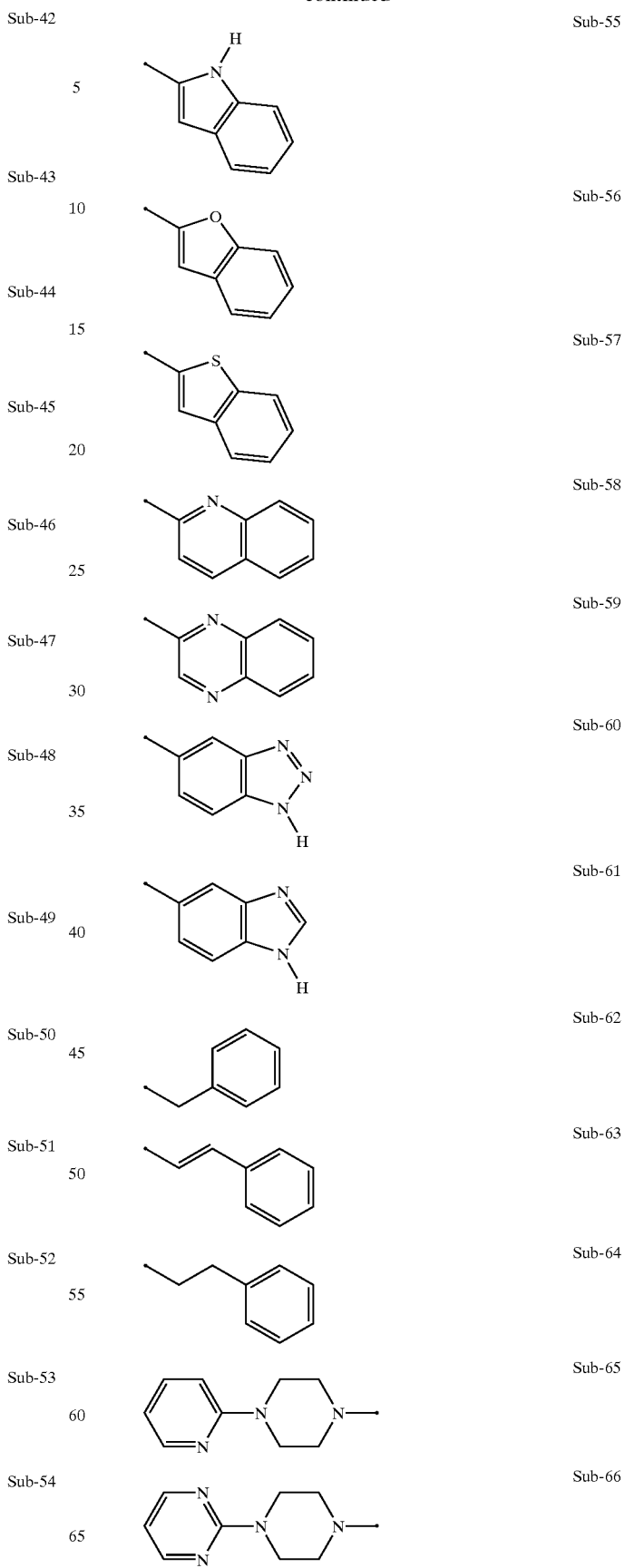

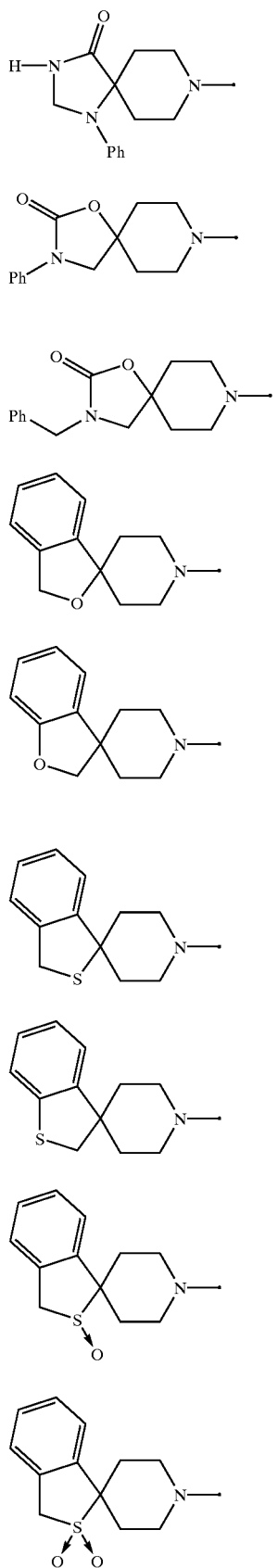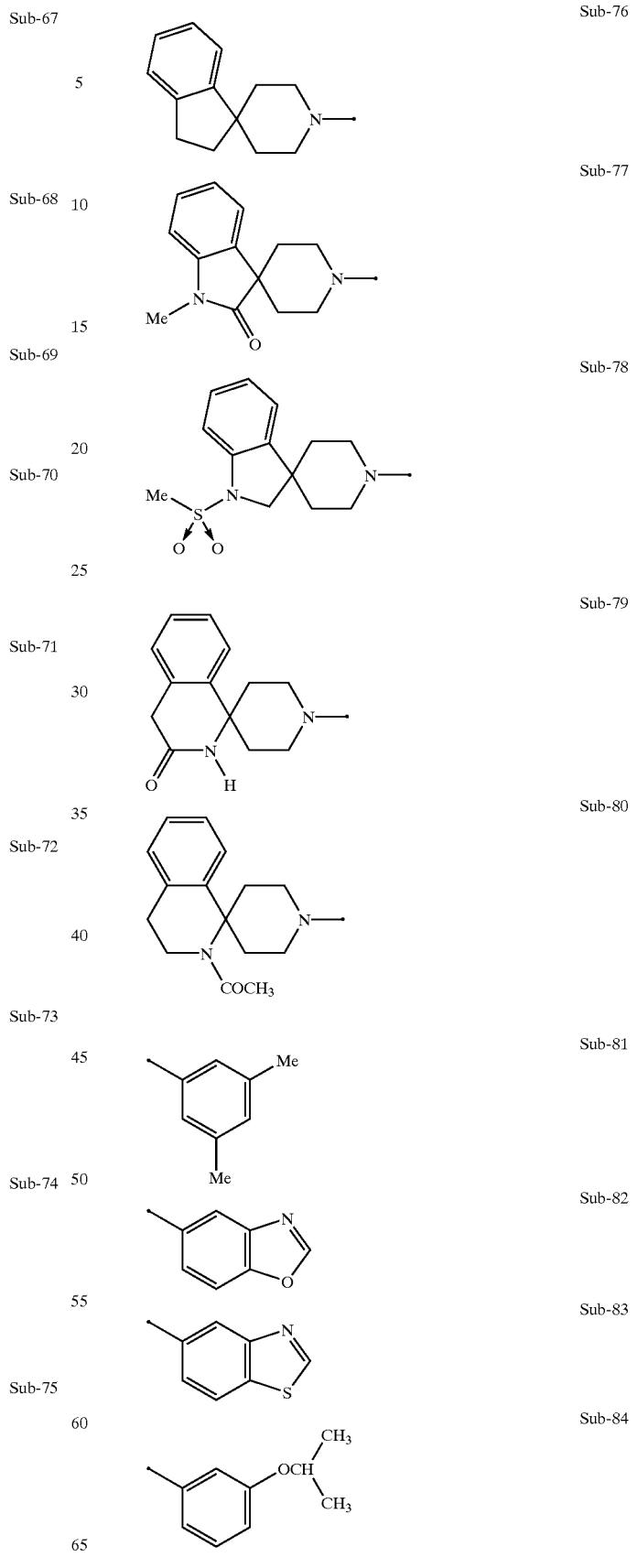

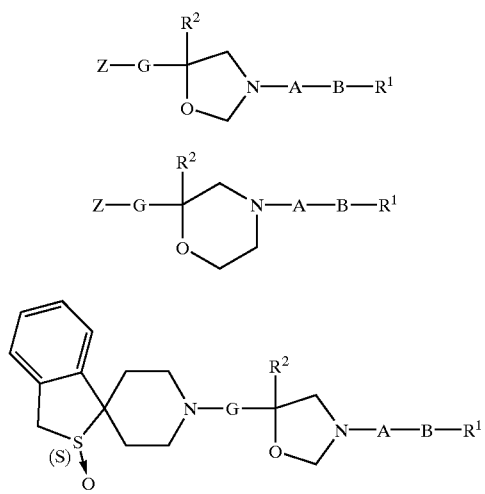

TABLE 1

| Cpd. No. | R¹ | R² | A | B | Z |
|---|---|---|---|---|---|
| 1-1 | Sub-33 | 3,4-diClPh | CH₂ | Single bond | Sub-1 |
| 1-2 | Sub-33 | 3,4-diClPh | CH₂ | Single bond | Sub-2 |
| 1-3 | Sub-33 | 3,4-diClPh | CH₂ | Single bond | Sub-3 |
| 1-4 | Sub-33 | 3,4-diClPh | CH₂ | Single bond | Sub-4 |
| 1-5 | Sub-33 | 3,4-diClPh | CH₂ | Single bond | Sub-5 |
| 1-6 | Sub-33 | 3,4-diClPh | CH₂ | Single bond | Sub-6 |
| 1-7 | Sub-33 | 3,4-diClPh | CH₂ | Single bond | Sub-7 |
| 1-8 | Sub-33 | 3,4-diClPh | CH₂ | Single bond | Sub-8 |
| 1-9 | Sub-33 | 3,4-diClPh | CH₂ | Single bond | Sub-9 |
| 1-10 | Sub-33 | 3,4-diClPh | CH₂ | Single bond | Sub-10 |
| 1-11 | Sub-33 | 3,4-diClPh | CH₂ | Single bond | Sub-11 |
| 1-12 | Sub-33 | 3,4-diClPh | CH₂ | Single bond | Sub-12 |
| 1-13 | Sub-33 | 3,4-diClPh | CH₂ | Single bond | Sub-13 |
| 1-14 | Sub-33 | 3,4-diClPh | CH₂ | Single bond | Sub-14 |
| 1-15 | Sub-33 | 3,4-diClPh | CH₂ | Single bond | Sub-15 |
| 1-16 | Sub-33 | 3,4-diClPh | CH₂ | Single bond | Sub-16 |
| 1-17 | Sub-33 | 3,4-diClPh | CH₂ | Single bond | Sub-17 |
| 1-18 | Sub-33 | 3,4-diClPh | CH₂ | Single bond | Sub-18 |
| 1-19 | Sub-33 | 3,4-diClPh | CH₂ | Single bond | Sub-19 |
| 1-20 | Sub-33 | 3,4-diClPh | CH₂ | Single bond | Sub-20 |
| 1-21 | Sub-33 | 3,4-diClPh | CH₂ | Single bond | Sub-21 |
| 1-22 | Sub-33 | 3,4-diClPh | CH₂ | Single bond | Sub-22 |
| 1-23 | Sub-33 | 3,4-diClPh | CH₂ | Single bond | Sub-23 |
| 1-24 | Sub-33 | 3,4-diClPh | CH₂ | Single bond | Sub-24 |
| 1-25 | Sub-33 | 3,4-diClPh | CH₂ | Single bond | Sub-25 |
| 1-26 | Sub-33 | 3,4-diClPh | CH₂ | Single bond | Sub-26 |
| 1-27 | Sub-33 | 3,4-diClPh | CH₂ | Single bond | Sub-27 |
| 1-28 | Sub-33 | 3,4-diClPh | CH₂ | Single bond | Sub-28 |
| 1-29 | Sub-33 | 3,4-diClPh | CH₂ | Single bond | Sub-29 |
| 1-30 | Sub-33 | 3,4-diClPh | CH₂ | Single bond | Sub-30 |
| 1-31 | Sub-33 | 3,4-diClPh | CH₂ | Single bond | Sub-31 |
| 1-32 | Sub-33 | 3,4-diClPh | CH₂ | Single bond | Sub-32 |
| 1-33 | Sub-34 | 3,4-diClPh | CH₂ | Single bond | Sub-1 |
| 1-34 | Sub-34 | 3,4-diClPh | CH₂ | Single bond | Sub-2 |
| 1-35 | Sub-34 | 3,4-diClPh | CH₂ | Single bond | Sub-3 |
| 1-36 | Sub-34 | 3,4-diClPh | CH₂ | Single bond | Sub-4 |
| 1-37 | Sub-34 | 3,4-diClPh | CH₂ | Single bond | Sub-5 |
| 1-38 | Sub-34 | 3,4-diClPh | CH₂ | Single bond | Sub-6 |
| 1-39 | Sub-34 | 3,4-diClPh | CH₂ | Single bond | Sub-7 |
| 1-40 | Sub-34 | 3,4-diClPh | CH₂ | Single bond | Sub-8 |
| 1-41 | Sub-34 | 3,4-diClPh | CH₂ | Single bond | Sub-9 |
| 1-42 | Sub-34 | 3,4-diClPh | CH₂ | Single bond | Sub-10 |
| 1-43 | Sub-34 | 3,4-diClPh | CH₂ | Single bond | Sub-11 |
| 1-44 | Sub-34 | 3,4-diClPh | CH₂ | Single bond | Sub-12 |
| 1-45 | Sub-34 | 3,4-diClPh | CH₂ | Single bond | Sub-13 |
| 1-46 | Sub-34 | 3,4-diClPh | CH₂ | Single bond | Sub-14 |
| 1-47 | Sub-34 | 3,4-diClPh | CH₂ | Single bond | Sub-15 |
| 1-48 | Sub-34 | 3,4-diClPh | CH₂ | Single bond | Sub-16 |
| 1-49 | Sub-34 | 3,4-diClPh | CH₂ | Single bond | Sub-17 |
| 1-50 | Sub-34 | 3,4-diClPh | CH₂ | Single bond | Sub-18 |
| 1-51 | Sub-34 | 3,4-diClPh | CH₂ | Single bond | Sub-19 |
| 1-52 | Sub-34 | 3,4-diClPh | CH₂ | Single bond | Sub-20 |
| 1-53 | Sub-34 | 3,4-diClPh | CH₂ | Single bond | Sub-21 |
| 1-54 | Sub-34 | 3,4-diClPh | CH₂ | Single bond | Sub-22 |
| 1-55 | Sub-34 | 3,4-diClPh | CH₂ | Single bond | Sub-23 |
| 1-56 | Sub-34 | 3,4-diClPh | CH₂ | Single bond | Sub-24 |
| 1-57 | Sub-34 | 3,4-diClPh | CH₂ | Single bond | Sub-25 |
| 1-58 | Sub-34 | 3,4-diClPh | CH₂ | Single bond | Sub-26 |
| 1-59 | Sub-34 | 3,4-diClPh | CH₂ | Single bond | Sub-27 |
| 1-60 | Sub-34 | 3,4-diClPh | CH₂ | Single bond | Sub-28 |
| 1-61 | Sub-34 | 3,4-diClPh | CH₂ | Single bond | Sub-29 |
| 1-62 | Sub-34 | 3,4-diClPh | CH₂ | Single bond | Sub-30 |
| 1-63 | Sub-34 | 3,4-diClPh | CH₂ | Single bond | Sub-31 |
| 1-64 | Sub-34 | 3,4-diClPh | CH₂ | Single bond | Sub-32 |
| 1-65 | Sub-35 | 3,4-diClPh | CH₂ | Single bond | Sub-1 |
| 1-66 | Sub-35 | 3,4-diClPh | CH₂ | Single bond | Sub-2 |
| 1-67 | Sub-35 | 3,4-diClPh | CH₂ | Single bond | Sub-3 |
| 1-68 | Sub-35 | 3,4-diClPh | CH₂ | Single bond | Sub-4 |
| 1-69 | Sub-35 | 3,4-diClPh | CH₂ | Single bond | Sub-5 |
| 1-70 | Sub-35 | 3,4-diClPh | CH₂ | Single bond | Sub-6 |
| 1-71 | Sub-35 | 3,4-diClPh | CH₂ | Single bond | Sub-7 |
| 1-72 | Sub-35 | 3,4-diClPh | CH₂ | Single bond | Sub-8 |
| 1-73 | Sub-35 | 3,4-diClPh | CH₂ | Single bond | Sub-9 |
| 1-74 | Sub-35 | 3,4-diClPh | CH₂ | Single bond | Sub-10 |
| 1-75 | Sub-35 | 3,4-diClPh | CH₂ | Single bond | Sub-11 |
| 1-76 | Sub-35 | 3,4-diClPh | CH₂ | Single bond | Sub-12 |
| 1-77 | Sub-35 | 3,4-diClPh | CH₂ | Single bond | Sub-13 |
| 1-78 | Sub-35 | 3,4-diClPh | CH₂ | Single bond | Sub-14 |
| 1-79 | Sub-35 | 3,4-diClPh | CH₂ | Single bond | Sub-15 |
| 1-80 | Sub-35 | 3,4-diClPh | CH₂ | Single bond | Sub-16 |
| 1-81 | Sub-35 | 3,4-diClPh | CH₂ | Single bond | Sub-17 |
| 1-82 | Sub-35 | 3,4-diClPh | CH₂ | Single bond | Sub-18 |
| 1-83 | Sub-35 | 3,4-diClPh | CH₂ | Single bond | Sub-19 |
| 1-84 | Sub-35 | 3,4-diClPh | CH₂ | Single bond | Sub-20 |
| 1-85 | Sub-35 | 3,4-diClPh | CH₂ | Single bond | Sub-21 |
| 1-86 | Sub-35 | 3,4-diClPh | CH₂ | Single bond | Sub-22 |
| 1-87 | Sub-35 | 3,4-diClPh | CH₂ | Single bond | Sub-23 |
| 1-88 | Sub-35 | 3,4-diClPh | CH₂ | Single bond | Sub-24 |
| 1-89 | Sub-35 | 3,4-diClPh | CH₂ | Single bond | Sub-25 |
| 1-90 | Sub-35 | 3,4-diClPh | CH₂ | Single bond | Sub-26 |
| 1-91 | Sub-35 | 3,4-diClPh | CH₂ | Single bond | Sub-27 |
| 1-92 | Sub-35 | 3,4-diClPh | CH₂ | Single bond | Sub-28 |
| 1-93 | Sub-35 | 3,4-diClPh | CH₂ | Single bond | Sub-29 |
| 1-94 | Sub-35 | 3,4-diClPh | CH₂ | Single bond | Sub-30 |
| 1-95 | Sub-35 | 3,4-diClPh | CH₂ | Single bond | Sub-31 |
| 1-96 | Sub-35 | 3,4-diClPh | CH₂ | Single bond | Sub-32 |
| 1-97 | Sub-36 | 3,4-diClPh | CH₂ | Single bond | Sub-1 |
| 1-98 | Sub-36 | 3,4-diClPh | CH₂ | Single bond | Sub-2 |
| 1-99 | Sub-36 | 3,4-diClPh | CH₂ | Single bond | Sub-3 |
| 1-100 | Sub-36 | 3,4-diClPh | CH₂ | Single bond | Sub-4 |
| 1-101 | Sub-36 | 3,4-diClPh | CH₂ | Single bond | Sub-5 |
| 1-102 | Sub-36 | 3,4-diClPh | CH₂ | Single bond | Sub-6 |
| 1-103 | Sub-36 | 3,4-diClPh | CH₂ | Single bond | Sub-7 |
| 1-104 | Sub-36 | 3,4-diClPh | CH₂ | Single bond | Sub-8 |
| 1-105 | Sub-36 | 3,4-diClPh | CH₂ | Single bond | Sub-9 |
| 1-106 | Sub-36 | 3,4-diClPh | CH₂ | Single bond | Sub-10 |
| 1-107 | Sub-36 | 3,4-diClPh | CH₂ | Single bond | Sub-11 |
| 1-108 | Sub-36 | 3,4-diClPh | CH₂ | Single bond | Sub-12 |
| 1-109 | Sub-36 | 3,4-diClPh | CH₂ | Single bond | Sub-13 |
| 1-110 | Sub-36 | 3,4-diClPh | CH₂ | Single bond | Sub-14 |
| 1-111 | Sub-36 | 3,4-diClPh | CH₂ | Single bond | Sub-15 |
| 1-112 | Sub-36 | 3,4-diClPh | CH₂ | Single bond | Sub-16 |
| 1-113 | Sub-36 | 3,4-diClPh | CH₂ | Single bond | Sub-17 |
| 1-114 | Sub-36 | 3,4-diClPh | CH₂ | Single bond | Sub-18 |
| 1-115 | Sub-36 | 3,4-diClPh | CH₂ | Single bond | Sub-19 |
| 1-116 | Sub-36 | 3,4-diClPh | CH₂ | Single bond | Sub-20 |
| 1-117 | Sub-36 | 3,4-diClPh | CH₂ | Single bond | Sub-21 |
| 1-118 | Sub-36 | 3,4-diClPh | CH₂ | Single bond | Sub-22 |
| 1-119 | Sub-36 | 3,4-diClPh | CH₂ | Single bond | Sub-23 |
| 1-120 | Sub-36 | 3,4-diClPh | CH₂ | Single bond | Sub-24 |
| 1-121 | Sub-36 | 3,4-diClPh | CH₂ | Single bond | Sub-25 |
| 1-122 | Sub-36 | 3,4-diClPh | CH₂ | Single bond | Sub-26 |
| 1-123 | Sub-36 | 3,4-diClPh | CH₂ | Single bond | Sub-27 |
| 1-124 | Sub-36 | 3,4-diClPh | CH₂ | Single bond | Sub-28 |
| 1-125 | Sub-36 | 3,4-diClPh | CH₂ | Single bond | Sub-29 |

| Cpd. No. | R¹ | R² | A | B | Z |
|---|---|---|---|---|---|
| 1-126 | Sub-36 | 3,4-diClPh | CH₂ | Single bond | Sub-30 |
| 1-127 | Sub-36 | 3,4-diClPh | CH₂ | Single bond | Sub-31 |
| 1-128 | Sub-36 | 3,4-diClPh | CH₂ | Single bond | Sub-32 |
| 1-129 | Sub-37 | 3,4-diClPh | CH₂ | Single bond | Sub-1 |
| 1-130 | Sub-37 | 3,4-diClPh | CH₂ | Single bond | Sub-2 |
| 1-131 | Sub-37 | 3,4-diClPh | CH₂ | Single bond | Sub-3 |
| 1-132 | Sub-37 | 3,4-diClPh | CH₂ | Single bond | Sub-4 |
| 1-133 | Sub-37 | 3,4-diClPh | CH₂ | Single bond | Sub-5 |
| 1-134 | Sub-37 | 3,4-diClPh | CH₂ | Single bond | Sub-6 |
| 1-135 | Sub-37 | 3,4-diClPh | CH₂ | Single bond | Sub-7 |
| 1-136 | Sub-37 | 3,4-diClPh | CH₂ | Single bond | Sub-8 |
| 1-137 | Sub-37 | 3,4-diClPh | CH₂ | Single bond | Sub-9 |
| 1-138 | Sub-37 | 3,4-diClPh | CH₂ | Single bond | Sub-10 |
| 1-139 | Sub-37 | 3,4-diClPh | CH₂ | Single bond | Sub-11 |
| 1-140 | Sub-37 | 3,4-diClPh | CH₂ | Single bond | Sub-12 |
| 1-141 | Sub-37 | 3,4-diClPh | CH₂ | Single bond | Sub-13 |
| 1-142 | Sub-37 | 3,4-diClPh | CH₂ | Single bond | Sub-14 |
| 1-143 | Sub-37 | 3,4-diClPh | CH₂ | Single bond | Sub-15 |
| 1-144 | Sub-37 | 3,4-diClPh | CH₂ | Single bond | Sub-16 |
| 1-145 | Sub-37 | 3,4-diClPh | CH₂ | Single bond | Sub-17 |
| 1-146 | Sub-37 | 3,4-diClPh | CH₂ | Single bond | Sub-18 |
| 1-147 | Sub-37 | 3,4-diClPh | CH₂ | Single bond | Sub-19 |
| 1-148 | Sub-37 | 3,4-diClPh | CH₂ | Single bond | Sub-20 |
| 1-149 | Sub-37 | 3,4-diClPh | CH₂ | Single bond | Sub-21 |
| 1-150 | Sub-37 | 3,4-diClPh | CH₂ | Single bond | Sub-22 |
| 1-151 | Sub-37 | 3,4-diClPh | CH₂ | Single bond | Sub-23 |
| 1-152 | Sub-37 | 3,4-diClPh | CH₂ | Single bond | Sub-24 |
| 1-153 | Sub-37 | 3,4-diClPh | CH₂ | Single bond | Sub-25 |
| 1-154 | Sub-37 | 3,4-diClPh | CH₂ | Single bond | Sub-26 |
| 1-155 | Sub-37 | 3,4-diClPh | CH₂ | Single bond | Sub-27 |
| 1-156 | Sub-37 | 3,4-diClPh | CH₂ | Single bond | Sub-28 |
| 1-157 | Sub-37 | 3,4-diClPh | CH₂ | Single bond | Sub-29 |
| 1-158 | Sub-37 | 3,4-diClPh | CH₂ | Single bond | Sub-30 |
| 1-159 | Sub-37 | 3,4-diClPh | CH₂ | Single bond | Sub-31 |
| 1-160 | Sub-37 | 3,4-diClPh | CH₂ | Single bond | Sub-32 |
| 1-161 | Sub-38 | 3,4-diClPh | CH₂ | Single bond | Sub-1 |
| 1-162 | Sub-38 | 3,4-diClPh | CH₂ | Single bond | Sub-2 |
| 1-163 | Sub-38 | 3,4-diClPh | CH₂ | Single bond | Sub-3 |
| 1-164 | Sub-38 | 3,4-diClPh | CH₂ | Single bond | Sub-4 |
| 1-165 | Sub-38 | 3,4-diClPh | CH₂ | Single bond | Sub-5 |
| 1-166 | Sub-38 | 3,4-diClPh | CH₂ | Single bond | Sub-6 |
| 1-167 | Sub-38 | 3,4-diClPh | CH₂ | Single bond | Sub-7 |
| 1-168 | Sub-38 | 3,4-diClPh | CH₂ | Single bond | Sub-8 |
| 1-169 | Sub-38 | 3,4-diClPh | CH₂ | Single bond | Sub-9 |
| 1-170 | Sub-38 | 3,4-diClPh | CH₂ | Single bond | Sub-10 |
| 1-171 | Sub-38 | 3,4-diClPh | CH₂ | Single bond | Sub-11 |
| 1-172 | Sub-38 | 3,4-diClPh | CH₂ | Single bond | Sub-12 |
| 1-173 | Sub-38 | 3,4-diClPh | CH₂ | Single bond | Sub-13 |
| 1-174 | Sub-38 | 3,4-diClPh | CH₂ | Single bond | Sub-14 |
| 1-175 | Sub-38 | 3,4-diClPh | CH₂ | Single bond | Sub-15 |
| 1-176 | Sub-38 | 3,4-diClPh | CH₂ | Single bond | Sub-16 |
| 1-177 | Sub-38 | 3,4-diClPh | CH₂ | Single bond | Sub-17 |
| 1-178 | Sub-38 | 3,4-diClPh | CH₂ | Single bond | Sub-18 |
| 1-179 | Sub-38 | 3,4-diClPh | CH₂ | Single bond | Sub-19 |
| 1-180 | Sub-38 | 3,4-diClPh | CH₂ | Single bond | Sub-20 |
| 1-181 | Sub-38 | 3,4-diClPh | CH₂ | Single bond | Sub-21 |
| 1-182 | Sub-38 | 3,4-diClPh | CH₂ | Single bond | Sub-22 |
| 1-183 | Sub-38 | 3,4-diClPh | CH₂ | Single bond | Sub-23 |
| 1-184 | Sub-38 | 3,4-diClPh | CH₂ | Single bond | Sub-24 |
| 1-185 | Sub-38 | 3,4-diClPh | CH₂ | Single bond | Sub-25 |
| 1-186 | Sub-38 | 3,4-diClPh | CH₂ | Single bond | Sub-26 |
| 1-187 | Sub-38 | 3,4-diClPh | CH₂ | Single bond | Sub-27 |
| 1-188 | Sub-38 | 3,4-diClPh | CH₂ | Single bond | Sub-28 |
| 1-189 | Sub-38 | 3,4-diClPh | CH₂ | Single bond | Sub-29 |
| 1-190 | Sub-38 | 3,4-diClPh | CH₂ | Single bond | Sub-30 |
| 1-191 | Sub-38 | 3,4-diClPh | CH₂ | Single bond | Sub-31 |
| 1-192 | Sub-38 | 3,4-diClPh | CH₂ | Single bond | Sub-32 |
| 1-193 | Sub-39 | 3,4-diClPh | CH₂ | Single bond | Sub-1 |
| 1-194 | Sub-39 | 3,4-diClPh | CH₂ | Single bond | Sub-2 |
| 1-195 | Sub-39 | 3,4-diClPh | CH₂ | Single bond | Sub-3 |
| 1-196 | Sub-39 | 3,4-diClPh | CH₂ | Single bond | Sub-4 |
| 1-197 | Sub-39 | 3,4-diClPh | CH₂ | Single bond | Sub-5 |
| 1-198 | Sub-39 | 3,4-diClPh | CH₂ | Single bond | Sub-6 |
| 1-199 | Sub-39 | 3,4-diClPh | CH₂ | Single bond | Sub-7 |
| 1-200 | Sub-39 | 3,4-diClPh | CH₂ | Single bond | Sub-8 |
| 1-201 | Sub-39 | 3,4-diClPh | CH₂ | Single bond | Sub-9 |
| 1-202 | Sub-39 | 3,4-diClPh | CH₂ | Single bond | Sub-10 |
| 1-203 | Sub-39 | 3,4-diClPh | CH₂ | Single bond | Sub-11 |
| 1-204 | Sub-39 | 3,4-diClPh | CH₂ | Single bond | Sub-12 |
| 1-205 | Sub-39 | 3,4-diClPh | CH₂ | Single bond | Sub-13 |
| 1-206 | Sub-39 | 3,4-diClPh | CH₂ | Single bond | Sub-14 |
| 1-207 | Sub-39 | 3,4-diClPh | CH₂ | Single bond | Sub-15 |
| 1-208 | Sub-39 | 3,4-diClPh | CH₂ | Single bond | Sub-16 |
| 1-209 | Sub-39 | 3,4-diClPh | CH₂ | Single bond | Sub-17 |
| 1-210 | Sub-39 | 3,4-diClPh | CH₂ | Single bond | Sub-18 |
| 1-211 | Sub-39 | 3,4-diClPh | CH₂ | Single bond | Sub-19 |
| 1-212 | Sub-39 | 3,4-diClPh | CH₂ | Single bond | Sub-20 |
| 1-213 | Sub-39 | 3,4-diClPh | CH₂ | Single bond | Sub-21 |
| 1-214 | Sub-39 | 3,4-diClPh | CH₂ | Single bond | Sub-22 |
| 1-215 | Sub-39 | 3,4-diClPh | CH₂ | Single bond | Sub-23 |
| 1-216 | Sub-39 | 3,4-diClPh | CH₂ | Single bond | Sub-24 |
| 1-217 | Sub-39 | 3,4-diClPh | CH₂ | Single bond | Sub-25 |
| 1-218 | Sub-39 | 3,4-diClPh | CH₂ | Single bond | Sub-26 |
| 1-219 | Sub-39 | 3,4-diClPh | CH₂ | Single bond | Sub-27 |
| 1-220 | Sub-39 | 3,4-diClPh | CH₂ | Single bond | Sub-28 |
| 1-221 | Sub-39 | 3,4-diClPh | CH₂ | Single bond | Sub-29 |
| 1-222 | Sub-39 | 3,4-diClPh | CH₂ | Single bond | Sub-30 |
| 1-223 | Sub-39 | 3,4-diClPh | CH₂ | Single bond | Sub-31 |
| 1-224 | Sub-39 | 3,4-diClPh | CH₂ | Single bond | Sub-32 |
| 1-225 | Sub-40 | 3,4-diClPh | CH₂ | Single bond | Sub-1 |
| 1-226 | Sub-40 | 3,4-diClPh | CH₂ | Single bond | Sub-2 |
| 1-227 | Sub-40 | 3,4-diClPh | CH₂ | Single bond | Sub-3 |
| 1-228 | Sub-40 | 3,4-diClPh | CH₂ | Single bond | Sub-4 |
| 1-229 | Sub-40 | 3,4-diClPh | CH₂ | Single bond | Sub-5 |
| 1-230 | Sub-40 | 3,4-diClPh | CH₂ | Single bond | Sub-6 |
| 1-231 | Sub-40 | 3,4-diClPh | CH₂ | Single bond | Sub-7 |
| 1-232 | Sub-40 | 3,4-diClPh | CH₂ | Single bond | Sub-8 |
| 1-233 | Sub-40 | 3,4-diClPh | CH₂ | Single bond | Sub-9 |
| 1-234 | Sub-40 | 3,4-diClPh | CH₂ | Single bond | Sub-10 |
| 1-235 | Sub-40 | 3,4-diClPh | CH₂ | Single bond | Sub-11 |
| 1-236 | Sub-40 | 3,4-diClPh | CH₂ | Single bond | Sub-12 |
| 1-237 | Sub-40 | 3,4-diClPh | CH₂ | Single bond | Sub-13 |
| 1-238 | Sub-40 | 3,4-diClPh | CH₂ | Single bond | Sub-14 |
| 1-239 | Sub-40 | 3,4-diClPh | CH₂ | Single bond | Sub-15 |
| 1-240 | Sub-40 | 3,4-diClPh | CH₂ | Single bond | Sub-16 |
| 1-241 | Sub-40 | 3,4-diClPh | CH₂ | Single bond | Sub-17 |
| 1-242 | Sub-40 | 3,4-diClPh | CH₂ | Single bond | Sub-18 |
| 1-243 | Sub-40 | 3,4-diClPh | CH₂ | Single bond | Sub-19 |
| 1-244 | Sub-40 | 3,4-diClPh | CH₂ | Single bond | Sub-20 |
| 1-245 | Sub-40 | 3,4-diClPh | CH₂ | Single bond | Sub-21 |
| 1-246 | Sub-40 | 3,4-diClPh | CH₂ | Single bond | Sub-22 |
| 1-247 | Sub-40 | 3,4-diClPh | CH₂ | Single bond | Sub-23 |
| 1-248 | Sub-40 | 3,4-diClPh | CH₂ | Single bond | Sub-24 |
| 1-249 | Sub-40 | 3,4-diClPh | CH₂ | Single bond | Sub-25 |
| 1-250 | Sub-40 | 3,4-diClPh | CH₂ | Single bond | Sub-26 |
| 1-251 | Sub-40 | 3,4-diClPh | CH₂ | Single bond | Sub-27 |
| 1-252 | Sub-40 | 3,4-diClPh | CH₂ | Single bond | Sub-28 |
| 1-253 | Sub-40 | 3,4-diClPh | CH₂ | Single bond | Sub-29 |
| 1-254 | Sub-40 | 3,4-diClPh | CH₂ | Single bond | Sub-30 |
| 1-255 | Sub-40 | 3,4-diClPh | CH₂ | Single bond | Sub-31 |
| 1-256 | Sub-40 | 3,4-diClPh | CH₂ | Single bond | Sub-32 |
| 1-257 | Sub-41 | 3,4-diClPh | CH₂ | Single bond | Sub-1 |
| 1-258 | Sub-41 | 3,4-diClPh | CH₂ | Single bond | Sub-2 |
| 1-259 | Sub-41 | 3,4-diClPh | CH₂ | Single bond | Sub-3 |
| 1-260 | Sub-41 | 3,4-diClPh | CH₂ | Single bond | Sub-4 |
| 1-261 | Sub-41 | 3,4-diClPh | CH₂ | Single bond | Sub-5 |
| 1-262 | Sub-41 | 3,4-diClPh | CH₂ | Single bond | Sub-6 |
| 1-263 | Sub-41 | 3,4-diClPh | CH₂ | Single bond | Sub-7 |
| 1-264 | Sub-41 | 3,4-diClPh | CH₂ | Single bond | Sub-8 |
| 1-265 | Sub-41 | 3,4-diClPh | CH₂ | Single bond | Sub-9 |
| 1-266 | Sub-41 | 3,4-diClPh | CH₂ | Single bond | Sub-10 |
| 1-267 | Sub-41 | 3,4-diClPh | CH₂ | Single bond | Sub-11 |
| 1-268 | Sub-41 | 3,4-diClPh | CH₂ | Single bond | Sub-12 |
| 1-269 | Sub-41 | 3,4-diClPh | CH₂ | Single bond | Sub-13 |
| 1-270 | Sub-41 | 3,4-diClPh | CH₂ | Single bond | Sub-14 |
| 1-271 | Sub-41 | 3,4-diClPh | CH₂ | Single bond | Sub-15 |
| 1-272 | Sub-41 | 3,4-diClPh | CH₂ | Single bond | Sub-16 |
| 1-273 | Sub-41 | 3,4-diClPh | CH₂ | Single bond | Sub-17 |
| 1-274 | Sub-41 | 3,4-diClPh | CH₂ | Single bond | Sub-18 |
| 1-275 | Sub-41 | 3,4-diClPh | CH₂ | Single bond | Sub-19 |
| 1-276 | Sub-41 | 3,4-diClPh | CH₂ | Single bond | Sub-20 |
| 1-277 | Sub-41 | 3,4-diClPh | CH₂ | Single bond | Sub-21 |

TABLE 1-continued

| Cpd. No. | R¹ | R² | A | B | Z |
|---|---|---|---|---|---|
| 1-278 | Sub-41 | 3,4-diClPh | CH₂ | Single bond | Sub-22 |
| 1-279 | Sub-41 | 3,4-diClPh | CH₂ | Single bond | Sub-23 |
| 1-280 | Sub-41 | 3,4-diClPh | CH₂ | Single bond | Sub-24 |
| 1-281 | Sub-41 | 3,4-diClPh | CH₂ | Single bond | Sub-25 |
| 1-282 | Sub-41 | 3,4-diClPh | CH₂ | Single bond | Sub-26 |
| 1-283 | Sub-41 | 3,4-diClPh | CH₂ | Single bond | Sub-27 |
| 1-284 | Sub-41 | 3,4-diClPh | CH₂ | Single bond | Sub-28 |
| 1-285 | Sub-41 | 3,4-diClPh | CH₂ | Single bond | Sub-29 |
| 1-286 | Sub-41 | 3,4-diClPh | CH₂ | Single bond | Sub-30 |
| 1-287 | Sub-41 | 3,4-diClPh | CH₂ | Single bond | Sub-31 |
| 1-288 | Sub-41 | 3,4-diClPh | CH₂ | Single bond | Sub-32 |
| 1-289 | Sub-42 | 3,4-diClPh | CH₂ | Single bond | Sub-1 |
| 1-290 | Sub-42 | 3,4-diClPh | CH₂ | Single bond | Sub-2 |
| 1-291 | Sub-42 | 3,4-diClPh | CH₂ | Single bond | Sub-3 |
| 1-292 | Sub-42 | 3,4-diClPh | CH₂ | Single bond | Sub-4 |
| 1-293 | Sub-42 | 3,4-diClPh | CH₂ | Single bond | Sub-5 |
| 1-294 | Sub-42 | 3,4-diClPh | CH₂ | Single bond | Sub-6 |
| 1-295 | Sub-42 | 3,4-diClPh | CH₂ | Single bond | Sub-7 |
| 1-296 | Sub-42 | 3,4-diClPh | CH₂ | Single bond | Sub-8 |
| 1-297 | Sub-42 | 3,4-diClPh | CH₂ | Single bond | Sub-9 |
| 1-298 | Sub-42 | 3,4-diClPh | CH₂ | Single bond | Sub-10 |
| 1-299 | Sub-42 | 3,4-diClPh | CH₂ | Single bond | Sub-11 |
| 1-300 | Sub-42 | 3,4-diClPh | CH₂ | Single bond | Sub-12 |
| 1-301 | Sub-42 | 3,4-diClPh | CH₂ | Single bond | Sub-13 |
| 1-302 | Sub-42 | 3,4-diClPh | CH₂ | Single bond | Sub-14 |
| 1-303 | Sub-42 | 3,4-diClPh | CH₂ | Single bond | Sub-15 |
| 1-304 | Sub-42 | 3,4-diClPh | CH₂ | Single bond | Sub-16 |
| 1-305 | Sub-42 | 3,4-diClPh | CH₂ | Single bond | Sub-17 |
| 1-306 | Sub-42 | 3,4-diClPh | CH₂ | Single bond | Sub-18 |
| 1-307 | Sub-42 | 3,4-diClPh | CH₂ | Single bond | Sub-19 |
| 1-308 | Sub-42 | 3,4-diClPh | CH₂ | Single bond | Sub-20 |
| 1-309 | Sub-42 | 3,4-diClPh | CH₂ | Single bond | Sub-21 |
| 1-310 | Sub-42 | 3,4-diClPh | CH₂ | Single bond | Sub-22 |
| 1-311 | Sub-42 | 3,4-diClPh | CH₂ | Single bond | Sub-23 |
| 1-312 | Sub-42 | 3,4-diClPh | CH₂ | Single bond | Sub-24 |
| 1-313 | Sub-42 | 3,4-diClPh | CH₂ | Single bond | Sub-25 |
| 1-314 | Sub-42 | 3,4-diClPh | CH₂ | Single bond | Sub-26 |
| 1-315 | Sub-42 | 3,4-diClPh | CH₂ | Single bond | Sub-27 |
| 1-316 | Sub-42 | 3,4-diClPh | CH₂ | Single bond | Sub-28 |
| 1-317 | Sub-42 | 3,4-diClPh | CH₂ | Single bond | Sub-29 |
| 1-318 | Sub-42 | 3,4-diClPh | CH₂ | Single bond | Sub-30 |
| 1-319 | Sub-42 | 3,4-diClPh | CH₂ | Single bond | Sub-31 |
| 1-320 | Sub-42 | 3,4-diClPh | CH₂ | Single bond | Sub-32 |
| 1-321 | Sub-43 | 3,4-diClPh | CH₂ | Single bond | Sub-1 |
| 1-322 | Sub-43 | 3,4-diClPh | CH₂ | Single bond | Sub-2 |
| 1-323 | Sub-43 | 3,4-diClPh | CH₂ | Single bond | Sub-3 |
| 1-324 | Sub-43 | 3,4-diClPh | CH₂ | Single bond | Sub-4 |
| 1-325 | Sub-43 | 3,4-diClPh | CH₂ | Single bond | Sub-5 |
| 1-326 | Sub-43 | 3,4-diClPh | CH₂ | Single bond | Sub-6 |
| 1-327 | Sub-43 | 3,4-diClPh | CH₂ | Single bond | Sub-7 |
| 1-328 | Sub-43 | 3,4-diClPh | CH₂ | Single bond | Sub-8 |
| 1-329 | Sub-43 | 3,4-diClPh | CH₂ | Single bond | Sub-9 |
| 1-340 | Sub-43 | 3,4-diClPh | CH₂ | Single bond | Sub-10 |
| 1-341 | Sub-43 | 3,4-diClPh | CH₂ | Single bond | Sub-11 |
| 1-342 | Sub-43 | 3,4-diClPh | CH₂ | Single bond | Sub-12 |
| 1-343 | Sub-43 | 3,4-diClPh | CH₂ | Single bond | Sub-13 |
| 1-344 | Sub-43 | 3,4-diClPh | CH₂ | Single bond | Sub-14 |
| 1-345 | Sub-43 | 3,4-diClPh | CH₂ | Single bond | Sub-15 |
| 1-346 | Sub-43 | 3,4-diClPh | CH₂ | Single bond | Sub-16 |
| 1-347 | Sub-43 | 3,4-diClPh | CH₂ | Single bond | Sub-17 |
| 1-348 | Sub-43 | 3,4-diClPh | CH₂ | Single bond | Sub-18 |
| 1-349 | Sub-43 | 3,4-diClPh | CH₂ | Single bond | Sub-19 |
| 1-340 | Sub-43 | 3,4-diClPh | CH₂ | Single bond | Sub-20 |
| 1-341 | Sub-43 | 3,4-diClPh | CH₂ | Single bond | Sub-21 |
| 1-342 | Sub-43 | 3,4-diClPh | CH₂ | Single bond | Sub-22 |
| 1-343 | Sub-43 | 3,4-diClPh | CH₂ | Single bond | Sub-23 |
| 1-344 | Sub-43 | 3,4-diClPh | CH₂ | Single bond | Sub-24 |
| 1-345 | Sub-43 | 3,4-diClPh | CH₂ | Single bond | Sub-25 |
| 1-346 | Sub-43 | 3,4-diClPh | CH₂ | Single bond | Sub-26 |
| 1-347 | Sub-43 | 3,4-diClPh | CH₂ | Single bond | Sub-27 |
| 1-348 | Sub-43 | 3,4-diClPh | CH₂ | Single bond | Sub-28 |
| 1-349 | Sub-43 | 3,4-diClPh | CH₂ | Single bond | Sub-29 |
| 1-350 | Sub-43 | 3,4-diClPh | CH₂ | Single bond | Sub-30 |
| 1-351 | Sub-43 | 3,4-diClPh | CH₂ | Single bond | Sub-31 |
| 1-352 | Sub-43 | 3,4-diClPh | CH₂ | Single bond | Sub-32 |
| 1-353 | Sub-44 | 3,4-diClPh | CH₂ | Single bond | Sub-1 |
| 1-354 | Sub-44 | 3,4-diClPh | CH₂ | Single bond | Sub-2 |
| 1-355 | Sub-44 | 3,4-diClPh | CH₂ | Single bond | Sub-3 |
| 1-356 | Sub-44 | 3,4-diClPh | CH₂ | Single bond | Sub-4 |
| 1-357 | Sub-44 | 3,4-diClPh | CH₂ | Single bond | Sub-5 |
| 1-358 | Sub-44 | 3,4-diClPh | CH₂ | Single bond | Sub-6 |
| 1-359 | Sub-44 | 3,4-diClPh | CH₂ | Single bond | Sub-7 |
| 1-360 | Sub-44 | 3,4-diClPh | CH₂ | Single bond | Sub-8 |
| 1-361 | Sub-44 | 3,4-diClPh | CH₂ | Single bond | Sub-9 |
| 1-362 | Sub-44 | 3,4-diClPh | CH₂ | Single bond | Sub-10 |
| 1-363 | Sub-44 | 3,4-diClPh | CH₂ | Single bond | Sub-11 |
| 1-364 | Sub-44 | 3,4-diClPh | CH₂ | Single bond | Sub-12 |
| 1-365 | Sub-44 | 3,4-diClPh | CH₂ | Single bond | Sub-13 |
| 1-366 | Sub-44 | 3,4-diClPh | CH₂ | Single bond | Sub-14 |
| 1-367 | Sub-44 | 3,4-diClPh | CH₂ | Single bond | Sub-15 |
| 1-368 | Sub-44 | 3,4-diClPh | CH₂ | Single bond | Sub-16 |
| 1-369 | Sub-44 | 3,4-diClPh | CH₂ | Single bond | Sub-17 |
| 1-370 | Sub-44 | 3,4-diClPh | CH₂ | Single bond | Sub-18 |
| 1-371 | Sub-44 | 3,4-diClPh | CH₂ | Single bond | Sub-19 |
| 1-372 | Sub-44 | 3,4-diClPh | CH₂ | Single bond | Sub-20 |
| 1-373 | Sub-44 | 3,4-diClPh | CH₂ | Single bond | Sub-21 |
| 1-374 | Sub-44 | 3,4-diClPh | CH₂ | Single bond | Sub-22 |
| 1-375 | Sub-44 | 3,4-diClPh | CH₂ | Single bond | Sub-23 |
| 1-376 | Sub-44 | 3,4-diClPh | CH₂ | Single bond | Sub-24 |
| 1-377 | Sub-44 | 3,4-diClPh | CH₂ | Single bond | Sub-25 |
| 1-378 | Sub-44 | 3,4-diClPh | CH₂ | Single bond | Sub-26 |
| 1-379 | Sub-44 | 3,4-diClPh | CH₂ | Single bond | Sub-27 |
| 1-380 | Sub-44 | 3,4-diClPh | CH₂ | Single bond | Sub-28 |
| 1-381 | Sub-44 | 3,4-diClPh | CH₂ | Single bond | Sub-29 |
| 1-382 | Sub-44 | 3,4-diClPh | CH₂ | Single bond | Sub-30 |
| 1-383 | Sub-44 | 3,4-diClPh | CH₂ | Single bond | Sub-31 |
| 1-384 | Sub-44 | 3,4-diClPh | CH₂ | Single bond | Sub-32 |
| 1-385 | Sub-45 | 3,4-diClPh | CH₂ | Single bond | Sub-1 |
| 1-386 | Sub-45 | 3,4-diClPh | CH₂ | Single bond | Sub-2 |
| 1-387 | Sub-45 | 3,4-diClPh | CH₂ | Single bond | Sub-3 |
| 1-388 | Sub-45 | 3,4-diClPh | CH₂ | Single bond | Sub-4 |
| 1-389 | Sub-45 | 3,4-diClPh | CH₂ | Single bond | Sub-5 |
| 1-390 | Sub-45 | 3,4-diClPh | CH₂ | Single bond | Sub-6 |
| 1-391 | Sub-45 | 3,4-diClPh | CH₂ | Single bond | Sub-7 |
| 1-392 | Sub-45 | 3,4-diClPh | CH₂ | Single bond | Sub-8 |
| 1-393 | Sub-45 | 3,4-diClPh | CH₂ | Single bond | Sub-9 |
| 1-394 | Sub-45 | 3,4-diClPh | CH₂ | Single bond | Sub-10 |
| 1-395 | Sub-45 | 3,4-diClPh | CH₂ | Single bond | Sub-11 |
| 1-396 | Sub-45 | 3,4-diClPh | CH₂ | Single bond | Sub-12 |
| 1-397 | Sub-45 | 3,4-diClPh | CH₂ | Single bond | Sub-13 |
| 1-398 | Sub-45 | 3,4-diClPh | CH₂ | Single bond | Sub-14 |
| 1-399 | Sub-45 | 3,4-diClPh | CH₂ | Single bond | Sub-15 |
| 1-400 | Sub-45 | 3,4-diClPh | CH₂ | Single bond | Sub-16 |
| 1-401 | Sub-45 | 3,4-diClPh | CH₂ | Single bond | Sub-17 |
| 1-402 | Sub-45 | 3,4-diClPh | CH₂ | Single bond | Sub-18 |
| 1-403 | Sub-45 | 3,4-diClPh | CH₂ | Single bond | Sub-19 |
| 1-404 | Sub-45 | 3,4-diClPh | CH₂ | Single bond | Sub-20 |
| 1-405 | Sub-45 | 3,4-diClPh | CH₂ | Single bond | Sub-21 |
| 1-406 | Sub-45 | 3,4-diClPh | CH₂ | Single bond | Sub-22 |
| 1-407 | Sub-45 | 3,4-diClPh | CH₂ | Single bond | Sub-23 |
| 1-408 | Sub-45 | 3,4-diClPh | CH₂ | Single bond | Sub-24 |
| 1-409 | Sub-45 | 3,4-diClPh | CH₂ | Single bond | Sub-25 |
| 1-410 | Sub-45 | 3,4-diClPh | CH₂ | Single bond | Sub-26 |
| 1-411 | Sub-45 | 3,4-diClPh | CH₂ | Single bond | Sub-27 |
| 1-412 | Sub-45 | 3,4-diClPh | CH₂ | Single bond | Sub-28 |
| 1-413 | Sub-45 | 3,4-diClPh | CH₂ | Single bond | Sub-29 |
| 1-414 | Sub-45 | 3,4-diClPh | CH₂ | Single bond | Sub-30 |
| 1-415 | Sub-45 | 3,4-diClPh | CH₂ | Single bond | Sub-31 |
| 1-416 | Sub-45 | 3,4-diClPh | CH₂ | Single bond | Sub-32 |
| 1-417 | Sub-46 | 3,4-diClPh | CH₂ | Single bond | Sub-1 |
| 1-418 | Sub-46 | 3,4-diClPh | CH₂ | Single bond | Sub-2 |
| 1-419 | Sub-46 | 3,4-diClPh | CH₂ | Single bond | Sub-3 |
| 1-420 | Sub-46 | 3,4-diClPh | CH₂ | Single bond | Sub-4 |
| 1-421 | Sub-46 | 3,4-diClPh | CH₂ | Single bond | Sub-5 |
| 1-422 | Sub-46 | 3,4-diClPh | CH₂ | Single bond | Sub-6 |
| 1-423 | Sub-46 | 3,4-diClPh | CH₂ | Single bond | Sub-7 |
| 1-424 | Sub-46 | 3,4-diClPh | CH₂ | Single bond | Sub-8 |
| 1-425 | Sub-46 | 3,4-diClPh | CH₂ | Single bond | Sub-9 |
| 1-426 | Sub-46 | 3,4-diClPh | CH₂ | Single bond | Sub-10 |
| 1-427 | Sub-46 | 3,4-diClPh | CH₂ | Single bond | Sub-11 |
| 1-428 | Sub-46 | 3,4-diClPh | CH₂ | Single bond | Sub-12 |
| 1-429 | Sub-46 | 3,4-diClPh | CH₂ | Single bond | Sub-13 |

TABLE 1-continued

| Cpd. No. | R¹ | R² | A | B | Z |
|---|---|---|---|---|---|
| 1-430 | Sub-46 | 3,4-diClPh | CH$_2$ | Single bond | Sub-14 |
| 1-431 | Sub-46 | 3,4-diClPh | CH$_2$ | Single bond | Sub-15 |
| 1-432 | Sub-46 | 3,4-diClPh | CH$_2$ | Single bond | Sub-16 |
| 1-433 | Sub-46 | 3,4-diClPh | CH$_2$ | Single bond | Sub-17 |
| 1-434 | Sub-46 | 3,4-diClPh | CH$_2$ | Single bond | Sub-18 |
| 1-435 | Sub-46 | 3,4-diClPh | CH$_2$ | Single bond | Sub-19 |
| 1-436 | Sub-46 | 3,4-diClPh | CH$_2$ | Single bond | Sub-20 |
| 1-437 | Sub-46 | 3,4-diClPh | CH$_2$ | Single bond | Sub-21 |
| 1-438 | Sub-46 | 3,4-diClPh | CH$_2$ | Single bond | Sub-22 |
| 1-439 | Sub-46 | 3,4-diClPh | CH$_2$ | Single bond | Sub-23 |
| 1-440 | Sub-46 | 3,4-diClPh | CH$_2$ | Single bond | Sub-24 |
| 1-441 | Sub-46 | 3,4-diClPh | CH$_2$ | Single bond | Sub-25 |
| 1-442 | Sub-46 | 3,4-diClPh | CH$_2$ | Single bond | Sub-26 |
| 1-443 | Sub-46 | 3,4-diClPh | CH$_2$ | Single bond | Sub-27 |
| 1-444 | Sub-46 | 3,4-diClPh | CH$_2$ | Single bond | Sub-28 |
| 1-445 | Sub-46 | 3,4-diClPh | CH$_2$ | Single bond | Sub-29 |
| 1-446 | Sub-46 | 3,4-diClPh | CH$_2$ | Single bond | Sub-30 |
| 1-447 | Sub-46 | 3,4-diClPh | CH$_2$ | Single bond | Sub-31 |
| 1-448 | Sub-46 | 3,4-diClPh | CH$_2$ | Single bond | Sub-32 |
| 1-449 | Sub-47 | 3,4-diClPh | CH$_2$ | Single bond | Sub-1 |
| 1-450 | Sub-47 | 3,4-diClPh | CH$_2$ | Single bond | Sub-2 |
| 1-451 | Sub-47 | 3,4-diClPh | CH$_2$ | Single bond | Sub-3 |
| 1-452 | Sub-47 | 3,4-diClPh | CH$_2$ | Single bond | Sub-4 |
| 1-453 | Sub-47 | 3,4-diClPh | CH$_2$ | Single bond | Sub-5 |
| 1-454 | Sub-47 | 3,4-diClPh | CH$_2$ | Single bond | Sub-6 |
| 1-455 | Sub-47 | 3,4-diClPh | CH$_2$ | Single bond | Sub-7 |
| 1-456 | Sub-47 | 3,4-diClPh | CH$_2$ | Single bond | Sub-8 |
| 1-457 | Sub-47 | 3,4-diClPh | CH$_2$ | Single bond | Sub-9 |
| 1-458 | Sub-47 | 3,4-diClPh | CH$_2$ | Single bond | Sub-10 |
| 1-459 | Sub-47 | 3,4-diClPh | CH$_2$ | Single bond | Sub-11 |
| 1-460 | Sub-47 | 3,4-diClPh | CH$_2$ | Single bond | Sub-12 |
| 1-461 | Sub-47 | 3,4-diClPh | CH$_2$ | Single bond | Sub-13 |
| 1-462 | Sub-47 | 3,4-diClPh | CH$_2$ | Single bond | Sub-14 |
| 1-463 | Sub-47 | 3,4-diClPh | CH$_2$ | Single bond | Sub-15 |
| 1-464 | Sub-47 | 3,4-diClPh | CH$_2$ | Single bond | Sub-16 |
| 1-465 | Sub-47 | 3,4-diClPh | CH$_2$ | Single bond | Sub-17 |
| 1-466 | Sub-47 | 3,4-diClPh | CH$_2$ | Single bond | Sub-18 |
| 1-467 | Sub-47 | 3,4-diClPh | CH$_2$ | Single bond | Sub-19 |
| 1-468 | Sub-47 | 3,4-diClPh | CH$_2$ | Single bond | Sub-20 |
| 1-469 | Sub-47 | 3,4-diClPh | CH$_2$ | Single bond | Sub-21 |
| 1-470 | Sub-47 | 3,4-diClPh | CH$_2$ | Single bond | Sub-22 |
| 1-471 | Sub-47 | 3,4-diClPh | CH$_2$ | Single bond | Sub-23 |
| 1-472 | Sub-47 | 3,4-diClPh | CH$_2$ | Single bond | Sub-24 |
| 1-473 | Sub-47 | 3,4-diClPh | CH$_2$ | Single bond | Sub-25 |
| 1-474 | Sub-47 | 3,4-diClPh | CH$_2$ | Single bond | Sub-26 |
| 1-475 | Sub-47 | 3,4-diClPh | CH$_2$ | Single bond | Sub-27 |
| 1-476 | Sub-47 | 3,4-diClPh | CH$_2$ | Single bond | Sub-28 |
| 1-477 | Sub-47 | 3,4-diClPh | CH$_2$ | Single bond | Sub-29 |
| 1-478 | Sub-47 | 3,4-diClPh | CH$_2$ | Single bond | Sub-30 |
| 1-479 | Sub-47 | 3,4-diClPh | CH$_2$ | Single bond | Sub-31 |
| 1-480 | Sub-47 | 3,4-diClPh | CH$_2$ | Single bond | Sub-32 |
| 1-481 | Sub-48 | 3,4-diClPh | CH$_2$ | Single bond | Sub-1 |
| 1-482 | Sub-48 | 3,4-diClPh | CH$_2$ | Single bond | Sub-2 |
| 1-483 | Sub-48 | 3,4-diClPh | CH$_2$ | Single bond | Sub-3 |
| 1-484 | Sub-48 | 3,4-diClPh | CH$_2$ | Single bond | Sub-4 |
| 1-485 | Sub-48 | 3,4-diClPh | CH$_2$ | Single bond | Sub-5 |
| 1-486 | Sub-48 | 3,4-diClPh | CH$_2$ | Single bond | Sub-6 |
| 1-487 | Sub-48 | 3,4-diClPh | CH$_2$ | Single bond | Sub-7 |
| 1-488 | Sub-48 | 3,4-diClPh | CH$_2$ | Single bond | Sub-8 |
| 1-489 | Sub-48 | 3,4-diClPh | CH$_2$ | Single bond | Sub-9 |
| 1-490 | Sub-48 | 3,4-diClPh | CH$_2$ | Single bond | Sub-10 |
| 1-491 | Sub-48 | 3,4-diClPh | CH$_2$ | Single bond | Sub-11 |
| 1-492 | Sub-48 | 3,4-diClPh | CH$_2$ | Single bond | Sub-12 |
| 1-493 | Sub-48 | 3,4-diClPh | CH$_2$ | Single bond | Sub-13 |
| 1-494 | Sub-48 | 3,4-diClPh | CH$_2$ | Single bond | Sub-14 |
| 1-495 | Sub-48 | 3,4-diClPh | CH$_2$ | Single bond | Sub-15 |
| 1-496 | Sub-48 | 3,4-diClPh | CH$_2$ | Single bond | Sub-16 |
| 1-497 | Sub-48 | 3,4-diClPh | CH$_2$ | Single bond | Sub-17 |
| 1-498 | Sub-48 | 3,4-diClPh | CH$_2$ | Single bond | Sub-18 |
| 1-499 | Sub-48 | 3,4-diClPh | CH$_2$ | Single bond | Sub-19 |
| 1-500 | Sub-48 | 3,4-diClPh | CH$_2$ | Single bond | Sub-20 |
| 1-501 | Sub-48 | 3,4-diClPh | CH$_2$ | Single bond | Sub-21 |
| 1-502 | Sub-48 | 3,4-diClPh | CH$_2$ | Single bond | Sub-22 |
| 1-503 | Sub-48 | 3,4-diClPh | CH$_2$ | Single bond | Sub-23 |
| 1-504 | Sub-48 | 3,4-diClPh | CH$_2$ | Single bond | Sub-24 |
| 1-505 | Sub-48 | 3,4-diClPh | CH$_2$ | Single bond | Sub-25 |
| 1-506 | Sub-48 | 3,4-diClPh | CH$_2$ | Single bond | Sub-26 |
| 1-507 | Sub-48 | 3,4-diClPh | CH$_2$ | Single bond | Sub-27 |
| 1-508 | Sub-48 | 3,4-diClPh | CH$_2$ | Single bond | Sub-28 |
| 1-509 | Sub-48 | 3,4-diClPh | CH$_2$ | Single bond | Sub-29 |
| 1-510 | Sub-48 | 3,4-diClPh | CH$_2$ | Single bond | Sub-30 |
| 1-511 | Sub-48 | 3,4-diClPh | CH$_2$ | Single bond | Sub-31 |
| 1-512 | Sub-48 | 3,4-diClPh | CH$_2$ | Single bond | Sub-32 |
| 1-513 | Sub-49 | 3,4-diClPh | CH$_2$ | Single bond | Sub-1 |
| 1-514 | Sub-49 | 3,4-diClPh | CH$_2$ | Single bond | Sub-2 |
| 1-515 | Sub-49 | 3,4-diClPh | CH$_2$ | Single bond | Sub-3 |
| 1-516 | Sub-49 | 3,4-diClPh | CH$_2$ | Single bond | Sub-4 |
| 1-517 | Sub-49 | 3,4-diClPh | CH$_2$ | Single bond | Sub-5 |
| 1-518 | Sub-49 | 3,4-diClPh | CH$_2$ | Single bond | Sub-6 |
| 1-519 | Sub-49 | 3,4-diClPh | CH$_2$ | Single bond | Sub-7 |
| 1-520 | Sub-49 | 3,4-diClPh | CH$_2$ | Single bond | Sub-8 |
| 1-521 | Sub-49 | 3,4-diClPh | CH$_2$ | Single bond | Sub-9 |
| 1-522 | Sub-49 | 3,4-diClPh | CH$_2$ | Single bond | Sub-10 |
| 1-523 | Sub-49 | 3,4-diClPh | CH$_2$ | Single bond | Sub-11 |
| 1-524 | Sub-49 | 3,4-diClPh | CH$_2$ | Single bond | Sub-12 |
| 1-525 | Sub-49 | 3,4-diClPh | CH$_2$ | Single bond | Sub-13 |
| 1-526 | Sub-49 | 3,4-diClPh | CH$_2$ | Single bond | Sub-14 |
| 1-527 | Sub-49 | 3,4-diClPh | CH$_2$ | Single bond | Sub-15 |
| 1-528 | Sub-49 | 3,4-diClPh | CH$_2$ | Single bond | Sub-16 |
| 1-529 | Sub-49 | 3,4-diClPh | CH$_2$ | Single bond | Sub-17 |
| 1-530 | Sub-49 | 3,4-diClPh | CH$_2$ | Single bond | Sub-18 |
| 1-531 | Sub-49 | 3,4-diClPh | CH$_2$ | Single bond | Sub-19 |
| 1-532 | Sub-49 | 3,4-diClPh | CH$_2$ | Single bond | Sub-20 |
| 1-533 | Sub-49 | 3,4-diClPh | CH$_2$ | Single bond | Sub-21 |
| 1-534 | Sub-49 | 3,4-diClPh | CH$_2$ | Single bond | Sub-22 |
| 1-535 | Sub-49 | 3,4-diClPh | CH$_2$ | Single bond | Sub-23 |
| 1-536 | Sub-49 | 3,4-diClPh | CH$_2$ | Single bond | Sub-24 |
| 1-537 | Sub-49 | 3,4-diClPh | CH$_2$ | Single bond | Sub-25 |
| 1-538 | Sub-49 | 3,4-diClPh | CH$_2$ | Single bond | Sub-26 |
| 1-539 | Sub-49 | 3,4-diClPh | CH$_2$ | Single bond | Sub-27 |
| 1-540 | Sub-49 | 3,4-diClPh | CH$_2$ | Single bond | Sub-28 |
| 1-541 | Sub-49 | 3,4-diClPh | CH$_2$ | Single bond | Sub-29 |
| 1-542 | Sub-49 | 3,4-diClPh | CH$_2$ | Single bond | Sub-30 |
| 1-543 | Sub-49 | 3,4-diClPh | CH$_2$ | Single bond | Sub-31 |
| 1-544 | Sub-49 | 3,4-diClPh | CH$_2$ | Single bond | Sub-32 |
| 1-545 | Sub-50 | 3,4-diClPh | CH$_2$ | Single bond | Sub-1 |
| 1-546 | Sub-50 | 3,4-diClPh | CH$_2$ | Single bond | Sub-2 |
| 1-547 | Sub-50 | 3,4-diClPh | CH$_2$ | Single bond | Sub-3 |
| 1-548 | Sub-50 | 3,4-diClPh | CH$_2$ | Single bond | Sub-4 |
| 1-549 | Sub-50 | 3,4-diClPh | CH$_2$ | Single bond | Sub-5 |
| 1-550 | Sub-50 | 3,4-diClPh | CH$_2$ | Single bond | Sub-6 |
| 1-551 | Sub-50 | 3,4-diClPh | CH$_2$ | Single bond | Sub-7 |
| 1-552 | Sub-50 | 3,4-diClPh | CH$_2$ | Single bond | Sub-8 |
| 1-553 | Sub-50 | 3,4-diClPh | CH$_2$ | Single bond | Sub-9 |
| 1-554 | Sub-50 | 3,4-diClPh | CH$_2$ | Single bond | Sub-10 |
| 1-555 | Sub-50 | 3,4-diClPh | CH$_2$ | Single bond | Sub-11 |
| 1-556 | Sub-50 | 3,4-diClPh | CH$_2$ | Single bond | Sub-12 |
| 1-557 | Sub-50 | 3,4-diClPh | CH$_2$ | Single bond | Sub-13 |
| 1-558 | Sub-50 | 3,4-diClPh | CH$_2$ | Single bond | Sub-14 |
| 1-559 | Sub-50 | 3,4-diClPh | CH$_2$ | Single bond | Sub-15 |
| 1-560 | Sub-50 | 3,4-diClPh | CH$_2$ | Single bond | Sub-16 |
| 1-561 | Sub-50 | 3,4-diClPh | CH$_2$ | Single bond | Sub-17 |
| 1-562 | Sub-50 | 3,4-diClPh | CH$_2$ | Single bond | Sub-18 |
| 1-563 | Sub-50 | 3,4-diClPh | CH$_2$ | Single bond | Sub-19 |
| 1-564 | Sub-50 | 3,4-diClPh | CH$_2$ | Single bond | Sub-20 |
| 1-565 | Sub-50 | 3,4-diClPh | CH$_2$ | Single bond | Sub-21 |
| 1-566 | Sub-50 | 3,4-diClPh | CH$_2$ | Single bond | Sub-22 |
| 1-567 | Sub-50 | 3,4-diClPh | CH$_2$ | Single bond | Sub-23 |
| 1-568 | Sub-50 | 3,4-diClPh | CH$_2$ | Single bond | Sub-24 |
| 1-569 | Sub-50 | 3,4-diClPh | CH$_2$ | Single bond | Sub-25 |
| 1-570 | Sub-50 | 3,4-diClPh | CH$_2$ | Single bond | Sub-26 |
| 1-571 | Sub-50 | 3,4-diClPh | CH$_2$ | Single bond | Sub-27 |
| 1-572 | Sub-50 | 3,4-diClPh | CH$_2$ | Single bond | Sub-28 |
| 1-573 | Sub-50 | 3,4-diClPh | CH$_2$ | Single bond | Sub-29 |
| 1-574 | Sub-50 | 3,4-diClPh | CH$_2$ | Single bond | Sub-30 |
| 1-575 | Sub-50 | 3,4-diClPh | CH$_2$ | Single bond | Sub-31 |
| 1-576 | Sub-50 | 3,4-diClPh | CH$_2$ | Single bond | Sub-32 |
| 1-577 | Sub-51 | 3,4-diClPh | CH$_2$ | Single bond | Sub-1 |
| 1-578 | Sub-51 | 3,4-diClPh | CH$_2$ | Single bond | Sub-2 |
| 1-579 | Sub-51 | 3,4-diClPh | CH$_2$ | Single bond | Sub-3 |
| 1-580 | Sub-51 | 3,4-diClPh | CH$_2$ | Single bond | Sub-4 |
| 1-581 | Sub-51 | 3,4-diClPh | CH$_2$ | Single bond | Sub-5 |

TABLE 1-continued

| Cpd. No. | R¹ | R² | A | B | Z |
|---|---|---|---|---|---|
| 1-582 | Sub-51 | 3,4-diClPh | $CH_2$ | Single bond | Sub-6 |
| 1-583 | Sub-51 | 3,4-diClPh | $CH_2$ | Single bond | Sub-7 |
| 1-584 | Sub-51 | 3,4-diClPh | $CH_2$ | Single bond | Sub-8 |
| 1-585 | Sub-51 | 3,4-diClPh | $CH_2$ | Single bond | Sub-9 |
| 1-586 | Sub-51 | 3,4-diClPh | $CH_2$ | Single bond | Sub-10 |
| 1-587 | Sub-51 | 3,4-diClPh | $CH_2$ | Single bond | Sub-11 |
| 1-588 | Sub-51 | 3,4-diClPh | $CH_2$ | Single bond | Sub-12 |
| 1-589 | Sub-51 | 3,4-diClPh | $CH_2$ | Single bond | Sub-13 |
| 1-590 | Sub-51 | 3,4-diClPh | $CH_2$ | Single bond | Sub-14 |
| 1-591 | Sub-51 | 3,4-diClPh | $CH_2$ | Single bond | Sub-15 |
| 1-592 | Sub-51 | 3,4-diClPh | $CH_2$ | Single bond | Sub-16 |
| 1-593 | Sub-51 | 3,4-diClPh | $CH_2$ | Single bond | Sub-17 |
| 1-594 | Sub-51 | 3,4-diClPh | $CH_2$ | Single bond | Sub-18 |
| 1-595 | Sub-51 | 3,4-diClPh | $CH_2$ | Single bond | Sub-19 |
| 1-596 | Sub-51 | 3,4-diClPh | $CH_2$ | Single bond | Sub-20 |
| 1-597 | Sub-51 | 3,4-diClPh | $CH_2$ | Single bond | Sub-21 |
| 1-598 | Sub-51 | 3,4-diClPh | $CH_2$ | Single bond | Sub-22 |
| 1-599 | Sub-51 | 3,4-diClPh | $CH_2$ | Single bond | Sub-23 |
| 1-600 | Sub-51 | 3,4-diClPh | $CH_2$ | Single bond | Sub-24 |
| 1-601 | Sub-51 | 3,4-diClPh | $CH_2$ | Single bond | Sub-25 |
| 1-602 | Sub-51 | 3,4-diClPh | $CH_2$ | Single bond | Sub-26 |
| 1-603 | Sub-51 | 3,4-diClPh | $CH_2$ | Single bond | Sub-27 |
| 1-604 | Sub-51 | 3,4-diClPh | $CH_2$ | Single bond | Sub-28 |
| 1-605 | Sub-51 | 3,4-diClPh | $CH_2$ | Single bond | Sub-29 |
| 1-606 | Sub-51 | 3,4-diClPh | $CH_2$ | Single bond | Sub-30 |
| 1-607 | Sub-51 | 3,4-diClPh | $CH_2$ | Single bond | Sub-31 |
| 1-608 | Sub-51 | 3,4-diClPh | $CH_2$ | Single bond | Sub-32 |
| 1-609 | Sub-52 | 3,4-diClPh | $CH_2$ | Single bond | Sub-1 |
| 1-610 | Sub-52 | 3,4-diClPh | $CH_2$ | Single bond | Sub-2 |
| 1-611 | Sub-52 | 3,4-diClPh | $CH_2$ | Single bond | Sub-3 |
| 1-612 | Sub-52 | 3,4-diClPh | $CH_2$ | Single bond | Sub-4 |
| 1-613 | Sub-52 | 3,4-diClPh | $CH_2$ | Single bond | Sub-5 |
| 1-614 | Sub-52 | 3,4-diClPh | $CH_2$ | Single bond | Sub-6 |
| 1-615 | Sub-52 | 3,4-diClPh | $CH_2$ | Single bond | Sub-7 |
| 1-616 | Sub-52 | 3,4-diClPh | $CH_2$ | Single bond | Sub-8 |
| 1-617 | Sub-52 | 3,4-diClPh | $CH_2$ | Single bond | Sub-9 |
| 1-618 | Sub-52 | 3,4-diClPh | $CH_2$ | Single bond | Sub-10 |
| 1-619 | Sub-52 | 3,4-diClPh | $CH_2$ | Single bond | Sub-11 |
| 1-620 | Sub-52 | 3,4-diClPh | $CH_2$ | Single bond | Sub-12 |
| 1-621 | Sub-52 | 3,4-diClPh | $CH_2$ | Single bond | Sub-13 |
| 1-622 | Sub-52 | 3,4-diClPh | $CH_2$ | Single bond | Sub-14 |
| 1-623 | Sub-52 | 3,4-diClPh | $CH_2$ | Single bond | Sub-15 |
| 1-624 | Sub-52 | 3,4-diClPh | $CH_2$ | Single bond | Sub-16 |
| 1-625 | Sub-52 | 3,4-diClPh | $CH_2$ | Single bond | Sub-17 |
| 1-626 | Sub-52 | 3,4-diClPh | $CH_2$ | Single bond | Sub-18 |
| 1-627 | Sub-52 | 3,4-diClPh | $CH_2$ | Single bond | Sub-19 |
| 1-628 | Sub-52 | 3,4-diClPh | $CH_2$ | Single bond | Sub-20 |
| 1-629 | Sub-52 | 3,4-diClPh | $CH_2$ | Single bond | Sub-21 |
| 1-630 | Sub-52 | 3,4-diClPh | $CH_2$ | Single bond | Sub-22 |
| 1-631 | Sub-52 | 3,4-diClPh | $CH_2$ | Single bond | Sub-23 |
| 1-632 | Sub-52 | 3,4-diClPh | $CH_2$ | Single bond | Sub-24 |
| 1-633 | Sub-52 | 3,4-diClPh | $CH_2$ | Single bond | Sub-25 |
| 1-634 | Sub-52 | 3,4-diClPh | $CH_2$ | Single bond | Sub-26 |
| 1-635 | Sub-52 | 3,4-diClPh | $CH_2$ | Single bond | Sub-27 |
| 1-636 | Sub-52 | 3,4-diClPh | $CH_2$ | Single bond | Sub-28 |
| 1-637 | Sub-52 | 3,4-diClPh | $CH_2$ | Single bond | Sub-29 |
| 1-638 | Sub-52 | 3,4-diClPh | $CH_2$ | Single bond | Sub-30 |
| 1-639 | Sub-52 | 3,4-diClPh | $CH_2$ | Single bond | Sub-31 |
| 1-640 | Sub-52 | 3,4-diClPh | $CH_2$ | Single bond | Sub-32 |
| 1-641 | Sub-53 | 3,4-diClPh | $CH_2$ | Single bond | Sub-1 |
| 1-642 | Sub-53 | 3,4-diClPh | $CH_2$ | Single bond | Sub-2 |
| 1-643 | Sub-53 | 3,4-diClPh | $CH_2$ | Single bond | Sub-3 |
| 1-644 | Sub-53 | 3,4-diClPh | $CH_2$ | Single bond | Sub-4 |
| 1-645 | Sub-53 | 3,4-diClPh | $CH_2$ | Single bond | Sub-5 |
| 1-646 | Sub-53 | 3,4-diClPh | $CH_2$ | Single bond | Sub-6 |
| 1-647 | Sub-53 | 3,4-diClPh | $CH_2$ | Single bond | Sub-7 |
| 1-648 | Sub-53 | 3,4-diClPh | $CH_2$ | Single bond | Sub-8 |
| 1-649 | Sub-53 | 3,4-diClPh | $CH_2$ | Single bond | Sub-9 |
| 1-650 | Sub-53 | 3,4-diClPh | $CH_2$ | Single bond | Sub-10 |
| 1-651 | Sub-53 | 3,4-diClPh | $CH_2$ | Single bond | Sub-11 |
| 1-652 | Sub-53 | 3,4-diClPh | $CH_2$ | Single bond | Sub-12 |
| 1-653 | Sub-53 | 3,4-diClPh | $CH_2$ | Single bond | Sub-13 |
| 1-654 | Sub-53 | 3,4-diClPh | $CH_2$ | Single bond | Sub-14 |
| 1-655 | Sub-53 | 3,4-diClPh | $CH_2$ | Single bond | Sub-15 |
| 1-656 | Sub-53 | 3,4-diClPh | $CH_2$ | Single bond | Sub-16 |
| 1-657 | Sub-53 | 3,4-diClPh | $CH_2$ | Single bond | Sub-17 |
| 1-658 | Sub-53 | 3,4-diClPh | $CH_2$ | Single bond | Sub-18 |
| 1-659 | Sub-53 | 3,4-diClPh | $CH_2$ | Single bond | Sub-19 |
| 1-660 | Sub-53 | 3,4-diClPh | $CH_2$ | Single bond | Sub-20 |
| 1-661 | Sub-53 | 3,4-diClPh | $CH_2$ | Single bond | Sub-21 |
| 1-662 | Sub-53 | 3,4-diClPh | $CH_2$ | Single bond | Sub-22 |
| 1-663 | Sub-53 | 3,4-diClPh | $CH_2$ | Single bond | Sub-23 |
| 1-664 | Sub-53 | 3,4-diClPh | $CH_2$ | Single bond | Sub-24 |
| 1-665 | Sub-53 | 3,4-diClPh | $CH_2$ | Single bond | Sub-25 |
| 1-666 | Sub-53 | 3,4-diClPh | $CH_2$ | Single bond | Sub-26 |
| 1-667 | Sub-53 | 3,4-diClPh | $CH_2$ | Single bond | Sub-27 |
| 1-668 | Sub-53 | 3,4-diClPh | $CH_2$ | Single bond | Sub-28 |
| 1-669 | Sub-53 | 3,4-diClPh | $CH_2$ | Single bond | Sub-29 |
| 1-670 | Sub-53 | 3,4-diClPh | $CH_2$ | Single bond | Sub-30 |
| 1-671 | Sub-53 | 3,4-diClPh | $CH_2$ | Single bond | Sub-31 |
| 1-672 | Sub-53 | 3,4-diClPh | $CH_2$ | Single bond | Sub-32 |
| 1-673 | Sub-54 | 3,4-diClPh | $CH_2$ | Single bond | Sub-1 |
| 1-674 | Sub-54 | 3,4-diClPh | $CH_2$ | Single bond | Sub-2 |
| 1-675 | Sub-54 | 3,4-diClPh | $CH_2$ | Single bond | Sub-3 |
| 1-676 | Sub-54 | 3,4-diClPh | $CH_2$ | Single bond | Sub-4 |
| 1-677 | Sub-54 | 3,4-diClPh | $CH_2$ | Single bond | Sub-5 |
| 1-678 | Sub-54 | 3,4-diClPh | $CH_2$ | Single bond | Sub-6 |
| 1-679 | Sub-54 | 3,4-diClPh | $CH_2$ | Single bond | Sub-7 |
| 1-680 | Sub-54 | 3,4-diClPh | $CH_2$ | Single bond | Sub-8 |
| 1-681 | Sub-54 | 3,4-diClPh | $CH_2$ | Single bond | Sub-9 |
| 1-682 | Sub-54 | 3,4-diClPh | $CH_2$ | Single bond | Sub-10 |
| 1-683 | Sub-54 | 3,4-diClPh | $CH_2$ | Single bond | Sub-11 |
| 1-684 | Sub-54 | 3,4-diClPh | $CH_2$ | Single bond | Sub-12 |
| 1-685 | Sub-54 | 3,4-diClPh | $CH_2$ | Single bond | Sub-13 |
| 1-686 | Sub-54 | 3,4-diClPh | $CH_2$ | Single bond | Sub-14 |
| 1-687 | Sub-54 | 3,4-diClPh | $CH_2$ | Single bond | Sub-15 |
| 1-688 | Sub-54 | 3,4-diClPh | $CH_2$ | Single bond | Sub-16 |
| 1-689 | Sub-54 | 3,4-diClPh | $CH_2$ | Single bond | Sub-17 |
| 1-690 | Sub-54 | 3,4-diClPh | $CH_2$ | Single bond | Sub-18 |
| 1-691 | Sub-54 | 3,4-diClPh | $CH_2$ | Single bond | Sub-19 |
| 1-692 | Sub-54 | 3,4-diClPh | $CH_2$ | Single bond | Sub-20 |
| 1-693 | Sub-54 | 3,4-diClPh | $CH_2$ | Single bond | Sub-21 |
| 1-694 | Sub-54 | 3,4-diClPh | $CH_2$ | Single bond | Sub-22 |
| 1-695 | Sub-54 | 3,4-diClPh | $CH_2$ | Single bond | Sub-23 |
| 1-696 | Sub-54 | 3,4-diClPh | $CH_2$ | Single bond | Sub-24 |
| 1-697 | Sub-54 | 3,4-diClPh | $CH_2$ | Single bond | Sub-25 |
| 1-698 | Sub-54 | 3,4-diClPh | $CH_2$ | Single bond | Sub-26 |
| 1-699 | Sub-54 | 3,4-diClPh | $CH_2$ | Single bond | Sub-27 |
| 1-700 | Sub-54 | 3,4-diClPh | $CH_2$ | Single bond | Sub-28 |
| 1-701 | Sub-54 | 3,4-diClPh | $CH_2$ | Single bond | Sub-29 |
| 1-702 | Sub-54 | 3,4-diClPh | $CH_2$ | Single bond | Sub-30 |
| 1-703 | Sub-54 | 3,4-diClPh | $CH_2$ | Single bond | Sub-31 |
| 1-704 | Sub-54 | 3,4-diClPh | $CH_2$ | Single bond | Sub-32 |
| 1-705 | Sub-55 | 3,4-diClPh | $CH_2$ | Single bond | Sub-1 |
| 1-706 | Sub-55 | 3,4-diClPh | $CH_2$ | Single bond | Sub-2 |
| 1-707 | Sub-55 | 3,4-diClPh | $CH_2$ | Single bond | Sub-3 |
| 1-708 | Sub-55 | 3,4-diClPh | $CH_2$ | Single bond | Sub-4 |
| 1-709 | Sub-55 | 3,4-diClPh | $CH_2$ | Single bond | Sub-5 |
| 1-710 | Sub-55 | 3,4-diClPh | $CH_2$ | Single bond | Sub-6 |
| 1-711 | Sub-55 | 3,4-diClPh | $CH_2$ | Single bond | Sub-7 |
| 1-712 | Sub-55 | 3,4-diClPh | $CH_2$ | Single bond | Sub-8 |
| 1-713 | Sub-55 | 3,4-diClPh | $CH_2$ | Single bond | Sub-9 |
| 1-714 | Sub-55 | 3,4-diClPh | $CH_2$ | Single bond | Sub-10 |
| 1-715 | Sub-55 | 3,4-diClPh | $CH_2$ | Single bond | Sub-11 |
| 1-716 | Sub-55 | 3,4-diClPh | $CH_2$ | Single bond | Sub-12 |
| 1-717 | Sub-55 | 3,4-diClPh | $CH_2$ | Single bond | Sub-13 |
| 1-718 | Sub-55 | 3,4-diClPh | $CH_2$ | Single bond | Sub-14 |
| 1-719 | Sub-55 | 3,4-diClPh | $CH_2$ | Single bond | Sub-15 |
| 1-720 | Sub-55 | 3,4-diClPh | $CH_2$ | Single bond | Sub-16 |
| 1-721 | Sub-55 | 3,4-diClPh | $CH_2$ | Single bond | Sub-17 |
| 1-722 | Sub-55 | 3,4-diClPh | $CH_2$ | Single bond | Sub-18 |
| 1-723 | Sub-55 | 3,4-diClPh | $CH_2$ | Single bond | Sub-19 |
| 1-724 | Sub-55 | 3,4-diClPh | $CH_2$ | Single bond | Sub-20 |
| 1-725 | Sub-55 | 3,4-diClPh | $CH_2$ | Single bond | Sub-21 |
| 1-726 | Sub-55 | 3,4-diClPh | $CH_2$ | Single bond | Sub-22 |
| 1-727 | Sub-55 | 3,4-diClPh | $CH_2$ | Single bond | Sub-23 |
| 1-728 | Sub-55 | 3,4-diClPh | $CH_2$ | Single bond | Sub-24 |
| 1-729 | Sub-55 | 3,4-diClPh | $CH_2$ | Single bond | Sub-25 |
| 1-730 | Sub-55 | 3,4-diClPh | $CH_2$ | Single bond | Sub-26 |
| 1-731 | Sub-55 | 3,4-diClPh | $CH_2$ | Single bond | Sub-27 |
| 1-732 | Sub-55 | 3,4-diClPh | $CH_2$ | Single bond | Sub-28 |
| 1-733 | Sub-55 | 3,4-diClPh | $CH_2$ | Single bond | Sub-29 |

TABLE 1-continued

| Cpd. No. | R¹ | R² | A | B | Z |
|---|---|---|---|---|---|
| 1-734 | Sub-55 | 3,4-diClPh | CH$_2$ | Single bond | Sub-30 |
| 1-735 | Sub-55 | 3,4-diClPh | CH$_2$ | Single bond | Sub-31 |
| 1-736 | Sub-55 | 3,4-diClPh | CH$_2$ | Single bond | Sub-32 |
| 1-737 | Sub-56 | 3,4-diClPh | CH$_2$ | Single bond | Sub-1 |
| 1-738 | Sub-56 | 3,4-diClPh | CH$_2$ | Single bond | Sub-2 |
| 1-739 | Sub-56 | 3,4-diClPh | CH$_2$ | Single bond | Sub-3 |
| 1-740 | Sub-56 | 3,4-diClPh | CH$_2$ | Single bond | Sub-4 |
| 1-741 | Sub-56 | 3,4-diClPh | CH$_2$ | Single bond | Sub-5 |
| 1-742 | Sub-56 | 3,4-diClPh | CH$_2$ | Single bond | Sub-6 |
| 1-743 | Sub-56 | 3,4-diClPh | CH$_2$ | Single bond | Sub-7 |
| 1-744 | Sub-56 | 3,4-diClPh | CH$_2$ | Single bond | Sub-8 |
| 1-745 | Sub-56 | 3,4-diClPh | CH$_2$ | Single bond | Sub-9 |
| 1-746 | Sub-56 | 3,4-diClPh | CH$_2$ | Single bond | Sub-10 |
| 1-747 | Sub-56 | 3,4-diClPh | CH$_2$ | Single bond | Sub-11 |
| 1-748 | Sub-56 | 3,4-diClPh | CH$_2$ | Single bond | Sub-12 |
| 1-749 | Sub-56 | 3,4-diClPh | CH$_2$ | Single bond | Sub-13 |
| 1-750 | Sub-56 | 3,4-diClPh | CH$_2$ | Single bond | Sub-14 |
| 1-751 | Sub-56 | 3,4-diClPh | CH$_2$ | Single bond | Sub-15 |
| 1-752 | Sub-56 | 3,4-diClPh | CH$_2$ | Single bond | Sub-16 |
| 1-753 | Sub-56 | 3,4-diClPh | CH$_2$ | Single bond | Sub-17 |
| 1-754 | Sub-56 | 3,4-diClPh | CH$_2$ | Single bond | Sub-18 |
| 1-755 | Sub-56 | 3,4-diClPh | CH$_2$ | Single bond | Sub-19 |
| 1-756 | Sub-56 | 3,4-diClPh | CH$_2$ | Single bond | Sub-20 |
| 1-757 | Sub-56 | 3,4-diClPh | CH$_2$ | Single bond | Sub-21 |
| 1-758 | Sub-56 | 3,4-diClPh | CH$_2$ | Single bond | Sub-22 |
| 1-759 | Sub-56 | 3,4-diClPh | CH$_2$ | Single bond | Sub-23 |
| 1-760 | Sub-56 | 3,4-diClPh | CH$_2$ | Single bond | Sub-24 |
| 1-761 | Sub-56 | 3,4-diClPh | CH$_2$ | Single bond | Sub-25 |
| 1-762 | Sub-56 | 3,4-diClPh | CH$_2$ | Single bond | Sub-26 |
| 1-763 | Sub-56 | 3,4-diClPh | CH$_2$ | Single bond | Sub-27 |
| 1-764 | Sub-56 | 3,4-diClPh | CH$_2$ | Single bond | Sub-28 |
| 1-765 | Sub-56 | 3,4-diClPh | CH$_2$ | Single bond | Sub-29 |
| 1-766 | Sub-56 | 3,4-diClPh | CH$_2$ | Single bond | Sub-30 |
| 1-767 | Sub-56 | 3,4-diClPh | CH$_2$ | Single bond | Sub-31 |
| 1-768 | Sub-56 | 3,4-diClPh | CH$_2$ | Single bond | Sub-32 |
| 1-769 | Sub-57 | 3,4-diClPh | CH$_2$ | Single bond | Sub-1 |
| 1-770 | Sub-57 | 3,4-diClPh | CH$_2$ | Single bond | Sub-2 |
| 1-771 | Sub-57 | 3,4-diClPh | CH$_2$ | Single bond | Sub-3 |
| 1-772 | Sub-57 | 3,4-diClPh | CH$_2$ | Single bond | Sub-4 |
| 1-773 | Sub-57 | 3,4-diClPh | CH$_2$ | Single bond | Sub-5 |
| 1-774 | Sub-57 | 3,4-diClPh | CH$_2$ | Single bond | Sub-6 |
| 1-775 | Sub-57 | 3,4-diClPh | CH$_2$ | Single bond | Sub-7 |
| 1-776 | Sub-57 | 3,4-diClPh | CH$_2$ | Single bond | Sub-8 |
| 1-777 | Sub-57 | 3,4-diClPh | CH$_2$ | Single bond | Sub-9 |
| 1-778 | Sub-57 | 3,4-diClPh | CH$_2$ | Single bond | Sub-10 |
| 1-779 | Sub-57 | 3,4-diClPh | CH$_2$ | Single bond | Sub-11 |
| 1-780 | Sub-57 | 3,4-diClPh | CH$_2$ | Single bond | Sub-12 |
| 1-781 | Sub-57 | 3,4-diClPh | CH$_2$ | Single bond | Sub-13 |
| 1-782 | Sub-57 | 3,4-diClPh | CH$_2$ | Single bond | Sub-14 |
| 1-783 | Sub-57 | 3,4-diClPh | CH$_2$ | Single bond | Sub-15 |
| 1-784 | Sub-57 | 3,4-diClPh | CH$_2$ | Single bond | Sub-16 |
| 1-785 | Sub-57 | 3,4-diClPh | CH$_2$ | Single bond | Sub-17 |
| 1-786 | Sub-57 | 3,4-diClPh | CH$_2$ | Single bond | Sub-18 |
| 1-787 | Sub-57 | 3,4-diClPh | CH$_2$ | Single bond | Sub-19 |
| 1-788 | Sub-57 | 3,4-diClPh | CH$_2$ | Single bond | Sub-20 |
| 1-789 | Sub-57 | 3,4-diClPh | CH$_2$ | Single bond | Sub-21 |
| 1-790 | Sub-57 | 3,4-diClPh | CH$_2$ | Single bond | Sub-22 |
| 1-791 | Sub-57 | 3,4-diClPh | CH$_2$ | Single bond | Sub-23 |
| 1-792 | Sub-57 | 3,4-diClPh | CH$_2$ | Single bond | Sub-24 |
| 1-793 | Sub-57 | 3,4-diClPh | CH$_2$ | Single bond | Sub-25 |
| 1-794 | Sub-57 | 3,4-diClPh | CH$_2$ | Single bond | Sub-26 |
| 1-795 | Sub-57 | 3,4-diClPh | CH$_2$ | Single bond | Sub-27 |
| 1-796 | Sub-57 | 3,4-diClPh | CH$_2$ | Single bond | Sub-28 |
| 1-797 | Sub-57 | 3,4-diClPh | CH$_2$ | Single bond | Sub-29 |
| 1-798 | Sub-57 | 3,4-diClPh | CH$_2$ | Single bond | Sub-30 |
| 1-799 | Sub-57 | 3,4-diClPh | CH$_2$ | Single bond | Sub-31 |
| 1-800 | Sub-57 | 3,4-diClPh | CH$_2$ | Single bond | Sub-32 |
| 1-801 | Sub-58 | 3,4-diClPh | CH$_2$ | Single bond | Sub-1 |
| 1-802 | Sub-58 | 3,4-diClPh | CH$_2$ | Single bond | Sub-2 |
| 1-803 | Sub-58 | 3,4-diClPh | CH$_2$ | Single bond | Sub-3 |
| 1-804 | Sub-58 | 3,4-diClPh | CH$_2$ | Single bond | Sub-4 |
| 1-805 | Sub-58 | 3,4-diClPh | CH$_2$ | Single bond | Sub-5 |
| 1-806 | Sub-58 | 3,4-diClPh | CH$_2$ | Single bond | Sub-6 |
| 1-807 | Sub-58 | 3,4-diClPh | CH$_2$ | Single bond | Sub-7 |
| 1-808 | Sub-58 | 3,4-diClPh | CH$_2$ | Single bond | Sub-8 |
| 1-809 | Sub-58 | 3,4-diClPh | CH$_2$ | Single bond | Sub-9 |
| 1-810 | Sub-58 | 3,4-diClPh | CH$_2$ | Single bond | Sub-10 |
| 1-811 | Sub-58 | 3,4-diClPh | CH$_2$ | Single bond | Sub-11 |
| 1-812 | Sub-58 | 3,4-diClPh | CH$_2$ | Single bond | Sub-12 |
| 1-813 | Sub-58 | 3,4-diClPh | CH$_2$ | Single bond | Sub-13 |
| 1-814 | Sub-58 | 3,4-diClPh | CH$_2$ | Single bond | Sub-14 |
| 1-815 | Sub-58 | 3,4-diClPh | CH$_2$ | Single bond | Sub-15 |
| 1-816 | Sub-58 | 3,4-diClPh | CH$_2$ | Single bond | Sub-16 |
| 1-817 | Sub-58 | 3,4-diClPh | CH$_2$ | Single bond | Sub-17 |
| 1-818 | Sub-58 | 3,4-diClPh | CH$_2$ | Single bond | Sub-18 |
| 1-819 | Sub-58 | 3,4-diClPh | CH$_2$ | Single bond | Sub-19 |
| 1-820 | Sub-58 | 3,4-diClPh | CH$_2$ | Single bond | Sub-20 |
| 1-821 | Sub-58 | 3,4-diClPh | CH$_2$ | Single bond | Sub-21 |
| 1-822 | Sub-58 | 3,4-diClPh | CH$_2$ | Single bond | Sub-22 |
| 1-823 | Sub-58 | 3,4-diClPh | CH$_2$ | Single bond | Sub-23 |
| 1-824 | Sub-58 | 3,4-diClPh | CH$_2$ | Single bond | Sub-24 |
| 1-825 | Sub-58 | 3,4-diClPh | CH$_2$ | Single bond | Sub-25 |
| 1-826 | Sub-58 | 3,4-diClPh | CH$_2$ | Single bond | Sub-26 |
| 1-827 | Sub-58 | 3,4-diClPh | CH$_2$ | Single bond | Sub-27 |
| 1-828 | Sub-58 | 3,4-diClPh | CH$_2$ | Single bond | Sub-28 |
| 1-829 | Sub-58 | 3,4-diClPh | CH$_2$ | Single bond | Sub-29 |
| 1-830 | Sub-58 | 3,4-diClPh | CH$_2$ | Single bond | Sub-30 |
| 1-831 | Sub-58 | 3,4-diClPh | CH$_2$ | Single bond | Sub-31 |
| 1-832 | Sub-58 | 3,4-diClPh | CH$_2$ | Single bond | Sub-32 |
| 1-833 | Sub-59 | 3,4-diClPh | CH$_2$ | Single bond | Sub-1 |
| 1-834 | Sub-59 | 3,4-diClPh | CH$_2$ | Single bond | Sub-2 |
| 1-835 | Sub-59 | 3,4-diClPh | CH$_2$ | Single bond | Sub-3 |
| 1-836 | Sub-59 | 3,4-diClPh | CH$_2$ | Single bond | Sub-4 |
| 1-837 | Sub-59 | 3,4-diClPh | CH$_2$ | Single bond | Sub-5 |
| 1-838 | Sub-59 | 3,4-diClPh | CH$_2$ | Single bond | Sub-6 |
| 1-839 | Sub-59 | 3,4-diClPh | CH$_2$ | Single bond | Sub-7 |
| 1-840 | Sub-59 | 3,4-diClPh | CH$_2$ | Single bond | Sub-8 |
| 1-841 | Sub-59 | 3,4-diClPh | CH$_2$ | Single bond | Sub-9 |
| 1-842 | Sub-59 | 3,4-diClPh | CH$_2$ | Single bond | Sub-10 |
| 1-843 | Sub-59 | 3,4-diClPh | CH$_2$ | Single bond | Sub-11 |
| 1-844 | Sub-59 | 3,4-diClPh | CH$_2$ | Single bond | Sub-12 |
| 1-845 | Sub-59 | 3,4-diClPh | CH$_2$ | Single bond | Sub-13 |
| 1-846 | Sub-59 | 3,4-diClPh | CH$_2$ | Single bond | Sub-14 |
| 1-847 | Sub-59 | 3,4-diClPh | CH$_2$ | Single bond | Sub-15 |
| 1-848 | Sub-59 | 3,4-diClPh | CH$_2$ | Single bond | Sub-16 |
| 1-849 | Sub-59 | 3,4-diClPh | CH$_2$ | Single bond | Sub-17 |
| 1-850 | Sub-59 | 3,4-diClPh | CH$_2$ | Single bond | Sub-18 |
| 1-851 | Sub-59 | 3,4-diClPh | CH$_2$ | Single bond | Sub-19 |
| 1-852 | Sub-59 | 3,4-diClPh | CH$_2$ | Single bond | Sub-20 |
| 1-853 | Sub-59 | 3,4-diClPh | CH$_2$ | Single bond | Sub-21 |
| 1-854 | Sub-59 | 3,4-diClPh | CH$_2$ | Single bond | Sub-22 |
| 1-855 | Sub-59 | 3,4-diClPh | CH$_2$ | Single bond | Sub-23 |
| 1-856 | Sub-59 | 3,4-diClPh | CH$_2$ | Single bond | Sub-24 |
| 1-857 | Sub-59 | 3,4-diClPh | CH$_2$ | Single bond | Sub-25 |
| 1-858 | Sub-59 | 3,4-diClPh | CH$_2$ | Single bond | Sub-26 |
| 1-859 | Sub-59 | 3,4-diClPh | CH$_2$ | Single bond | Sub-27 |
| 1-860 | Sub-59 | 3,4-diClPh | CH$_2$ | Single bond | Sub-28 |
| 1-861 | Sub-59 | 3,4-diClPh | CH$_2$ | Single bond | Sub-29 |
| 1-862 | Sub-59 | 3,4-diClPh | CH$_2$ | Single bond | Sub-30 |
| 1-863 | Sub-59 | 3,4-diClPh | CH$_2$ | Single bond | Sub-31 |
| 1-864 | Sub-59 | 3,4-diClPh | CH$_2$ | Single bond | Sub-32 |
| 1-865 | Sub-60 | 3,4-diClPh | CH$_2$ | Single bond | Sub-1 |
| 1-866 | Sub-60 | 3,4-diClPh | CH$_2$ | Single bond | Sub-2 |
| 1-867 | Sub-60 | 3,4-diClPh | CH$_2$ | Single bond | Sub-3 |
| 1-868 | Sub-60 | 3,4-diClPh | CH$_2$ | Single bond | Sub-4 |
| 1-869 | Sub-60 | 3,4-diClPh | CH$_2$ | Single bond | Sub-5 |
| 1-870 | Sub-60 | 3,4-diClPh | CH$_2$ | Single bond | Sub-6 |
| 1-871 | Sub-60 | 3,4-diClPh | CH$_2$ | Single bond | Sub-7 |
| 1-872 | Sub-60 | 3,4-diClPh | CH$_2$ | Single bond | Sub-8 |
| 1-873 | Sub-60 | 3,4-diClPh | CH$_2$ | Single bond | Sub-9 |
| 1-874 | Sub-60 | 3,4-diClPh | CH$_2$ | Single bond | Sub-10 |
| 1-875 | Sub-60 | 3,4-diClPh | CH$_2$ | Single bond | Sub-11 |
| 1-876 | Sub-60 | 3,4-diClPh | CH$_2$ | Single bond | Sub-12 |
| 1-877 | Sub-60 | 3,4-diClPh | CH$_2$ | Single bond | Sub-13 |
| 1-878 | Sub-60 | 3,4-diClPh | CH$_2$ | Single bond | Sub-14 |
| 1-879 | Sub-60 | 3,4-diClPh | CH$_2$ | Single bond | Sub-15 |
| 1-880 | Sub-60 | 3,4-diClPh | CH$_2$ | Single bond | Sub-16 |
| 1-881 | Sub-60 | 3,4-diClPh | CH$_2$ | Single bond | Sub-17 |
| 1-882 | Sub-60 | 3,4-diClPh | CH$_2$ | Single bond | Sub-18 |
| 1-883 | Sub-60 | 3,4-diClPh | CH$_2$ | Single bond | Sub-19 |
| 1-884 | Sub-60 | 3,4-diClPh | CH$_2$ | Single bond | Sub-20 |
| 1-885 | Sub-60 | 3,4-diClPh | CH$_2$ | Single bond | Sub-21 |

TABLE 1-continued

| Cpd. No. | R¹ | R² | A | B | Z |
|---|---|---|---|---|---|
| 1-886 | Sub-60 | 3,4-diClPh | CH$_2$ | Single bond | Sub-22 |
| 1-887 | Sub-60 | 3,4-diClPh | CH$_2$ | Single bond | Sub-23 |
| 1-888 | Sub-60 | 3,4-diClPh | CH$_2$ | Single bond | Sub-24 |
| 1-889 | Sub-60 | 3,4-diClPh | CH$_2$ | Single bond | Sub-25 |
| 1-890 | Sub-60 | 3,4-diClPh | CH$_2$ | Single bond | Sub-26 |
| 1-891 | Sub-60 | 3,4-diClPh | CH$_2$ | Single bond | Sub-27 |
| 1-892 | Sub-60 | 3,4-diClPh | CH$_2$ | Single bond | Sub-28 |
| 1-893 | Sub-60 | 3,4-diClPh | CH$_2$ | Single bond | Sub-29 |
| 1-894 | Sub-60 | 3,4-diClPh | CH$_2$ | Single bond | Sub-30 |
| 1-895 | Sub-60 | 3,4-diClPh | CH$_2$ | Single bond | Sub-31 |
| 1-896 | Sub-60 | 3,4-diClPh | CH$_2$ | Single bond | Sub-32 |
| 1-897 | Sub-61 | 3,4-diClPh | CH$_2$ | Single bond | Sub-1 |
| 1-898 | Sub-61 | 3,4-diClPh | CH$_2$ | Single bond | Sub-2 |
| 1-899 | Sub-61 | 3,4-diClPh | CH$_2$ | Single bond | Sub-3 |
| 1-900 | Sub-61 | 3,4-diClPh | CH$_2$ | Single bond | Sub-4 |
| 1-901 | Sub-61 | 3,4-diClPh | CH$_2$ | Single bond | Sub-5 |
| 1-902 | Sub-61 | 3,4-diClPh | CH$_2$ | Single bond | Sub-6 |
| 1-903 | Sub-61 | 3,4-diClPh | CH$_2$ | Single bond | Sub-7 |
| 1-904 | Sub-61 | 3,4-diClPh | CH$_2$ | Single bond | Sub-8 |
| 1-905 | Sub-61 | 3,4-diClPh | CH$_2$ | Single bond | Sub-9 |
| 1-906 | Sub-61 | 3,4-diClPh | CH$_2$ | Single bond | Sub-10 |
| 1-907 | Sub-61 | 3,4-diClPh | CH$_2$ | Single bond | Sub-11 |
| 1-908 | Sub-61 | 3,4-diClPh | CH$_2$ | Single bond | Sub-12 |
| 1-909 | Sub-61 | 3,4-diClPh | CH$_2$ | Single bond | Sub-13 |
| 1-910 | Sub-61 | 3,4-diClPh | CH$_2$ | Single bond | Sub-14 |
| 1-911 | Sub-61 | 3,4-diClPh | CH$_2$ | Single bond | Sub-15 |
| 1-912 | Sub-61 | 3,4-diClPh | CH$_2$ | Single bond | Sub-16 |
| 1-913 | Sub-61 | 3,4-diClPh | CH$_2$ | Single bond | Sub-17 |
| 1-914 | Sub-61 | 3,4-diClPh | CH$_2$ | Single bond | Sub-18 |
| 1-915 | Sub-61 | 3,4-diClPh | CH$_2$ | Single bond | Sub-19 |
| 1-916 | Sub-61 | 3,4-diClPh | CH$_2$ | Single bond | Sub-20 |
| 1-917 | Sub-61 | 3,4-diClPh | CH$_2$ | Single bond | Sub-21 |
| 1-918 | Sub-61 | 3,4-diClPh | CH$_2$ | Single bond | Sub-22 |
| 1-919 | Sub-61 | 3,4-diClPh | CH$_2$ | Single bond | Sub-23 |
| 1-920 | Sub-61 | 3,4-diClPh | CH$_2$ | Single bond | Sub-24 |
| 1-921 | Sub-61 | 3,4-diClPh | CH$_2$ | Single bond | Sub-25 |
| 1-922 | Sub-61 | 3,4-diClPh | CH$_2$ | Single bond | Sub-26 |
| 1-923 | Sub-61 | 3,4-diClPh | CH$_2$ | Single bond | Sub-27 |
| 1-924 | Sub-61 | 3,4-diClPh | CH$_2$ | Single bond | Sub-28 |
| 1-925 | Sub-61 | 3,4-diClPh | CH$_2$ | Single bond | Sub-29 |
| 1-926 | Sub-61 | 3,4-diClPh | CH$_2$ | Single bond | Sub-30 |
| 1-927 | Sub-61 | 3,4-diClPh | CH$_2$ | Single bond | Sub-31 |
| 1-928 | Sub-61 | 3,4-diClPh | CH$_2$ | Single bond | Sub-32 |
| 1-929 | Sub-62 | 3,4-diClPh | CH$_2$ | Single bond | Sub-1 |
| 1-930 | Sub-62 | 3,4-diClPh | CH$_2$ | Single bond | Sub-2 |
| 1-931 | Sub-62 | 3,4-diClPh | CH$_2$ | Single bond | Sub-3 |
| 1-932 | Sub-62 | 3,4-diClPh | CH$_2$ | Single bond | Sub-4 |
| 1-933 | Sub-62 | 3,4-diClPh | CH$_2$ | Single bond | Sub-5 |
| 1-934 | Sub-62 | 3,4-diClPh | CH$_2$ | Single bond | Sub-6 |
| 1-935 | Sub-62 | 3,4-diClPh | CH$_2$ | Single bond | Sub-7 |
| 1-936 | Sub-62 | 3,4-diClPh | CH$_2$ | Single bond | Sub-8 |
| 1-937 | Sub-62 | 3,4-diClPh | CH$_2$ | Single bond | Sub-9 |
| 1-938 | Sub-62 | 3,4-diClPh | CH$_2$ | Single bond | Sub-10 |
| 1-939 | Sub-62 | 3,4-diClPh | CH$_2$ | Single bond | Sub-11 |
| 1-940 | Sub-62 | 3,4-diClPh | CH$_2$ | Single bond | Sub-12 |
| 1-941 | Sub-62 | 3,4-diClPh | CH$_2$ | Single bond | Sub-13 |
| 1-942 | Sub-62 | 3,4-diClPh | CH$_2$ | Single bond | Sub-14 |
| 1-943 | Sub-62 | 3,4-diClPh | CH$_2$ | Single bond | Sub-15 |
| 1-944 | Sub-62 | 3,4-diClPh | CH$_2$ | Single bond | Sub-16 |
| 1-945 | Sub-62 | 3,4-diClPh | CH$_2$ | Single bond | Sub-17 |
| 1-946 | Sub-62 | 3,4-diClPh | CH$_2$ | Single bond | Sub-18 |
| 1-947 | Sub-62 | 3,4-diClPh | CH$_2$ | Single bond | Sub-19 |
| 1-948 | Sub-62 | 3,4-diClPh | CH$_2$ | Single bond | Sub-20 |
| 1-949 | Sub-62 | 3,4-diClPh | CH$_2$ | Single bond | Sub-21 |
| 1-950 | Sub-62 | 3,4-diClPh | CH$_2$ | Single bond | Sub-22 |
| 1-951 | Sub-62 | 3,4-diClPh | CH$_2$ | Single bond | Sub-23 |
| 1-952 | Sub-62 | 3,4-diClPh | CH$_2$ | Single bond | Sub-24 |
| 1-953 | Sub-62 | 3,4-diClPh | CH$_2$ | Single bond | Sub-25 |
| 1-954 | Sub-62 | 3,4-diClPh | CH$_2$ | Single bond | Sub-26 |
| 1-955 | Sub-62 | 3,4-diClPh | CH$_2$ | Single bond | Sub-27 |
| 1-956 | Sub-62 | 3,4-diClPh | CH$_2$ | Single bond | Sub-28 |
| 1-957 | Sub-62 | 3,4-diClPh | CH$_2$ | Single bond | Sub-29 |
| 1-958 | Sub-62 | 3,4-diClPh | CH$_2$ | Single bond | Sub-30 |
| 1-959 | Sub-62 | 3,4-diClPh | CH$_2$ | Single bond | Sub-31 |
| 1-960 | Sub-62 | 3,4-diClPh | CH$_2$ | Single bond | Sub-32 |
| 1-961 | Sub-63 | 3,4-diClPh | CH$_2$ | Single bond | Sub-1 |
| 1-962 | Sub-63 | 3,4-diClPh | CH$_2$ | Single bond | Sub-2 |
| 1-963 | Sub-63 | 3,4-diClPh | CH$_2$ | Single bond | Sub-3 |
| 1-964 | Sub-63 | 3,4-diClPh | CH$_2$ | Single bond | Sub-4 |
| 1-965 | Sub-63 | 3,4-diClPh | CH$_2$ | Single bond | Sub-5 |
| 1-966 | Sub-63 | 3,4-diClPh | CH$_2$ | Single bond | Sub-6 |
| 1-967 | Sub-63 | 3,4-diClPh | CH$_2$ | Single bond | Sub-7 |
| 1-968 | Sub-63 | 3,4-diClPh | CH$_2$ | Single bond | Sub-8 |
| 1-969 | Sub-63 | 3,4-diClPh | CH$_2$ | Single bond | Sub-9 |
| 1-970 | Sub-63 | 3,4-diClPh | CH$_2$ | Single bond | Sub-10 |
| 1-971 | Sub-63 | 3,4-diClPh | CH$_2$ | Single bond | Sub-11 |
| 1-972 | Sub-63 | 3,4-diClPh | CH$_2$ | Single bond | Sub-12 |
| 1-973 | Sub-63 | 3,4-diClPh | CH$_2$ | Single bond | Sub-13 |
| 1-974 | Sub-63 | 3,4-diClPh | CH$_2$ | Single bond | Sub-14 |
| 1-975 | Sub-63 | 3,4-diClPh | CH$_2$ | Single bond | Sub-15 |
| 1-976 | Sub-63 | 3,4-diClPh | CH$_2$ | Single bond | Sub-16 |
| 1-977 | Sub-63 | 3,4-diClPh | CH$_2$ | Single bond | Sub-17 |
| 1-978 | Sub-63 | 3,4-diClPh | CH$_2$ | Single bond | Sub-18 |
| 1-979 | Sub-63 | 3,4-diClPh | CH$_2$ | Single bond | Sub-19 |
| 1-980 | Sub-63 | 3,4-diClPh | CH$_2$ | Single bond | Sub-20 |
| 1-981 | Sub-63 | 3,4-diClPh | CH$_2$ | Single bond | Sub-21 |
| 1-982 | Sub-63 | 3,4-diClPh | CH$_2$ | Single bond | Sub-22 |
| 1-983 | Sub-63 | 3,4-diClPh | CH$_2$ | Single bond | Sub-23 |
| 1-984 | Sub-63 | 3,4-diClPh | CH$_2$ | Single bond | Sub-24 |
| 1-985 | Sub-63 | 3,4-diClPh | CH$_2$ | Single bond | Sub-25 |
| 1-986 | Sub-63 | 3,4-diClPh | CH$_2$ | Single bond | Sub-26 |
| 1-987 | Sub-63 | 3,4-diClPh | CH$_2$ | Single bond | Sub-27 |
| 1-988 | Sub-63 | 3,4-diClPh | CH$_2$ | Single bond | Sub-28 |
| 1-989 | Sub-63 | 3,4-diClPh | CH$_2$ | Single bond | Sub-29 |
| 1-990 | Sub-63 | 3,4-diClPh | CH$_2$ | Single bond | Sub-30 |
| 1-991 | Sub-63 | 3,4-diClPh | CH$_2$ | Single bond | Sub-31 |
| 1-992 | Sub-63 | 3,4-diClPh | CH$_2$ | Single bond | Sub-32 |
| 1-993 | Sub-64 | 3,4-diClPh | CH$_2$ | Single bond | Sub-1 |
| 1-994 | Sub-64 | 3,4-diClPh | CH$_2$ | Single bond | Sub-2 |
| 1-995 | Sub-64 | 3,4-diClPh | CH$_2$ | Single bond | Sub-3 |
| 1-996 | Sub-64 | 3,4-diClPh | CH$_2$ | Single bond | Sub-4 |
| 1-997 | Sub-64 | 3,4-diClPh | CH$_2$ | Single bond | Sub-5 |
| 1-998 | Sub-64 | 3,4-diClPh | CH$_2$ | Single bond | Sub-6 |
| 1-999 | Sub-64 | 3,4-diClPh | CH$_2$ | Single bond | Sub-7 |
| 1-1000 | Sub-64 | 3,4-diClPh | CH$_2$ | Single bond | Sub-8 |
| 1-1001 | Sub-64 | 3,4-diClPh | CH$_2$ | Single bond | Sub-9 |
| 1-1002 | Sub-64 | 3,4-diClPh | CH$_2$ | Single bond | Sub-10 |
| 1-1003 | Sub-64 | 3,4-diClPh | CH$_2$ | Single bond | Sub-11 |
| 1-1004 | Sub-64 | 3,4-diClPh | CH$_2$ | Single bond | Sub-12 |
| 1-1005 | Sub-64 | 3,4-diClPh | CH$_2$ | Single bond | Sub-13 |
| 1-1006 | Sub-64 | 3,4-diClPh | CH$_2$ | Single bond | Sub-14 |
| 1-1007 | Sub-64 | 3,4-diClPh | CH$_2$ | Single bond | Sub-15 |
| 1-1008 | Sub-64 | 3,4-diClPh | CH$_2$ | Single bond | Sub-16 |
| 1-1009 | Sub-64 | 3,4-diClPh | CH$_2$ | Single bond | Sub-17 |
| 1-1010 | Sub-64 | 3,4-diClPh | CH$_2$ | Single bond | Sub-18 |
| 1-1011 | Sub-64 | 3,4-diClPh | CH$_2$ | Single bond | Sub-19 |
| 1-1012 | Sub-64 | 3,4-diClPh | CH$_2$ | Single bond | Sub-20 |
| 1-1013 | Sub-64 | 3,4-diClPh | CH$_2$ | Single bond | Sub-21 |
| 1-1014 | Sub-64 | 3,4-diClPh | CH$_2$ | Single bond | Sub-22 |
| 1-1015 | Sub-64 | 3,4-diClPh | CH$_2$ | Single bond | Sub-23 |
| 1-1016 | Sub-64 | 3,4-diClPh | CH$_2$ | Single bond | Sub-24 |
| 1-1017 | Sub-64 | 3,4-diClPh | CH$_2$ | Single bond | Sub-25 |
| 1-1018 | Sub-64 | 3,4-diClPh | CH$_2$ | Single bond | Sub-26 |
| 1-1019 | Sub-64 | 3,4-diClPh | CH$_2$ | Single bond | Sub-27 |
| 1-1020 | Sub-64 | 3,4-diClPh | CH$_2$ | Single bond | Sub-28 |
| 1-1021 | Sub-64 | 3,4-diClPh | CH$_2$ | Single bond | Sub-29 |
| 1-1022 | Sub-64 | 3,4-diClPh | CH$_2$ | Single bond | Sub-30 |
| 1-1023 | Sub-64 | 3,4-diClPh | CH$_2$ | Single bond | Sub-31 |
| 1-1024 | Sub-64 | 3,4-diClPh | CH$_2$ | Single bond | Sub-32 |
| 1-1025 | Sub-33 | 3,4-diClPh | CO | Single bond | Sub-1 |
| 1-1026 | Sub-33 | 3,4-diClPh | CO | Single bond | Sub-2 |
| 1-1027 | Sub-33 | 3,4-diClPh | CO | Single bond | Sub-3 |
| 1-1028 | Sub-33 | 3,4-diClPh | CO | Single bond | Sub-4 |
| 1-1029 | Sub-33 | 3,4-diClPh | CO | Single bond | Sub-5 |
| 1-1030 | Sub-33 | 3,4-diClPh | CO | Single bond | Sub-6 |
| 1-1031 | Sub-33 | 3,4-diClPh | CO | Single bond | Sub-7 |
| 1-1032 | Sub-33 | 3,4-diClPh | CO | Single bond | Sub-8 |
| 1-1033 | Sub-33 | 3,4-diClPh | CO | Single bond | Sub-9 |
| 1-1034 | Sub-33 | 3,4-diClPh | CO | Single bond | Sub-10 |
| 1-1035 | Sub-33 | 3,4-diClPh | CO | Single bond | Sub-11 |
| 1-1036 | Sub-33 | 3,4-diClPh | CO | Single bond | Sub-12 |
| 1-1037 | Sub-33 | 3,4-diClPh | CO | Single bond | Sub-13 |

TABLE 1-continued

| Cpd. No. | R¹ | R² | A | B | Z |
|---|---|---|---|---|---|
| 1-1038 | Sub-33 | 3,4-diClPh | CO | Single bond | Sub-14 |
| 1-1039 | Sub-33 | 3,4-diClPh | CO | Single bond | Sub-15 |
| 1-1040 | Sub-33 | 3,4-diClPh | CO | Single bond | Sub-16 |
| 1-1041 | Sub-33 | 3,4-diClPh | CO | Single bond | Sub-17 |
| 1-1042 | Sub-33 | 3,4-diClPh | CO | Single bond | Sub-18 |
| 1-1043 | Sub-33 | 3,4-diClPh | CO | Single bond | Sub-19 |
| 1-1044 | Sub-33 | 3,4-diClPh | CO | Single bond | Sub-20 |
| 1-1045 | Sub-33 | 3,4-diClPh | CO | Single bond | Sub-21 |
| 1-1046 | Sub-33 | 3,4-diClPh | CO | Single bond | Sub-22 |
| 1-1047 | Sub-33 | 3,4-diClPh | CO | Single bond | Sub-23 |
| 1-1048 | Sub-33 | 3,4-diClPh | CO | Single bond | Sub-24 |
| 1-1049 | Sub-33 | 3,4-diClPh | CO | Single bond | Sub-25 |
| 1-1050 | Sub-33 | 3,4-diClPh | CO | Single bond | Sub-26 |
| 1-1051 | Sub-33 | 3,4-diClPh | CO | Single bond | Sub-27 |
| 1-1052 | Sub-33 | 3,4-diClPh | CO | Single bond | Sub-28 |
| 1-1053 | Sub-33 | 3,4-diClPh | CO | Single bond | Sub-29 |
| 1-1054 | Sub-33 | 3,4-diClPh | CO | Single bond | Sub-30 |
| 1-1055 | Sub-33 | 3,4-diClPh | CO | Single bond | Sub-31 |
| 1-1056 | Sub-33 | 3,4-diClPh | CO | Single bond | Sub-32 |
| 1-1057 | Sub-34 | 3,4-diClPh | CO | Single bond | Sub-1 |
| 1-1058 | Sub-34 | 3,4-diClPh | CO | Single bond | Sub-2 |
| 1-1059 | Sub-34 | 3,4-diClPh | CO | Single bond | Sub-3 |
| 1-1060 | Sub-34 | 3,4-diClPh | CO | Single bond | Sub-4 |
| 1-1061 | Sub-34 | 3,4-diClPh | CO | Single bond | Sub-5 |
| 1-1062 | Sub-34 | 3,4-diClPh | CO | Single bond | Sub-6 |
| 1-1063 | Sub-34 | 3,4-diClPh | CO | Single bond | Sub-7 |
| 1-1064 | Sub-34 | 3,4-diClPh | CO | Single bond | Sub-8 |
| 1-1065 | Sub-34 | 3,4-diClPh | CO | Single bond | Sub-9 |
| 1-1066 | Sub-34 | 3,4-diClPh | CO | Single bond | Sub-10 |
| 1-1067 | Sub-34 | 3,4-diClPh | CO | Single bond | Sub-11 |
| 1-1068 | Sub-34 | 3,4-diClPh | CO | Single bond | Sub-12 |
| 1-1069 | Sub-34 | 3,4-diClPh | CO | Single bond | Sub-13 |
| 1-1070 | Sub-34 | 3,4-diClPh | CO | Single bond | Sub-14 |
| 1-1071 | Sub-34 | 3,4-diClPh | CO | Single bond | Sub-15 |
| 1-1072 | Sub-34 | 3,4-diClPh | CO | Single bond | Sub-16 |
| 1-1073 | Sub-34 | 3,4-diClPh | CO | Single bond | Sub-17 |
| 1-1074 | Sub-34 | 3,4-diClPh | CO | Single bond | Sub-18 |
| 1-1075 | Sub-34 | 3,4-diClPh | CO | Single bond | Sub-19 |
| 1-1076 | Sub-34 | 3,4-diClPh | CO | Single bond | Sub-20 |
| 1-1077 | Sub-34 | 3,4-diClPh | CO | Single bond | Sub-21 |
| 1-1078 | Sub-34 | 3,4-diClPh | CO | Single bond | Sub-22 |
| 1-1079 | Sub-34 | 3,4-diClPh | CO | Single bond | Sub-23 |
| 1-1080 | Sub-34 | 3,4-diClPh | CO | Single bond | Sub-24 |
| 1-1081 | Sub-34 | 3,4-diClPh | CO | Single bond | Sub-25 |
| 1-1082 | Sub-34 | 3,4-diClPh | CO | Single bond | Sub-26 |
| 1-1083 | Sub-34 | 3,4-diClPh | CO | Single bond | Sub-27 |
| 1-1084 | Sub-34 | 3,4-diClPh | CO | Single bond | Sub-28 |
| 1-1085 | Sub-34 | 3,4-diClPh | CO | Single bond | Sub-29 |
| 1-1086 | Sub-34 | 3,4-diClPh | CO | Single bond | Sub-30 |
| 1-1087 | Sub-34 | 3,4-diClPh | CO | Single bond | Sub-31 |
| 1-1088 | Sub-34 | 3,4-diClPh | CO | Single bond | Sub-32 |
| 1-1089 | Sub-35 | 3,4-diClPh | CO | Single bond | Sub-1 |
| 1-1090 | Sub-35 | 3,4-diClPh | CO | Single bond | Sub-2 |
| 1-1091 | Sub-35 | 3,4-diClPh | CO | Single bond | Sub-3 |
| 1-1092 | Sub-35 | 3,4-diClPh | CO | Single bond | Sub-4 |
| 1-1093 | Sub-35 | 3,4-diClPh | CO | Single bond | Sub-5 |
| 1-1094 | Sub-35 | 3,4-diClPh | CO | Single bond | Sub-6 |
| 1-1095 | Sub-35 | 3,4-diClPh | CO | Single bond | Sub-7 |
| 1-1096 | Sub-35 | 3,4-diClPh | CO | Single bond | Sub-8 |
| 1-1097 | Sub-35 | 3,4-diClPh | CO | Single bond | Sub-9 |
| 1-1098 | Sub-35 | 3,4-diClPh | CO | Single bond | Sub-10 |
| 1-1099 | Sub-35 | 3,4-diClPh | CO | Single bond | Sub-11 |
| 1-1100 | Sub-35 | 3,4-diClPh | CO | Single bond | Sub-12 |
| 1-1101 | Sub-35 | 3,4-diClPh | CO | Single bond | Sub-13 |
| 1-1102 | Sub-35 | 3,4-diClPh | CO | Single bond | Sub-14 |
| 1-1103 | Sub-35 | 3,4-diClPh | CO | Single bond | Sub-15 |
| 1-1104 | Sub-35 | 3,4-diClPh | CO | Single bond | Sub-16 |
| 1-1105 | Sub-35 | 3,4-diClPh | CO | Single bond | Sub-17 |
| 1-1106 | Sub-35 | 3,4-diClPh | CO | Single bond | Sub-18 |
| 1-1107 | Sub-35 | 3,4-diClPh | CO | Single bond | Sub-19 |
| 1-1108 | Sub-35 | 3,4-diClPh | CO | Single bond | Sub-20 |
| 1-1109 | Sub-35 | 3,4-diClPh | CO | Single bond | Sub-21 |
| 1-1110 | Sub-35 | 3,4-diClPh | CO | Single bond | Sub-22 |
| 1-1111 | Sub-35 | 3,4-diClPh | CO | Single bond | Sub-23 |
| 1-1112 | Sub-35 | 3,4-diClPh | CO | Single bond | Sub-24 |
| 1-1113 | Sub-35 | 3,4-diClPh | CO | Single bond | Sub-25 |
| 1-1114 | Sub-35 | 3,4-diClPh | CO | Single bond | Sub-26 |
| 1-1115 | Sub-35 | 3,4-diClPh | CO | Single bond | Sub-27 |
| 1-1116 | Sub-35 | 3,4-diClPh | CO | Single bond | Sub-28 |
| 1-1117 | Sub-35 | 3,4-diClPh | CO | Single bond | Sub-29 |
| 1-1118 | Sub-35 | 3,4-diClPh | CO | Single bond | Sub-30 |
| 1-1119 | Sub-35 | 3,4-diClPh | CO | Single bond | Sub-31 |
| 1-1120 | Sub-35 | 3,4-diClPh | CO | Single bond | Sub-32 |
| 1-1121 | Sub-36 | 3,4-diClPh | CO | Single bond | Sub-1 |
| 1-1122 | Sub-36 | 3,4-diClPh | CO | Single bond | Sub-2 |
| 1-1123 | Sub-36 | 3,4-diClPh | CO | Single bond | Sub-3 |
| 1-1124 | Sub-36 | 3,4-diClPh | CO | Single bond | Sub-4 |
| 1-1125 | Sub-36 | 3,4-diClPh | CO | Single bond | Sub-5 |
| 1-1126 | Sub-36 | 3,4-diClPh | CO | Single bond | Sub-6 |
| 1-1127 | Sub-36 | 3,4-diClPh | CO | Single bond | Sub-7 |
| 1-1128 | Sub-36 | 3,4-diClPh | CO | Single bond | Sub-8 |
| 1-1129 | Sub-36 | 3,4-diClPh | CO | Single bond | Sub-9 |
| 1-1130 | Sub-36 | 3,4-diClPh | CO | Single bond | Sub-10 |
| 1-1131 | Sub-36 | 3,4-diClPh | CO | Single bond | Sub-11 |
| 1-1132 | Sub-36 | 3,4-diClPh | CO | Single bond | Sub-12 |
| 1-1133 | Sub-36 | 3,4-diClPh | CO | Single bond | Sub-13 |
| 1-1134 | Sub-36 | 3,4-diClPh | CO | Single bond | Sub-14 |
| 1-1135 | Sub-36 | 3,4-diClPh | CO | Single bond | Sub-15 |
| 1-1136 | Sub-36 | 3,4-diClPh | CO | Single bond | Sub-16 |
| 1-1137 | Sub-36 | 3,4-diClPh | CO | Single bond | Sub-17 |
| 1-1138 | Sub-36 | 3,4-diClPh | CO | Single bond | Sub-18 |
| 1-1139 | Sub-36 | 3,4-diClPh | CO | Single bond | Sub-19 |
| 1-1140 | Sub-36 | 3,4-diClPh | CO | Single bond | Sub-20 |
| 1-1141 | Sub-36 | 3,4-diClPh | CO | Single bond | Sub-21 |
| 1-1142 | Sub-36 | 3,4-diClPh | CO | Single bond | Sub-22 |
| 1-1143 | Sub-36 | 3,4-diClPh | CO | Single bond | Sub-23 |
| 1-1144 | Sub-36 | 3,4-diClPh | CO | Single bond | Sub-24 |
| 1-1145 | Sub-36 | 3,4-diClPh | CO | Single bond | Sub-25 |
| 1-1146 | Sub-36 | 3,4-diClPh | CO | Single bond | Sub-26 |
| 1-1147 | Sub-36 | 3,4-diClPh | CO | Single bond | Sub-27 |
| 1-1148 | Sub-36 | 3,4-diClPh | CO | Single bond | Sub-28 |
| 1-1149 | Sub-36 | 3,4-diClPh | CO | Single bond | Sub-29 |
| 1-1150 | Sub-36 | 3,4-diClPh | CO | Single bond | Sub-30 |
| 1-1151 | Sub-36 | 3,4-diClPh | CO | Single bond | Sub-31 |
| 1-1152 | Sub-36 | 3,4-diClPh | CO | Single bond | Sub-32 |
| 1-1153 | Sub-37 | 3,4-diClPh | CO | Single bond | Sub-1 |
| 1-1154 | Sub-37 | 3,4-diClPh | CO | Single bond | Sub-2 |
| 1-1155 | Sub-37 | 3,4-diClPh | CO | Single bond | Sub-3 |
| 1-1156 | Sub-37 | 3,4-diClPh | CO | Single bond | Sub-4 |
| 1-1157 | Sub-37 | 3,4-diClPh | CO | Single bond | Sub-5 |
| 1-1158 | Sub-37 | 3,4-diClPh | CO | Single bond | Sub-6 |
| 1-1159 | Sub-37 | 3,4-diClPh | CO | Single bond | Sub-7 |
| 1-1160 | Sub-37 | 3,4-diClPh | CO | Single bond | Sub-8 |
| 1-1161 | Sub-37 | 3,4-diClPh | CO | Single bond | Sub-9 |
| 1-1162 | Sub-37 | 3,4-diClPh | CO | Single bond | Sub-10 |
| 1-1163 | Sub-37 | 3,4-diClPh | CO | Single bond | Sub-11 |
| 1-1164 | Sub-37 | 3,4-diClPh | CO | Single bond | Sub-12 |
| 1-1165 | Sub-37 | 3,4-diClPh | CO | Single bond | Sub-13 |
| 1-1166 | Sub-37 | 3,4-diClPh | CO | Single bond | Sub-14 |
| 1-1167 | Sub-37 | 3,4-diClPh | CO | Single bond | Sub-15 |
| 1-1168 | Sub-37 | 3,4-diClPh | CO | Single bond | Sub-16 |
| 1-1169 | Sub-37 | 3,4-diClPh | CO | Single bond | Sub-17 |
| 1-1170 | Sub-37 | 3,4-diClPh | CO | Single bond | Sub-18 |
| 1-1171 | Sub-37 | 3,4-diClPh | CO | Single bond | Sub-19 |
| 1-1172 | Sub-37 | 3,4-diClPh | CO | Single bond | Sub-20 |
| 1-1173 | Sub-37 | 3,4-diClPh | CO | Single bond | Sub-21 |
| 1-1174 | Sub-37 | 3,4-diClPh | CO | Single bond | Sub-22 |
| 1-1175 | Sub-37 | 3,4-diClPh | CO | Single bond | Sub-23 |
| 1-1176 | Sub-37 | 3,4-diClPh | CO | Single bond | Sub-24 |
| 1-1177 | Sub-37 | 3,4-diClPh | CO | Single bond | Sub-25 |
| 1-1178 | Sub-37 | 3,4-diClPh | CO | Single bond | Sub-26 |
| 1-1179 | Sub-37 | 3,4-diClPh | CO | Single bond | Sub-27 |
| 1-1180 | Sub-37 | 3,4-diClPh | CO | Single bond | Sub-28 |
| 1-1181 | Sub-37 | 3,4-diClPh | CO | Single bond | Sub-29 |
| 1-1182 | Sub-37 | 3,4-diClPh | CO | Single bond | Sub-30 |
| 1-1183 | Sub-37 | 3,4-diClPh | CO | Single bond | Sub-31 |
| 1-1184 | Sub-37 | 3,4-diClPh | CO | Single bond | Sub-32 |
| 1-1185 | Sub-38 | 3,4-diClPh | CO | Single bond | Sub-1 |
| 1-1186 | Sub-38 | 3,4-diClPh | CO | Single bond | Sub-2 |
| 1-1187 | Sub-38 | 3,4-diClPh | CO | Single bond | Sub-3 |
| 1-1188 | Sub-38 | 3,4-diClPh | CO | Single bond | Sub-4 |
| 1-1189 | Sub-38 | 3,4-diClPh | CO | Single bond | Sub-5 |

TABLE 1-continued

| Cpd. No. | R¹ | R² | A | B | Z |
|---|---|---|---|---|---|
| 1-1190 | Sub-38 | 3,4-diClPh | CO | Single bond | Sub-6 |
| 1-1191 | Sub-38 | 3,4-diClPh | CO | Single bond | Sub-7 |
| 1-1192 | Sub-38 | 3,4-diClPh | CO | Single bond | Sub-8 |
| 1-1193 | Sub-38 | 3,4-diClPh | CO | Single bond | Sub-9 |
| 1-1194 | Sub-38 | 3,4-diClPh | CO | Single bond | Sub-10 |
| 1-1195 | Sub-38 | 3,4-diClPh | CO | Single bond | Sub-11 |
| 1-1196 | Sub-38 | 3,4-diClPh | CO | Single bond | Sub-12 |
| 1-1197 | Sub-38 | 3,4-diClPh | CO | Single bond | Sub-13 |
| 1-1198 | Sub-38 | 3,4-diClPh | CO | Single bond | Sub-14 |
| 1-1199 | Sub-38 | 3,4-diClPh | CO | Single bond | Sub-15 |
| 1-1200 | Sub-38 | 3,4-diClPh | CO | Single bond | Sub-16 |
| 1-1201 | Sub-38 | 3,4-diClPh | CO | Single bond | Sub-17 |
| 1-1202 | Sub-38 | 3,4-diClPh | CO | Single bond | Sub-18 |
| 1-1203 | Sub-38 | 3,4-diClPh | CO | Single bond | Sub-19 |
| 1-1204 | Sub-38 | 3,4-diClPh | CO | Single bond | Sub-20 |
| 1-1205 | Sub-38 | 3,4-diClPh | CO | Single bond | Sub-21 |
| 1-1206 | Sub-38 | 3,4-diClPh | CO | Single bond | Sub-22 |
| 1-1207 | Sub-38 | 3,4-diClPh | CO | Single bond | Sub-23 |
| 1-1208 | Sub-38 | 3,4-diClPh | CO | Single bond | Sub-24 |
| 1-1209 | Sub-38 | 3,4-diClPh | CO | Single bond | Sub-25 |
| 1-1210 | Sub-38 | 3,4-diClPh | CO | Single bond | Sub-26 |
| 1-1211 | Sub-38 | 3,4-diClPh | CO | Single bond | Sub-27 |
| 1-1212 | Sub-38 | 3,4-diClPh | CO | Single bond | Sub-28 |
| 1-1213 | Sub-38 | 3,4-diClPh | CO | Single bond | Sub-29 |
| 1-1214 | Sub-38 | 3,4-diClPh | CO | Single bond | Sub-30 |
| 1-1215 | Sub-38 | 3,4-diClPh | CO | Single bond | Sub-31 |
| 1-1216 | Sub-38 | 3,4-diClPh | CO | Single bond | Sub-32 |
| 1-1217 | Sub-39 | 3,4-diClPh | CO | Single bond | Sub-1 |
| 1-1218 | Sub-39 | 3,4-diClPh | CO | Single bond | Sub-2 |
| 1-1219 | Sub-39 | 3,4-diClPh | CO | Single bond | Sub-3 |
| 1-1220 | Sub-39 | 3,4-diClPh | CO | Single bond | Sub-4 |
| 1-1221 | Sub-39 | 3,4-diClPh | CO | Single bond | Sub-5 |
| 1-1222 | Sub-39 | 3,4-diClPh | CO | Single bond | Sub-6 |
| 1-1223 | Sub-39 | 3,4-diClPh | CO | Single bond | Sub-7 |
| 1-1224 | Sub-39 | 3,4-diClPh | CO | Single bond | Sub-8 |
| 1-1225 | Sub-39 | 3,4-diClPh | CO | Single bond | Sub-9 |
| 1-1226 | Sub-39 | 3,4-diClPh | CO | Single bond | Sub-10 |
| 1-1227 | Sub-39 | 3,4-diClPh | CO | Single bond | Sub-11 |
| 1-1228 | Sub-39 | 3,4-diClPh | CO | Single bond | Sub-12 |
| 1-1229 | Sub-39 | 3,4-diClPh | CO | Single bond | Sub-13 |
| 1-1230 | Sub-39 | 3,4-diClPh | CO | Single bond | Sub-14 |
| 1-1231 | Sub-39 | 3,4-diClPh | CO | Single bond | Sub-15 |
| 1-1232 | Sub-39 | 3,4-diClPh | CO | Single bond | Sub-16 |
| 1-1233 | Sub-39 | 3,4-diClPh | CO | Single bond | Sub-17 |
| 1-1234 | Sub-39 | 3,4-diClPh | CO | Single bond | Sub-18 |
| 1-1235 | Sub-39 | 3,4-diClPh | CO | Single bond | Sub-19 |
| 1-1236 | Sub-39 | 3,4-diClPh | CO | Single bond | Sub-20 |
| 1-1237 | Sub-39 | 3,4-diClPh | CO | Single bond | Sub-21 |
| 1-1238 | Sub-39 | 3,4-diClPh | CO | Single bond | Sub-22 |
| 1-1239 | Sub-39 | 3,4-diClPh | CO | Single bond | Sub-23 |
| 1-1240 | Sub-39 | 3,4-diClPh | CO | Single bond | Sub-24 |
| 1-1241 | Sub-39 | 3,4-diClPh | CO | Single bond | Sub-25 |
| 1-1242 | Sub-39 | 3,4-diClPh | CO | Single bond | Sub-26 |
| 1-1243 | Sub-39 | 3,4-diClPh | CO | Single bond | Sub-27 |
| 1-1244 | Sub-39 | 3,4-diClPh | CO | Single bond | Sub-28 |
| 1-1245 | Sub-39 | 3,4-diClPh | CO | Single bond | Sub-29 |
| 1-1246 | Sub-39 | 3,4-diClPh | CO | Single bond | Sub-30 |
| 1-1247 | Sub-39 | 3,4-diClPh | CO | Single bond | Sub-31 |
| 1-1248 | Sub-39 | 3,4-diClPh | CO | Single bond | Sub-32 |
| 1-1249 | Sub-40 | 3,4-diClPh | CO | Single bond | Sub-1 |
| 1-1250 | Sub-40 | 3,4-diClPh | CO | Single bond | Sub-2 |
| 1-1251 | Sub-40 | 3,4-diClPh | CO | Single bond | Sub-3 |
| 1-1252 | Sub-40 | 3,4-diClPh | CO | Single bond | Sub-4 |
| 1-1253 | Sub-40 | 3,4-diClPh | CO | Single bond | Sub-5 |
| 1-1254 | Sub-40 | 3,4-diClPh | CO | Single bond | Sub-6 |
| 1-1255 | Sub-40 | 3,4-diClPh | CO | Single bond | Sub-7 |
| 1-1256 | Sub-40 | 3,4-diClPh | CO | Single bond | Sub-8 |
| 1-1257 | Sub-40 | 3,4-diClPh | CO | Single bond | Sub-9 |
| 1-1258 | Sub-40 | 3,4-diClPh | CO | Single bond | Sub-10 |
| 1-1259 | Sub-40 | 3,4-diClPh | CO | Single bond | Sub-11 |
| 1-1260 | Sub-40 | 3,4-diClPh | CO | Single bond | Sub-12 |
| 1-1261 | Sub-40 | 3,4-diClPh | CO | Single bond | Sub-13 |
| 1-1262 | Sub-40 | 3,4-diClPh | CO | Single bond | Sub-14 |
| 1-1263 | Sub-40 | 3,4-diClPh | CO | Single bond | Sub-15 |
| 1-1264 | Sub-40 | 3,4-diClPh | CO | Single bond | Sub-16 |
| 1-1265 | Sub-40 | 3,4-diClPh | CO | Single bond | Sub-17 |
| 1-1266 | Sub-40 | 3,4-diClPh | CO | Single bond | Sub-18 |
| 1-1267 | Sub-40 | 3,4-diClPh | CO | Single bond | Sub-19 |
| 1-1268 | Sub-40 | 3,4-diClPh | CO | Single bond | Sub-20 |
| 1-1269 | Sub-40 | 3,4-diClPh | CO | Single bond | Sub-21 |
| 1-1270 | Sub-40 | 3,4-diClPh | CO | Single bond | Sub-22 |
| 1-1271 | Sub-40 | 3,4-diClPh | CO | Single bond | Sub-23 |
| 1-1272 | Sub-40 | 3,4-diClPh | CO | Single bond | Sub-24 |
| 1-1273 | Sub-40 | 3,4-diClPh | CO | Single bond | Sub-25 |
| 1-1274 | Sub-40 | 3,4-diClPh | CO | Single bond | Sub-26 |
| 1-1275 | Sub-40 | 3,4-diClPh | CO | Single bond | Sub-27 |
| 1-1276 | Sub-40 | 3,4-diClPh | CO | Single bond | Sub-28 |
| 1-1277 | Sub-40 | 3,4-diClPh | CO | Single bond | Sub-29 |
| 1-1278 | Sub-40 | 3,4-diClPh | CO | Single bond | Sub-30 |
| 1-1279 | Sub-40 | 3,4-diClPh | CO | Single bond | Sub-31 |
| 1-1280 | Sub-40 | 3,4-diClPh | CO | Single bond | Sub-32 |
| 1-1281 | Sub-41 | 3,4-diClPh | CO | Single bond | Sub-1 |
| 1-1282 | Sub-41 | 3,4-diClPh | CO | Single bond | Sub-2 |
| 1-1283 | Sub-41 | 3,4-diClPh | CO | Single bond | Sub-3 |
| 1-1284 | Sub-41 | 3,4-diClPh | CO | Single bond | Sub-4 |
| 1-1285 | Sub-41 | 3,4-diClPh | CO | Single bond | Sub-5 |
| 1-1286 | Sub-41 | 3,4-diClPh | CO | Single bond | Sub-6 |
| 1-1287 | Sub-41 | 3,4-diClPh | CO | Single bond | Sub-7 |
| 1-1288 | Sub-41 | 3,4-diClPh | CO | Single bond | Sub-8 |
| 1-1289 | Sub-41 | 3,4-diClPh | CO | Single bond | Sub-9 |
| 1-1290 | Sub-41 | 3,4-diClPh | CO | Single bond | Sub-10 |
| 1-1291 | Sub-41 | 3,4-diClPh | CO | Single bond | Sub-11 |
| 1-1292 | Sub-41 | 3,4-diClPh | CO | Single bond | Sub-12 |
| 1-1293 | Sub-41 | 3,4-diClPh | CO | Single bond | Sub-13 |
| 1-1294 | Sub-41 | 3,4-diClPh | CO | Single bond | Sub-14 |
| 1-1295 | Sub-41 | 3,4-diClPh | CO | Single bond | Sub-15 |
| 1-1296 | Sub-41 | 3,4-diClPh | CO | Single bond | Sub-16 |
| 1-1297 | Sub-41 | 3,4-diClPh | CO | Single bond | Sub-17 |
| 1-1298 | Sub-41 | 3,4-diClPh | CO | Single bond | Sub-18 |
| 1-1299 | Sub-41 | 3,4-diClPh | CO | Single bond | Sub-19 |
| 1-1300 | Sub-41 | 3,4-diClPh | CO | Single bond | Sub-20 |
| 1-1301 | Sub-41 | 3,4-diClPh | CO | Single bond | Sub-21 |
| 1-1302 | Sub-41 | 3,4-diClPh | CO | Single bond | Sub-22 |
| 1-1303 | Sub-41 | 3,4-diClPh | CO | Single bond | Sub-23 |
| 1-1304 | Sub-41 | 3,4-diClPh | CO | Single bond | Sub-24 |
| 1-1305 | Sub-41 | 3,4-diClPh | CO | Single bond | Sub-25 |
| 1-1306 | Sub-41 | 3,4-diClPh | CO | Single bond | Sub-26 |
| 1-1307 | Sub-41 | 3,4-diClPh | CO | Single bond | Sub-27 |
| 1-1308 | Sub-41 | 3,4-diClPh | CO | Single bond | Sub-28 |
| 1-1309 | Sub-41 | 3,4-diClPh | CO | Single bond | Sub-29 |
| 1-1310 | Sub-41 | 3,4-diClPh | CO | Single bond | Sub-30 |
| 1-1311 | Sub-41 | 3,4-diClPh | CO | Single bond | Sub-31 |
| 1-1312 | Sub-41 | 3,4-diClPh | CO | Single bond | Sub-32 |
| 1-1313 | Sub-42 | 3,4-diClPh | CO | Single bond | Sub-1 |
| 1-1314 | Sub-42 | 3,4-diClPh | CO | Single bond | Sub-2 |
| 1-1315 | Sub-42 | 3,4-diClPh | CO | Single bond | Sub-3 |
| 1-1316 | Sub-42 | 3,4-diClPh | CO | Single bond | Sub-4 |
| 1-1317 | Sub-42 | 3,4-diClPh | CO | Single bond | Sub-5 |
| 1-1318 | Sub-42 | 3,4-diClPh | CO | Single bond | Sub-6 |
| 1-1319 | Sub-42 | 3,4-diClPh | CO | Single bond | Sub-7 |
| 1-1320 | Sub-42 | 3,4-diClPh | CO | Single bond | Sub-8 |
| 1-1321 | Sub-42 | 3,4-diClPh | CO | Single bond | Sub-9 |
| 1-1322 | Sub-42 | 3,4-diClPh | CO | Single bond | Sub-10 |
| 1-1323 | Sub-42 | 3,4-diClPh | CO | Single bond | Sub-11 |
| 1-1324 | Sub-42 | 3,4-diClPh | CO | Single bond | Sub-12 |
| 1-1325 | Sub-42 | 3,4-diClPh | CO | Single bond | Sub-13 |
| 1-1326 | Sub-42 | 3,4-diClPh | CO | Single bond | Sub-14 |
| 1-1327 | Sub-42 | 3,4-diClPh | CO | Single bond | Sub-15 |
| 1-1328 | Sub-42 | 3,4-diClPh | CO | Single bond | Sub-16 |
| 1-1329 | Sub-42 | 3,4-diClPh | CO | Single bond | Sub-17 |
| 1-1330 | Sub-42 | 3,4-diClPh | CO | Single bond | Sub-18 |
| 1-1331 | Sub-42 | 3,4-diClPh | CO | Single bond | Sub-19 |
| 1-1332 | Sub-42 | 3,4-diClPh | CO | Single bond | Sub-20 |
| 1-1333 | Sub-42 | 3,4-diClPh | CO | Single bond | Sub-21 |
| 1-1334 | Sub-42 | 3,4-diClPh | CO | Single bond | Sub-22 |
| 1-1335 | Sub-42 | 3,4-diClPh | CO | Single bond | Sub-23 |
| 1-1336 | Sub-42 | 3,4-diClPh | CO | Single bond | Sub-24 |
| 1-1337 | Sub-42 | 3,4-diClPh | CO | Single bond | Sub-25 |
| 1-1338 | Sub-42 | 3,4-diClPh | CO | Single bond | Sub-26 |
| 1-1339 | Sub-42 | 3,4-diClPh | CO | Single bond | Sub-27 |
| 1-1340 | Sub-42 | 3,4-diClPh | CO | Single bond | Sub-28 |
| 1-1341 | Sub-42 | 3,4-diClPh | CO | Single bond | Sub-29 |

TABLE 1-continued

| Cpd. No. | R¹ | R² | A | B | Z |
|---|---|---|---|---|---|
| 1-1342 | Sub-42 | 3,4-diClPh | CO | Single bond | Sub-30 |
| 1-1343 | Sub-42 | 3,4-diClPh | CO | Single bond | Sub-31 |
| 1-1344 | Sub-42 | 3,4-diClPh | CO | Single bond | Sub-32 |
| 1-1345 | Sub-43 | 3,4-diClPh | CO | Single bond | Sub-1 |
| 1-1346 | Sub-43 | 3,4-diClPh | CO | Single bond | Sub-2 |
| 1-1347 | Sub-43 | 3,4-diClPh | CO | Single bond | Sub-3 |
| 1-1348 | Sub-43 | 3,4-diClPh | CO | Single bond | Sub-4 |
| 1-1349 | Sub-43 | 3,4-diClPh | CO | Single bond | Sub-5 |
| 1-1350 | Sub-43 | 3,4-diClPh | CO | Single bond | Sub-6 |
| 1-1351 | Sub-43 | 3,4-diClPh | CO | Single bond | Sub-7 |
| 1-1352 | Sub-43 | 3,4-diClPh | CO | Single bond | Sub-8 |
| 1-1353 | Sub-43 | 3,4-diClPh | CO | Single bond | Sub-9 |
| 1-1354 | Sub-43 | 3,4-diClPh | CO | Single bond | Sub-10 |
| 1-1355 | Sub-43 | 3,4-diClPh | CO | Single bond | Sub-11 |
| 1-1356 | Sub-43 | 3,4-diClPh | CO | Single bond | Sub-12 |
| 1-1357 | Sub-43 | 3,4-diClPh | CO | Single bond | Sub-13 |
| 1-1358 | Sub-43 | 3,4-diClPh | CO | Single bond | Sub-14 |
| 1-1359 | Sub-43 | 3,4-diClPh | CO | Single bond | Sub-15 |
| 1-1360 | Sub-43 | 3,4-diClPh | CO | Single bond | Sub-16 |
| 1-1361 | Sub-43 | 3,4-diClPh | CO | Single bond | Sub-17 |
| 1-1362 | Sub-43 | 3,4-diClPh | CO | Single bond | Sub-18 |
| 1-1363 | Sub-43 | 3,4-diClPh | CO | Single bond | Sub-19 |
| 1-1364 | Sub-43 | 3,4-diClPh | CO | Single bond | Sub-20 |
| 1-1365 | Sub-43 | 3,4-diClPh | CO | Single bond | Sub-21 |
| 1-1366 | Sub-43 | 3,4-diClPh | CO | Single bond | Sub-22 |
| 1-1367 | Sub-43 | 3,4-diClPh | CO | Single bond | Sub-23 |
| 1-1368 | Sub-43 | 3,4-diClPh | CO | Single bond | Sub-24 |
| 1-1369 | Sub-43 | 3,4-diClPh | CO | Single bond | Sub-25 |
| 1-1370 | Sub-43 | 3,4-diClPh | CO | Single bond | Sub-26 |
| 1-1371 | Sub-43 | 3,4-diClPh | CO | Single bond | Sub-27 |
| 1-1372 | Sub-43 | 3,4-diClPh | CO | Single bond | Sub-28 |
| 1-1373 | Sub-43 | 3,4-diClPh | CO | Single bond | Sub-29 |
| 1-1374 | Sub-43 | 3,4-diClPh | CO | Single bond | Sub-30 |
| 1-1375 | Sub-43 | 3,4-diClPh | CO | Single bond | Sub-31 |
| 1-1376 | Sub-43 | 3,4-diClPh | CO | Single bond | Sub-32 |
| 1-1377 | Sub-44 | 3,4-diClPh | CO | Single bond | Sub-1 |
| 1-1378 | Sub-44 | 3,4-diClPh | CO | Single bond | Sub-2 |
| 1-1379 | Sub-44 | 3,4-diClPh | CO | Single bond | Sub-3 |
| 1-1380 | Sub-44 | 3,4-diClPh | CO | Single bond | Sub-4 |
| 1-1381 | Sub-44 | 3,4-diClPh | CO | Single bond | Sub-5 |
| 1-1382 | Sub-44 | 3,4-diClPh | CO | Single bond | Sub-6 |
| 1-1383 | Sub-44 | 3,4-diClPh | CO | Single bond | Sub-7 |
| 1-1384 | Sub-44 | 3,4-diClPh | CO | Single bond | Sub-8 |
| 1-1385 | Sub-44 | 3,4-diClPh | CO | Single bond | Sub-9 |
| 1-1386 | Sub-44 | 3,4-diClPh | CO | Single bond | Sub-10 |
| 1-1387 | Sub-44 | 3,4-diClPh | CO | Single bond | Sub-11 |
| 1-1388 | Sub-44 | 3,4-diClPh | CO | Single bond | Sub-12 |
| 1-1389 | Sub-44 | 3,4-diClPh | CO | Single bond | Sub-13 |
| 1-1390 | Sub-44 | 3,4-diClPh | CO | Single bond | Sub-14 |
| 1-1391 | Sub-44 | 3,4-diClPh | CO | Single bond | Sub-15 |
| 1-1392 | Sub-44 | 3,4-diClPh | CO | Single bond | Sub-16 |
| 1-1393 | Sub-44 | 3,4-diClPh | CO | Single bond | Sub-17 |
| 1-1394 | Sub-44 | 3,4-diClPh | CO | Single bond | Sub-18 |
| 1-1395 | Sub-44 | 3,4-diClPh | CO | Single bond | Sub-19 |
| 1-1396 | Sub-44 | 3,4-diClPh | CO | Single bond | Sub-20 |
| 1-1397 | Sub-44 | 3,4-diClPh | CO | Single bond | Sub-21 |
| 1-1398 | Sub-44 | 3,4-diClPh | CO | Single bond | Sub-22 |
| 1-1399 | Sub-44 | 3,4-diClPh | CO | Single bond | Sub-23 |
| 1-1400 | Sub-44 | 3,4-diClPh | CO | Single bond | Sub-24 |
| 1-1401 | Sub-44 | 3,4-diClPh | CO | Single bond | Sub-25 |
| 1-1402 | Sub-44 | 3,4-diClPh | CO | Single bond | Sub-26 |
| 1-1403 | Sub-44 | 3,4-diClPh | CO | Single bond | Sub-27 |
| 1-1404 | Sub-44 | 3,4-diClPh | CO | Single bond | Sub-28 |
| 1-1405 | Sub-44 | 3,4-diClPh | CO | Single bond | Sub-29 |
| 1-1406 | Sub-44 | 3,4-diClPh | CO | Single bond | Sub-30 |
| 1-1407 | Sub-44 | 3,4-diClPh | CO | Single bond | Sub-31 |
| 1-1408 | Sub-44 | 3,4-diClPh | CO | Single bond | Sub-32 |
| 1-1409 | Sub-45 | 3,4-diClPh | CO | Single bond | Sub-1 |
| 1-1410 | Sub-45 | 3,4-diClPh | CO | Single bond | Sub-2 |
| 1-1411 | Sub-45 | 3,4-diClPh | CO | Single bond | Sub-3 |
| 1-1412 | Sub-45 | 3,4-diClPh | CO | Single bond | Sub-4 |
| 1-1413 | Sub-45 | 3,4-diClPh | CO | Single bond | Sub-5 |
| 1-1414 | Sub-45 | 3,4-diClPh | CO | Single bond | Sub-6 |
| 1-1415 | Sub-45 | 3,4-diClPh | CO | Single bond | Sub-7 |
| 1-1416 | Sub-45 | 3,4-diClPh | CO | Single bond | Sub-8 |
| 1-1417 | Sub-45 | 3,4-diClPh | CO | Single bond | Sub-9 |
| 1-1418 | Sub-45 | 3,4-diClPh | CO | Single bond | Sub-10 |
| 1-1419 | Sub-45 | 3,4-diClPh | CO | Single bond | Sub-11 |
| 1-1420 | Sub-45 | 3,4-diClPh | CO | Single bond | Sub-12 |
| 1-1421 | Sub-45 | 3,4-diClPh | CO | Single bond | Sub-13 |
| 1-1422 | Sub-45 | 3,4-diClPh | CO | Single bond | Sub-14 |
| 1-1423 | Sub-45 | 3,4-diClPh | CO | Single bond | Sub-15 |
| 1-1424 | Sub-45 | 3,4-diClPh | CO | Single bond | Sub-16 |
| 1-1425 | Sub-45 | 3,4-diClPh | CO | Single bond | Sub-17 |
| 1-1426 | Sub-45 | 3,4-diClPh | CO | Single bond | Sub-18 |
| 1-1427 | Sub-45 | 3,4-diClPh | CO | Single bond | Sub-19 |
| 1-1428 | Sub-45 | 3,4-diClPh | CO | Single bond | Sub-20 |
| 1-1429 | Sub-45 | 3,4-diClPh | CO | Single bond | Sub-21 |
| 1-1430 | Sub-45 | 3,4-diClPh | CO | Single bond | Sub-22 |
| 1-1431 | Sub-45 | 3,4-diClPh | CO | Single bond | Sub-23 |
| 1-1432 | Sub-45 | 3,4-diClPh | CO | Single bond | Sub-24 |
| 1-1433 | Sub-45 | 3,4-diClPh | CO | Single bond | Sub-25 |
| 1-1434 | Sub-45 | 3,4-diClPh | CO | Single bond | Sub-26 |
| 1-1435 | Sub-45 | 3,4-diClPh | CO | Single bond | Sub-27 |
| 1-1436 | Sub-45 | 3,4-diClPh | CO | Single bond | Sub-28 |
| 1-1437 | Sub-45 | 3,4-diClPh | CO | Single bond | Sub-29 |
| 1-1438 | Sub-45 | 3,4-diClPh | CO | Single bond | Sub-30 |
| 1-1439 | Sub-45 | 3,4-diClPh | CO | Single bond | Sub-31 |
| 1-1440 | Sub-45 | 3,4-diClPh | CO | Single bond | Sub-32 |
| 1-1441 | Sub-46 | 3,4-diClPh | CO | Single bond | Sub-1 |
| 1-1442 | Sub-46 | 3,4-diClPh | CO | Single bond | Sub-2 |
| 1-1443 | Sub-46 | 3,4-diClPh | CO | Single bond | Sub-3 |
| 1-1444 | Sub-46 | 3,4-diClPh | CO | Single bond | Sub-4 |
| 1-1445 | Sub-46 | 3,4-diClPh | CO | Single bond | Sub-5 |
| 1-1446 | Sub-46 | 3,4-diClPh | CO | Single bond | Sub-6 |
| 1-1447 | Sub-46 | 3,4-diClPh | CO | Single bond | Sub-7 |
| 1-1448 | Sub-46 | 3,4-diClPh | CO | Single bond | Sub-8 |
| 1-1449 | Sub-46 | 3,4-diClPh | CO | Single bond | Sub-9 |
| 1-1450 | Sub-46 | 3,4-diClPh | CO | Single bond | Sub-10 |
| 1-1451 | Sub-46 | 3,4-diClPh | CO | Single bond | Sub-11 |
| 1-1452 | Sub-46 | 3,4-diClPh | CO | Single bond | Sub-12 |
| 1-1453 | Sub-46 | 3,4-diClPh | CO | Single bond | Sub-13 |
| 1-1454 | Sub-46 | 3,4-diClPh | CO | Single bond | Sub-14 |
| 1-1455 | Sub-46 | 3,4-diClPh | CO | Single bond | Sub-15 |
| 1-1456 | Sub-46 | 3,4-diClPh | CO | Single bond | Sub-16 |
| 1-1457 | Sub-46 | 3,4-diClPh | CO | Single bond | Sub-17 |
| 1-1458 | Sub-46 | 3,4-diClPh | CO | Single bond | Sub-18 |
| 1-1459 | Sub-46 | 3,4-diClPh | CO | Single bond | Sub-19 |
| 1-1460 | Sub-46 | 3,4-diClPh | CO | Single bond | Sub-20 |
| 1-1461 | Sub-46 | 3,4-diClPh | CO | Single bond | Sub-21 |
| 1-1462 | Sub-46 | 3,4-diClPh | CO | Single bond | Sub-22 |
| 1-1463 | Sub-46 | 3,4-diClPh | CO | Single bond | Sub-23 |
| 1-1464 | Sub-46 | 3,4-diClPh | CO | Single bond | Sub-24 |
| 1-1465 | Sub-46 | 3,4-diClPh | CO | Single bond | Sub-25 |
| 1-1466 | Sub-46 | 3,4-diClPh | CO | Single bond | Sub-26 |
| 1-1467 | Sub-46 | 3,4-diClPh | CO | Single bond | Sub-27 |
| 1-1468 | Sub-46 | 3,4-diClPh | CO | Single bond | Sub-28 |
| 1-1469 | Sub-46 | 3,4-diClPh | CO | Single bond | Sub-29 |
| 1-1470 | Sub-46 | 3,4-diClPh | CO | Single bond | Sub-30 |
| 1-1471 | Sub-46 | 3,4-diClPh | CO | Single bond | Sub-31 |
| 1-1472 | Sub-46 | 3,4-diClPh | CO | Single bond | Sub-32 |
| 1-1473 | Sub-47 | 3,4-diClPh | CO | Single bond | Sub-1 |
| 1-1474 | Sub-47 | 3,4-diClPh | CO | Single bond | Sub-2 |
| 1-1475 | Sub-47 | 3,4-diClPh | CO | Single bond | Sub-3 |
| 1-1476 | Sub-47 | 3,4-diClPh | CO | Single bond | Sub-4 |
| 1-1477 | Sub-47 | 3,4-diClPh | CO | Single bond | Sub-5 |
| 1-1478 | Sub-47 | 3,4-diClPh | CO | Single bond | Sub-6 |
| 1-1479 | Sub-47 | 3,4-diClPh | CO | Single bond | Sub-7 |
| 1-1480 | Sub-47 | 3,4-diClPh | CO | Single bond | Sub-8 |
| 1-1481 | Sub-47 | 3,4-diClPh | CO | Single bond | Sub-9 |
| 1-1482 | Sub-47 | 3,4-diClPh | CO | Single bond | Sub-10 |
| 1-1483 | Sub-47 | 3,4-diClPh | CO | Single bond | Sub-11 |
| 1-1484 | Sub-47 | 3,4-diClPh | CO | Single bond | Sub-12 |
| 1-1485 | Sub-47 | 3,4-diClPh | CO | Single bond | Sub-13 |
| 1-1486 | Sub-47 | 3,4-diClPh | CO | Single bond | Sub-14 |
| 1-1487 | Sub-47 | 3,4-diClPh | CO | Single bond | Sub-15 |
| 1-1488 | Sub-47 | 3,4-diClPh | CO | Single bond | Sub-16 |
| 1-1489 | Sub-47 | 3,4-diClPh | CO | Single bond | Sub-17 |
| 1-1490 | Sub-47 | 3,4-diClPh | CO | Single bond | Sub-18 |
| 1-1491 | Sub-47 | 3,4-diClPh | CO | Single bond | Sub-19 |
| 1-1492 | Sub-47 | 3,4-diClPh | CO | Single bond | Sub-20 |
| 1-1493 | Sub-47 | 3,4-diClPh | CO | Single bond | Sub-21 |

TABLE 1-continued

| Cpd. No. | R¹ | R² | A | B | Z |
|---|---|---|---|---|---|
| 1-1494 | Sub-47 | 3,4-diClPh | CO | Single bond | Sub-22 |
| 1-1495 | Sub-47 | 3,4-diClPh | CO | Single bond | Sub-23 |
| 1-1496 | Sub-47 | 3,4-diClPh | CO | Single bond | Sub-24 |
| 1-1497 | Sub-47 | 3,4-diClPh | CO | Single bond | Sub-25 |
| 1-1498 | Sub-47 | 3,4-diClPh | CO | Single bond | Sub-26 |
| 1-1499 | Sub-47 | 3,4-diClPh | CO | Single bond | Sub-27 |
| 1-1500 | Sub-47 | 3,4-diClPh | CO | Single bond | Sub-28 |
| 1-1501 | Sub-47 | 3,4-diClPh | CO | Single bond | Sub-29 |
| 1-1502 | Sub-47 | 3,4-diClPh | CO | Single bond | Sub-30 |
| 1-1503 | Sub-47 | 3,4-diClPh | CO | Single bond | Sub-31 |
| 1-1504 | Sub-47 | 3,4-diClPh | CO | Single bond | Sub-32 |
| 1-1505 | Sub-48 | 3,4-diClPh | CO | Single bond | Sub-1 |
| 1-1506 | Sub-48 | 3,4-diClPh | CO | Single bond | Sub-2 |
| 1-1507 | Sub-48 | 3,4-diClPh | CO | Single bond | Sub-3 |
| 1-1508 | Sub-48 | 3,4-diClPh | CO | Single bond | Sub-4 |
| 1-1509 | Sub-48 | 3,4-diClPh | CO | Single bond | Sub-5 |
| 1-1510 | Sub-48 | 3,4-diClPh | CO | Single bond | Sub-6 |
| 1-1511 | Sub-48 | 3,4-diClPh | CO | Single bond | Sub-7 |
| 1-1512 | Sub-48 | 3,4-diClPh | CO | Single bond | Sub-8 |
| 1-1513 | Sub-48 | 3,4-diClPh | CO | Single bond | Sub-9 |
| 1-1514 | Sub-48 | 3,4-diClPh | CO | Single bond | Sub-10 |
| 1-1515 | Sub-48 | 3,4-diClPh | CO | Single bond | Sub-11 |
| 1-1516 | Sub-48 | 3,4-diClPh | CO | Single bond | Sub-12 |
| 1-1517 | Sub-48 | 3,4-diClPh | CO | Single bond | Sub-13 |
| 1-1518 | Sub-48 | 3,4-diClPh | CO | Single bond | Sub-14 |
| 1-1519 | Sub-48 | 3,4-diClPh | CO | Single bond | Sub-15 |
| 1-1520 | Sub-48 | 3,4-diClPh | CO | Single bond | Sub-16 |
| 1-1521 | Sub-48 | 3,4-diClPh | CO | Single bond | Sub-17 |
| 1-1522 | Sub-48 | 3,4-diClPh | CO | Single bond | Sub-18 |
| 1-1523 | Sub-48 | 3,4-diClPh | CO | Single bond | Sub-19 |
| 1-1524 | Sub-48 | 3,4-diClPh | CO | Single bond | Sub-20 |
| 1-1525 | Sub-48 | 3,4-diClPh | CO | Single bond | Sub-21 |
| 1-1526 | Sub-48 | 3,4-diClPh | CO | Single bond | Sub-22 |
| 1-1527 | Sub-48 | 3,4-diClPh | CO | Single bond | Sub-23 |
| 1-1528 | Sub-48 | 3,4-diClPh | CO | Single bond | Sub-24 |
| 1-1529 | Sub-48 | 3,4-diClPh | CO | Single bond | Sub-25 |
| 1-1530 | Sub-48 | 3,4-diClPh | CO | Single bond | Sub-26 |
| 1-1531 | Sub-48 | 3,4-diClPh | CO | Single bond | Sub-27 |
| 1-1532 | Sub-48 | 3,4-diClPh | CO | Single bond | Sub-28 |
| 1-1533 | Sub-48 | 3,4-diClPh | CO | Single bond | Sub-29 |
| 1-1534 | Sub-48 | 3,4-diClPh | CO | Single bond | Sub-30 |
| 1-1535 | Sub-48 | 3,4-diClPh | CO | Single bond | Sub-31 |
| 1-1536 | Sub-48 | 3,4-diClPh | CO | Single bond | Sub-32 |
| 1-1537 | Sub-49 | 3,4-diClPh | CO | Single bond | Sub-1 |
| 1-1538 | Sub-49 | 3,4-diClPh | CO | Single bond | Sub-2 |
| 1-1539 | Sub-49 | 3,4-diClPh | CO | Single bond | Sub-3 |
| 1-1540 | Sub-49 | 3,4-diClPh | CO | Single bond | Sub-4 |
| 1-1541 | Sub-49 | 3,4-diClPh | CO | Single bond | Sub-5 |
| 1-1542 | Sub-49 | 3,4-diClPh | CO | Single bond | Sub-6 |
| 1-1543 | Sub-49 | 3,4-diClPh | CO | Single bond | Sub-7 |
| 1-1544 | Sub-49 | 3,4-diClPh | CO | Single bond | Sub-8 |
| 1-1545 | Sub-49 | 3,4-diClPh | CO | Single bond | Sub-9 |
| 1-1546 | Sub-49 | 3,4-diClPh | CO | Single bond | Sub-10 |
| 1-1547 | Sub-49 | 3,4-diClPh | CO | Single bond | Sub-11 |
| 1-1548 | Sub-49 | 3,4-diClPh | CO | Single bond | Sub-12 |
| 1-1549 | Sub-49 | 3,4-diClPh | CO | Single bond | Sub-13 |
| 1-1550 | Sub-49 | 3,4-diClPh | CO | Single bond | Sub-14 |
| 1-1551 | Sub-49 | 3,4-diClPh | CO | Single bond | Sub-15 |
| 1-1552 | Sub-49 | 3,4-diClPh | CO | Single bond | Sub-16 |
| 1-1553 | Sub-49 | 3,4-diClPh | CO | Single bond | Sub-17 |
| 1-1554 | Sub-49 | 3,4-diClPh | CO | Single bond | Sub-18 |
| 1-1555 | Sub-49 | 3,4-diClPh | CO | Single bond | Sub-19 |
| 1-1556 | Sub-49 | 3,4-diClPh | CO | Single bond | Sub-20 |
| 1-1557 | Sub-49 | 3,4-diClPh | CO | Single bond | Sub-21 |
| 1-1558 | Sub-49 | 3,4-diClPh | CO | Single bond | Sub-22 |
| 1-1559 | Sub-49 | 3,4-diClPh | CO | Single bond | Sub-23 |
| 1-1560 | Sub-49 | 3,4-diClPh | CO | Single bond | Sub-24 |
| 1-1561 | Sub-49 | 3,4-diClPh | CO | Single bond | Sub-25 |
| 1-1562 | Sub-49 | 3,4-diClPh | CO | Single bond | Sub-26 |
| 1-1563 | Sub-49 | 3,4-diClPh | CO | Single bond | Sub-27 |
| 1-1564 | Sub-49 | 3,4-diClPh | CO | Single bond | Sub-28 |
| 1-1565 | Sub-49 | 3,4-diClPh | CO | Single bond | Sub-29 |
| 1-1566 | Sub-49 | 3,4-diClPh | CO | Single bond | Sub-30 |
| 1-1567 | Sub-49 | 3,4-diClPh | CO | Single bond | Sub-31 |
| 1-1568 | Sub-49 | 3,4-diClPh | CO | Single bond | Sub-32 |
| 1-1569 | Sub-50 | 3,4-diClPh | CO | Single bond | Sub-1 |
| 1-1570 | Sub-50 | 3,4-diClPh | CO | Single bond | Sub-2 |
| 1-1571 | Sub-50 | 3,4-diClPh | CO | Single bond | Sub-3 |
| 1-1572 | Sub-50 | 3,4-diClPh | CO | Single bond | Sub-4 |
| 1-1573 | Sub-50 | 3,4-diClPh | CO | Single bond | Sub-5 |
| 1-1574 | Sub-50 | 3,4-diClPh | CO | Single bond | Sub-6 |
| 1-1575 | Sub-50 | 3,4-diClPh | CO | Single bond | Sub-7 |
| 1-1576 | Sub-50 | 3,4-diClPh | CO | Single bond | Sub-8 |
| 1-1577 | Sub-50 | 3,4-diClPh | CO | Single bond | Sub-9 |
| 1-1578 | Sub-50 | 3,4-diClPh | CO | Single bond | Sub-10 |
| 1-1579 | Sub-50 | 3,4-diClPh | CO | Single bond | Sub-11 |
| 1-1580 | Sub-50 | 3,4-diClPh | CO | Single bond | Sub-12 |
| 1-1581 | Sub-50 | 3,4-diClPh | CO | Single bond | Sub-13 |
| 1-1582 | Sub-50 | 3,4-diClPh | CO | Single bond | Sub-14 |
| 1-1583 | Sub-50 | 3,4-diClPh | CO | Single bond | Sub-15 |
| 1-1584 | Sub-50 | 3,4-diClPh | CO | Single bond | Sub-16 |
| 1-1585 | Sub-50 | 3,4-diClPh | CO | Single bond | Sub-17 |
| 1-1586 | Sub-50 | 3,4-diClPh | CO | Single bond | Sub-18 |
| 1-1587 | Sub-50 | 3,4-diClPh | CO | Single bond | Sub-19 |
| 1-1588 | Sub-50 | 3,4-diClPh | CO | Single bond | Sub-20 |
| 1-1589 | Sub-50 | 3,4-diClPh | CO | Single bond | Sub-21 |
| 1-1590 | Sub-50 | 3,4-diClPh | CO | Single bond | Sub-22 |
| 1-1591 | Sub-50 | 3,4-diClPh | CO | Single bond | Sub-23 |
| 1-1592 | Sub-50 | 3,4-diClPh | CO | Single bond | Sub-24 |
| 1-1593 | Sub-50 | 3,4-diClPh | CO | Single bond | Sub-25 |
| 1-1594 | Sub-50 | 3,4-diClPh | CO | Single bond | Sub-26 |
| 1-1595 | Sub-50 | 3,4-diClPh | CO | Single bond | Sub-27 |
| 1-1596 | Sub-50 | 3,4-diClPh | CO | Single bond | Sub-28 |
| 1-1597 | Sub-50 | 3,4-diClPh | CO | Single bond | Sub-29 |
| 1-1598 | Sub-50 | 3,4-diClPh | CO | Single bond | Sub-30 |
| 1-1599 | Sub-50 | 3,4-diClPh | CO | Single bond | Sub-31 |
| 1-1600 | Sub-50 | 3,4-diClPh | CO | Single bond | Sub-32 |
| 1-1601 | Sub-51 | 3,4-diClPh | CO | Single bond | Sub-1 |
| 1-1602 | Sub-51 | 3,4-diClPh | CO | Single bond | Sub-2 |
| 1-1603 | Sub-51 | 3,4-diClPh | CO | Single bond | Sub-3 |
| 1-1604 | Sub-51 | 3,4-diClPh | CO | Single bond | Sub-4 |
| 1-1605 | Sub-51 | 3,4-diClPh | CO | Single bond | Sub-5 |
| 1-1606 | Sub-51 | 3,4-diClPh | CO | Single bond | Sub-6 |
| 1-1607 | Sub-51 | 3,4-diClPh | CO | Single bond | Sub-7 |
| 1-1608 | Sub-51 | 3,4-diClPh | CO | Single bond | Sub-8 |
| 1-1609 | Sub-51 | 3,4-diClPh | CO | Single bond | Sub-9 |
| 1-1610 | Sub-51 | 3,4-diClPh | CO | Single bond | Sub-10 |
| 1-1611 | Sub-51 | 3,4-diClPh | CO | Single bond | Sub-11 |
| 1-1612 | Sub-51 | 3,4-diClPh | CO | Single bond | Sub-12 |
| 1-1613 | Sub-51 | 3,4-diClPh | CO | Single bond | Sub-13 |
| 1-1614 | Sub-51 | 3,4-diClPh | CO | Single bond | Sub-14 |
| 1-1615 | Sub-51 | 3,4-diClPh | CO | Single bond | Sub-15 |
| 1-1616 | Sub-51 | 3,4-diClPh | CO | Single bond | Sub-16 |
| 1-1617 | Sub-51 | 3,4-diClPh | CO | Single bond | Sub-17 |
| 1-1618 | Sub-51 | 3,4-diClPh | CO | Single bond | Sub-18 |
| 1-1619 | Sub-51 | 3,4-diClPh | CO | Single bond | Sub-19 |
| 1-1620 | Sub-51 | 3,4-diClPh | CO | Single bond | Sub-20 |
| 1-1621 | Sub-51 | 3,4-diClPh | CO | Single bond | Sub-21 |
| 1-1622 | Sub-51 | 3,4-diClPh | CO | Single bond | Sub-22 |
| 1-1623 | Sub-51 | 3,4-diClPh | CO | Single bond | Sub-23 |
| 1-1624 | Sub-51 | 3,4-diClPh | CO | Single bond | Sub-24 |
| 1-1625 | Sub-51 | 3,4-diClPh | CO | Single bond | Sub-25 |
| 1-1626 | Sub-51 | 3,4-diClPh | CO | Single bond | Sub-26 |
| 1-1627 | Sub-51 | 3,4-diClPh | CO | Single bond | Sub-27 |
| 1-1628 | Sub-51 | 3,4-diClPh | CO | Single bond | Sub-28 |
| 1-1629 | Sub-51 | 3,4-diClPh | CO | Single bond | Sub-29 |
| 1-1630 | Sub-51 | 3,4-diClPh | CO | Single bond | Sub-30 |
| 1-1631 | Sub-51 | 3,4-diClPh | CO | Single bond | Sub-31 |
| 1-1632 | Sub-51 | 3,4-diClPh | CO | Single bond | Sub-32 |
| 1-1633 | Sub-52 | 3,4-diClPh | CO | Single bond | Sub-1 |
| 1-1634 | Sub-52 | 3,4-diClPh | CO | Single bond | Sub-2 |
| 1-1635 | Sub-52 | 3,4-diClPh | CO | Single bond | Sub-3 |
| 1-1636 | Sub-52 | 3,4-diClPh | CO | Single bond | Sub-4 |
| 1-1637 | Sub-52 | 3,4-diClPh | CO | Single bond | Sub-5 |
| 1-1638 | Sub-52 | 3,4-diClPh | CO | Single bond | Sub-6 |
| 1-1639 | Sub-52 | 3,4-diClPh | CO | Single bond | Sub-7 |
| 1-1640 | Sub-52 | 3,4-diClPh | CO | Single bond | Sub-8 |
| 1-1641 | Sub-52 | 3,4-diClPh | CO | Single bond | Sub-9 |
| 1-1642 | Sub-52 | 3,4-diClPh | CO | Single bond | Sub-10 |
| 1-1643 | Sub-52 | 3,4-diClPh | CO | Single bond | Sub-11 |
| 1-1644 | Sub-52 | 3,4-diClPh | CO | Single bond | Sub-12 |
| 1-1645 | Sub-52 | 3,4-diClPh | CO | Single bond | Sub-13 |

TABLE 1-continued

| Cpd. No. | R¹ | R² | A | B | Z |
|---|---|---|---|---|---|
| 1-1646 | Sub-52 | 3,4-diClPh | CO | Single bond | Sub-14 |
| 1-1647 | Sub-52 | 3,4-diClPh | CO | Single bond | Sub-15 |
| 1-1648 | Sub-52 | 3,4-diClPh | CO | Single bond | Sub-16 |
| 1-1649 | Sub-52 | 3,4-diClPh | CO | Single bond | Sub-17 |
| 1-1650 | Sub-52 | 3,4-diClPh | CO | Single bond | Sub-18 |
| 1-1651 | Sub-52 | 3,4-diClPh | CO | Single bond | Sub-19 |
| 1-1652 | Sub-52 | 3,4-diClPh | CO | Single bond | Sub-20 |
| 1-1653 | Sub-52 | 3,4-diClPh | CO | Single bond | Sub-21 |
| 1-1654 | Sub-52 | 3,4-diClPh | CO | Single bond | Sub-22 |
| 1-1655 | Sub-52 | 3,4-diClPh | CO | Single bond | Sub-23 |
| 1-1656 | Sub-52 | 3,4-diClPh | CO | Single bond | Sub-24 |
| 1-1657 | Sub-52 | 3,4-diClPh | CO | Single bond | Sub-25 |
| 1-1658 | Sub-52 | 3,4-diClPh | CO | Single bond | Sub-26 |
| 1-1659 | Sub-52 | 3,4-diClPh | CO | Single bond | Sub-27 |
| 1-1660 | Sub-52 | 3,4-diClPh | CO | Single bond | Sub-28 |
| 1-1661 | Sub-52 | 3,4-diClPh | CO | Single bond | Sub-29 |
| 1-1662 | Sub-52 | 3,4-diClPh | CO | Single bond | Sub-30 |
| 1-1663 | Sub-52 | 3,4-diClPh | CO | Single bond | Sub-31 |
| 1-1664 | Sub-52 | 3,4-diClPh | CO | Single bond | Sub-32 |
| 1-1665 | Sub-53 | 3,4-diClPh | CO | Single bond | Sub-1 |
| 1-1666 | Sub-53 | 3,4-diClPh | CO | Single bond | Sub-2 |
| 1-1667 | Sub-53 | 3,4-diClPh | CO | Single bond | Sub-3 |
| 1-1668 | Sub-53 | 3,4-diClPh | CO | Single bond | Sub-4 |
| 1-1669 | Sub-53 | 3,4-diClPh | CO | Single bond | Sub-5 |
| 1-1670 | Sub-53 | 3,4-diClPh | CO | Single bond | Sub-6 |
| 1-1671 | Sub-53 | 3,4-diClPh | CO | Single bond | Sub-7 |
| 1-1672 | Sub-53 | 3,4-diClPh | CO | Single bond | Sub-8 |
| 1-1673 | Sub-53 | 3,4-diClPh | CO | Single bond | Sub-9 |
| 1-1674 | Sub-53 | 3,4-diClPh | CO | Single bond | Sub-10 |
| 1-1675 | Sub-53 | 3,4-diClPh | CO | Single bond | Sub-11 |
| 1-1676 | Sub-53 | 3,4-diClPh | CO | Single bond | Sub-12 |
| 1-1677 | Sub-53 | 3,4-diClPh | CO | Single bond | Sub-13 |
| 1-1678 | Sub-53 | 3,4-diClPh | CO | Single bond | Sub-14 |
| 1-1679 | Sub-53 | 3,4-diClPh | CO | Single bond | Sub-15 |
| 1-1680 | Sub-53 | 3,4-diClPh | CO | Single bond | Sub-16 |
| 1-1681 | Sub-53 | 3,4-diClPh | CO | Single bond | Sub-17 |
| 1-1682 | Sub-53 | 3,4-diClPh | CO | Single bond | Sub-18 |
| 1-1683 | Sub-53 | 3,4-diClPh | CO | Single bond | Sub-19 |
| 1-1684 | Sub-53 | 3,4-diClPh | CO | Single bond | Sub-20 |
| 1-1685 | Sub-53 | 3,4-diClPh | CO | Single bond | Sub-21 |
| 1-1686 | Sub-53 | 3,4-diClPh | CO | Single bond | Sub-22 |
| 1-1687 | Sub-53 | 3,4-diClPh | CO | Single bond | Sub-23 |
| 1-1688 | Sub-53 | 3,4-diClPh | CO | Single bond | Sub-24 |
| 1-1689 | Sub-53 | 3,4-diClPh | CO | Single bond | Sub-25 |
| 1-1690 | Sub-53 | 3,4-diClPh | CO | Single bond | Sub-26 |
| 1-1691 | Sub-53 | 3,4-diClPh | CO | Single bond | Sub-27 |
| 1-1692 | Sub-53 | 3,4-diClPh | CO | Single bond | Sub-28 |
| 1-1693 | Sub-53 | 3,4-diClPh | CO | Single bond | Sub-29 |
| 1-1694 | Sub-53 | 3,4-diClPh | CO | Single bond | Sub-30 |
| 1-1695 | Sub-53 | 3,4-diClPh | CO | Single bond | Sub-31 |
| 1-1696 | Sub-53 | 3,4-diClPh | CO | Single bond | Sub-32 |
| 1-1697 | Sub-54 | 3,4-diClPh | CO | Single bond | Sub-1 |
| 1-1698 | Sub-54 | 3,4-diClPh | CO | Single bond | Sub-2 |
| 1-1699 | Sub-54 | 3,4-diClPh | CO | Single bond | Sub-3 |
| 1-1700 | Sub-54 | 3,4-diClPh | CO | Single bond | Sub-4 |
| 1-1701 | Sub-54 | 3,4-diClPh | CO | Single bond | Sub-5 |
| 1-1702 | Sub-54 | 3,4-diClPh | CO | Single bond | Sub-6 |
| 1-1703 | Sub-54 | 3,4-diClPh | CO | Single bond | Sub-7 |
| 1-1704 | Sub-54 | 3,4-diClPh | CO | Single bond | Sub-8 |
| 1-1705 | Sub-54 | 3,4-diClPh | CO | Single bond | Sub-9 |
| 1-1706 | Sub-54 | 3,4-diClPh | CO | Single bond | Sub-10 |
| 1-1707 | Sub-54 | 3,4-diClPh | CO | Single bond | Sub-11 |
| 1-1708 | Sub-54 | 3,4-diClPh | CO | Single bond | Sub-12 |
| 1-1709 | Sub-54 | 3,4-diClPh | CO | Single bond | Sub-13 |
| 1-1710 | Sub-54 | 3,4-diClPh | CO | Single bond | Sub-14 |
| 1-1711 | Sub-54 | 3,4-diClPh | CO | Single bond | Sub-15 |
| 1-1712 | Sub-54 | 3,4-diClPh | CO | Single bond | Sub-16 |
| 1-1713 | Sub-54 | 3,4-diClPh | CO | Single bond | Sub-17 |
| 1-1714 | Sub-54 | 3,4-diClPh | CO | Single bond | Sub-18 |
| 1-1715 | Sub-54 | 3,4-diClPh | CO | Single bond | Sub-19 |
| 1-1716 | Sub-54 | 3,4-diClPh | CO | Single bond | Sub-20 |
| 1-1717 | Sub-54 | 3,4-diClPh | CO | Single bond | Sub-21 |
| 1-1718 | Sub-54 | 3,4-diClPh | CO | Single bond | Sub-22 |
| 1-1719 | Sub-54 | 3,4-diClPh | CO | Single bond | Sub-23 |
| 1-1720 | Sub-54 | 3,4-diClPh | CO | Single bond | Sub-24 |
| 1-1721 | Sub-54 | 3,4-diClPh | CO | Single bond | Sub-25 |
| 1-1722 | Sub-54 | 3,4-diClPh | CO | Single bond | Sub-26 |
| 1-1723 | Sub-54 | 3,4-diClPh | CO | Single bond | Sub-27 |
| 1-1724 | Sub-54 | 3,4-diClPh | CO | Single bond | Sub-28 |
| 1-1725 | Sub-54 | 3,4-diClPh | CO | Single bond | Sub-29 |
| 1-1726 | Sub-54 | 3,4-diClPh | CO | Single bond | Sub-30 |
| 1-1727 | Sub-54 | 3,4-diClPh | CO | Single bond | Sub-31 |
| 1-1728 | Sub-54 | 3,4-diClPh | CO | Single bond | Sub-32 |
| 1-1729 | Sub-55 | 3,4-diClPh | CO | Single bond | Sub-1 |
| 1-1730 | Sub-55 | 3,4-diClPh | CO | Single bond | Sub-2 |
| 1-1731 | Sub-55 | 3,4-diClPh | CO | Single bond | Sub-3 |
| 1-1732 | Sub-55 | 3,4-diClPh | CO | Single bond | Sub-4 |
| 1-1733 | Sub-55 | 3,4-diClPh | CO | Single bond | Sub-5 |
| 1-1734 | Sub-55 | 3,4-diClPh | CO | Single bond | Sub-6 |
| 1-1735 | Sub-55 | 3,4-diClPh | CO | Single bond | Sub-7 |
| 1-1736 | Sub-55 | 3,4-diClPh | CO | Single bond | Sub-8 |
| 1-1737 | Sub-55 | 3,4-diClPh | CO | Single bond | Sub-9 |
| 1-1738 | Sub-55 | 3,4-diClPh | CO | Single bond | Sub-10 |
| 1-1739 | Sub-55 | 3,4-diClPh | CO | Single bond | Sub-11 |
| 1-1740 | Sub-55 | 3,4-diClPh | CO | Single bond | Sub-12 |
| 1-1741 | Sub-55 | 3,4-diClPh | CO | Single bond | Sub-13 |
| 1-1742 | Sub-55 | 3,4-diClPh | CO | Single bond | Sub-14 |
| 1-1743 | Sub-55 | 3,4-diClPh | CO | Single bond | Sub-15 |
| 1-1744 | Sub-55 | 3,4-diClPh | CO | Single bond | Sub-16 |
| 1-1745 | Sub-55 | 3,4-diClPh | CO | Single bond | Sub-17 |
| 1-1746 | Sub-55 | 3,4-diClPh | CO | Single bond | Sub-18 |
| 1-1747 | Sub-55 | 3,4-diClPh | CO | Single bond | Sub-19 |
| 1-1748 | Sub-55 | 3,4-diClPh | CO | Single bond | Sub-20 |
| 1-1749 | Sub-55 | 3,4-diClPh | CO | Single bond | Sub-21 |
| 1-1750 | Sub-55 | 3,4-diClPh | CO | Single bond | Sub-22 |
| 1-1751 | Sub-55 | 3,4-diClPh | CO | Single bond | Sub-23 |
| 1-1752 | Sub-55 | 3,4-diClPh | CO | Single bond | Sub-24 |
| 1-1753 | Sub-55 | 3,4-diClPh | CO | Single bond | Sub-25 |
| 1-1754 | Sub-55 | 3,4-diClPh | CO | Single bond | Sub-26 |
| 1-1755 | Sub-55 | 3,4-diClPh | CO | Single bond | Sub-27 |
| 1-1756 | Sub-55 | 3,4-diClPh | CO | Single bond | Sub-28 |
| 1-1757 | Sub-55 | 3,4-diClPh | CO | Single bond | Sub-29 |
| 1-1758 | Sub-55 | 3,4-diClPh | CO | Single bond | Sub-30 |
| 1-1759 | Sub-55 | 3,4-diClPh | CO | Single bond | Sub-31 |
| 1-1760 | Sub-55 | 3,4-diClPh | CO | Single bond | Sub-32 |
| 1-1761 | Sub-56 | 3,4-diClPh | CO | Single bond | Sub-1 |
| 1-1762 | Sub-56 | 3,4-diClPh | CO | Single bond | Sub-2 |
| 1-1763 | Sub-56 | 3,4-diClPh | CO | Single bond | Sub-3 |
| 1-1764 | Sub-56 | 3,4-diClPh | CO | Single bond | Sub-4 |
| 1-1765 | Sub-56 | 3,4-diClPh | CO | Single bond | Sub-5 |
| 1-1766 | Sub-56 | 3,4-diClPh | CO | Single bond | Sub-6 |
| 1-1767 | Sub-56 | 3,4-diClPh | CO | Single bond | Sub-7 |
| 1-1768 | Sub-56 | 3,4-diClPh | CO | Single bond | Sub-8 |
| 1-1769 | Sub-56 | 3,4-diClPh | CO | Single bond | Sub-9 |
| 1-1770 | Sub-56 | 3,4-diClPh | CO | Single bond | Sub-10 |
| 1-1771 | Sub-56 | 3,4-diClPh | CO | Single bond | Sub-11 |
| 1-1772 | Sub-56 | 3,4-diClPh | CO | Single bond | Sub-12 |
| 1-1773 | Sub-56 | 3,4-diClPh | CO | Single bond | Sub-13 |
| 1-1774 | Sub-56 | 3,4-diClPh | CO | Single bond | Sub-14 |
| 1-1775 | Sub-56 | 3,4-diClPh | CO | Single bond | Sub-15 |
| 1-1776 | Sub-56 | 3,4-diClPh | CO | Single bond | Sub-16 |
| 1-1777 | Sub-56 | 3,4-diClPh | CO | Single bond | Sub-17 |
| 1-1778 | Sub-56 | 3,4-diClPh | CO | Single bond | Sub-18 |
| 1-1779 | Sub-56 | 3,4-diClPh | CO | Single bond | Sub-19 |
| 1-1780 | Sub-56 | 3,4-diClPh | CO | Single bond | Sub-20 |
| 1-1781 | Sub-56 | 3,4-diClPh | CO | Single bond | Sub-21 |
| 1-1782 | Sub-56 | 3,4-diClPh | CO | Single bond | Sub-22 |
| 1-1783 | Sub-56 | 3,4-diClPh | CO | Single bond | Sub-23 |
| 1-1784 | Sub-56 | 3,4-diClPh | CO | Single bond | Sub-24 |
| 1-1785 | Sub-56 | 3,4-diClPh | CO | Single bond | Sub-25 |
| 1-1786 | Sub-56 | 3,4-diClPh | CO | Single bond | Sub-26 |
| 1-1787 | Sub-56 | 3,4-diClPh | CO | Single bond | Sub-27 |
| 1-1788 | Sub-56 | 3,4-diClPh | CO | Single bond | Sub-28 |
| 1-1789 | Sub-56 | 3,4-diClPh | CO | Single bond | Sub-29 |
| 1-1790 | Sub-56 | 3,4-diClPh | CO | Single bond | Sub-30 |
| 1-1791 | Sub-56 | 3,4-diClPh | CO | Single bond | Sub-31 |
| 1-1792 | Sub-56 | 3,4-diClPh | CO | Single bond | Sub-32 |
| 1-1793 | Sub-57 | 3,4-diClPh | CO | Single bond | Sub-1 |
| 1-1794 | Sub-57 | 3,4-diClPh | CO | Single bond | Sub-2 |
| 1-1795 | Sub-57 | 3,4-diClPh | CO | Single bond | Sub-3 |
| 1-1796 | Sub-57 | 3,4-diClPh | CO | Single bond | Sub-4 |
| 1-1797 | Sub-57 | 3,4-diClPh | CO | Single bond | Sub-5 |

TABLE 1-continued

| Cpd. No. | R¹ | R² | A | B | Z |
|---|---|---|---|---|---|
| 1-1798 | Sub-57 | 3,4-diClPh | CO | Single bond | Sub-6 |
| 1-1799 | Sub-57 | 3,4-diClPh | CO | Single bond | Sub-7 |
| 1-1800 | Sub-57 | 3,4-diClPh | CO | Single bond | Sub-8 |
| 1-1801 | Sub-57 | 3,4-diClPh | CO | Single bond | Sub-9 |
| 1-1802 | Sub-57 | 3,4-diClPh | CO | Single bond | Sub-10 |
| 1-1803 | Sub-57 | 3,4-diClPh | CO | Single bond | Sub-11 |
| 1-1804 | Sub-57 | 3,4-diClPh | CO | Single bond | Sub-12 |
| 1-1805 | Sub-57 | 3,4-diClPh | CO | Single bond | Sub-13 |
| 1-1806 | Sub-57 | 3,4-diClPh | CO | Single bond | Sub-14 |
| 1-1807 | Sub-57 | 3,4-diClPh | CO | Single bond | Sub-15 |
| 1-1808 | Sub-57 | 3,4-diClPh | CO | Single bond | Sub-16 |
| 1-1809 | Sub-57 | 3,4-diClPh | CO | Single bond | Sub-17 |
| 1-1810 | Sub-57 | 3,4-diClPh | CO | Single bond | Sub-18 |
| 1-1811 | Sub-57 | 3,4-diClPh | CO | Single bond | Sub-19 |
| 1-1812 | Sub-57 | 3,4-diClPh | CO | Single bond | Sub-20 |
| 1-1813 | Sub-57 | 3,4-diClPh | CO | Single bond | Sub-21 |
| 1-1814 | Sub-57 | 3,4-diClPh | CO | Single bond | Sub-22 |
| 1-1815 | Sub-57 | 3,4-diClPh | CO | Single bond | Sub-23 |
| 1-1816 | Sub-57 | 3,4-diClPh | CO | Single bond | Sub-24 |
| 1-1817 | Sub-57 | 3,4-diClPh | CO | Single bond | Sub-25 |
| 1-1818 | Sub-57 | 3,4-diClPh | CO | Single bond | Sub-26 |
| 1-1819 | Sub-57 | 3,4-diClPh | CO | Single bond | Sub-27 |
| 1-1820 | Sub-57 | 3,4-diClPh | CO | Single bond | Sub-28 |
| 1-1821 | Sub-57 | 3,4-diClPh | CO | Single bond | Sub-29 |
| 1-1822 | Sub-57 | 3,4-diClPh | CO | Single bond | Sub-30 |
| 1-1823 | Sub-57 | 3,4-diClPh | CO | Single bond | Sub-31 |
| 1-1824 | Sub-57 | 3,4-diClPh | CO | Single bond | Sub-32 |
| 1-1825 | Sub-58 | 3,4-diClPh | CO | Single bond | Sub-1 |
| 1-1826 | Sub-58 | 3,4-diClPh | CO | Single bond | Sub-2 |
| 1-1827 | Sub-58 | 3,4-diClPh | CO | Single bond | Sub-3 |
| 1-1828 | Sub-58 | 3,4-diClPh | CO | Single bond | Sub-4 |
| 1-1829 | Sub-58 | 3,4-diClPh | CO | Single bond | Sub-5 |
| 1-1830 | Sub-58 | 3,4-diClPh | CO | Single bond | Sub-6 |
| 1-1831 | Sub-58 | 3,4-diClPh | CO | Single bond | Sub-7 |
| 1-1832 | Sub-58 | 3,4-diClPh | CO | Single bond | Sub-8 |
| 1-1833 | Sub-58 | 3,4-diClPh | CO | Single bond | Sub-9 |
| 1-1834 | Sub-58 | 3,4-diClPh | CO | Single bond | Sub-10 |
| 1-1835 | Sub-58 | 3,4-diClPh | CO | Single bond | Sub-11 |
| 1-1836 | Sub-58 | 3,4-diClPh | CO | Single bond | Sub-12 |
| 1-1837 | Sub-58 | 3,4-diClPh | CO | Single bond | Sub-13 |
| 1-1838 | Sub-58 | 3,4-diClPh | CO | Single bond | Sub-14 |
| 1-1839 | Sub-58 | 3,4-diClPh | CO | Single bond | Sub-15 |
| 1-1840 | Sub-58 | 3,4-diClPh | CO | Single bond | Sub-16 |
| 1-1841 | Sub-58 | 3,4-diClPh | CO | Single bond | Sub-17 |
| 1-1842 | Sub-58 | 3,4-diClPh | CO | Single bond | Sub-18 |
| 1-1843 | Sub-58 | 3,4-diClPh | CO | Single bond | Sub-19 |
| 1-1844 | Sub-58 | 3,4-diClPh | CO | Single bond | Sub-20 |
| 1-1845 | Sub-58 | 3,4-diClPh | CO | Single bond | Sub-21 |
| 1-1846 | Sub-58 | 3,4-diClPh | CO | Single bond | Sub-22 |
| 1-1847 | Sub-58 | 3,4-diClPh | CO | Single bond | Sub-23 |
| 1-1848 | Sub-58 | 3,4-diClPh | CO | Single bond | Sub-24 |
| 1-1849 | Sub-58 | 3,4-diClPh | CO | Single bond | Sub-25 |
| 1-1850 | Sub-58 | 3,4-diClPh | CO | Single bond | Sub-26 |
| 1-1851 | Sub-58 | 3,4-diClPh | CO | Single bond | Sub-27 |
| 1-1852 | Sub-58 | 3,4-diClPh | CO | Single bond | Sub-28 |
| 1-1853 | Sub-58 | 3,4-diClPh | CO | Single bond | Sub-29 |
| 1-1854 | Sub-58 | 3,4-diClPh | CO | Single bond | Sub-30 |
| 1-1855 | Sub-58 | 3,4-diClPh | CO | Single bond | Sub-31 |
| 1-1856 | Sub-58 | 3,4-diClPh | CO | Single bond | Sub-32 |
| 1-1857 | Sub-59 | 3,4-diClPh | CO | Single bond | Sub-1 |
| 1-1858 | Sub-59 | 3,4-diClPh | CO | Single bond | Sub-2 |
| 1-1859 | Sub-59 | 3,4-diClPh | CO | Single bond | Sub-3 |
| 1-1860 | Sub-59 | 3,4-diClPh | CO | Single bond | Sub-4 |
| 1-1861 | Sub-59 | 3,4-diClPh | CO | Single bond | Sub-5 |
| 1-1862 | Sub-59 | 3,4-diClPh | CO | Single bond | Sub-6 |
| 1-1863 | Sub-59 | 3,4-diClPh | CO | Single bond | Sub-7 |
| 1-1864 | Sub-59 | 3,4-diClPh | CO | Single bond | Sub-8 |
| 1-1865 | Sub-59 | 3,4-diClPh | CO | Single bond | Sub-9 |
| 1-1866 | Sub-59 | 3,4-diClPh | CO | Single bond | Sub-10 |
| 1-1867 | Sub-59 | 3,4-diClPh | CO | Single bond | Sub-11 |
| 1-1868 | Sub-59 | 3,4-diClPh | CO | Single bond | Sub-12 |
| 1-1869 | Sub-59 | 3,4-diClPh | CO | Single bond | Sub-13 |
| 1-1870 | Sub-59 | 3,4-diClPh | CO | Single bond | Sub-14 |
| 1-1871 | Sub-59 | 3,4-diClPh | CO | Single bond | Sub-15 |
| 1-1872 | Sub-59 | 3,4-diClPh | CO | Single bond | Sub-16 |
| 1-1873 | Sub-59 | 3,4-diClPh | CO | Single bond | Sub-17 |
| 1-1874 | Sub-59 | 3,4-diClPh | CO | Single bond | Sub-18 |
| 1-1875 | Sub-59 | 3,4-diClPh | CO | Single bond | Sub-19 |
| 1-1876 | Sub-59 | 3,4-diClPh | CO | Single bond | Sub-20 |
| 1-1877 | Sub-59 | 3,4-diClPh | CO | Single bond | Sub-21 |
| 1-1878 | Sub-59 | 3,4-diClPh | CO | Single bond | Sub-22 |
| 1-1879 | Sub-59 | 3,4-diClPh | CO | Single bond | Sub-23 |
| 1-1880 | Sub-59 | 3,4-diClPh | CO | Single bond | Sub-24 |
| 1-1881 | Sub-59 | 3,4-diClPh | CO | Single bond | Sub-25 |
| 1-1882 | Sub-59 | 3,4-diClPh | CO | Single bond | Sub-26 |
| 1-1883 | Sub-59 | 3,4-diClPh | CO | Single bond | Sub-27 |
| 1-1884 | Sub-59 | 3,4-diClPh | CO | Single bond | Sub-28 |
| 1-1885 | Sub-59 | 3,4-diClPh | CO | Single bond | Sub-29 |
| 1-1886 | Sub-59 | 3,4-diClPh | CO | Single bond | Sub-30 |
| 1-1887 | Sub-59 | 3,4-diClPh | CO | Single bond | Sub-31 |
| 1-1888 | Sub-59 | 3,4-diClPh | CO | Single bond | Sub-32 |
| 1-1889 | Sub-60 | 3,4-diClPh | CO | Single bond | Sub-1 |
| 1-1890 | Sub-60 | 3,4-diClPh | CO | Single bond | Sub-2 |
| 1-1891 | Sub-60 | 3,4-diClPh | CO | Single bond | Sub-3 |
| 1-1892 | Sub-60 | 3,4-diClPh | CO | Single bond | Sub-4 |
| 1-1893 | Sub-60 | 3,4-diClPh | CO | Single bond | Sub-5 |
| 1-1894 | Sub-60 | 3,4-diClPh | CO | Single bond | Sub-6 |
| 1-1895 | Sub-60 | 3,4-diClPh | CO | Single bond | Sub-7 |
| 1-1896 | Sub-60 | 3,4-diClPh | CO | Single bond | Sub-8 |
| 1-1897 | Sub-60 | 3,4-diClPh | CO | Single bond | Sub-9 |
| 1-1898 | Sub-60 | 3,4-diClPh | CO | Single bond | Sub-10 |
| 1-1899 | Sub-60 | 3,4-diClPh | CO | Single bond | Sub-11 |
| 1-1900 | Sub-60 | 3,4-diClPh | CO | Single bond | Sub-12 |
| 1-1901 | Sub-60 | 3,4-diClPh | CO | Single bond | Sub-13 |
| 1-1902 | Sub-60 | 3,4-diClPh | CO | Single bond | Sub-14 |
| 1-1903 | Sub-60 | 3,4-diClPh | CO | Single bond | Sub-15 |
| 1-1904 | Sub-60 | 3,4-diClPh | CO | Single bond | Sub-16 |
| 1-1905 | Sub-60 | 3,4-diClPh | CO | Single bond | Sub-17 |
| 1-1906 | Sub-60 | 3,4-diClPh | CO | Single bond | Sub-18 |
| 1-1907 | Sub-60 | 3,4-diClPh | CO | Single bond | Sub-19 |
| 1-1908 | Sub-60 | 3,4-diClPh | CO | Single bond | Sub-20 |
| 1-1909 | Sub-60 | 3,4-diClPh | CO | Single bond | Sub-21 |
| 1-1910 | Sub-60 | 3,4-diClPh | CO | Single bond | Sub-22 |
| 1-1911 | Sub-60 | 3,4-diClPh | CO | Single bond | Sub-23 |
| 1-1912 | Sub-60 | 3,4-diClPh | CO | Single bond | Sub-24 |
| 1-1913 | Sub-60 | 3,4-diClPh | CO | Single bond | Sub-25 |
| 1-1914 | Sub-60 | 3,4-diClPh | CO | Single bond | Sub-26 |
| 1-1915 | Sub-60 | 3,4-diClPh | CO | Single bond | Sub-27 |
| 1-1916 | Sub-60 | 3,4-diClPh | CO | Single bond | Sub-28 |
| 1-1917 | Sub-60 | 3,4-diClPh | CO | Single bond | Sub-29 |
| 1-1918 | Sub-60 | 3,4-diClPh | CO | Single bond | Sub-30 |
| 1-1919 | Sub-60 | 3,4-diClPh | CO | Single bond | Sub-31 |
| 1-1920 | Sub-60 | 3,4-diClPh | CO | Single bond | Sub-32 |
| 1-1921 | Sub-61 | 3,4-diClPh | CO | Single bond | Sub-1 |
| 1-1922 | Sub-61 | 3,4-diClPh | CO | Single bond | Sub-2 |
| 1-1923 | Sub-61 | 3,4-diClPh | CO | Single bond | Sub-3 |
| 1-1924 | Sub-61 | 3,4-diClPh | CO | Single bond | Sub-4 |
| 1-1925 | Sub-61 | 3,4-diClPh | CO | Single bond | Sub-5 |
| 1-1926 | Sub-61 | 3,4-diClPh | CO | Single bond | Sub-6 |
| 1-1927 | Sub-61 | 3,4-diClPh | CO | Single bond | Sub-7 |
| 1-1928 | Sub-61 | 3,4-diClPh | CO | Single bond | Sub-8 |
| 1-1929 | Sub-61 | 3,4-diClPh | CO | Single bond | Sub-9 |
| 1-1930 | Sub-61 | 3,4-diClPh | CO | Single bond | Sub-10 |
| 1-1931 | Sub-61 | 3,4-diClPh | CO | Single bond | Sub-11 |
| 1-1932 | Sub-61 | 3,4-diClPh | CO | Single bond | Sub-12 |
| 1-1933 | Sub-61 | 3,4-diClPh | CO | Single bond | Sub-13 |
| 1-1934 | Sub-61 | 3,4-diClPh | CO | Single bond | Sub-14 |
| 1-1935 | Sub-61 | 3,4-diClPh | CO | Single bond | Sub-15 |
| 1-1936 | Sub-61 | 3,4-diClPh | CO | Single bond | Sub-16 |
| 1-1937 | Sub-61 | 3,4-diClPh | CO | Single bond | Sub-17 |
| 1-1938 | Sub-61 | 3,4-diClPh | CO | Single bond | Sub-18 |
| 1-1939 | Sub-61 | 3,4-diClPh | CO | Single bond | Sub-19 |
| 1-1940 | Sub-61 | 3,4-diClPh | CO | Single bond | Sub-20 |
| 1-1941 | Sub-61 | 3,4-diClPh | CO | Single bond | Sub-21 |
| 1-1942 | Sub-61 | 3,4-diClPh | CO | Single bond | Sub-22 |
| 1-1943 | Sub-61 | 3,4-diClPh | CO | Single bond | Sub-23 |
| 1-1944 | Sub-61 | 3,4-diClPh | CO | Single bond | Sub-24 |
| 1-1945 | Sub-61 | 3,4-diClPh | CO | Single bond | Sub-25 |
| 1-1946 | Sub-61 | 3,4-diClPh | CO | Single bond | Sub-26 |
| 1-1947 | Sub-61 | 3,4-diClPh | CO | Single bond | Sub-27 |
| 1-1948 | Sub-61 | 3,4-diClPh | CO | Single bond | Sub-28 |
| 1-1949 | Sub-61 | 3,4-diClPh | CO | Single bond | Sub-29 |

TABLE 1-continued

| Cpd. No. | R¹ | R² | A | B | Z |
|---|---|---|---|---|---|
| 1-1950 | Sub-61 | 3,4-diClPh | CO | Single bond | Sub-30 |
| 1-1951 | Sub-61 | 3,4-diClPh | CO | Single bond | Sub-31 |
| 1-1952 | Sub-61 | 3,4-diClPh | CO | Single bond | Sub-32 |
| 1-1953 | Sub-62 | 3,4-diClPh | CO | Single bond | Sub-1 |
| 1-1954 | Sub-62 | 3,4-diClPh | CO | Single bond | Sub-2 |
| 1-1955 | Sub-62 | 3,4-diClPh | CO | Single bond | Sub-3 |
| 1-1956 | Sub-62 | 3,4-diClPh | CO | Single bond | Sub-4 |
| 1-1957 | Sub-62 | 3,4-diClPh | CO | Single bond | Sub-5 |
| 1-1958 | Sub-62 | 3,4-diClPh | CO | Single bond | Sub-6 |
| 1-1959 | Sub-62 | 3,4-diClPh | CO | Single bond | Sub-7 |
| 1-1960 | Sub-62 | 3,4-diClPh | CO | Single bond | Sub-8 |
| 1-1961 | Sub-62 | 3,4-diClPh | CO | Single bond | Sub-9 |
| 1-1962 | Sub-62 | 3,4-diClPh | CO | Single bond | Sub-10 |
| 1-1963 | Sub-62 | 3,4-diClPh | CO | Single bond | Sub-11 |
| 1-1964 | Sub-62 | 3,4-diClPh | CO | Single bond | Sub-12 |
| 1-1965 | Sub-62 | 3,4-diClPh | CO | Single bond | Sub-13 |
| 1-1966 | Sub-62 | 3,4-diClPh | CO | Single bond | Sub-14 |
| 1-1967 | Sub-62 | 3,4-diClPh | CO | Single bond | Sub-15 |
| 1-1968 | Sub-62 | 3,4-diClPh | CO | Single bond | Sub-16 |
| 1-1969 | Sub-62 | 3,4-diClPh | CO | Single bond | Sub-17 |
| 1-1970 | Sub-62 | 3,4-diClPh | CO | Single bond | Sub-18 |
| 1-1971 | Sub-62 | 3,4-diClPh | CO | Single bond | Sub-19 |
| 1-1972 | Sub-62 | 3,4-diClPh | CO | Single bond | Sub-20 |
| 1-1973 | Sub-62 | 3,4-diClPh | CO | Single bond | Sub-21 |
| 1-1974 | Sub-62 | 3,4-diClPh | CO | Single bond | Sub-22 |
| 1-1975 | Sub-62 | 3,4-diClPh | CO | Single bond | Sub-23 |
| 1-1976 | Sub-62 | 3,4-diClPh | CO | Single bond | Sub-24 |
| 1-1977 | Sub-62 | 3,4-diClPh | CO | Single bond | Sub-25 |
| 1-1978 | Sub-62 | 3,4-diClPh | CO | Single bond | Sub-26 |
| 1-1979 | Sub-62 | 3,4-diClPh | CO | Single bond | Sub-27 |
| 1-1980 | Sub-62 | 3,4-diClPh | CO | Single bond | Sub-28 |
| 1-1981 | Sub-62 | 3,4-diClPh | CO | Single bond | Sub-29 |
| 1-1982 | Sub-62 | 3,4-diClPh | CO | Single bond | Sub-30 |
| 1-1983 | Sub-62 | 3,4-diClPh | CO | Single bond | Sub-31 |
| 1-1984 | Sub-62 | 3,4-diClPh | CO | Single bond | Sub-32 |
| 1-1985 | Sub-63 | 3,4-diClPh | CO | Single bond | Sub-1 |
| 1-1986 | Sub-63 | 3,4-diClPh | CO | Single bond | Sub-2 |
| 1-1987 | Sub-63 | 3,4-diClPh | CO | Single bond | Sub-3 |
| 1-1988 | Sub-63 | 3,4-diClPh | CO | Single bond | Sub-4 |
| 1-1989 | Sub-63 | 3,4-diClPh | CO | Single bond | Sub-5 |
| 1-1990 | Sub-63 | 3,4-diClPh | CO | Single bond | Sub-6 |
| 1-1991 | Sub-63 | 3,4-diClPh | CO | Single bond | Sub-7 |
| 1-1992 | Sub-63 | 3,4-diClPh | CO | Single bond | Sub-8 |
| 1-1993 | Sub-63 | 3,4-diClPh | CO | Single bond | Sub-9 |
| 1-1994 | Sub-63 | 3,4-diClPh | CO | Single bond | Sub-10 |
| 1-1995 | Sub-63 | 3,4-diClPh | CO | Single bond | Sub-11 |
| 1-1996 | Sub-63 | 3,4-diClPh | CO | Single bond | Sub-12 |
| 1-1997 | Sub-63 | 3,4-diClPh | CO | Single bond | Sub-13 |
| 1-1998 | Sub-63 | 3,4-diClPh | CO | Single bond | Sub-14 |
| 1-1999 | Sub-63 | 3,4-diClPh | CO | Single bond | Sub-15 |
| 1-2000 | Sub-63 | 3,4-diClPh | CO | Single bond | Sub-16 |
| 1-2001 | Sub-63 | 3,4-diClPh | CO | Single bond | Sub-17 |
| 1-2002 | Sub-63 | 3,4-diClPh | CO | Single bond | Sub-18 |
| 1-2003 | Sub-63 | 3,4-diClPh | CO | Single bond | Sub-19 |
| 1-2004 | Sub-63 | 3,4-diClPh | CO | Single bond | Sub-20 |
| 1-2005 | Sub-63 | 3,4-diClPh | CO | Single bond | Sub-21 |
| 1-2006 | Sub-63 | 3,4-diClPh | CO | Single bond | Sub-22 |
| 1-2007 | Sub-63 | 3,4-diClPh | CO | Single bond | Sub-23 |
| 1-2008 | Sub-63 | 3,4-diClPh | CO | Single bond | Sub-24 |
| 1-2009 | Sub-63 | 3,4-diClPh | CO | Single bond | Sub-25 |
| 1-2010 | Sub-63 | 3,4-diClPh | CO | Single bond | Sub-26 |
| 1-2011 | Sub-63 | 3,4-diClPh | CO | Single bond | Sub-27 |
| 1-2012 | Sub-63 | 3,4-diClPh | CO | Single bond | Sub-28 |
| 1-2013 | Sub-63 | 3,4-diClPh | CO | Single bond | Sub-29 |
| 1-2014 | Sub-63 | 3,4-diClPh | CO | Single bond | Sub-30 |
| 1-2015 | Sub-63 | 3,4-diClPh | CO | Single bond | Sub-31 |
| 1-2016 | Sub-63 | 3,4-diClPh | CO | Single bond | Sub-32 |
| 1-2017 | Sub-64 | 3,4-diClPh | CO | Single bond | Sub-1 |
| 1-2018 | Sub-64 | 3,4-diClPh | CO | Single bond | Sub-2 |
| 1-2019 | Sub-64 | 3,4-diClPh | CO | Single bond | Sub-3 |
| 1-2020 | Sub-64 | 3,4-diClPh | CO | Single bond | Sub-4 |
| 1-2021 | Sub-64 | 3,4-diClPh | CO | Single bond | Sub-5 |
| 1-2022 | Sub-64 | 3,4-diClPh | CO | Single bond | Sub-6 |
| 1-2023 | Sub-64 | 3,4-diClPh | CO | Single bond | Sub-7 |
| 1-2024 | Sub-64 | 3,4-diClPh | CO | Single bond | Sub-8 |
| 1-2025 | Sub-64 | 3,4-diClPh | CO | Single bond | Sub-9 |
| 1-2026 | Sub-64 | 3,4-diClPh | CO | Single bond | Sub-10 |
| 1-2027 | Sub-64 | 3,4-diClPh | CO | Single bond | Sub-11 |
| 1-2028 | Sub-64 | 3,4-diClPh | CO | Single bond | Sub-12 |
| 1-2029 | Sub-64 | 3,4-diClPh | CO | Single bond | Sub-13 |
| 1-2030 | Sub-64 | 3,4-diClPh | CO | Single bond | Sub-14 |
| 1-2031 | Sub-64 | 3,4-diClPh | CO | Single bond | Sub-15 |
| 1-2032 | Sub-64 | 3,4-diClPh | CO | Single bond | Sub-16 |
| 1-2033 | Sub-64 | 3,4-diClPh | CO | Single bond | Sub-17 |
| 1-2034 | Sub-64 | 3,4-diClPh | CO | Single bond | Sub-18 |
| 1-2035 | Sub-64 | 3,4-diClPh | CO | Single bond | Sub-19 |
| 1-2036 | Sub-64 | 3,4-diClPh | CO | Single bond | Sub-20 |
| 1-2037 | Sub-64 | 3,4-diClPh | CO | Single bond | Sub-21 |
| 1-2038 | Sub-64 | 3,4-diClPh | CO | Single bond | Sub-22 |
| 1-2039 | Sub-64 | 3,4-diClPh | CO | Single bond | Sub-23 |
| 1-2040 | Sub-64 | 3,4-diClPh | CO | Single bond | Sub-24 |
| 1-2041 | Sub-64 | 3,4-diClPh | CO | Single bond | Sub-25 |
| 1-2042 | Sub-64 | 3,4-diClPh | CO | Single bond | Sub-26 |
| 1-2043 | Sub-64 | 3,4-diClPh | CO | Single bond | Sub-27 |
| 1-2044 | Sub-64 | 3,4-diClPh | CO | Single bond | Sub-28 |
| 1-2045 | Sub-64 | 3,4-diClPh | CO | Single bond | Sub-29 |
| 1-2046 | Sub-64 | 3,4-diClPh | CO | Single bond | Sub-30 |
| 1-2047 | Sub-64 | 3,4-diClPh | CO | Single bond | Sub-31 |
| 1-2048 | Sub-64 | 3,4-diClPh | CO | Single bond | Sub-32 |
| 1-2049 | Sub-33 | 3,4-diClPh | SO$_2$ | Single bond | Sub-1 |
| 1-2050 | Sub-33 | 3,4-diClPh | SO$_2$ | Single bond | Sub-2 |
| 1-2051 | Sub-33 | 3,4-diClPh | SO$_2$ | Single bond | Sub-3 |
| 1-2052 | Sub-33 | 3,4-diClPh | SO$_2$ | Single bond | Sub-4 |
| 1-2053 | Sub-33 | 3,4-diClPh | SO$_2$ | Single bond | Sub-5 |
| 1-2054 | Sub-33 | 3,4-diClPh | SO$_2$ | Single bond | Sub-6 |
| 1-2055 | Sub-33 | 3,4-diClPh | SO$_2$ | Single bond | Sub-7 |
| 1-2056 | Sub-33 | 3,4-diClPh | SO$_2$ | Single bond | Sub-8 |
| 1-2057 | Sub-33 | 3,4-diClPh | SO$_2$ | Single bond | Sub-9 |
| 1-2058 | Sub-33 | 3,4-diClPh | SO$_2$ | Single bond | Sub-10 |
| 1-2059 | Sub-33 | 3,4-diClPh | SO$_2$ | Single bond | Sub-11 |
| 1-2060 | Sub-33 | 3,4-diClPh | SO$_2$ | Single bond | Sub-12 |
| 1-2061 | Sub-33 | 3,4-diClPh | SO$_2$ | Single bond | Sub-13 |
| 1-2062 | Sub-33 | 3,4-diClPh | SO$_2$ | Single bond | Sub-14 |
| 1-2063 | Sub-33 | 3,4-diClPh | SO$_2$ | Single bond | Sub-15 |
| 1-2064 | Sub-33 | 3,4-diClPh | SO$_2$ | Single bond | Sub-16 |
| 1-2065 | Sub-33 | 3,4-diClPh | SO$_2$ | Single bond | Sub-17 |
| 1-2066 | Sub-33 | 3,4-diClPh | SO$_2$ | Single bond | Sub-18 |
| 1-2067 | Sub-33 | 3,4-diClPh | SO$_2$ | Single bond | Sub-19 |
| 1-2068 | Sub-33 | 3,4-diClPh | SO$_2$ | Single bond | Sub-20 |
| 1-2069 | Sub-33 | 3,4-diClPh | SO$_2$ | Single bond | Sub-21 |
| 1-2070 | Sub-33 | 3,4-diClPh | SO$_2$ | Single bond | Sub-22 |
| 1-2071 | Sub-33 | 3,4-diClPh | SO$_2$ | Single bond | Sub-23 |
| 1-2072 | Sub-33 | 3,4-diClPh | SO$_2$ | Single bond | Sub-24 |
| 1-2073 | Sub-33 | 3,4-diClPh | SO$_2$ | Single bond | Sub-25 |
| 1-2074 | Sub-33 | 3,4-diClPh | SO$_2$ | Single bond | Sub-26 |
| 1-2075 | Sub-33 | 3,4-diClPh | SO$_2$ | Single bond | Sub-27 |
| 1-2076 | Sub-33 | 3,4-diClPh | SO$_2$ | Single bond | Sub-28 |
| 1-2077 | Sub-33 | 3,4-diClPh | SO$_2$ | Single bond | Sub-29 |
| 1-2078 | Sub-33 | 3,4-diClPh | SO$_2$ | Single bond | Sub-30 |
| 1-2079 | Sub-33 | 3,4-diClPh | SO$_2$ | Single bond | Sub-31 |
| 1-2080 | Sub-33 | 3,4-diClPh | SO$_2$ | Single bond | Sub-32 |
| 1-2081 | Sub-34 | 3,4-diClPh | SO$_2$ | Single bond | Sub-1 |
| 1-2082 | Sub-34 | 3,4-diClPh | SO$_2$ | Single bond | Sub-2 |
| 1-2083 | Sub-34 | 3,4-diClPh | SO$_2$ | Single bond | Sub-3 |
| 1-2084 | Sub-34 | 3,4-diClPh | SO$_2$ | Single bond | Sub-4 |
| 1-2085 | Sub-34 | 3,4-diClPh | SO$_2$ | Single bond | Sub-5 |
| 1-2086 | Sub-34 | 3,4-diClPh | SO$_2$ | Single bond | Sub-6 |
| 1-2087 | Sub-34 | 3,4-diClPh | SO$_2$ | Single bond | Sub-7 |
| 1-2088 | Sub-34 | 3,4-diClPh | SO$_2$ | Single bond | Sub-8 |
| 1-2089 | Sub-34 | 3,4-diClPh | SO$_2$ | Single bond | Sub-9 |
| 1-2090 | Sub-34 | 3,4-diClPh | SO$_2$ | Single bond | Sub-10 |
| 1-2091 | Sub-34 | 3,4-diClPh | SO$_2$ | Single bond | Sub-11 |
| 1-2092 | Sub-34 | 3,4-diClPh | SO$_2$ | Single bond | Sub-12 |
| 1-2093 | Sub-34 | 3,4-diClPh | SO$_2$ | Single bond | Sub-13 |
| 1-2094 | Sub-34 | 3,4-diClPh | SO$_2$ | Single bond | Sub-14 |
| 1-2095 | Sub-34 | 3,4-diClPh | SO$_2$ | Single bond | Sub-15 |
| 1-2096 | Sub-34 | 3,4-diClPh | SO$_2$ | Single bond | Sub-16 |
| 1-2097 | Sub-34 | 3,4-diClPh | SO$_2$ | Single bond | Sub-17 |
| 1-2098 | Sub-34 | 3,4-diClPh | SO$_2$ | Single bond | Sub-18 |
| 1-2099 | Sub-34 | 3,4-diClPh | SO$_2$ | Single bond | Sub-19 |
| 1-2100 | Sub-34 | 3,4-diClPh | SO$_2$ | Single bond | Sub-20 |
| 1-2101 | Sub-34 | 3,4-diClPh | SO$_2$ | Single bond | Sub-21 |

TABLE 1-continued

| Cpd. No. | R¹ | R² | A | B | Z |
|---|---|---|---|---|---|
| 1-2102 | Sub-34 | 3,4-diClPh | SO$_2$ | Single bond | Sub-22 |
| 1-2103 | Sub-34 | 3,4-diClPh | SO$_2$ | Single bond | Sub-23 |
| 1-2104 | Sub-34 | 3,4-diClPh | SO$_2$ | Single bond | Sub-24 |
| 1-2105 | Sub-34 | 3,4-diClPh | SO$_2$ | Single bond | Sub-25 |
| 1-2106 | Sub-34 | 3,4-diClPh | SO$_2$ | Single bond | Sub-26 |
| 1-2107 | Sub-34 | 3,4-diClPh | SO$_2$ | Single bond | Sub-27 |
| 1-2108 | Sub-34 | 3,4-diClPh | SO$_2$ | Single bond | Sub-28 |
| 1-2109 | Sub-34 | 3,4-diClPh | SO$_2$ | Single bond | Sub-29 |
| 1-2110 | Sub-34 | 3,4-diClPh | SO$_2$ | Single bond | Sub-30 |
| 1-2111 | Sub-34 | 3,4-diClPh | SO$_2$ | Single bond | Sub-31 |
| 1-2112 | Sub-34 | 3,4-diClPh | SO$_2$ | Single bond | Sub-32 |
| 1-2113 | Sub-35 | 3,4-diClPh | SO$_2$ | Single bond | Sub-1 |
| 1-2114 | Sub-35 | 3,4-diClPh | SO$_2$ | Single bond | Sub-2 |
| 1-2115 | Sub-35 | 3,4-diClPh | SO$_2$ | Single bond | Sub-3 |
| 1-2116 | Sub-35 | 3,4-diClPh | SO$_2$ | Single bond | Sub-4 |
| 1-2117 | Sub-35 | 3,4-diClPh | SO$_2$ | Single bond | Sub-5 |
| 1-2118 | Sub-35 | 3,4-diClPh | SO$_2$ | Single bond | Sub-6 |
| 1-2119 | Sub-35 | 3,4-diClPh | SO$_2$ | Single bond | Sub-7 |
| 1-2121 | Sub-35 | 3,4-diClPh | SO$_2$ | Single bond | Sub-8 |
| 1-2121 | Sub-35 | 3,4-diClPh | SO$_2$ | Single bond | Sub-9 |
| 1-2122 | Sub-35 | 3,4-diClPh | SO$_2$ | Single bond | Sub-10 |
| 1-2123 | Sub-35 | 3,4-diClPh | SO$_2$ | Single bond | Sub-11 |
| 1-2124 | Sub-35 | 3,4-diClPh | SO$_2$ | Single bond | Sub-12 |
| 1-2125 | Sub-35 | 3,4-diClPh | SO$_2$ | Single bond | Sub-13 |
| 1-2126 | Sub-35 | 3,4-diClPh | SO$_2$ | Single bond | Sub-14 |
| 1-2127 | Sub-35 | 3,4-diClPh | SO$_2$ | Single bond | Sub-15 |
| 1-2128 | Sub-35 | 3,4-diClPh | SO$_2$ | Single bond | Sub-16 |
| 1-2129 | Sub-35 | 3,4-diClPh | SO$_2$ | Single bond | Sub-17 |
| 1-2130 | Sub-35 | 3,4-diClPh | SO$_2$ | Single bond | Sub-18 |
| 1-2131 | Sub-35 | 3,4-diClPh | SO$_2$ | Single bond | Sub-19 |
| 1-2132 | Sub-35 | 3,4-diClPh | SO$_2$ | Single bond | Sub-20 |
| 1-2133 | Sub-35 | 3,4-diClPh | SO$_2$ | Single bond | Sub-21 |
| 1-2134 | Sub-35 | 3,4-diClPh | SO$_2$ | Single bond | Sub-22 |
| 1-2135 | Sub-35 | 3,4-diClPh | SO$_2$ | Single bond | Sub-23 |
| 1-2136 | Sub-35 | 3,4-diClPh | SO$_2$ | Single bond | Sub-24 |
| 1-2137 | Sub-35 | 3,4-diClPh | SO$_2$ | Single bond | Sub-25 |
| 1-2138 | Sub-35 | 3,4-diClPh | SO$_2$ | Single bond | Sub-26 |
| 1-2139 | Sub-35 | 3,4-diClPh | SO$_2$ | Single bond | Sub-27 |
| 1-2140 | Sub-35 | 3,4-diClPh | SO$_2$ | Single bond | Sub-28 |
| 1-2141 | Sub-35 | 3,4-diClPh | SO$_2$ | Single bond | Sub-29 |
| 1-2142 | Sub-35 | 3,4-diClPh | SO$_2$ | Single bond | Sub-30 |
| 1-2143 | Sub-35 | 3,4-diClPh | SO$_2$ | Single bond | Sub-31 |
| 1-2144 | Sub-35 | 3,4-diClPh | SO$_2$ | Single bond | Sub-32 |
| 1-2145 | Sub-36 | 3,4-diClPh | SO$_2$ | Single bond | Sub-1 |
| 1-2146 | Sub-36 | 3,4-diClPh | SO$_2$ | Single bond | Sub-2 |
| 1-2147 | Sub-36 | 3,4-diClPh | SO$_2$ | Single bond | Sub-3 |
| 1-2148 | Sub-36 | 3,4-diClPh | SO$_2$ | Single bond | Sub-4 |
| 1-2149 | Sub-36 | 3,4-diClPh | SO$_2$ | Single bond | Sub-5 |
| 1-2150 | Sub-36 | 3,4-diClPh | SO$_2$ | Single bond | Sub-6 |
| 1-2151 | Sub-36 | 3,4-diClPh | SO$_2$ | Single bond | Sub-7 |
| 1-2152 | Sub-36 | 3,4-diClPh | SO$_2$ | Single bond | Sub-8 |
| 1-2153 | Sub-36 | 3,4-diClPh | SO$_2$ | Single bond | Sub-9 |
| 1-2154 | Sub-36 | 3,4-diClPh | SO$_2$ | Single bond | Sub-10 |
| 1-2155 | Sub-36 | 3,4-diClPh | SO$_2$ | Single bond | Sub-11 |
| 1-2156 | Sub-36 | 3,4-diClPh | SO$_2$ | Single bond | Sub-12 |
| 1-2157 | Sub-36 | 3,4-diClPh | SO$_2$ | Single bond | Sub-13 |
| 1-2158 | Sub-36 | 3,4-diClPh | SO$_2$ | Single bond | Sub-14 |
| 1-2159 | Sub-36 | 3,4-diClPh | SO$_2$ | Single bond | Sub-15 |
| 1-2160 | Sub-36 | 3,4-diClPh | SO$_2$ | Single bond | Sub-16 |
| 1-2161 | Sub-36 | 3,4-diClPh | SO$_2$ | Single bond | Sub-17 |
| 1-2162 | Sub-36 | 3,4-diClPh | SO$_2$ | Single bond | Sub-18 |
| 1-2163 | Sub-36 | 3,4-diClPh | SO$_2$ | Single bond | Sub-19 |
| 1-2164 | Sub-36 | 3,4-diClPh | SO$_2$ | Single bond | Sub-20 |
| 1-2165 | Sub-36 | 3,4-diClPh | SO$_2$ | Single bond | Sub-21 |
| 1-2166 | Sub-36 | 3,4-diClPh | SO$_2$ | Single bond | Sub-22 |
| 1-2167 | Sub-36 | 3,4-diClPh | SO$_2$ | Single bond | Sub-23 |
| 1-2168 | Sub-36 | 3,4-diClPh | SO$_2$ | Single bond | Sub-24 |
| 1-2169 | Sub-36 | 3,4-diClPh | SO$_2$ | Single bond | Sub-25 |
| 1-2170 | Sub-36 | 3,4-diClPh | SO$_2$ | Single bond | Sub-26 |
| 1-2171 | Sub-36 | 3,4-diClPh | SO$_2$ | Single bond | Sub-27 |
| 1-2172 | Sub-36 | 3,4-diClPh | SO$_2$ | Single bond | Sub-28 |
| 1-2173 | Sub-36 | 3,4-diClPh | SO$_2$ | Single bond | Sub-29 |
| 1-2174 | Sub-36 | 3,4-diClPh | SO$_2$ | Single bond | Sub-30 |
| 1-2175 | Sub-36 | 3,4-diClPh | SO$_2$ | Single bond | Sub-31 |
| 1-2176 | Sub-36 | 3,4-diClPh | SO$_2$ | Single bond | Sub-32 |
| 1-2177 | Sub-37 | 3,4-diClPh | SO$_2$ | Single bond | Sub-1 |
| 1-2178 | Sub-37 | 3,4-diClPh | SO$_2$ | Single bond | Sub-2 |
| 1-2179 | Sub-37 | 3,4-diClPh | SO$_2$ | Single bond | Sub-3 |
| 1-2180 | Sub-37 | 3,4-diClPh | SO$_2$ | Single bond | Sub-4 |
| 1-2181 | Sub-37 | 3,4-diClPh | SO$_2$ | Single bond | Sub-5 |
| 1-2182 | Sub-37 | 3,4-diClPh | SO$_2$ | Single bond | Sub-6 |
| 1-2183 | Sub-37 | 3,4-diClPh | SO$_2$ | Single bond | Sub-7 |
| 1-2184 | Sub-37 | 3,4-diClPh | SO$_2$ | Single bond | Sub-8 |
| 1-2185 | Sub-37 | 3,4-diClPh | SO$_2$ | Single bond | Sub-9 |
| 1-2186 | Sub-37 | 3,4-diClPh | SO$_2$ | Single bond | Sub-10 |
| 1-2187 | Sub-37 | 3,4-diClPh | SO$_2$ | Single bond | Sub-11 |
| 1-2188 | Sub-37 | 3,4-diClPh | SO$_2$ | Single bond | Sub-12 |
| 1-2189 | Sub-37 | 3,4-diClPh | SO$_2$ | Single bond | Sub-13 |
| 1-2190 | Sub-37 | 3,4-diClPh | SO$_2$ | Single bond | Sub-14 |
| 1-2191 | Sub-37 | 3,4-diClPh | SO$_2$ | Single bond | Sub-15 |
| 1-2192 | Sub-37 | 3,4-diClPh | SO$_2$ | Single bond | Sub-16 |
| 1-2193 | Sub-37 | 3,4-diClPh | SO$_2$ | Single bond | Sub-17 |
| 1-2194 | Sub-37 | 3,4-diClPh | SO$_2$ | Single bond | Sub-18 |
| 1-2195 | Sub-37 | 3,4-diClPh | SO$_2$ | Single bond | Sub-19 |
| 1-2196 | Sub-37 | 3,4-diClPh | SO$_2$ | Single bond | Sub-20 |
| 1-2197 | Sub-37 | 3,4-diClPh | SO$_2$ | Single bond | Sub-21 |
| 1-2198 | Sub-37 | 3,4-diClPh | SO$_2$ | Single bond | Sub-22 |
| 1-2199 | Sub-37 | 3,4-diClPh | SO$_2$ | Single bond | Sub-23 |
| 1-2200 | Sub-37 | 3,4-diClPh | SO$_2$ | Single bond | Sub-24 |
| 1-2201 | Sub-37 | 3,4-diClPh | SO$_2$ | Single bond | Sub-25 |
| 1-2202 | Sub-37 | 3,4-diClPh | SO$_2$ | Single bond | Sub-26 |
| 1-2203 | Sub-37 | 3,4-diClPh | SO$_2$ | Single bond | Sub-27 |
| 1-2204 | Sub-37 | 3,4-diClPh | SO$_2$ | Single bond | Sub-28 |
| 1-2205 | Sub-37 | 3,4-diClPh | SO$_2$ | Single bond | Sub-29 |
| 1-2206 | Sub-37 | 3,4-diClPh | SO$_2$ | Single bond | Sub-30 |
| 1-2207 | Sub-37 | 3,4-diClPh | SO$_2$ | Single bond | Sub-31 |
| 1-2208 | Sub-37 | 3,4-diClPh | SO$_2$ | Single bond | Sub-32 |
| 1-2209 | Sub-38 | 3,4-diClPh | SO$_2$ | Single bond | Sub-1 |
| 1-2210 | Sub-38 | 3,4-diClPh | SO$_2$ | Single bond | Sub-2 |
| 1-2211 | Sub-38 | 3,4-diClPh | SO$_2$ | Single bond | Sub-3 |
| 1-2212 | Sub-38 | 3,4-diClPh | SO$_2$ | Single bond | Sub-4 |
| 1-2213 | Sub-38 | 3,4-diClPh | SO$_2$ | Single bond | Sub-5 |
| 1-2214 | Sub-38 | 3,4-diClPh | SO$_2$ | Single bond | Sub-6 |
| 1-2215 | Sub-38 | 3,4-diClPh | SO$_2$ | Single bond | Sub-7 |
| 1-2216 | Sub-38 | 3,4-diClPh | SO$_2$ | Single bond | Sub-8 |
| 1-2217 | Sub-38 | 3,4-diClPh | SO$_2$ | Single bond | Sub-9 |
| 1-2218 | Sub-38 | 3,4-diClPh | SO$_2$ | Single bond | Sub-10 |
| 1-2219 | Sub-38 | 3,4-diClPh | SO$_2$ | Single bond | Sub-11 |
| 1-2221 | Sub-38 | 3,4-diClPh | SO$_2$ | Single bond | Sub-12 |
| 1-2221 | Sub-38 | 3,4-diClPh | SO$_2$ | Single bond | Sub-13 |
| 1-2222 | Sub-38 | 3,4-diClPh | SO$_2$ | Single bond | Sub-14 |
| 1-2223 | Sub-38 | 3,4-diClPh | SO$_2$ | Single bond | Sub-15 |
| 1-2224 | Sub-38 | 3,4-diClPh | SO$_2$ | Single bond | Sub-16 |
| 1-2225 | Sub-38 | 3,4-diClPh | SO$_2$ | Single bond | Sub-17 |
| 1-2226 | Sub-38 | 3,4-diClPh | SO$_2$ | Single bond | Sub-18 |
| 1-2227 | Sub-38 | 3,4-diClPh | SO$_2$ | Single bond | Sub-19 |
| 1-2228 | Sub-38 | 3,4-diClPh | SO$_2$ | Single bond | Sub-20 |
| 1-2229 | Sub-38 | 3,4-diClPh | SO$_2$ | Single bond | Sub-21 |
| 1-2230 | Sub-38 | 3,4-diClPh | SO$_2$ | Single bond | Sub-22 |
| 1-2231 | Sub-38 | 3,4-diClPh | SO$_2$ | Single bond | Sub-23 |
| 1-2232 | Sub-38 | 3,4-diClPh | SO$_2$ | Single bond | Sub-24 |
| 1-2233 | Sub-38 | 3,4-diClPh | SO$_2$ | Single bond | Sub-25 |
| 1-2234 | Sub-38 | 3,4-diClPh | SO$_2$ | Single bond | Sub-26 |
| 1-2235 | Sub-38 | 3,4-diClPh | SO$_2$ | Single bond | Sub-27 |
| 1-2236 | Sub-38 | 3,4-diClPh | SO$_2$ | Single bond | Sub-28 |
| 1-2237 | Sub-38 | 3,4-diClPh | SO$_2$ | Single bond | Sub-29 |
| 1-2238 | Sub-38 | 3,4-diClPh | SO$_2$ | Single bond | Sub-30 |
| 1-2239 | Sub-38 | 3,4-diClPh | SO$_2$ | Single bond | Sub-31 |
| 1-2240 | Sub-38 | 3,4-diClPh | SO$_2$ | Single bond | Sub-32 |
| 1-2241 | Sub-39 | 3,4-diClPh | SO$_2$ | Single bond | Sub-1 |
| 1-2242 | Sub-39 | 3,4-diClPh | SO$_2$ | Single bond | Sub-2 |
| 1-2243 | Sub-39 | 3,4-diClPh | SO$_2$ | Single bond | Sub-3 |
| 1-2244 | Sub-39 | 3,4-diClPh | SO$_2$ | Single bond | Sub-4 |
| 1-2245 | Sub-39 | 3,4-diClPh | SO$_2$ | Single bond | Sub-5 |
| 1-2246 | Sub-39 | 3,4-diClPh | SO$_2$ | Single bond | Sub-6 |
| 1-2247 | Sub-39 | 3,4-diClPh | SO$_2$ | Single bond | Sub-7 |
| 1-2248 | Sub-39 | 3,4-diClPh | SO$_2$ | Single bond | Sub-8 |
| 1-2249 | Sub-39 | 3,4-diClPh | SO$_2$ | Single bond | Sub-9 |
| 1-2250 | Sub-39 | 3,4-diClPh | SO$_2$ | Single bond | Sub-10 |
| 1-2251 | Sub-39 | 3,4-diClPh | SO$_2$ | Single bond | Sub-11 |
| 1-2252 | Sub-39 | 3,4-diClPh | SO$_2$ | Single bond | Sub-12 |
| 1-2253 | Sub-39 | 3,4-diClPh | SO$_2$ | Single bond | Sub-13 |

TABLE 1-continued

| Cpd. No. | R¹ | R² | A | B | Z |
|---|---|---|---|---|---|
| 1-2254 | Sub-39 | 3,4-diClPh | SO$_2$ | Single bond | Sub-14 |
| 1-2255 | Sub-39 | 3,4-diClPh | SO$_2$ | Single bond | Sub-15 |
| 1-2256 | Sub-39 | 3,4-diClPh | SO$_2$ | Single bond | Sub-16 |
| 1-2257 | Sub-39 | 3,4-diClPh | SO$_2$ | Single bond | Sub-17 |
| 1-2258 | Sub-39 | 3,4-diClPh | SO$_2$ | Single bond | Sub-18 |
| 1-2259 | Sub-39 | 3,4-diClPh | SO$_2$ | Single bond | Sub-19 |
| 1-2260 | Sub-39 | 3,4-diClPh | SO$_2$ | Single bond | Sub-20 |
| 1-2261 | Sub-39 | 3,4-diClPh | SO$_2$ | Single bond | Sub-21 |
| 1-2262 | Sub-39 | 3,4-diClPh | SO$_2$ | Single bond | Sub-22 |
| 1-2263 | Sub-39 | 3,4-diClPh | SO$_2$ | Single bond | Sub-23 |
| 1-2264 | Sub-39 | 3,4-diClPh | SO$_2$ | Single bond | Sub-24 |
| 1-2265 | Sub-39 | 3,4-diClPh | SO$_2$ | Single bond | Sub-25 |
| 1-2266 | Sub-39 | 3,4-diClPh | SO$_2$ | Single bond | Sub-26 |
| 1-2267 | Sub-39 | 3,4-diClPh | SO$_2$ | Single bond | Sub-27 |
| 1-2268 | Sub-39 | 3,4-diClPh | SO$_2$ | Single bond | Sub-28 |
| 1-2269 | Sub-39 | 3,4-diClPh | SO$_2$ | Single bond | Sub-29 |
| 1-2270 | Sub-39 | 3,4-diClPh | SO$_2$ | Single bond | Sub-30 |
| 1-2271 | Sub-39 | 3,4-diClPh | SO$_2$ | Single bond | Sub-31 |
| 1-2272 | Sub-39 | 3,4-diClPh | SO$_2$ | Single bond | Sub-32 |
| 1-2273 | Sub-40 | 3,4-diClPh | SO$_2$ | Single bond | Sub-1 |
| 1-2274 | Sub-40 | 3,4-diClPh | SO$_2$ | Single bond | Sub-2 |
| 1-2275 | Sub-40 | 3,4-diClPh | SO$_2$ | Single bond | Sub-3 |
| 1-2276 | Sub-40 | 3,4-diClPh | SO$_2$ | Single bond | Sub-4 |
| 1-2277 | Sub-40 | 3,4-diClPh | SO$_2$ | Single bond | Sub-5 |
| 1-2278 | Sub-40 | 3,4-diClPh | SO$_2$ | Single bond | Sub-6 |
| 1-2279 | Sub-40 | 3,4-diClPh | SO$_2$ | Single bond | Sub-7 |
| 1-2280 | Sub-40 | 3,4-diClPh | SO$_2$ | Single bond | Sub-8 |
| 1-2281 | Sub-40 | 3,4-diClPh | SO$_2$ | Single bond | Sub-9 |
| 1-2282 | Sub-40 | 3,4-diClPh | SO$_2$ | Single bond | Sub-10 |
| 1-2283 | Sub-40 | 3,4-diClPh | SO$_2$ | Single bond | Sub-11 |
| 1-2284 | Sub-40 | 3,4-diClPh | SO$_2$ | Single bond | Sub-12 |
| 1-2285 | Sub-40 | 3,4-diClPh | SO$_2$ | Single bond | Sub-13 |
| 1-2286 | Sub-40 | 3,4-diClPh | SO$_2$ | Single bond | Sub-14 |
| 1-2287 | Sub-40 | 3,4-diClPh | SO$_2$ | Single bond | Sub-15 |
| 1-2288 | Sub-40 | 3,4-diClPh | SO$_2$ | Single bond | Sub-16 |
| 1-2289 | Sub-40 | 3,4-diClPh | SO$_2$ | Single bond | Sub-17 |
| 1-2290 | Sub-40 | 3,4-diClPh | SO$_2$ | Single bond | Sub-18 |
| 1-2291 | Sub-40 | 3,4-diClPh | SO$_2$ | Single bond | Sub-19 |
| 1-2292 | Sub-40 | 3,4-diClPh | SO$_2$ | Single bond | Sub-20 |
| 1-2293 | Sub-40 | 3,4-diClPh | SO$_2$ | Single bond | Sub-21 |
| 1-2294 | Sub-40 | 3,4-diClPh | SO$_2$ | Single bond | Sub-22 |
| 1-2295 | Sub-40 | 3,4-diClPh | SO$_2$ | Single bond | Sub-23 |
| 1-2296 | Sub-40 | 3,4-diClPh | SO$_2$ | Single bond | Sub-24 |
| 1-2297 | Sub-40 | 3,4-diClPh | SO$_2$ | Single bond | Sub-25 |
| 1-2298 | Sub-40 | 3,4-diClPh | SO$_2$ | Single bond | Sub-26 |
| 1-2299 | Sub-40 | 3,4-diClPh | SO$_2$ | Single bond | Sub-27 |
| 1-2300 | Sub-40 | 3,4-diClPh | SO$_2$ | Single bond | Sub-28 |
| 1-2301 | Sub-40 | 3,4-diClPh | SO$_2$ | Single bond | Sub-29 |
| 1-2302 | Sub-40 | 3,4-diClPh | SO$_2$ | Single bond | Sub-30 |
| 1-2303 | Sub-40 | 3,4-diClPh | SO$_2$ | Single bond | Sub-31 |
| 1-2304 | Sub-40 | 3,4-diClPh | SO$_2$ | Single bond | Sub-32 |
| 1-2305 | Sub-41 | 3,4-diClPh | SO$_2$ | Single bond | Sub-1 |
| 1-2306 | Sub-41 | 3,4-diClPh | SO$_2$ | Single bond | Sub-2 |
| 1-2307 | Sub-41 | 3,4-diClPh | SO$_2$ | Single bond | Sub-3 |
| 1-2308 | Sub-41 | 3,4-diClPh | SO$_2$ | Single bond | Sub-4 |
| 1-2309 | Sub-41 | 3,4-diClPh | SO$_2$ | Single bond | Sub-5 |
| 1-2310 | Sub-41 | 3,4-diClPh | SO$_2$ | Single bond | Sub-6 |
| 1-2311 | Sub-41 | 3,4-diClPh | SO$_2$ | Single bond | Sub-7 |
| 1-2312 | Sub-41 | 3,4-diClPh | SO$_2$ | Single bond | Sub-8 |
| 1-2313 | Sub-41 | 3,4-diClPh | SO$_2$ | Single bond | Sub-9 |
| 1-2314 | Sub-41 | 3,4-diClPh | SO$_2$ | Single bond | Sub-10 |
| 1-2315 | Sub-41 | 3,4-diClPh | SO$_2$ | Single bond | Sub-11 |
| 1-2316 | Sub-41 | 3,4-diClPh | SO$_2$ | Single bond | Sub-12 |
| 1-2317 | Sub-41 | 3,4-diClPh | SO$_2$ | Single bond | Sub-13 |
| 1-2318 | Sub-41 | 3,4-diClPh | SO$_2$ | Single bond | Sub-14 |
| 1-2319 | Sub-41 | 3,4-diClPh | SO$_2$ | Single bond | Sub-15 |
| 1-2321 | Sub-41 | 3,4-diClPh | SO$_2$ | Single bond | Sub-16 |
| 1-2321 | Sub-41 | 3,4-diClPh | SO$_2$ | Single bond | Sub-17 |
| 1-2322 | Sub-41 | 3,4-diClPh | SO$_2$ | Single bond | Sub-18 |
| 1-2323 | Sub-41 | 3,4-diClPh | SO$_2$ | Single bond | Sub-19 |
| 1-2324 | Sub-41 | 3,4-diClPh | SO$_2$ | Single bond | Sub-20 |
| 1-2325 | Sub-41 | 3,4-diClPh | SO$_2$ | Single bond | Sub-21 |
| 1-2326 | Sub-41 | 3,4-diClPh | SO$_2$ | Single bond | Sub-22 |
| 1-2327 | Sub-41 | 3,4-diClPh | SO$_2$ | Single bond | Sub-23 |
| 1-2328 | Sub-41 | 3,4-diClPh | SO$_2$ | Single bond | Sub-24 |
| 1-2329 | Sub-41 | 3,4-diClPh | SO$_2$ | Single bond | Sub-25 |
| 1-2330 | Sub-41 | 3,4-diClPh | SO$_2$ | Single bond | Sub-26 |
| 1-2331 | Sub-41 | 3,4-diClPh | SO$_2$ | Single bond | Sub-27 |
| 1-2332 | Sub-41 | 3,4-diClPh | SO$_2$ | Single bond | Sub-28 |
| 1-2333 | Sub-41 | 3,4-diClPh | SO$_2$ | Single bond | Sub-29 |
| 1-2334 | Sub-41 | 3,4-diClPh | SO$_2$ | Single bond | Sub-30 |
| 1-2335 | Sub-41 | 3,4-diClPh | SO$_2$ | Single bond | Sub-31 |
| 1-2336 | Sub-41 | 3,4-diClPh | SO$_2$ | Single bond | Sub-32 |
| 1-2337 | Sub-42 | 3,4-diClPh | SO$_2$ | Single bond | Sub-1 |
| 1-2338 | Sub-42 | 3,4-diClPh | SO$_2$ | Single bond | Sub-2 |
| 1-2339 | Sub-42 | 3,4-diClPh | SO$_2$ | Single bond | Sub-3 |
| 1-2340 | Sub-42 | 3,4-diClPh | SO$_2$ | Single bond | Sub-4 |
| 1-2341 | Sub-42 | 3,4-diClPh | SO$_2$ | Single bond | Sub-5 |
| 1-2342 | Sub-42 | 3,4-diClPh | SO$_2$ | Single bond | Sub-6 |
| 1-2343 | Sub-42 | 3,4-diClPh | SO$_2$ | Single bond | Sub-7 |
| 1-2344 | Sub-42 | 3,4-diClPh | SO$_2$ | Single bond | Sub-8 |
| 1-2345 | Sub-42 | 3,4-diClPh | SO$_2$ | Single bond | Sub-9 |
| 1-2346 | Sub-42 | 3,4-diClPh | SO$_2$ | Single bond | Sub-10 |
| 1-2347 | Sub-42 | 3,4-diClPh | SO$_2$ | Single bond | Sub-11 |
| 1-2348 | Sub-42 | 3,4-diClPh | SO$_2$ | Single bond | Sub-12 |
| 1-2349 | Sub-42 | 3,4-diClPh | SO$_2$ | Single bond | Sub-13 |
| 1-2350 | Sub-42 | 3,4-diClPh | SO$_2$ | Single bond | Sub-14 |
| 1-2351 | Sub-42 | 3,4-diClPh | SO$_2$ | Single bond | Sub-15 |
| 1-2352 | Sub-42 | 3,4-diClPh | SO$_2$ | Single bond | Sub-16 |
| 1-2353 | Sub-42 | 3,4-diClPh | SO$_2$ | Single bond | Sub-17 |
| 1-2354 | Sub-42 | 3,4-diClPh | SO$_2$ | Single bond | Sub-18 |
| 1-2355 | Sub-42 | 3,4-diClPh | SO$_2$ | Single bond | Sub-19 |
| 1-2356 | Sub-42 | 3,4-diClPh | SO$_2$ | Single bond | Sub-20 |
| 1-2357 | Sub-42 | 3,4-diClPh | SO$_2$ | Single bond | Sub-21 |
| 1-2358 | Sub-42 | 3,4-diClPh | SO$_2$ | Single bond | Sub-22 |
| 1-2359 | Sub-42 | 3,4-diClPh | SO$_2$ | Single bond | Sub-23 |
| 1-2360 | Sub-42 | 3,4-diClPh | SO$_2$ | Single bond | Sub-24 |
| 1-2361 | Sub-42 | 3,4-diClPh | SO$_2$ | Single bond | Sub-25 |
| 1-2362 | Sub-42 | 3,4-diClPh | SO$_2$ | Single bond | Sub-26 |
| 1-2363 | Sub-42 | 3,4-diClPh | SO$_2$ | Single bond | Sub-27 |
| 1-2364 | Sub-42 | 3,4-diClPh | SO$_2$ | Single bond | Sub-28 |
| 1-2365 | Sub-42 | 3,4-diClPh | SO$_2$ | Single bond | Sub-29 |
| 1-2366 | Sub-42 | 3,4-diClPh | SO$_2$ | Single bond | Sub-30 |
| 1-2367 | Sub-42 | 3,4-diClPh | SO$_2$ | Single bond | Sub-31 |
| 1-2368 | Sub-42 | 3,4-diClPh | SO$_2$ | Single bond | Sub-32 |
| 1-2369 | Sub-43 | 3,4-diClPh | SO$_2$ | Single bond | Sub-1 |
| 1-2370 | Sub-43 | 3,4-diClPh | SO$_2$ | Single bond | Sub-2 |
| 1-2371 | Sub-43 | 3,4-diClPh | SO$_2$ | Single bond | Sub-3 |
| 1-2372 | Sub-43 | 3,4-diClPh | SO$_2$ | Single bond | Sub-4 |
| 1-2373 | Sub-43 | 3,4-diClPh | SO$_2$ | Single bond | Sub-5 |
| 1-2374 | Sub-43 | 3,4-diClPh | SO$_2$ | Single bond | Sub-6 |
| 1-2375 | Sub-43 | 3,4-diClPh | SO$_2$ | Single bond | Sub-7 |
| 1-2376 | Sub-43 | 3,4-diClPh | SO$_2$ | Single bond | Sub-8 |
| 1-2377 | Sub-43 | 3,4-diClPh | SO$_2$ | Single bond | Sub-9 |
| 1-2378 | Sub-43 | 3,4-diClPh | SO$_2$ | Single bond | Sub-10 |
| 1-2379 | Sub-43 | 3,4-diClPh | SO$_2$ | Single bond | Sub-11 |
| 1-2380 | Sub-43 | 3,4-diClPh | SO$_2$ | Single bond | Sub-12 |
| 1-2381 | Sub-43 | 3,4-diClPh | SO$_2$ | Single bond | Sub-13 |
| 1-2382 | Sub-43 | 3,4-diClPh | SO$_2$ | Single bond | Sub-14 |
| 1-2383 | Sub-43 | 3,4-diClPh | SO$_2$ | Single bond | Sub-15 |
| 1-2384 | Sub-43 | 3,4-diClPh | SO$_2$ | Single bond | Sub-16 |
| 1-2385 | Sub-43 | 3,4-diClPh | SO$_2$ | Single bond | Sub-17 |
| 1-2386 | Sub-43 | 3,4-diClPh | SO$_2$ | Single bond | Sub-18 |
| 1-2387 | Sub-43 | 3,4-diClPh | SO$_2$ | Single bond | Sub-19 |
| 1-2388 | Sub-43 | 3,4-diClPh | SO$_2$ | Single bond | Sub-20 |
| 1-2389 | Sub-43 | 3,4-diClPh | SO$_2$ | Single bond | Sub-21 |
| 1-2390 | Sub-43 | 3,4-diClPh | SO$_2$ | Single bond | Sub-22 |
| 1-2391 | Sub-43 | 3,4-diClPh | SO$_2$ | Single bond | Sub-23 |
| 1-2392 | Sub-43 | 3,4-diClPh | SO$_2$ | Single bond | Sub-24 |
| 1-2393 | Sub-43 | 3,4-diClPh | SO$_2$ | Single bond | Sub-25 |
| 1-2394 | Sub-43 | 3,4-diClPh | SO$_2$ | Single bond | Sub-26 |
| 1-2395 | Sub-43 | 3,4-diClPh | SO$_2$ | Single bond | Sub-27 |
| 1-2396 | Sub-43 | 3,4-diClPh | SO$_2$ | Single bond | Sub-28 |
| 1-2397 | Sub-43 | 3,4-diClPh | SO$_2$ | Single bond | Sub-29 |
| 1-2398 | Sub-43 | 3,4-diClPh | SO$_2$ | Single bond | Sub-30 |
| 1-2399 | Sub-43 | 3,4-diClPh | SO$_2$ | Single bond | Sub-31 |
| 1-2400 | Sub-43 | 3,4-diClPh | SO$_2$ | Single bond | Sub-32 |
| 1-2401 | Sub-44 | 3,4-diClPh | SO$_2$ | Single bond | Sub-1 |
| 1-2402 | Sub-44 | 3,4-diClPh | SO$_2$ | Single bond | Sub-2 |
| 1-2403 | Sub-44 | 3,4-diClPh | SO$_2$ | Single bond | Sub-3 |
| 1-2404 | Sub-44 | 3,4-diClPh | SO$_2$ | Single bond | Sub-4 |
| 1-2405 | Sub-44 | 3,4-diClPh | SO$_2$ | Single bond | Sub-5 |

TABLE 1-continued

| Cpd. No. | R¹ | R² | A | B | Z |
|---|---|---|---|---|---|
| 1-2406 | Sub-44 | 3,4-diClPh | SO₂ | Single bond | Sub-6 |
| 1-2407 | Sub-44 | 3,4-diClPh | SO₂ | Single bond | Sub-7 |
| 1-2408 | Sub-44 | 3,4-diClPh | SO₂ | Single bond | Sub-8 |
| 1-2409 | Sub-44 | 3,4-diClPh | SO₂ | Single bond | Sub-9 |
| 1-2410 | Sub-44 | 3,4-diClPh | SO₂ | Single bond | Sub-10 |
| 1-2411 | Sub-44 | 3,4-diClPh | SO₂ | Single bond | Sub-11 |
| 1-2412 | Sub-44 | 3,4-diClPh | SO₂ | Single bond | Sub-12 |
| 1-2413 | Sub-44 | 3,4-diClPh | SO₂ | Single bond | Sub-13 |
| 1-2414 | Sub-44 | 3,4-diClPh | SO₂ | Single bond | Sub-14 |
| 1-2415 | Sub-44 | 3,4-diClPh | SO₂ | Single bond | Sub-15 |
| 1-2416 | Sub-44 | 3,4-diClPh | SO₂ | Single bond | Sub-16 |
| 1-2417 | Sub-44 | 3,4-diClPh | SO₂ | Single bond | Sub-17 |
| 1-2418 | Sub-44 | 3,4-diClPh | SO₂ | Single bond | Sub-18 |
| 1-2419 | Sub-44 | 3,4-diClPh | SO₂ | Single bond | Sub-19 |
| 1-2420 | Sub-44 | 3,4-diClPh | SO₂ | Single bond | Sub-20 |
| 1-2421 | Sub-44 | 3,4-diClPh | SO₂ | Single bond | Sub-21 |
| 1-2422 | Sub-44 | 3,4-diClPh | SO₂ | Single bond | Sub-22 |
| 1-2423 | Sub-44 | 3,4-diClPh | SO₂ | Single bond | Sub-23 |
| 1-2424 | Sub-44 | 3,4-diClPh | SO₂ | Single bond | Sub-24 |
| 1-2425 | Sub-44 | 3,4-diClPh | SO₂ | Single bond | Sub-25 |
| 1-2426 | Sub-44 | 3,4-diClPh | SO₂ | Single bond | Sub-26 |
| 1-2427 | Sub-44 | 3,4-diClPh | SO₂ | Single bond | Sub-27 |
| 1-2428 | Sub-44 | 3,4-diClPh | SO₂ | Single bond | Sub-28 |
| 1-2429 | Sub-44 | 3,4-diClPh | SO₂ | Single bond | Sub-29 |
| 1-2430 | Sub-44 | 3,4-diClPh | SO₂ | Single bond | Sub-30 |
| 1-2431 | Sub-44 | 3,4-diClPh | SO₂ | Single bond | Sub-31 |
| 1-2432 | Sub-44 | 3,4-diClPh | SO₂ | Single bond | Sub-32 |
| 1-2433 | Sub-45 | 3,4-diClPh | SO₂ | Single bond | Sub-1 |
| 1-2434 | Sub-45 | 3,4-diClPh | SO₂ | Single bond | Sub-2 |
| 1-2435 | Sub-45 | 3,4-diClPh | SO₂ | Single bond | Sub-3 |
| 1-2436 | Sub-45 | 3,4-diClPh | SO₂ | Single bond | Sub-4 |
| 1-2437 | Sub-45 | 3,4-diClPh | SO₂ | Single bond | Sub-5 |
| 1-2438 | Sub-45 | 3,4-diClPh | SO₂ | Single bond | Sub-6 |
| 1-2439 | Sub-45 | 3,4-diClPh | SO₂ | Single bond | Sub-7 |
| 1-2440 | Sub-45 | 3,4-diClPh | SO₂ | Single bond | Sub-8 |
| 1-2441 | Sub-45 | 3,4-diClPh | SO₂ | Single bond | Sub-9 |
| 1-2442 | Sub-45 | 3,4-diClPh | SO₂ | Single bond | Sub-10 |
| 1-2443 | Sub-45 | 3,4-diClPh | SO₂ | Single bond | Sub-11 |
| 1-2444 | Sub-45 | 3,4-diClPh | SO₂ | Single bond | Sub-12 |
| 1-2445 | Sub-45 | 3,4-diClPh | SO₂ | Single bond | Sub-13 |
| 1-2446 | Sub-45 | 3,4-diClPh | SO₂ | Single bond | Sub-14 |
| 1-2447 | Sub-45 | 3,4-diClPh | SO₂ | Single bond | Sub-15 |
| 1-2448 | Sub-45 | 3,4-diClPh | SO₂ | Single bond | Sub-16 |
| 1-2449 | Sub-45 | 3,4-diClPh | SO₂ | Single bond | Sub-17 |
| 1-2450 | Sub-45 | 3,4-diClPh | SO₂ | Single bond | Sub-18 |
| 1-2451 | Sub-45 | 3,4-diClPh | SO₂ | Single bond | Sub-19 |
| 1-2452 | Sub-45 | 3,4-diClPh | SO₂ | Single bond | Sub-20 |
| 1-2453 | Sub-45 | 3,4-diClPh | SO₂ | Single bond | Sub-21 |
| 1-2454 | Sub-45 | 3,4-diClPh | SO₂ | Single bond | Sub-22 |
| 1-2455 | Sub-45 | 3,4-diClPh | SO₂ | Single bond | Sub-23 |
| 1-2456 | Sub-45 | 3,4-diClPh | SO₂ | Single bond | Sub-24 |
| 1-2457 | Sub-45 | 3,4-diClPh | SO₂ | Single bond | Sub-25 |
| 1-2458 | Sub-45 | 3,4-diClPh | SO₂ | Single bond | Sub-26 |
| 1-2459 | Sub-45 | 3,4-diClPh | SO₂ | Single bond | Sub-27 |
| 1-2460 | Sub-45 | 3,4-diClPh | SO₂ | Single bond | Sub-28 |
| 1-2461 | Sub-45 | 3,4-diClPh | SO₂ | Single bond | Sub-29 |
| 1-2462 | Sub-45 | 3,4-diClPh | SO₂ | Single bond | Sub-30 |
| 1-2463 | Sub-45 | 3,4-diClPh | SO₂ | Single bond | Sub-31 |
| 1-2464 | Sub-45 | 3,4-diClPh | SO₂ | Single bond | Sub-32 |
| 1-2465 | Sub-46 | 3,4-diClPh | SO₂ | Single bond | Sub-1 |
| 1-2466 | Sub-46 | 3,4-diClPh | SO₂ | Single bond | Sub-2 |
| 1-2467 | Sub-46 | 3,4-diClPh | SO₂ | Single bond | Sub-3 |
| 1-2468 | Sub-46 | 3,4-diClPh | SO₂ | Single bond | Sub-4 |
| 1-2469 | Sub-46 | 3,4-diClPh | SO₂ | Single bond | Sub-5 |
| 1-2470 | Sub-46 | 3,4-diClPh | SO₂ | Single bond | Sub-6 |
| 1-2471 | Sub-46 | 3,4-diClPh | SO₂ | Single bond | Sub-7 |
| 1-2472 | Sub-46 | 3,4-diClPh | SO₂ | Single bond | Sub-8 |
| 1-2473 | Sub-46 | 3,4-diClPh | SO₂ | Single bond | Sub-9 |
| 1-2474 | Sub-46 | 3,4-diClPh | SO₂ | Single bond | Sub-10 |
| 1-2475 | Sub-46 | 3,4-diClPh | SO₂ | Single bond | Sub-11 |
| 1-2476 | Sub-46 | 3,4-diClPh | SO₂ | Single bond | Sub-12 |
| 1-2477 | Sub-46 | 3,4-diClPh | SO₂ | Single bond | Sub-13 |
| 1-2478 | Sub-46 | 3,4-diClPh | SO₂ | Single bond | Sub-14 |
| 1-2479 | Sub-46 | 3,4-diClPh | SO₂ | Single bond | Sub-15 |
| 1-2480 | Sub-46 | 3,4-diClPh | SO₂ | Single bond | Sub-16 |
| 1-2481 | Sub-46 | 3,4-diClPh | SO₂ | Single bond | Sub-17 |
| 1-2482 | Sub-46 | 3,4-diClPh | SO₂ | Single bond | Sub-18 |
| 1-2483 | Sub-46 | 3,4-diClPh | SO₂ | Single bond | Sub-19 |
| 1-2484 | Sub-46 | 3,4-diClPh | SO₂ | Single bond | Sub-20 |
| 1-2485 | Sub-46 | 3,4-diClPh | SO₂ | Single bond | Sub-21 |
| 1-2486 | Sub-46 | 3,4-diClPh | SO₂ | Single bond | Sub-22 |
| 1-2487 | Sub-46 | 3,4-diClPh | SO₂ | Single bond | Sub-23 |
| 1-2488 | Sub-46 | 3,4-diClPh | SO₂ | Single bond | Sub-24 |
| 1-2489 | Sub-46 | 3,4-diClPh | SO₂ | Single bond | Sub-25 |
| 1-2490 | Sub-46 | 3,4-diClPh | SO₂ | Single bond | Sub-26 |
| 1-2491 | Sub-46 | 3,4-diClPh | SO₂ | Single bond | Sub-27 |
| 1-2492 | Sub-46 | 3,4-diClPh | SO₂ | Single bond | Sub-28 |
| 1-2493 | Sub-46 | 3,4-diClPh | SO₂ | Single bond | Sub-29 |
| 1-2494 | Sub-46 | 3,4-diClPh | SO₂ | Single bond | Sub-30 |
| 1-2495 | Sub-46 | 3,4-diClPh | SO₂ | Single bond | Sub-31 |
| 1-2496 | Sub-46 | 3,4-diClPh | SO₂ | Single bond | Sub-32 |
| 1-2497 | Sub-47 | 3,4-diClPh | SO₂ | Single bond | Sub-1 |
| 1-2498 | Sub-47 | 3,4-diClPh | SO₂ | Single bond | Sub-2 |
| 1-2499 | Sub-47 | 3,4-diClPh | SO₂ | Single bond | Sub-3 |
| 1-2500 | Sub-47 | 3,4-diClPh | SO₂ | Single bond | Sub-4 |
| 1-2501 | Sub-47 | 3,4-diClPh | SO₂ | Single bond | Sub-5 |
| 1-2502 | Sub-47 | 3,4-diClPh | SO₂ | Single bond | Sub-6 |
| 1-2503 | Sub-47 | 3,4-diClPh | SO₂ | Single bond | Sub-7 |
| 1-2504 | Sub-47 | 3,4-diClPh | SO₂ | Single bond | Sub-8 |
| 1-2505 | Sub-47 | 3,4-diClPh | SO₂ | Single bond | Sub-9 |
| 1-2506 | Sub-47 | 3,4-diClPh | SO₂ | Single bond | Sub-10 |
| 1-2507 | Sub-47 | 3,4-diClPh | SO₂ | Single bond | Sub-11 |
| 1-2508 | Sub-47 | 3,4-diClPh | SO₂ | Single bond | Sub-12 |
| 1-2509 | Sub-47 | 3,4-diClPh | SO₂ | Single bond | Sub-13 |
| 1-2510 | Sub-47 | 3,4-diClPh | SO₂ | Single bond | Sub-14 |
| 1-2511 | Sub-47 | 3,4-diClPh | SO₂ | Single bond | Sub-15 |
| 1-2512 | Sub-47 | 3,4-diClPh | SO₂ | Single bond | Sub-16 |
| 1-2513 | Sub-47 | 3,4-diClPh | SO₂ | Single bond | Sub-17 |
| 1-2514 | Sub-47 | 3,4-diClPh | SO₂ | Single bond | Sub-18 |
| 1-2515 | Sub-47 | 3,4-diClPh | SO₂ | Single bond | Sub-19 |
| 1-2516 | Sub-47 | 3,4-diClPh | SO₂ | Single bond | Sub-20 |
| 1-2517 | Sub-47 | 3,4-diClPh | SO₂ | Single bond | Sub-21 |
| 1-2518 | Sub-47 | 3,4-diClPh | SO₂ | Single bond | Sub-22 |
| 1-2519 | Sub-47 | 3,4-diClPh | SO₂ | Single bond | Sub-23 |
| 1-2521 | Sub-47 | 3,4-diClPh | SO₂ | Single bond | Sub-24 |
| 1-2521 | Sub-47 | 3,4-diClPh | SO₂ | Single bond | Sub-25 |
| 1-2522 | Sub-47 | 3,4-diClPh | SO₂ | Single bond | Sub-26 |
| 1-2523 | Sub-47 | 3,4-diClPh | SO₂ | Single bond | Sub-27 |
| 1-2524 | Sub-47 | 3,4-diClPh | SO₂ | Single bond | Sub-28 |
| 1-2525 | Sub-47 | 3,4-diClPh | SO₂ | Single bond | Sub-29 |
| 1-2526 | Sub-47 | 3,4-diClPh | SO₂ | Single bond | Sub-30 |
| 1-2527 | Sub-47 | 3,4-diClPh | SO₂ | Single bond | Sub-31 |
| 1-2528 | Sub-47 | 3,4-diClPh | SO₂ | Single bond | Sub-32 |
| 1-2529 | Sub-48 | 3,4-diClPh | SO₂ | Single bond | Sub-1 |
| 1-2530 | Sub-48 | 3,4-diClPh | SO₂ | Single bond | Sub-2 |
| 1-2531 | Sub-48 | 3,4-diClPh | SO₂ | Single bond | Sub-3 |
| 1-2532 | Sub-48 | 3,4-diClPh | SO₂ | Single bond | Sub-4 |
| 1-2533 | Sub-48 | 3,4-diClPh | SO₂ | Single bond | Sub-5 |
| 1-2534 | Sub-48 | 3,4-diClPh | SO₂ | Single bond | Sub-6 |
| 1-2535 | Sub-48 | 3,4-diClPh | SO₂ | Single bond | Sub-7 |
| 1-2536 | Sub-48 | 3,4-diClPh | SO₂ | Single bond | Sub-8 |
| 1-2537 | Sub-48 | 3,4-diClPh | SO₂ | Single bond | Sub-9 |
| 1-2538 | Sub-48 | 3,4-diClPh | SO₂ | Single bond | Sub-10 |
| 1-2539 | Sub-48 | 3,4-diClPh | SO₂ | Single bond | Sub-11 |
| 1-2540 | Sub-48 | 3,4-diClPh | SO₂ | Single bond | Sub-12 |
| 1-2541 | Sub-48 | 3,4-diClPh | SO₂ | Single bond | Sub-13 |
| 1-2542 | Sub-48 | 3,4-diClPh | SO₂ | Single bond | Sub-14 |
| 1-2543 | Sub-48 | 3,4-diClPh | SO₂ | Single bond | Sub-15 |
| 1-2544 | Sub-48 | 3,4-diClPh | SO₂ | Single bond | Sub-16 |
| 1-2545 | Sub-48 | 3,4-diClPh | SO₂ | Single bond | Sub-17 |
| 1-2546 | Sub-48 | 3,4-diClPh | SO₂ | Single bond | Sub-18 |
| 1-2547 | Sub-48 | 3,4-diClPh | SO₂ | Single bond | Sub-19 |
| 1-2548 | Sub-48 | 3,4-diClPh | SO₂ | Single bond | Sub-20 |
| 1-2549 | Sub-48 | 3,4-diClPh | SO₂ | Single bond | Sub-21 |
| 1-2550 | Sub-48 | 3,4-diClPh | SO₂ | Single bond | Sub-22 |
| 1-2551 | Sub-48 | 3,4-diClPh | SO₂ | Single bond | Sub-23 |
| 1-2552 | Sub-48 | 3,4-diClPh | SO₂ | Single bond | Sub-24 |
| 1-2553 | Sub-48 | 3,4-diClPh | SO₂ | Single bond | Sub-25 |
| 1-2554 | Sub-48 | 3,4-diClPh | SO₂ | Single bond | Sub-26 |
| 1-2555 | Sub-48 | 3,4-diClPh | SO₂ | Single bond | Sub-27 |
| 1-2556 | Sub-48 | 3,4-diClPh | SO₂ | Single bond | Sub-28 |
| 1-2557 | Sub-48 | 3,4-diClPh | SO₂ | Single bond | Sub-29 |

TABLE 1-continued

| Cpd. No. | R¹ | R² | A | B | Z |
|---|---|---|---|---|---|
| 1-2558 | Sub-48 | 3,4-diClPh | SO₂ | Single bond | Sub-30 |
| 1-2559 | Sub-48 | 3,4-diClPh | SO₂ | Single bond | Sub-31 |
| 1-2560 | Sub-48 | 3,4-diClPh | SO₂ | Single bond | Sub-32 |
| 1-2561 | Sub-49 | 3,4-diClPh | SO₂ | Single bond | Sub-1 |
| 1-2562 | Sub-49 | 3,4-diClPh | SO₂ | Single bond | Sub-2 |
| 1-2563 | Sub-49 | 3,4-diClPh | SO₂ | Single bond | Sub-3 |
| 1-2564 | Sub-49 | 3,4-diClPh | SO₂ | Single bond | Sub-4 |
| 1-2565 | Sub-49 | 3,4-diClPh | SO₂ | Single bond | Sub-5 |
| 1-2566 | Sub-49 | 3,4-diClPh | SO₂ | Single bond | Sub-6 |
| 1-2567 | Sub-49 | 3,4-diClPh | SO₂ | Single bond | Sub-7 |
| 1-2568 | Sub-49 | 3,4-diClPh | SO₂ | Single bond | Sub-8 |
| 1-2569 | Sub-49 | 3,4-diClPh | SO₂ | Single bond | Sub-9 |
| 1-2570 | Sub-49 | 3,4-diClPh | SO₂ | Single bond | Sub-10 |
| 1-2571 | Sub-49 | 3,4-diClPh | SO₂ | Single bond | Sub-11 |
| 1-2572 | Sub-49 | 3,4-diClPh | SO₂ | Single bond | Sub-12 |
| 1-2573 | Sub-49 | 3,4-diClPh | SO₂ | Single bond | Sub-13 |
| 1-2574 | Sub-49 | 3,4-diClPh | SO₂ | Single bond | Sub-14 |
| 1-2575 | Sub-49 | 3,4-diClPh | SO₂ | Single bond | Sub-15 |
| 1-2576 | Sub-49 | 3,4-diClPh | SO₂ | Single bond | Sub-16 |
| 1-2577 | Sub-49 | 3,4-diClPh | SO₂ | Single bond | Sub-17 |
| 1-2578 | Sub-49 | 3,4-diClPh | SO₂ | Single bond | Sub-18 |
| 1-2579 | Sub-49 | 3,4-diClPh | SO₂ | Single bond | Sub-19 |
| 1-2580 | Sub-49 | 3,4-diClPh | SO₂ | Single bond | Sub-20 |
| 1-2581 | Sub-49 | 3,4-diClPh | SO₂ | Single bond | Sub-21 |
| 1-2582 | Sub-49 | 3,4-diClPh | SO₂ | Single bond | Sub-22 |
| 1-2583 | Sub-49 | 3,4-diClPh | SO₂ | Single bond | Sub-23 |
| 1-2584 | Sub-49 | 3,4-diClPh | SO₂ | Single bond | Sub-24 |
| 1-2585 | Sub-49 | 3,4-diClPh | SO₂ | Single bond | Sub-25 |
| 1-2586 | Sub-49 | 3,4-diClPh | SO₂ | Single bond | Sub-26 |
| 1-2587 | Sub-49 | 3,4-diClPh | SO₂ | Single bond | Sub-27 |
| 1-2588 | Sub-49 | 3,4-diClPh | SO₂ | Single bond | Sub-28 |
| 1-2589 | Sub-49 | 3,4-diClPh | SO₂ | Single bond | Sub-29 |
| 1-2590 | Sub-49 | 3,4-diClPh | SO₂ | Single bond | Sub-30 |
| 1-2591 | Sub-49 | 3,4-diClPh | SO₂ | Single bond | Sub-31 |
| 1-2592 | Sub-49 | 3,4-diClPh | SO₂ | Single bond | Sub-32 |
| 1-2593 | Sub-50 | 3,4-diClPh | SO₂ | Single bond | Sub-1 |
| 1-2594 | Sub-50 | 3,4-diClPh | SO₂ | Single bond | Sub-2 |
| 1-2595 | Sub-50 | 3,4-diClPh | SO₂ | Single bond | Sub-3 |
| 1-2596 | Sub-50 | 3,4-diClPh | SO₂ | Single bond | Sub-4 |
| 1-2597 | Sub-50 | 3,4-diClPh | SO₂ | Single bond | Sub-5 |
| 1-2598 | Sub-50 | 3,4-diClPh | SO₂ | Single bond | Sub-6 |
| 1-2599 | Sub-50 | 3,4-diClPh | SO₂ | Single bond | Sub-7 |
| 1-2600 | Sub-50 | 3,4-diClPh | SO₂ | Single bond | Sub-8 |
| 1-2601 | Sub-50 | 3,4-diClPh | SO₂ | Single bond | Sub-9 |
| 1-2602 | Sub-50 | 3,4-diClPh | SO₂ | Single bond | Sub-10 |
| 1-2603 | Sub-50 | 3,4-diClPh | SO₂ | Single bond | Sub-11 |
| 1-2604 | Sub-50 | 3,4-diClPh | SO₂ | Single bond | Sub-12 |
| 1-2605 | Sub-50 | 3,4-diClPh | SO₂ | Single bond | Sub-13 |
| 1-2606 | Sub-50 | 3,4-diClPh | SO₂ | Single bond | Sub-14 |
| 1-2607 | Sub-50 | 3,4-diClPh | SO₂ | Single bond | Sub-15 |
| 1-2608 | Sub-50 | 3,4-diClPh | SO₂ | Single bond | Sub-16 |
| 1-2609 | Sub-50 | 3,4-diClPh | SO₂ | Single bond | Sub-17 |
| 1-2610 | Sub-50 | 3,4-diClPh | SO₂ | Single bond | Sub-18 |
| 1-2611 | Sub-50 | 3,4-diClPh | SO₂ | Single bond | Sub-19 |
| 1-2612 | Sub-50 | 3,4-diClPh | SO₂ | Single bond | Sub-20 |
| 1-2613 | Sub-50 | 3,4-diClPh | SO₂ | Single bond | Sub-21 |
| 1-2614 | Sub-50 | 3,4-diClPh | SO₂ | Single bond | Sub-22 |
| 1-2615 | Sub-50 | 3,4-diClPh | SO₂ | Single bond | Sub-23 |
| 1-2616 | Sub-50 | 3,4-diClPh | SO₂ | Single bond | Sub-24 |
| 1-2617 | Sub-50 | 3,4-diClPh | SO₂ | Single bond | Sub-25 |
| 1-2618 | Sub-50 | 3,4-diClPh | SO₂ | Single bond | Sub-26 |
| 1-2619 | Sub-50 | 3,4-diClPh | SO₂ | Single bond | Sub-27 |
| 1-2621 | Sub-50 | 3,4-diClPh | SO₂ | Single bond | Sub-28 |
| 1-2621 | Sub-50 | 3,4-diClPh | SO₂ | Single bond | Sub-29 |
| 1-2622 | Sub-50 | 3,4-diClPh | SO₂ | Single bond | Sub-30 |
| 1-2623 | Sub-50 | 3,4-diClPh | SO₂ | Single bond | Sub-31 |
| 1-2624 | Sub-50 | 3,4-diClPh | SO₂ | Single bond | Sub-32 |
| 1-2625 | Sub-51 | 3,4-diClPh | SO₂ | Single bond | Sub-1 |
| 1-2626 | Sub-51 | 3,4-diClPh | SO₂ | Single bond | Sub-2 |
| 1-2627 | Sub-51 | 3,4-diClPh | SO₂ | Single bond | Sub-3 |
| 1-2628 | Sub-51 | 3,4-diClPh | SO₂ | Single bond | Sub-4 |
| 1-2629 | Sub-51 | 3,4-diClPh | SO₂ | Single bond | Sub-5 |
| 1-2630 | Sub-51 | 3,4-diClPh | SO₂ | Single bond | Sub-6 |
| 1-2631 | Sub-51 | 3,4-diClPh | SO₂ | Single bond | Sub-7 |
| 1-2632 | Sub-51 | 3,4-diClPh | SO₂ | Single bond | Sub-8 |
| 1-2633 | Sub-51 | 3,4-diClPh | SO₂ | Single bond | Sub-9 |
| 1-2634 | Sub-51 | 3,4-diClPh | SO₂ | Single bond | Sub-10 |
| 1-2635 | Sub-51 | 3,4-diClPh | SO₂ | Single bond | Sub-11 |
| 1-2636 | Sub-51 | 3,4-diClPh | SO₂ | Single bond | Sub-12 |
| 1-2637 | Sub-51 | 3,4-diClPh | SO₂ | Single bond | Sub-13 |
| 1-2638 | Sub-51 | 3,4-diClPh | SO₂ | Single bond | Sub-14 |
| 1-2639 | Sub-51 | 3,4-diClPh | SO₂ | Single bond | Sub-15 |
| 1-2640 | Sub-51 | 3,4-diClPh | SO₂ | Single bond | Sub-16 |
| 1-2641 | Sub-51 | 3,4-diClPh | SO₂ | Single bond | Sub-17 |
| 1-2642 | Sub-51 | 3,4-diClPh | SO₂ | Single bond | Sub-18 |
| 1-2643 | Sub-51 | 3,4-diClPh | SO₂ | Single bond | Sub-19 |
| 1-2644 | Sub-51 | 3,4-diClPh | SO₂ | Single bond | Sub-20 |
| 1-2645 | Sub-51 | 3,4-diClPh | SO₂ | Single bond | Sub-21 |
| 1-2646 | Sub-51 | 3,4-diClPh | SO₂ | Single bond | Sub-22 |
| 1-2647 | Sub-51 | 3,4-diClPh | SO₂ | Single bond | Sub-23 |
| 1-2648 | Sub-51 | 3,4-diClPh | SO₂ | Single bond | Sub-24 |
| 1-2649 | Sub-51 | 3,4-diClPh | SO₂ | Single bond | Sub-25 |
| 1-2650 | Sub-51 | 3,4-diClPh | SO₂ | Single bond | Sub-26 |
| 1-2651 | Sub-51 | 3,4-diClPh | SO₂ | Single bond | Sub-27 |
| 1-2652 | Sub-51 | 3,4-diClPh | SO₂ | Single bond | Sub-28 |
| 1-2653 | Sub-51 | 3,4-diClPh | SO₂ | Single bond | Sub-29 |
| 1-2654 | Sub-51 | 3,4-diClPh | SO₂ | Single bond | Sub-30 |
| 1-2655 | Sub-51 | 3,4-diClPh | SO₂ | Single bond | Sub-31 |
| 1-2656 | Sub-51 | 3,4-diClPh | SO₂ | Single bond | Sub-32 |
| 1-2657 | Sub-52 | 3,4-diClPh | SO₂ | Single bond | Sub-1 |
| 1-2658 | Sub-52 | 3,4-diClPh | SO₂ | Single bond | Sub-2 |
| 1-2659 | Sub-52 | 3,4-diClPh | SO₂ | Single bond | Sub-3 |
| 1-2660 | Sub-52 | 3,4-diClPh | SO₂ | Single bond | Sub-4 |
| 1-2661 | Sub-52 | 3,4-diClPh | SO₂ | Single bond | Sub-5 |
| 1-2662 | Sub-52 | 3,4-diClPh | SO₂ | Single bond | Sub-6 |
| 1-2663 | Sub-52 | 3,4-diClPh | SO₂ | Single bond | Sub-7 |
| 1-2664 | Sub-52 | 3,4-diClPh | SO₂ | Single bond | Sub-8 |
| 1-2665 | Sub-52 | 3,4-diClPh | SO₂ | Single bond | Sub-9 |
| 1-2666 | Sub-52 | 3,4-diClPh | SO₂ | Single bond | Sub-10 |
| 1-2667 | Sub-52 | 3,4-diClPh | SO₂ | Single bond | Sub-11 |
| 1-2668 | Sub-52 | 3,4-diClPh | SO₂ | Single bond | Sub-12 |
| 1-2669 | Sub-52 | 3,4-diClPh | SO₂ | Single bond | Sub-13 |
| 1-2670 | Sub-52 | 3,4-diClPh | SO₂ | Single bond | Sub-14 |
| 1-2671 | Sub-52 | 3,4-diClPh | SO₂ | Single bond | Sub-15 |
| 1-2672 | Sub-52 | 3,4-diClPh | SO₂ | Single bond | Sub-16 |
| 1-2673 | Sub-52 | 3,4-diClPh | SO₂ | Single bond | Sub-17 |
| 1-2674 | Sub-52 | 3,4-diClPh | SO₂ | Single bond | Sub-18 |
| 1-2675 | Sub-52 | 3,4-diClPh | SO₂ | Single bond | Sub-19 |
| 1-2676 | Sub-52 | 3,4-diClPh | SO₂ | Single bond | Sub-20 |
| 1-2677 | Sub-52 | 3,4-diClPh | SO₂ | Single bond | Sub-21 |
| 1-2678 | Sub-52 | 3,4-diClPh | SO₂ | Single bond | Sub-22 |
| 1-2679 | Sub-52 | 3,4-diClPh | SO₂ | Single bond | Sub-23 |
| 1-2680 | Sub-52 | 3,4-diClPh | SO₂ | Single bond | Sub-24 |
| 1-2681 | Sub-52 | 3,4-diClPh | SO₂ | Single bond | Sub-25 |
| 1-2682 | Sub-52 | 3,4-diClPh | SO₂ | Single bond | Sub-26 |
| 1-2683 | Sub-52 | 3,4-diClPh | SO₂ | Single bond | Sub-27 |
| 1-2684 | Sub-52 | 3,4-diClPh | SO₂ | Single bond | Sub-28 |
| 1-2685 | Sub-52 | 3,4-diClPh | SO₂ | Single bond | Sub-29 |
| 1-2686 | Sub-52 | 3,4-diClPh | SO₂ | Single bond | Sub-30 |
| 1-2687 | Sub-52 | 3,4-diClPh | SO₂ | Single bond | Sub-31 |
| 1-2688 | Sub-52 | 3,4-diClPh | SO₂ | Single bond | Sub-32 |
| 1-2689 | Sub-53 | 3,4-diClPh | SO₂ | Single bond | Sub-1 |
| 1-2690 | Sub-53 | 3,4-diClPh | SO₂ | Single bond | Sub-2 |
| 1-2691 | Sub-53 | 3,4-diClPh | SO₂ | Single bond | Sub-3 |
| 1-2692 | Sub-53 | 3,4-diClPh | SO₂ | Single bond | Sub-4 |
| 1-2693 | Sub-53 | 3,4-diClPh | SO₂ | Single bond | Sub-5 |
| 1-2694 | Sub-53 | 3,4-diClPh | SO₂ | Single bond | Sub-6 |
| 1-2695 | Sub-53 | 3,4-diClPh | SO₂ | Single bond | Sub-7 |
| 1-2696 | Sub-53 | 3,4-diClPh | SO₂ | Single bond | Sub-8 |
| 1-2697 | Sub-53 | 3,4-diClPh | SO₂ | Single bond | Sub-9 |
| 1-2698 | Sub-53 | 3,4-diClPh | SO₂ | Single bond | Sub-10 |
| 1-2699 | Sub-53 | 3,4-diClPh | SO₂ | Single bond | Sub-11 |
| 1-2700 | Sub-53 | 3,4-diClPh | SO₂ | Single bond | Sub-12 |
| 1-2701 | Sub-53 | 3,4-diClPh | SO₂ | Single bond | Sub-13 |
| 1-2702 | Sub-53 | 3,4-diClPh | SO₂ | Single bond | Sub-14 |
| 1-2703 | Sub-53 | 3,4-diClPh | SO₂ | Single bond | Sub-15 |
| 1-2704 | Sub-53 | 3,4-diClPh | SO₂ | Single bond | Sub-16 |
| 1-2705 | Sub-53 | 3,4-diClPh | SO₂ | Single bond | Sub-17 |
| 1-2706 | Sub-53 | 3,4-diClPh | SO₂ | Single bond | Sub-18 |
| 1-2707 | Sub-53 | 3,4-diClPh | SO₂ | Single bond | Sub-19 |
| 1-2708 | Sub-53 | 3,4-diClPh | SO₂ | Single bond | Sub-20 |
| 1-2709 | Sub-53 | 3,4-diClPh | SO₂ | Single bond | Sub-21 |

TABLE 1-continued

| Cpd. No. | R¹ | R² | A | B | Z |
|---|---|---|---|---|---|
| 1-2710 | Sub-53 | 3,4-diClPh | $SO_2$ | Single bond | Sub-22 |
| 1-2711 | Sub-53 | 3,4-diClPh | $SO_2$ | Single bond | Sub-23 |
| 1-2712 | Sub-53 | 3,4-diClPh | $SO_2$ | Single bond | Sub-24 |
| 1-2713 | Sub-53 | 3,4-diClPh | $SO_2$ | Single bond | Sub-25 |
| 1-2714 | Sub-53 | 3,4-diClPh | $SO_2$ | Single bond | Sub-26 |
| 1-2715 | Sub-53 | 3,4-diClPh | $SO_2$ | Single bond | Sub-27 |
| 1-2716 | Sub-53 | 3,4-diClPh | $SO_2$ | Single bond | Sub-28 |
| 1-2717 | Sub-53 | 3,4-diClPh | $SO_2$ | Single bond | Sub-29 |
| 1-2718 | Sub-53 | 3,4-diClPh | $SO_2$ | Single bond | Sub-30 |
| 1-2719 | Sub-53 | 3,4-diClPh | $SO_2$ | Single bond | Sub-31 |
| 1-2721 | Sub-53 | 3,4-diClPh | $SO_2$ | Single bond | Sub-32 |
| 1-2721 | Sub-54 | 3,4-diClPh | $SO_2$ | Single bond | Sub-1 |
| 1-2722 | Sub-54 | 3,4-diClPh | $SO_2$ | Single bond | Sub-2 |
| 1-2723 | Sub-54 | 3,4-diClPh | $SO_2$ | Single bond | Sub-3 |
| 1-2724 | Sub-54 | 3,4-diClPh | $SO_2$ | Single bond | Sub-4 |
| 1-2725 | Sub-54 | 3,4-diClPh | $SO_2$ | Single bond | Sub-5 |
| 1-2726 | Sub-54 | 3,4-diClPh | $SO_2$ | Single bond | Sub-6 |
| 1-2727 | Sub-54 | 3,4-diClPh | $SO_2$ | Single bond | Sub-7 |
| 1-2728 | Sub-54 | 3,4-diClPh | $SO_2$ | Single bond | Sub-8 |
| 1-2729 | Sub-54 | 3,4-diClPh | $SO_2$ | Single bond | Sub-9 |
| 1-2730 | Sub-54 | 3,4-diClPh | $SO_2$ | Single bond | Sub-10 |
| 1-2731 | Sub-54 | 3,4-diClPh | $SO_2$ | Single bond | Sub-11 |
| 1-2732 | Sub-54 | 3,4-diClPh | $SO_2$ | Single bond | Sub-12 |
| 1-2733 | Sub-54 | 3,4-diClPh | $SO_2$ | Single bond | Sub-13 |
| 1-2734 | Sub-54 | 3,4-diClPh | $SO_2$ | Single bond | Sub-14 |
| 1-2735 | Sub-54 | 3,4-diClPh | $SO_2$ | Single bond | Sub-15 |
| 1-2736 | Sub-54 | 3,4-diClPh | $SO_2$ | Single bond | Sub-16 |
| 1-2737 | Sub-54 | 3,4-diClPh | $SO_2$ | Single bond | Sub-17 |
| 1-2738 | Sub-54 | 3,4-diClPh | $SO_2$ | Single bond | Sub-18 |
| 1-2739 | Sub-54 | 3,4-diClPh | $SO_2$ | Single bond | Sub-19 |
| 1-2740 | Sub-54 | 3,4-diClPh | $SO_2$ | Single bond | Sub-20 |
| 1-2741 | Sub-54 | 3,4-diClPh | $SO_2$ | Single bond | Sub-21 |
| 1-2742 | Sub-54 | 3,4-diClPh | $SO_2$ | Single bond | Sub-22 |
| 1-2743 | Sub-54 | 3,4-diClPh | $SO_2$ | Single bond | Sub-23 |
| 1-2744 | Sub-54 | 3,4-diClPh | $SO_2$ | Single bond | Sub-24 |
| 1-2745 | Sub-54 | 3,4-diClPh | $SO_2$ | Single bond | Sub-25 |
| 1-2746 | Sub-54 | 3,4-diClPh | $SO_2$ | Single bond | Sub-26 |
| 1-2747 | Sub-54 | 3,4-diClPh | $SO_2$ | Single bond | Sub-27 |
| 1-2748 | Sub-54 | 3,4-diClPh | $SO_2$ | Single bond | Sub-28 |
| 1-2749 | Sub-54 | 3,4-diClPh | $SO_2$ | Single bond | Sub-29 |
| 1-2750 | Sub-54 | 3,4-diClPh | $SO_2$ | Single bond | Sub-30 |
| 1-2751 | Sub-54 | 3,4-diClPh | $SO_2$ | Single bond | Sub-31 |
| 1-2752 | Sub-54 | 3,4-diClPh | $SO_2$ | Single bond | Sub-32 |
| 1-2753 | Sub-55 | 3,4-diClPh | $SO_2$ | Single bond | Sub-1 |
| 1-2754 | Sub-55 | 3,4-diClPh | $SO_2$ | Single bond | Sub-2 |
| 1-2755 | Sub-55 | 3,4-diClPh | $SO_2$ | Single bond | Sub-3 |
| 1-2756 | Sub-55 | 3,4-diClPh | $SO_2$ | Single bond | Sub-4 |
| 1-2757 | Sub-55 | 3,4-diClPh | $SO_2$ | Single bond | Sub-5 |
| 1-2758 | Sub-55 | 3,4-diClPh | $SO_2$ | Single bond | Sub-6 |
| 1-2759 | Sub-55 | 3,4-diClPh | $SO_2$ | Single bond | Sub-7 |
| 1-2760 | Sub-55 | 3,4-diClPh | $SO_2$ | Single bond | Sub-8 |
| 1-2761 | Sub-55 | 3,4-diClPh | $SO_2$ | Single bond | Sub-9 |
| 1-2762 | Sub-55 | 3,4-diClPh | $SO_2$ | Single bond | Sub-10 |
| 1-2763 | Sub-55 | 3,4-diClPh | $SO_2$ | Single bond | Sub-11 |
| 1-2764 | Sub-55 | 3,4-diClPh | $SO_2$ | Single bond | Sub-12 |
| 1-2765 | Sub-55 | 3,4-diClPh | $SO_2$ | Single bond | Sub-13 |
| 1-2766 | Sub-55 | 3,4-diClPh | $SO_2$ | Single bond | Sub-14 |
| 1-2767 | Sub-55 | 3,4-diClPh | $SO_2$ | Single bond | Sub-15 |
| 1-2768 | Sub-55 | 3,4-diClPh | $SO_2$ | Single bond | Sub-16 |
| 1-2769 | Sub-55 | 3,4-diClPh | $SO_2$ | Single bond | Sub-17 |
| 1-2770 | Sub-55 | 3,4-diClPh | $SO_2$ | Single bond | Sub-18 |
| 1-2771 | Sub-55 | 3,4-diClPh | $SO_2$ | Single bond | Sub-19 |
| 1-2772 | Sub-55 | 3,4-diClPh | $SO_2$ | Single bond | Sub-20 |
| 1-2773 | Sub-55 | 3,4-diClPh | $SO_2$ | Single bond | Sub-21 |
| 1-2774 | Sub-55 | 3,4-diClPh | $SO_2$ | Single bond | Sub-22 |
| 1-2775 | Sub-55 | 3,4-diClPh | $SO_2$ | Single bond | Sub-23 |
| 1-2776 | Sub-55 | 3,4-diClPh | $SO_2$ | Single bond | Sub-24 |
| 1-2777 | Sub-55 | 3,4-diClPh | $SO_2$ | Single bond | Sub-25 |
| 1-2778 | Sub-55 | 3,4-diClPh | $SO_2$ | Single bond | Sub-26 |
| 1-2779 | Sub-55 | 3,4-diClPh | $SO_2$ | Single bond | Sub-27 |
| 1-2780 | Sub-55 | 3,4-diClPh | $SO_2$ | Single bond | Sub-28 |
| 1-2781 | Sub-55 | 3,4-diClPh | $SO_2$ | Single bond | Sub-29 |
| 1-2782 | Sub-55 | 3,4-diClPh | $SO_2$ | Single bond | Sub-30 |
| 1-2783 | Sub-55 | 3,4-diClPh | $SO_2$ | Single bond | Sub-31 |
| 1-2784 | Sub-55 | 3,4-diClPh | $SO_2$ | Single bond | Sub-32 |
| 1-2785 | Sub-56 | 3,4-diClPh | $SO_2$ | Single bond | Sub-1 |
| 1-2786 | Sub-56 | 3,4-diClPh | $SO_2$ | Single bond | Sub-2 |
| 1-2787 | Sub-56 | 3,4-diClPh | $SO_2$ | Single bond | Sub-3 |
| 1-2788 | Sub-56 | 3,4-diClPh | $SO_2$ | Single bond | Sub-4 |
| 1-2789 | Sub-56 | 3,4-diClPh | $SO_2$ | Single bond | Sub-5 |
| 1-2790 | Sub-56 | 3,4-diClPh | $SO_2$ | Single bond | Sub-6 |
| 1-2791 | Sub-56 | 3,4-diClPh | $SO_2$ | Single bond | Sub-7 |
| 1-2792 | Sub-56 | 3,4-diClPh | $SO_2$ | Single bond | Sub-8 |
| 1-2793 | Sub-56 | 3,4-diClPh | $SO_2$ | Single bond | Sub-9 |
| 1-2794 | Sub-56 | 3,4-diClPh | $SO_2$ | Single bond | Sub-10 |
| 1-2795 | Sub-56 | 3,4-diClPh | $SO_2$ | Single bond | Sub-11 |
| 1-2796 | Sub-56 | 3,4-diClPh | $SO_2$ | Single bond | Sub-12 |
| 1-2797 | Sub-56 | 3,4-diClPh | $SO_2$ | Single bond | Sub-13 |
| 1-2798 | Sub-56 | 3,4-diClPh | $SO_2$ | Single bond | Sub-14 |
| 1-2799 | Sub-56 | 3,4-diClPh | $SO_2$ | Single bond | Sub-15 |
| 1-2800 | Sub-56 | 3,4-diClPh | $SO_2$ | Single bond | Sub-16 |
| 1-2801 | Sub-56 | 3,4-diClPh | $SO_2$ | Single bond | Sub-17 |
| 1-2802 | Sub-56 | 3,4-diClPh | $SO_2$ | Single bond | Sub-18 |
| 1-2803 | Sub-56 | 3,4-diClPh | $SO_2$ | Single bond | Sub-19 |
| 1-2804 | Sub-56 | 3,4-diClPh | $SO_2$ | Single bond | Sub-20 |
| 1-2805 | Sub-56 | 3,4-diClPh | $SO_2$ | Single bond | Sub-21 |
| 1-2806 | Sub-56 | 3,4-diClPh | $SO_2$ | Single bond | Sub-22 |
| 1-2807 | Sub-56 | 3,4-diClPh | $SO_2$ | Single bond | Sub-23 |
| 1-2808 | Sub-56 | 3,4-diClPh | $SO_2$ | Single bond | Sub-24 |
| 1-2809 | Sub-56 | 3,4-diClPh | $SO_2$ | Single bond | Sub-25 |
| 1-2810 | Sub-56 | 3,4-diClPh | $SO_2$ | Single bond | Sub-26 |
| 1-2811 | Sub-56 | 3,4-diClPh | $SO_2$ | Single bond | Sub-27 |
| 1-2812 | Sub-56 | 3,4-diClPh | $SO_2$ | Single bond | Sub-28 |
| 1-2813 | Sub-56 | 3,4-diClPh | $SO_2$ | Single bond | Sub-29 |
| 1-2814 | Sub-56 | 3,4-diClPh | $SO_2$ | Single bond | Sub-30 |
| 1-2815 | Sub-56 | 3,4-diClPh | $SO_2$ | Single bond | Sub-31 |
| 1-2816 | Sub-56 | 3,4-diClPh | $SO_2$ | Single bond | Sub-32 |
| 1-2817 | Sub-57 | 3,4-diClPh | $SO_2$ | Single bond | Sub-1 |
| 1-2818 | Sub-57 | 3,4-diClPh | $SO_2$ | Single bond | Sub-2 |
| 1-2819 | Sub-57 | 3,4-diClPh | $SO_2$ | Single bond | Sub-3 |
| 1-2821 | Sub-57 | 3,4-diClPh | $SO_2$ | Single bond | Sub-4 |
| 1-2821 | Sub-57 | 3,4-diClPh | $SO_2$ | Single bond | Sub-5 |
| 1-2822 | Sub-57 | 3,4-diClPh | $SO_2$ | Single bond | Sub-6 |
| 1-2823 | Sub-57 | 3,4-diClPh | $SO_2$ | Single bond | Sub-7 |
| 1-2824 | Sub-57 | 3,4-diClPh | $SO_2$ | Single bond | Sub-8 |
| 1-2825 | Sub-57 | 3,4-diClPh | $SO_2$ | Single bond | Sub-9 |
| 1-2826 | Sub-57 | 3,4-diClPh | $SO_2$ | Single bond | Sub-10 |
| 1-2827 | Sub-57 | 3,4-diClPh | $SO_2$ | Single bond | Sub-11 |
| 1-2828 | Sub-57 | 3,4-diClPh | $SO_2$ | Single bond | Sub-12 |
| 1-2829 | Sub-57 | 3,4-diClPh | $SO_2$ | Single bond | Sub-13 |
| 1-2830 | Sub-57 | 3,4-diClPh | $SO_2$ | Single bond | Sub-14 |
| 1-2831 | Sub-57 | 3,4-diClPh | $SO_2$ | Single bond | Sub-15 |
| 1-2832 | Sub-57 | 3,4-diClPh | $SO_2$ | Single bond | Sub-16 |
| 1-2833 | Sub-57 | 3,4-diClPh | $SO_2$ | Single bond | Sub-17 |
| 1-2834 | Sub-57 | 3,4-diClPh | $SO_2$ | Single bond | Sub-18 |
| 1-2835 | Sub-57 | 3,4-diClPh | $SO_2$ | Single bond | Sub-19 |
| 1-2836 | Sub-57 | 3,4-diClPh | $SO_2$ | Single bond | Sub-20 |
| 1-2837 | Sub-57 | 3,4-diClPh | $SO_2$ | Single bond | Sub-21 |
| 1-2838 | Sub-57 | 3,4-diClPh | $SO_2$ | Single bond | Sub-22 |
| 1-2839 | Sub-57 | 3,4-diClPh | $SO_2$ | Single bond | Sub-23 |
| 1-2840 | Sub-57 | 3,4-diClPh | $SO_2$ | Single bond | Sub-24 |
| 1-2841 | Sub-57 | 3,4-diClPh | $SO_2$ | Single bond | Sub-25 |
| 1-2842 | Sub-57 | 3,4-diClPh | $SO_2$ | Single bond | Sub-26 |
| 1-2843 | Sub-57 | 3,4-diClPh | $SO_2$ | Single bond | Sub-27 |
| 1-2844 | Sub-57 | 3,4-diClPh | $SO_2$ | Single bond | Sub-28 |
| 1-2845 | Sub-57 | 3,4-diClPh | $SO_2$ | Single bond | Sub-29 |
| 1-2846 | Sub-57 | 3,4-diClPh | $SO_2$ | Single bond | Sub-30 |
| 1-2847 | Sub-57 | 3,4-diClPh | $SO_2$ | Single bond | Sub-31 |
| 1-2848 | Sub-57 | 3,4-diClPh | $SO_2$ | Single bond | Sub-32 |
| 1-2849 | Sub-58 | 3,4-diClPh | $SO_2$ | Single bond | Sub-1 |
| 1-2850 | Sub-58 | 3,4-diClPh | $SO_2$ | Single bond | Sub-2 |
| 1-2851 | Sub-58 | 3,4-diClPh | $SO_2$ | Single bond | Sub-3 |
| 1-2852 | Sub-58 | 3,4-diClPh | $SO_2$ | Single bond | Sub-4 |
| 1-2853 | Sub-58 | 3,4-diClPh | $SO_2$ | Single bond | Sub-5 |
| 1-2854 | Sub-58 | 3,4-diClPh | $SO_2$ | Single bond | Sub-6 |
| 1-2855 | Sub-58 | 3,4-diClPh | $SO_2$ | Single bond | Sub-7 |
| 1-2856 | Sub-58 | 3,4-diClPh | $SO_2$ | Single bond | Sub-8 |
| 1-2857 | Sub-58 | 3,4-diClPh | $SO_2$ | Single bond | Sub-9 |
| 1-2858 | Sub-58 | 3,4-diClPh | $SO_2$ | Single bond | Sub-10 |
| 1-2859 | Sub-58 | 3,4-diClPh | $SO_2$ | Single bond | Sub-11 |
| 1-2860 | Sub-58 | 3,4-diClPh | $SO_2$ | Single bond | Sub-12 |
| 1-2861 | Sub-58 | 3,4-diClPh | $SO_2$ | Single bond | Sub-13 |

TABLE 1-continued

| Cpd. No. | R¹ | R² | A | B | Z |
|---|---|---|---|---|---|
| 1-2862 | Sub-58 | 3,4-diClPh | SO₂ | Single bond | Sub-14 |
| 1-2863 | Sub-58 | 3,4-diClPh | SO₂ | Single bond | Sub-15 |
| 1-2864 | Sub-58 | 3,4-diClPh | SO₂ | Single bond | Sub-16 |
| 1-2865 | Sub-58 | 3,4-diClPh | SO₂ | Single bond | Sub-17 |
| 1-2866 | Sub-58 | 3,4-diClPh | SO₂ | Single bond | Sub-18 |
| 1-2867 | Sub-58 | 3,4-diClPh | SO₂ | Single bond | Sub-19 |
| 1-2868 | Sub-58 | 3,4-diClPh | SO₂ | Single bond | Sub-20 |
| 1-2869 | Sub-58 | 3,4-diClPh | SO₂ | Single bond | Sub-21 |
| 1-2870 | Sub-58 | 3,4-diClPh | SO₂ | Single bond | Sub-22 |
| 1-2871 | Sub-58 | 3,4-diClPh | SO₂ | Single bond | Sub-23 |
| 1-2872 | Sub-58 | 3,4-diClPh | SO₂ | Single bond | Sub-24 |
| 1-2873 | Sub-58 | 3,4-diClPh | SO₂ | Single bond | Sub-25 |
| 1-2874 | Sub-58 | 3,4-diClPh | SO₂ | Single bond | Sub-26 |
| 1-2875 | Sub-58 | 3,4-diClPh | SO₂ | Single bond | Sub-27 |
| 1-2876 | Sub-58 | 3,4-diClPh | SO₂ | Single bond | Sub-28 |
| 1-2877 | Sub-58 | 3,4-diClPh | SO₂ | Single bond | Sub-29 |
| 1-2878 | Sub-58 | 3,4-diClPh | SO₂ | Single bond | Sub-30 |
| 1-2879 | Sub-58 | 3,4-diClPh | SO₂ | Single bond | Sub-31 |
| 1-2880 | Sub-58 | 3,4-diClPh | SO₂ | Single bond | Sub-32 |
| 1-2881 | Sub-59 | 3,4-diClPh | SO₂ | Single bond | Sub-1 |
| 1-2882 | Sub-59 | 3,4-diClPh | SO₂ | Single bond | Sub-2 |
| 1-2883 | Sub-59 | 3,4-diClPh | SO₂ | Single bond | Sub-3 |
| 1-2884 | Sub-59 | 3,4-diClPh | SO₂ | Single bond | Sub-4 |
| 1-2885 | Sub-59 | 3,4-diClPh | SO₂ | Single bond | Sub-5 |
| 1-2886 | Sub-59 | 3,4-diClPh | SO₂ | Single bond | Sub-6 |
| 1-2887 | Sub-59 | 3,4-diClPh | SO₂ | Single bond | Sub-7 |
| 1-2888 | Sub-59 | 3,4-diClPh | SO₂ | Single bond | Sub-8 |
| 1-2889 | Sub-59 | 3,4-diClPh | SO₂ | Single bond | Sub-9 |
| 1-2890 | Sub-59 | 3,4-diClPh | SO₂ | Single bond | Sub-10 |
| 1-2891 | Sub-59 | 3,4-diClPh | SO₂ | Single bond | Sub-11 |
| 1-2892 | Sub-59 | 3,4-diClPh | SO₂ | Single bond | Sub-12 |
| 1-2893 | Sub-59 | 3,4-diClPh | SO₂ | Single bond | Sub-13 |
| 1-2894 | Sub-59 | 3,4-diClPh | SO₂ | Single bond | Sub-14 |
| 1-2895 | Sub-59 | 3,4-diClPh | SO₂ | Single bond | Sub-15 |
| 1-2896 | Sub-59 | 3,4-diClPh | SO₂ | Single bond | Sub-16 |
| 1-2897 | Sub-59 | 3,4-diClPh | SO₂ | Single bond | Sub-17 |
| 1-2898 | Sub-59 | 3,4-diClPh | SO₂ | Single bond | Sub-18 |
| 1-2899 | Sub-59 | 3,4-diClPh | SO₂ | Single bond | Sub-19 |
| 1-2900 | Sub-59 | 3,4-diClPh | SO₂ | Single bond | Sub-20 |
| 1-2901 | Sub-59 | 3,4-diClPh | SO₂ | Single bond | Sub-21 |
| 1-2902 | Sub-59 | 3,4-diClPh | SO₂ | Single bond | Sub-22 |
| 1-2903 | Sub-59 | 3,4-diClPh | SO₂ | Single bond | Sub-23 |
| 1-2904 | Sub-59 | 3,4-diClPh | SO₂ | Single bond | Sub-24 |
| 1-2905 | Sub-59 | 3,4-diClPh | SO₂ | Single bond | Sub-25 |
| 1-2906 | Sub-59 | 3,4-diClPh | SO₂ | Single bond | Sub-26 |
| 1-2907 | Sub-59 | 3,4-diClPh | SO₂ | Single bond | Sub-27 |
| 1-2908 | Sub-59 | 3,4-diClPh | SO₂ | Single bond | Sub-28 |
| 1-2909 | Sub-59 | 3,4-diClPh | SO₂ | Single bond | Sub-29 |
| 1-2910 | Sub-59 | 3,4-diClPh | SO₂ | Single bond | Sub-30 |
| 1-2911 | Sub-59 | 3,4-diClPh | SO₂ | Single bond | Sub-31 |
| 1-2912 | Sub-59 | 3,4-diClPh | SO₂ | Single bond | Sub-32 |
| 1-2913 | Sub-60 | 3,4-diClPh | SO₂ | Single bond | Sub-1 |
| 1-2914 | Sub-60 | 3,4-diClPh | SO₂ | Single bond | Sub-2 |
| 1-2915 | Sub-60 | 3,4-diClPh | SO₂ | Single bond | Sub-3 |
| 1-2916 | Sub-60 | 3,4-diClPh | SO₂ | Single bond | Sub-4 |
| 1-2917 | Sub-60 | 3,4-diClPh | SO₂ | Single bond | Sub-5 |
| 1-2918 | Sub-60 | 3,4-diClPh | SO₂ | Single bond | Sub-6 |
| 1-2919 | Sub-60 | 3,4-diClPh | SO₂ | Single bond | Sub-7 |
| 1-2921 | Sub-60 | 3,4-diClPh | SO₂ | Single bond | Sub-8 |
| 1-2921 | Sub-60 | 3,4-diClPh | SO₂ | Single bond | Sub-9 |
| 1-2922 | Sub-60 | 3,4-diClPh | SO₂ | Single bond | Sub-10 |
| 1-2923 | Sub-60 | 3,4-diClPh | SO₂ | Single bond | Sub-11 |
| 1-2924 | Sub-60 | 3,4-diClPh | SO₂ | Single bond | Sub-12 |
| 1-2925 | Sub-60 | 3,4-diClPh | SO₂ | Single bond | Sub-13 |
| 1-2926 | Sub-60 | 3,4-diClPh | SO₂ | Single bond | Sub-14 |
| 1-2927 | Sub-60 | 3,4-diClPh | SO₂ | Single bond | Sub-15 |
| 1-2928 | Sub-60 | 3,4-diClPh | SO₂ | Single bond | Sub-16 |
| 1-2929 | Sub-60 | 3,4-diClPh | SO₂ | Single bond | Sub-17 |
| 1-2930 | Sub-60 | 3,4-diClPh | SO₂ | Single bond | Sub-18 |
| 1-2931 | Sub-60 | 3,4-diClPh | SO₂ | Single bond | Sub-19 |
| 1-2932 | Sub-60 | 3,4-diClPh | SO₂ | Single bond | Sub-20 |
| 1-2933 | Sub-60 | 3,4-diClPh | SO₂ | Single bond | Sub-21 |
| 1-2934 | Sub-60 | 3,4-diClPh | SO₂ | Single bond | Sub-22 |
| 1-2935 | Sub-60 | 3,4-diClPh | SO₂ | Single bond | Sub-23 |
| 1-2936 | Sub-60 | 3,4-diClPh | SO₂ | Single bond | Sub-24 |
| 1-2937 | Sub-60 | 3,4-diClPh | SO₂ | Single bond | Sub-25 |
| 1-2938 | Sub-60 | 3,4-diClPh | SO₂ | Single bond | Sub-26 |
| 1-2939 | Sub-60 | 3,4-diClPh | SO₂ | Single bond | Sub-27 |
| 1-2940 | Sub-60 | 3,4-diClPh | SO₂ | Single bond | Sub-28 |
| 1-2941 | Sub-60 | 3,4-diClPh | SO₂ | Single bond | Sub-29 |
| 1-2942 | Sub-60 | 3,4-diClPh | SO₂ | Single bond | Sub-30 |
| 1-2943 | Sub-60 | 3,4-diClPh | SO₂ | Single bond | Sub-31 |
| 1-2944 | Sub-60 | 3,4-diClPh | SO₂ | Single bond | Sub-32 |
| 1-2945 | Sub-61 | 3,4-diClPh | SO₂ | Single bond | Sub-1 |
| 1-2946 | Sub-61 | 3,4-diClPh | SO₂ | Single bond | Sub-2 |
| 1-2947 | Sub-61 | 3,4-diClPh | SO₂ | Single bond | Sub-3 |
| 1-2948 | Sub-61 | 3,4-diClPh | SO₂ | Single bond | Sub-4 |
| 1-2949 | Sub-61 | 3,4-diClPh | SO₂ | Single bond | Sub-5 |
| 1-2950 | Sub-61 | 3,4-diClPh | SO₂ | Single bond | Sub-6 |
| 1-2951 | Sub-61 | 3,4-diClPh | SO₂ | Single bond | Sub-7 |
| 1-2952 | Sub-61 | 3,4-diClPh | SO₂ | Single bond | Sub-8 |
| 1-2953 | Sub-61 | 3,4-diClPh | SO₂ | Single bond | Sub-9 |
| 1-2954 | Sub-61 | 3,4-diClPh | SO₂ | Single bond | Sub-10 |
| 1-2955 | Sub-61 | 3,4-diClPh | SO₂ | Single bond | Sub-11 |
| 1-2956 | Sub-61 | 3,4-diClPh | SO₂ | Single bond | Sub-12 |
| 1-2957 | Sub-61 | 3,4-diClPh | SO₂ | Single bond | Sub-13 |
| 1-2958 | Sub-61 | 3,4-diClPh | SO₂ | Single bond | Sub-14 |
| 1-2959 | Sub-61 | 3,4-diClPh | SO₂ | Single bond | Sub-15 |
| 1-2960 | Sub-61 | 3,4-diClPh | SO₂ | Single bond | Sub-16 |
| 1-2961 | Sub-61 | 3,4-diClPh | SO₂ | Single bond | Sub-17 |
| 1-2962 | Sub-61 | 3,4-diClPh | SO₂ | Single bond | Sub-18 |
| 1-2963 | Sub-61 | 3,4-diClPh | SO₂ | Single bond | Sub-19 |
| 1-2964 | Sub-61 | 3,4-diClPh | SO₂ | Single bond | Sub-20 |
| 1-2965 | Sub-61 | 3,4-diClPh | SO₂ | Single bond | Sub-21 |
| 1-2966 | Sub-61 | 3,4-diClPh | SO₂ | Single bond | Sub-22 |
| 1-2967 | Sub-61 | 3,4-diClPh | SO₂ | Single bond | Sub-23 |
| 1-2968 | Sub-61 | 3,4-diClPh | SO₂ | Single bond | Sub-24 |
| 1-2969 | Sub-61 | 3,4-diClPh | SO₂ | Single bond | Sub-25 |
| 1-2970 | Sub-61 | 3,4-diClPh | SO₂ | Single bond | Sub-26 |
| 1-2971 | Sub-61 | 3,4-diClPh | SO₂ | Single bond | Sub-27 |
| 1-2972 | Sub-61 | 3,4-diClPh | SO₂ | Single bond | Sub-28 |
| 1-2973 | Sub-61 | 3,4-diClPh | SO₂ | Single bond | Sub-29 |
| 1-2974 | Sub-61 | 3,4-diClPh | SO₂ | Single bond | Sub-30 |
| 1-2975 | Sub-61 | 3,4-diClPh | SO₂ | Single bond | Sub-31 |
| 1-2976 | Sub-61 | 3,4-diClPh | SO₂ | Single bond | Sub-32 |
| 1-2977 | Sub-62 | 3,4-diClPh | SO₂ | Single bond | Sub-1 |
| 1-2978 | Sub-62 | 3,4-diClPh | SO₂ | Single bond | Sub-2 |
| 1-2979 | Sub-62 | 3,4-diClPh | SO₂ | Single bond | Sub-3 |
| 1-2980 | Sub-62 | 3,4-diClPh | SO₂ | Single bond | Sub-4 |
| 1-2981 | Sub-62 | 3,4-diClPh | SO₂ | Single bond | Sub-5 |
| 1-2982 | Sub-62 | 3,4-diClPh | SO₂ | Single bond | Sub-6 |
| 1-2983 | Sub-62 | 3,4-diClPh | SO₂ | Single bond | Sub-7 |
| 1-2984 | Sub-62 | 3,4-diClPh | SO₂ | Single bond | Sub-8 |
| 1-2985 | Sub-62 | 3,4-diClPh | SO₂ | Single bond | Sub-9 |
| 1-2986 | Sub-62 | 3,4-diClPh | SO₂ | Single bond | Sub-10 |
| 1-2987 | Sub-62 | 3,4-diClPh | SO₂ | Single bond | Sub-11 |
| 1-2988 | Sub-62 | 3,4-diClPh | SO₂ | Single bond | Sub-12 |
| 1-2989 | Sub-62 | 3,4-diClPh | SO₂ | Single bond | Sub-13 |
| 1-2990 | Sub-62 | 3,4-diClPh | SO₂ | Single bond | Sub-14 |
| 1-2991 | Sub-62 | 3,4-diClPh | SO₂ | Single bond | Sub-15 |
| 1-2992 | Sub-62 | 3,4-diClPh | SO₂ | Single bond | Sub-16 |
| 1-2993 | Sub-62 | 3,4-diClPh | SO₂ | Single bond | Sub-17 |
| 1-2994 | Sub-62 | 3,4-diClPh | SO₂ | Single bond | Sub-18 |
| 1-2995 | Sub-62 | 3,4-diClPh | SO₂ | Single bond | Sub-19 |
| 1-2996 | Sub-62 | 3,4-diClPh | SO₂ | Single bond | Sub-20 |
| 1-2997 | Sub-62 | 3,4-diClPh | SO₂ | Single bond | Sub-21 |
| 1-2998 | Sub-62 | 3,4-diClPh | SO₂ | Single bond | Sub-22 |
| 1-2999 | Sub-62 | 3,4-diClPh | SO₂ | Single bond | Sub-23 |
| 1-3000 | Sub-62 | 3,4-diClPh | SO₂ | Single bond | Sub-24 |
| 1-3001 | Sub-62 | 3,4-diClPh | SO₂ | Single bond | Sub-25 |
| 1-3002 | Sub-62 | 3,4-diClPh | SO₂ | Single bond | Sub-26 |
| 1-3003 | Sub-62 | 3,4-diClPh | SO₂ | Single bond | Sub-27 |
| 1-3004 | Sub-62 | 3,4-diClPh | SO₂ | Single bond | Sub-28 |
| 1-3005 | Sub-62 | 3,4-diClPh | SO₂ | Single bond | Sub-29 |
| 1-3006 | Sub-62 | 3,4-diClPh | SO₂ | Single bond | Sub-30 |
| 1-3007 | Sub-62 | 3,4-diClPh | SO₂ | Single bond | Sub-31 |
| 1-3008 | Sub-62 | 3,4-diClPh | SO₂ | Single bond | Sub-32 |
| 1-3009 | Sub-63 | 3,4-diClPh | SO₂ | Single bond | Sub-1 |
| 1-3010 | Sub-63 | 3,4-diClPh | SO₂ | Single bond | Sub-2 |
| 1-3011 | Sub-63 | 3,4-diClPh | SO₂ | Single bond | Sub-3 |
| 1-3012 | Sub-63 | 3,4-diClPh | SO₂ | Single bond | Sub-4 |
| 1-3013 | Sub-63 | 3,4-diClPh | SO₂ | Single bond | Sub-5 |

TABLE 1-continued

| Cpd. No. | R¹ | R² | A | B | Z |
|---|---|---|---|---|---|
| 1-3014 | Sub-63 | 3,4-diClPh | SO$_2$ | Single bond | Sub-6 |
| 1-3015 | Sub-63 | 3,4-diClPh | SO$_2$ | Single bond | Sub-7 |
| 1-3016 | Sub-63 | 3,4-diClPh | SO$_2$ | Single bond | Sub-8 |
| 1-3017 | Sub-63 | 3,4-diClPh | SO$_2$ | Single bond | Sub-9 |
| 1-3018 | Sub-63 | 3,4-diClPh | SO$_2$ | Single bond | Sub-10 |
| 1-3019 | Sub-63 | 3,4-diClPh | SO$_2$ | Single bond | Sub-11 |
| 1-3020 | Sub-63 | 3,4-diClPh | SO$_2$ | Single bond | Sub-12 |
| 1-3021 | Sub-63 | 3,4-diClPh | SO$_2$ | Single bond | Sub-13 |
| 1-3022 | Sub-63 | 3,4-diClPh | SO$_2$ | Single bond | Sub-14 |
| 1-3023 | Sub-63 | 3,4-diClPh | SO$_2$ | Single bond | Sub-15 |
| 1-3024 | Sub-63 | 3,4-diClPh | SO$_2$ | Single bond | Sub-16 |
| 1-3025 | Sub-63 | 3,4-diClPh | SO$_2$ | Single bond | Sub-17 |
| 1-3026 | Sub-63 | 3,4-diClPh | SO$_2$ | Single bond | Sub-18 |
| 1-3027 | Sub-63 | 3,4-diClPh | SO$_2$ | Single bond | Sub-19 |
| 1-3028 | Sub-63 | 3,4-diClPh | SO$_2$ | Single bond | Sub-20 |
| 1-3029 | Sub-63 | 3,4-diClPh | SO$_2$ | Single bond | Sub-21 |
| 1-3030 | Sub-63 | 3,4-diClPh | SO$_2$ | Single bond | Sub-22 |
| 1-3031 | Sub-63 | 3,4-diClPh | SO$_2$ | Single bond | Sub-23 |
| 1-3032 | Sub-63 | 3,4-diClPh | SO$_2$ | Single bond | Sub-24 |
| 1-3033 | Sub-63 | 3,4-diClPh | SO$_2$ | Single bond | Sub-25 |
| 1-3034 | Sub-63 | 3,4-diClPh | SO$_2$ | Single bond | Sub-26 |
| 1-3035 | Sub-63 | 3,4-diClPh | SO$_2$ | Single bond | Sub-27 |
| 1-3036 | Sub-63 | 3,4-diClPh | SO$_2$ | Single bond | Sub-28 |
| 1-3037 | Sub-63 | 3,4-diClPh | SO$_2$ | Single bond | Sub-29 |
| 1-3038 | Sub-63 | 3,4-diClPh | SO$_2$ | Single bond | Sub-30 |
| 1-3039 | Sub-63 | 3,4-diClPh | SO$_2$ | Single bond | Sub-31 |
| 1-3040 | Sub-63 | 3,4-diClPh | SO$_2$ | Single bond | Sub-32 |
| 1-3041 | Sub-64 | 3,4-diClPh | SO$_2$ | Single bond | Sub-1 |
| 1-3042 | Sub-64 | 3,4-diClPh | SO$_2$ | Single bond | Sub-2 |
| 1-3043 | Sub-64 | 3,4-diClPh | SO$_2$ | Single bond | Sub-3 |
| 1-3044 | Sub-64 | 3,4-diClPh | SO$_2$ | Single bond | Sub-4 |
| 1-3045 | Sub-64 | 3,4-diClPh | SO$_2$ | Single bond | Sub-5 |
| 1-3046 | Sub-64 | 3,4-diClPh | SO$_2$ | Single bond | Sub-6 |
| 1-3047 | Sub-64 | 3,4-diClPh | SO$_2$ | Single bond | Sub-7 |
| 1-3048 | Sub-64 | 3,4-diClPh | SO$_2$ | Single bond | Sub-8 |
| 1-3049 | Sub-64 | 3,4-diClPh | SO$_2$ | Single bond | Sub-9 |
| 1-3050 | Sub-64 | 3,4-diClPh | SO$_2$ | Single bond | Sub-10 |
| 1-3051 | Sub-64 | 3,4-diClPh | SO$_2$ | Single bond | Sub-11 |
| 1-3052 | Sub-64 | 3,4-diClPh | SO$_2$ | Single bond | Sub-12 |
| 1-3053 | Sub-64 | 3,4-diClPh | SO$_2$ | Single bond | Sub-13 |
| 1-3054 | Sub-64 | 3,4-diClPh | SO$_2$ | Single bond | Sub-14 |
| 1-3055 | Sub-64 | 3,4-diClPh | SO$_2$ | Single bond | Sub-15 |
| 1-3056 | Sub-64 | 3,4-diClPh | SO$_2$ | Single bond | Sub-16 |
| 1-3057 | Sub-64 | 3,4-diClPh | SO$_2$ | Single bond | Sub-17 |
| 1-3058 | Sub-64 | 3,4-diClPh | SO$_2$ | Single bond | Sub-18 |
| 1-3059 | Sub-64 | 3,4-diClPh | SO$_2$ | Single bond | Sub-19 |
| 1-3060 | Sub-64 | 3,4-diClPh | SO$_2$ | Single bond | Sub-20 |
| 1-3061 | Sub-64 | 3,4-diClPh | SO$_2$ | Single bond | Sub-21 |
| 1-3062 | Sub-64 | 3,4-diClPh | SO$_2$ | Single bond | Sub-22 |
| 1-3063 | Sub-64 | 3,4-diClPh | SO$_2$ | Single bond | Sub-23 |
| 1-3064 | Sub-64 | 3,4-diClPh | SO$_2$ | Single bond | Sub-24 |
| 1-3065 | Sub-64 | 3,4-diClPh | SO$_2$ | Single bond | Sub-25 |
| 1-3066 | Sub-64 | 3,4-diClPh | SO$_2$ | Single bond | Sub-26 |
| 1-3067 | Sub-64 | 3,4-diClPh | SO$_2$ | Single bond | Sub-27 |
| 1-3068 | Sub-64 | 3,4-diClPh | SO$_2$ | Single bond | Sub-28 |
| 1-3069 | Sub-64 | 3,4-diClPh | SO$_2$ | Single bond | Sub-29 |
| 1-3070 | Sub-64 | 3,4-diClPh | SO$_2$ | Single bond | Sub-30 |
| 1-3071 | Sub-64 | 3,4-diClPh | SO$_2$ | Single bond | Sub-31 |
| 1-3072 | Sub-64 | 3,4-diClPh | SO$_2$ | Single bond | Sub-32 |
| 1-3073 | Sub-33 | 3,4-diClPh | CO | CH$_2$ | Sub-1 |
| 1-3074 | Sub-33 | 3,4-diClPh | CO | CH$_2$ | Sub-2 |
| 1-3075 | Sub-33 | 3,4-diClPh | CO | CH$_2$ | Sub-3 |
| 1-3076 | Sub-33 | 3,4-diClPh | CO | CH$_2$ | Sub-4 |
| 1-3077 | Sub-33 | 3,4-diClPh | CO | CH$_2$ | Sub-5 |
| 1-3078 | Sub-33 | 3,4-diClPh | CO | CH$_2$ | Sub-6 |
| 1-3079 | Sub-33 | 3,4-diClPh | CO | CH$_2$ | Sub-7 |
| 1-3080 | Sub-33 | 3,4-diClPh | CO | CH$_2$ | Sub-8 |
| 1-3081 | Sub-33 | 3,4-diClPh | CO | CH$_2$ | Sub-9 |
| 1-3082 | Sub-33 | 3,4-diClPh | CO | CH$_2$ | Sub-10 |
| 1-3083 | Sub-33 | 3,4-diClPh | CO | CH$_2$ | Sub-11 |
| 1-3084 | Sub-33 | 3,4-diClPh | CO | CH$_2$ | Sub-12 |
| 1-3085 | Sub-33 | 3,4-diClPh | CO | CH$_2$ | Sub-13 |
| 1-3086 | Sub-33 | 3,4-diClPh | CO | CH$_2$ | Sub-14 |
| 1-3087 | Sub-33 | 3,4-diClPh | CO | CH$_2$ | Sub-15 |
| 1-3088 | Sub-33 | 3,4-diClPh | CO | CH$_2$ | Sub-16 |
| 1-3089 | Sub-33 | 3,4-diClPh | CO | CH$_2$ | Sub-17 |
| 1-3090 | Sub-33 | 3,4-diClPh | CO | CH$_2$ | Sub-18 |
| 1-3091 | Sub-33 | 3,4-diClPh | CO | CH$_2$ | Sub-19 |
| 1-3092 | Sub-33 | 3,4-diClPh | CO | CH$_2$ | Sub-20 |
| 1-3093 | Sub-33 | 3,4-diClPh | CO | CH$_2$ | Sub-21 |
| 1-3094 | Sub-33 | 3,4-diClPh | CO | CH$_2$ | Sub-22 |
| 1-3095 | Sub-33 | 3,4-diClPh | CO | CH$_2$ | Sub-23 |
| 1-3096 | Sub-33 | 3,4-diClPh | CO | CH$_2$ | Sub-24 |
| 1-3097 | Sub-33 | 3,4-diClPh | CO | CH$_2$ | Sub-25 |
| 1-3098 | Sub-33 | 3,4-diClPh | CO | CH$_2$ | Sub-26 |
| 1-3099 | Sub-33 | 3,4-diClPh | CO | CH$_2$ | Sub-27 |
| 1-3100 | Sub-33 | 3,4-diClPh | CO | CH$_2$ | Sub-28 |
| 1-3101 | Sub-33 | 3,4-diClPh | CO | CH$_2$ | Sub-29 |
| 1-3102 | Sub-33 | 3,4-diClPh | CO | CH$_2$ | Sub-30 |
| 1-3103 | Sub-33 | 3,4-diClPh | CO | CH$_2$ | Sub-31 |
| 1-3104 | Sub-33 | 3,4-diClPh | CO | CH$_2$ | Sub-32 |
| 1-3105 | Sub-34 | 3,4-diClPh | CO | CH$_2$ | Sub-1 |
| 1-3106 | Sub-34 | 3,4-diClPh | CO | CH$_2$ | Sub-2 |
| 1-3107 | Sub-34 | 3,4-diClPh | CO | CH$_2$ | Sub-3 |
| 1-3108 | Sub-34 | 3,4-diClPh | CO | CH$_2$ | Sub-4 |
| 1-3109 | Sub-34 | 3,4-diClPh | CO | CH$_2$ | Sub-5 |
| 1-3110 | Sub-34 | 3,4-diClPh | CO | CH$_2$ | Sub-6 |
| 1-3111 | Sub-34 | 3,4-diClPh | CO | CH$_2$ | Sub-7 |
| 1-3112 | Sub-34 | 3,4-diClPh | CO | CH$_2$ | Sub-8 |
| 1-3113 | Sub-34 | 3,4-diClPh | CO | CH$_2$ | Sub-9 |
| 1-3114 | Sub-34 | 3,4-diClPh | CO | CH$_2$ | Sub-10 |
| 1-3115 | Sub-34 | 3,4-diClPh | CO | CH$_2$ | Sub-11 |
| 1-3116 | Sub-34 | 3,4-diClPh | CO | CH$_2$ | Sub-12 |
| 1-3117 | Sub-34 | 3,4-diClPh | CO | CH$_2$ | Sub-13 |
| 1-3118 | Sub-34 | 3,4-diClPh | CO | CH$_2$ | Sub-14 |
| 1-3119 | Sub-34 | 3,4-diClPh | CO | CH$_2$ | Sub-15 |
| 1-3120 | Sub-34 | 3,4-diClPh | CO | CH$_2$ | Sub-16 |
| 1-3121 | Sub-34 | 3,4-diClPh | CO | CH$_2$ | Sub-17 |
| 1-3122 | Sub-34 | 3,4-diClPh | CO | CH$_2$ | Sub-18 |
| 1-3123 | Sub-34 | 3,4-diClPh | CO | CH$_2$ | Sub-19 |
| 1-3124 | Sub-34 | 3,4-diClPh | CO | CH$_2$ | Sub-20 |
| 1-3125 | Sub-34 | 3,4-diClPh | CO | CH$_2$ | Sub-21 |
| 1-3126 | Sub-34 | 3,4-diClPh | CO | CH$_2$ | Sub-22 |
| 1-3127 | Sub-34 | 3,4-diClPh | CO | CH$_2$ | Sub-23 |
| 1-3128 | Sub-34 | 3,4-diClPh | CO | CH$_2$ | Sub-24 |
| 1-3129 | Sub-34 | 3,4-diClPh | CO | CH$_2$ | Sub-25 |
| 1-3130 | Sub-34 | 3,4-diClPh | CO | CH$_2$ | Sub-26 |
| 1-3131 | Sub-34 | 3,4-diClPh | CO | CH$_2$ | Sub-27 |
| 1-3132 | Sub-34 | 3,4-diClPh | CO | CH$_2$ | Sub-28 |
| 1-3133 | Sub-34 | 3,4-diClPh | CO | CH$_2$ | Sub-29 |
| 1-3134 | Sub-34 | 3,4-diClPh | CO | CH$_2$ | Sub-30 |
| 1-3135 | Sub-34 | 3,4-diClPh | CO | CH$_2$ | Sub-31 |
| 1-3136 | Sub-34 | 3,4-diClPh | CO | CH$_2$ | Sub-32 |
| 1-3137 | Sub-35 | 3,4-diClPh | CO | CH$_2$ | Sub-1 |
| 1-3138 | Sub-35 | 3,4-diClPh | CO | CH$_2$ | Sub-2 |
| 1-3139 | Sub-35 | 3,4-diClPh | CO | CH$_2$ | Sub-3 |
| 1-3140 | Sub-35 | 3,4-diClPh | CO | CH$_2$ | Sub-4 |
| 1-3141 | Sub-35 | 3,4-diClPh | CO | CH$_2$ | Sub-5 |
| 1-3142 | Sub-35 | 3,4-diClPh | CO | CH$_2$ | Sub-6 |
| 1-3143 | Sub-35 | 3,4-diClPh | CO | CH$_2$ | Sub-7 |
| 1-3144 | Sub-35 | 3,4-diClPh | CO | CH$_2$ | Sub-8 |
| 1-3145 | Sub-35 | 3,4-diClPh | CO | CH$_2$ | Sub-9 |
| 1-3146 | Sub-35 | 3,4-diClPh | CO | CH$_2$ | Sub-10 |
| 1-3147 | Sub-35 | 3,4-diClPh | CO | CH$_2$ | Sub-11 |
| 1-3148 | Sub-35 | 3,4-diClPh | CO | CH$_2$ | Sub-12 |
| 1-3149 | Sub-35 | 3,4-diClPh | CO | CH$_2$ | Sub-13 |
| 1-3150 | Sub-35 | 3,4-diClPh | CO | CH$_2$ | Sub-14 |
| 1-3151 | Sub-35 | 3,4-diClPh | CO | CH$_2$ | Sub-15 |
| 1-3152 | Sub-35 | 3,4-diClPh | CO | CH$_2$ | Sub-16 |
| 1-3153 | Sub-35 | 3,4-diClPh | CO | CH$_2$ | Sub-17 |
| 1-3154 | Sub-35 | 3,4-diClPh | CO | CH$_2$ | Sub-18 |
| 1-3155 | Sub-35 | 3,4-diClPh | CO | CH$_2$ | Sub-19 |
| 1-3156 | Sub-35 | 3,4-diClPh | CO | CH$_2$ | Sub-20 |
| 1-3157 | Sub-35 | 3,4-diClPh | CO | CH$_2$ | Sub-21 |
| 1-3158 | Sub-35 | 3,4-diClPh | CO | CH$_2$ | Sub-22 |
| 1-3159 | Sub-35 | 3,4-diClPh | CO | CH$_2$ | Sub-23 |
| 1-3160 | Sub-35 | 3,4-diClPh | CO | CH$_2$ | Sub-24 |
| 1-3161 | Sub-35 | 3,4-diClPh | CO | CH$_2$ | Sub-25 |
| 1-3162 | Sub-35 | 3,4-diClPh | CO | CH$_2$ | Sub-26 |
| 1-3163 | Sub-35 | 3,4-diClPh | CO | CH$_2$ | Sub-27 |
| 1-3164 | Sub-35 | 3,4-diClPh | CO | CH$_2$ | Sub-28 |
| 1-3165 | Sub-35 | 3,4-diClPh | CO | CH$_2$ | Sub-29 |

TABLE 1-continued

| Cpd. No. | R¹ | R² | A | B | Z |
|---|---|---|---|---|---|
| 1-3166 | Sub-35 | 3,4-diClPh | CO | $CH_2$ | Sub-30 |
| 1-3167 | Sub-35 | 3,4-diClPh | CO | $CH_2$ | Sub-31 |
| 1-3168 | Sub-35 | 3,4-diClPh | CO | $CH_2$ | Sub-32 |
| 1-3169 | Sub-36 | 3,4-diClPh | CO | $CH_2$ | Sub-1 |
| 1-3170 | Sub-36 | 3,4-diClPh | CO | $CH_2$ | Sub-2 |
| 1-3171 | Sub-36 | 3,4-diClPh | CO | $CH_2$ | Sub-3 |
| 1-3172 | Sub-36 | 3,4-diClPh | CO | $CH_2$ | Sub-4 |
| 1-3173 | Sub-36 | 3,4-diClPh | CO | $CH_2$ | Sub-5 |
| 1-3174 | Sub-36 | 3,4-diClPh | CO | $CH_2$ | Sub-6 |
| 1-3175 | Sub-36 | 3,4-diClPh | CO | $CH_2$ | Sub-7 |
| 1-3176 | Sub-36 | 3,4-diClPh | CO | $CH_2$ | Sub-8 |
| 1-3177 | Sub-36 | 3,4-diClPh | CO | $CH_2$ | Sub-9 |
| 1-3178 | Sub-36 | 3,4-diClPh | CO | $CH_2$ | Sub-10 |
| 1-3179 | Sub-36 | 3,4-diClPh | CO | $CH_2$ | Sub-11 |
| 1-3180 | Sub-36 | 3,4-diClPh | CO | $CH_2$ | Sub-12 |
| 1-3181 | Sub-36 | 3,4-diClPh | CO | $CH_2$ | Sub-13 |
| 1-3182 | Sub-36 | 3,4-diClPh | CO | $CH_2$ | Sub-14 |
| 1-3183 | Sub-36 | 3,4-diClPh | CO | $CH_2$ | Sub-15 |
| 1-3184 | Sub-36 | 3,4-diClPh | CO | $CH_2$ | Sub-16 |
| 1-3185 | Sub-36 | 3,4-diClPh | CO | $CH_2$ | Sub-17 |
| 1-3186 | Sub-36 | 3,4-diClPh | CO | $CH_2$ | Sub-18 |
| 1-3187 | Sub-36 | 3,4-diClPh | CO | $CH_2$ | Sub-19 |
| 1-3188 | Sub-36 | 3,4-diClPh | CO | $CH_2$ | Sub-20 |
| 1-3189 | Sub-36 | 3,4-diClPh | CO | $CH_2$ | Sub-21 |
| 1-3190 | Sub-36 | 3,4-diClPh | CO | $CH_2$ | Sub-22 |
| 1-3191 | Sub-36 | 3,4-diClPh | CO | $CH_2$ | Sub-23 |
| 1-3192 | Sub-36 | 3,4-diClPh | CO | $CH_2$ | Sub-24 |
| 1-3193 | Sub-36 | 3,4-diClPh | CO | $CH_2$ | Sub-25 |
| 1-3194 | Sub-36 | 3,4-diClPh | CO | $CH_2$ | Sub-26 |
| 1-3195 | Sub-36 | 3,4-diClPh | CO | $CH_2$ | Sub-27 |
| 1-3196 | Sub-36 | 3,4-diClPh | CO | $CH_2$ | Sub-28 |
| 1-3197 | Sub-36 | 3,4-diClPh | CO | $CH_2$ | Sub-29 |
| 1-3198 | Sub-36 | 3,4-diClPh | CO | $CH_2$ | Sub-30 |
| 1-3199 | Sub-36 | 3,4-diClPh | CO | $CH_2$ | Sub-31 |
| 1-3200 | Sub-36 | 3,4-diClPh | CO | $CH_2$ | Sub-32 |
| 1-3201 | Sub-37 | 3,4-diClPh | CO | $CH_2$ | Sub-1 |
| 1-3202 | Sub-37 | 3,4-diClPh | CO | $CH_2$ | Sub-2 |
| 1-3203 | Sub-37 | 3,4-diClPh | CO | $CH_2$ | Sub-3 |
| 1-3204 | Sub-37 | 3,4-diClPh | CO | $CH_2$ | Sub-4 |
| 1-3205 | Sub-37 | 3,4-diClPh | CO | $CH_2$ | Sub-5 |
| 1-3206 | Sub-37 | 3,4-diClPh | CO | $CH_2$ | Sub-6 |
| 1-3207 | Sub-37 | 3,4-diClPh | CO | $CH_2$ | Sub-7 |
| 1-3208 | Sub-37 | 3,4-diClPh | CO | $CH_2$ | Sub-8 |
| 1-3209 | Sub-37 | 3,4-diClPh | CO | $CH_2$ | Sub-9 |
| 1-3210 | Sub-37 | 3,4-diClPh | CO | $CH_2$ | Sub-10 |
| 1-3211 | Sub-37 | 3,4-diClPh | CO | $CH_2$ | Sub-11 |
| 1-3212 | Sub-37 | 3,4-diClPh | CO | $CH_2$ | Sub-12 |
| 1-3213 | Sub-37 | 3,4-diClPh | CO | $CH_2$ | Sub-13 |
| 1-3214 | Sub-37 | 3,4-diClPh | CO | $CH_2$ | Sub-14 |
| 1-3215 | Sub-37 | 3,4-diClPh | CO | $CH_2$ | Sub-15 |
| 1-3216 | Sub-37 | 3,4-diClPh | CO | $CH_2$ | Sub-16 |
| 1-3217 | Sub-37 | 3,4-diClPh | CO | $CH_2$ | Sub-17 |
| 1-3218 | Sub-37 | 3,4-diClPh | CO | $CH_2$ | Sub-18 |
| 1-3219 | Sub-37 | 3,4-diClPh | CO | $CH_2$ | Sub-19 |
| 1-3220 | Sub-37 | 3,4-diClPh | CO | $CH_2$ | Sub-20 |
| 1-3221 | Sub-37 | 3,4-diClPh | CO | $CH_2$ | Sub-21 |
| 1-3222 | Sub-37 | 3,4-diClPh | CO | $CH_2$ | Sub-22 |
| 1-3223 | Sub-37 | 3,4-diClPh | CO | $CH_2$ | Sub-23 |
| 1-3224 | Sub-37 | 3,4-diClPh | CO | $CH_2$ | Sub-24 |
| 1-3225 | Sub-37 | 3,4-diClPh | CO | $CH_2$ | Sub-25 |
| 1-3226 | Sub-37 | 3,4-diClPh | CO | $CH_2$ | Sub-26 |
| 1-3227 | Sub-37 | 3,4-diClPh | CO | $CH_2$ | Sub-27 |
| 1-3228 | Sub-37 | 3,4-diClPh | CO | $CH_2$ | Sub-28 |
| 1-3229 | Sub-37 | 3,4-diClPh | CO | $CH_2$ | Sub-29 |
| 1-3230 | Sub-37 | 3,4-diClPh | CO | $CH_2$ | Sub-30 |
| 1-3231 | Sub-37 | 3,4-diClPh | CO | $CH_2$ | Sub-31 |
| 1-3232 | Sub-37 | 3,4-diClPh | CO | $CH_2$ | Sub-32 |
| 1-3233 | Sub-38 | 3,4-diClPh | CO | $CH_2$ | Sub-1 |
| 1-3234 | Sub-38 | 3,4-diClPh | CO | $CH_2$ | Sub-2 |
| 1-3235 | Sub-38 | 3,4-diClPh | CO | $CH_2$ | Sub-3 |
| 1-3236 | Sub-38 | 3,4-diClPh | CO | $CH_2$ | Sub-4 |
| 1-3237 | Sub-38 | 3,4-diClPh | CO | $CH_2$ | Sub-5 |
| 1-3238 | Sub-38 | 3,4-diClPh | CO | $CH_2$ | Sub-6 |
| 1-3239 | Sub-38 | 3,4-diClPh | CO | $CH_2$ | Sub-7 |
| 1-3240 | Sub-38 | 3,4-diClPh | CO | $CH_2$ | Sub-8 |
| 1-3241 | Sub-38 | 3,4-diClPh | CO | $CH_2$ | Sub-9 |
| 1-3242 | Sub-38 | 3,4-diClPh | CO | $CH_2$ | Sub-10 |
| 1-3243 | Sub-38 | 3,4-diClPh | CO | $CH_2$ | Sub-11 |
| 1-3244 | Sub-38 | 3,4-diClPh | CO | $CH_2$ | Sub-12 |
| 1-3245 | Sub-38 | 3,4-diClPh | CO | $CH_2$ | Sub-13 |
| 1-3246 | Sub-38 | 3,4-diClPh | CO | $CH_2$ | Sub-14 |
| 1-3247 | Sub-38 | 3,4-diClPh | CO | $CH_2$ | Sub-15 |
| 1-3248 | Sub-38 | 3,4-diClPh | CO | $CH_2$ | Sub-16 |
| 1-3249 | Sub-38 | 3,4-diClPh | CO | $CH_2$ | Sub-17 |
| 1-3250 | Sub-38 | 3,4-diClPh | CO | $CH_2$ | Sub-18 |
| 1-3251 | Sub-38 | 3,4-diClPh | CO | $CH_2$ | Sub-19 |
| 1-3252 | Sub-38 | 3,4-diClPh | CO | $CH_2$ | Sub-20 |
| 1-3253 | Sub-38 | 3,4-diClPh | CO | $CH_2$ | Sub-21 |
| 1-3254 | Sub-38 | 3,4-diClPh | CO | $CH_2$ | Sub-22 |
| 1-3255 | Sub-38 | 3,4-diClPh | CO | $CH_2$ | Sub-23 |
| 1-3256 | Sub-38 | 3,4-diClPh | CO | $CH_2$ | Sub-24 |
| 1-3257 | Sub-38 | 3,4-diClPh | CO | $CH_2$ | Sub-25 |
| 1-3258 | Sub-38 | 3,4-diClPh | CO | $CH_2$ | Sub-26 |
| 1-3259 | Sub-38 | 3,4-diClPh | CO | $CH_2$ | Sub-27 |
| 1-3260 | Sub-38 | 3,4-diClPh | CO | $CH_2$ | Sub-28 |
| 1-3261 | Sub-38 | 3,4-diClPh | CO | $CH_2$ | Sub-29 |
| 1-3262 | Sub-38 | 3,4-diClPh | CO | $CH_2$ | Sub-30 |
| 1-3263 | Sub-38 | 3,4-diClPh | CO | $CH_2$ | Sub-31 |
| 1-3264 | Sub-38 | 3,4-diClPh | CO | $CH_2$ | Sub-32 |
| 1-3265 | Sub-39 | 3,4-diClPh | CO | $CH_2$ | Sub-1 |
| 1-3266 | Sub-39 | 3,4-diClPh | CO | $CH_2$ | Sub-2 |
| 1-3267 | Sub-39 | 3,4-diClPh | CO | $CH_2$ | Sub-3 |
| 1-3268 | Sub-39 | 3,4-diClPh | CO | $CH_2$ | Sub-4 |
| 1-3269 | Sub-39 | 3,4-diClPh | CO | $CH_2$ | Sub-5 |
| 1-3270 | Sub-39 | 3,4-diClPh | CO | $CH_2$ | Sub-6 |
| 1-3271 | Sub-39 | 3,4-diClPh | CO | $CH_2$ | Sub-7 |
| 1-3272 | Sub-39 | 3,4-diClPh | CO | $CH_2$ | Sub-8 |
| 1-3273 | Sub-39 | 3,4-diClPh | CO | $CH_2$ | Sub-9 |
| 1-3274 | Sub-39 | 3,4-diClPh | CO | $CH_2$ | Sub-10 |
| 1-3275 | Sub-39 | 3,4-diClPh | CO | $CH_2$ | Sub-11 |
| 1-3276 | Sub-39 | 3,4-diClPh | CO | $CH_2$ | Sub-12 |
| 1-3277 | Sub-39 | 3,4-diClPh | CO | $CH_2$ | Sub-13 |
| 1-3278 | Sub-39 | 3,4-diClPh | CO | $CH_2$ | Sub-14 |
| 1-3279 | Sub-39 | 3,4-diClPh | CO | $CH_2$ | Sub-15 |
| 1-3280 | Sub-39 | 3,4-diClPh | CO | $CH_2$ | Sub-16 |
| 1-3281 | Sub-39 | 3,4-diClPh | CO | $CH_2$ | Sub-17 |
| 1-3282 | Sub-39 | 3,4-diClPh | CO | $CH_2$ | Sub-18 |
| 1-3283 | Sub-39 | 3,4-diClPh | CO | $CH_2$ | Sub-19 |
| 1-3284 | Sub-39 | 3,4-diClPh | CO | $CH_2$ | Sub-20 |
| 1-3285 | Sub-39 | 3,4-diClPh | CO | $CH_2$ | Sub-21 |
| 1-3286 | Sub-39 | 3,4-diClPh | CO | $CH_2$ | Sub-22 |
| 1-3287 | Sub-39 | 3,4-diClPh | CO | $CH_2$ | Sub-23 |
| 1-3288 | Sub-39 | 3,4-diClPh | CO | $CH_2$ | Sub-24 |
| 1-3289 | Sub-39 | 3,4-diClPh | CO | $CH_2$ | Sub-25 |
| 1-3290 | Sub-39 | 3,4-diClPh | CO | $CH_2$ | Sub-26 |
| 1-3291 | Sub-39 | 3,4-diClPh | CO | $CH_2$ | Sub-27 |
| 1-3292 | Sub-39 | 3,4-diClPh | CO | $CH_2$ | Sub-28 |
| 1-3293 | Sub-39 | 3,4-diClPh | CO | $CH_2$ | Sub-29 |
| 1-3294 | Sub-39 | 3,4-diClPh | CO | $CH_2$ | Sub-30 |
| 1-3295 | Sub-39 | 3,4-diClPh | CO | $CH_2$ | Sub-31 |
| 1-3296 | Sub-39 | 3,4-diClPh | CO | $CH_2$ | Sub-32 |
| 1-3297 | Sub-40 | 3,4-diClPh | CO | $CH_2$ | Sub-1 |
| 1-3298 | Sub-40 | 3,4-diClPh | CO | $CH_2$ | Sub-2 |
| 1-3299 | Sub-40 | 3,4-diClPh | CO | $CH_2$ | Sub-3 |
| 1-3300 | Sub-40 | 3,4-diClPh | CO | $CH_2$ | Sub-4 |
| 1-3301 | Sub-40 | 3,4-diClPh | CO | $CH_2$ | Sub-5 |
| 1-3302 | Sub-40 | 3,4-diClPh | CO | $CH_2$ | Sub-6 |
| 1-3303 | Sub-40 | 3,4-diClPh | CO | $CH_2$ | Sub-7 |
| 1-3304 | Sub-40 | 3,4-diClPh | CO | $CH_2$ | Sub-8 |
| 1-3305 | Sub-40 | 3,4-diClPh | CO | $CH_2$ | Sub-9 |
| 1-3306 | Sub-40 | 3,4-diClPh | CO | $CH_2$ | Sub-10 |
| 1-3307 | Sub-40 | 3,4-diClPh | CO | $CH_2$ | Sub-11 |
| 1-3308 | Sub-40 | 3,4-diClPh | CO | $CH_2$ | Sub-12 |
| 1-3309 | Sub-40 | 3,4-diClPh | CO | $CH_2$ | Sub-13 |
| 1-3310 | Sub-40 | 3,4-diClPh | CO | $CH_2$ | Sub-14 |
| 1-3311 | Sub-40 | 3,4-diClPh | CO | $CH_2$ | Sub-15 |
| 1-3312 | Sub-40 | 3,4-diClPh | CO | $CH_2$ | Sub-16 |
| 1-3313 | Sub-40 | 3,4-diClPh | CO | $CH_2$ | Sub-17 |
| 1-3314 | Sub-40 | 3,4-diClPh | CO | $CH_2$ | Sub-18 |
| 1-3315 | Sub-40 | 3,4-diClPh | CO | $CH_2$ | Sub-19 |
| 1-3316 | Sub-40 | 3,4-diClPh | CO | $CH_2$ | Sub-20 |
| 1-3317 | Sub-40 | 3,4-diClPh | CO | $CH_2$ | Sub-21 |

TABLE 1-continued

| Cpd. No. | R¹ | R² | A | B | Z |
|---|---|---|---|---|---|
| 1-3318 | Sub-40 | 3,4-diClPh | CO | CH$_2$ | Sub-22 |
| 1-3319 | Sub-40 | 3,4-diClPh | CO | CH$_2$ | Sub-23 |
| 1-3320 | Sub-40 | 3,4-diClPh | CO | CH$_2$ | Sub-24 |
| 1-3321 | Sub-40 | 3,4-diClPh | CO | CH$_2$ | Sub-25 |
| 1-3322 | Sub-40 | 3,4-diClPh | CO | CH$_2$ | Sub-26 |
| 1-3323 | Sub-40 | 3,4-diClPh | CO | CH$_2$ | Sub-27 |
| 1-3324 | Sub-40 | 3,4-diClPh | CO | CH$_2$ | Sub-28 |
| 1-3325 | Sub-40 | 3,4-diClPh | CO | CH$_2$ | Sub-29 |
| 1-3326 | Sub-40 | 3,4-diClPh | CO | CH$_2$ | Sub-30 |
| 1-3327 | Sub-40 | 3,4-diClPh | CO | CH$_2$ | Sub-31 |
| 1-3328 | Sub-40 | 3,4-diClPh | CO | CH$_2$ | Sub-32 |
| 1-3329 | Sub-41 | 3,4-diClPh | CO | CH$_2$ | Sub-1 |
| 1-3330 | Sub-41 | 3,4-diClPh | CO | CH$_2$ | Sub-2 |
| 1-3331 | Sub-41 | 3,4-diClPh | CO | CH$_2$ | Sub-3 |
| 1-3332 | Sub-41 | 3,4-diClPh | CO | CH$_2$ | Sub-4 |
| 1-3333 | Sub-41 | 3,4-diClPh | CO | CH$_2$ | Sub-5 |
| 1-3334 | Sub-41 | 3,4-diClPh | CO | CH$_2$ | Sub-6 |
| 1-3335 | Sub-41 | 3,4-diClPh | CO | CH$_2$ | Sub-7 |
| 1-3336 | Sub-41 | 3,4-diClPh | CO | CH$_2$ | Sub-8 |
| 1-3337 | Sub-41 | 3,4-diClPh | CO | CH$_2$ | Sub-9 |
| 1-3338 | Sub-41 | 3,4-diClPh | CO | CH$_2$ | Sub-10 |
| 1-3339 | Sub-41 | 3,4-diClPh | CO | CH$_2$ | Sub-11 |
| 1-3340 | Sub-41 | 3,4-diClPh | CO | CH$_2$ | Sub-12 |
| 1-3341 | Sub-41 | 3,4-diClPh | CO | CH$_2$ | Sub-13 |
| 1-3342 | Sub-41 | 3,4-diClPh | CO | CH$_2$ | Sub-14 |
| 1-3343 | Sub-41 | 3,4-diClPh | CO | CH$_2$ | Sub-15 |
| 1-3344 | Sub-41 | 3,4-diClPh | CO | CH$_2$ | Sub-16 |
| 1-3345 | Sub-41 | 3,4-diClPh | CO | CH$_2$ | Sub-17 |
| 1-3346 | Sub-41 | 3,4-diClPh | CO | CH$_2$ | Sub-18 |
| 1-3347 | Sub-41 | 3,4-diClPh | CO | CH$_2$ | Sub-19 |
| 1-3348 | Sub-41 | 3,4-diClPh | CO | CH$_2$ | Sub-20 |
| 1-3349 | Sub-41 | 3,4-diClPh | CO | CH$_2$ | Sub-21 |
| 1-3350 | Sub-41 | 3,4-diClPh | CO | CH$_2$ | Sub-22 |
| 1-3351 | Sub-41 | 3,4-diClPh | CO | CH$_2$ | Sub-23 |
| 1-3352 | Sub-41 | 3,4-diClPh | CO | CH$_2$ | Sub-24 |
| 1-3353 | Sub-41 | 3,4-diClPh | CO | CH$_2$ | Sub-25 |
| 1-3354 | Sub-41 | 3,4-diClPh | CO | CH$_2$ | Sub-26 |
| 1-3355 | Sub-41 | 3,4-diClPh | CO | CH$_2$ | Sub-27 |
| 1-3356 | Sub-41 | 3,4-diClPh | CO | CH$_2$ | Sub-28 |
| 1-3357 | Sub-41 | 3,4-diClPh | CO | CH$_2$ | Sub-29 |
| 1-3358 | Sub-41 | 3,4-diClPh | CO | CH$_2$ | Sub-30 |
| 1-3359 | Sub-41 | 3,4-diClPh | CO | CH$_2$ | Sub-31 |
| 1-3360 | Sub-41 | 3,4-diClPh | CO | CH$_2$ | Sub-32 |
| 1-3361 | Sub-42 | 3,4-diClPh | CO | CH$_2$ | Sub-1 |
| 1-3362 | Sub-42 | 3,4-diClPh | CO | CH$_2$ | Sub-2 |
| 1-3363 | Sub-42 | 3,4-diClPh | CO | CH$_2$ | Sub-3 |
| 1-3364 | Sub-42 | 3,4-diClPh | CO | CH$_2$ | Sub-4 |
| 1-3365 | Sub-42 | 3,4-diClPh | CO | CH$_2$ | Sub-5 |
| 1-3366 | Sub-42 | 3,4-diClPh | CO | CH$_2$ | Sub-6 |
| 1-3367 | Sub-42 | 3,4-diClPh | CO | CH$_2$ | Sub-7 |
| 1-3368 | Sub-42 | 3,4-diClPh | CO | CH$_2$ | Sub-8 |
| 1-3369 | Sub-42 | 3,4-diClPh | CO | CH$_2$ | Sub-9 |
| 1-3370 | Sub-42 | 3,4-diClPh | CO | CH$_2$ | Sub-10 |
| 1-3371 | Sub-42 | 3,4-diClPh | CO | CH$_2$ | Sub-11 |
| 1-3372 | Sub-42 | 3,4-diClPh | CO | CH$_2$ | Sub-12 |
| 1-3373 | Sub-42 | 3,4-diClPh | CO | CH$_2$ | Sub-13 |
| 1-3374 | Sub-42 | 3,4-diClPh | CO | CH$_2$ | Sub-14 |
| 1-3375 | Sub-42 | 3,4-diClPh | CO | CH$_2$ | Sub-15 |
| 1-3376 | Sub-42 | 3,4-diClPh | CO | CH$_2$ | Sub-16 |
| 1-3377 | Sub-42 | 3,4-diClPh | CO | CH$_2$ | Sub-17 |
| 1-3378 | Sub-42 | 3,4-diClPh | CO | CH$_2$ | Sub-18 |
| 1-3379 | Sub-42 | 3,4-diClPh | CO | CH$_2$ | Sub-19 |
| 1-3380 | Sub-42 | 3,4-diClPh | CO | CH$_2$ | Sub-20 |
| 1-3381 | Sub-42 | 3,4-diClPh | CO | CH$_2$ | Sub-21 |
| 1-3382 | Sub-42 | 3,4-diClPh | CO | CH$_2$ | Sub-22 |
| 1-3383 | Sub-42 | 3,4-diClPh | CO | CH$_2$ | Sub-23 |
| 1-3384 | Sub-42 | 3,4-diClPh | CO | CH$_2$ | Sub-24 |
| 1-3385 | Sub-42 | 3,4-diClPh | CO | CH$_2$ | Sub-25 |
| 1-3386 | Sub-42 | 3,4-diClPh | CO | CH$_2$ | Sub-26 |
| 1-3387 | Sub-42 | 3,4-diClPh | CO | CH$_2$ | Sub-27 |
| 1-3388 | Sub-42 | 3,4-diClPh | CO | CH$_2$ | Sub-28 |
| 1-3389 | Sub-42 | 3,4-diClPh | CO | CH$_2$ | Sub-29 |
| 1-3390 | Sub-42 | 3,4-diClPh | CO | CH$_2$ | Sub-30 |
| 1-3391 | Sub-42 | 3,4-diClPh | CO | CH$_2$ | Sub-31 |
| 1-3392 | Sub-42 | 3,4-diClPh | CO | CH$_2$ | Sub-32 |
| 1-3393 | Sub-43 | 3,4-diClPh | CO | CH$_2$ | Sub-1 |
| 1-3394 | Sub-43 | 3,4-diClPh | CO | CH$_2$ | Sub-2 |
| 1-3395 | Sub-43 | 3,4-diClPh | CO | CH$_2$ | Sub-3 |
| 1-3396 | Sub-43 | 3,4-diClPh | CO | CH$_2$ | Sub-4 |
| 1-3397 | Sub-43 | 3,4-diClPh | CO | CH$_2$ | Sub-5 |
| 1-3398 | Sub-43 | 3,4-diClPh | CO | CH$_2$ | Sub-6 |
| 1-3399 | Sub-43 | 3,4-diClPh | CO | CH$_2$ | Sub-7 |
| 1-3400 | Sub-43 | 3,4-diClPh | CO | CH$_2$ | Sub-8 |
| 1-3401 | Sub-43 | 3,4-diClPh | CO | CH$_2$ | Sub-9 |
| 1-3402 | Sub-43 | 3,4-diClPh | CO | CH$_2$ | Sub-10 |
| 1-3403 | Sub-43 | 3,4-diClPh | CO | CH$_2$ | Sub-11 |
| 1-3404 | Sub-43 | 3,4-diClPh | CO | CH$_2$ | Sub-12 |
| 1-3405 | Sub-43 | 3,4-diClPh | CO | CH$_2$ | Sub-13 |
| 1-3406 | Sub-43 | 3,4-diClPh | CO | CH$_2$ | Sub-14 |
| 1-3407 | Sub-43 | 3,4-diClPh | CO | CH$_2$ | Sub-15 |
| 1-3408 | Sub-43 | 3,4-diClPh | CO | CH$_2$ | Sub-16 |
| 1-3409 | Sub-43 | 3,4-diClPh | CO | CH$_2$ | Sub-17 |
| 1-3410 | Sub-43 | 3,4-diClPh | CO | CH$_2$ | Sub-18 |
| 1-3411 | Sub-43 | 3,4-diClPh | CO | CH$_2$ | Sub-19 |
| 1-3412 | Sub-43 | 3,4-diClPh | CO | CH$_2$ | Sub-20 |
| 1-3413 | Sub-43 | 3,4-diClPh | CO | CH$_2$ | Sub-21 |
| 1-3414 | Sub-43 | 3,4-diClPh | CO | CH$_2$ | Sub-22 |
| 1-3415 | Sub-43 | 3,4-diClPh | CO | CH$_2$ | Sub-23 |
| 1-3416 | Sub-43 | 3,4-diClPh | CO | CH$_2$ | Sub-24 |
| 1-3417 | Sub-43 | 3,4-diClPh | CO | CH$_2$ | Sub-25 |
| 1-3418 | Sub-43 | 3,4-diClPh | CO | CH$_2$ | Sub-26 |
| 1-3419 | Sub-43 | 3,4-diClPh | CO | CH$_2$ | Sub-27 |
| 1-3420 | Sub-43 | 3,4-diClPh | CO | CH$_2$ | Sub-28 |
| 1-3421 | Sub-43 | 3,4-diClPh | CO | CH$_2$ | Sub-29 |
| 1-3422 | Sub-43 | 3,4-diClPh | CO | CH$_2$ | Sub-30 |
| 1-3423 | Sub-43 | 3,4-diClPh | CO | CH$_2$ | Sub-31 |
| 1-3424 | Sub-43 | 3,4-diClPh | CO | CH$_2$ | Sub-32 |
| 1-3425 | Sub-44 | 3,4-diClPh | CO | CH$_2$ | Sub-1 |
| 1-3426 | Sub-44 | 3,4-diClPh | CO | CH$_2$ | Sub-2 |
| 1-3427 | Sub-44 | 3,4-diClPh | CO | CH$_2$ | Sub-3 |
| 1-3428 | Sub-44 | 3,4-diClPh | CO | CH$_2$ | Sub-4 |
| 1-3429 | Sub-44 | 3,4-diClPh | CO | CH$_2$ | Sub-5 |
| 1-3430 | Sub-44 | 3,4-diClPh | CO | CH$_2$ | Sub-6 |
| 1-3431 | Sub-44 | 3,4-diClPh | CO | CH$_2$ | Sub-7 |
| 1-3432 | Sub-44 | 3,4-diClPh | CO | CH$_2$ | Sub-8 |
| 1-3433 | Sub-44 | 3,4-diClPh | CO | CH$_2$ | Sub-9 |
| 1-3434 | Sub-44 | 3,4-diClPh | CO | CH$_2$ | Sub-10 |
| 1-3435 | Sub-44 | 3,4-diClPh | CO | CH$_2$ | Sub-11 |
| 1-3436 | Sub-44 | 3,4-diClPh | CO | CH$_2$ | Sub-12 |
| 1-3437 | Sub-44 | 3,4-diClPh | CO | CH$_2$ | Sub-13 |
| 1-3438 | Sub-44 | 3,4-diClPh | CO | CH$_2$ | Sub-14 |
| 1-3439 | Sub-44 | 3,4-diClPh | CO | CH$_2$ | Sub-15 |
| 1-3440 | Sub-44 | 3,4-diClPh | CO | CH$_2$ | Sub-16 |
| 1-3441 | Sub-44 | 3,4-diClPh | CO | CH$_2$ | Sub-17 |
| 1-3442 | Sub-44 | 3,4-diClPh | CO | CH$_2$ | Sub-18 |
| 1-3443 | Sub-44 | 3,4-diClPh | CO | CH$_2$ | Sub-19 |
| 1-3444 | Sub-44 | 3,4-diClPh | CO | CH$_2$ | Sub-20 |
| 1-3445 | Sub-44 | 3,4-diClPh | CO | CH$_2$ | Sub-21 |
| 1-3446 | Sub-44 | 3,4-diClPh | CO | CH$_2$ | Sub-22 |
| 1-3447 | Sub-44 | 3,4-diClPh | CO | CH$_2$ | Sub-23 |
| 1-3448 | Sub-44 | 3,4-diClPh | CO | CH$_2$ | Sub-24 |
| 1-3449 | Sub-44 | 3,4-diClPh | CO | CH$_2$ | Sub-25 |
| 1-3450 | Sub-44 | 3,4-diClPh | CO | CH$_2$ | Sub-26 |
| 1-3451 | Sub-44 | 3,4-diClPh | CO | CH$_2$ | Sub-27 |
| 1-3452 | Sub-44 | 3,4-diClPh | CO | CH$_2$ | Sub-28 |
| 1-3453 | Sub-44 | 3,4-diClPh | CO | CH$_2$ | Sub-29 |
| 1-3454 | Sub-44 | 3,4-diClPh | CO | CH$_2$ | Sub-30 |
| 1-3455 | Sub-44 | 3,4-diClPh | CO | CH$_2$ | Sub-31 |
| 1-3456 | Sub-44 | 3,4-diClPh | CO | CH$_2$ | Sub-32 |
| 1-3457 | Sub-45 | 3,4-diClPh | CO | CH$_2$ | Sub-1 |
| 1-3458 | Sub-45 | 3,4-diClPh | CO | CH$_2$ | Sub-2 |
| 1-3459 | Sub-45 | 3,4-diClPh | CO | CH$_2$ | Sub-3 |
| 1-3460 | Sub-45 | 3,4-diClPh | CO | CH$_2$ | Sub-4 |
| 1-3461 | Sub-45 | 3,4-diClPh | CO | CH$_2$ | Sub-5 |
| 1-3462 | Sub-45 | 3,4-diClPh | CO | CH$_2$ | Sub-6 |
| 1-3463 | Sub-45 | 3,4-diClPh | CO | CH$_2$ | Sub-7 |
| 1-3464 | Sub-45 | 3,4-diClPh | CO | CH$_2$ | Sub-8 |
| 1-3465 | Sub-45 | 3,4-diClPh | CO | CH$_2$ | Sub-9 |
| 1-3466 | Sub-45 | 3,4-diClPh | CO | CH$_2$ | Sub-10 |
| 1-3467 | Sub-45 | 3,4-diClPh | CO | CH$_2$ | Sub-11 |
| 1-3468 | Sub-45 | 3,4-diClPh | CO | CH$_2$ | Sub-12 |
| 1-3469 | Sub-45 | 3,4-diClPh | CO | CH$_2$ | Sub-13 |

TABLE 1-continued

| Cpd. No. | R¹ | R² | A | B | Z |
|---|---|---|---|---|---|
| 1-3470 | Sub-45 | 3,4-diClPh | CO | CH$_2$ | Sub-14 |
| 1-3471 | Sub-45 | 3,4-diClPh | CO | CH$_2$ | Sub-15 |
| 1-3472 | Sub-45 | 3,4-diClPh | CO | CH$_2$ | Sub-16 |
| 1-3473 | Sub-45 | 3,4-diClPh | CO | CH$_2$ | Sub-17 |
| 1-3474 | Sub-45 | 3,4-diClPh | CO | CH$_2$ | Sub-18 |
| 1-3475 | Sub-45 | 3,4-diClPh | CO | CH$_2$ | Sub-19 |
| 1-3476 | Sub-45 | 3,4-diClPh | CO | CH$_2$ | Sub-20 |
| 1-3477 | Sub-45 | 3,4-diClPh | CO | CH$_2$ | Sub-21 |
| 1-3478 | Sub-45 | 3,4-diClPh | CO | CH$_2$ | Sub-22 |
| 1-3479 | Sub-45 | 3,4-diClPh | CO | CH$_2$ | Sub-23 |
| 1-3480 | Sub-45 | 3,4-diClPh | CO | CH$_2$ | Sub-24 |
| 1-3481 | Sub-45 | 3,4-diClPh | CO | CH$_2$ | Sub-25 |
| 1-3482 | Sub-45 | 3,4-diClPh | CO | CH$_2$ | Sub-26 |
| 1-3483 | Sub-45 | 3,4-diClPh | CO | CH$_2$ | Sub-27 |
| 1-3484 | Sub-45 | 3,4-diClPh | CO | CH$_2$ | Sub-28 |
| 1-3485 | Sub-45 | 3,4-diClPh | CO | CH$_2$ | Sub-29 |
| 1-3486 | Sub-45 | 3,4-diClPh | CO | CH$_2$ | Sub-30 |
| 1-3487 | Sub-45 | 3,4-diClPh | CO | CH$_2$ | Sub-31 |
| 1-3488 | Sub-45 | 3,4-diClPh | CO | CH$_2$ | Sub-32 |
| 1-3489 | Sub-46 | 3,4-diClPh | CO | CH$_2$ | Sub-1 |
| 1-3490 | Sub-46 | 3,4-diClPh | CO | CH$_2$ | Sub-2 |
| 1-3491 | Sub-46 | 3,4-diClPh | CO | CH$_2$ | Sub-3 |
| 1-3492 | Sub-46 | 3,4-diClPh | CO | CH$_2$ | Sub-4 |
| 1-3493 | Sub-46 | 3,4-diClPh | CO | CH$_2$ | Sub-5 |
| 1-3494 | Sub-46 | 3,4-diClPh | CO | CH$_2$ | Sub-6 |
| 1-3495 | Sub-46 | 3,4-diClPh | CO | CH$_2$ | Sub-7 |
| 1-3496 | Sub-46 | 3,4-diClPh | CO | CH$_2$ | Sub-8 |
| 1-3497 | Sub-46 | 3,4-diClPh | CO | CH$_2$ | Sub-9 |
| 1-3498 | Sub-46 | 3,4-diClPh | CO | CH$_2$ | Sub-10 |
| 1-3499 | Sub-46 | 3,4-diClPh | CO | CH$_2$ | Sub-11 |
| 1-3500 | Sub-46 | 3,4-diClPh | CO | CH$_2$ | Sub-12 |
| 1-3501 | Sub-46 | 3,4-diClPh | CO | CH$_2$ | Sub-13 |
| 1-3502 | Sub-46 | 3,4-diClPh | CO | CH$_2$ | Sub-14 |
| 1-3503 | Sub-46 | 3,4-diClPh | CO | CH$_2$ | Sub-15 |
| 1-3504 | Sub-46 | 3,4-diClPh | CO | CH$_2$ | Sub-16 |
| 1-3505 | Sub-46 | 3,4-diClPh | CO | CH$_2$ | Sub-17 |
| 1-3506 | Sub-46 | 3,4-diClPh | CO | CH$_2$ | Sub-18 |
| 1-3507 | Sub-46 | 3,4-diClPh | CO | CH$_2$ | Sub-19 |
| 1-3508 | Sub-46 | 3,4-diClPh | CO | CH$_2$ | Sub-20 |
| 1-3509 | Sub-46 | 3,4-diClPh | CO | CH$_2$ | Sub-21 |
| 1-3510 | Sub-46 | 3,4-diClPh | CO | CH$_2$ | Sub-22 |
| 1-3511 | Sub-46 | 3,4-diClPh | CO | CH$_2$ | Sub-23 |
| 1-3512 | Sub-46 | 3,4-diClPh | CO | CH$_2$ | Sub-24 |
| 1-3513 | Sub-46 | 3,4-diClPh | CO | CH$_2$ | Sub-25 |
| 1-3514 | Sub-46 | 3,4-diClPh | CO | CH$_2$ | Sub-26 |
| 1-3515 | Sub-46 | 3,4-diClPh | CO | CH$_2$ | Sub-27 |
| 1-3516 | Sub-46 | 3,4-diClPh | CO | CH$_2$ | Sub-28 |
| 1-3517 | Sub-46 | 3,4-diClPh | CO | CH$_2$ | Sub-29 |
| 1-3518 | Sub-46 | 3,4-diClPh | CO | CH$_2$ | Sub-30 |
| 1-3519 | Sub-46 | 3,4-diClPh | CO | CH$_2$ | Sub-31 |
| 1-3520 | Sub-46 | 3,4-diClPh | CO | CH$_2$ | Sub-32 |
| 1-3521 | Sub-47 | 3,4-diClPh | CO | CH$_2$ | Sub-1 |
| 1-3522 | Sub-47 | 3,4-diClPh | CO | CH$_2$ | Sub-2 |
| 1-3523 | Sub-47 | 3,4-diClPh | CO | CH$_2$ | Sub-3 |
| 1-3524 | Sub-47 | 3,4-diClPh | CO | CH$_2$ | Sub-4 |
| 1-3525 | Sub-47 | 3,4-diClPh | CO | CH$_2$ | Sub-5 |
| 1-3526 | Sub-47 | 3,4-diClPh | CO | CH$_2$ | Sub-6 |
| 1-3527 | Sub-47 | 3,4-diClPh | CO | CH$_2$ | Sub-7 |
| 1-3528 | Sub-47 | 3,4-diClPh | CO | CH$_2$ | Sub-8 |
| 1-3529 | Sub-47 | 3,4-diClPh | CO | CH$_2$ | Sub-9 |
| 1-3530 | Sub-47 | 3,4-diClPh | CO | CH$_2$ | Sub-10 |
| 1-3531 | Sub-47 | 3,4-diClPh | CO | CH$_2$ | Sub-11 |
| 1-3532 | Sub-47 | 3,4-diClPh | CO | CH$_2$ | Sub-12 |
| 1-3533 | Sub-47 | 3,4-diClPh | CO | CH$_2$ | Sub-13 |
| 1-3534 | Sub-47 | 3,4-diClPh | CO | CH$_2$ | Sub-14 |
| 1-3535 | Sub-47 | 3,4-diClPh | CO | CH$_2$ | Sub-15 |
| 1-3536 | Sub-47 | 3,4-diClPh | CO | CH$_2$ | Sub-16 |
| 1-3537 | Sub-47 | 3,4-diClPh | CO | CH$_2$ | Sub-17 |
| 1-3538 | Sub-47 | 3,4-diClPh | CO | CH$_2$ | Sub-18 |
| 1-3539 | Sub-47 | 3,4-diClPh | CO | CH$_2$ | Sub-19 |
| 1-3540 | Sub-47 | 3,4-diClPh | CO | CH$_2$ | Sub-20 |
| 1-3541 | Sub-47 | 3,4-diClPh | CO | CH$_2$ | Sub-21 |
| 1-3542 | Sub-47 | 3,4-diClPh | CO | CH$_2$ | Sub-22 |
| 1-3543 | Sub-47 | 3,4-diClPh | CO | CH$_2$ | Sub-23 |
| 1-3544 | Sub-47 | 3,4-diClPh | CO | CH$_2$ | Sub-24 |
| 1-3545 | Sub-47 | 3,4-diClPh | CO | CH$_2$ | Sub-25 |
| 1-3546 | Sub-47 | 3,4-diClPh | CO | CH$_2$ | Sub-26 |
| 1-3547 | Sub-47 | 3,4-diClPh | CO | CH$_2$ | Sub-27 |
| 1-3548 | Sub-47 | 3,4-diClPh | CO | CH$_2$ | Sub-28 |
| 1-3549 | Sub-47 | 3,4-diClPh | CO | CH$_2$ | Sub-29 |
| 1-3550 | Sub-47 | 3,4-diClPh | CO | CH$_2$ | Sub-30 |
| 1-3551 | Sub-47 | 3,4-diClPh | CO | CH$_2$ | Sub-31 |
| 1-3552 | Sub-47 | 3,4-diClPh | CO | CH$_2$ | Sub-32 |
| 1-3553 | Sub-48 | 3,4-diClPh | CO | CH$_2$ | Sub-1 |
| 1-3554 | Sub-48 | 3,4-diClPh | CO | CH$_2$ | Sub-2 |
| 1-3555 | Sub-48 | 3,4-diClPh | CO | CH$_2$ | Sub-3 |
| 1-3556 | Sub-48 | 3,4-diClPh | CO | CH$_2$ | Sub-4 |
| 1-3557 | Sub-48 | 3,4-diClPh | CO | CH$_2$ | Sub-5 |
| 1-3558 | Sub-48 | 3,4-diClPh | CO | CH$_2$ | Sub-6 |
| 1-3559 | Sub-48 | 3,4-diClPh | CO | CH$_2$ | Sub-7 |
| 1-3560 | Sub-48 | 3,4-diClPh | CO | CH$_2$ | Sub-8 |
| 1-3561 | Sub-48 | 3,4-diClPh | CO | CH$_2$ | Sub-9 |
| 1-3562 | Sub-48 | 3,4-diClPh | CO | CH$_2$ | Sub-10 |
| 1-3563 | Sub-48 | 3,4-diClPh | CO | CH$_2$ | Sub-11 |
| 1-3564 | Sub-48 | 3,4-diClPh | CO | CH$_2$ | Sub-12 |
| 1-3565 | Sub-48 | 3,4-diClPh | CO | CH$_2$ | Sub-13 |
| 1-3566 | Sub-48 | 3,4-diClPh | CO | CH$_2$ | Sub-14 |
| 1-3567 | Sub-48 | 3,4-diClPh | CO | CH$_2$ | Sub-15 |
| 1-3568 | Sub-48 | 3,4-diClPh | CO | CH$_2$ | Sub-16 |
| 1-3569 | Sub-48 | 3,4-diClPh | CO | CH$_2$ | Sub-17 |
| 1-3570 | Sub-48 | 3,4-diClPh | CO | CH$_2$ | Sub-18 |
| 1-3571 | Sub-48 | 3,4-diClPh | CO | CH$_2$ | Sub-19 |
| 1-3572 | Sub-48 | 3,4-diClPh | CO | CH$_2$ | Sub-20 |
| 1-3573 | Sub-48 | 3,4-diClPh | CO | CH$_2$ | Sub-21 |
| 1-3574 | Sub-48 | 3,4-diClPh | CO | CH$_2$ | Sub-22 |
| 1-3575 | Sub-48 | 3,4-diClPh | CO | CH$_2$ | Sub-23 |
| 1-3576 | Sub-48 | 3,4-diClPh | CO | CH$_2$ | Sub-24 |
| 1-3577 | Sub-48 | 3,4-diClPh | CO | CH$_2$ | Sub-25 |
| 1-3578 | Sub-48 | 3,4-diClPh | CO | CH$_2$ | Sub-26 |
| 1-3579 | Sub-48 | 3,4-diClPh | CO | CH$_2$ | Sub-27 |
| 1-3580 | Sub-48 | 3,4-diClPh | CO | CH$_2$ | Sub-28 |
| 1-3581 | Sub-48 | 3,4-diClPh | CO | CH$_2$ | Sub-29 |
| 1-3582 | Sub-48 | 3,4-diClPh | CO | CH$_2$ | Sub-30 |
| 1-3583 | Sub-48 | 3,4-diClPh | CO | CH$_2$ | Sub-31 |
| 1-3584 | Sub-48 | 3,4-diClPh | CO | CH$_2$ | Sub-32 |
| 1-3585 | Sub-49 | 3,4-diClPh | CO | CH$_2$ | Sub-1 |
| 1-3586 | Sub-49 | 3,4-diClPh | CO | CH$_2$ | Sub-2 |
| 1-3587 | Sub-49 | 3,4-diClPh | CO | CH$_2$ | Sub-3 |
| 1-3588 | Sub-49 | 3,4-diClPh | CO | CH$_2$ | Sub-4 |
| 1-3589 | Sub-49 | 3,4-diClPh | CO | CH$_2$ | Sub-5 |
| 1-3590 | Sub-49 | 3,4-diClPh | CO | CH$_2$ | Sub-6 |
| 1-3591 | Sub-49 | 3,4-diClPh | CO | CH$_2$ | Sub-7 |
| 1-3592 | Sub-49 | 3,4-diClPh | CO | CH$_2$ | Sub-8 |
| 1-3593 | Sub-49 | 3,4-diClPh | CO | CH$_2$ | Sub-9 |
| 1-3594 | Sub-49 | 3,4-diClPh | CO | CH$_2$ | Sub-10 |
| 1-3595 | Sub-49 | 3,4-diClPh | CO | CH$_2$ | Sub-11 |
| 1-3596 | Sub-49 | 3,4-diClPh | CO | CH$_2$ | Sub-12 |
| 1-3597 | Sub-49 | 3,4-diClPh | CO | CH$_2$ | Sub-13 |
| 1-3598 | Sub-49 | 3,4-diClPh | CO | CH$_2$ | Sub-14 |
| 1-3599 | Sub-49 | 3,4-diClPh | CO | CH$_2$ | Sub-15 |
| 1-3600 | Sub-49 | 3,4-diClPh | CO | CH$_2$ | Sub-16 |
| 1-3601 | Sub-49 | 3,4-diClPh | CO | CH$_2$ | Sub-17 |
| 1-3602 | Sub-49 | 3,4-diClPh | CO | CH$_2$ | Sub-18 |
| 1-3603 | Sub-49 | 3,4-diClPh | CO | CH$_2$ | Sub-19 |
| 1-3604 | Sub-49 | 3,4-diClPh | CO | CH$_2$ | Sub-20 |
| 1-3605 | Sub-49 | 3,4-diClPh | CO | CH$_2$ | Sub-21 |
| 1-3606 | Sub-49 | 3,4-diClPh | CO | CH$_2$ | Sub-22 |
| 1-3607 | Sub-49 | 3,4-diClPh | CO | CH$_2$ | Sub-23 |
| 1-3608 | Sub-49 | 3,4-diClPh | CO | CH$_2$ | Sub-24 |
| 1-3609 | Sub-49 | 3,4-diClPh | CO | CH$_2$ | Sub-25 |
| 1-3610 | Sub-49 | 3,4-diClPh | CO | CH$_2$ | Sub-26 |
| 1-3611 | Sub-49 | 3,4-diClPh | CO | CH$_2$ | Sub-27 |
| 1-3612 | Sub-49 | 3,4-diClPh | CO | CH$_2$ | Sub-28 |
| 1-3613 | Sub-49 | 3,4-diClPh | CO | CH$_2$ | Sub-29 |
| 1-3614 | Sub-49 | 3,4-diClPh | CO | CH$_2$ | Sub-30 |
| 1-3615 | Sub-49 | 3,4-diClPh | CO | CH$_2$ | Sub-31 |
| 1-3616 | Sub-49 | 3,4-diClPh | CO | CH$_2$ | Sub-32 |
| 1-3617 | Sub-50 | 3,4-diClPh | CO | CH$_2$ | Sub-1 |
| 1-3618 | Sub-50 | 3,4-diClPh | CO | CH$_2$ | Sub-2 |
| 1-3619 | Sub-50 | 3,4-diClPh | CO | CH$_2$ | Sub-3 |
| 1-3620 | Sub-50 | 3,4-diClPh | CO | CH$_2$ | Sub-4 |
| 1-3621 | Sub-50 | 3,4-diClPh | CO | CH$_2$ | Sub-5 |

TABLE 1-continued

| Cpd. No. | R¹ | R² | A | B | Z |
|---|---|---|---|---|---|
| 1-3622 | Sub-50 | 3,4-diClPh | CO | CH₂ | Sub-6 |
| 1-3623 | Sub-50 | 3,4-diClPh | CO | CH₂ | Sub-7 |
| 1-3624 | Sub-50 | 3,4-diClPh | CO | CH₂ | Sub-8 |
| 1-3625 | Sub-50 | 3,4-diClPh | CO | CH₂ | Sub-9 |
| 1-3626 | Sub-50 | 3,4-diClPh | CO | CH₂ | Sub-10 |
| 1-3627 | Sub-50 | 3,4-diClPh | CO | CH₂ | Sub-11 |
| 1-3628 | Sub-50 | 3,4-diClPh | CO | CH₂ | Sub-12 |
| 1-3629 | Sub-50 | 3,4-diClPh | CO | CH₂ | Sub-13 |
| 1-3630 | Sub-50 | 3,4-diClPh | CO | CH₂ | Sub-14 |
| 1-3631 | Sub-50 | 3,4-diClPh | CO | CH₂ | Sub-15 |
| 1-3632 | Sub-50 | 3,4-diClPh | CO | CH₂ | Sub-16 |
| 1-3633 | Sub-50 | 3,4-diClPh | CO | CH₂ | Sub-17 |
| 1-3634 | Sub-50 | 3,4-diClPh | CO | CH₂ | Sub-18 |
| 1-3635 | Sub-50 | 3,4-diClPh | CO | CH₂ | Sub-19 |
| 1-3636 | Sub-50 | 3,4-diClPh | CO | CH₂ | Sub-20 |
| 1-3637 | Sub-50 | 3,4-diClPh | CO | CH₂ | Sub-21 |
| 1-3638 | Sub-50 | 3,4-diClPh | CO | CH₂ | Sub-22 |
| 1-3639 | Sub-50 | 3,4-diClPh | CO | CH₂ | Sub-23 |
| 1-3640 | Sub-50 | 3,4-diClPh | CO | CH₂ | Sub-24 |
| 1-3641 | Sub-50 | 3,4-diClPh | CO | CH₂ | Sub-25 |
| 1-3642 | Sub-50 | 3,4-diClPh | CO | CH₂ | Sub-26 |
| 1-3643 | Sub-50 | 3,4-diClPh | CO | CH₂ | Sub-27 |
| 1-3644 | Sub-50 | 3,4-diClPh | CO | CH₂ | Sub-28 |
| 1-3645 | Sub-50 | 3,4-diClPh | CO | CH₂ | Sub-29 |
| 1-3646 | Sub-50 | 3,4-diClPh | CO | CH₂ | Sub-30 |
| 1-3647 | Sub-50 | 3,4-diClPh | CO | CH₂ | Sub-31 |
| 1-3648 | Sub-50 | 3,4-diClPh | CO | CH₂ | Sub-32 |
| 1-3649 | Sub-51 | 3,4-diClPh | CO | CH₂ | Sub-1 |
| 1-3650 | Sub-51 | 3,4-diClPh | CO | CH₂ | Sub-2 |
| 1-3651 | Sub-51 | 3,4-diClPh | CO | CH₂ | Sub-3 |
| 1-3652 | Sub-51 | 3,4-diClPh | CO | CH₂ | Sub-4 |
| 1-3653 | Sub-51 | 3,4-diClPh | CO | CH₂ | Sub-5 |
| 1-3654 | Sub-51 | 3,4-diClPh | CO | CH₂ | Sub-6 |
| 1-3655 | Sub-51 | 3,4-diClPh | CO | CH₂ | Sub-7 |
| 1-3656 | Sub-51 | 3,4-diClPh | CO | CH₂ | Sub-8 |
| 1-3657 | Sub-51 | 3,4-diClPh | CO | CH₂ | Sub-9 |
| 1-3658 | Sub-51 | 3,4-diClPh | CO | CH₂ | Sub-10 |
| 1-3659 | Sub-51 | 3,4-diClPh | CO | CH₂ | Sub-11 |
| 1-3660 | Sub-51 | 3,4-diClPh | CO | CH₂ | Sub-12 |
| 1-3661 | Sub-51 | 3,4-diClPh | CO | CH₂ | Sub-13 |
| 1-3662 | Sub-51 | 3,4-diClPh | CO | CH₂ | Sub-14 |
| 1-3663 | Sub-51 | 3,4-diClPh | CO | CH₂ | Sub-15 |
| 1-3664 | Sub-51 | 3,4-diClPh | CO | CH₂ | Sub-16 |
| 1-3665 | Sub-51 | 3,4-diClPh | CO | CH₂ | Sub-17 |
| 1-3666 | Sub-51 | 3,4-diClPh | CO | CH₂ | Sub-18 |
| 1-3667 | Sub-51 | 3,4-diClPh | CO | CH₂ | Sub-19 |
| 1-3668 | Sub-51 | 3,4-diClPh | CO | CH₂ | Sub-20 |
| 1-3669 | Sub-51 | 3,4-diClPh | CO | CH₂ | Sub-21 |
| 1-3670 | Sub-51 | 3,4-diClPh | CO | CH₂ | Sub-22 |
| 1-3671 | Sub-51 | 3,4-diClPh | CO | CH₂ | Sub-23 |
| 1-3672 | Sub-51 | 3,4-diClPh | CO | CH₂ | Sub-24 |
| 1-3673 | Sub-51 | 3,4-diClPh | CO | CH₂ | Sub-25 |
| 1-3674 | Sub-51 | 3,4-diClPh | CO | CH₂ | Sub-26 |
| 1-3675 | Sub-51 | 3,4-diClPh | CO | CH₂ | Sub-27 |
| 1-3676 | Sub-51 | 3,4-diClPh | CO | CH₂ | Sub-28 |
| 1-3677 | Sub-51 | 3,4-diClPh | CO | CH₂ | Sub-29 |
| 1-3678 | Sub-51 | 3,4-diClPh | CO | CH₂ | Sub-30 |
| 1-3679 | Sub-51 | 3,4-diClPh | CO | CH₂ | Sub-31 |
| 1-3680 | Sub-51 | 3,4-diClPh | CO | CH₂ | Sub-32 |
| 1-3681 | Sub-52 | 3,4-diClPh | CO | CH₂ | Sub-1 |
| 1-3682 | Sub-52 | 3,4-diClPh | CO | CH₂ | Sub-2 |
| 1-3683 | Sub-52 | 3,4-diClPh | CO | CH₂ | Sub-3 |
| 1-3684 | Sub-52 | 3,4-diClPh | CO | CH₂ | Sub-4 |
| 1-3685 | Sub-52 | 3,4-diClPh | CO | CH₂ | Sub-5 |
| 1-3686 | Sub-52 | 3,4-diClPh | CO | CH₂ | Sub-6 |
| 1-3687 | Sub-52 | 3,4-diClPh | CO | CH₂ | Sub-7 |
| 1-3688 | Sub-52 | 3,4-diClPh | CO | CH₂ | Sub-8 |
| 1-3689 | Sub-52 | 3,4-diClPh | CO | CH₂ | Sub-9 |
| 1-3690 | Sub-52 | 3,4-diClPh | CO | CH₂ | Sub-10 |
| 1-3691 | Sub-52 | 3,4-diClPh | CO | CH₂ | Sub-11 |
| 1-3692 | Sub-52 | 3,4-diClPh | CO | CH₂ | Sub-12 |
| 1-3693 | Sub-52 | 3,4-diClPh | CO | CH₂ | Sub-13 |
| 1-3694 | Sub-52 | 3,4-diClPh | CO | CH₂ | Sub-14 |
| 1-3695 | Sub-52 | 3,4-diClPh | CO | CH₂ | Sub-15 |
| 1-3696 | Sub-52 | 3,4-diClPh | CO | CH₂ | Sub-16 |
| 1-3697 | Sub-52 | 3,4-diClPh | CO | CH₂ | Sub-17 |
| 1-3698 | Sub-52 | 3,4-diClPh | CO | CH₂ | Sub-18 |
| 1-3699 | Sub-52 | 3,4-diClPh | CO | CH₂ | Sub-19 |
| 1-3700 | Sub-52 | 3,4-diClPh | CO | CH₂ | Sub-20 |
| 1-3701 | Sub-52 | 3,4-diClPh | CO | CH₂ | Sub-21 |
| 1-3702 | Sub-52 | 3,4-diClPh | CO | CH₂ | Sub-22 |
| 1-3703 | Sub-52 | 3,4-diClPh | CO | CH₂ | Sub-23 |
| 1-3704 | Sub-52 | 3,4-diClPh | CO | CH₂ | Sub-24 |
| 1-3705 | Sub-52 | 3,4-diClPh | CO | CH₂ | Sub-25 |
| 1-3706 | Sub-52 | 3,4-diClPh | CO | CH₂ | Sub-26 |
| 1-3707 | Sub-52 | 3,4-diClPh | CO | CH₂ | Sub-27 |
| 1-3708 | Sub-52 | 3,4-diClPh | CO | CH₂ | Sub-28 |
| 1-3709 | Sub-52 | 3,4-diClPh | CO | CH₂ | Sub-29 |
| 1-3710 | Sub-52 | 3,4-diClPh | CO | CH₂ | Sub-30 |
| 1-3711 | Sub-52 | 3,4-diClPh | CO | CH₂ | Sub-31 |
| 1-3712 | Sub-52 | 3,4-diClPh | CO | CH₂ | Sub-32 |
| 1-3713 | Sub-53 | 3,4-diClPh | CO | CH₂ | Sub-1 |
| 1-3714 | Sub-53 | 3,4-diClPh | CO | CH₂ | Sub-2 |
| 1-3715 | Sub-53 | 3,4-diClPh | CO | CH₂ | Sub-3 |
| 1-3716 | Sub-53 | 3,4-diClPh | CO | CH₂ | Sub-4 |
| 1-3717 | Sub-53 | 3,4-diClPh | CO | CH₂ | Sub-5 |
| 1-3718 | Sub-53 | 3,4-diClPh | CO | CH₂ | Sub-6 |
| 1-3719 | Sub-53 | 3,4-diClPh | CO | CH₂ | Sub-7 |
| 1-3720 | Sub-53 | 3,4-diClPh | CO | CH₂ | Sub-8 |
| 1-3721 | Sub-53 | 3,4-diClPh | CO | CH₂ | Sub-9 |
| 1-3722 | Sub-53 | 3,4-diClPh | CO | CH₂ | Sub-10 |
| 1-3723 | Sub-53 | 3,4-diClPh | CO | CH₂ | Sub-11 |
| 1-3724 | Sub-53 | 3,4-diClPh | CO | CH₂ | Sub-12 |
| 1-3725 | Sub-53 | 3,4-diClPh | CO | CH₂ | Sub-13 |
| 1-3726 | Sub-53 | 3,4-diClPh | CO | CH₂ | Sub-14 |
| 1-3727 | Sub-53 | 3,4-diClPh | CO | CH₂ | Sub-15 |
| 1-3728 | Sub-53 | 3,4-diClPh | CO | CH₂ | Sub-16 |
| 1-3729 | Sub-53 | 3,4-diClPh | CO | CH₂ | Sub-17 |
| 1-3730 | Sub-53 | 3,4-diClPh | CO | CH₂ | Sub-18 |
| 1-3731 | Sub-53 | 3,4-diClPh | CO | CH₂ | Sub-19 |
| 1-3732 | Sub-53 | 3,4-diClPh | CO | CH₂ | Sub-20 |
| 1-3733 | Sub-53 | 3,4-diClPh | CO | CH₂ | Sub-21 |
| 1-3734 | Sub-53 | 3,4-diClPh | CO | CH₂ | Sub-22 |
| 1-3735 | Sub-53 | 3,4-diClPh | CO | CH₂ | Sub-23 |
| 1-3736 | Sub-53 | 3,4-diClPh | CO | CH₂ | Sub-24 |
| 1-3737 | Sub-53 | 3,4-diClPh | CO | CH₂ | Sub-25 |
| 1-3738 | Sub-53 | 3,4-diClPh | CO | CH₂ | Sub-26 |
| 1-3739 | Sub-53 | 3,4-diClPh | CO | CH₂ | Sub-27 |
| 1-3740 | Sub-53 | 3,4-diClPh | CO | CH₂ | Sub-28 |
| 1-3741 | Sub-53 | 3,4-diClPh | CO | CH₂ | Sub-29 |
| 1-3742 | Sub-53 | 3,4-diClPh | CO | CH₂ | Sub-30 |
| 1-3743 | Sub-53 | 3,4-diClPh | CO | CH₂ | Sub-31 |
| 1-3744 | Sub-53 | 3,4-diClPh | CO | CH₂ | Sub-32 |
| 1-3745 | Sub-54 | 3,4-diClPh | CO | CH₂ | Sub-1 |
| 1-3746 | Sub-54 | 3,4-diClPh | CO | CH₂ | Sub-2 |
| 1-3747 | Sub-54 | 3,4-diClPh | CO | CH₂ | Sub-3 |
| 1-3748 | Sub-54 | 3,4-diClPh | CO | CH₂ | Sub-4 |
| 1-3749 | Sub-54 | 3,4-diClPh | CO | CH₂ | Sub-5 |
| 1-3750 | Sub-54 | 3,4-diClPh | CO | CH₂ | Sub-6 |
| 1-3751 | Sub-54 | 3,4-diClPh | CO | CH₂ | Sub-7 |
| 1-3752 | Sub-54 | 3,4-diClPh | CO | CH₂ | Sub-8 |
| 1-3753 | Sub-54 | 3,4-diClPh | CO | CH₂ | Sub-9 |
| 1-3754 | Sub-54 | 3,4-diClPh | CO | CH₂ | Sub-10 |
| 1-3755 | Sub-54 | 3,4-diClPh | CO | CH₂ | Sub-11 |
| 1-3756 | Sub-54 | 3,4-diClPh | CO | CH₂ | Sub-12 |
| 1-3757 | Sub-54 | 3,4-diClPh | CO | CH₂ | Sub-13 |
| 1-3758 | Sub-54 | 3,4-diClPh | CO | CH₂ | Sub-14 |
| 1-3759 | Sub-54 | 3,4-diClPh | CO | CH₂ | Sub-15 |
| 1-3760 | Sub-54 | 3,4-diClPh | CO | CH₂ | Sub-16 |
| 1-3761 | Sub-54 | 3,4-diClPh | CO | CH₂ | Sub-17 |
| 1-3762 | Sub-54 | 3,4-diClPh | CO | CH₂ | Sub-18 |
| 1-3763 | Sub-54 | 3,4-diClPh | CO | CH₂ | Sub-19 |
| 1-3764 | Sub-54 | 3,4-diClPh | CO | CH₂ | Sub-20 |
| 1-3765 | Sub-54 | 3,4-diClPh | CO | CH₂ | Sub-21 |
| 1-3766 | Sub-54 | 3,4-diClPh | CO | CH₂ | Sub-22 |
| 1-3767 | Sub-54 | 3,4-diClPh | CO | CH₂ | Sub-23 |
| 1-3768 | Sub-54 | 3,4-diClPh | CO | CH₂ | Sub-24 |
| 1-3769 | Sub-54 | 3,4-diClPh | CO | CH₂ | Sub-25 |
| 1-3770 | Sub-54 | 3,4-diClPh | CO | CH₂ | Sub-26 |
| 1-3771 | Sub-54 | 3,4-diClPh | CO | CH₂ | Sub-27 |
| 1-3772 | Sub-54 | 3,4-diClPh | CO | CH₂ | Sub-28 |
| 1-3773 | Sub-54 | 3,4-diClPh | CO | CH₂ | Sub-29 |

TABLE 1-continued

| Cpd. No. | R¹ | R² | A | B | Z |
|---|---|---|---|---|---|
| 1-3774 | Sub-54 | 3,4-diClPh | CO | $CH_2$ | Sub-30 |
| 1-3775 | Sub-54 | 3,4-diClPh | CO | $CH_2$ | Sub-31 |
| 1-3776 | Sub-54 | 3,4-diClPh | CO | $CH_2$ | Sub-32 |
| 1-3777 | Sub-55 | 3,4-diClPh | CO | $CH_2$ | Sub-1 |
| 1-3778 | Sub-55 | 3,4-diClPh | CO | $CH_2$ | Sub-2 |
| 1-3779 | Sub-55 | 3,4-diClPh | CO | $CH_2$ | Sub-3 |
| 1-3780 | Sub-55 | 3,4-diClPh | CO | $CH_2$ | Sub-4 |
| 1-3781 | Sub-55 | 3,4-diClPh | CO | $CH_2$ | Sub-5 |
| 1-3782 | Sub-55 | 3,4-diClPh | CO | $CH_2$ | Sub-6 |
| 1-3783 | Sub-55 | 3,4-diClPh | CO | $CH_2$ | Sub-7 |
| 1-3784 | Sub-55 | 3,4-diClPh | CO | $CH_2$ | Sub-8 |
| 1-3785 | Sub-55 | 3,4-diClPh | CO | $CH_2$ | Sub-9 |
| 1-3786 | Sub-55 | 3,4-diClPh | CO | $CH_2$ | Sub-10 |
| 1-3787 | Sub-55 | 3,4-diClPh | CO | $CH_2$ | Sub-11 |
| 1-3788 | Sub-55 | 3,4-diClPh | CO | $CH_2$ | Sub-12 |
| 1-3789 | Sub-55 | 3,4-diClPh | CO | $CH_2$ | Sub-13 |
| 1-3790 | Sub-55 | 3,4-diClPh | CO | $CH_2$ | Sub-14 |
| 1-3791 | Sub-55 | 3,4-diClPh | CO | $CH_2$ | Sub-15 |
| 1-3792 | Sub-55 | 3,4-diClPh | CO | $CH_2$ | Sub-16 |
| 1-3793 | Sub-55 | 3,4-diClPh | CO | $CH_2$ | Sub-17 |
| 1-3794 | Sub-55 | 3,4-diClPh | CO | $CH_2$ | Sub-18 |
| 1-3795 | Sub-55 | 3,4-diClPh | CO | $CH_2$ | Sub-19 |
| 1-3796 | Sub-55 | 3,4-diClPh | CO | $CH_2$ | Sub-20 |
| 1-3797 | Sub-55 | 3,4-diClPh | CO | $CH_2$ | Sub-21 |
| 1-3798 | Sub-55 | 3,4-diClPh | CO | $CH_2$ | Sub-22 |
| 1-3799 | Sub-55 | 3,4-diClPh | CO | $CH_2$ | Sub-23 |
| 1-3800 | Sub-55 | 3,4-diClPh | CO | $CH_2$ | Sub-24 |
| 1-3801 | Sub-55 | 3,4-diClPh | CO | $CH_2$ | Sub-25 |
| 1-3802 | Sub-55 | 3,4-diClPh | CO | $CH_2$ | Sub-26 |
| 1-3803 | Sub-55 | 3,4-diClPh | CO | $CH_2$ | Sub-27 |
| 1-3804 | Sub-55 | 3,4-diClPh | CO | $CH_2$ | Sub-28 |
| 1-3805 | Sub-55 | 3,4-diClPh | CO | $CH_2$ | Sub-29 |
| 1-3806 | Sub-55 | 3,4-diClPh | CO | $CH_2$ | Sub-30 |
| 1-3807 | Sub-55 | 3,4-diClPh | CO | $CH_2$ | Sub-31 |
| 1-3808 | Sub-55 | 3,4-diClPh | CO | $CH_2$ | Sub-32 |
| 1-3809 | Sub-56 | 3,4-diClPh | CO | $CH_2$ | Sub-1 |
| 1-3810 | Sub-56 | 3,4-diClPh | CO | $CH_2$ | Sub-2 |
| 1-3811 | Sub-56 | 3,4-diClPh | CO | $CH_2$ | Sub-3 |
| 1-3812 | Sub-56 | 3,4-diClPh | CO | $CH_2$ | Sub-4 |
| 1-3813 | Sub-56 | 3,4-diClPh | CO | $CH_2$ | Sub-5 |
| 1-3814 | Sub-56 | 3,4-diClPh | CO | $CH_2$ | Sub-6 |
| 1-3815 | Sub-56 | 3,4-diClPh | CO | $CH_2$ | Sub-7 |
| 1-3816 | Sub-56 | 3,4-diClPh | CO | $CH_2$ | Sub-8 |
| 1-3817 | Sub-56 | 3,4-diClPh | CO | $CH_2$ | Sub-9 |
| 1-3818 | Sub-56 | 3,4-diClPh | CO | $CH_2$ | Sub-10 |
| 1-3819 | Sub-56 | 3,4-diClPh | CO | $CH_2$ | Sub-11 |
| 1-3820 | Sub-56 | 3,4-diClPh | CO | $CH_2$ | Sub-12 |
| 1-3821 | Sub-56 | 3,4-diClPh | CO | $CH_2$ | Sub-13 |
| 1-3822 | Sub-56 | 3,4-diClPh | CO | $CH_2$ | Sub-14 |
| 1-3823 | Sub-56 | 3,4-diClPh | CO | $CH_2$ | Sub-15 |
| 1-3824 | Sub-56 | 3,4-diClPh | CO | $CH_2$ | Sub-16 |
| 1-3825 | Sub-56 | 3,4-diClPh | CO | $CH_2$ | Sub-17 |
| 1-3826 | Sub-56 | 3,4-diClPh | CO | $CH_2$ | Sub-18 |
| 1-3827 | Sub-56 | 3,4-diClPh | CO | $CH_2$ | Sub-19 |
| 1-3828 | Sub-56 | 3,4-diClPh | CO | $CH_2$ | Sub-20 |
| 1-3829 | Sub-56 | 3,4-diClPh | CO | $CH_2$ | Sub-21 |
| 1-3830 | Sub-56 | 3,4-diClPh | CO | $CH_2$ | Sub-22 |
| 1-3831 | Sub-56 | 3,4-diClPh | CO | $CH_2$ | Sub-23 |
| 1-3832 | Sub-56 | 3,4-diClPh | CO | $CH_2$ | Sub-24 |
| 1-3833 | Sub-56 | 3,4-diClPh | CO | $CH_2$ | Sub-25 |
| 1-3834 | Sub-56 | 3,4-diClPh | CO | $CH_2$ | Sub-26 |
| 1-3835 | Sub-56 | 3,4-diClPh | CO | $CH_2$ | Sub-27 |
| 1-3836 | Sub-56 | 3,4-diClPh | CO | $CH_2$ | Sub-28 |
| 1-3837 | Sub-56 | 3,4-diClPh | CO | $CH_2$ | Sub-29 |
| 1-3838 | Sub-56 | 3,4-diClPh | CO | $CH_2$ | Sub-30 |
| 1-3839 | Sub-56 | 3,4-diClPh | CO | $CH_2$ | Sub-31 |
| 1-3840 | Sub-56 | 3,4-diClPh | CO | $CH_2$ | Sub-32 |
| 1-3841 | Sub-57 | 3,4-diClPh | CO | $CH_2$ | Sub-1 |
| 1-3842 | Sub-57 | 3,4-diClPh | CO | $CH_2$ | Sub-2 |
| 1-3843 | Sub-57 | 3,4-diClPh | CO | $CH_2$ | Sub-3 |
| 1-3844 | Sub-57 | 3,4-diClPh | CO | $CH_2$ | Sub-4 |
| 1-3845 | Sub-57 | 3,4-diClPh | CO | $CH_2$ | Sub-5 |
| 1-3846 | Sub-57 | 3,4-diClPh | CO | $CH_2$ | Sub-6 |
| 1-3847 | Sub-57 | 3,4-diClPh | CO | $CH_2$ | Sub-7 |
| 1-3848 | Sub-57 | 3,4-diClPh | CO | $CH_2$ | Sub-8 |
| 1-3849 | Sub-57 | 3,4-diClPh | CO | $CH_2$ | Sub-9 |
| 1-3850 | Sub-57 | 3,4-diClPh | CO | $CH_2$ | Sub-10 |
| 1-3851 | Sub-57 | 3,4-diClPh | CO | $CH_2$ | Sub-11 |
| 1-3852 | Sub-57 | 3,4-diClPh | CO | $CH_2$ | Sub-12 |
| 1-3853 | Sub-57 | 3,4-diClPh | CO | $CH_2$ | Sub-13 |
| 1-3854 | Sub-57 | 3,4-diClPh | CO | $CH_2$ | Sub-14 |
| 1-3855 | Sub-57 | 3,4-diClPh | CO | $CH_2$ | Sub-15 |
| 1-3856 | Sub-57 | 3,4-diClPh | CO | $CH_2$ | Sub-16 |
| 1-3857 | Sub-57 | 3,4-diClPh | CO | $CH_2$ | Sub-17 |
| 1-3858 | Sub-57 | 3,4-diClPh | CO | $CH_2$ | Sub-18 |
| 1-3859 | Sub-57 | 3,4-diClPh | CO | $CH_2$ | Sub-19 |
| 1-3860 | Sub-57 | 3,4-diClPh | CO | $CH_2$ | Sub-20 |
| 1-3861 | Sub-57 | 3,4-diClPh | CO | $CH_2$ | Sub-21 |
| 1-3862 | Sub-57 | 3,4-diClPh | CO | $CH_2$ | Sub-22 |
| 1-3863 | Sub-57 | 3,4-diClPh | CO | $CH_2$ | Sub-23 |
| 1-3864 | Sub-57 | 3,4-diClPh | CO | $CH_2$ | Sub-24 |
| 1-3865 | Sub-57 | 3,4-diClPh | CO | $CH_2$ | Sub-25 |
| 1-3866 | Sub-57 | 3,4-diClPh | CO | $CH_2$ | Sub-26 |
| 1-3867 | Sub-57 | 3,4-diClPh | CO | $CH_2$ | Sub-27 |
| 1-3868 | Sub-57 | 3,4-diClPh | CO | $CH_2$ | Sub-28 |
| 1-3869 | Sub-57 | 3,4-diClPh | CO | $CH_2$ | Sub-29 |
| 1-3870 | Sub-57 | 3,4-diClPh | CO | $CH_2$ | Sub-30 |
| 1-3871 | Sub-57 | 3,4-diClPh | CO | $CH_2$ | Sub-31 |
| 1-3872 | Sub-57 | 3,4-diClPh | CO | $CH_2$ | Sub-32 |
| 1-3873 | Sub-58 | 3,4-diClPh | CO | $CH_2$ | Sub-1 |
| 1-3874 | Sub-58 | 3,4-diClPh | CO | $CH_2$ | Sub-2 |
| 1-3875 | Sub-58 | 3,4-diClPh | CO | $CH_2$ | Sub-3 |
| 1-3876 | Sub-58 | 3,4-diClPh | CO | $CH_2$ | Sub-4 |
| 1-3877 | Sub-58 | 3,4-diClPh | CO | $CH_2$ | Sub-5 |
| 1-3878 | Sub-58 | 3,4-diClPh | CO | $CH_2$ | Sub-6 |
| 1-3879 | Sub-58 | 3,4-diClPh | CO | $CH_2$ | Sub-7 |
| 1-3880 | Sub-58 | 3,4-diClPh | CO | $CH_2$ | Sub-8 |
| 1-3881 | Sub-58 | 3,4-diClPh | CO | $CH_2$ | Sub-9 |
| 1-3882 | Sub-58 | 3,4-diClPh | CO | $CH_2$ | Sub-10 |
| 1-3883 | Sub-58 | 3,4-diClPh | CO | $CH_2$ | Sub-11 |
| 1-3884 | Sub-58 | 3,4-diClPh | CO | $CH_2$ | Sub-12 |
| 1-3885 | Sub-58 | 3,4-diClPh | CO | $CH_2$ | Sub-13 |
| 1-3886 | Sub-58 | 3,4-diClPh | CO | $CH_2$ | Sub-14 |
| 1-3887 | Sub-58 | 3,4-diClPh | CO | $CH_2$ | Sub-15 |
| 1-3888 | Sub-58 | 3,4-diClPh | CO | $CH_2$ | Sub-16 |
| 1-3889 | Sub-58 | 3,4-diClPh | CO | $CH_2$ | Sub-17 |
| 1-3890 | Sub-58 | 3,4-diClPh | CO | $CH_2$ | Sub-18 |
| 1-3891 | Sub-58 | 3,4-diClPh | CO | $CH_2$ | Sub-19 |
| 1-3892 | Sub-58 | 3,4-diClPh | CO | $CH_2$ | Sub-20 |
| 1-3893 | Sub-58 | 3,4-diClPh | CO | $CH_2$ | Sub-21 |
| 1-3894 | Sub-58 | 3,4-diClPh | CO | $CH_2$ | Sub-22 |
| 1-3895 | Sub-58 | 3,4-diClPh | CO | $CH_2$ | Sub-23 |
| 1-3896 | Sub-58 | 3,4-diClPh | CO | $CH_2$ | Sub-24 |
| 1-3897 | Sub-58 | 3,4-diClPh | CO | $CH_2$ | Sub-25 |
| 1-3898 | Sub-58 | 3,4-diClPh | CO | $CH_2$ | Sub-26 |
| 1-3899 | Sub-58 | 3,4-diClPh | CO | $CH_2$ | Sub-27 |
| 1-3900 | Sub-58 | 3,4-diClPh | CO | $CH_2$ | Sub-28 |
| 1-3901 | Sub-58 | 3,4-diClPh | CO | $CH_2$ | Sub-29 |
| 1-3902 | Sub-58 | 3,4-diClPh | CO | $CH_2$ | Sub-30 |
| 1-3903 | Sub-58 | 3,4-diClPh | CO | $CH_2$ | Sub-31 |
| 1-3904 | Sub-58 | 3,4-diClPh | CO | $CH_2$ | Sub-32 |
| 1-3905 | Sub-59 | 3,4-diClPh | CO | $CH_2$ | Sub-1 |
| 1-3906 | Sub-59 | 3,4-diClPh | CO | $CH_2$ | Sub-2 |
| 1-3907 | Sub-59 | 3,4-diClPh | CO | $CH_2$ | Sub-3 |
| 1-3908 | Sub-59 | 3,4-diClPh | CO | $CH_2$ | Sub-4 |
| 1-3909 | Sub-59 | 3,4-diClPh | CO | $CH_2$ | Sub-5 |
| 1-3910 | Sub-59 | 3,4-diClPh | CO | $CH_2$ | Sub-6 |
| 1-3911 | Sub-59 | 3,4-diClPh | CO | $CH_2$ | Sub-7 |
| 1-3912 | Sub-59 | 3,4-diClPh | CO | $CH_2$ | Sub-8 |
| 1-3913 | Sub-59 | 3,4-diClPh | CO | $CH_2$ | Sub-9 |
| 1-3914 | Sub-59 | 3,4-diClPh | CO | $CH_2$ | Sub-10 |
| 1-3915 | Sub-59 | 3,4-diClPh | CO | $CH_2$ | Sub-11 |
| 1-3916 | Sub-59 | 3,4-diClPh | CO | $CH_2$ | Sub-12 |
| 1-3917 | Sub-59 | 3,4-diClPh | CO | $CH_2$ | Sub-13 |
| 1-3918 | Sub-59 | 3,4-diClPh | CO | $CH_2$ | Sub-14 |
| 1-3919 | Sub-59 | 3,4-diClPh | CO | $CH_2$ | Sub-15 |
| 1-3920 | Sub-59 | 3,4-diClPh | CO | $CH_2$ | Sub-16 |
| 1-3921 | Sub-59 | 3,4-diClPh | CO | $CH_2$ | Sub-17 |
| 1-3922 | Sub-59 | 3,4-diClPh | CO | $CH_2$ | Sub-18 |
| 1-3923 | Sub-59 | 3,4-diClPh | CO | $CH_2$ | Sub-19 |
| 1-3924 | Sub-59 | 3,4-diClPh | CO | $CH_2$ | Sub-20 |
| 1-3925 | Sub-59 | 3,4-diClPh | CO | $CH_2$ | Sub-21 |

TABLE 1-continued

| Cpd. No. | R¹ | R² | A | B | Z |
|---|---|---|---|---|---|
| 1-3926 | Sub-59 | 3,4-diClPh | CO | CH₂ | Sub-22 |
| 1-3927 | Sub-59 | 3,4-diClPh | CO | CH₂ | Sub-23 |
| 1-3928 | Sub-59 | 3,4-diClPh | CO | CH₂ | Sub-24 |
| 1-3929 | Sub-59 | 3,4-diClPh | CO | CH₂ | Sub-25 |
| 1-3930 | Sub-59 | 3,4-diClPh | CO | CH₂ | Sub-26 |
| 1-3931 | Sub-59 | 3,4-diClPh | CO | CH₂ | Sub-27 |
| 1-3932 | Sub-59 | 3,4-diClPh | CO | CH₂ | Sub-28 |
| 1-3933 | Sub-59 | 3,4-diClPh | CO | CH₂ | Sub-29 |
| 1-3934 | Sub-59 | 3,4-diClPh | CO | CH₂ | Sub-30 |
| 1-3935 | Sub-59 | 3,4-diClPh | CO | CH₂ | Sub-31 |
| 1-3936 | Sub-59 | 3,4-diClPh | CO | CH₂ | Sub-32 |
| 1-3937 | Sub-60 | 3,4-diClPh | CO | CH₂ | Sub-1 |
| 1-3938 | Sub-60 | 3,4-diClPh | CO | CH₂ | Sub-2 |
| 1-3939 | Sub-60 | 3,4-diClPh | CO | CH₂ | Sub-3 |
| 1-3940 | Sub-60 | 3,4-diClPh | CO | CH₂ | Sub-4 |
| 1-3941 | Sub-60 | 3,4-diClPh | CO | CH₂ | Sub-5 |
| 1-3942 | Sub-60 | 3,4-diClPh | CO | CH₂ | Sub-6 |
| 1-3943 | Sub-60 | 3,4-diClPh | CO | CH₂ | Sub-7 |
| 1-3944 | Sub-60 | 3,4-diClPh | CO | CH₂ | Sub-8 |
| 1-3945 | Sub-60 | 3,4-diClPh | CO | CH₂ | Sub-9 |
| 1-3946 | Sub-60 | 3,4-diClPh | CO | CH₂ | Sub-10 |
| 1-3947 | Sub-60 | 3,4-diClPh | CO | CH₂ | Sub-11 |
| 1-3948 | Sub-60 | 3,4-diClPh | CO | CH₂ | Sub-12 |
| 1-3949 | Sub-60 | 3,4-diClPh | CO | CH₂ | Sub-13 |
| 1-3950 | Sub-60 | 3,4-diClPh | CO | CH₂ | Sub-14 |
| 1-3951 | Sub-60 | 3,4-diClPh | CO | CH₂ | Sub-15 |
| 1-3952 | Sub-60 | 3,4-diClPh | CO | CH₂ | Sub-16 |
| 1-3953 | Sub-60 | 3,4-diClPh | CO | CH₂ | Sub-17 |
| 1-3954 | Sub-60 | 3,4-diClPh | CO | CH₂ | Sub-18 |
| 1-3955 | Sub-60 | 3,4-diClPh | CO | CH₂ | Sub-19 |
| 1-3956 | Sub-60 | 3,4-diClPh | CO | CH₂ | Sub-20 |
| 1-3957 | Sub-60 | 3,4-diClPh | CO | CH₂ | Sub-21 |
| 1-3958 | Sub-60 | 3,4-diClPh | CO | CH₂ | Sub-22 |
| 1-3959 | Sub-60 | 3,4-diClPh | CO | CH₂ | Sub-23 |
| 1-3960 | Sub-60 | 3,4-diClPh | CO | CH₂ | Sub-24 |
| 1-3961 | Sub-60 | 3,4-diClPh | CO | CH₂ | Sub-25 |
| 1-3962 | Sub-60 | 3,4-diClPh | CO | CH₂ | Sub-26 |
| 1-3963 | Sub-60 | 3,4-diClPh | CO | CH₂ | Sub-27 |
| 1-3964 | Sub-60 | 3,4-diClPh | CO | CH₂ | Sub-28 |
| 1-3965 | Sub-60 | 3,4-diClPh | CO | CH₂ | Sub-29 |
| 1-3966 | Sub-60 | 3,4-diClPh | CO | CH₂ | Sub-30 |
| 1-3967 | Sub-60 | 3,4-diClPh | CO | CH₂ | Sub-31 |
| 1-3968 | Sub-60 | 3,4-diClPh | CO | CH₂ | Sub-32 |
| 1-3969 | Sub-61 | 3,4-diClPh | CO | CH₂ | Sub-1 |
| 1-3970 | Sub-61 | 3,4-diClPh | CO | CH₂ | Sub-2 |
| 1-3971 | Sub-61 | 3,4-diClPh | CO | CH₂ | Sub-3 |
| 1-3972 | Sub-61 | 3,4-diClPh | CO | CH₂ | Sub-4 |
| 1-3973 | Sub-61 | 3,4-diClPh | CO | CH₂ | Sub-5 |
| 1-3974 | Sub-61 | 3,4-diClPh | CO | CH₂ | Sub-6 |
| 1-3975 | Sub-61 | 3,4-diClPh | CO | CH₂ | Sub-7 |
| 1-3976 | Sub-61 | 3,4-diClPh | CO | CH₂ | Sub-8 |
| 1-3977 | Sub-61 | 3,4-diClPh | CO | CH₂ | Sub-9 |
| 1-3978 | Sub-61 | 3,4-diClPh | CO | CH₂ | Sub-10 |
| 1-3979 | Sub-61 | 3,4-diClPh | CO | CH₂ | Sub-11 |
| 1-3980 | Sub-61 | 3,4-diClPh | CO | CH₂ | Sub-12 |
| 1-3981 | Sub-61 | 3,4-diClPh | CO | CH₂ | Sub-13 |
| 1-3982 | Sub-61 | 3,4-diClPh | CO | CH₂ | Sub-14 |
| 1-3983 | Sub-61 | 3,4-diClPh | CO | CH₂ | Sub-15 |
| 1-3984 | Sub-61 | 3,4-diClPh | CO | CH₂ | Sub-16 |
| 1-3985 | Sub-61 | 3,4-diClPh | CO | CH₂ | Sub-17 |
| 1-3986 | Sub-61 | 3,4-diClPh | CO | CH₂ | Sub-18 |
| 1-3987 | Sub-61 | 3,4-diClPh | CO | CH₂ | Sub-19 |
| 1-3988 | Sub-61 | 3,4-diClPh | CO | CH₂ | Sub-20 |
| 1-3989 | Sub-61 | 3,4-diClPh | CO | CH₂ | Sub-21 |
| 1-3990 | Sub-61 | 3,4-diClPh | CO | CH₂ | Sub-22 |
| 1-3991 | Sub-61 | 3,4-diClPh | CO | CH₂ | Sub-23 |
| 1-3992 | Sub-61 | 3,4-diClPh | CO | CH₂ | Sub-24 |
| 1-3993 | Sub-61 | 3,4-diClPh | CO | CH₂ | Sub-25 |
| 1-3994 | Sub-61 | 3,4-diClPh | CO | CH₂ | Sub-26 |
| 1-3995 | Sub-61 | 3,4-diClPh | CO | CH₂ | Sub-27 |
| 1-3996 | Sub-61 | 3,4-diClPh | CO | CH₂ | Sub-28 |
| 1-3997 | Sub-61 | 3,4-diClPh | CO | CH₂ | Sub-29 |
| 1-3998 | Sub-61 | 3,4-diClPh | CO | CH₂ | Sub-30 |
| 1-3999 | Sub-61 | 3,4-diClPh | CO | CH₂ | Sub-31 |
| 1-4000 | Sub-61 | 3,4-diClPh | CO | CH₂ | Sub-32 |
| 1-4001 | Sub-62 | 3,4-diClPh | CO | CH₂ | Sub-1 |
| 1-4002 | Sub-62 | 3,4-diClPh | CO | CH₂ | Sub-2 |
| 1-4003 | Sub-62 | 3,4-diClPh | CO | CH₂ | Sub-3 |
| 1-4004 | Sub-62 | 3,4-diClPh | CO | CH₂ | Sub-4 |
| 1-4005 | Sub-62 | 3,4-diClPh | CO | CH₂ | Sub-5 |
| 1-4006 | Sub-62 | 3,4-diClPh | CO | CH₂ | Sub-6 |
| 1-4007 | Sub-62 | 3,4-diClPh | CO | CH₂ | Sub-7 |
| 1-4008 | Sub-62 | 3,4-diClPh | CO | CH₂ | Sub-8 |
| 1-4009 | Sub-62 | 3,4-diClPh | CO | CH₂ | Sub-9 |
| 1-4010 | Sub-62 | 3,4-diClPh | CO | CH₂ | Sub-10 |
| 1-4011 | Sub-62 | 3,4-diClPh | CO | CH₂ | Sub-11 |
| 1-4012 | Sub-62 | 3,4-diClPh | CO | CH₂ | Sub-12 |
| 1-4013 | Sub-62 | 3,4-diClPh | CO | CH₂ | Sub-13 |
| 1-4014 | Sub-62 | 3,4-diClPh | CO | CH₂ | Sub-14 |
| 1-4015 | Sub-62 | 3,4-diClPh | CO | CH₂ | Sub-15 |
| 1-4016 | Sub-62 | 3,4-diClPh | CO | CH₂ | Sub-16 |
| 1-4017 | Sub-62 | 3,4-diClPh | CO | CH₂ | Sub-17 |
| 1-4018 | Sub-62 | 3,4-diClPh | CO | CH₂ | Sub-18 |
| 1-4019 | Sub-62 | 3,4-diClPh | CO | CH₂ | Sub-19 |
| 1-4020 | Sub-62 | 3,4-diClPh | CO | CH₂ | Sub-20 |
| 1-4021 | Sub-62 | 3,4-diClPh | CO | CH₂ | Sub-21 |
| 1-4022 | Sub-62 | 3,4-diClPh | CO | CH₂ | Sub-22 |
| 1-4023 | Sub-62 | 3,4-diClPh | CO | CH₂ | Sub-23 |
| 1-4024 | Sub-62 | 3,4-diClPh | CO | CH₂ | Sub-24 |
| 1-4025 | Sub-62 | 3,4-diClPh | CO | CH₂ | Sub-25 |
| 1-4026 | Sub-62 | 3,4-diClPh | CO | CH₂ | Sub-26 |
| 1-4027 | Sub-62 | 3,4-diClPh | CO | CH₂ | Sub-27 |
| 1-4028 | Sub-62 | 3,4-diClPh | CO | CH₂ | Sub-28 |
| 1-4029 | Sub-62 | 3,4-diClPh | CO | CH₂ | Sub-29 |
| 1-4030 | Sub-62 | 3,4-diClPh | CO | CH₂ | Sub-30 |
| 1-4031 | Sub-62 | 3,4-diClPh | CO | CH₂ | Sub-31 |
| 1-4032 | Sub-62 | 3,4-diClPh | CO | CH₂ | Sub-32 |
| 1-4033 | Sub-63 | 3,4-diClPh | CO | CH₂ | Sub-1 |
| 1-4034 | Sub-63 | 3,4-diClPh | CO | CH₂ | Sub-2 |
| 1-4035 | Sub-63 | 3,4-diClPh | CO | CH₂ | Sub-3 |
| 1-4036 | Sub-63 | 3,4-diClPh | CO | CH₂ | Sub-4 |
| 1-4037 | Sub-63 | 3,4-diClPh | CO | CH₂ | Sub-5 |
| 1-4038 | Sub-63 | 3,4-diClPh | CO | CH₂ | Sub-6 |
| 1-4039 | Sub-63 | 3,4-diClPh | CO | CH₂ | Sub-7 |
| 1-4040 | Sub-63 | 3,4-diClPh | CO | CH₂ | Sub-8 |
| 1-4041 | Sub-63 | 3,4-diClPh | CO | CH₂ | Sub-9 |
| 1-4042 | Sub-63 | 3,4-diClPh | CO | CH₂ | Sub-10 |
| 1-4043 | Sub-63 | 3,4-diClPh | CO | CH₂ | Sub-11 |
| 1-4044 | Sub-63 | 3,4-diClPh | CO | CH₂ | Sub-12 |
| 1-4045 | Sub-63 | 3,4-diClPh | CO | CH₂ | Sub-13 |
| 1-4046 | Sub-63 | 3,4-diClPh | CO | CH₂ | Sub-14 |
| 1-4047 | Sub-63 | 3,4-diClPh | CO | CH₂ | Sub-15 |
| 1-4048 | Sub-63 | 3,4-diClPh | CO | CH₂ | Sub-16 |
| 1-4049 | Sub-63 | 3,4-diClPh | CO | CH₂ | Sub-17 |
| 1-4050 | Sub-63 | 3,4-diClPh | CO | CH₂ | Sub-18 |
| 1-4051 | Sub-63 | 3,4-diClPh | CO | CH₂ | Sub-19 |
| 1-4052 | Sub-63 | 3,4-diClPh | CO | CH₂ | Sub-20 |
| 1-4053 | Sub-63 | 3,4-diClPh | CO | CH₂ | Sub-21 |
| 1-4054 | Sub-63 | 3,4-diClPh | CO | CH₂ | Sub-22 |
| 1-4055 | Sub-63 | 3,4-diClPh | CO | CH₂ | Sub-23 |
| 1-4056 | Sub-63 | 3,4-diClPh | CO | CH₂ | Sub-24 |
| 1-4057 | Sub-63 | 3,4-diClPh | CO | CH₂ | Sub-25 |
| 1-4058 | Sub-63 | 3,4-diClPh | CO | CH₂ | Sub-26 |
| 1-4059 | Sub-63 | 3,4-diClPh | CO | CH₂ | Sub-27 |
| 1-4060 | Sub-63 | 3,4-diClPh | CO | CH₂ | Sub-28 |
| 1-4061 | Sub-63 | 3,4-diClPh | CO | CH₂ | Sub-29 |
| 1-4062 | Sub-63 | 3,4-diClPh | CO | CH₂ | Sub-30 |
| 1-4063 | Sub-63 | 3,4-diClPh | CO | CH₂ | Sub-31 |
| 1-4064 | Sub-63 | 3,4-diClPh | CO | CH₂ | Sub-32 |
| 1-4065 | Sub-64 | 3,4-diClPh | CO | CH₂ | Sub-1 |
| 1-4066 | Sub-64 | 3,4-diClPh | CO | CH₂ | Sub-2 |
| 1-4067 | Sub-64 | 3,4-diClPh | CO | CH₂ | Sub-3 |
| 1-4068 | Sub-64 | 3,4-diClPh | CO | CH₂ | Sub-4 |
| 1-4069 | Sub-64 | 3,4-diClPh | CO | CH₂ | Sub-5 |
| 1-4070 | Sub-64 | 3,4-diClPh | CO | CH₂ | Sub-6 |
| 1-4071 | Sub-64 | 3,4-diClPh | CO | CH₂ | Sub-7 |
| 1-4072 | Sub-64 | 3,4-diClPh | CO | CH₂ | Sub-8 |
| 1-4073 | Sub-64 | 3,4-diClPh | CO | CH₂ | Sub-9 |
| 1-4074 | Sub-64 | 3,4-diClPh | CO | CH₂ | Sub-10 |
| 1-4075 | Sub-64 | 3,4-diClPh | CO | CH₂ | Sub-11 |
| 1-4076 | Sub-64 | 3,4-diClPh | CO | CH₂ | Sub-12 |
| 1-4077 | Sub-64 | 3,4-diClPh | CO | CH₂ | Sub-13 |

TABLE 1-continued

| Cpd. No. | R¹ | R² | A | B | Z |
|---|---|---|---|---|---|
| 1-4078 | Sub-64 | 3,4-diClPh | CO | $CH_2$ | Sub-14 |
| 1-4079 | Sub-64 | 3,4-diClPh | CO | $CH_2$ | Sub-15 |
| 1-4080 | Sub-64 | 3,4-diClPh | CO | $CH_2$ | Sub-16 |
| 1-4081 | Sub-64 | 3,4-diClPh | CO | $CH_2$ | Sub-17 |
| 1-4082 | Sub-64 | 3,4-diClPh | CO | $CH_2$ | Sub-18 |
| 1-4083 | Sub-64 | 3,4-diClPh | CO | $CH_2$ | Sub-19 |
| 1-4084 | Sub-64 | 3,4-diClPh | CO | $CH_2$ | Sub-20 |
| 1-4085 | Sub-64 | 3,4-diClPh | CO | $CH_2$ | Sub-21 |
| 1-4086 | Sub-64 | 3,4-diClPh | CO | $CH_2$ | Sub-22 |
| 1-4087 | Sub-64 | 3,4-diClPh | CO | $CH_2$ | Sub-23 |
| 1-4088 | Sub-64 | 3,4-diClPh | CO | $CH_2$ | Sub-24 |
| 1-4089 | Sub-64 | 3,4-diClPh | CO | $CH_2$ | Sub-25 |
| 1-4090 | Sub-64 | 3,4-diClPh | CO | $CH_2$ | Sub-26 |
| 1-4091 | Sub-64 | 3,4-diClPh | CO | $CH_2$ | Sub-27 |
| 1-4092 | Sub-64 | 3,4-diClPh | CO | $CH_2$ | Sub-28 |
| 1-4093 | Sub-64 | 3,4-diClPh | CO | $CH_2$ | Sub-29 |
| 1-4094 | Sub-64 | 3,4-diClPh | CO | $CH_2$ | Sub-30 |
| 1-4095 | Sub-64 | 3,4-diClPh | CO | $CH_2$ | Sub-31 |
| 1-4096 | Sub-64 | 3,4-diClPh | CO | $CH_2$ | Sub-32 |

TABLE 2

| Cpd. No. | R¹ | R² | A | B | Z |
|---|---|---|---|---|---|
| 2-1 | Sub-33 | 3,4-diClPh | $CH_2$ | Single bond | Sub-1 |
| 2-2 | Sub-33 | 3,4-diClPh | $CH_2$ | Single bond | Sub-2 |
| 2-3 | Sub-33 | 3,4-diClPh | $CH_2$ | Single bond | Sub-3 |
| 2-4 | Sub-33 | 3,4-diClPh | $CH_2$ | Single bond | Sub-4 |
| 2-5 | Sub-33 | 3,4-diClPh | $CH_2$ | Single bond | Sub-5 |
| 2-6 | Sub-33 | 3,4-diClPh | $CH_2$ | Single bond | Sub-6 |
| 2-7 | Sub-33 | 3,4-diClPh | $CH_2$ | Single bond | Sub-7 |
| 2-8 | Sub-33 | 3,4-diClPh | $CH_2$ | Single bond | Sub-8 |
| 2-9 | Sub-33 | 3,4-diClPh | $CH_2$ | Single bond | Sub-9 |
| 2-10 | Sub-33 | 3,4-diClPh | $CH_2$ | Single bond | Sub-10 |
| 2-11 | Sub-33 | 3,4-diClPh | $CH_2$ | Single bond | Sub-11 |
| 2-12 | Sub-33 | 3,4-diClPh | $CH_2$ | Single bond | Sub-12 |
| 2-13 | Sub-33 | 3,4-diClPh | $CH_2$ | Single bond | Sub-13 |
| 2-14 | Sub-33 | 3,4-diClPh | $CH_2$ | Single bond | Sub-14 |
| 2-15 | Sub-33 | 3,4-diClPh | $CH_2$ | Single bond | Sub-15 |
| 2-16 | Sub-33 | 3,4-diClPh | $CH_2$ | Single bond | Sub-16 |
| 2-17 | Sub-33 | 3,4-diClPh | $CH_2$ | Single bond | Sub-17 |
| 2-18 | Sub-33 | 3,4-diClPh | $CH_2$ | Single bond | Sub-18 |
| 2-19 | Sub-33 | 3,4-diClPh | $CH_2$ | Single bond | Sub-19 |
| 2-20 | Sub-33 | 3,4-diClPh | $CH_2$ | Single bond | Sub-20 |
| 2-21 | Sub-33 | 3,4-diClPh | $CH_2$ | Single bond | Sub-21 |
| 2-22 | Sub-33 | 3,4-diClPh | $CH_2$ | Single bond | Sub-22 |
| 2-23 | Sub-33 | 3,4-diClPh | $CH_2$ | Single bond | Sub-23 |
| 2-24 | Sub-33 | 3,4-diClPh | $CH_2$ | Single bond | Sub-24 |
| 2-25 | Sub-33 | 3,4-diClPh | $CH_2$ | Single bond | Sub-25 |
| 2-26 | Sub-33 | 3,4-diClPh | $CH_2$ | Single bond | Sub-26 |
| 2-27 | Sub-33 | 3,4-diClPh | $CH_2$ | Single bond | Sub-27 |
| 2-28 | Sub-33 | 3,4-diClPh | $CH_2$ | Single bond | Sub-28 |
| 2-29 | Sub-33 | 3,4-diClPh | $CH_2$ | Single bond | Sub-29 |
| 2-30 | Sub-33 | 3,4-diClPh | $CH_2$ | Single bond | Sub-30 |
| 2-31 | Sub-33 | 3,4-diClPh | $CH_2$ | Single bond | Sub-31 |
| 2-32 | Sub-33 | 3,4-diClPh | $CH_2$ | Single bond | Sub-32 |
| 2-33 | Sub-33 | 3,4-diClPh | $CH_2$ | Single bond | Sub-65 |
| 2-34 | Sub-33 | 3,4-diClPh | $CH_2$ | Single bond | Sub-66 |
| 2-35 | Sub-33 | 3,4-diClPh | $CH_2$ | Single bond | Sub-67 |
| 2-36 | Sub-33 | 3,4-diClPh | $CH_2$ | Single bond | Sub-68 |
| 2-37 | Sub-33 | 3,4-diClPh | $CH_2$ | Single bond | Sub-69 |
| 2-38 | Sub-33 | 3,4-diClPh | $CH_2$ | Single bond | Sub-70 |
| 2-39 | Sub-33 | 3,4-diClPh | $CH_2$ | Single bond | Sub-71 |
| 2-40 | Sub-33 | 3,4-diClPh | $CH_2$ | Single bond | Sub-72 |
| 2-41 | Sub-33 | 3,4-diClPh | $CH_2$ | Single bond | Sub-73 |
| 2-42 | Sub-33 | 3,4-diClPh | $CH_2$ | Single bond | Sub-74 |
| 2-43 | Sub-33 | 3,4-diClPh | $CH_2$ | Single bond | Sub-75 |
| 2-44 | Sub-33 | 3,4-diClPh | $CH_2$ | Single bond | Sub-76 |
| 2-45 | Sub-33 | 3,4-diClPh | $CH_2$ | Single bond | Sub-77 |
| 2-46 | Sub-33 | 3,4-diClPh | $CH_2$ | Single bond | Sub-78 |
| 2-47 | Sub-33 | 3,4-diClPh | $CH_2$ | Single bond | Sub-79 |
| 2-48 | Sub-33 | 3,4-diClPh | $CH_2$ | Single bond | Sub-80 |
| 2-49 | Sub-34 | 3,4-diClPh | $CH_2$ | Single bond | Sub-1 |

TABLE 2-continued

| Cpd. No. | R¹ | R² | A | B | Z |
|---|---|---|---|---|---|
| 2-50 | Sub-34 | 3,4-diClPh | $CH_2$ | Single bond | Sub-2 |
| 2-51 | Sub-34 | 3,4-diClPh | $CH_2$ | Single bond | Sub-3 |
| 2-52 | Sub-34 | 3,4-diClPh | $CH_2$ | Single bond | Sub-4 |
| 2-53 | Sub-34 | 3,4-diClPh | $CH_2$ | Single bond | Sub-5 |
| 2-54 | Sub-34 | 3,4-diClPh | $CH_2$ | Single bond | Sub-6 |
| 2-55 | Sub-34 | 3,4-diClPh | $CH_2$ | Single bond | Sub-7 |
| 2-56 | Sub-34 | 3,4-diClPh | $CH_2$ | Single bond | Sub-8 |
| 2-57 | Sub-34 | 3,4-diClPh | $CH_2$ | Single bond | Sub-9 |
| 2-58 | Sub-34 | 3,4-diClPh | $CH_2$ | Single bond | Sub-10 |
| 2-59 | Sub-34 | 3,4-diClPh | $CH_2$ | Single bond | Sub-11 |
| 2-60 | Sub-34 | 3,4-diClPh | $CH_2$ | Single bond | Sub-12 |
| 2-61 | Sub-34 | 3,4-diClPh | $CH_2$ | Single bond | Sub-13 |
| 2-62 | Sub-34 | 3,4-diClPh | $CH_2$ | Single bond | Sub-14 |
| 2-63 | Sub-34 | 3,4-diClPh | $CH_2$ | Single bond | Sub-15 |
| 2-64 | Sub-34 | 3,4-diClPh | $CH_2$ | Single bond | Sub-16 |
| 2-65 | Sub-34 | 3,4-diClPh | $CH_2$ | Single bond | Sub-17 |
| 2-66 | Sub-34 | 3,4-diClPh | $CH_2$ | Single bond | Sub-18 |
| 2-67 | Sub-34 | 3,4-diClPh | $CH_2$ | Single bond | Sub-19 |
| 2-68 | Sub-34 | 3,4-diClPh | $CH_2$ | Single bond | Sub-20 |
| 2-69 | Sub-34 | 3,4-diClPh | $CH_2$ | Single bond | Sub-21 |
| 2-70 | Sub-34 | 3,4-diClPh | $CH_2$ | Single bond | Sub-22 |
| 2-71 | Sub-34 | 3,4-diClPh | $CH_2$ | Single bond | Sub-23 |
| 2-72 | Sub-34 | 3,4-diClPh | $CH_2$ | Single bond | Sub-24 |
| 2-73 | Sub-34 | 3,4-diClPh | $CH_2$ | Single bond | Sub-25 |
| 2-74 | Sub-34 | 3,4-diClPh | $CH_2$ | Single bond | Sub-26 |
| 2-75 | Sub-34 | 3,4-diClPh | $CH_2$ | Single bond | Sub-27 |
| 2-76 | Sub-34 | 3,4-diClPh | $CH_2$ | Single bond | Sub-28 |
| 2-77 | Sub-34 | 3,4-diClPh | $CH_2$ | Single bond | Sub-29 |
| 2-78 | Sub-34 | 3,4-diClPh | $CH_2$ | Single bond | Sub-30 |
| 2-79 | Sub-34 | 3,4-diClPh | $CH_2$ | Single bond | Sub-31 |
| 2-80 | Sub-34 | 3,4-diClPh | $CH_2$ | Single bond | Sub-32 |
| 2-81 | Sub-34 | 3,4-diClPh | $CH_2$ | Single bond | Sub-65 |
| 2-82 | Sub-34 | 3,4-diClPh | $CH_2$ | Single bond | Sub-66 |
| 2-83 | Sub-34 | 3,4-diClPh | $CH_2$ | Single bond | Sub-67 |
| 2-84 | Sub-34 | 3,4-diClPh | $CH_2$ | Single bond | Sub-68 |
| 2-85 | Sub-34 | 3,4-diClPh | $CH_2$ | Single bond | Sub-69 |
| 2-86 | Sub-34 | 3,4-diClPh | $CH_2$ | Single bond | Sub-70 |
| 2-87 | Sub-34 | 3,4-diClPh | $CH_2$ | Single bond | Sub-71 |
| 2-88 | Sub-34 | 3,4-diClPh | $CH_2$ | Single bond | Sub-72 |
| 2-89 | Sub-34 | 3,4-diClPh | $CH_2$ | Single bond | Sub-73 |
| 2-90 | Sub-34 | 3,4-diClPh | $CH_2$ | Single bond | Sub-74 |
| 2-91 | Sub-34 | 3,4-diClPh | $CH_2$ | Single bond | Sub-75 |
| 2-92 | Sub-34 | 3,4-diClPh | $CH_2$ | Single bond | Sub-76 |
| 2-93 | Sub-34 | 3,4-diClPh | $CH_2$ | Single bond | Sub-77 |
| 2-94 | Sub-34 | 3,4-diClPh | $CH_2$ | Single bond | Sub-78 |
| 2-95 | Sub-34 | 3,4-diClPh | $CH_2$ | Single bond | Sub-79 |
| 2-96 | Sub-34 | 3,4-diClPh | $CH_2$ | Single bond | Sub-80 |
| 2-97 | Sub-35 | 3,4-diClPh | $CH_2$ | Single bond | Sub-1 |
| 2-98 | Sub-35 | 3,4-diClPh | $CH_2$ | Single bond | Sub-2 |
| 2-99 | Sub-35 | 3,4-diClPh | $CH_2$ | Single bond | Sub-3 |
| 2-100 | Sub-35 | 3,4-diClPh | $CH_2$ | Single bond | Sub-4 |
| 2-101 | Sub-35 | 3,4-diClPh | $CH_2$ | Single bond | Sub-5 |
| 2-102 | Sub-35 | 3,4-diClPh | $CH_2$ | Single bond | Sub-6 |
| 2-103 | Sub-35 | 3,4-diClPh | $CH_2$ | Single bond | Sub-7 |
| 2-104 | Sub-35 | 3,4-diClPh | $CH_2$ | Single bond | Sub-8 |
| 2-105 | Sub-35 | 3,4-diClPh | $CH_2$ | Single bond | Sub-9 |
| 2-106 | Sub-35 | 3,4-diClPh | $CH_2$ | Single bond | Sub-10 |
| 2-107 | Sub-35 | 3,4-diClPh | $CH_2$ | Single bond | Sub-11 |
| 2-108 | Sub-35 | 3,4-diClPh | $CH_2$ | Single bond | Sub-12 |
| 2-109 | Sub-35 | 3,4-diClPh | $CH_2$ | Single bond | Sub-13 |
| 2-110 | Sub-35 | 3,4-diClPh | $CH_2$ | Single bond | Sub-14 |
| 2-111 | Sub-35 | 3,4-diClPh | $CH_2$ | Single bond | Sub-15 |
| 2-112 | Sub-35 | 3,4-diClPh | $CH_2$ | Single bond | Sub-16 |
| 2-113 | Sub-35 | 3,4-diClPh | $CH_2$ | Single bond | Sub-17 |
| 2-114 | Sub-35 | 3,4-diClPh | $CH_2$ | Single bond | Sub-18 |
| 2-115 | Sub-35 | 3,4-diClPh | $CH_2$ | Single bond | Sub-19 |
| 2-116 | Sub-35 | 3,4-diClPh | $CH_2$ | Single bond | Sub-20 |
| 2-117 | Sub-35 | 3,4-diClPh | $CH_2$ | Single bond | Sub-21 |
| 2-118 | Sub-35 | 3,4-diClPh | $CH_2$ | Single bond | Sub-22 |
| 2-119 | Sub-35 | 3,4-diClPh | $CH_2$ | Single bond | Sub-23 |
| 2-120 | Sub-35 | 3,4-diClPh | $CH_2$ | Single bond | Sub-24 |
| 2-121 | Sub-35 | 3,4-diClPh | $CH_2$ | Single bond | Sub-25 |
| 2-122 | Sub-35 | 3,4-diClPh | $CH_2$ | Single bond | Sub-26 |
| 2-123 | Sub-35 | 3,4-diClPh | $CH_2$ | Single bond | Sub-27 |
| 2-124 | Sub-35 | 3,4-diClPh | $CH_2$ | Single bond | Sub-28 |
| 2-125 | Sub-35 | 3,4-diClPh | $CH_2$ | Single bond | Sub-29 |
| 2-126 | Sub-35 | 3,4-diClPh | $CH_2$ | Single bond | Sub-30 |

TABLE 2-continued

| Cpd. No. | R¹ | R² | A | B | Z |
|---|---|---|---|---|---|
| 2-127 | Sub-35 | 3,4-diClPh | CH$_2$ | Single bond | Sub-31 |
| 2-128 | Sub-35 | 3,4-diClPh | CH$_2$ | Single bond | Sub-32 |
| 2-129 | Sub-35 | 3,4-diClPh | CH$_2$ | Single bond | Sub-65 |
| 2-130 | Sub-35 | 3,4-diClPh | CH$_2$ | Single bond | Sub-66 |
| 2-131 | Sub-35 | 3,4-diClPh | CH$_2$ | Single bond | Sub-67 |
| 2-132 | Sub-35 | 3,4-diClPh | CH$_2$ | Single bond | Sub-68 |
| 2-133 | Sub-35 | 3,4-diClPh | CH$_2$ | Single bond | Sub-69 |
| 2-134 | Sub-35 | 3,4-diClPh | CH$_2$ | Single bond | Sub-70 |
| 2-135 | Sub-35 | 3,4-diClPh | CH$_2$ | Single bond | Sub-71 |
| 2-136 | Sub-35 | 3,4-diClPh | CH$_2$ | Single bond | Sub-72 |
| 2-137 | Sub-35 | 3,4-diClPh | CH$_2$ | Single bond | Sub-73 |
| 2-138 | Sub-35 | 3,4-diClPh | CH$_2$ | Single bond | Sub-74 |
| 2-139 | Sub-35 | 3,4-diClPh | CH$_2$ | Single bond | Sub-75 |
| 2-140 | Sub-35 | 3,4-diClPh | CH$_2$ | Single bond | Sub-76 |
| 2-141 | Sub-35 | 3,4-diClPh | CH$_2$ | Single bond | Sub-77 |
| 2-142 | Sub-35 | 3,4-diClPh | CH$_2$ | Single bond | Sub-78 |
| 2-143 | Sub-35 | 3,4-diClPh | CH$_2$ | Single bond | Sub-79 |
| 2-144 | Sub-35 | 3,4-diClPh | CH$_2$ | Single bond | Sub-80 |
| 2-145 | Sub-36 | 3,4-diClPh | CH$_2$ | Single bond | Sub-1 |
| 2-146 | Sub-36 | 3,4-diClPh | CH$_2$ | Single bond | Sub-2 |
| 2-147 | Sub-36 | 3,4-diClPh | CH$_2$ | Single bond | Sub-3 |
| 2-148 | Sub-36 | 3,4-diClPh | CH$_2$ | Single bond | Sub-4 |
| 2-149 | Sub-36 | 3,4-diClPh | CH$_2$ | Single bond | Sub-5 |
| 2-150 | Sub-36 | 3,4-diClPh | CH$_2$ | Single bond | Sub-6 |
| 2-151 | Sub-36 | 3,4-diClPh | CH$_2$ | Single bond | Sub-7 |
| 2-152 | Sub-36 | 3,4-diClPh | CH$_2$ | Single bond | Sub-8 |
| 2-153 | Sub-36 | 3,4-diClPh | CH$_2$ | Single bond | Sub-9 |
| 2-154 | Sub-36 | 3,4-diClPh | CH$_2$ | Single bond | Sub-10 |
| 2-155 | Sub-36 | 3,4-diClPh | CH$_2$ | Single bond | Sub-11 |
| 2-156 | Sub-36 | 3,4-diClPh | CH$_2$ | Single bond | Sub-12 |
| 2-157 | Sub-36 | 3,4-diClPh | CH$_2$ | Single bond | Sub-13 |
| 2-158 | Sub-36 | 3,4-diClPh | CH$_2$ | Single bond | Sub-14 |
| 2-159 | Sub-36 | 3,4-diClPh | CH$_2$ | Single bond | Sub-15 |
| 2-160 | Sub-36 | 3,4-diClPh | CH$_2$ | Single bond | Sub-16 |
| 2-161 | Sub-36 | 3,4-diClPh | CH$_2$ | Single bond | Sub-17 |
| 2-162 | Sub-36 | 3,4-diClPh | CH$_2$ | Single bond | Sub-18 |
| 2-163 | Sub-36 | 3,4-diClPh | CH$_2$ | Single bond | Sub-19 |
| 2-164 | Sub-36 | 3,4-diClPh | CH$_2$ | Single bond | Sub-20 |
| 2-165 | Sub-36 | 3,4-diClPh | CH$_2$ | Single bond | Sub-21 |
| 2-166 | Sub-36 | 3,4-diClPh | CH$_2$ | Single bond | Sub-22 |
| 2-167 | Sub-36 | 3,4-diClPh | CH$_2$ | Single bond | Sub-23 |
| 2-168 | Sub-36 | 3,4-diClPh | CH$_2$ | Single bond | Sub-24 |
| 2-169 | Sub-36 | 3,4-diClPh | CH$_2$ | Single bond | Sub-25 |
| 2-170 | Sub-36 | 3,4-diClPh | CH$_2$ | Single bond | Sub-26 |
| 2-171 | Sub-36 | 3,4-diClPh | CH$_2$ | Single bond | Sub-27 |
| 2-172 | Sub-36 | 3,4-diClPh | CH$_2$ | Single bond | Sub-28 |
| 2-173 | Sub-36 | 3,4-diClPh | CH$_2$ | Single bond | Sub-29 |
| 2-174 | Sub-36 | 3,4-diClPh | CH$_2$ | Single bond | Sub-30 |
| 2-175 | Sub-36 | 3,4-diClPh | CH$_2$ | Single bond | Sub-31 |
| 2-176 | Sub-36 | 3,4-diClPh | CH$_2$ | Single bond | Sub-32 |
| 2-177 | Sub-36 | 3,4-diClPh | CH$_2$ | Single bond | Sub-65 |
| 2-178 | Sub-36 | 3,4-diClPh | CH$_2$ | Single bond | Sub-66 |
| 2-179 | Sub-36 | 3,4-diClPh | CH$_2$ | Single bond | Sub-67 |
| 2-180 | Sub-36 | 3,4-diClPh | CH$_2$ | Single bond | Sub-68 |
| 2-181 | Sub-36 | 3,4-diClPh | CH$_2$ | Single bond | Sub-69 |
| 2-182 | Sub-36 | 3,4-diClPh | CH$_2$ | Single bond | Sub-70 |
| 2-183 | Sub-36 | 3,4-diClPh | CH$_2$ | Single bond | Sub-71 |
| 2-184 | Sub-36 | 3,4-diClPh | CH$_2$ | Single bond | Sub-72 |
| 2-185 | Sub-36 | 3,4-diClPh | CH$_2$ | Single bond | Sub-73 |
| 2-186 | Sub-36 | 3,4-diClPh | CH$_2$ | Single bond | Sub-74 |
| 2-187 | Sub-36 | 3,4-diClPh | CH$_2$ | Single bond | Sub-75 |
| 2-188 | Sub-36 | 3,4-diClPh | CH$_2$ | Single bond | Sub-76 |
| 2-189 | Sub-36 | 3,4-diClPh | CH$_2$ | Single bond | Sub-77 |
| 2-190 | Sub-36 | 3,4-diClPh | CH$_2$ | Single bond | Sub-78 |
| 2-191 | Sub-36 | 3,4-diClPh | CH$_2$ | Single bond | Sub-79 |
| 2-192 | Sub-36 | 3,4-diClPh | CH$_2$ | Single bond | Sub-80 |
| 2-193 | Sub-37 | 3,4-diClPh | CH$_2$ | Single bond | Sub-1 |
| 2-194 | Sub-37 | 3,4-diClPh | CH$_2$ | Single bond | Sub-2 |
| 2-195 | Sub-37 | 3,4-diClPh | CH$_2$ | Single bond | Sub-3 |
| 2-196 | Sub-37 | 3,4-diClPh | CH$_2$ | Single bond | Sub-4 |
| 2-197 | Sub-37 | 3,4-diClPh | CH$_2$ | Single bond | Sub-5 |
| 2-198 | Sub-37 | 3,4-diClPh | CH$_2$ | Single bond | Sub-6 |
| 2-199 | Sub-37 | 3,4-diClPh | CH$_2$ | Single bond | Sub-7 |
| 2-200 | Sub-37 | 3,4-diClPh | CH$_2$ | Single bond | Sub-8 |
| 2-201 | Sub-37 | 3,4-diClPh | CH$_2$ | Single bond | Sub-9 |
| 2-202 | Sub-37 | 3,4-diClPh | CH$_2$ | Single bond | Sub-10 |
| 2-203 | Sub-37 | 3,4-diClPh | CH$_2$ | Single bond | Sub-11 |
| 2-204 | Sub-37 | 3,4-diClPh | CH$_2$ | Single bond | Sub-12 |
| 2-205 | Sub-37 | 3,4-diClPh | CH$_2$ | Single bond | Sub-13 |
| 2-206 | Sub-37 | 3,4-diClPh | CH$_2$ | Single bond | Sub-14 |
| 2-207 | Sub-37 | 3,4-diClPh | CH$_2$ | Single bond | Sub-15 |
| 2-208 | Sub-37 | 3,4-diClPh | CH$_2$ | Single bond | Sub-16 |
| 2-209 | Sub-37 | 3,4-diClPh | CH$_2$ | Single bond | Sub-17 |
| 2-210 | Sub-37 | 3,4-diClPh | CH$_2$ | Single bond | Sub-18 |
| 2-211 | Sub-37 | 3,4-diClPh | CH$_2$ | Single bond | Sub-19 |
| 2-212 | Sub-37 | 3,4-diClPh | CH$_2$ | Single bond | Sub-20 |
| 2-213 | Sub-37 | 3,4-diClPh | CH$_2$ | Single bond | Sub-21 |
| 2-214 | Sub-37 | 3,4-diClPh | CH$_2$ | Single bond | Sub-22 |
| 2-215 | Sub-37 | 3,4-diClPh | CH$_2$ | Single bond | Sub-23 |
| 2-216 | Sub-37 | 3,4-diClPh | CH$_2$ | Single bond | Sub-24 |
| 2-217 | Sub-37 | 3,4-diClPh | CH$_2$ | Single bond | Sub-25 |
| 2-218 | Sub-37 | 3,4-diClPh | CH$_2$ | Single bond | Sub-26 |
| 2-219 | Sub-37 | 3,4-diClPh | CH$_2$ | Single bond | Sub-27 |
| 2-220 | Sub-37 | 3,4-diClPh | CH$_2$ | Single bond | Sub-28 |
| 2-221 | Sub-37 | 3,4-diClPh | CH$_2$ | Single bond | Sub-29 |
| 2-222 | Sub-37 | 3,4-diClPh | CH$_2$ | Single bond | Sub-30 |
| 2-223 | Sub-37 | 3,4-diClPh | CH$_2$ | Single bond | Sub-31 |
| 2-224 | Sub-37 | 3,4-diClPh | CH$_2$ | Single bond | Sub-32 |
| 2-225 | Sub-37 | 3,4-diClPh | CH$_2$ | Single bond | Sub-65 |
| 2-226 | Sub-37 | 3,4-diClPh | CH$_2$ | Single bond | Sub-66 |
| 2-227 | Sub-37 | 3,4-diClPh | CH$_2$ | Single bond | Sub-67 |
| 2-228 | Sub-37 | 3,4-diClPh | CH$_2$ | Single bond | Sub-68 |
| 2-229 | Sub-37 | 3,4-diClPh | CH$_2$ | Single bond | Sub-69 |
| 2-230 | Sub-37 | 3,4-diClPh | CH$_2$ | Single bond | Sub-70 |
| 2-231 | Sub-37 | 3,4-diClPh | CH$_2$ | Single bond | Sub-71 |
| 2-232 | Sub-37 | 3,4-diClPh | CH$_2$ | Single bond | Sub-72 |
| 2-233 | Sub-37 | 3,4-diClPh | CH$_2$ | Single bond | Sub-73 |
| 2-234 | Sub-37 | 3,4-diClPh | CH$_2$ | Single bond | Sub-74 |
| 2-235 | Sub-37 | 3,4-diClPh | CH$_2$ | Single bond | Sub-75 |
| 2-236 | Sub-37 | 3,4-diClPh | CH$_2$ | Single bond | Sub-76 |
| 2-237 | Sub-37 | 3,4-diClPh | CH$_2$ | Single bond | Sub-77 |
| 2-238 | Sub-37 | 3,4-diClPh | CH$_2$ | Single bond | Sub-78 |
| 2-239 | Sub-37 | 3,4-diClPh | CH$_2$ | Single bond | Sub-79 |
| 2-240 | Sub-37 | 3,4-diClPh | CH$_2$ | Single bond | Sub-80 |
| 2-241 | Sub-38 | 3,4-diClPh | CH$_2$ | Single bond | Sub-1 |
| 2-242 | Sub-38 | 3,4-diClPh | CH$_2$ | Single bond | Sub-2 |
| 2-243 | Sub-38 | 3,4-diClPh | CH$_2$ | Single bond | Sub-3 |
| 2-244 | Sub-38 | 3,4-diClPh | CH$_2$ | Single bond | Sub-4 |
| 2-245 | Sub-38 | 3,4-diClPh | CH$_2$ | Single bond | Sub-5 |
| 2-246 | Sub-38 | 3,4-diClPh | CH$_2$ | Single bond | Sub-6 |
| 2-247 | Sub-38 | 3,4-diClPh | CH$_2$ | Single bond | Sub-7 |
| 2-248 | Sub-38 | 3,4-diClPh | CH$_2$ | Single bond | Sub-8 |
| 2-249 | Sub-38 | 3,4-diClPh | CH$_2$ | Single bond | Sub-9 |
| 2-250 | Sub-38 | 3,4-diClPh | CH$_2$ | Single bond | Sub-10 |
| 2-251 | Sub-38 | 3,4-diClPh | CH$_2$ | Single bond | Sub-11 |
| 2-252 | Sub-38 | 3,4-diClPh | CH$_2$ | Single bond | Sub-12 |
| 2-253 | Sub-38 | 3,4-diClPh | CH$_2$ | Single bond | Sub-13 |
| 2-254 | Sub-38 | 3,4-diClPh | CH$_2$ | Single bond | Sub-14 |
| 2-255 | Sub-38 | 3,4-diClPh | CH$_2$ | Single bond | Sub-15 |
| 2-256 | Sub-38 | 3,4-diClPh | CH$_2$ | Single bond | Sub-16 |
| 2-257 | Sub-38 | 3,4-diClPh | CH$_2$ | Single bond | Sub-17 |
| 2-258 | Sub-38 | 3,4-diClPh | CH$_2$ | Single bond | Sub-18 |
| 2-259 | Sub-38 | 3,4-diClPh | CH$_2$ | Single bond | Sub-19 |
| 2-260 | Sub-38 | 3,4-diClPh | CH$_2$ | Single bond | Sub-20 |
| 2-261 | Sub-38 | 3,4-diClPh | CH$_2$ | Single bond | Sub-21 |
| 2-262 | Sub-38 | 3,4-diClPh | CH$_2$ | Single bond | Sub-22 |
| 2-263 | Sub-38 | 3,4-diClPh | CH$_2$ | Single bond | Sub-23 |
| 2-264 | Sub-38 | 3,4-diClPh | CH$_2$ | Single bond | Sub-24 |
| 2-265 | Sub-38 | 3,4-diClPh | CH$_2$ | Single bond | Sub-25 |
| 2-266 | Sub-38 | 3,4-diClPh | CH$_2$ | Single bond | Sub-26 |
| 2-267 | Sub-38 | 3,4-diClPh | CH$_2$ | Single bond | Sub-27 |
| 2-268 | Sub-38 | 3,4-diClPh | CH$_2$ | Single bond | Sub-28 |
| 2-269 | Sub-38 | 3,4-diClPh | CH$_2$ | Single bond | Sub-29 |
| 2-270 | Sub-38 | 3,4-diClPh | CH$_2$ | Single bond | Sub-30 |
| 2-271 | Sub-38 | 3,4-diClPh | CH$_2$ | Single bond | Sub-31 |
| 2-272 | Sub-38 | 3,4-diClPh | CH$_2$ | Single bond | Sub-32 |
| 2-273 | Sub-38 | 3,4-diClPh | CH$_2$ | Single bond | Sub-65 |
| 2-274 | Sub-38 | 3,4-diClPh | CH$_2$ | Single bond | Sub-66 |
| 2-275 | Sub-38 | 3,4-diClPh | CH$_2$ | Single bond | Sub-67 |
| 2-276 | Sub-38 | 3,4-diClPh | CH$_2$ | Single bond | Sub-68 |
| 2-277 | Sub-38 | 3,4-diClPh | CH$_2$ | Single bond | Sub-69 |
| 2-278 | Sub-38 | 3,4-diClPh | CH$_2$ | Single bond | Sub-70 |
| 2-279 | Sub-38 | 3,4-diClPh | CH$_2$ | Single bond | Sub-71 |
| 2-280 | Sub-38 | 3,4-diClPh | CH$_2$ | Single bond | Sub-72 |

TABLE 2-continued

| Cpd. No. | R¹ | R² | A | B | Z |
|---|---|---|---|---|---|
| 2-281 | Sub-38 | 3,4-diClPh | CH₂ | Single bond | Sub-73 |
| 2-282 | Sub-38 | 3,4-diClPh | CH₂ | Single bond | Sub-74 |
| 2-283 | Sub-38 | 3,4-diClPh | CH₂ | Single bond | Sub-75 |
| 2-284 | Sub-38 | 3,4-diClPh | CH₂ | Single bond | Sub-76 |
| 2-285 | Sub-38 | 3,4-diClPh | CH₂ | Single bond | Sub-77 |
| 2-286 | Sub-38 | 3,4-diClPh | CH₂ | Single bond | Sub-78 |
| 2-287 | Sub-38 | 3,4-diClPh | CH₂ | Single bond | Sub-79 |
| 2-288 | Sub-38 | 3,4-diClPh | CH₂ | Single bond | Sub-80 |
| 2-289 | Sub-39 | 3,4-diClPh | CH₂ | Single bond | Sub-1 |
| 2-290 | Sub-39 | 3,4-diClPh | CH₂ | Single bond | Sub-2 |
| 2-291 | Sub-39 | 3,4-diClPh | CH₂ | Single bond | Sub-3 |
| 2-292 | Sub-39 | 3,4-diClPh | CH₂ | Single bond | Sub-4 |
| 2-293 | Sub-39 | 3,4-diClPh | CH₂ | Single bond | Sub-5 |
| 2-294 | Sub-39 | 3,4-diClPh | CH₂ | Single bond | Sub-6 |
| 2-295 | Sub-39 | 3,4-diClPh | CH₂ | Single bond | Sub-7 |
| 2-296 | Sub-39 | 3,4-diClPh | CH₂ | Single bond | Sub-8 |
| 2-297 | Sub-39 | 3,4-diClPh | CH₂ | Single bond | Sub-9 |
| 2-298 | Sub-39 | 3,4-diClPh | CH₂ | Single bond | Sub-10 |
| 2-299 | Sub-39 | 3,4-diClPh | CH₂ | Single bond | Sub-11 |
| 2-300 | Sub-39 | 3,4-diClPh | CH₂ | Single bond | Sub-12 |
| 2-301 | Sub-39 | 3,4-diClPh | CH₂ | Single bond | Sub-13 |
| 2-302 | Sub-39 | 3,4-diClPh | CH₂ | Single bond | Sub-14 |
| 2-303 | Sub-39 | 3,4-diClPh | CH₂ | Single bond | Sub-15 |
| 2-304 | Sub-39 | 3,4-diClPh | CH₂ | Single bond | Sub-16 |
| 2-305 | Sub-39 | 3,4-diClPh | CH₂ | Single bond | Sub-17 |
| 2-306 | Sub-39 | 3,4-diClPh | CH₂ | Single bond | Sub-18 |
| 2-307 | Sub-39 | 3,4-diClPh | CH₂ | Single bond | Sub-19 |
| 2-308 | Sub-39 | 3,4-diClPh | CH₂ | Single bond | Sub-20 |
| 2-309 | Sub-39 | 3,4-diClPh | CH₂ | Single bond | Sub-21 |
| 2-310 | Sub-39 | 3,4-diClPh | CH₂ | Single bond | Sub-22 |
| 2-311 | Sub-39 | 3,4-diClPh | CH₂ | Single bond | Sub-23 |
| 2-312 | Sub-39 | 3,4-diClPh | CH₂ | Single bond | Sub-24 |
| 2-313 | Sub-39 | 3,4-diClPh | CH₂ | Single bond | Sub-25 |
| 2-314 | Sub-39 | 3,4-diClPh | CH₂ | Single bond | Sub-26 |
| 2-315 | Sub-39 | 3,4-diClPh | CH₂ | Single bond | Sub-27 |
| 2-316 | Sub-39 | 3,4-diClPh | CH₂ | Single bond | Sub-28 |
| 2-317 | Sub-39 | 3,4-diClPh | CH₂ | Single bond | Sub-29 |
| 2-318 | Sub-39 | 3,4-diClPh | CH₂ | Single bond | Sub-30 |
| 2-319 | Sub-39 | 3,4-diClPh | CH₂ | Single bond | Sub-31 |
| 2-320 | Sub-39 | 3,4-diClPh | CH₂ | Single bond | Sub-32 |
| 2-321 | Sub-39 | 3,4-diClPh | CH₂ | Single bond | Sub-65 |
| 2-322 | Sub-39 | 3,4-diClPh | CH₂ | Single bond | Sub-66 |
| 2-323 | Sub-39 | 3,4-diClPh | CH₂ | Single bond | Sub-67 |
| 2-324 | Sub-39 | 3,4-diClPh | CH₂ | Single bond | Sub-68 |
| 2-325 | Sub-39 | 3,4-diClPh | CH₂ | Single bond | Sub-69 |
| 2-326 | Sub-39 | 3,4-diClPh | CH₂ | Single bond | Sub-70 |
| 2-327 | Sub-39 | 3,4-diClPh | CH₂ | Single bond | Sub-71 |
| 2-328 | Sub-39 | 3,4-diClPh | CH₂ | Single bond | Sub-72 |
| 2-329 | Sub-39 | 3,4-diClPh | CH₂ | Single bond | Sub-73 |
| 2-330 | Sub-39 | 3,4-diClPh | CH₂ | Single bond | Sub-74 |
| 2-331 | Sub-39 | 3,4-diClPh | CH₂ | Single bond | Sub-75 |
| 2-332 | Sub-39 | 3,4-diClPh | CH₂ | Single bond | Sub-76 |
| 2-333 | Sub-39 | 3,4-diClPh | CH₂ | Single bond | Sub-77 |
| 2-334 | Sub-39 | 3,4-diClPh | CH₂ | Single bond | Sub-78 |
| 2-335 | Sub-39 | 3,4-diClPh | CH₂ | Single bond | Sub-79 |
| 2-336 | Sub-39 | 3,4-diClPh | CH₂ | Single bond | Sub-80 |
| 2-337 | Sub-40 | 3,4-diClPh | CH₂ | Single bond | Sub-1 |
| 2-338 | Sub-40 | 3,4-diClPh | CH₂ | Single bond | Sub-2 |
| 2-339 | Sub-40 | 3,4-diClPh | CH₂ | Single bond | Sub-3 |
| 2-340 | Sub-40 | 3,4-diClPh | CH₂ | Single bond | Sub-4 |
| 2-341 | Sub-40 | 3,4-diClPh | CH₂ | Single bond | Sub-5 |
| 2-342 | Sub-40 | 3,4-diClPh | CH₂ | Single bond | Sub-6 |
| 2-343 | Sub-40 | 3,4-diClPh | CH₂ | Single bond | Sub-7 |
| 2-344 | Sub-40 | 3,4-diClPh | CH₂ | Single bond | Sub-8 |
| 2-345 | Sub-40 | 3,4-diClPh | CH₂ | Single bond | Sub-9 |
| 2-346 | Sub-40 | 3,4-diClPh | CH₂ | Single bond | Sub-10 |
| 2-347 | Sub-40 | 3,4-diClPh | CH₂ | Single bond | Sub-11 |
| 2-348 | Sub-40 | 3,4-diClPh | CH₂ | Single bond | Sub-12 |
| 2-349 | Sub-40 | 3,4-diClPh | CH₂ | Single bond | Sub-13 |
| 2-350 | Sub-40 | 3,4-diClPh | CH₂ | Single bond | Sub-14 |
| 2-351 | Sub-40 | 3,4-diClPh | CH₂ | Single bond | Sub-15 |
| 2-352 | Sub-40 | 3,4-diClPh | CH₂ | Single bond | Sub-16 |
| 2-353 | Sub-40 | 3,4-diClPh | CH₂ | Single bond | Sub-17 |
| 2-354 | Sub-40 | 3,4-diClPh | CH₂ | Single bond | Sub-18 |
| 2-355 | Sub-40 | 3,4-diClPh | CH₂ | Single bond | Sub-19 |
| 2-356 | Sub-40 | 3,4-diClPh | CH₂ | Single bond | Sub-20 |
| 2-357 | Sub-40 | 3,4-diClPh | CH₂ | Single bond | Sub-21 |
| 2-358 | Sub-40 | 3,4-diClPh | CH₂ | Single bond | Sub-22 |
| 2-359 | Sub-40 | 3,4-diClPh | CH₂ | Single bond | Sub-23 |
| 2-360 | Sub-40 | 3,4-diClPh | CH₂ | Single bond | Sub-24 |
| 2-361 | Sub-40 | 3,4-diClPh | CH₂ | Single bond | Sub-25 |
| 2-362 | Sub-40 | 3,4-diClPh | CH₂ | Single bond | Sub-26 |
| 2-363 | Sub-40 | 3,4-diClPh | CH₂ | Single bond | Sub-27 |
| 2-364 | Sub-40 | 3,4-diClPh | CH₂ | Single bond | Sub-28 |
| 2-365 | Sub-40 | 3,4-diClPh | CH₂ | Single bond | Sub-29 |
| 2-366 | Sub-40 | 3,4-diClPh | CH₂ | Single bond | Sub-30 |
| 2-367 | Sub-40 | 3,4-diClPh | CH₂ | Single bond | Sub-31 |
| 2-368 | Sub-40 | 3,4-diClPh | CH₂ | Single bond | Sub-32 |
| 2-369 | Sub-40 | 3,4-diClPh | CH₂ | Single bond | Sub-65 |
| 2-370 | Sub-40 | 3,4-diClPh | CH₂ | Single bond | Sub-66 |
| 2-371 | Sub-40 | 3,4-diClPh | CH₂ | Single bond | Sub-67 |
| 2-372 | Sub-40 | 3,4-diClPh | CH₂ | Single bond | Sub-68 |
| 2-373 | Sub-40 | 3,4-diClPh | CH₂ | Single bond | Sub-69 |
| 2-374 | Sub-40 | 3,4-diClPh | CH₂ | Single bond | Sub-70 |
| 2-375 | Sub-40 | 3,4-diClPh | CH₂ | Single bond | Sub-71 |
| 2-376 | Sub-40 | 3,4-diClPh | CH₂ | Single bond | Sub-72 |
| 2-377 | Sub-40 | 3,4-diClPh | CH₂ | Single bond | Sub-73 |
| 2-378 | Sub-40 | 3,4-diClPh | CH₂ | Single bond | Sub-74 |
| 2-379 | Sub-40 | 3,4-diClPh | CH₂ | Single bond | Sub-75 |
| 2-380 | Sub-40 | 3,4-diClPh | CH₂ | Single bond | Sub-76 |
| 2-381 | Sub-40 | 3,4-diClPh | CH₂ | Single bond | Sub-77 |
| 2-382 | Sub-40 | 3,4-diClPh | CH₂ | Single bond | Sub-78 |
| 2-383 | Sub-40 | 3,4-diClPh | CH₂ | Single bond | Sub-79 |
| 2-384 | Sub-40 | 3,4-diClPh | CH₂ | Single bond | Sub-80 |
| 2-385 | Sub-41 | 3,4-diClPh | CH₂ | Single bond | Sub-1 |
| 2-386 | Sub-41 | 3,4-diClPh | CH₂ | Single bond | Sub-2 |
| 2-387 | Sub-41 | 3,4-diClPh | CH₂ | Single bond | Sub-3 |
| 2-388 | Sub-41 | 3,4-diClPh | CH₂ | Single bond | Sub-4 |
| 2-389 | Sub-41 | 3,4-diClPh | CH₂ | Single bond | Sub-5 |
| 2-390 | Sub-41 | 3,4-diClPh | CH₂ | Single bond | Sub-6 |
| 2-391 | Sub-41 | 3,4-diClPh | CH₂ | Single bond | Sub-7 |
| 2-392 | Sub-41 | 3,4-diClPh | CH₂ | Single bond | Sub-8 |
| 2-393 | Sub-41 | 3,4-diClPh | CH₂ | Single bond | Sub-9 |
| 2-394 | Sub-41 | 3,4-diClPh | CH₂ | Single bond | Sub-10 |
| 2-395 | Sub-41 | 3,4-diClPh | CH₂ | Single bond | Sub-11 |
| 2-396 | Sub-41 | 3,4-diClPh | CH₂ | Single bond | Sub-12 |
| 2-397 | Sub-41 | 3,4-diClPh | CH₂ | Single bond | Sub-13 |
| 2-398 | Sub-41 | 3,4-diClPh | CH₂ | Single bond | Sub-14 |
| 2-399 | Sub-41 | 3,4-diClPh | CH₂ | Single bond | Sub-15 |
| 2-400 | Sub-41 | 3,4-diClPh | CH₂ | Single bond | Sub-16 |
| 2-401 | Sub-41 | 3,4-diClPh | CH₂ | Single bond | Sub-17 |
| 2-402 | Sub-41 | 3,4-diClPh | CH₂ | Single bond | Sub-18 |
| 2-403 | Sub-41 | 3,4-diClPh | CH₂ | Single bond | Sub-19 |
| 2-404 | Sub-41 | 3,4-diClPh | CH₂ | Single bond | Sub-20 |
| 2-405 | Sub-41 | 3,4-diClPh | CH₂ | Single bond | Sub-21 |
| 2-406 | Sub-41 | 3,4-diClPh | CH₂ | Single bond | Sub-22 |
| 2-407 | Sub-41 | 3,4-diClPh | CH₂ | Single bond | Sub-23 |
| 2-408 | Sub-41 | 3,4-diClPh | CH₂ | Single bond | Sub-24 |
| 2-409 | Sub-41 | 3,4-diClPh | CH₂ | Single bond | Sub-25 |
| 2-410 | Sub-41 | 3,4-diClPh | CH₂ | Single bond | Sub-26 |
| 2-411 | Sub-41 | 3,4-diClPh | CH₂ | Single bond | Sub-27 |
| 2-412 | Sub-41 | 3,4-diClPh | CH₂ | Single bond | Sub-28 |
| 2-413 | Sub-41 | 3,4-diClPh | CH₂ | Single bond | Sub-29 |
| 2-414 | Sub-41 | 3,4-diClPh | CH₂ | Single bond | Sub-30 |
| 2-415 | Sub-41 | 3,4-diClPh | CH₂ | Single bond | Sub-31 |
| 2-416 | Sub-41 | 3,4-diClPh | CH₂ | Single bond | Sub-32 |
| 2-417 | Sub-41 | 3,4-diClPh | CH₂ | Single bond | Sub-65 |
| 2-418 | Sub-41 | 3,4-diClPh | CH₂ | Single bond | Sub-66 |
| 2-419 | Sub-41 | 3,4-diClPh | CH₂ | Single bond | Sub-67 |
| 2-420 | Sub-41 | 3,4-diClPh | CH₂ | Single bond | Sub-68 |
| 2-421 | Sub-41 | 3,4-diClPh | CH₂ | Single bond | Sub-69 |
| 2-422 | Sub-41 | 3,4-diClPh | CH₂ | Single bond | Sub-70 |
| 2-423 | Sub-41 | 3,4-diClPh | CH₂ | Single bond | Sub-71 |
| 2-424 | Sub-41 | 3,4-diClPh | CH₂ | Single bond | Sub-72 |
| 2-425 | Sub-41 | 3,4-diClPh | CH₂ | Single bond | Sub-73 |
| 2-426 | Sub-41 | 3,4-diClPh | CH₂ | Single bond | Sub-74 |
| 2-427 | Sub-41 | 3,4-diClPh | CH₂ | Single bond | Sub-75 |
| 2-428 | Sub-41 | 3,4-diClPh | CH₂ | Single bond | Sub-76 |
| 2-429 | Sub-41 | 3,4-diClPh | CH₂ | Single bond | Sub-77 |
| 2-430 | Sub-41 | 3,4-diClPh | CH₂ | Single bond | Sub-78 |
| 2-431 | Sub-41 | 3,4-diClPh | CH₂ | Single bond | Sub-79 |
| 2-432 | Sub-41 | 3,4-diClPh | CH₂ | Single bond | Sub-80 |
| 2-433 | Sub-42 | 3,4-diClPh | CH₂ | Single bond | Sub-1 |
| 2-434 | Sub-42 | 3,4-diClPh | CH₂ | Single bond | Sub-2 |

TABLE 2-continued

| Cpd. No. | R¹ | R² | A | B | Z |
|---|---|---|---|---|---|
| 2-435 | Sub-42 | 3,4-diClPh | $CH_2$ | Single bond | Sub-3 |
| 2-436 | Sub-42 | 3,4-diClPh | $CH_2$ | Single bond | Sub-4 |
| 2-437 | Sub-42 | 3,4-diClPh | $CH_2$ | Single bond | Sub-5 |
| 2-438 | Sub-42 | 3,4-diClPh | $CH_2$ | Single bond | Sub-6 |
| 2-439 | Sub-42 | 3,4-diClPh | $CH_2$ | Single bond | Sub-7 |
| 2-440 | Sub-42 | 3,4-diClPh | $CH_2$ | Single bond | Sub-8 |
| 2-441 | Sub-42 | 3,4-diClPh | $CH_2$ | Single bond | Sub-9 |
| 2-442 | Sub-42 | 3,4-diClPh | $CH_2$ | Single bond | Sub-10 |
| 2-443 | Sub-42 | 3,4-diClPh | $CH_2$ | Single bond | Sub-11 |
| 2-444 | Sub-42 | 3,4-diClPh | $CH_2$ | Single bond | Sub-12 |
| 2-445 | Sub-42 | 3,4-diClPh | $CH_2$ | Single bond | Sub-13 |
| 2-446 | Sub-42 | 3,4-diClPh | $CH_2$ | Single bond | Sub-14 |
| 2-447 | Sub-42 | 3,4-diClPh | $CH_2$ | Single bond | Sub-15 |
| 2-448 | Sub-42 | 3,4-diClPh | $CH_2$ | Single bond | Sub-16 |
| 2-449 | Sub-42 | 3,4-diClPh | $CH_2$ | Single bond | Sub-17 |
| 2-450 | Sub-42 | 3,4-diClPh | $CH_2$ | Single bond | Sub-18 |
| 2-451 | Sub-42 | 3,4-diClPh | $CH_2$ | Single bond | Sub-19 |
| 2-452 | Sub-42 | 3,4-diClPh | $CH_2$ | Single bond | Sub-20 |
| 2-453 | Sub-42 | 3,4-diClPh | $CH_2$ | Single bond | Sub-21 |
| 2-454 | Sub-42 | 3,4-diClPh | $CH_2$ | Single bond | Sub-22 |
| 2-455 | Sub-42 | 3,4-diClPh | $CH_2$ | Single bond | Sub-23 |
| 2-456 | Sub-42 | 3,4-diClPh | $CH_2$ | Single bond | Sub-24 |
| 2-457 | Sub-42 | 3,4-diClPh | $CH_2$ | Single bond | Sub-25 |
| 2-458 | Sub-42 | 3,4-diClPh | $CH_2$ | Single bond | Sub-26 |
| 2-459 | Sub-42 | 3,4-diClPh | $CH_2$ | Single bond | Sub-27 |
| 2-460 | Sub-42 | 3,4-diClPh | $CH_2$ | Single bond | Sub-28 |
| 2-461 | Sub-42 | 3,4-diClPh | $CH_2$ | Single bond | Sub-29 |
| 2-462 | Sub-42 | 3,4-diClPh | $CH_2$ | Single bond | Sub-30 |
| 2-463 | Sub-42 | 3,4-diClPh | $CH_2$ | Single bond | Sub-31 |
| 2-464 | Sub-42 | 3,4-diClPh | $CH_2$ | Single bond | Sub-32 |
| 2-465 | Sub-42 | 3,4-diClPh | $CH_2$ | Single bond | Sub-65 |
| 2-466 | Sub-42 | 3,4-diClPh | $CH_2$ | Single bond | Sub-66 |
| 2-467 | Sub-42 | 3,4-diClPh | $CH_2$ | Single bond | Sub-67 |
| 2-468 | Sub-42 | 3,4-diClPh | $CH_2$ | Single bond | Sub-68 |
| 2-469 | Sub-42 | 3,4-diClPh | $CH_2$ | Single bond | Sub-69 |
| 2-470 | Sub-42 | 3,4-diClPh | $CH_2$ | Single bond | Sub-70 |
| 2-471 | Sub-42 | 3,4-diClPh | $CH_2$ | Single bond | Sub-71 |
| 2-472 | Sub-42 | 3,4-diClPh | $CH_2$ | Single bond | Sub-72 |
| 2-473 | Sub-42 | 3,4-diClPh | $CH_2$ | Single bond | Sub-73 |
| 2-474 | Sub-42 | 3,4-diClPh | $CH_2$ | Single bond | Sub-74 |
| 2-475 | Sub-42 | 3,4-diClPh | $CH_2$ | Single bond | Sub-75 |
| 2-476 | Sub-42 | 3,4-diClPh | $CH_2$ | Single bond | Sub-76 |
| 2-477 | Sub-42 | 3,4-diClPh | $CH_2$ | Single bond | Sub-77 |
| 2-478 | Sub-42 | 3,4-diClPh | $CH_2$ | Single bond | Sub-78 |
| 2-479 | Sub-42 | 3,4-diClPh | $CH_2$ | Single bond | Sub-79 |
| 2-480 | Sub-42 | 3,4-diClPh | $CH_2$ | Single bond | Sub-80 |
| 2-481 | Sub-43 | 3,4-diClPh | $CH_2$ | Single bond | Sub-1 |
| 2-482 | Sub-43 | 3,4-diClPh | $CH_2$ | Single bond | Sub-2 |
| 2-483 | Sub-43 | 3,4-diClPh | $CH_2$ | Single bond | Sub-3 |
| 2-484 | Sub-43 | 3,4-diClPh | $CH_2$ | Single bond | Sub-4 |
| 2-485 | Sub-43 | 3,4-diClPh | $CH_2$ | Single bond | Sub-5 |
| 2-486 | Sub-43 | 3,4-diClPh | $CH_2$ | Single bond | Sub-6 |
| 2-487 | Sub-43 | 3,4-diClPh | $CH_2$ | Single bond | Sub-7 |
| 2-488 | Sub-43 | 3,4-diClPh | $CH_2$ | Single bond | Sub-8 |
| 2-489 | Sub-43 | 3,4-diClPh | $CH_2$ | Single bond | Sub-9 |
| 2-490 | Sub-43 | 3,4-diClPh | $CH_2$ | Single bond | Sub-10 |
| 2-491 | Sub-43 | 3,4-diClPh | $CH_2$ | Single bond | Sub-11 |
| 2-492 | Sub-43 | 3,4-diClPh | $CH_2$ | Single bond | Sub-12 |
| 2-493 | Sub-43 | 3,4-diClPh | $CH_2$ | Single bond | Sub-13 |
| 2-494 | Sub-43 | 3,4-diClPh | $CH_2$ | Single bond | Sub-14 |
| 2-495 | Sub-43 | 3,4-diClPh | $CH_2$ | Single bond | Sub-15 |
| 2-496 | Sub-43 | 3,4-diClPh | $CH_2$ | Single bond | Sub-16 |
| 2-497 | Sub-43 | 3,4-diClPh | $CH_2$ | Single bond | Sub-17 |
| 2-498 | Sub-43 | 3,4-diClPh | $CH_2$ | Single bond | Sub-18 |
| 2-499 | Sub-43 | 3,4-diClPh | $CH_2$ | Single bond | Sub-19 |
| 2-500 | Sub-43 | 3,4-diClPh | $CH_2$ | Single bond | Sub-20 |
| 2-501 | Sub-43 | 3,4-diClPh | $CH_2$ | Single bond | Sub-21 |
| 2-502 | Sub-43 | 3,4-diClPh | $CH_2$ | Single bond | Sub-22 |
| 2-503 | Sub-43 | 3,4-diClPh | $CH_2$ | Single bond | Sub-23 |
| 2-504 | Sub-43 | 3,4-diClPh | $CH_2$ | Single bond | Sub-24 |
| 2-505 | Sub-43 | 3,4-diClPh | $CH_2$ | Single bond | Sub-25 |
| 2-506 | Sub-43 | 3,4-diClPh | $CH_2$ | Single bond | Sub-26 |
| 2-507 | Sub-43 | 3,4-diClPh | $CH_2$ | Single bond | Sub-27 |
| 2-508 | Sub-43 | 3,4-diClPh | $CH_2$ | Single bond | Sub-28 |
| 2-509 | Sub-43 | 3,4-diClPh | $CH_2$ | Single bond | Sub-29 |
| 2-510 | Sub-43 | 3,4-diClPh | $CH_2$ | Single bond | Sub-30 |
| 2-511 | Sub-43 | 3,4-diClPh | $CH_2$ | Single bond | Sub-31 |
| 2-512 | Sub-43 | 3,4-diClPh | $CH_2$ | Single bond | Sub-32 |
| 2-513 | Sub-43 | 3,4-diClPh | $CH_2$ | Single bond | Sub-65 |
| 2-514 | Sub-43 | 3,4-diClPh | $CH_2$ | Single bond | Sub-66 |
| 2-515 | Sub-43 | 3,4-diClPh | $CH_2$ | Single bond | Sub-67 |
| 2-516 | Sub-43 | 3,4-diClPh | $CH_2$ | Single bond | Sub-68 |
| 2-517 | Sub-43 | 3,4-diClPh | $CH_2$ | Single bond | Sub-69 |
| 2-518 | Sub-43 | 3,4-diClPh | $CH_2$ | Single bond | Sub-70 |
| 2-519 | Sub-43 | 3,4-diClPh | $CH_2$ | Single bond | Sub-71 |
| 2-520 | Sub-43 | 3,4-diClPh | $CH_2$ | Single bond | Sub-72 |
| 2-521 | Sub-43 | 3,4-diClPh | $CH_2$ | Single bond | Sub-73 |
| 2-522 | Sub-43 | 3,4-diClPh | $CH_2$ | Single bond | Sub-74 |
| 2-523 | Sub-43 | 3,4-diClPh | $CH_2$ | Single bond | Sub-75 |
| 2-524 | Sub-43 | 3,4-diClPh | $CH_2$ | Single bond | Sub-76 |
| 2-525 | Sub-43 | 3,4-diClPh | $CH_2$ | Single bond | Sub-77 |
| 2-526 | Sub-43 | 3,4-diClPh | $CH_2$ | Single bond | Sub-78 |
| 2-527 | Sub-43 | 3,4-diClPh | $CH_2$ | Single bond | Sub-79 |
| 2-528 | Sub-43 | 3,4-diClPh | $CH_2$ | Single bond | Sub-80 |
| 2-529 | Sub-44 | 3,4-diClPh | $CH_2$ | Single bond | Sub-1 |
| 2-530 | Sub-44 | 3,4-diClPh | $CH_2$ | Single bond | Sub-2 |
| 2-531 | Sub-44 | 3,4-diClPh | $CH_2$ | Single bond | Sub-3 |
| 2-532 | Sub-44 | 3,4-diClPh | $CH_2$ | Single bond | Sub-4 |
| 2-533 | Sub-44 | 3,4-diClPh | $CH_2$ | Single bond | Sub-5 |
| 2-534 | Sub-44 | 3,4-diClPh | $CH_2$ | Single bond | Sub-6 |
| 2-535 | Sub-44 | 3,4-diClPh | $CH_2$ | Single bond | Sub-7 |
| 2-536 | Sub-44 | 3,4-diClPh | $CH_2$ | Single bond | Sub-8 |
| 2-537 | Sub-44 | 3,4-diClPh | $CH_2$ | Single bond | Sub-9 |
| 2-538 | Sub-44 | 3,4-diClPh | $CH_2$ | Single bond | Sub-10 |
| 2-539 | Sub-44 | 3,4-diClPh | $CH_2$ | Single bond | Sub-11 |
| 2-540 | Sub-44 | 3,4-diClPh | $CH_2$ | Single bond | Sub-12 |
| 2-541 | Sub-44 | 3,4-diClPh | $CH_2$ | Single bond | Sub-13 |
| 2-542 | Sub-44 | 3,4-diClPh | $CH_2$ | Single bond | Sub-14 |
| 2-543 | Sub-44 | 3,4-diClPh | $CH_2$ | Single bond | Sub-15 |
| 2-544 | Sub-44 | 3,4-diClPh | $CH_2$ | Single bond | Sub-16 |
| 2-545 | Sub-44 | 3,4-diClPh | $CH_2$ | Single bond | Sub-17 |
| 2-546 | Sub-44 | 3,4-diClPh | $CH_2$ | Single bond | Sub-18 |
| 2-547 | Sub-44 | 3,4-diClPh | $CH_2$ | Single bond | Sub-19 |
| 2-548 | Sub-44 | 3,4-diClPh | $CH_2$ | Single bond | Sub-20 |
| 2-549 | Sub-44 | 3,4-diClPh | $CH_2$ | Single bond | Sub-21 |
| 2-550 | Sub-44 | 3,4-diClPh | $CH_2$ | Single bond | Sub-22 |
| 2-551 | Sub-44 | 3,4-diClPh | $CH_2$ | Single bond | Sub-23 |
| 2-552 | Sub-44 | 3,4-diClPh | $CH_2$ | Single bond | Sub-24 |
| 2-553 | Sub-44 | 3,4-diClPh | $CH_2$ | Single bond | Sub-25 |
| 2-554 | Sub-44 | 3,4-diClPh | $CH_2$ | Single bond | Sub-26 |
| 2-555 | Sub-44 | 3,4-diClPh | $CH_2$ | Single bond | Sub-27 |
| 2-556 | Sub-44 | 3,4-diClPh | $CH_2$ | Single bond | Sub-28 |
| 2-557 | Sub-44 | 3,4-diClPh | $CH_2$ | Single bond | Sub-29 |
| 2-558 | Sub-44 | 3,4-diClPh | $CH_2$ | Single bond | Sub-30 |
| 2-559 | Sub-44 | 3,4-diClPh | $CH_2$ | Single bond | Sub-31 |
| 2-560 | Sub-44 | 3,4-diClPh | $CH_2$ | Single bond | Sub-32 |
| 2-561 | Sub-44 | 3,4-diClPh | $CH_2$ | Single bond | Sub-65 |
| 2-562 | Sub-44 | 3,4-diClPh | $CH_2$ | Single bond | Sub-66 |
| 2-563 | Sub-44 | 3,4-diClPh | $CH_2$ | Single bond | Sub-67 |
| 2-564 | Sub-44 | 3,4-diClPh | $CH_2$ | Single bond | Sub-68 |
| 2-565 | Sub-44 | 3,4-diClPh | $CH_2$ | Single bond | Sub-69 |
| 2-566 | Sub-44 | 3,4-diClPh | $CH_2$ | Single bond | Sub-70 |
| 2-567 | Sub-44 | 3,4-diClPh | $CH_2$ | Single bond | Sub-71 |
| 2-568 | Sub-44 | 3,4-diClPh | $CH_2$ | Single bond | Sub-72 |
| 2-569 | Sub-44 | 3,4-diClPh | $CH_2$ | Single bond | Sub-73 |
| 2-570 | Sub-44 | 3,4-diClPh | $CH_2$ | Single bond | Sub-74 |
| 2-571 | Sub-44 | 3,4-diClPh | $CH_2$ | Single bond | Sub-75 |
| 2-572 | Sub-44 | 3,4-diClPh | $CH_2$ | Single bond | Sub-76 |
| 2-573 | Sub-44 | 3,4-diClPh | $CH_2$ | Single bond | Sub-77 |
| 2-574 | Sub-44 | 3,4-diClPh | $CH_2$ | Single bond | Sub-78 |
| 2-575 | Sub-44 | 3,4-diClPh | $CH_2$ | Single bond | Sub-79 |
| 2-576 | Sub-44 | 3,4-diClPh | $CH_2$ | Single bond | Sub-80 |
| 2-577 | Sub-45 | 3,4-diClPh | $CH_2$ | Single bond | Sub-1 |
| 2-578 | Sub-45 | 3,4-diClPh | $CH_2$ | Single bond | Sub-2 |
| 2-579 | Sub-45 | 3,4-diClPh | $CH_2$ | Single bond | Sub-3 |
| 2-580 | Sub-45 | 3,4-diClPh | $CH_2$ | Single bond | Sub-4 |
| 2-581 | Sub-45 | 3,4-diClPh | $CH_2$ | Single bond | Sub-5 |
| 2-582 | Sub-45 | 3,4-diClPh | $CH_2$ | Single bond | Sub-6 |
| 2-583 | Sub-45 | 3,4-diClPh | $CH_2$ | Single bond | Sub-7 |
| 2-584 | Sub-45 | 3,4-diClPh | $CH_2$ | Single bond | Sub-8 |
| 2-585 | Sub-45 | 3,4-diClPh | $CH_2$ | Single bond | Sub-9 |
| 2-586 | Sub-45 | 3,4-diClPh | $CH_2$ | Single bond | Sub-10 |
| 2-587 | Sub-45 | 3,4-diClPh | $CH_2$ | Single bond | Sub-11 |
| 2-588 | Sub-45 | 3,4-diClPh | $CH_2$ | Single bond | Sub-12 |

TABLE 2-continued

| Cpd. No. | R¹ | R² | A | B | Z |
|---|---|---|---|---|---|
| 2-589 | Sub-45 | 3,4-diClPh | CH$_2$ | Single bond | Sub-13 |
| 2-590 | Sub-45 | 3,4-diClPh | CH$_2$ | Single bond | Sub-14 |
| 2-591 | Sub-45 | 3,4-diClPh | CH$_2$ | Single bond | Sub-15 |
| 2-592 | Sub-45 | 3,4-diClPh | CH$_2$ | Single bond | Sub-16 |
| 2-593 | Sub-45 | 3,4-diClPh | CH$_2$ | Single bond | Sub-17 |
| 2-594 | Sub-45 | 3,4-diClPh | CH$_2$ | Single bond | Sub-18 |
| 2-595 | Sub-45 | 3,4-diClPh | CH$_2$ | Single bond | Sub-19 |
| 2-596 | Sub-45 | 3,4-diClPh | CH$_2$ | Single bond | Sub-20 |
| 2-597 | Sub-45 | 3,4-diClPh | CH$_2$ | Single bond | Sub-21 |
| 2-598 | Sub-45 | 3,4-diClPh | CH$_2$ | Single bond | Sub-22 |
| 2-599 | Sub-45 | 3,4-diClPh | CH$_2$ | Single bond | Sub-23 |
| 2-600 | Sub-45 | 3,4-diClPh | CH$_2$ | Single bond | Sub-24 |
| 2-601 | Sub-45 | 3,4-diClPh | CH$_2$ | Single bond | Sub-25 |
| 2-602 | Sub-45 | 3,4-diClPh | CH$_2$ | Single bond | Sub-26 |
| 2-603 | Sub-45 | 3,4-diClPh | CH$_2$ | Single bond | Sub-27 |
| 2-604 | Sub-45 | 3,4-diClPh | CH$_2$ | Single bond | Sub-28 |
| 2-605 | Sub-45 | 3,4-diClPh | CH$_2$ | Single bond | Sub-29 |
| 2-606 | Sub-45 | 3,4-diClPh | CH$_2$ | Single bond | Sub-30 |
| 2-607 | Sub-45 | 3,4-diClPh | CH$_2$ | Single bond | Sub-31 |
| 2-608 | Sub-45 | 3,4-diClPh | CH$_2$ | Single bond | Sub-32 |
| 2-609 | Sub-45 | 3,4-diClPh | CH$_2$ | Single bond | Sub-65 |
| 2-610 | Sub-45 | 3,4-diClPh | CH$_2$ | Single bond | Sub-66 |
| 2-611 | Sub-45 | 3,4-diClPh | CH$_2$ | Single bond | Sub-67 |
| 2-612 | Sub-45 | 3,4-diClPh | CH$_2$ | Single bond | Sub-68 |
| 2-613 | Sub-45 | 3,4-diClPh | CH$_2$ | Single bond | Sub-69 |
| 2-614 | Sub-45 | 3,4-diClPh | CH$_2$ | Single bond | Sub-70 |
| 2-615 | Sub-45 | 3,4-diClPh | CH$_2$ | Single bond | Sub-71 |
| 2-616 | Sub-45 | 3,4-diClPh | CH$_2$ | Single bond | Sub-72 |
| 2-617 | Sub-45 | 3,4-diClPh | CH$_2$ | Single bond | Sub-73 |
| 2-618 | Sub-45 | 3,4-diClPh | CH$_2$ | Single bond | Sub-74 |
| 2-619 | Sub-45 | 3,4-diClPh | CH$_2$ | Single bond | Sub-75 |
| 2-620 | Sub-45 | 3,4-diClPh | CH$_2$ | Single bond | Sub-76 |
| 2-621 | Sub-45 | 3,4-diClPh | CH$_2$ | Single bond | Sub-77 |
| 2-622 | Sub-45 | 3,4-diClPh | CH$_2$ | Single bond | Sub-78 |
| 2-623 | Sub-45 | 3,4-diClPh | CH$_2$ | Single bond | Sub-79 |
| 2-624 | Sub-45 | 3,4-diClPh | CH$_2$ | Single bond | Sub-80 |
| 2-625 | Sub-46 | 3,4-diClPh | CH$_2$ | Single bond | Sub-1 |
| 2-626 | Sub-46 | 3,4-diClPh | CH$_2$ | Single bond | Sub-2 |
| 2-627 | Sub-46 | 3,4-diClPh | CH$_2$ | Single bond | Sub-3 |
| 2-628 | Sub-46 | 3,4-diClPh | CH$_2$ | Single bond | Sub-4 |
| 2-629 | Sub-46 | 3,4-diClPh | CH$_2$ | Single bond | Sub-5 |
| 2-630 | Sub-46 | 3,4-diClPh | CH$_2$ | Single bond | Sub-6 |
| 2-631 | Sub-46 | 3,4-diClPh | CH$_2$ | Single bond | Sub-7 |
| 2-632 | Sub-46 | 3,4-diClPh | CH$_2$ | Single bond | Sub-8 |
| 2-633 | Sub-46 | 3,4-diClPh | CH$_2$ | Single bond | Sub-9 |
| 2-634 | Sub-46 | 3,4-diClPh | CH$_2$ | Single bond | Sub-10 |
| 2-635 | Sub-46 | 3,4-diClPh | CH$_2$ | Single bond | Sub-11 |
| 2-636 | Sub-46 | 3,4-diClPh | CH$_2$ | Single bond | Sub-12 |
| 2-637 | Sub-46 | 3,4-diClPh | CH$_2$ | Single bond | Sub-13 |
| 2-638 | Sub-46 | 3,4-diClPh | CH$_2$ | Single bond | Sub-14 |
| 2-639 | Sub-46 | 3,4-diClPh | CH$_2$ | Single bond | Sub-15 |
| 2-640 | Sub-46 | 3,4-diClPh | CH$_2$ | Single bond | Sub-16 |
| 2-641 | Sub-46 | 3,4-diClPh | CH$_2$ | Single bond | Sub-17 |
| 2-642 | Sub-46 | 3,4-diClPh | CH$_2$ | Single bond | Sub-18 |
| 2-643 | Sub-46 | 3,4-diClPh | CH$_2$ | Single bond | Sub-19 |
| 2-644 | Sub-46 | 3,4-diClPh | CH$_2$ | Single bond | Sub-20 |
| 2-645 | Sub-46 | 3,4-diClPh | CH$_2$ | Single bond | Sub-21 |
| 2-646 | Sub-46 | 3,4-diClPh | CH$_2$ | Single bond | Sub-22 |
| 2-647 | Sub-46 | 3,4-diClPh | CH$_2$ | Single bond | Sub-23 |
| 2-648 | Sub-46 | 3,4-diClPh | CH$_2$ | Single bond | Sub-24 |
| 2-649 | Sub-46 | 3,4-diClPh | CH$_2$ | Single bond | Sub-25 |
| 2-650 | Sub-46 | 3,4-diClPh | CH$_2$ | Single bond | Sub-26 |
| 2-651 | Sub-46 | 3,4-diClPh | CH$_2$ | Single bond | Sub-27 |
| 2-652 | Sub-46 | 3,4-diClPh | CH$_2$ | Single bond | Sub-28 |
| 2-653 | Sub-46 | 3,4-diClPh | CH$_2$ | Single bond | Sub-29 |
| 2-654 | Sub-46 | 3,4-diClPh | CH$_2$ | Single bond | Sub-30 |
| 2-655 | Sub-46 | 3,4-diClPh | CH$_2$ | Single bond | Sub-31 |
| 2-656 | Sub-46 | 3,4-diClPh | CH$_2$ | Single bond | Sub-32 |
| 2-657 | Sub-46 | 3,4-diClPh | CH$_2$ | Single bond | Sub-65 |
| 2-658 | Sub-46 | 3,4-diClPh | CH$_2$ | Single bond | Sub-66 |
| 2-659 | Sub-46 | 3,4-diClPh | CH$_2$ | Single bond | Sub-67 |
| 2-660 | Sub-46 | 3,4-diClPh | CH$_2$ | Single bond | Sub-68 |
| 2-661 | Sub-46 | 3,4-diClPh | CH$_2$ | Single bond | Sub-69 |
| 2-662 | Sub-46 | 3,4-diClPh | CH$_2$ | Single bond | Sub-70 |
| 2-663 | Sub-46 | 3,4-diClPh | CH$_2$ | Single bond | Sub-71 |
| 2-664 | Sub-46 | 3,4-diClPh | CH$_2$ | Single bond | Sub-72 |
| 2-665 | Sub-46 | 3,4-diClPh | CH$_2$ | Single bond | Sub-73 |
| 2-666 | Sub-46 | 3,4-diClPh | CH$_2$ | Single bond | Sub-74 |
| 2-667 | Sub-46 | 3,4-diClPh | CH$_2$ | Single bond | Sub-75 |
| 2-668 | Sub-46 | 3,4-diClPh | CH$_2$ | Single bond | Sub-76 |
| 2-669 | Sub-46 | 3,4-diClPh | CH$_2$ | Single bond | Sub-77 |
| 2-670 | Sub-46 | 3,4-diClPh | CH$_2$ | Single bond | Sub-78 |
| 2-671 | Sub-46 | 3,4-diClPh | CH$_2$ | Single bond | Sub-79 |
| 2-672 | Sub-46 | 3,4-diClPh | CH$_2$ | Single bond | Sub-80 |
| 2-673 | Sub-47 | 3,4-diClPh | CH$_2$ | Single bond | Sub-1 |
| 2-674 | Sub-47 | 3,4-diClPh | CH$_2$ | Single bond | Sub-2 |
| 2-675 | Sub-47 | 3,4-diClPh | CH$_2$ | Single bond | Sub-3 |
| 2-676 | Sub-47 | 3,4-diClPh | CH$_2$ | Single bond | Sub-4 |
| 2-677 | Sub-47 | 3,4-diClPh | CH$_2$ | Single bond | Sub-5 |
| 2-678 | Sub-47 | 3,4-diClPh | CH$_2$ | Single bond | Sub-6 |
| 2-679 | Sub-47 | 3,4-diClPh | CH$_2$ | Single bond | Sub-7 |
| 2-680 | Sub-47 | 3,4-diClPh | CH$_2$ | Single bond | Sub-8 |
| 2-681 | Sub-47 | 3,4-diClPh | CH$_2$ | Single bond | Sub-9 |
| 2-682 | Sub-47 | 3,4-diClPh | CH$_2$ | Single bond | Sub-10 |
| 2-683 | Sub-47 | 3,4-diClPh | CH$_2$ | Single bond | Sub-11 |
| 2-684 | Sub-47 | 3,4-diClPh | CH$_2$ | Single bond | Sub-12 |
| 2-685 | Sub-47 | 3,4-diClPh | CH$_2$ | Single bond | Sub-13 |
| 2-686 | Sub-47 | 3,4-diClPh | CH$_2$ | Single bond | Sub-14 |
| 2-687 | Sub-47 | 3,4-diClPh | CH$_2$ | Single bond | Sub-15 |
| 2-688 | Sub-47 | 3,4-diClPh | CH$_2$ | Single bond | Sub-16 |
| 2-689 | Sub-47 | 3,4-diClPh | CH$_2$ | Single bond | Sub-17 |
| 2-690 | Sub-47 | 3,4-diClPh | CH$_2$ | Single bond | Sub-18 |
| 2-691 | Sub-47 | 3,4-diClPh | CH$_2$ | Single bond | Sub-19 |
| 2-692 | Sub-47 | 3,4-diClPh | CH$_2$ | Single bond | Sub-20 |
| 2-693 | Sub-47 | 3,4-diClPh | CH$_2$ | Single bond | Sub-21 |
| 2-694 | Sub-47 | 3,4-diClPh | CH$_2$ | Single bond | Sub-22 |
| 2-695 | Sub-47 | 3,4-diClPh | CH$_2$ | Single bond | Sub-23 |
| 2-696 | Sub-47 | 3,4-diClPh | CH$_2$ | Single bond | Sub-24 |
| 2-697 | Sub-47 | 3,4-diClPh | CH$_2$ | Single bond | Sub-25 |
| 2-698 | Sub-47 | 3,4-diClPh | CH$_2$ | Single bond | Sub-26 |
| 2-699 | Sub-47 | 3,4-diClPh | CH$_2$ | Single bond | Sub-27 |
| 2-700 | Sub-47 | 3,4-diClPh | CH$_2$ | Single bond | Sub-28 |
| 2-701 | Sub-47 | 3,4-diClPh | CH$_2$ | Single bond | Sub-29 |
| 2-702 | Sub-47 | 3,4-diClPh | CH$_2$ | Single bond | Sub-30 |
| 2-703 | Sub-47 | 3,4-diClPh | CH$_2$ | Single bond | Sub-31 |
| 2-704 | Sub-47 | 3,4-diClPh | CH$_2$ | Single bond | Sub-32 |
| 2-705 | Sub-47 | 3,4-diClPh | CH$_2$ | Single bond | Sub-65 |
| 2-706 | Sub-47 | 3,4-diClPh | CH$_2$ | Single bond | Sub-66 |
| 2-707 | Sub-47 | 3,4-diClPh | CH$_2$ | Single bond | Sub-67 |
| 2-708 | Sub-47 | 3,4-diClPh | CH$_2$ | Single bond | Sub-68 |
| 2-709 | Sub-47 | 3,4-diClPh | CH$_2$ | Single bond | Sub-69 |
| 2-710 | Sub-47 | 3,4-diClPh | CH$_2$ | Single bond | Sub-70 |
| 2-711 | Sub-47 | 3,4-diClPh | CH$_2$ | Single bond | Sub-71 |
| 2-712 | Sub-47 | 3,4-diClPh | CH$_2$ | Single bond | Sub-72 |
| 2-713 | Sub-47 | 3,4-diClPh | CH$_2$ | Single bond | Sub-73 |
| 2-714 | Sub-47 | 3,4-diClPh | CH$_2$ | Single bond | Sub-74 |
| 2-715 | Sub-47 | 3,4-diClPh | CH$_2$ | Single bond | Sub-75 |
| 2-716 | Sub-47 | 3,4-diClPh | CH$_2$ | Single bond | Sub-76 |
| 2-717 | Sub-47 | 3,4-diClPh | CH$_2$ | Single bond | Sub-77 |
| 2-718 | Sub-47 | 3,4-diClPh | CH$_2$ | Single bond | Sub-78 |
| 2-719 | Sub-47 | 3,4-diClPh | CH$_2$ | Single bond | Sub-79 |
| 2-720 | Sub-47 | 3,4-diClPh | CH$_2$ | Single bond | Sub-80 |
| 2-721 | Sub-81 | 3,4-diClPh | CH$_2$ | Single bond | Sub-1 |
| 2-722 | Sub-81 | 3,4-diClPh | CH$_2$ | Single bond | Sub-2 |
| 2-723 | Sub-81 | 3,4-diClPh | CH$_2$ | Single bond | Sub-3 |
| 2-724 | Sub-81 | 3,4-diClPh | CH$_2$ | Single bond | Sub-4 |
| 2-725 | Sub-81 | 3,4-diClPh | CH$_2$ | Single bond | Sub-5 |
| 2-726 | Sub-81 | 3,4-diClPh | CH$_2$ | Single bond | Sub-6 |
| 2-727 | Sub-81 | 3,4-diClPh | CH$_2$ | Single bond | Sub-7 |
| 2-728 | Sub-81 | 3,4-diClPh | CH$_2$ | Single bond | Sub-8 |
| 2-729 | Sub-81 | 3,4-diClPh | CH$_2$ | Single bond | Sub-9 |
| 2-730 | Sub-81 | 3,4-diClPh | CH$_2$ | Single bond | Sub-10 |
| 2-731 | Sub-81 | 3,4-diClPh | CH$_2$ | Single bond | Sub-11 |
| 2-732 | Sub-81 | 3,4-diClPh | CH$_2$ | Single bond | Sub-12 |
| 2-733 | Sub-81 | 3,4-diClPh | CH$_2$ | Single bond | Sub-13 |
| 2-734 | Sub-81 | 3,4-diClPh | CH$_2$ | Single bond | Sub-14 |
| 2-735 | Sub-81 | 3,4-diClPh | CH$_2$ | Single bond | Sub-15 |
| 2-736 | Sub-81 | 3,4-diClPh | CH$_2$ | Single bond | Sub-16 |
| 2-737 | Sub-81 | 3,4-diClPh | CH$_2$ | Single bond | Sub-17 |
| 2-738 | Sub-81 | 3,4-diClPh | CH$_2$ | Single bond | Sub-18 |
| 2-739 | Sub-81 | 3,4-diClPh | CH$_2$ | Single bond | Sub-19 |
| 2-740 | Sub-81 | 3,4-diClPh | CH$_2$ | Single bond | Sub-20 |
| 2-741 | Sub-81 | 3,4-diClPh | CH$_2$ | Single bond | Sub-21 |
| 2-742 | Sub-81 | 3,4-diClPh | CH$_2$ | Single bond | Sub-22 |

TABLE 2-continued

| Cpd. No. | R¹ | R² | A | B | Z |
|---|---|---|---|---|---|
| 2-743 | Sub-81 | 3,4-diClPh | CH₂ | Single bond | Sub-23 |
| 2-744 | Sub-81 | 3,4-diClPh | CH₂ | Single bond | Sub-24 |
| 2-745 | Sub-81 | 3,4-diClPh | CH₂ | Single bond | Sub-25 |
| 2-746 | Sub-81 | 3,4-diClPh | CH₂ | Single bond | Sub-26 |
| 2-747 | Sub-81 | 3,4-diClPh | CH₂ | Single bond | Sub-27 |
| 2-748 | Sub-81 | 3,4-diClPh | CH₂ | Single bond | Sub-28 |
| 2-749 | Sub-81 | 3,4-diClPh | CH₂ | Single bond | Sub-29 |
| 2-750 | Sub-81 | 3,4-diClPh | CH₂ | Single bond | Sub-30 |
| 2-751 | Sub-81 | 3,4-diClPh | CH₂ | Single bond | Sub-31 |
| 2-752 | Sub-81 | 3,4-diClPh | CH₂ | Single bond | Sub-32 |
| 2-753 | Sub-81 | 3,4-diClPh | CH₂ | Single bond | Sub-65 |
| 2-754 | Sub-81 | 3,4-diClPh | CH₂ | Single bond | Sub-66 |
| 2-755 | Sub-81 | 3,4-diClPh | CH₂ | Single bond | Sub-67 |
| 2-756 | Sub-81 | 3,4-diClPh | CH₂ | Single bond | Sub-68 |
| 2-757 | Sub-81 | 3,4-diClPh | CH₂ | Single bond | Sub-69 |
| 2-758 | Sub-81 | 3,4-diClPh | CH₂ | Single bond | Sub-70 |
| 2-759 | Sub-81 | 3,4-diClPh | CH₂ | Single bond | Sub-71 |
| 2-760 | Sub-81 | 3,4-diClPh | CH₂ | Single bond | Sub-72 |
| 2-761 | Sub-81 | 3,4-diClPh | CH₂ | Single bond | Sub-73 |
| 2-762 | Sub-81 | 3,4-diClPh | CH₂ | Single bond | Sub-74 |
| 2-763 | Sub-81 | 3,4-diClPh | CH₂ | Single bond | Sub-75 |
| 2-764 | Sub-81 | 3,4-diClPh | CH₂ | Single bond | Sub-76 |
| 2-765 | Sub-81 | 3,4-diClPh | CH₂ | Single bond | Sub-77 |
| 2-766 | Sub-81 | 3,4-diClPh | CH₂ | Single bond | Sub-78 |
| 2-767 | Sub-81 | 3,4-diClPh | CH₂ | Single bond | Sub-79 |
| 2-768 | Sub-81 | 3,4-diClPh | CH₂ | Single bond | Sub-80 |
| 2-769 | Sub-48 | 3,4-diClPh | CH₂ | Single bond | Sub-1 |
| 2-770 | Sub-48 | 3,4-diClPh | CH₂ | Single bond | Sub-2 |
| 2-771 | Sub-48 | 3,4-diClPh | CH₂ | Single bond | Sub-3 |
| 2-772 | Sub-48 | 3,4-diClPh | CH₂ | Single bond | Sub-4 |
| 2-773 | Sub-48 | 3,4-diClPh | CH₂ | Single bond | Sub-5 |
| 2-774 | Sub-48 | 3,4-diClPh | CH₂ | Single bond | Sub-6 |
| 2-775 | Sub-48 | 3,4-diClPh | CH₂ | Single bond | Sub-7 |
| 2-776 | Sub-48 | 3,4-diClPh | CH₂ | Single bond | Sub-8 |
| 2-777 | Sub-48 | 3,4-diClPh | CH₂ | Single bond | Sub-9 |
| 2-778 | Sub-48 | 3,4-diClPh | CH₂ | Single bond | Sub-10 |
| 2-779 | Sub-48 | 3,4-diClPh | CH₂ | Single bond | Sub-11 |
| 2-780 | Sub-48 | 3,4-diClPh | CH₂ | Single bond | Sub-12 |
| 2-781 | Sub-48 | 3,4-diClPh | CH₂ | Single bond | Sub-13 |
| 2-782 | Sub-48 | 3,4-diClPh | CH₂ | Single bond | Sub-14 |
| 2-783 | Sub-48 | 3,4-diClPh | CH₂ | Single bond | Sub-15 |
| 2-784 | Sub-48 | 3,4-diClPh | CH₂ | Single bond | Sub-16 |
| 2-785 | Sub-48 | 3,4-diClPh | CH₂ | Single bond | Sub-17 |
| 2-786 | Sub-48 | 3,4-diClPh | CH₂ | Single bond | Sub-18 |
| 2-787 | Sub-48 | 3,4-diClPh | CH₂ | Single bond | Sub-19 |
| 2-788 | Sub-48 | 3,4-diClPh | CH₂ | Single bond | Sub-20 |
| 2-789 | Sub-48 | 3,4-diClPh | CH₂ | Single bond | Sub-21 |
| 2-790 | Sub-48 | 3,4-diClPh | CH₂ | Single bond | Sub-22 |
| 2-791 | Sub-48 | 3,4-diClPh | CH₂ | Single bond | Sub-23 |
| 2-792 | Sub-48 | 3,4-diClPh | CH₂ | Single bond | Sub-24 |
| 2-793 | Sub-48 | 3,4-diClPh | CH₂ | Single bond | Sub-25 |
| 2-794 | Sub-48 | 3,4-diClPh | CH₂ | Single bond | Sub-26 |
| 2-795 | Sub-48 | 3,4-diClPh | CH₂ | Single bond | Sub-27 |
| 2-796 | Sub-48 | 3,4-diClPh | CH₂ | Single bond | Sub-28 |
| 2-797 | Sub-48 | 3,4-diClPh | CH₂ | Single bond | Sub-29 |
| 2-798 | Sub-48 | 3,4-diClPh | CH₂ | Single bond | Sub-30 |
| 2-799 | Sub-48 | 3,4-diClPh | CH₂ | Single bond | Sub-31 |
| 2-800 | Sub-48 | 3,4-diClPh | CH₂ | Single bond | Sub-32 |
| 2-801 | Sub-48 | 3,4-diClPh | CH₂ | Single bond | Sub-65 |
| 2-802 | Sub-48 | 3,4-diClPh | CH₂ | Single bond | Sub-66 |
| 2-803 | Sub-48 | 3,4-diClPh | CH₂ | Single bond | Sub-67 |
| 2-804 | Sub-48 | 3,4-diClPh | CH₂ | Single bond | Sub-68 |
| 2-805 | Sub-48 | 3,4-diClPh | CH₂ | Single bond | Sub-69 |
| 2-806 | Sub-48 | 3,4-diClPh | CH₂ | Single bond | Sub-70 |
| 2-807 | Sub-48 | 3,4-diClPh | CH₂ | Single bond | Sub-71 |
| 2-808 | Sub-48 | 3,4-diClPh | CH₂ | Single bond | Sub-72 |
| 2-809 | Sub-48 | 3,4-diClPh | CH₂ | Single bond | Sub-73 |
| 2-810 | Sub-48 | 3,4-diClPh | CH₂ | Single bond | Sub-74 |
| 2-811 | Sub-48 | 3,4-diClPh | CH₂ | Single bond | Sub-75 |
| 2-812 | Sub-48 | 3,4-diClPh | CH₂ | Single bond | Sub-76 |
| 2-813 | Sub-48 | 3,4-diClPh | CH₂ | Single bond | Sub-77 |
| 2-814 | Sub-48 | 3,4-diClPh | CH₂ | Single bond | Sub-78 |
| 2-815 | Sub-48 | 3,4-diClPh | CH₂ | Single bond | Sub-79 |
| 2-816 | Sub-48 | 3,4-diClPh | CH₂ | Single bond | Sub-80 |
| 2-817 | Sub-49 | 3,4-diClPh | CH₂ | Single bond | Sub-1 |
| 2-818 | Sub-49 | 3,4-diClPh | CH₂ | Single bond | Sub-2 |
| 2-819 | Sub-49 | 3,4-diClPh | CH₂ | Single bond | Sub-3 |
| 2-820 | Sub-49 | 3,4-diClPh | CH₂ | Single bond | Sub-4 |
| 2-821 | Sub-49 | 3,4-diClPh | CH₂ | Single bond | Sub-5 |
| 2-822 | Sub-49 | 3,4-diClPh | CH₂ | Single bond | Sub-6 |
| 2-823 | Sub-49 | 3,4-diClPh | CH₂ | Single bond | Sub-7 |
| 2-824 | Sub-49 | 3,4-diClPh | CH₂ | Single bond | Sub-8 |
| 2-825 | Sub-49 | 3,4-diClPh | CH₂ | Single bond | Sub-9 |
| 2-826 | Sub-49 | 3,4-diClPh | CH₂ | Single bond | Sub-10 |
| 2-827 | Sub-49 | 3,4-diClPh | CH₂ | Single bond | Sub-11 |
| 2-828 | Sub-49 | 3,4-diClPh | CH₂ | Single bond | Sub-12 |
| 2-829 | Sub-49 | 3,4-diClPh | CH₂ | Single bond | Sub-13 |
| 2-830 | Sub-49 | 3,4-diClPh | CH₂ | Single bond | Sub-14 |
| 2-831 | Sub-49 | 3,4-diClPh | CH₂ | Single bond | Sub-15 |
| 2-832 | Sub-49 | 3,4-diClPh | CH₂ | Single bond | Sub-16 |
| 2-833 | Sub-49 | 3,4-diClPh | CH₂ | Single bond | Sub-17 |
| 2-834 | Sub-49 | 3,4-diClPh | CH₂ | Single bond | Sub-18 |
| 2-835 | Sub-49 | 3,4-diClPh | CH₂ | Single bond | Sub-19 |
| 2-836 | Sub-49 | 3,4-diClPh | CH₂ | Single bond | Sub-20 |
| 2-837 | Sub-49 | 3,4-diClPh | CH₂ | Single bond | Sub-21 |
| 2-838 | Sub-49 | 3,4-diClPh | CH₂ | Single bond | Sub-22 |
| 2-839 | Sub-49 | 3,4-diClPh | CH₂ | Single bond | Sub-23 |
| 2-840 | Sub-49 | 3,4-diClPh | CH₂ | Single bond | Sub-24 |
| 2-841 | Sub-49 | 3,4-diClPh | CH₂ | Single bond | Sub-25 |
| 2-842 | Sub-49 | 3,4-diClPh | CH₂ | Single bond | Sub-26 |
| 2-843 | Sub-49 | 3,4-diClPh | CH₂ | Single bond | Sub-27 |
| 2-844 | Sub-49 | 3,4-diClPh | CH₂ | Single bond | Sub-28 |
| 2-845 | Sub-49 | 3,4-diClPh | CH₂ | Single bond | Sub-29 |
| 2-846 | Sub-49 | 3,4-diClPh | CH₂ | Single bond | Sub-30 |
| 2-847 | Sub-49 | 3,4-diClPh | CH₂ | Single bond | Sub-31 |
| 2-848 | Sub-49 | 3,4-diClPh | CH₂ | Single bond | Sub-32 |
| 2-849 | Sub-49 | 3,4-diClPh | CH₂ | Single bond | Sub-65 |
| 2-850 | Sub-49 | 3,4-diClPh | CH₂ | Single bond | Sub-66 |
| 2-851 | Sub-49 | 3,4-diClPh | CH₂ | Single bond | Sub-67 |
| 2-852 | Sub-49 | 3,4-diClPh | CH₂ | Single bond | Sub-68 |
| 2-853 | Sub-49 | 3,4-diClPh | CH₂ | Single bond | Sub-69 |
| 2-854 | Sub-49 | 3,4-diClPh | CH₂ | Single bond | Sub-70 |
| 2-855 | Sub-49 | 3,4-diClPh | CH₂ | Single bond | Sub-71 |
| 2-856 | Sub-49 | 3,4-diClPh | CH₂ | Single bond | Sub-72 |
| 2-857 | Sub-49 | 3,4-diClPh | CH₂ | Single bond | Sub-73 |
| 2-858 | Sub-49 | 3,4-diClPh | CH₂ | Single bond | Sub-74 |
| 2-859 | Sub-49 | 3,4-diClPh | CH₂ | Single bond | Sub-75 |
| 2-860 | Sub-49 | 3,4-diClPh | CH₂ | Single bond | Sub-76 |
| 2-861 | Sub-49 | 3,4-diClPh | CH₂ | Single bond | Sub-77 |
| 2-862 | Sub-49 | 3,4-diClPh | CH₂ | Single bond | Sub-78 |
| 2-863 | Sub-49 | 3,4-diClPh | CH₂ | Single bond | Sub-79 |
| 2-864 | Sub-49 | 3,4-diClPh | CH₂ | Single bond | Sub-80 |
| 2-865 | Sub-50 | 3,4-diClPh | CH₂ | Single bond | Sub-1 |
| 2-866 | Sub-50 | 3,4-diClPh | CH₂ | Single bond | Sub-2 |
| 2-867 | Sub-50 | 3,4-diClPh | CH₂ | Single bond | Sub-3 |
| 2-868 | Sub-50 | 3,4-diClPh | CH₂ | Single bond | Sub-4 |
| 2-869 | Sub-50 | 3,4-diClPh | CH₂ | Single bond | Sub-5 |
| 2-870 | Sub-50 | 3,4-diClPh | CH₂ | Single bond | Sub-6 |
| 2-871 | Sub-50 | 3,4-diClPh | CH₂ | Single bond | Sub-7 |
| 2-872 | Sub-50 | 3,4-diClPh | CH₂ | Single bond | Sub-8 |
| 2-873 | Sub-50 | 3,4-diClPh | CH₂ | Single bond | Sub-9 |
| 2-874 | Sub-50 | 3,4-diClPh | CH₂ | Single bond | Sub-10 |
| 2-875 | Sub-50 | 3,4-diClPh | CH₂ | Single bond | Sub-11 |
| 2-876 | Sub-50 | 3,4-diClPh | CH₂ | Single bond | Sub-12 |
| 2-877 | Sub-50 | 3,4-diClPh | CH₂ | Single bond | Sub-13 |
| 2-878 | Sub-50 | 3,4-diClPh | CH₂ | Single bond | Sub-14 |
| 2-879 | Sub-50 | 3,4-diClPh | CH₂ | Single bond | Sub-15 |
| 2-880 | Sub-50 | 3,4-diClPh | CH₂ | Single bond | Sub-16 |
| 2-881 | Sub-50 | 3,4-diClPh | CH₂ | Single bond | Sub-17 |
| 2-882 | Sub-50 | 3,4-diClPh | CH₂ | Single bond | Sub-18 |
| 2-883 | Sub-50 | 3,4-diClPh | CH₂ | Single bond | Sub-19 |
| 2-884 | Sub-50 | 3,4-diClPh | CH₂ | Single bond | Sub-20 |
| 2-885 | Sub-50 | 3,4-diClPh | CH₂ | Single bond | Sub-21 |
| 2-886 | Sub-50 | 3,4-diClPh | CH₂ | Single bond | Sub-22 |
| 2-887 | Sub-50 | 3,4-diClPh | CH₂ | Single bond | Sub-23 |
| 2-888 | Sub-50 | 3,4-diClPh | CH₂ | Single bond | Sub-24 |
| 2-889 | Sub-50 | 3,4-diClPh | CH₂ | Single bond | Sub-25 |
| 2-890 | Sub-50 | 3,4-diClPh | CH₂ | Single bond | Sub-26 |
| 2-891 | Sub-50 | 3,4-diClPh | CH₂ | Single bond | Sub-27 |
| 2-892 | Sub-50 | 3,4-diClPh | CH₂ | Single bond | Sub-28 |
| 2-893 | Sub-50 | 3,4-diClPh | CH₂ | Single bond | Sub-29 |
| 2-894 | Sub-50 | 3,4-diClPh | CH₂ | Single bond | Sub-30 |
| 2-895 | Sub-50 | 3,4-diClPh | CH₂ | Single bond | Sub-31 |
| 2-896 | Sub-50 | 3,4-diClPh | CH₂ | Single bond | Sub-32 |

TABLE 2-continued

| Cpd. No. | R¹ | R² | A | B | Z |
|---|---|---|---|---|---|
| 2-897 | Sub-50 | 3,4-diClPh | CH₂ | Single bond | Sub-65 |
| 2-898 | Sub-50 | 3,4-diClPh | CH₂ | Single bond | Sub-66 |
| 2-899 | Sub-50 | 3,4-diClPh | CH₂ | Single bond | Sub-67 |
| 2-900 | Sub-50 | 3,4-diClPh | CH₂ | Single bond | Sub-68 |
| 2-901 | Sub-50 | 3,4-diClPh | CH₂ | Single bond | Sub-69 |
| 2-902 | Sub-50 | 3,4-diClPh | CH₂ | Single bond | Sub-70 |
| 2-903 | Sub-50 | 3,4-diClPh | CH₂ | Single bond | Sub-71 |
| 2-904 | Sub-50 | 3,4-diClPh | CH₂ | Single bond | Sub-72 |
| 2-905 | Sub-50 | 3,4-diClPh | CH₂ | Single bond | Sub-73 |
| 2-906 | Sub-50 | 3,4-diClPh | CH₂ | Single bond | Sub-74 |
| 2-907 | Sub-50 | 3,4-diClPh | CH₂ | Single bond | Sub-75 |
| 2-908 | Sub-50 | 3,4-diClPh | CH₂ | Single bond | Sub-76 |
| 2-909 | Sub-50 | 3,4-diClPh | CH₂ | Single bond | Sub-77 |
| 2-910 | Sub-50 | 3,4-diClPh | CH₂ | Single bond | Sub-78 |
| 2-911 | Sub-50 | 3,4-diClPh | CH₂ | Single bond | Sub-79 |
| 2-912 | Sub-50 | 3,4-diClPh | CH₂ | Single bond | Sub-80 |
| 2-913 | Sub-51 | 3,4-diClPh | CH₂ | Single bond | Sub-1 |
| 2-914 | Sub-51 | 3,4-diClPh | CH₂ | Single bond | Sub-2 |
| 2-915 | Sub-51 | 3,4-diClPh | CH₂ | Single bond | Sub-3 |
| 2-916 | Sub-51 | 3,4-diClPh | CH₂ | Single bond | Sub-4 |
| 2-917 | Sub-51 | 3,4-diClPh | CH₂ | Single bond | Sub-5 |
| 2-918 | Sub-51 | 3,4-diClPh | CH₂ | Single bond | Sub-6 |
| 2-919 | Sub-51 | 3,4-diClPh | CH₂ | Single bond | Sub-7 |
| 2-920 | Sub-51 | 3,4-diClPh | CH₂ | Single bond | Sub-8 |
| 2-921 | Sub-51 | 3,4-diClPh | CH₂ | Single bond | Sub-9 |
| 2-922 | Sub-51 | 3,4-diClPh | CH₂ | Single bond | Sub-10 |
| 2-923 | Sub-51 | 3,4-diClPh | CH₂ | Single bond | Sub-11 |
| 2-924 | Sub-51 | 3,4-diClPh | CH₂ | Single bond | Sub-12 |
| 2-925 | Sub-51 | 3,4-diClPh | CH₂ | Single bond | Sub-13 |
| 2-926 | Sub-51 | 3,4-diClPh | CH₂ | Single bond | Sub-14 |
| 2-927 | Sub-51 | 3,4-diClPh | CH₂ | Single bond | Sub-15 |
| 2-928 | Sub-51 | 3,4-diClPh | CH₂ | Single bond | Sub-16 |
| 2-929 | Sub-51 | 3,4-diClPh | CH₂ | Single bond | Sub-17 |
| 2-930 | Sub-51 | 3,4-diClPh | CH₂ | Single bond | Sub-18 |
| 2-931 | Sub-51 | 3,4-diClPh | CH₂ | Single bond | Sub-19 |
| 2-932 | Sub-51 | 3,4-diClPh | CH₂ | Single bond | Sub-20 |
| 2-933 | Sub-51 | 3,4-diClPh | CH₂ | Single bond | Sub-21 |
| 2-934 | Sub-51 | 3,4-diClPh | CH₂ | Single bond | Sub-22 |
| 2-935 | Sub-51 | 3,4-diClPh | CH₂ | Single bond | Sub-23 |
| 2-936 | Sub-51 | 3,4-diClPh | CH₂ | Single bond | Sub-24 |
| 2-937 | Sub-51 | 3,4-diClPh | CH₂ | Single bond | Sub-25 |
| 2-938 | Sub-51 | 3,4-diClPh | CH₂ | Single bond | Sub-26 |
| 2-939 | Sub-51 | 3,4-diClPh | CH₂ | Single bond | Sub-27 |
| 2-940 | Sub-51 | 3,4-diClPh | CH₂ | Single bond | Sub-28 |
| 2-941 | Sub-51 | 3,4-diClPh | CH₂ | Single bond | Sub-29 |
| 2-942 | Sub-51 | 3,4-diClPh | CH₂ | Single bond | Sub-30 |
| 2-943 | Sub-51 | 3,4-diClPh | CH₂ | Single bond | Sub-31 |
| 2-944 | Sub-51 | 3,4-diClPh | CH₂ | Single bond | Sub-32 |
| 2-945 | Sub-51 | 3,4-diClPh | CH₂ | Single bond | Sub-65 |
| 2-946 | Sub-51 | 3,4-diClPh | CH₂ | Single bond | Sub-66 |
| 2-947 | Sub-51 | 3,4-diClPh | CH₂ | Single bond | Sub-67 |
| 2-948 | Sub-51 | 3,4-diClPh | CH₂ | Single bond | Sub-68 |
| 2-949 | Sub-51 | 3,4-diClPh | CH₂ | Single bond | Sub-69 |
| 2-950 | Sub-51 | 3,4-diClPh | CH₂ | Single bond | Sub-70 |
| 2-951 | Sub-51 | 3,4-diClPh | CH₂ | Single bond | Sub-71 |
| 2-952 | Sub-51 | 3,4-diClPh | CH₂ | Single bond | Sub-72 |
| 2-953 | Sub-51 | 3,4-diClPh | CH₂ | Single bond | Sub-73 |
| 2-954 | Sub-51 | 3,4-diClPh | CH₂ | Single bond | Sub-74 |
| 2-955 | Sub-51 | 3,4-diClPh | CH₂ | Single bond | Sub-75 |
| 2-956 | Sub-51 | 3,4-diClPh | CH₂ | Single bond | Sub-76 |
| 2-957 | Sub-51 | 3,4-diClPh | CH₂ | Single bond | Sub-77 |
| 2-958 | Sub-51 | 3,4-diClPh | CH₂ | Single bond | Sub-78 |
| 2-959 | Sub-51 | 3,4-diClPh | CH₂ | Single bond | Sub-79 |
| 2-960 | Sub-51 | 3,4-diClPh | CH₂ | Single bond | Sub-80 |
| 2-961 | Sub-52 | 3,4-diClPh | CH₂ | Single bond | Sub-1 |
| 2-962 | Sub-52 | 3,4-diClPh | CH₂ | Single bond | Sub-2 |
| 2-963 | Sub-52 | 3,4-diClPh | CH₂ | Single bond | Sub-3 |
| 2-964 | Sub-52 | 3,4-diClPh | CH₂ | Single bond | Sub-4 |
| 2-965 | Sub-52 | 3,4-diClPh | CH₂ | Single bond | Sub-5 |
| 2-966 | Sub-52 | 3,4-diClPh | CH₂ | Single bond | Sub-6 |
| 2-967 | Sub-52 | 3,4-diClPh | CH₂ | Single bond | Sub-7 |
| 2-968 | Sub-52 | 3,4-diClPh | CH₂ | Single bond | Sub-8 |
| 2-969 | Sub-52 | 3,4-diClPh | CH₂ | Single bond | Sub-9 |
| 2-970 | Sub-52 | 3,4-diClPh | CH₂ | Single bond | Sub-10 |
| 2-971 | Sub-52 | 3,4-diClPh | CH₂ | Single bond | Sub-11 |
| 2-972 | Sub-52 | 3,4-diClPh | CH₂ | Single bond | Sub-12 |
| 2-973 | Sub-52 | 3,4-diClPh | CH₂ | Single bond | Sub-13 |
| 2-974 | Sub-52 | 3,4-diClPh | CH₂ | Single bond | Sub-14 |
| 2-975 | Sub-52 | 3,4-diClPh | CH₂ | Single bond | Sub-15 |
| 2-976 | Sub-52 | 3,4-diClPh | CH₂ | Single bond | Sub-16 |
| 2-977 | Sub-52 | 3,4-diClPh | CH₂ | Single bond | Sub-17 |
| 2-978 | Sub-52 | 3,4-diClPh | CH₂ | Single bond | Sub-18 |
| 2-979 | Sub-52 | 3,4-diClPh | CH₂ | Single bond | Sub-19 |
| 2-980 | Sub-52 | 3,4-diClPh | CH₂ | Single bond | Sub-20 |
| 2-981 | Sub-52 | 3,4-diClPh | CH₂ | Single bond | Sub-21 |
| 2-982 | Sub-52 | 3,4-diClPh | CH₂ | Single bond | Sub-22 |
| 2-983 | Sub-52 | 3,4-diClPh | CH₂ | Single bond | Sub-23 |
| 2-984 | Sub-52 | 3,4-diClPh | CH₂ | Single bond | Sub-24 |
| 2-985 | Sub-52 | 3,4-diClPh | CH₂ | Single bond | Sub-25 |
| 2-986 | Sub-52 | 3,4-diClPh | CH₂ | Single bond | Sub-26 |
| 2-987 | Sub-52 | 3,4-diClPh | CH₂ | Single bond | Sub-27 |
| 2-988 | Sub-52 | 3,4-diClPh | CH₂ | Single bond | Sub-28 |
| 2-989 | Sub-52 | 3,4-diClPh | CH₂ | Single bond | Sub-29 |
| 2-990 | Sub-52 | 3,4-diClPh | CH₂ | Single bond | Sub-30 |
| 2-991 | Sub-52 | 3,4-diClPh | CH₂ | Single bond | Sub-31 |
| 2-992 | Sub-52 | 3,4-diClPh | CH₂ | Single bond | Sub-32 |
| 2-993 | Sub-52 | 3,4-diClPh | CH₂ | Single bond | Sub-65 |
| 2-994 | Sub-52 | 3,4-diClPh | CH₂ | Single bond | Sub-66 |
| 2-995 | Sub-52 | 3,4-diClPh | CH₂ | Single bond | Sub-67 |
| 2-996 | Sub-52 | 3,4-diClPh | CH₂ | Single bond | Sub-68 |
| 2-997 | Sub-52 | 3,4-diClPh | CH₂ | Single bond | Sub-69 |
| 2-998 | Sub-52 | 3,4-diClPh | CH₂ | Single bond | Sub-70 |
| 2-999 | Sub-52 | 3,4-diClPh | CH₂ | Single bond | Sub-71 |
| 2-1000 | Sub-52 | 3,4-diClPh | CH₂ | Single bond | Sub-72 |
| 2-1001 | Sub-52 | 3,4-diClPh | CH₂ | Single bond | Sub-73 |
| 2-1002 | Sub-52 | 3,4-diClPh | CH₂ | Single bond | Sub-74 |
| 2-1003 | Sub-52 | 3,4-diClPh | CH₂ | Single bond | Sub-75 |
| 2-1004 | Sub-52 | 3,4-diClPh | CH₂ | Single bond | Sub-76 |
| 2-1005 | Sub-52 | 3,4-diClPh | CH₂ | Single bond | Sub-77 |
| 2-1006 | Sub-52 | 3,4-diClPh | CH₂ | Single bond | Sub-78 |
| 2-1007 | Sub-52 | 3,4-diClPh | CH₂ | Single bond | Sub-79 |
| 2-1008 | Sub-52 | 3,4-diClPh | CH₂ | Single bond | Sub-80 |
| 2-1009 | Sub-53 | 3,4-diClPh | CH₂ | Single bond | Sub-1 |
| 2-1010 | Sub-53 | 3,4-diClPh | CH₂ | Single bond | Sub-2 |
| 2-1011 | Sub-53 | 3,4-diClPh | CH₂ | Single bond | Sub-3 |
| 2-1012 | Sub-53 | 3,4-diClPh | CH₂ | Single bond | Sub-4 |
| 2-1013 | Sub-53 | 3,4-diClPh | CH₂ | Single bond | Sub-5 |
| 2-1014 | Sub-53 | 3,4-diClPh | CH₂ | Single bond | Sub-6 |
| 2-1015 | Sub-53 | 3,4-diClPh | CH₂ | Single bond | Sub-7 |
| 2-1016 | Sub-53 | 3,4-diClPh | CH₂ | Single bond | Sub-8 |
| 2-1017 | Sub-53 | 3,4-diClPh | CH₂ | Single bond | Sub-9 |
| 2-1018 | Sub-53 | 3,4-diClPh | CH₂ | Single bond | Sub-10 |
| 2-1019 | Sub-53 | 3,4-diClPh | CH₂ | Single bond | Sub-11 |
| 2-1020 | Sub-53 | 3,4-diClPh | CH₂ | Single bond | Sub-12 |
| 2-1021 | Sub-53 | 3,4-diClPh | CH₂ | Single bond | Sub-13 |
| 2-1022 | Sub-53 | 3,4-diClPh | CH₂ | Single bond | Sub-14 |
| 2-1023 | Sub-53 | 3,4-diClPh | CH₂ | Single bond | Sub-15 |
| 2-1024 | Sub-53 | 3,4-diClPh | CH₂ | Single bond | Sub-16 |
| 2-1025 | Sub-53 | 3,4-diClPh | CH₂ | Single bond | Sub-17 |
| 2-1026 | Sub-53 | 3,4-diClPh | CH₂ | Single bond | Sub-18 |
| 2-1027 | Sub-53 | 3,4-diClPh | CH₂ | Single bond | Sub-19 |
| 2-1028 | Sub-53 | 3,4-diClPh | CH₂ | Single bond | Sub-20 |
| 2-1029 | Sub-53 | 3,4-diClPh | CH₂ | Single bond | Sub-21 |
| 2-1030 | Sub-53 | 3,4-diClPh | CH₂ | Single bond | Sub-22 |
| 2-1031 | Sub-53 | 3,4-diClPh | CH₂ | Single bond | Sub-23 |
| 2-1032 | Sub-53 | 3,4-diClPh | CH₂ | Single bond | Sub-24 |
| 2-1033 | Sub-53 | 3,4-diClPh | CH₂ | Single bond | Sub-25 |
| 2-1034 | Sub-53 | 3,4-diClPh | CH₂ | Single bond | Sub-26 |
| 2-1035 | Sub-53 | 3,4-diClPh | CH₂ | Single bond | Sub-27 |
| 2-1036 | Sub-53 | 3,4-diClPh | CH₂ | Single bond | Sub-28 |
| 2-1037 | Sub-53 | 3,4-diClPh | CH₂ | Single bond | Sub-29 |
| 2-1038 | Sub-53 | 3,4-diClPh | CH₂ | Single bond | Sub-30 |
| 2-1039 | Sub-53 | 3,4-diClPh | CH₂ | Single bond | Sub-31 |
| 2-1040 | Sub-53 | 3,4-diClPh | CH₂ | Single bond | Sub-32 |
| 2-1041 | Sub-53 | 3,4-diClPh | CH₂ | Single bond | Sub-65 |
| 2-1042 | Sub-53 | 3,4-diClPh | CH₂ | Single bond | Sub-66 |
| 2-1043 | Sub-53 | 3,4-diClPh | CH₂ | Single bond | Sub-67 |
| 2-1044 | Sub-53 | 3,4-diClPh | CH₂ | Single bond | Sub-68 |
| 2-1045 | Sub-53 | 3,4-diClPh | CH₂ | Single bond | Sub-69 |
| 2-1046 | Sub-53 | 3,4-diClPh | CH₂ | Single bond | Sub-70 |
| 2-1047 | Sub-53 | 3,4-diClPh | CH₂ | Single bond | Sub-71 |
| 2-1048 | Sub-53 | 3,4-diClPh | CH₂ | Single bond | Sub-72 |
| 2-1049 | Sub-53 | 3,4-diClPh | CH₂ | Single bond | Sub-73 |
| 2-1050 | Sub-53 | 3,4-diClPh | CH₂ | Single bond | Sub-74 |

TABLE 2-continued

| Cpd. No. | R¹ | R² | A | B | Z |
|---|---|---|---|---|---|
| 2-1051 | Sub-53 | 3,4-diClPh | CH₂ | Single bond | Sub-75 |
| 2-1052 | Sub-53 | 3,4-diClPh | CH₂ | Single bond | Sub-76 |
| 2-1053 | Sub-53 | 3,4-diClPh | CH₂ | Single bond | Sub-77 |
| 2-1054 | Sub-53 | 3,4-diClPh | CH₂ | Single bond | Sub-78 |
| 2-1055 | Sub-53 | 3,4-diClPh | CH₂ | Single bond | Sub-79 |
| 2-1056 | Sub-53 | 3,4-diClPh | CH₂ | Single bond | Sub-80 |
| 2-1057 | Sub-54 | 3,4-diClPh | CH₂ | Single bond | Sub-1 |
| 2-1058 | Sub-54 | 3,4-diClPh | CH₂ | Single bond | Sub-2 |
| 2-1059 | Sub-54 | 3,4-diClPh | CH₂ | Single bond | Sub-3 |
| 2-1060 | Sub-54 | 3,4-diClPh | CH₂ | Single bond | Sub-4 |
| 2-1061 | Sub-54 | 3,4-diClPh | CH₂ | Single bond | Sub-5 |
| 2-1062 | Sub-54 | 3,4-diClPh | CH₂ | Single bond | Sub-6 |
| 2-1063 | Sub-54 | 3,4-diClPh | CH₂ | Single bond | Sub-7 |
| 2-1064 | Sub-54 | 3,4-diClPh | CH₂ | Single bond | Sub-8 |
| 2-1065 | Sub-54 | 3,4-diClPh | CH₂ | Single bond | Sub-9 |
| 2-1066 | Sub-54 | 3,4-diClPh | CH₂ | Single bond | Sub-10 |
| 2-1067 | Sub-54 | 3,4-diClPh | CH₂ | Single bond | Sub-11 |
| 2-1068 | Sub-54 | 3,4-diClPh | CH₂ | Single bond | Sub-12 |
| 2-1069 | Sub-54 | 3,4-diClPh | CH₂ | Single bond | Sub-13 |
| 2-1070 | Sub-54 | 3,4-diClPh | CH₂ | Single bond | Sub-14 |
| 2-1071 | Sub-54 | 3,4-diClPh | CH₂ | Single bond | Sub-15 |
| 2-1072 | Sub-54 | 3,4-diClPh | CH₂ | Single bond | Sub-16 |
| 2-1073 | Sub-54 | 3,4-diClPh | CH₂ | Single bond | Sub-17 |
| 2-1074 | Sub-54 | 3,4-diClPh | CH₂ | Single bond | Sub-18 |
| 2-1075 | Sub-54 | 3,4-diClPh | CH₂ | Single bond | Sub-19 |
| 2-1076 | Sub-54 | 3,4-diClPh | CH₂ | Single bond | Sub-20 |
| 2-1077 | Sub-54 | 3,4-diClPh | CH₂ | Single bond | Sub-21 |
| 2-1078 | Sub-54 | 3,4-diClPh | CH₂ | Single bond | Sub-22 |
| 2-1079 | Sub-54 | 3,4-diClPh | CH₂ | Single bond | Sub-23 |
| 2-1080 | Sub-54 | 3,4-diClPh | CH₂ | Single bond | Sub-24 |
| 2-1081 | Sub-54 | 3,4-diClPh | CH₂ | Single bond | Sub-25 |
| 2-1082 | Sub-54 | 3,4-diClPh | CH₂ | Single bond | Sub-26 |
| 2-1083 | Sub-54 | 3,4-diClPh | CH₂ | Single bond | Sub-27 |
| 2-1084 | Sub-54 | 3,4-diClPh | CH₂ | Single bond | Sub-28 |
| 2-1085 | Sub-54 | 3,4-diClPh | CH₂ | Single bond | Sub-29 |
| 2-1086 | Sub-54 | 3,4-diClPh | CH₂ | Single bond | Sub-30 |
| 2-1087 | Sub-54 | 3,4-diClPh | CH₂ | Single bond | Sub-31 |
| 2-1088 | Sub-54 | 3,4-diClPh | CH₂ | Single bond | Sub-32 |
| 2-1089 | Sub-54 | 3,4-diClPh | CH₂ | Single bond | Sub-65 |
| 2-1090 | Sub-54 | 3,4-diClPh | CH₂ | Single bond | Sub-66 |
| 2-1091 | Sub-54 | 3,4-diClPh | CH₂ | Single bond | Sub-67 |
| 2-1092 | Sub-54 | 3,4-diClPh | CH₂ | Single bond | Sub-68 |
| 2-1093 | Sub-54 | 3,4-diClPh | CH₂ | Single bond | Sub-69 |
| 2-1094 | Sub-54 | 3,4-diClPh | CH₂ | Single bond | Sub-70 |
| 2-1095 | Sub-54 | 3,4-diClPh | CH₂ | Single bond | Sub-71 |
| 2-1096 | Sub-54 | 3,4-diClPh | CH₂ | Single bond | Sub-72 |
| 2-1097 | Sub-54 | 3,4-diClPh | CH₂ | Single bond | Sub-73 |
| 2-1098 | Sub-54 | 3,4-diClPh | CH₂ | Single bond | Sub-74 |
| 2-1099 | Sub-54 | 3,4-diClPh | CH₂ | Single bond | Sub-75 |
| 2-1100 | Sub-54 | 3,4-diClPh | CH₂ | Single bond | Sub-76 |
| 2-1101 | Sub-54 | 3,4-diClPh | CH₂ | Single bond | Sub-77 |
| 2-1102 | Sub-54 | 3,4-diClPh | CH₂ | Single bond | Sub-78 |
| 2-1103 | Sub-54 | 3,4-diClPh | CH₂ | Single bond | Sub-79 |
| 2-1104 | Sub-54 | 3,4-diClPh | CH₂ | Single bond | Sub-80 |
| 2-1105 | Sub-55 | 3,4-diClPh | CH₂ | Single bond | Sub-1 |
| 2-1106 | Sub-55 | 3,4-diClPh | CH₂ | Single bond | Sub-2 |
| 2-1107 | Sub-55 | 3,4-diClPh | CH₂ | Single bond | Sub-3 |
| 2-1108 | Sub-55 | 3,4-diClPh | CH₂ | Single bond | Sub-4 |
| 2-1109 | Sub-55 | 3,4-diClPh | CH₂ | Single bond | Sub-5 |
| 2-1110 | Sub-55 | 3,4-diClPh | CH₂ | Single bond | Sub-6 |
| 2-1111 | Sub-55 | 3,4-diClPh | CH₂ | Single bond | Sub-7 |
| 2-1112 | Sub-55 | 3,4-diClPh | CH₂ | Single bond | Sub-8 |
| 2-1113 | Sub-55 | 3,4-diClPh | CH₂ | Single bond | Sub-9 |
| 2-1114 | Sub-55 | 3,4-diClPh | CH₂ | Single bond | Sub-10 |
| 2-1115 | Sub-55 | 3,4-diClPh | CH₂ | Single bond | Sub-11 |
| 2-1116 | Sub-55 | 3,4-diClPh | CH₂ | Single bond | Sub-12 |
| 2-1117 | Sub-55 | 3,4-diClPh | CH₂ | Single bond | Sub-13 |
| 2-1118 | Sub-55 | 3,4-diClPh | CH₂ | Single bond | Sub-14 |
| 2-1119 | Sub-55 | 3,4-diClPh | CH₂ | Single bond | Sub-15 |
| 2-1120 | Sub-55 | 3,4-diClPh | CH₂ | Single bond | Sub-16 |
| 2-1121 | Sub-55 | 3,4-diClPh | CH₂ | Single bond | Sub-17 |
| 2-1122 | Sub-55 | 3,4-diClPh | CH₂ | Single bond | Sub-18 |
| 2-1123 | Sub-55 | 3,4-diClPh | CH₂ | Single bond | Sub-19 |
| 2-1124 | Sub-55 | 3,4-diClPh | CH₂ | Single bond | Sub-20 |
| 2-1125 | Sub-55 | 3,4-diClPh | CH₂ | Single bond | Sub-21 |
| 2-1126 | Sub-55 | 3,4-diClPh | CH₂ | Single bond | Sub-22 |
| 2-1127 | Sub-55 | 3,4-diClPh | CH₂ | Single bond | Sub-23 |
| 2-1128 | Sub-55 | 3,4-diClPh | CH₂ | Single bond | Sub-24 |
| 2-1129 | Sub-55 | 3,4-diClPh | CH₂ | Single bond | Sub-25 |
| 2-1130 | Sub-55 | 3,4-diClPh | CH₂ | Single bond | Sub-26 |
| 2-1131 | Sub-55 | 3,4-diClPh | CH₂ | Single bond | Sub-27 |
| 2-1132 | Sub-55 | 3,4-diClPh | CH₂ | Single bond | Sub-28 |
| 2-1133 | Sub-55 | 3,4-diClPh | CH₂ | Single bond | Sub-29 |
| 2-1134 | Sub-55 | 3,4-diClPh | CH₂ | Single bond | Sub-30 |
| 2-1135 | Sub-55 | 3,4-diClPh | CH₂ | Single bond | Sub-31 |
| 2-1136 | Sub-55 | 3,4-diClPh | CH₂ | Single bond | Sub-32 |
| 2-1137 | Sub-55 | 3,4-diClPh | CH₂ | Single bond | Sub-65 |
| 2-1138 | Sub-55 | 3,4-diClPh | CH₂ | Single bond | Sub-66 |
| 2-1139 | Sub-55 | 3,4-diClPh | CH₂ | Single bond | Sub-67 |
| 2-1140 | Sub-55 | 3,4-diClPh | CH₂ | Single bond | Sub-68 |
| 2-1141 | Sub-55 | 3,4-diClPh | CH₂ | Single bond | Sub-69 |
| 2-1142 | Sub-55 | 3,4-diClPh | CH₂ | Single bond | Sub-70 |
| 2-1143 | Sub-55 | 3,4-diClPh | CH₂ | Single bond | Sub-71 |
| 2-1144 | Sub-55 | 3,4-diClPh | CH₂ | Single bond | Sub-72 |
| 2-1145 | Sub-55 | 3,4-diClPh | CH₂ | Single bond | Sub-73 |
| 2-1146 | Sub-55 | 3,4-diClPh | CH₂ | Single bond | Sub-74 |
| 2-1147 | Sub-55 | 3,4-diClPh | CH₂ | Single bond | Sub-75 |
| 2-1148 | Sub-55 | 3,4-diClPh | CH₂ | Single bond | Sub-76 |
| 2-1149 | Sub-55 | 3,4-diClPh | CH₂ | Single bond | Sub-77 |
| 2-1150 | Sub-55 | 3,4-diClPh | CH₂ | Single bond | Sub-78 |
| 2-1151 | Sub-55 | 3,4-diClPh | CH₂ | Single bond | Sub-79 |
| 2-1152 | Sub-55 | 3,4-diClPh | CH₂ | Single bond | Sub-80 |
| 2-1153 | Sub-56 | 3,4-diClPh | CH₂ | Single bond | Sub-1 |
| 2-1154 | Sub-56 | 3,4-diClPh | CH₂ | Single bond | Sub-2 |
| 2-1155 | Sub-56 | 3,4-diClPh | CH₂ | Single bond | Sub-3 |
| 2-1156 | Sub-56 | 3,4-diClPh | CH₂ | Single bond | Sub-4 |
| 2-1157 | Sub-56 | 3,4-diClPh | CH₂ | Single bond | Sub-5 |
| 2-1158 | Sub-56 | 3,4-diClPh | CH₂ | Single bond | Sub-6 |
| 2-1159 | Sub-56 | 3,4-diClPh | CH₂ | Single bond | Sub-7 |
| 2-1160 | Sub-56 | 3,4-diClPh | CH₂ | Single bond | Sub-8 |
| 2-1161 | Sub-56 | 3,4-diClPh | CH₂ | Single bond | Sub-9 |
| 2-1162 | Sub-56 | 3,4-diClPh | CH₂ | Single bond | Sub-10 |
| 2-1163 | Sub-56 | 3,4-diClPh | CH₂ | Single bond | Sub-11 |
| 2-1164 | Sub-56 | 3,4-diClPh | CH₂ | Single bond | Sub-12 |
| 2-1165 | Sub-56 | 3,4-diClPh | CH₂ | Single bond | Sub-13 |
| 2-1166 | Sub-56 | 3,4-diClPh | CH₂ | Single bond | Sub-14 |
| 2-1167 | Sub-56 | 3,4-diClPh | CH₂ | Single bond | Sub-15 |
| 2-1168 | Sub-56 | 3,4-diClPh | CH₂ | Single bond | Sub-16 |
| 2-1169 | Sub-56 | 3,4-diClPh | CH₂ | Single bond | Sub-17 |
| 2-1170 | Sub-56 | 3,4-diClPh | CH₂ | Single bond | Sub-18 |
| 2-1171 | Sub-56 | 3,4-diClPh | CH₂ | Single bond | Sub-19 |
| 2-1172 | Sub-56 | 3,4-diClPh | CH₂ | Single bond | Sub-20 |
| 2-1173 | Sub-56 | 3,4-diClPh | CH₂ | Single bond | Sub-21 |
| 2-1174 | Sub-56 | 3,4-diClPh | CH₂ | Single bond | Sub-22 |
| 2-1175 | Sub-56 | 3,4-diClPh | CH₂ | Single bond | Sub-23 |
| 2-1176 | Sub-56 | 3,4-diClPh | CH₂ | Single bond | Sub-24 |
| 2-1177 | Sub-56 | 3,4-diClPh | CH₂ | Single bond | Sub-25 |
| 2-1178 | Sub-56 | 3,4-diClPh | CH₂ | Single bond | Sub-26 |
| 2-1179 | Sub-56 | 3,4-diClPh | CH₂ | Single bond | Sub-27 |
| 2-1180 | Sub-56 | 3,4-diClPh | CH₂ | Single bond | Sub-28 |
| 2-1181 | Sub-56 | 3,4-diClPh | CH₂ | Single bond | Sub-29 |
| 2-1182 | Sub-56 | 3,4-diClPh | CH₂ | Single bond | Sub-30 |
| 2-1183 | Sub-56 | 3,4-diClPh | CH₂ | Single bond | Sub-31 |
| 2-1184 | Sub-56 | 3,4-diClPh | CH₂ | Single bond | Sub-32 |
| 2-1185 | Sub-56 | 3,4-diClPh | CH₂ | Single bond | Sub-65 |
| 2-1186 | Sub-56 | 3,4-diClPh | CH₂ | Single bond | Sub-66 |
| 2-1187 | Sub-56 | 3,4-diClPh | CH₂ | Single bond | Sub-67 |
| 2-1188 | Sub-56 | 3,4-diClPh | CH₂ | Single bond | Sub-68 |
| 2-1189 | Sub-56 | 3,4-diClPh | CH₂ | Single bond | Sub-69 |
| 2-1190 | Sub-56 | 3,4-diClPh | CH₂ | Single bond | Sub-70 |
| 2-1191 | Sub-56 | 3,4-diClPh | CH₂ | Single bond | Sub-71 |
| 2-1192 | Sub-56 | 3,4-diClPh | CH₂ | Single bond | Sub-72 |
| 2-1193 | Sub-56 | 3,4-diClPh | CH₂ | Single bond | Sub-73 |
| 2-1194 | Sub-56 | 3,4-diClPh | CH₂ | Single bond | Sub-74 |
| 2-1195 | Sub-56 | 3,4-diClPh | CH₂ | Single bond | Sub-75 |
| 2-1196 | Sub-56 | 3,4-diClPh | CH₂ | Single bond | Sub-76 |
| 2-1197 | Sub-56 | 3,4-diClPh | CH₂ | Single bond | Sub-77 |
| 2-1198 | Sub-56 | 3,4-diClPh | CH₂ | Single bond | Sub-78 |
| 2-1199 | Sub-56 | 3,4-diClPh | CH₂ | Single bond | Sub-79 |
| 2-1200 | Sub-56 | 3,4-diClPh | CH₂ | Single bond | Sub-80 |
| 2-1201 | Sub-57 | 3,4-diClPh | CH₂ | Single bond | Sub-1 |
| 2-1202 | Sub-57 | 3,4-diClPh | CH₂ | Single bond | Sub-2 |
| 2-1203 | Sub-57 | 3,4-diClPh | CH₂ | Single bond | Sub-3 |
| 2-1204 | Sub-57 | 3,4-diClPh | CH₂ | Single bond | Sub-4 |

TABLE 2-continued

| Cpd. No. | R¹ | R² | A | B | Z |
|---|---|---|---|---|---|
| 2-1205 | Sub-57 | 3,4-diClPh | CH$_2$ | Single bond | Sub-5 |
| 2-1206 | Sub-57 | 3,4-diClPh | CH$_2$ | Single bond | Sub-6 |
| 2-1207 | Sub-57 | 3,4-diClPh | CH$_2$ | Single bond | Sub-7 |
| 2-1208 | Sub-57 | 3,4-diClPh | CH$_2$ | Single bond | Sub-8 |
| 2-1209 | Sub-57 | 3,4-diClPh | CH$_2$ | Single bond | Sub-9 |
| 2-1210 | Sub-57 | 3,4-diClPh | CH$_2$ | Single bond | Sub-10 |
| 2-1211 | Sub-57 | 3,4-diClPh | CH$_2$ | Single bond | Sub-11 |
| 2-1212 | Sub-57 | 3,4-diClPh | CH$_2$ | Single bond | Sub-12 |
| 2-1213 | Sub-57 | 3,4-diClPh | CH$_2$ | Single bond | Sub-13 |
| 2-1214 | Sub-57 | 3,4-diClPh | CH$_2$ | Single bond | Sub-14 |
| 2-1215 | Sub-57 | 3,4-diClPh | CH$_2$ | Single bond | Sub-15 |
| 2-1216 | Sub-57 | 3,4-diClPh | CH$_2$ | Single bond | Sub-16 |
| 2-1217 | Sub-57 | 3,4-diClPh | CH$_2$ | Single bond | Sub-17 |
| 2-1218 | Sub-57 | 3,4-diClPh | CH$_2$ | Single bond | Sub-18 |
| 2-1219 | Sub-57 | 3,4-diClPh | CH$_2$ | Single bond | Sub-19 |
| 2-1220 | Sub-57 | 3,4-diClPh | CH$_2$ | Single bond | Sub-20 |
| 2-1221 | Sub-57 | 3,4-diClPh | CH$_2$ | Single bond | Sub-21 |
| 2-1222 | Sub-57 | 3,4-diClPh | CH$_2$ | Single bond | Sub-22 |
| 2-1223 | Sub-57 | 3,4-diClPh | CH$_2$ | Single bond | Sub-23 |
| 2-1224 | Sub-57 | 3,4-diClPh | CH$_2$ | Single bond | Sub-24 |
| 2-1225 | Sub-57 | 3,4-diClPh | CH$_2$ | Single bond | Sub-25 |
| 2-1226 | Sub-57 | 3,4-diClPh | CH$_2$ | Single bond | Sub-26 |
| 2-1227 | Sub-57 | 3,4-diClPh | CH$_2$ | Single bond | Sub-27 |
| 2-1228 | Sub-57 | 3,4-diClPh | CH$_2$ | Single bond | Sub-28 |
| 2-1229 | Sub-57 | 3,4-diClPh | CH$_2$ | Single bond | Sub-29 |
| 2-1230 | Sub-57 | 3,4-diClPh | CH$_2$ | Single bond | Sub-30 |
| 2-1231 | Sub-57 | 3,4-diClPh | CH$_2$ | Single bond | Sub-31 |
| 2-1232 | Sub-57 | 3,4-diClPh | CH$_2$ | Single bond | Sub-32 |
| 2-1233 | Sub-57 | 3,4-diClPh | CH$_2$ | Single bond | Sub-65 |
| 2-1234 | Sub-57 | 3,4-diClPh | CH$_2$ | Single bond | Sub-66 |
| 2-1235 | Sub-57 | 3,4-diClPh | CH$_2$ | Single bond | Sub-67 |
| 2-1236 | Sub-57 | 3,4-diClPh | CH$_2$ | Single bond | Sub-68 |
| 2-1237 | Sub-57 | 3,4-diClPh | CH$_2$ | Single bond | Sub-69 |
| 2-1238 | Sub-57 | 3,4-diClPh | CH$_2$ | Single bond | Sub-70 |
| 2-1239 | Sub-57 | 3,4-diClPh | CH$_2$ | Single bond | Sub-71 |
| 2-1240 | Sub-57 | 3,4-diClPh | CH$_2$ | Single bond | Sub-72 |
| 2-1241 | Sub-57 | 3,4-diClPh | CH$_2$ | Single bond | Sub-73 |
| 2-1242 | Sub-57 | 3,4-diClPh | CH$_2$ | Single bond | Sub-74 |
| 2-1243 | Sub-57 | 3,4-diClPh | CH$_2$ | Single bond | Sub-75 |
| 2-1244 | Sub-57 | 3,4-diClPh | CH$_2$ | Single bond | Sub-76 |
| 2-1245 | Sub-57 | 3,4-diClPh | CH$_2$ | Single bond | Sub-77 |
| 2-1246 | Sub-57 | 3,4-diClPh | CH$_2$ | Single bond | Sub-78 |
| 2-1247 | Sub-57 | 3,4-diClPh | CH$_2$ | Single bond | Sub-79 |
| 2-1248 | Sub-57 | 3,4-diClPh | CH$_2$ | Single bond | Sub-80 |
| 2-1249 | Sub-58 | 3,4-diClPh | CH$_2$ | Single bond | Sub-1 |
| 2-1250 | Sub-58 | 3,4-diClPh | CH$_2$ | Single bond | Sub-2 |
| 2-1251 | Sub-58 | 3,4-diClPh | CH$_2$ | Single bond | Sub-3 |
| 2-1252 | Sub-58 | 3,4-diClPh | CH$_2$ | Single bond | Sub-4 |
| 2-1253 | Sub-58 | 3,4-diClPh | CH$_2$ | Single bond | Sub-5 |
| 2-1254 | Sub-58 | 3,4-diClPh | CH$_2$ | Single bond | Sub-6 |
| 2-1255 | Sub-58 | 3,4-diClPh | CH$_2$ | Single bond | Sub-7 |
| 2-1256 | Sub-58 | 3,4-diClPh | CH$_2$ | Single bond | Sub-8 |
| 2-1257 | Sub-58 | 3,4-diClPh | CH$_2$ | Single bond | Sub-9 |
| 2-1258 | Sub-58 | 3,4-diClPh | CH$_2$ | Single bond | Sub-10 |
| 2-1259 | Sub-58 | 3,4-diClPh | CH$_2$ | Single bond | Sub-11 |
| 2-1260 | Sub-58 | 3,4-diClPh | CH$_2$ | Single bond | Sub-12 |
| 2-1261 | Sub-58 | 3,4-diClPh | CH$_2$ | Single bond | Sub-13 |
| 2-1262 | Sub-58 | 3,4-diClPh | CH$_2$ | Single bond | Sub-14 |
| 2-1263 | Sub-58 | 3,4-diClPh | CH$_2$ | Single bond | Sub-15 |
| 2-1264 | Sub-58 | 3,4-diClPh | CH$_2$ | Single bond | Sub-16 |
| 2-1265 | Sub-58 | 3,4-diClPh | CH$_2$ | Single bond | Sub-17 |
| 2-1266 | Sub-58 | 3,4-diClPh | CH$_2$ | Single bond | Sub-18 |
| 2-1267 | Sub-58 | 3,4-diClPh | CH$_2$ | Single bond | Sub-19 |
| 2-1268 | Sub-58 | 3,4-diClPh | CH$_2$ | Single bond | Sub-20 |
| 2-1269 | Sub-58 | 3,4-diClPh | CH$_2$ | Single bond | Sub-21 |
| 2-1270 | Sub-58 | 3,4-diClPh | CH$_2$ | Single bond | Sub-22 |
| 2-1271 | Sub-58 | 3,4-diClPh | CH$_2$ | Single bond | Sub-23 |
| 2-1272 | Sub-58 | 3,4-diClPh | CH$_2$ | Single bond | Sub-24 |
| 2-1273 | Sub-58 | 3,4-diClPh | CH$_2$ | Single bond | Sub-25 |
| 2-1274 | Sub-58 | 3,4-diClPh | CH$_2$ | Single bond | Sub-26 |
| 2-1275 | Sub-58 | 3,4-diClPh | CH$_2$ | Single bond | Sub-27 |
| 2-1276 | Sub-58 | 3,4-diClPh | CH$_2$ | Single bond | Sub-28 |
| 2-1277 | Sub-58 | 3,4-diClPh | CH$_2$ | Single bond | Sub-29 |
| 2-1278 | Sub-58 | 3,4-diClPh | CH$_2$ | Single bond | Sub-30 |
| 2-1279 | Sub-58 | 3,4-diClPh | CH$_2$ | Single bond | Sub-31 |
| 2-1280 | Sub-58 | 3,4-diClPh | CH$_2$ | Single bond | Sub-32 |
| 2-1281 | Sub-58 | 3,4-diClPh | CH$_2$ | Single bond | Sub-65 |
| 2-1282 | Sub-58 | 3,4-diClPh | CH$_2$ | Single bond | Sub-66 |
| 2-1283 | Sub-58 | 3,4-diClPh | CH$_2$ | Single bond | Sub-67 |
| 2-1284 | Sub-58 | 3,4-diClPh | CH$_2$ | Single bond | Sub-68 |
| 2-1285 | Sub-58 | 3,4-diClPh | CH$_2$ | Single bond | Sub-69 |
| 2-1286 | Sub-58 | 3,4-diClPh | CH$_2$ | Single bond | Sub-70 |
| 2-1287 | Sub-58 | 3,4-diClPh | CH$_2$ | Single bond | Sub-71 |
| 2-1288 | Sub-58 | 3,4-diClPh | CH$_2$ | Single bond | Sub-72 |
| 2-1289 | Sub-58 | 3,4-diClPh | CH$_2$ | Single bond | Sub-73 |
| 2-1290 | Sub-58 | 3,4-diClPh | CH$_2$ | Single bond | Sub-74 |
| 2-1291 | Sub-58 | 3,4-diClPh | CH$_2$ | Single bond | Sub-75 |
| 2-1292 | Sub-58 | 3,4-diClPh | CH$_2$ | Single bond | Sub-76 |
| 2-1293 | Sub-58 | 3,4-diClPh | CH$_2$ | Single bond | Sub-77 |
| 2-1294 | Sub-58 | 3,4-diClPh | CH$_2$ | Single bond | Sub-78 |
| 2-1295 | Sub-58 | 3,4-diClPh | CH$_2$ | Single bond | Sub-79 |
| 2-1296 | Sub-58 | 3,4-diClPh | CH$_2$ | Single bond | Sub-80 |
| 2-1297 | Sub-59 | 3,4-diClPh | CH$_2$ | Single bond | Sub-1 |
| 2-1298 | Sub-59 | 3,4-diClPh | CH$_2$ | Single bond | Sub-2 |
| 2-1299 | Sub-59 | 3,4-diClPh | CH$_2$ | Single bond | Sub-3 |
| 2-1300 | Sub-59 | 3,4-diClPh | CH$_2$ | Single bond | Sub-4 |
| 2-1301 | Sub-59 | 3,4-diClPh | CH$_2$ | Single bond | Sub-5 |
| 2-1302 | Sub-59 | 3,4-diClPh | CH$_2$ | Single bond | Sub-6 |
| 2-1303 | Sub-59 | 3,4-diClPh | CH$_2$ | Single bond | Sub-7 |
| 2-1304 | Sub-59 | 3,4-diClPh | CH$_2$ | Single bond | Sub-8 |
| 2-1305 | Sub-59 | 3,4-diClPh | CH$_2$ | Single bond | Sub-9 |
| 2-1306 | Sub-59 | 3,4-diClPh | CH$_2$ | Single bond | Sub-10 |
| 2-1307 | Sub-59 | 3,4-diClPh | CH$_2$ | Single bond | Sub-11 |
| 2-1308 | Sub-59 | 3,4-diClPh | CH$_2$ | Single bond | Sub-12 |
| 2-1309 | Sub-59 | 3,4-diClPh | CH$_2$ | Single bond | Sub-13 |
| 2-1310 | Sub-59 | 3,4-diClPh | CH$_2$ | Single bond | Sub-14 |
| 2-1311 | Sub-59 | 3,4-diClPh | CH$_2$ | Single bond | Sub-15 |
| 2-1312 | Sub-59 | 3,4-diClPh | CH$_2$ | Single bond | Sub-16 |
| 2-1313 | Sub-59 | 3,4-diClPh | CH$_2$ | Single bond | Sub-17 |
| 2-1314 | Sub-59 | 3,4-diClPh | CH$_2$ | Single bond | Sub-18 |
| 2-1315 | Sub-59 | 3,4-diClPh | CH$_2$ | Single bond | Sub-19 |
| 2-1316 | Sub-59 | 3,4-diClPh | CH$_2$ | Single bond | Sub-20 |
| 2-1317 | Sub-59 | 3,4-diClPh | CH$_2$ | Single bond | Sub-21 |
| 2-1318 | Sub-59 | 3,4-diClPh | CH$_2$ | Single bond | Sub-22 |
| 2-1319 | Sub-59 | 3,4-diClPh | CH$_2$ | Single bond | Sub-23 |
| 2-1320 | Sub-59 | 3,4-diClPh | CH$_2$ | Single bond | Sub-24 |
| 2-1321 | Sub-59 | 3,4-diClPh | CH$_2$ | Single bond | Sub-25 |
| 2-1322 | Sub-59 | 3,4-diClPh | CH$_2$ | Single bond | Sub-26 |
| 2-1323 | Sub-59 | 3,4-diClPh | CH$_2$ | Single bond | Sub-27 |
| 2-1324 | Sub-59 | 3,4-diClPh | CH$_2$ | Single bond | Sub-28 |
| 2-1325 | Sub-59 | 3,4-diClPh | CH$_2$ | Single bond | Sub-29 |
| 2-1326 | Sub-59 | 3,4-diClPh | CH$_2$ | Single bond | Sub-30 |
| 2-1327 | Sub-59 | 3,4-diClPh | CH$_2$ | Single bond | Sub-31 |
| 2-1328 | Sub-59 | 3,4-diClPh | CH$_2$ | Single bond | Sub-32 |
| 2-1329 | Sub-59 | 3,4-diClPh | CH$_2$ | Single bond | Sub-65 |
| 2-1330 | Sub-59 | 3,4-diClPh | CH$_2$ | Single bond | Sub-66 |
| 2-1331 | Sub-59 | 3,4-diClPh | CH$_2$ | Single bond | Sub-67 |
| 2-1332 | Sub-59 | 3,4-diClPh | CH$_2$ | Single bond | Sub-68 |
| 2-1333 | Sub-59 | 3,4-diClPh | CH$_2$ | Single bond | Sub-69 |
| 2-1334 | Sub-59 | 3,4-diClPh | CH$_2$ | Single bond | Sub-70 |
| 2-1335 | Sub-59 | 3,4-diClPh | CH$_2$ | Single bond | Sub-71 |
| 2-1336 | Sub-59 | 3,4-diClPh | CH$_2$ | Single bond | Sub-72 |
| 2-1337 | Sub-59 | 3,4-diClPh | CH$_2$ | Single bond | Sub-73 |
| 2-1338 | Sub-59 | 3,4-diClPh | CH$_2$ | Single bond | Sub-74 |
| 2-1339 | Sub-59 | 3,4-diClPh | CH$_2$ | Single bond | Sub-75 |
| 2-1340 | Sub-59 | 3,4-diClPh | CH$_2$ | Single bond | Sub-76 |
| 2-1341 | Sub-59 | 3,4-diClPh | CH$_2$ | Single bond | Sub-77 |
| 2-1342 | Sub-59 | 3,4-diClPh | CH$_2$ | Single bond | Sub-78 |
| 2-1343 | Sub-59 | 3,4-diClPh | CH$_2$ | Single bond | Sub-79 |
| 2-1344 | Sub-59 | 3,4-diClPh | CH$_2$ | Single bond | Sub-80 |
| 2-1345 | Sub-82 | 3,4-diClPh | CH$_2$ | Single bond | Sub-1 |
| 2-1346 | Sub-82 | 3,4-diClPh | CH$_2$ | Single bond | Sub-2 |
| 2-1347 | Sub-82 | 3,4-diClPh | CH$_2$ | Single bond | Sub-3 |
| 2-1348 | Sub-82 | 3,4-diClPh | CH$_2$ | Single bond | Sub-4 |
| 2-1349 | Sub-82 | 3,4-diClPh | CH$_2$ | Single bond | Sub-5 |
| 2-1350 | Sub-82 | 3,4-diClPh | CH$_2$ | Single bond | Sub-6 |
| 2-1351 | Sub-82 | 3,4-diClPh | CH$_2$ | Single bond | Sub-7 |
| 2-1352 | Sub-82 | 3,4-diClPh | CH$_2$ | Single bond | Sub-8 |
| 2-1353 | Sub-82 | 3,4-diClPh | CH$_2$ | Single bond | Sub-9 |
| 2-1354 | Sub-82 | 3,4-diClPh | CH$_2$ | Single bond | Sub-10 |
| 2-1355 | Sub-82 | 3,4-diClPh | CH$_2$ | Single bond | Sub-11 |
| 2-1356 | Sub-82 | 3,4-diClPh | CH$_2$ | Single bond | Sub-12 |
| 2-1357 | Sub-82 | 3,4-diClPh | CH$_2$ | Single bond | Sub-13 |
| 2-1358 | Sub-82 | 3,4-diClPh | CH$_2$ | Single bond | Sub-14 |

TABLE 2-continued

| Cpd. No. | R¹ | R² | A | B | Z |
|---|---|---|---|---|---|
| 2-1359 | Sub-82 | 3,4-diClPh | CH$_2$ | Single bond | Sub-15 |
| 2-1360 | Sub-82 | 3,4-diClPh | CH$_2$ | Single bond | Sub-16 |
| 2-1361 | Sub-82 | 3,4-diClPh | CH$_2$ | Single bond | Sub-17 |
| 2-1362 | Sub-82 | 3,4-diClPh | CH$_2$ | Single bond | Sub-18 |
| 2-1363 | Sub-82 | 3,4-diClPh | CH$_2$ | Single bond | Sub-19 |
| 2-1364 | Sub-82 | 3,4-diClPh | CH$_2$ | Single bond | Sub-20 |
| 2-1365 | Sub-82 | 3,4-diClPh | CH$_2$ | Single bond | Sub-21 |
| 2-1366 | Sub-82 | 3,4-diClPh | CH$_2$ | Single bond | Sub-22 |
| 2-1367 | Sub-82 | 3,4-diClPh | CH$_2$ | Single bond | Sub-23 |
| 2-1368 | Sub-82 | 3,4-diClPh | CH$_2$ | Single bond | Sub-24 |
| 2-1369 | Sub-82 | 3,4-diClPh | CH$_2$ | Single bond | Sub-25 |
| 2-1370 | Sub-82 | 3,4-diClPh | CH$_2$ | Single bond | Sub-26 |
| 2-1371 | Sub-82 | 3,4-diClPh | CH$_2$ | Single bond | Sub-27 |
| 2-1372 | Sub-82 | 3,4-diClPh | CH$_2$ | Single bond | Sub-28 |
| 2-1373 | Sub-82 | 3,4-diClPh | CH$_2$ | Single bond | Sub-29 |
| 2-1374 | Sub-82 | 3,4-diClPh | CH$_2$ | Single bond | Sub-30 |
| 2-1375 | Sub-82 | 3,4-diClPh | CH$_2$ | Single bond | Sub-31 |
| 2-1376 | Sub-82 | 3,4-diClPh | CH$_2$ | Single bond | Sub-32 |
| 2-1377 | Sub-82 | 3,4-diClPh | CH$_2$ | Single bond | Sub-65 |
| 2-1378 | Sub-82 | 3,4-diClPh | CH$_2$ | Single bond | Sub-66 |
| 2-1379 | Sub-82 | 3,4-diClPh | CH$_2$ | Single bond | Sub-67 |
| 2-1380 | Sub-82 | 3,4-diClPh | CH$_2$ | Single bond | Sub-68 |
| 2-1381 | Sub-82 | 3,4-diClPh | CH$_2$ | Single bond | Sub-69 |
| 2-1382 | Sub-82 | 3,4-diClPh | CH$_2$ | Single bond | Sub-70 |
| 2-1383 | Sub-82 | 3,4-diClPh | CH$_2$ | Single bond | Sub-71 |
| 2-1384 | Sub-82 | 3,4-diClPh | CH$_2$ | Single bond | Sub-72 |
| 2-1385 | Sub-82 | 3,4-diClPh | CH$_2$ | Single bond | Sub-73 |
| 2-1386 | Sub-82 | 3,4-diClPh | CH$_2$ | Single bond | Sub-74 |
| 2-1387 | Sub-82 | 3,4-diClPh | CH$_2$ | Single bond | Sub-75 |
| 2-1388 | Sub-82 | 3,4-diClPh | CH$_2$ | Single bond | Sub-76 |
| 2-1389 | Sub-82 | 3,4-diClPh | CH$_2$ | Single bond | Sub-77 |
| 2-1390 | Sub-82 | 3,4-diClPh | CH$_2$ | Single bond | Sub-78 |
| 2-1391 | Sub-82 | 3,4-diClPh | CH$_2$ | Single bond | Sub-79 |
| 2-1392 | Sub-82 | 3,4-diClPh | CH$_2$ | Single bond | Sub-80 |
| 2-1393 | Sub-83 | 3,4-diClPh | CH$_2$ | Single bond | Sub-1 |
| 2-1394 | Sub-83 | 3,4-diClPh | CH$_2$ | Single bond | Sub-2 |
| 2-1395 | Sub-83 | 3,4-diClPh | CH$_2$ | Single bond | Sub-3 |
| 2-1396 | Sub-83 | 3,4-diClPh | CH$_2$ | Single bond | Sub-4 |
| 2-1397 | Sub-83 | 3,4-diClPh | CH$_2$ | Single bond | Sub-5 |
| 2-1398 | Sub-83 | 3,4-diClPh | CH$_2$ | Single bond | Sub-6 |
| 2-1399 | Sub-83 | 3,4-diClPh | CH$_2$ | Single bond | Sub-7 |
| 2-1400 | Sub-83 | 3,4-diClPh | CH$_2$ | Single bond | Sub-8 |
| 2-1401 | Sub-83 | 3,4-diClPh | CH$_2$ | Single bond | Sub-9 |
| 2-1402 | Sub-83 | 3,4-diClPh | CH$_2$ | Single bond | Sub-10 |
| 2-1403 | Sub-83 | 3,4-diClPh | CH$_2$ | Single bond | Sub-11 |
| 2-1404 | Sub-83 | 3,4-diClPh | CH$_2$ | Single bond | Sub-12 |
| 2-1405 | Sub-83 | 3,4-diClPh | CH$_2$ | Single bond | Sub-13 |
| 2-1406 | Sub-83 | 3,4-diClPh | CH$_2$ | Single bond | Sub-14 |
| 2-1407 | Sub-83 | 3,4-diClPh | CH$_2$ | Single bond | Sub-15 |
| 2-1408 | Sub-83 | 3,4-diClPh | CH$_2$ | Single bond | Sub-16 |
| 2-1409 | Sub-83 | 3,4-diClPh | CH$_2$ | Single bond | Sub-17 |
| 2-1410 | Sub-83 | 3,4-diClPh | CH$_2$ | Single bond | Sub-18 |
| 2-1411 | Sub-83 | 3,4-diClPh | CH$_2$ | Single bond | Sub-19 |
| 2-1412 | Sub-83 | 3,4-diClPh | CH$_2$ | Single bond | Sub-20 |
| 2-1413 | Sub-83 | 3,4-diClPh | CH$_2$ | Single bond | Sub-21 |
| 2-1414 | Sub-83 | 3,4-diClPh | CH$_2$ | Single bond | Sub-22 |
| 2-1415 | Sub-83 | 3,4-diClPh | CH$_2$ | Single bond | Sub-23 |
| 2-1416 | Sub-83 | 3,4-diClPh | CH$_2$ | Single bond | Sub-24 |
| 2-1417 | Sub-83 | 3,4-diClPh | CH$_2$ | Single bond | Sub-25 |
| 2-1418 | Sub-83 | 3,4-diClPh | CH$_2$ | Single bond | Sub-26 |
| 2-1419 | Sub-83 | 3,4-diClPh | CH$_2$ | Single bond | Sub-27 |
| 2-1420 | Sub-83 | 3,4-diClPh | CH$_2$ | Single bond | Sub-28 |
| 2-1421 | Sub-83 | 3,4-diClPh | CH$_2$ | Single bond | Sub-29 |
| 2-1422 | Sub-83 | 3,4-diClPh | CH$_2$ | Single bond | Sub-30 |
| 2-1423 | Sub-83 | 3,4-diClPh | CH$_2$ | Single bond | Sub-31 |
| 2-1424 | Sub-83 | 3,4-diClPh | CH$_2$ | Single bond | Sub-32 |
| 2-1425 | Sub-83 | 3,4-diClPh | CH$_2$ | Single bond | Sub-65 |
| 2-1426 | Sub-83 | 3,4-diClPh | CH$_2$ | Single bond | Sub-66 |
| 2-1427 | Sub-83 | 3,4-diClPh | CH$_2$ | Single bond | Sub-67 |
| 2-1428 | Sub-83 | 3,4-diClPh | CH$_2$ | Single bond | Sub-68 |
| 2-1429 | Sub-83 | 3,4-diClPh | CH$_2$ | Single bond | Sub-69 |
| 2-1430 | Sub-83 | 3,4-diClPh | CH$_2$ | Single bond | Sub-70 |
| 2-1431 | Sub-83 | 3,4-diClPh | CH$_2$ | Single bond | Sub-71 |
| 2-1432 | Sub-83 | 3,4-diClPh | CH$_2$ | Single bond | Sub-72 |
| 2-1433 | Sub-83 | 3,4-diClPh | CH$_2$ | Single bond | Sub-73 |
| 2-1434 | Sub-83 | 3,4-diClPh | CH$_2$ | Single bond | Sub-74 |
| 2-1435 | Sub-83 | 3,4-diClPh | CH$_2$ | Single bond | Sub-75 |
| 2-1436 | Sub-83 | 3,4-diClPh | CH$_2$ | Single bond | Sub-76 |
| 2-1437 | Sub-83 | 3,4-diClPh | CH$_2$ | Single bond | Sub-77 |
| 2-1438 | Sub-83 | 3,4-diClPh | CH$_2$ | Single bond | Sub-78 |
| 2-1439 | Sub-83 | 3,4-diClPh | CH$_2$ | Single bond | Sub-79 |
| 2-1440 | Sub-83 | 3,4-diClPh | CH$_2$ | Single bond | Sub-80 |
| 2-1441 | Sub-61 | 3,4-diClPh | CH$_2$ | Single bond | Sub-1 |
| 2-1442 | Sub-61 | 3,4-diClPh | CH$_2$ | Single bond | Sub-2 |
| 2-1443 | Sub-61 | 3,4-diClPh | CH$_2$ | Single bond | Sub-3 |
| 2-1444 | Sub-61 | 3,4-diClPh | CH$_2$ | Single bond | Sub-4 |
| 2-1445 | Sub-61 | 3,4-diClPh | CH$_2$ | Single bond | Sub-5 |
| 2-1446 | Sub-61 | 3,4-diClPh | CH$_2$ | Single bond | Sub-6 |
| 2-1447 | Sub-61 | 3,4-diClPh | CH$_2$ | Single bond | Sub-7 |
| 2-1448 | Sub-61 | 3,4-diClPh | CH$_2$ | Single bond | Sub-8 |
| 2-1449 | Sub-61 | 3,4-diClPh | CH$_2$ | Single bond | Sub-9 |
| 2-1450 | Sub-61 | 3,4-diClPh | CH$_2$ | Single bond | Sub-10 |
| 2-1451 | Sub-61 | 3,4-diClPh | CH$_2$ | Single bond | Sub-11 |
| 2-1452 | Sub-61 | 3,4-diClPh | CH$_2$ | Single bond | Sub-12 |
| 2-1453 | Sub-61 | 3,4-diClPh | CH$_2$ | Single bond | Sub-13 |
| 2-1454 | Sub-61 | 3,4-diClPh | CH$_2$ | Single bond | Sub-14 |
| 2-1455 | Sub-61 | 3,4-diClPh | CH$_2$ | Single bond | Sub-15 |
| 2-1456 | Sub-61 | 3,4-diClPh | CH$_2$ | Single bond | Sub-16 |
| 2-1457 | Sub-61 | 3,4-diClPh | CH$_2$ | Single bond | Sub-17 |
| 2-1458 | Sub-61 | 3,4-diClPh | CH$_2$ | Single bond | Sub-18 |
| 2-1459 | Sub-61 | 3,4-diClPh | CH$_2$ | Single bond | Sub-19 |
| 2-1460 | Sub-61 | 3,4-diClPh | CH$_2$ | Single bond | Sub-20 |
| 2-1461 | Sub-61 | 3,4-diClPh | CH$_2$ | Single bond | Sub-21 |
| 2-1462 | Sub-61 | 3,4-diClPh | CH$_2$ | Single bond | Sub-22 |
| 2-1463 | Sub-61 | 3,4-diClPh | CH$_2$ | Single bond | Sub-23 |
| 2-1464 | Sub-61 | 3,4-diClPh | CH$_2$ | Single bond | Sub-24 |
| 2-1465 | Sub-61 | 3,4-diClPh | CH$_2$ | Single bond | Sub-25 |
| 2-1466 | Sub-61 | 3,4-diClPh | CH$_2$ | Single bond | Sub-26 |
| 2-1467 | Sub-61 | 3,4-diClPh | CH$_2$ | Single bond | Sub-27 |
| 2-1468 | Sub-61 | 3,4-diClPh | CH$_2$ | Single bond | Sub-28 |
| 2-1469 | Sub-61 | 3,4-diClPh | CH$_2$ | Single bond | Sub-29 |
| 2-1470 | Sub-61 | 3,4-diClPh | CH$_2$ | Single bond | Sub-30 |
| 2-1471 | Sub-61 | 3,4-diClPh | CH$_2$ | Single bond | Sub-31 |
| 2-1472 | Sub-61 | 3,4-diClPh | CH$_2$ | Single bond | Sub-32 |
| 2-1473 | Sub-61 | 3,4-diClPh | CH$_2$ | Single bond | Sub-65 |
| 2-1474 | Sub-61 | 3,4-diClPh | CH$_2$ | Single bond | Sub-66 |
| 2-1475 | Sub-61 | 3,4-diClPh | CH$_2$ | Single bond | Sub-67 |
| 2-1476 | Sub-61 | 3,4-diClPh | CH$_2$ | Single bond | Sub-68 |
| 2-1477 | Sub-61 | 3,4-diClPh | CH$_2$ | Single bond | Sub-69 |
| 2-1478 | Sub-61 | 3,4-diClPh | CH$_2$ | Single bond | Sub-70 |
| 2-1479 | Sub-61 | 3,4-diClPh | CH$_2$ | Single bond | Sub-71 |
| 2-1480 | Sub-61 | 3,4-diClPh | CH$_2$ | Single bond | Sub-72 |
| 2-1481 | Sub-61 | 3,4-diClPh | CH$_2$ | Single bond | Sub-73 |
| 2-1482 | Sub-61 | 3,4-diClPh | CH$_2$ | Single bond | Sub-74 |
| 2-1483 | Sub-61 | 3,4-diClPh | CH$_2$ | Single bond | Sub-75 |
| 2-1484 | Sub-61 | 3,4-diClPh | CH$_2$ | Single bond | Sub-76 |
| 2-1485 | Sub-61 | 3,4-diClPh | CH$_2$ | Single bond | Sub-77 |
| 2-1486 | Sub-61 | 3,4-diClPh | CH$_2$ | Single bond | Sub-78 |
| 2-1487 | Sub-61 | 3,4-diClPh | CH$_2$ | Single bond | Sub-79 |
| 2-1488 | Sub-61 | 3,4-diClPh | CH$_2$ | Single bond | Sub-80 |
| 2-1489 | Sub-60 | 3,4-diClPh | CH$_2$ | Single bond | Sub-1 |
| 2-1490 | Sub-60 | 3,4-diClPh | CH$_2$ | Single bond | Sub-2 |
| 2-1491 | Sub-60 | 3,4-diClPh | CH$_2$ | Single bond | Sub-3 |
| 2-1492 | Sub-60 | 3,4-diClPh | CH$_2$ | Single bond | Sub-4 |
| 2-1493 | Sub-60 | 3,4-diClPh | CH$_2$ | Single bond | Sub-5 |
| 2-1494 | Sub-60 | 3,4-diClPh | CH$_2$ | Single bond | Sub-6 |
| 2-1495 | Sub-60 | 3,4-diClPh | CH$_2$ | Single bond | Sub-7 |
| 2-1496 | Sub-60 | 3,4-diClPh | CH$_2$ | Single bond | Sub-8 |
| 2-1497 | Sub-60 | 3,4-diClPh | CH$_2$ | Single bond | Sub-9 |
| 2-1498 | Sub-60 | 3,4-diClPh | CH$_2$ | Single bond | Sub-10 |
| 2-1499 | Sub-60 | 3,4-diClPh | CH$_2$ | Single bond | Sub-11 |
| 2-1500 | Sub-60 | 3,4-diClPh | CH$_2$ | Single bond | Sub-12 |
| 2-1501 | Sub-60 | 3,4-diClPh | CH$_2$ | Single bond | Sub-13 |
| 2-1502 | Sub-60 | 3,4-diClPh | CH$_2$ | Single bond | Sub-14 |
| 2-1503 | Sub-60 | 3,4-diClPh | CH$_2$ | Single bond | Sub-15 |
| 2-1504 | Sub-60 | 3,4-diClPh | CH$_2$ | Single bond | Sub-16 |
| 2-1505 | Sub-60 | 3,4-diClPh | CH$_2$ | Single bond | Sub-17 |
| 2-1506 | Sub-60 | 3,4-diClPh | CH$_2$ | Single bond | Sub-18 |
| 2-1507 | Sub-60 | 3,4-diClPh | CH$_2$ | Single bond | Sub-19 |
| 2-1508 | Sub-60 | 3,4-diClPh | CH$_2$ | Single bond | Sub-20 |
| 2-1509 | Sub-60 | 3,4-diClPh | CH$_2$ | Single bond | Sub-21 |
| 2-1510 | Sub-60 | 3,4-diClPh | CH$_2$ | Single bond | Sub-22 |
| 2-1511 | Sub-60 | 3,4-diClPh | CH$_2$ | Single bond | Sub-23 |
| 2-1512 | Sub-60 | 3,4-diClPh | CH$_2$ | Single bond | Sub-24 |

TABLE 2-continued

| Cpd. No. | R¹ | R² | A | B | Z |
|---|---|---|---|---|---|
| 2-1513 | Sub-60 | 3,4-diClPh | CH₂ | Single bond | Sub-25 |
| 2-1514 | Sub-60 | 3,4-diClPh | CH₂ | Single bond | Sub-26 |
| 2-1515 | Sub-60 | 3,4-diClPh | CH₂ | Single bond | Sub-27 |
| 2-1516 | Sub-60 | 3,4-diClPh | CH₂ | Single bond | Sub-28 |
| 2-1517 | Sub-60 | 3,4-diClPh | CH₂ | Single bond | Sub-29 |
| 2-1518 | Sub-60 | 3,4-diClPh | CH₂ | Single bond | Sub-30 |
| 2-1519 | Sub-60 | 3,4-diClPh | CH₂ | Single bond | Sub-31 |
| 2-1520 | Sub-60 | 3,4-diClPh | CH₂ | Single bond | Sub-32 |
| 2-1521 | Sub-60 | 3,4-diClPh | CH₂ | Single bond | Sub-65 |
| 2-1522 | Sub-60 | 3,4-diClPh | CH₂ | Single bond | Sub-66 |
| 2-1523 | Sub-60 | 3,4-diClPh | CH₂ | Single bond | Sub-67 |
| 2-1524 | Sub-60 | 3,4-diClPh | CH₂ | Single bond | Sub-68 |
| 2-1525 | Sub-60 | 3,4-diClPh | CH₂ | Single bond | Sub-69 |
| 2-1526 | Sub-60 | 3,4-diClPh | CH₂ | Single bond | Sub-70 |
| 2-1527 | Sub-60 | 3,4-diClPh | CH₂ | Single bond | Sub-71 |
| 2-1528 | Sub-60 | 3,4-diClPh | CH₂ | Single bond | Sub-72 |
| 2-1529 | Sub-60 | 3,4-diClPh | CH₂ | Single bond | Sub-73 |
| 2-1530 | Sub-60 | 3,4-diClPh | CH₂ | Single bond | Sub-74 |
| 2-1531 | Sub-60 | 3,4-diClPh | CH₂ | Single bond | Sub-75 |
| 2-1532 | Sub-60 | 3,4-diClPh | CH₂ | Single bond | Sub-76 |
| 2-1533 | Sub-60 | 3,4-diClPh | CH₂ | Single bond | Sub-77 |
| 2-1534 | Sub-60 | 3,4-diClPh | CH₂ | Single bond | Sub-78 |
| 2-1535 | Sub-60 | 3,4-diClPh | CH₂ | Single bond | Sub-79 |
| 2-1536 | Sub-60 | 3,4-diClPh | CH₂ | Single bond | Sub-80 |
| 2-1537 | Sub-33 | 3,4-diClPh | CO | Single bond or CH₂ | Sub-1 |
| 2-1538 | Sub-33 | 3,4-diClPh | CO | Single bond or CH₂ | Sub-2 |
| 2-1539 | Sub-33 | 3,4-diClPh | CO | Single bond or CH₂ | Sub-3 |
| 2-1540 | Sub-33 | 3,4-diClPh | CO | Single bond or CH₂ | Sub-4 |
| 2-1541 | Sub-33 | 3,4-diClPh | CO | Single bond or CH₂ | Sub-5 |
| 2-1542 | Sub-33 | 3,4-diClPh | CO | Single bond or CH₂ | Sub-6 |
| 2-1543 | Sub-33 | 3,4-diClPh | CO | Single bond or CH₂ | Sub-7 |
| 2-1544 | Sub-33 | 3,4-diClPh | CO | Single bond or CH₂ | Sub-8 |
| 2-1545 | Sub-33 | 3,4-diClPh | CO | Single bond or CH₂ | Sub-9 |
| 2-1546 | Sub-33 | 3,4-diClPh | CO | Single bond or CH₂ | Sub-10 |
| 2-1547 | Sub-33 | 3,4-diClPh | CO | Single bond or CH₂ | Sub-11 |
| 2-1548 | Sub-33 | 3,4-diClPh | CO | Single bond or CH₂ | Sub-12 |
| 2-1549 | Sub-33 | 3,4-diClPh | CO | Single bond or CH₂ | Sub-13 |
| 2-1550 | Sub-33 | 3,4-diClPh | CO | Single bond or CH₂ | Sub-14 |
| 2-1551 | Sub-33 | 3,4-diClPh | CO | Single bond or CH₂ | Sub-15 |
| 2-1552 | Sub-33 | 3,4-diClPh | CO | Single bond or CH₂ | Sub-16 |
| 2-1553 | Sub-33 | 3,4-diClPh | CO | Single bond or CH₂ | Sub-17 |
| 2-1554 | Sub-33 | 3,4-diClPh | CO | Single bond or CH₂ | Sub-18 |
| 2-1555 | Sub-33 | 3,4-diClPh | CO | Single bond or CH₂ | Sub-19 |
| 2-1556 | Sub-33 | 3,4-diClPh | CO | Single bond or CH₂ | Sub-20 |
| 2-1557 | Sub-33 | 3,4-diClPh | CO | Single bond or CH₂ | Sub-21 |
| 2-1558 | Sub-33 | 3,4-diClPh | CO | Single bond or CH₂ | Sub-22 |
| 2-1559 | Sub-33 | 3,4-diClPh | CO | Single bond or CH₂ | Sub-23 |
| 2-1560 | Sub-33 | 3,4-diClPh | CO | Single bond or CH₂ | Sub-24 |
| 2-1561 | Sub-33 | 3,4-diClPh | CO | Single bond or CH₂ | Sub-25 |
| 2-1562 | Sub-33 | 3,4-diClPh | CO | Single bond or CH₂ | Sub-26 |
| 2-1563 | Sub-33 | 3,4-diClPh | CO | Single bond or CH₂ | Sub-27 |
| 2-1564 | Sub-33 | 3,4-diClPh | CO | Single bond or CH₂ | Sub-28 |
| 2-1565 | Sub-33 | 3,4-diClPh | CO | Single bond or CH₂ | Sub-29 |
| 2-1566 | Sub-33 | 3,4-diClPh | CO | Single bond or CH₂ | Sub-30 |
| 2-1567 | Sub-33 | 3,4-diClPh | CO | Single bond or CH₂ | Sub-31 |
| 2-1568 | Sub-33 | 3,4-diClPh | CO | Single bond or CH₂ | Sub-32 |
| 2-1569 | Sub-33 | 3,4-diClPh | CO | Single bond or CH₂ | Sub-65 |
| 2-1570 | Sub-33 | 3,4-diClPh | CO | Single bond or CH₂ | Sub-66 |
| 2-1571 | Sub-33 | 3,4-diClPh | CO | Single bond or CH₂ | Sub-67 |
| 2-1572 | Sub-33 | 3,4-diClPh | CO | Single bond or CH₂ | Sub-68 |
| 2-1573 | Sub-33 | 3,4-diClPh | CO | Single bond or CH₂ | Sub-69 |
| 2-1574 | Sub-33 | 3,4-diClPh | CO | Single bond or CH₂ | Sub-70 |
| 2-1575 | Sub-33 | 3,4-diClPh | CO | Single bond or CH₂ | Sub-71 |
| 2-1576 | Sub-33 | 3,4-diClPh | CO | Single bond or CH₂ | Sub-72 |
| 2-1577 | Sub-33 | 3,4-diClPh | CO | Single bond or CH₂ | Sub-73 |
| 2-1578 | Sub-33 | 3,4-diClPh | CO | Single bond or CH₂ | Sub-74 |
| 2-1579 | Sub-33 | 3,4-diClPh | CO | Single bond or CH₂ | Sub-75 |
| 2-1580 | Sub-33 | 3,4-diClPh | CO | Single bond or CH₂ | Sub-76 |
| 2-1581 | Sub-33 | 3,4-diClPh | CO | Single bond or CH₂ | Sub-77 |
| 2-1582 | Sub-33 | 3,4-diClPh | CO | Single bond or CH₂ | Sub-78 |
| 2-1583 | Sub-33 | 3,4-diClPh | CO | Single bond or CH₂ | Sub-79 |
| 2-1584 | Sub-33 | 3,4-diClPh | CO | Single bond or CH₂ | Sub-80 |
| 2-1585 | Sub-34 | 3,4-diClPh | CO | Single bond or CH₂ | Sub-1 |
| 2-1586 | Sub-34 | 3,4-diClPh | CO | Single bond or CH₂ | Sub-2 |
| 2-1587 | Sub-34 | 3,4-diClPh | CO | Single bond or CH₂ | Sub-3 |
| 2-1588 | Sub-34 | 3,4-diClPh | CO | Single bond or CH₂ | Sub-4 |
| 2-1589 | Sub-34 | 3,4-diClPh | CO | Single bond or CH₂ | Sub-5 |
| 2-1590 | Sub-34 | 3,4-diClPh | CO | Single bond or CH₂ | Sub-6 |
| 2-1591 | Sub-34 | 3,4-diClPh | CO | Single bond or CH₂ | Sub-7 |
| 2-1592 | Sub-34 | 3,4-diClPh | CO | Single bond or CH₂ | Sub-8 |
| 2-1593 | Sub-34 | 3,4-diClPh | CO | Single bond or CH₂ | Sub-9 |
| 2-1594 | Sub-34 | 3,4-diClPh | CO | Single bond or CH₂ | Sub-10 |
| 2-1595 | Sub-34 | 3,4-diClPh | CO | Single bond or CH₂ | Sub-11 |
| 2-1596 | Sub-34 | 3,4-diClPh | CO | Single bond or CH₂ | Sub-12 |
| 2-1597 | Sub-34 | 3,4-diClPh | CO | Single bond or CH₂ | Sub-13 |
| 2-1598 | Sub-34 | 3,4-diClPh | CO | Single bond or CH₂ | Sub-14 |
| 2-1599 | Sub-34 | 3,4-diClPh | CO | Single bond or CH₂ | Sub-15 |
| 2-1600 | Sub-34 | 3,4-diClPh | CO | Single bond or CH₂ | Sub-16 |
| 2-1601 | Sub-34 | 3,4-diClPh | CO | Single bond or CH₂ | Sub-17 |
| 2-1602 | Sub-34 | 3,4-diClPh | CO | Single bond or CH₂ | Sub-18 |
| 2-1603 | Sub-34 | 3,4-diClPh | CO | Single bond or CH₂ | Sub-19 |
| 2-1604 | Sub-34 | 3,4-diClPh | CO | Single bond or CH₂ | Sub-20 |
| 2-1605 | Sub-34 | 3,4-diClPh | CO | Single bond or CH₂ | Sub-21 |
| 2-1606 | Sub-34 | 3,4-diClPh | CO | Single bond or CH₂ | Sub-22 |
| 2-1607 | Sub-34 | 3,4-diClPh | CO | Single bond or CH₂ | Sub-23 |
| 2-1608 | Sub-34 | 3,4-diClPh | CO | Single bond or CH₂ | Sub-24 |
| 2-1609 | Sub-34 | 3,4-diClPh | CO | Single bond or CH₂ | Sub-25 |
| 2-1610 | Sub-34 | 3,4-diClPh | CO | Single bond or CH₂ | Sub-26 |
| 2-1611 | Sub-34 | 3,4-diClPh | CO | Single bond or CH₂ | Sub-27 |
| 2-1612 | Sub-34 | 3,4-diClPh | CO | Single bond or CH₂ | Sub-28 |
| 2-1613 | Sub-34 | 3,4-diClPh | CO | Single bond or CH₂ | Sub-29 |
| 2-1614 | Sub-34 | 3,4-diClPh | CO | Single bond or CH₂ | Sub-30 |
| 2-1615 | Sub-34 | 3,4-diClPh | CO | Single bond or CH₂ | Sub-31 |
| 2-1616 | Sub-34 | 3,4-diClPh | CO | Single bond or CH₂ | Sub-32 |
| 2-1617 | Sub-34 | 3,4-diClPh | CO | Single bond or CH₂ | Sub-65 |
| 2-1618 | Sub-34 | 3,4-diClPh | CO | Single bond or CH₂ | Sub-66 |
| 2-1619 | Sub-34 | 3,4-diClPh | CO | Single bond or CH₂ | Sub-67 |
| 2-1620 | Sub-34 | 3,4-diClPh | CO | Single bond or CH₂ | Sub-68 |
| 2-1621 | Sub-34 | 3,4-diClPh | CO | Single bond or CH₂ | Sub-69 |
| 2-1622 | Sub-34 | 3,4-diClPh | CO | Single bond or CH₂ | Sub-70 |
| 2-1623 | Sub-34 | 3,4-diClPh | CO | Single bond or CH₂ | Sub-71 |
| 2-1624 | Sub-34 | 3,4-diClPh | CO | Single bond or CH₂ | Sub-72 |
| 2-1625 | Sub-34 | 3,4-diClPh | CO | Single bond or CH₂ | Sub-73 |
| 2-1626 | Sub-34 | 3,4-diClPh | CO | Single bond or CH₂ | Sub-74 |
| 2-1627 | Sub-34 | 3,4-diClPh | CO | Single bond or CH₂ | Sub-75 |
| 2-1628 | Sub-34 | 3,4-diClPh | CO | Single bond or CH₂ | Sub-76 |
| 2-1629 | Sub-34 | 3,4-diClPh | CO | Single bond or CH₂ | Sub-77 |
| 2-1630 | Sub-34 | 3,4-diClPh | CO | Single bond or CH₂ | Sub-78 |
| 2-1631 | Sub-34 | 3,4-diClPh | CO | Single bond or CH₂ | Sub-79 |
| 2-1632 | Sub-34 | 3,4-diClPh | CO | Single bond or CH₂ | Sub-80 |
| 2-1633 | Sub-35 | 3,4-diClPh | CO | Single bond or CH₂ | Sub-1 |
| 2-1634 | Sub-35 | 3,4-diClPh | CO | Single bond or CH₂ | Sub-2 |
| 2-1635 | Sub-35 | 3,4-diClPh | CO | Single bond or CH₂ | Sub-3 |
| 2-1636 | Sub-35 | 3,4-diClPh | CO | Single bond or CH₂ | Sub-4 |
| 2-1637 | Sub-35 | 3,4-diClPh | CO | Single bond or CH₂ | Sub-5 |
| 2-1638 | Sub-35 | 3,4-diClPh | CO | Single bond or CH₂ | Sub-6 |
| 2-1639 | Sub-35 | 3,4-diClPh | CO | Single bond or CH₂ | Sub-7 |
| 2-1640 | Sub-35 | 3,4-diClPh | CO | Single bond or CH₂ | Sub-8 |
| 2-1641 | Sub-35 | 3,4-diClPh | CO | Single bond or CH₂ | Sub-9 |
| 2-1642 | Sub-35 | 3,4-diClPh | CO | Single bond or CH₂ | Sub-10 |
| 2-1643 | Sub-35 | 3,4-diClPh | CO | Single bond or CH₂ | Sub-11 |
| 2-1644 | Sub-35 | 3,4-diClPh | CO | Single bond or CH₂ | Sub-12 |
| 2-1645 | Sub-35 | 3,4-diClPh | CO | Single bond or CH₂ | Sub-13 |
| 2-1646 | Sub-35 | 3,4-diClPh | CO | Single bond or CH₂ | Sub-14 |
| 2-1647 | Sub-35 | 3,4-diClPh | CO | Single bond or CH₂ | Sub-15 |
| 2-1648 | Sub-35 | 3,4-diClPh | CO | Single bond or CH₂ | Sub-16 |
| 2-1649 | Sub-35 | 3,4-diClPh | CO | Single bond or CH₂ | Sub-17 |
| 2-1650 | Sub-35 | 3,4-diClPh | CO | Single bond or CH₂ | Sub-18 |
| 2-1651 | Sub-35 | 3,4-diClPh | CO | Single bond or CH₂ | Sub-19 |
| 2-1652 | Sub-35 | 3,4-diClPh | CO | Single bond or CH₂ | Sub-20 |
| 2-1653 | Sub-35 | 3,4-diClPh | CO | Single bond or CH₂ | Sub-21 |
| 2-1654 | Sub-35 | 3,4-diClPh | CO | Single bond or CH₂ | Sub-22 |
| 2-1655 | Sub-35 | 3,4-diClPh | CO | Single bond or CH₂ | Sub-23 |
| 2-1656 | Sub-35 | 3,4-diClPh | CO | Single bond or CH₂ | Sub-24 |
| 2-1657 | Sub-35 | 3,4-diClPh | CO | Single bond or CH₂ | Sub-25 |
| 2-1658 | Sub-35 | 3,4-diClPh | CO | Single bond or CH₂ | Sub-26 |
| 2-1659 | Sub-35 | 3,4-diClPh | CO | Single bond or CH₂ | Sub-27 |
| 2-1660 | Sub-35 | 3,4-diClPh | CO | Single bond or CH₂ | Sub-28 |
| 2-1661 | Sub-35 | 3,4-diClPh | CO | Single bond or CH₂ | Sub-29 |
| 2-1662 | Sub-35 | 3,4-diClPh | CO | Single bond or CH₂ | Sub-30 |
| 2-1663 | Sub-35 | 3,4-diClPh | CO | Single bond or CH₂ | Sub-31 |
| 2-1664 | Sub-35 | 3,4-diClPh | CO | Single bond or CH₂ | Sub-32 |
| 2-1665 | Sub-35 | 3,4-diClPh | CO | Single bond or CH₂ | Sub-65 |
| 2-1666 | Sub-35 | 3,4-diClPh | CO | Single bond or CH₂ | Sub-66 |

TABLE 2-continued

| Cpd. No. | R¹ | R² | A | B | Z |
|---|---|---|---|---|---|
| 2-1667 | Sub-35 | 3,4-diClPh | CO | Single bond or CH₂ | Sub-67 |
| 2-1668 | Sub-35 | 3,4-diClPh | CO | Single bond or CH₂ | Sub-68 |
| 2-1669 | Sub-35 | 3,4-diClPh | CO | Single bond or CH₂ | Sub-69 |
| 2-1670 | Sub-35 | 3,4-diClPh | CO | Single bond or CH₂ | Sub-70 |
| 2-1671 | Sub-35 | 3,4-diClPh | CO | Single bond or CH₂ | Sub-71 |
| 2-1672 | Sub-35 | 3,4-diClPh | CO | Single bond or CH₂ | Sub-72 |
| 2-1673 | Sub-35 | 3,4-diClPh | CO | Single bond or CH₂ | Sub-73 |
| 2-1674 | Sub-35 | 3,4-diClPh | CO | Single bond or CH₂ | Sub-74 |
| 2-1675 | Sub-35 | 3,4-diClPh | CO | Single bond or CH₂ | Sub-75 |
| 2-1676 | Sub-35 | 3,4-diClPh | CO | Single bond or CH₂ | Sub-76 |
| 2-1677 | Sub-35 | 3,4-diClPh | CO | Single bond or CH₂ | Sub-77 |
| 2-1678 | Sub-35 | 3,4-diClPh | CO | Single bond or CH₂ | Sub-78 |
| 2-1679 | Sub-35 | 3,4-diClPh | CO | Single bond or CH₂ | Sub-79 |
| 2-1680 | Sub-35 | 3,4-diClPh | CO | Single bond or CH₂ | Sub-80 |
| 2-1681 | Sub-36 | 3,4-diClPh | CO | Single bond or CH₂ | Sub-1 |
| 2-1682 | Sub-36 | 3,4-diClPh | CO | Single bond or CH₂ | Sub-2 |
| 2-1683 | Sub-36 | 3,4-diClPh | CO | Single bond or CH₂ | Sub-3 |
| 2-1684 | Sub-36 | 3,4-diClPh | CO | Single bond or CH₂ | Sub-4 |
| 2-1685 | Sub-36 | 3,4-diClPh | CO | Single bond or CH₂ | Sub-5 |
| 2-1686 | Sub-36 | 3,4-diClPh | CO | Single bond or CH₂ | Sub-6 |
| 2-1687 | Sub-36 | 3,4-diClPh | CO | Single bond or CH₂ | Sub-7 |
| 2-1688 | Sub-36 | 3,4-diClPh | CO | Single bond or CH₂ | Sub-8 |
| 2-1689 | Sub-36 | 3,4-diClPh | CO | Single bond or CH₂ | Sub-9 |
| 2-1690 | Sub-36 | 3,4-diClPh | CO | Single bond or CH₂ | Sub-10 |
| 2-1691 | Sub-36 | 3,4-diClPh | CO | Single bond or CH₂ | Sub-11 |
| 2-1692 | Sub-36 | 3,4-diClPh | CO | Single bond or CH₂ | Sub-12 |
| 2-1693 | Sub-36 | 3,4-diClPh | CO | Single bond or CH₂ | Sub-13 |
| 2-1694 | Sub-36 | 3,4-diClPh | CO | Single bond or CH₂ | Sub-14 |
| 2-1695 | Sub-36 | 3,4-diClPh | CO | Single bond or CH₂ | Sub-15 |
| 2-1696 | Sub-36 | 3,4-diClPh | CO | Single bond or CH₂ | Sub-16 |
| 2-1697 | Sub-36 | 3,4-diClPh | CO | Single bond or CH₂ | Sub-17 |
| 2-1698 | Sub-36 | 3,4-diClPh | CO | Single bond or CH₂ | Sub-18 |
| 2-1699 | Sub-36 | 3,4-diClPh | CO | Single bond or CH₂ | Sub-19 |
| 2-1700 | Sub-36 | 3,4-diClPh | CO | Single bond or CH₂ | Sub-20 |
| 2-1701 | Sub-36 | 3,4-diClPh | CO | Single bond or CH₂ | Sub-21 |
| 2-1702 | Sub-36 | 3,4-diClPh | CO | Single bond or CH₂ | Sub-22 |
| 2-1703 | Sub-36 | 3,4-diClPh | CO | Single bond or CH₂ | Sub-23 |
| 2-1704 | Sub-36 | 3,4-diClPh | CO | Single bond or CH₂ | Sub-24 |
| 2-1705 | Sub-36 | 3,4-diClPh | CO | Single bond or CH₂ | Sub-25 |
| 2-1706 | Sub-36 | 3,4-diClPh | CO | Single bond or CH₂ | Sub-26 |
| 2-1707 | Sub-36 | 3,4-diClPh | CO | Single bond or CH₂ | Sub-27 |
| 2-1708 | Sub-36 | 3,4-diClPh | CO | Single bond or CH₂ | Sub-28 |
| 2-1709 | Sub-36 | 3,4-diClPh | CO | Single bond or CH₂ | Sub-29 |
| 2-1710 | Sub-36 | 3,4-diClPh | CO | Single bond or CH₂ | Sub-30 |
| 2-1711 | Sub-36 | 3,4-diClPh | CO | Single bond or CH₂ | Sub-31 |
| 2-1712 | Sub-36 | 3,4-diClPh | CO | Single bond or CH₂ | Sub-32 |
| 2-1713 | Sub-36 | 3,4-diClPh | CO | Single bond or CH₂ | Sub-65 |
| 2-1714 | Sub-36 | 3,4-diClPh | CO | Single bond or CH₂ | Sub-66 |
| 2-1715 | Sub-36 | 3,4-diClPh | CO | Single bond or CH₂ | Sub-67 |
| 2-1716 | Sub-36 | 3,4-diClPh | CO | Single bond or CH₂ | Sub-68 |
| 2-1717 | Sub-36 | 3,4-diClPh | CO | Single bond or CH₂ | Sub-69 |
| 2-1718 | Sub-36 | 3,4-diClPh | CO | Single bond or CH₂ | Sub-70 |
| 2-1719 | Sub-36 | 3,4-diClPh | CO | Single bond or CH₂ | Sub-71 |
| 2-1720 | Sub-36 | 3,4-diClPh | CO | Single bond or CH₂ | Sub-72 |
| 2-1721 | Sub-36 | 3,4-diClPh | CO | Single bond or CH₂ | Sub-73 |
| 2-1722 | Sub-36 | 3,4-diClPh | CO | Single bond or CH₂ | Sub-74 |
| 2-1723 | Sub-36 | 3,4-diClPh | CO | Single bond or CH₂ | Sub-75 |
| 2-1724 | Sub-36 | 3,4-diClPh | CO | Single bond or CH₂ | Sub-76 |
| 2-1725 | Sub-36 | 3,4-diClPh | CO | Single bond or CH₂ | Sub-77 |
| 2-1726 | Sub-36 | 3,4-diClPh | CO | Single bond or CH₂ | Sub-78 |
| 2-1727 | Sub-36 | 3,4-diClPh | CO | Single bond or CH₂ | Sub-79 |
| 2-1728 | Sub-36 | 3,4-diClPh | CO | Single bond or CH₂ | Sub-80 |
| 2-1729 | Sub-37 | 3,4-diClPh | CO | Single bond or CH₂ | Sub-1 |
| 2-1730 | Sub-37 | 3,4-diClPh | CO | Single bond or CH₂ | Sub-2 |
| 2-1731 | Sub-37 | 3,4-diClPh | CO | Single bond or CH₂ | Sub-3 |
| 2-1732 | Sub-37 | 3,4-diClPh | CO | Single bond or CH₂ | Sub-4 |
| 2-1733 | Sub-37 | 3,4-diClPh | CO | Single bond or CH₂ | Sub-5 |
| 2-1734 | Sub-37 | 3,4-diClPh | CO | Single bond or CH₂ | Sub-6 |
| 2-1735 | Sub-37 | 3,4-diClPh | CO | Single bond or CH₂ | Sub-7 |
| 2-1736 | Sub-37 | 3,4-diClPh | CO | Single bond or CH₂ | Sub-8 |
| 2-1737 | Sub-37 | 3,4-diClPh | CO | Single bond or CH₂ | Sub-9 |
| 2-1738 | Sub-37 | 3,4-diClPh | CO | Single bond or CH₂ | Sub-10 |
| 2-1739 | Sub-37 | 3,4-diClPh | CO | Single bond or CH₂ | Sub-11 |
| 2-1740 | Sub-37 | 3,4-diClPh | CO | Single bond or CH₂ | Sub-12 |
| 2-1741 | Sub-37 | 3,4-diClPh | CO | Single bond or CH₂ | Sub-13 |
| 2-1742 | Sub-37 | 3,4-diClPh | CO | Single bond or CH₂ | Sub-14 |
| 2-1743 | Sub-37 | 3,4-diClPh | CO | Single bond or CH₂ | Sub-15 |
| 2-1744 | Sub-37 | 3,4-diClPh | CO | Single bond or CH₂ | Sub-16 |
| 2-1745 | Sub-37 | 3,4-diClPh | CO | Single bond or CH₂ | Sub-17 |
| 2-1746 | Sub-37 | 3,4-diClPh | CO | Single bond or CH₂ | Sub-18 |
| 2-1747 | Sub-37 | 3,4-diClPh | CO | Single bond or CH₂ | Sub-19 |
| 2-1748 | Sub-37 | 3,4-diClPh | CO | Single bond or CH₂ | Sub-20 |
| 2-1749 | Sub-37 | 3,4-diClPh | CO | Single bond or CH₂ | Sub-21 |
| 2-1750 | Sub-37 | 3,4-diClPh | CO | Single bond or CH₂ | Sub-22 |
| 2-1751 | Sub-37 | 3,4-diClPh | CO | Single bond or CH₂ | Sub-23 |
| 2-1752 | Sub-37 | 3,4-diClPh | CO | Single bond or CH₂ | Sub-24 |
| 2-1753 | Sub-37 | 3,4-diClPh | CO | Single bond or CH₂ | Sub-25 |
| 2-1754 | Sub-37 | 3,4-diClPh | CO | Single bond or CH₂ | Sub-26 |
| 2-1755 | Sub-37 | 3,4-diClPh | CO | Single bond or CH₂ | Sub-27 |
| 2-1756 | Sub-37 | 3,4-diClPh | CO | Single bond or CH₂ | Sub-28 |
| 2-1757 | Sub-37 | 3,4-diClPh | CO | Single bond or CH₂ | Sub-29 |
| 2-1758 | Sub-37 | 3,4-diClPh | CO | Single bond or CH₂ | Sub-30 |
| 2-1759 | Sub-37 | 3,4-diClPh | CO | Single bond or CH₂ | Sub-31 |
| 2-1760 | Sub-37 | 3,4-diClPh | CO | Single bond or CH₂ | Sub-32 |
| 2-1761 | Sub-37 | 3,4-diClPh | CO | Single bond or CH₂ | Sub-65 |
| 2-1762 | Sub-37 | 3,4-diClPh | CO | Single bond or CH₂ | Sub-66 |
| 2-1763 | Sub-37 | 3,4-diClPh | CO | Single bond or CH₂ | Sub-67 |
| 2-1764 | Sub-37 | 3,4-diClPh | CO | Single bond or CH₂ | Sub-68 |
| 2-1765 | Sub-37 | 3,4-diClPh | CO | Single bond or CH₂ | Sub-69 |
| 2-1766 | Sub-37 | 3,4-diClPh | CO | Single bond or CH₂ | Sub-70 |
| 2-1767 | Sub-37 | 3,4-diClPh | CO | Single bond or CH₂ | Sub-71 |
| 2-1768 | Sub-37 | 3,4-diClPh | CO | Single bond or CH₂ | Sub-72 |
| 2-1769 | Sub-37 | 3,4-diClPh | CO | Single bond or CH₂ | Sub-73 |
| 2-1770 | Sub-37 | 3,4-diClPh | CO | Single bond or CH₂ | Sub-74 |
| 2-1771 | Sub-37 | 3,4-diClPh | CO | Single bond or CH₂ | Sub-75 |
| 2-1772 | Sub-37 | 3,4-diClPh | CO | Single bond or CH₂ | Sub-76 |
| 2-1773 | Sub-37 | 3,4-diClPh | CO | Single bond or CH₂ | Sub-77 |
| 2-1774 | Sub-37 | 3,4-diClPh | CO | Single bond or CH₂ | Sub-78 |
| 2-1775 | Sub-37 | 3,4-diClPh | CO | Single bond or CH₂ | Sub-79 |
| 2-1776 | Sub-37 | 3,4-diClPh | CO | Single bond or CH₂ | Sub-80 |
| 2-1777 | Sub-38 | 3,4-diClPh | CO | Single bond or CH₂ | Sub-1 |
| 2-1778 | Sub-38 | 3,4-diClPh | CO | Single bond or CH₂ | Sub-2 |
| 2-1779 | Sub-38 | 3,4-diClPh | CO | Single bond or CH₂ | Sub-3 |
| 2-1780 | Sub-38 | 3,4-diClPh | CO | Single bond or CH₂ | Sub-4 |
| 2-1781 | Sub-38 | 3,4-diClPh | CO | Single bond or CH₂ | Sub-5 |
| 2-1782 | Sub-38 | 3,4-diClPh | CO | Single bond or CH₂ | Sub-6 |
| 2-1783 | Sub-38 | 3,4-diClPh | CO | Single bond or CH₂ | Sub-7 |
| 2-1784 | Sub-38 | 3,4-diClPh | CO | Single bond or CH₂ | Sub-8 |
| 2-1785 | Sub-38 | 3,4-diClPh | CO | Single bond or CH₂ | Sub-9 |
| 2-1786 | Sub-38 | 3,4-diClPh | CO | Single bond or CH₂ | Sub-10 |
| 2-1787 | Sub-38 | 3,4-diClPh | CO | Single bond or CH₂ | Sub-11 |
| 2-1788 | Sub-38 | 3,4-diClPh | CO | Single bond or CH₂ | Sub-12 |
| 2-1789 | Sub-38 | 3,4-diClPh | CO | Single bond or CH₂ | Sub-13 |
| 2-1790 | Sub-38 | 3,4-diClPh | CO | Single bond or CH₂ | Sub-14 |
| 2-1791 | Sub-38 | 3,4-diClPh | CO | Single bond or CH₂ | Sub-15 |
| 2-1792 | Sub-38 | 3,4-diClPh | CO | Single bond or CH₂ | Sub-16 |
| 2-1793 | Sub-38 | 3,4-diClPh | CO | Single bond or CH₂ | Sub-17 |
| 2-1794 | Sub-38 | 3,4-diClPh | CO | Single bond or CH₂ | Sub-18 |
| 2-1795 | Sub-38 | 3,4-diClPh | CO | Single bond or CH₂ | Sub-19 |
| 2-1796 | Sub-38 | 3,4-diClPh | CO | Single bond or CH₂ | Sub-20 |
| 2-1797 | Sub-38 | 3,4-diClPh | CO | Single bond or CH₂ | Sub-21 |
| 2-1798 | Sub-38 | 3,4-diClPh | CO | Single bond or CH₂ | Sub-22 |
| 2-1799 | Sub-38 | 3,4-diClPh | CO | Single bond or CH₂ | Sub-23 |
| 2-1800 | Sub-38 | 3,4-diClPh | CO | Single bond or CH₂ | Sub-24 |
| 2-1801 | Sub-38 | 3,4-diClPh | CO | Single bond or CH₂ | Sub-25 |
| 2-1802 | Sub-38 | 3,4-diClPh | CO | Single bond or CH₂ | Sub-26 |
| 2-1803 | Sub-38 | 3,4-diClPh | CO | Single bond or CH₂ | Sub-27 |
| 2-1804 | Sub-38 | 3,4-diClPh | CO | Single bond or CH₂ | Sub-28 |
| 2-1805 | Sub-38 | 3,4-diClPh | CO | Single bond or CH₂ | Sub-29 |
| 2-1806 | Sub-38 | 3,4-diClPh | CO | Single bond or CH₂ | Sub-30 |
| 2-1807 | Sub-38 | 3,4-diClPh | CO | Single bond or CH₂ | Sub-31 |
| 2-1808 | Sub-38 | 3,4-diClPh | CO | Single bond or CH₂ | Sub-32 |
| 2-1809 | Sub-38 | 3,4-diClPh | CO | Single bond or CH₂ | Sub-65 |
| 2-1810 | Sub-38 | 3,4-diClPh | CO | Single bond or CH₂ | Sub-66 |
| 2-1811 | Sub-38 | 3,4-diClPh | CO | Single bond or CH₂ | Sub-67 |
| 2-1812 | Sub-38 | 3,4-diClPh | CO | Single bond or CH₂ | Sub-68 |
| 2-1813 | Sub-38 | 3,4-diClPh | CO | Single bond or CH₂ | Sub-69 |
| 2-1814 | Sub-38 | 3,4-diClPh | CO | Single bond or CH₂ | Sub-70 |
| 2-1815 | Sub-38 | 3,4-diClPh | CO | Single bond or CH₂ | Sub-71 |
| 2-1816 | Sub-38 | 3,4-diClPh | CO | Single bond or CH₂ | Sub-72 |
| 2-1817 | Sub-38 | 3,4-diClPh | CO | Single bond or CH₂ | Sub-73 |
| 2-1818 | Sub-38 | 3,4-diClPh | CO | Single bond or CH₂ | Sub-74 |
| 2-1819 | Sub-38 | 3,4-diClPh | CO | Single bond or CH₂ | Sub-75 |
| 2-1820 | Sub-38 | 3,4-diClPh | CO | Single bond or CH₂ | Sub-76 |

TABLE 2-continued

| Cpd. No. | R¹ | R² | A | B | Z |
|---|---|---|---|---|---|
| 2-1821 | Sub-38 | 3,4-diClPh | CO | Single bond or CH₂ | Sub-77 |
| 2-1822 | Sub-38 | 3,4-diClPh | CO | Single bond or CH₂ | Sub-78 |
| 2-1823 | Sub-38 | 3,4-diClPh | CO | Single bond or CH₂ | Sub-79 |
| 2-1824 | Sub-38 | 3,4-diClPh | CO | Single bond or CH₂ | Sub-80 |
| 2-1825 | Sub-39 | 3,4-diClPh | CO | Single bond or CH₂ | Sub-1 |
| 2-1826 | Sub-39 | 3,4-diClPh | CO | Single bond or CH₂ | Sub-2 |
| 2-1827 | Sub-39 | 3,4-diClPh | CO | Single bond or CH₂ | Sub-3 |
| 2-1828 | Sub-39 | 3,4-diClPh | CO | Single bond or CH₂ | Sub-4 |
| 2-1829 | Sub-39 | 3,4-diClPh | CO | Single bond or CH₂ | Sub-5 |
| 2-1830 | Sub-39 | 3,4-diClPh | CO | Single bond or CH₂ | Sub-6 |
| 2-1831 | Sub-39 | 3,4-diClPh | CO | Single bond or CH₂ | Sub-7 |
| 2-1832 | Sub-39 | 3,4-diClPh | CO | Single bond or CH₂ | Sub-8 |
| 2-1833 | Sub-39 | 3,4-diClPh | CO | Single bond or CH₂ | Sub-9 |
| 2-1834 | Sub-39 | 3,4-diClPh | CO | Single bond or CH₂ | Sub-10 |
| 2-1835 | Sub-39 | 3,4-diClPh | CO | Single bond or CH₂ | Sub-11 |
| 2-1836 | Sub-39 | 3,4-diClPh | CO | Single bond or CH₂ | Sub-12 |
| 2-1837 | Sub-39 | 3,4-diClPh | CO | Single bond or CH₂ | Sub-13 |
| 2-1838 | Sub-39 | 3,4-diClPh | CO | Single bond or CH₂ | Sub-14 |
| 2-1839 | Sub-39 | 3,4-diClPh | CO | Single bond or CH₂ | Sub-15 |
| 2-1840 | Sub-39 | 3,4-diClPh | CO | Single bond or CH₂ | Sub-16 |
| 2-1841 | Sub-39 | 3,4-diClPh | CO | Single bond or CH₂ | Sub-17 |
| 2-1842 | Sub-39 | 3,4-diClPh | CO | Single bond or CH₂ | Sub-18 |
| 2-1843 | Sub-39 | 3,4-diClPh | CO | Single bond or CH₂ | Sub-19 |
| 2-1844 | Sub-39 | 3,4-diClPh | CO | Single bond or CH₂ | Sub-20 |
| 2-1845 | Sub-39 | 3,4-diClPh | CO | Single bond or CH₂ | Sub-21 |
| 2-1846 | Sub-39 | 3,4-diClPh | CO | Single bond or CH₂ | Sub-22 |
| 2-1847 | Sub-39 | 3,4-diClPh | CO | Single bond or CH₂ | Sub-23 |
| 2-1848 | Sub-39 | 3,4-diClPh | CO | Single bond or CH₂ | Sub-24 |
| 2-1849 | Sub-39 | 3,4-diClPh | CO | Single bond or CH₂ | Sub-25 |
| 2-1850 | Sub-39 | 3,4-diClPh | CO | Single bond or CH₂ | Sub-26 |
| 2-1851 | Sub-39 | 3,4-diClPh | CO | Single bond or CH₂ | Sub-27 |
| 2-1852 | Sub-39 | 3,4-diClPh | CO | Single bond or CH₂ | Sub-28 |
| 2-1853 | Sub-39 | 3,4-diClPh | CO | Single bond or CH₂ | Sub-29 |
| 2-1854 | Sub-39 | 3,4-diClPh | CO | Single bond or CH₂ | Sub-30 |
| 2-1855 | Sub-39 | 3,4-diClPh | CO | Single bond or CH₂ | Sub-31 |
| 2-1856 | Sub-39 | 3,4-diClPh | CO | Single bond or CH₂ | Sub-32 |
| 2-1857 | Sub-39 | 3,4-diClPh | CO | Single bond or CH₂ | Sub-65 |
| 2-1858 | Sub-39 | 3,4-diClPh | CO | Single bond or CH₂ | Sub-66 |
| 2-1859 | Sub-39 | 3,4-diClPh | CO | Single bond or CH₂ | Sub-67 |
| 2-1860 | Sub-39 | 3,4-diClPh | CO | Single bond or CH₂ | Sub-68 |
| 2-1861 | Sub-39 | 3,4-diClPh | CO | Single bond or CH₂ | Sub-69 |
| 2-1862 | Sub-39 | 3,4-diClPh | CO | Single bond or CH₂ | Sub-70 |
| 2-1863 | Sub-39 | 3,4-diClPh | CO | Single bond or CH₂ | Sub-71 |
| 2-1864 | Sub-39 | 3,4-diClPh | CO | Single bond or CH₂ | Sub-72 |
| 2-1865 | Sub-39 | 3,4-diClPh | CO | Single bond or CH₂ | Sub-73 |
| 2-1866 | Sub-39 | 3,4-diClPh | CO | Single bond or CH₂ | Sub-74 |
| 2-1867 | Sub-39 | 3,4-diClPh | CO | Single bond or CH₂ | Sub-75 |
| 2-1868 | Sub-39 | 3,4-diClPh | CO | Single bond or CH₂ | Sub-76 |
| 2-1869 | Sub-39 | 3,4-diClPh | CO | Single bond or CH₂ | Sub-77 |
| 2-1870 | Sub-39 | 3,4-diClPh | CO | Single bond or CH₂ | Sub-78 |
| 2-1871 | Sub-39 | 3,4-diClPh | CO | Single bond or CH₂ | Sub-79 |
| 2-1872 | Sub-39 | 3,4-diClPh | CO | Single bond or CH₂ | Sub-80 |
| 2-1873 | Sub-40 | 3,4-diClPh | CO | Single bond or CH₂ | Sub-1 |
| 2-1874 | Sub-40 | 3,4-diClPh | CO | Single bond or CH₂ | Sub-2 |
| 2-1875 | Sub-40 | 3,4-diClPh | CO | Single bond or CH₂ | Sub-3 |
| 2-1876 | Sub-40 | 3,4-diClPh | CO | Single bond or CH₂ | Sub-4 |
| 2-1877 | Sub-40 | 3,4-diClPh | CO | Single bond or CH₂ | Sub-5 |
| 2-1878 | Sub-40 | 3,4-diClPh | CO | Single bond or CH₂ | Sub-6 |
| 2-1879 | Sub-40 | 3,4-diClPh | CO | Single bond or CH₂ | Sub-7 |
| 2-1880 | Sub-40 | 3,4-diClPh | CO | Single bond or CH₂ | Sub-8 |
| 2-1881 | Sub-40 | 3,4-diClPh | CO | Single bond or CH₂ | Sub-9 |
| 2-1882 | Sub-40 | 3,4-diClPh | CO | Single bond or CH₂ | Sub-10 |
| 2-1883 | Sub-40 | 3,4-diClPh | CO | Single bond or CH₂ | Sub-11 |
| 2-1884 | Sub-40 | 3,4-diClPh | CO | Single bond or CH₂ | Sub-12 |
| 2-1885 | Sub-40 | 3,4-diClPh | CO | Single bond or CH₂ | Sub-13 |
| 2-1886 | Sub-40 | 3,4-diClPh | CO | Single bond or CH₂ | Sub-14 |
| 2-1887 | Sub-40 | 3,4-diClPh | CO | Single bond or CH₂ | Sub-15 |
| 2-1888 | Sub-40 | 3,4-diClPh | CO | Single bond or CH₂ | Sub-16 |
| 2-1889 | Sub-40 | 3,4-diClPh | CO | Single bond or CH₂ | Sub-17 |
| 2-1890 | Sub-40 | 3,4-diClPh | CO | Single bond or CH₂ | Sub-18 |
| 2-1891 | Sub-40 | 3,4-diClPh | CO | Single bond or CH₂ | Sub-19 |
| 2-1892 | Sub-40 | 3,4-diClPh | CO | Single bond or CH₂ | Sub-20 |
| 2-1893 | Sub-40 | 3,4-diClPh | CO | Single bond or CH₂ | Sub-21 |
| 2-1894 | Sub-40 | 3,4-diClPh | CO | Single bond or CH₂ | Sub-22 |
| 2-1895 | Sub-40 | 3,4-diClPh | CO | Single bond or CH₂ | Sub-23 |
| 2-1896 | Sub-40 | 3,4-diClPh | CO | Single bond or CH₂ | Sub-24 |
| 2-1897 | Sub-40 | 3,4-diClPh | CO | Single bond or CH₂ | Sub-25 |
| 2-1898 | Sub-40 | 3,4-diClPh | CO | Single bond or CH₂ | Sub-26 |
| 2-1899 | Sub-40 | 3,4-diClPh | CO | Single bond or CH₂ | Sub-27 |
| 2-1900 | Sub-40 | 3,4-diClPh | CO | Single bond or CH₂ | Sub-28 |
| 2-1901 | Sub-40 | 3,4-diClPh | CO | Single bond or CH₂ | Sub-29 |
| 2-1902 | Sub-40 | 3,4-diClPh | CO | Single bond or CH₂ | Sub-30 |
| 2-1903 | Sub-40 | 3,4-diClPh | CO | Single bond or CH₂ | Sub-31 |
| 2-1904 | Sub-40 | 3,4-diClPh | CO | Single bond or CH₂ | Sub-32 |
| 2-1905 | Sub-40 | 3,4-diClPh | CO | Single bond or CH₂ | Sub-65 |
| 2-1906 | Sub-40 | 3,4-diClPh | CO | Single bond or CH₂ | Sub-66 |
| 2-1907 | Sub-40 | 3,4-diClPh | CO | Single bond or CH₂ | Sub-67 |
| 2-1908 | Sub-40 | 3,4-diClPh | CO | Single bond or CH₂ | Sub-68 |
| 2-1909 | Sub-40 | 3,4-diClPh | CO | Single bond or CH₂ | Sub-69 |
| 2-1910 | Sub-40 | 3,4-diClPh | CO | Single bond or CH₂ | Sub-70 |
| 2-1911 | Sub-40 | 3,4-diClPh | CO | Single bond or CH₂ | Sub-71 |
| 2-1912 | Sub-40 | 3,4-diClPh | CO | Single bond or CH₂ | Sub-72 |
| 2-1913 | Sub-40 | 3,4-diClPh | CO | Single bond or CH₂ | Sub-73 |
| 2-1914 | Sub-40 | 3,4-diClPh | CO | Single bond or CH₂ | Sub-74 |
| 2-1915 | Sub-40 | 3,4-diClPh | CO | Single bond or CH₂ | Sub-75 |
| 2-1916 | Sub-40 | 3,4-diClPh | CO | Single bond or CH₂ | Sub-76 |
| 2-1917 | Sub-40 | 3,4-diClPh | CO | Single bond or CH₂ | Sub-77 |
| 2-1918 | Sub-40 | 3,4-diClPh | CO | Single bond or CH₂ | Sub-78 |
| 2-1919 | Sub-40 | 3,4-diClPh | CO | Single bond or CH₂ | Sub-79 |
| 2-1920 | Sub-40 | 3,4-diClPh | CO | Single bond or CH₂ | Sub-80 |
| 2-1921 | Sub-41 | 3,4-diClPh | CO | Single bond or CH₂ | Sub-1 |
| 2-1922 | Sub-41 | 3,4-diClPh | CO | Single bond or CH₂ | Sub-2 |
| 2-1923 | Sub-41 | 3,4-diClPh | CO | Single bond or CH₂ | Sub-3 |
| 2-1924 | Sub-41 | 3,4-diClPh | CO | Single bond or CH₂ | Sub-4 |
| 2-1925 | Sub-41 | 3,4-diClPh | CO | Single bond or CH₂ | Sub-5 |
| 2-1926 | Sub-41 | 3,4-diClPh | CO | Single bond or CH₂ | Sub-6 |
| 2-1927 | Sub-41 | 3,4-diClPh | CO | Single bond or CH₂ | Sub-7 |
| 2-1928 | Sub-41 | 3,4-diClPh | CO | Single bond or CH₂ | Sub-8 |
| 2-1929 | Sub-41 | 3,4-diClPh | CO | Single bond or CH₂ | Sub-9 |
| 2-1930 | Sub-41 | 3,4-diClPh | CO | Single bond or CH₂ | Sub-10 |
| 2-1931 | Sub-41 | 3,4-diClPh | CO | Single bond or CH₂ | Sub-11 |
| 2-1932 | Sub-41 | 3,4-diClPh | CO | Single bond or CH₂ | Sub-12 |
| 2-1933 | Sub-41 | 3,4-diClPh | CO | Single bond or CH₂ | Sub-13 |
| 2-1934 | Sub-41 | 3,4-diClPh | CO | Single bond or CH₂ | Sub-14 |
| 2-1935 | Sub-41 | 3,4-diClPh | CO | Single bond or CH₂ | Sub-15 |
| 2-1936 | Sub-41 | 3,4-diClPh | CO | Single bond or CH₂ | Sub-16 |
| 2-1937 | Sub-41 | 3,4-diClPh | CO | Single bond or CH₂ | Sub-17 |
| 2-1938 | Sub-41 | 3,4-diClPh | CO | Single bond or CH₂ | Sub-18 |
| 2-1939 | Sub-41 | 3,4-diClPh | CO | Single bond or CH₂ | Sub-19 |
| 2-1940 | Sub-41 | 3,4-diClPh | CO | Single bond or CH₂ | Sub-20 |
| 2-1941 | Sub-41 | 3,4-diClPh | CO | Single bond or CH₂ | Sub-21 |
| 2-1942 | Sub-41 | 3,4-diClPh | CO | Single bond or CH₂ | Sub-22 |
| 2-1943 | Sub-41 | 3,4-diClPh | CO | Single bond or CH₂ | Sub-23 |
| 2-1944 | Sub-41 | 3,4-diClPh | CO | Single bond or CH₂ | Sub-24 |
| 2-1945 | Sub-41 | 3,4-diClPh | CO | Single bond or CH₂ | Sub-25 |
| 2-1946 | Sub-41 | 3,4-diClPh | CO | Single bond or CH₂ | Sub-26 |
| 2-1947 | Sub-41 | 3,4-diClPh | CO | Single bond or CH₂ | Sub-27 |
| 2-1948 | Sub-41 | 3,4-diClPh | CO | Single bond or CH₂ | Sub-28 |
| 2-1949 | Sub-41 | 3,4-diClPh | CO | Single bond or CH₂ | Sub-29 |
| 2-1950 | Sub-41 | 3,4-diClPh | CO | Single bond or CH₂ | Sub-30 |
| 2-1951 | Sub-41 | 3,4-diClPh | CO | Single bond or CH₂ | Sub-31 |
| 2-1952 | Sub-41 | 3,4-diClPh | CO | Single bond or CH₂ | Sub-32 |
| 2-1953 | Sub-41 | 3,4-diClPh | CO | Single bond or CH₂ | Sub-65 |
| 2-1954 | Sub-41 | 3,4-diClPh | CO | Single bond or CH₂ | Sub-66 |
| 2-1955 | Sub-41 | 3,4-diClPh | CO | Single bond or CH₂ | Sub-67 |
| 2-1956 | Sub-41 | 3,4-diClPh | CO | Single bond or CH₂ | Sub-68 |
| 2-1957 | Sub-41 | 3,4-diClPh | CO | Single bond or CH₂ | Sub-69 |
| 2-1958 | Sub-41 | 3,4-diClPh | CO | Single bond or CH₂ | Sub-70 |
| 2-1959 | Sub-41 | 3,4-diClPh | CO | Single bond or CH₂ | Sub-71 |
| 2-1960 | Sub-41 | 3,4-diClPh | CO | Single bond or CH₂ | Sub-72 |
| 2-1961 | Sub-41 | 3,4-diClPh | CO | Single bond or CH₂ | Sub-73 |
| 2-1962 | Sub-41 | 3,4-diClPh | CO | Single bond or CH₂ | Sub-74 |
| 2-1963 | Sub-41 | 3,4-diClPh | CO | Single bond or CH₂ | Sub-75 |
| 2-1964 | Sub-41 | 3,4-diClPh | CO | Single bond or CH₂ | Sub-76 |
| 2-1965 | Sub-41 | 3,4-diClPh | CO | Single bond or CH₂ | Sub-77 |
| 2-1966 | Sub-41 | 3,4-diClPh | CO | Single bond or CH₂ | Sub-78 |
| 2-1967 | Sub-41 | 3,4-diClPh | CO | Single bond or CH₂ | Sub-79 |
| 2-1968 | Sub-41 | 3,4-diClPh | CO | Single bond or CH₂ | Sub-80 |
| 2-1969 | Sub-42 | 3,4-diClPh | CO | Single bond or CH₂ | Sub-1 |
| 2-1970 | Sub-42 | 3,4-diClPh | CO | Single bond or CH₂ | Sub-2 |
| 2-1971 | Sub-42 | 3,4-diClPh | CO | Single bond or CH₂ | Sub-3 |
| 2-1972 | Sub-42 | 3,4-diClPh | CO | Single bond or CH₂ | Sub-4 |
| 2-1973 | Sub-42 | 3,4-diClPh | CO | Single bond or CH₂ | Sub-5 |
| 2-1974 | Sub-42 | 3,4-diClPh | CO | Single bond or CH₂ | Sub-6 |

TABLE 2-continued

| Cpd. No. | R¹ | R² | A | B | Z |
|---|---|---|---|---|---|
| 2-1975 | Sub-42 | 3,4-diClPh | CO | Single bond or CH₂ | Sub-7 |
| 2-1976 | Sub-42 | 3,4-diClPh | CO | Single bond or CH₂ | Sub-8 |
| 2-1977 | Sub-42 | 3,4-diClPh | CO | Single bond or CH₂ | Sub-9 |
| 2-1978 | Sub-42 | 3,4-diClPh | CO | Single bond or CH₂ | Sub-10 |
| 2-1979 | Sub-42 | 3,4-diClPh | CO | Single bond or CH₂ | Sub-11 |
| 2-1980 | Sub-42 | 3,4-diClPh | CO | Single bond or CH₂ | Sub-12 |
| 2-1981 | Sub-42 | 3,4-diClPh | CO | Single bond or CH₂ | Sub-13 |
| 2-1982 | Sub-42 | 3,4-diClPh | CO | Single bond or CH₂ | Sub-14 |
| 2-1983 | Sub-42 | 3,4-diClPh | CO | Single bond or CH₂ | Sub-15 |
| 2-1984 | Sub-42 | 3,4-diClPh | CO | Single bond or CH₂ | Sub-16 |
| 2-1985 | Sub-42 | 3,4-diClPh | CO | Single bond or CH₂ | Sub-17 |
| 2-1986 | Sub-42 | 3,4-diClPh | CO | Single bond or CH₂ | Sub-18 |
| 2-1987 | Sub-42 | 3,4-diClPh | CO | Single bond or CH₂ | Sub-19 |
| 2-1988 | Sub-42 | 3,4-diClPh | CO | Single bond or CH₂ | Sub-20 |
| 2-1989 | Sub-42 | 3,4-diClPh | CO | Single bond or CH₂ | Sub-21 |
| 2-1990 | Sub-42 | 3,4-diClPh | CO | Single bond or CH₂ | Sub-22 |
| 2-1991 | Sub-42 | 3,4-diClPh | CO | Single bond or CH₂ | Sub-23 |
| 2-1992 | Sub-42 | 3,4-diClPh | CO | Single bond or CH₂ | Sub-24 |
| 2-1993 | Sub-42 | 3,4-diClPh | CO | Single bond or CH₂ | Sub-25 |
| 2-1994 | Sub-42 | 3,4-diClPh | CO | Single bond or CH₂ | Sub-26 |
| 2-1995 | Sub-42 | 3,4-diClPh | CO | Single bond or CH₂ | Sub-27 |
| 2-1996 | Sub-42 | 3,4-diClPh | CO | Single bond or CH₂ | Sub-28 |
| 2-1997 | Sub-42 | 3,4-diClPh | CO | Single bond or CH₂ | Sub-29 |
| 2-1998 | Sub-42 | 3,4-diClPh | CO | Single bond or CH₂ | Sub-30 |
| 2-1999 | Sub-42 | 3,4-diClPh | CO | Single bond or CH₂ | Sub-31 |
| 2-2000 | Sub-42 | 3,4-diClPh | CO | Single bond or CH₂ | Sub-32 |
| 2-2001 | Sub-42 | 3,4-diClPh | CO | Single bond or CH₂ | Sub-65 |
| 2-2002 | Sub-42 | 3,4-diClPh | CO | Single bond or CH₂ | Sub-66 |
| 2-2003 | Sub-42 | 3,4-diClPh | CO | Single bond or CH₂ | Sub-67 |
| 2-2004 | Sub-42 | 3,4-diClPh | CO | Single bond or CH₂ | Sub-68 |
| 2-2005 | Sub-42 | 3,4-diClPh | CO | Single bond or CH₂ | Sub-69 |
| 2-2006 | Sub-42 | 3,4-diClPh | CO | Single bond or CH₂ | Sub-70 |
| 2-2007 | Sub-42 | 3,4-diClPh | CO | Single bond or CH₂ | Sub-71 |
| 2-2008 | Sub-42 | 3,4-diClPh | CO | Single bond or CH₂ | Sub-72 |
| 2-2009 | Sub-42 | 3,4-diClPh | CO | Single bond or CH₂ | Sub-73 |
| 2-2010 | Sub-42 | 3,4-diClPh | CO | Single bond or CH₂ | Sub-74 |
| 2-2011 | Sub-42 | 3,4-diClPh | CO | Single bond or CH₂ | Sub-75 |
| 2-2012 | Sub-42 | 3,4-diClPh | CO | Single bond or CH₂ | Sub-76 |
| 2-2013 | Sub-42 | 3,4-diClPh | CO | Single bond or CH₂ | Sub-77 |
| 2-2014 | Sub-42 | 3,4-diClPh | CO | Single bond or CH₂ | Sub-78 |
| 2-2015 | Sub-42 | 3,4-diClPh | CO | Single bond or CH₂ | Sub-79 |
| 2-2016 | Sub-42 | 3,4-diClPh | CO | Single bond or CH₂ | Sub-80 |
| 2-2017 | Sub-43 | 3,4-diClPh | CO | Single bond or CH₂ | Sub-1 |
| 2-2018 | Sub-43 | 3,4-diClPh | CO | Single bond or CH₂ | Sub-2 |
| 2-2019 | Sub-43 | 3,4-diClPh | CO | Single bond or CH₂ | Sub-3 |
| 2-2020 | Sub-43 | 3,4-diClPh | CO | Single bond or CH₂ | Sub-4 |
| 2-2021 | Sub-43 | 3,4-diClPh | CO | Single bond or CH₂ | Sub-5 |
| 2-2022 | Sub-43 | 3,4-diClPh | CO | Single bond or CH₂ | Sub-6 |
| 2-2023 | Sub-43 | 3,4-diClPh | CO | Single bond or CH₂ | Sub-7 |
| 2-2024 | Sub-43 | 3,4-diClPh | CO | Single bond or CH₂ | Sub-8 |
| 2-2025 | Sub-43 | 3,4-diClPh | CO | Single bond or CH₂ | Sub-9 |
| 2-2026 | Sub-43 | 3,4-diClPh | CO | Single bond or CH₂ | Sub-10 |
| 2-2027 | Sub-43 | 3,4-diClPh | CO | Single bond or CH₂ | Sub-11 |
| 2-2028 | Sub-43 | 3,4-diClPh | CO | Single bond or CH₂ | Sub-12 |
| 2-2029 | Sub-43 | 3,4-diClPh | CO | Single bond or CH₂ | Sub-13 |
| 2-2030 | Sub-43 | 3,4-diClPh | CO | Single bond or CH₂ | Sub-14 |
| 2-2031 | Sub-43 | 3,4-diClPh | CO | Single bond or CH₂ | Sub-15 |
| 2-2032 | Sub-43 | 3,4-diClPh | CO | Single bond or CH₂ | Sub-16 |
| 2-2033 | Sub-43 | 3,4-diClPh | CO | Single bond or CH₂ | Sub-17 |
| 2-2034 | Sub-43 | 3,4-diClPh | CO | Single bond or CH₂ | Sub-18 |
| 2-2035 | Sub-43 | 3,4-diClPh | CO | Single bond or CH₂ | Sub-19 |
| 2-2036 | Sub-43 | 3,4-diClPh | CO | Single bond or CH₂ | Sub-20 |
| 2-2037 | Sub-43 | 3,4-diClPh | CO | Single bond or CH₂ | Sub-21 |
| 2-2038 | Sub-43 | 3,4-diClPh | CO | Single bond or CH₂ | Sub-22 |
| 2-2039 | Sub-43 | 3,4-diClPh | CO | Single bond or CH₂ | Sub-23 |
| 2-2040 | Sub-43 | 3,4-diClPh | CO | Single bond or CH₂ | Sub-24 |
| 2-2041 | Sub-43 | 3,4-diClPh | CO | Single bond or CH₂ | Sub-25 |
| 2-2042 | Sub-43 | 3,4-diClPh | CO | Single bond or CH₂ | Sub-26 |
| 2-2043 | Sub-43 | 3,4-diClPh | CO | Single bond or CH₂ | Sub-27 |
| 2-2044 | Sub-43 | 3,4-diClPh | CO | Single bond or CH₂ | Sub-28 |
| 2-2045 | Sub-43 | 3,4-diClPh | CO | Single bond or CH₂ | Sub-29 |
| 2-2046 | Sub-43 | 3,4-diClPh | CO | Single bond or CH₂ | Sub-30 |
| 2-2047 | Sub-43 | 3,4-diClPh | CO | Single bond or CH₂ | Sub-31 |
| 2-2048 | Sub-43 | 3,4-diClPh | CO | Single bond or CH₂ | Sub-32 |
| 2-2049 | Sub-43 | 3,4-diClPh | CO | Single bond or CH₂ | Sub-65 |
| 2-2050 | Sub-43 | 3,4-diClPh | CO | Single bond or CH₂ | Sub-66 |
| 2-2051 | Sub-43 | 3,4-diClPh | CO | Single bond or CH₂ | Sub-67 |
| 2-2052 | Sub-43 | 3,4-diClPh | CO | Single bond or CH₂ | Sub-68 |
| 2-2053 | Sub-43 | 3,4-diClPh | CO | Single bond or CH₂ | Sub-69 |
| 2-2054 | Sub-43 | 3,4-diClPh | CO | Single bond or CH₂ | Sub-70 |
| 2-2055 | Sub-43 | 3,4-diClPh | CO | Single bond or CH₂ | Sub-71 |
| 2-2056 | Sub-43 | 3,4-diClPh | CO | Single bond or CH₂ | Sub-72 |
| 2-2057 | Sub-43 | 3,4-diClPh | CO | Single bond or CH₂ | Sub-73 |
| 2-2058 | Sub-43 | 3,4-diClPh | CO | Single bond or CH₂ | Sub-74 |
| 2-2059 | Sub-43 | 3,4-diClPh | CO | Single bond or CH₂ | Sub-75 |
| 2-2060 | Sub-43 | 3,4-diClPh | CO | Single bond or CH₂ | Sub-76 |
| 2-2061 | Sub-43 | 3,4-diClPh | CO | Single bond or CH₂ | Sub-77 |
| 2-2062 | Sub-43 | 3,4-diClPh | CO | Single bond or CH₂ | Sub-78 |
| 2-2063 | Sub-43 | 3,4-diClPh | CO | Single bond or CH₂ | Sub-79 |
| 2-2064 | Sub-43 | 3,4-diClPh | CO | Single bond or CH₂ | Sub-80 |
| 2-2065 | Sub-44 | 3,4-diClPh | CO | Single bond or CH₂ | Sub-1 |
| 2-2066 | Sub-44 | 3,4-diClPh | CO | Single bond or CH₂ | Sub-2 |
| 2-2067 | Sub-44 | 3,4-diClPh | CO | Single bond or CH₂ | Sub-3 |
| 2-2068 | Sub-44 | 3,4-diClPh | CO | Single bond or CH₂ | Sub-4 |
| 2-2069 | Sub-44 | 3,4-diClPh | CO | Single bond or CH₂ | Sub-5 |
| 2-2070 | Sub-44 | 3,4-diClPh | CO | Single bond or CH₂ | Sub-6 |
| 2-2071 | Sub-44 | 3,4-diClPh | CO | Single bond or CH₂ | Sub-7 |
| 2-2072 | Sub-44 | 3,4-diClPh | CO | Single bond or CH₂ | Sub-8 |
| 2-2073 | Sub-44 | 3,4-diClPh | CO | Single bond or CH₂ | Sub-9 |
| 2-2074 | Sub-44 | 3,4-diClPh | CO | Single bond or CH₂ | Sub-10 |
| 2-2075 | Sub-44 | 3,4-diClPh | CO | Single bond or CH₂ | Sub-11 |
| 2-2076 | Sub-44 | 3,4-diClPh | CO | Single bond or CH₂ | Sub-12 |
| 2-2077 | Sub-44 | 3,4-diClPh | CO | Single bond or CH₂ | Sub-13 |
| 2-2078 | Sub-44 | 3,4-diClPh | CO | Single bond or CH₂ | Sub-14 |
| 2-2079 | Sub-44 | 3,4-diClPh | CO | Single bond or CH₂ | Sub-15 |
| 2-2080 | Sub-44 | 3,4-diClPh | CO | Single bond or CH₂ | Sub-16 |
| 2-2081 | Sub-44 | 3,4-diClPh | CO | Single bond or CH₂ | Sub-17 |
| 2-2082 | Sub-44 | 3,4-diClPh | CO | Single bond or CH₂ | Sub-18 |
| 2-2083 | Sub-44 | 3,4-diClPh | CO | Single bond or CH₂ | Sub-19 |
| 2-2084 | Sub-44 | 3,4-diClPh | CO | Single bond or CH₂ | Sub-20 |
| 2-2085 | Sub-44 | 3,4-diClPh | CO | Single bond or CH₂ | Sub-21 |
| 2-2086 | Sub-44 | 3,4-diClPh | CO | Single bond or CH₂ | Sub-22 |
| 2-2087 | Sub-44 | 3,4-diClPh | CO | Single bond or CH₂ | Sub-23 |
| 2-2088 | Sub-44 | 3,4-diClPh | CO | Single bond or CH₂ | Sub-24 |
| 2-2089 | Sub-44 | 3,4-diClPh | CO | Single bond or CH₂ | Sub-25 |
| 2-2090 | Sub-44 | 3,4-diClPh | CO | Single bond or CH₂ | Sub-26 |
| 2-2091 | Sub-44 | 3,4-diClPh | CO | Single bond or CH₂ | Sub-27 |
| 2-2092 | Sub-44 | 3,4-diClPh | CO | Single bond or CH₂ | Sub-28 |
| 2-2093 | Sub-44 | 3,4-diClPh | CO | Single bond or CH₂ | Sub-29 |
| 2-2094 | Sub-44 | 3,4-diClPh | CO | Single bond or CH₂ | Sub-30 |
| 2-2095 | Sub-44 | 3,4-diClPh | CO | Single bond or CH₂ | Sub-31 |
| 2-2096 | Sub-44 | 3,4-diClPh | CO | Single bond or CH₂ | Sub-32 |
| 2-2097 | Sub-44 | 3,4-diClPh | CO | Single bond or CH₂ | Sub-65 |
| 2-2098 | Sub-44 | 3,4-diClPh | CO | Single bond or CH₂ | Sub-66 |
| 2-2099 | Sub-44 | 3,4-diClPh | CO | Single bond or CH₂ | Sub-67 |
| 2-2100 | Sub-44 | 3,4-diClPh | CO | Single bond or CH₂ | Sub-68 |
| 2-2101 | Sub-44 | 3,4-diClPh | CO | Single bond or CH₂ | Sub-69 |
| 2-2102 | Sub-44 | 3,4-diClPh | CO | Single bond or CH₂ | Sub-70 |
| 2-2103 | Sub-44 | 3,4-diClPh | CO | Single bond or CH₂ | Sub-71 |
| 2-2104 | Sub-44 | 3,4-diClPh | CO | Single bond or CH₂ | Sub-72 |
| 2-2105 | Sub-44 | 3,4-diClPh | CO | Single bond or CH₂ | Sub-73 |
| 2-2106 | Sub-44 | 3,4-diClPh | CO | Single bond or CH₂ | Sub-74 |
| 2-2107 | Sub-44 | 3,4-diClPh | CO | Single bond or CH₂ | Sub-75 |
| 2-2108 | Sub-44 | 3,4-diClPh | CO | Single bond or CH₂ | Sub-76 |
| 2-2109 | Sub-44 | 3,4-diClPh | CO | Single bond or CH₂ | Sub-77 |
| 2-2110 | Sub-44 | 3,4-diClPh | CO | Single bond or CH₂ | Sub-78 |
| 2-2111 | Sub-44 | 3,4-diClPh | CO | Single bond or CH₂ | Sub-79 |
| 2-2112 | Sub-44 | 3,4-diClPh | CO | Single bond or CH₂ | Sub-80 |
| 2-2113 | Sub-45 | 3,4-diClPh | CO | Single bond or CH₂ | Sub-1 |
| 2-2114 | Sub-45 | 3,4-diClPh | CO | Single bond or CH₂ | Sub-2 |
| 2-2115 | Sub-45 | 3,4-diClPh | CO | Single bond or CH₂ | Sub-3 |
| 2-2116 | Sub-45 | 3,4-diClPh | CO | Single bond or CH₂ | Sub-4 |
| 2-2117 | Sub-45 | 3,4-diClPh | CO | Single bond or CH₂ | Sub-5 |
| 2-2118 | Sub-45 | 3,4-diClPh | CO | Single bond or CH₂ | Sub-6 |
| 2-2119 | Sub-45 | 3,4-diClPh | CO | Single bond or CH₂ | Sub-7 |
| 2-2120 | Sub-45 | 3,4-diClPh | CO | Single bond or CH₂ | Sub-8 |
| 2-2121 | Sub-45 | 3,4-diClPh | CO | Single bond or CH₂ | Sub-9 |
| 2-2122 | Sub-45 | 3,4-diClPh | CO | Single bond or CH₂ | Sub-10 |
| 2-2123 | Sub-45 | 3,4-diClPh | CO | Single bond or CH₂ | Sub-11 |
| 2-2124 | Sub-45 | 3,4-diClPh | CO | Single bond or CH₂ | Sub-12 |
| 2-2125 | Sub-45 | 3,4-diClPh | CO | Single bond or CH₂ | Sub-13 |
| 2-2126 | Sub-45 | 3,4-diClPh | CO | Single bond or CH₂ | Sub-14 |
| 2-2127 | Sub-45 | 3,4-diClPh | CO | Single bond or CH₂ | Sub-15 |
| 2-2128 | Sub-45 | 3,4-diClPh | CO | Single bond or CH₂ | Sub-16 |

TABLE 2-continued

| Cpd. No. | R¹ | R² | A | B | Z |
|---|---|---|---|---|---|
| 2-2129 | Sub-45 | 3,4-diClPh | CO | Single bond or CH₂ | Sub-17 |
| 2-2130 | Sub-45 | 3,4-diClPh | CO | Single bond or CH₂ | Sub-18 |
| 2-2131 | Sub-45 | 3,4-diClPh | CO | Single bond or CH₂ | Sub-19 |
| 2-2132 | Sub-45 | 3,4-diClPh | CO | Single bond or CH₂ | Sub-20 |
| 2-2133 | Sub-45 | 3,4-diClPh | CO | Single bond or CH₂ | Sub-21 |
| 2-2134 | Sub-45 | 3,4-diClPh | CO | Single bond or CH₂ | Sub-22 |
| 2-2135 | Sub-45 | 3,4-diClPh | CO | Single bond or CH₂ | Sub-23 |
| 2-2136 | Sub-45 | 3,4-diClPh | CO | Single bond or CH₂ | Sub-24 |
| 2-2137 | Sub-45 | 3,4-diClPh | CO | Single bond or CH₂ | Sub-25 |
| 2-2138 | Sub-45 | 3,4-diClPh | CO | Single bond or CH₂ | Sub-26 |
| 2-2139 | Sub-45 | 3,4-diClPh | CO | Single bond or CH₂ | Sub-27 |
| 2-2140 | Sub-45 | 3,4-diClPh | CO | Single bond or CH₂ | Sub-28 |
| 2-2141 | Sub-45 | 3,4-diClPh | CO | Single bond or CH₂ | Sub-29 |
| 2-2142 | Sub-45 | 3,4-diClPh | CO | Single bond or CH₂ | Sub-30 |
| 2-2143 | Sub-45 | 3,4-diClPh | CO | Single bond or CH₂ | Sub-31 |
| 2-2144 | Sub-45 | 3,4-diClPh | CO | Single bond or CH₂ | Sub-32 |
| 2-2145 | Sub-45 | 3,4-diClPh | CO | Single bond or CH₂ | Sub-65 |
| 2-2146 | Sub-45 | 3,4-diClPh | CO | Single bond or CH₂ | Sub-66 |
| 2-2147 | Sub-45 | 3,4-diClPh | CO | Single bond or CH₂ | Sub-67 |
| 2-2148 | Sub-45 | 3,4-diClPh | CO | Single bond or CH₂ | Sub-68 |
| 2-2149 | Sub-45 | 3,4-diClPh | CO | Single bond or CH₂ | Sub-69 |
| 2-2150 | Sub-45 | 3,4-diClPh | CO | Single bond or CH₂ | Sub-70 |
| 2-2151 | Sub-45 | 3,4-diClPh | CO | Single bond or CH₂ | Sub-71 |
| 2-2152 | Sub-45 | 3,4-diClPh | CO | Single bond or CH₂ | Sub-72 |
| 2-2153 | Sub-45 | 3,4-diClPh | CO | Single bond or CH₂ | Sub-73 |
| 2-2154 | Sub-45 | 3,4-diClPh | CO | Single bond or CH₂ | Sub-74 |
| 2-2155 | Sub-45 | 3,4-diClPh | CO | Single bond or CH₂ | Sub-75 |
| 2-2156 | Sub-45 | 3,4-diClPh | CO | Single bond or CH₂ | Sub-76 |
| 2-2157 | Sub-45 | 3,4-diClPh | CO | Single bond or CH₂ | Sub-77 |
| 2-2158 | Sub-45 | 3,4-diClPh | CO | Single bond or CH₂ | Sub-78 |
| 2-2159 | Sub-45 | 3,4-diClPh | CO | Single bond or CH₂ | Sub-79 |
| 2-2160 | Sub-45 | 3,4-diClPh | CO | Single bond or CH₂ | Sub-80 |
| 2-2161 | Sub-46 | 3,4-diClPh | CO | Single bond or CH₂ | Sub-1 |
| 2-2162 | Sub-46 | 3,4-diClPh | CO | Single bond or CH₂ | Sub-2 |
| 2-2163 | Sub-46 | 3,4-diClPh | CO | Single bond or CH₂ | Sub-3 |
| 2-2164 | Sub-46 | 3,4-diClPh | CO | Single bond or CH₂ | Sub-4 |
| 2-2165 | Sub-46 | 3,4-diClPh | CO | Single bond or CH₂ | Sub-5 |
| 2-2166 | Sub-46 | 3,4-diClPh | CO | Single bond or CH₂ | Sub-6 |
| 2-2167 | Sub-46 | 3,4-diClPh | CO | Single bond or CH₂ | Sub-7 |
| 2-2168 | Sub-46 | 3,4-diClPh | CO | Single bond or CH₂ | Sub-8 |
| 2-2169 | Sub-46 | 3,4-diClPh | CO | Single bond or CH₂ | Sub-9 |
| 2-2170 | Sub-46 | 3,4-diClPh | CO | Single bond or CH₂ | Sub-10 |
| 2-2171 | Sub-46 | 3,4-diClPh | CO | Single bond or CH₂ | Sub-11 |
| 2-2172 | Sub-46 | 3,4-diClPh | CO | Single bond or CH₂ | Sub-12 |
| 2-2173 | Sub-46 | 3,4-diClPh | CO | Single bond or CH₂ | Sub-13 |
| 2-2174 | Sub-46 | 3,4-diClPh | CO | Single bond or CH₂ | Sub-14 |
| 2-2175 | Sub-46 | 3,4-diClPh | CO | Single bond or CH₂ | Sub-15 |
| 2-2176 | Sub-46 | 3,4-diClPh | CO | Single bond or CH₂ | Sub-16 |
| 2-2177 | Sub-46 | 3,4-diClPh | CO | Single bond or CH₂ | Sub-17 |
| 2-2178 | Sub-46 | 3,4-diClPh | CO | Single bond or CH₂ | Sub-18 |
| 2-2179 | Sub-46 | 3,4-diClPh | CO | Single bond or CH₂ | Sub-19 |
| 2-2180 | Sub-46 | 3,4-diClPh | CO | Single bond or CH₂ | Sub-20 |
| 2-2181 | Sub-46 | 3,4-diClPh | CO | Single bond or CH₂ | Sub-21 |
| 2-2182 | Sub-46 | 3,4-diClPh | CO | Single bond or CH₂ | Sub-22 |
| 2-2183 | Sub-46 | 3,4-diClPh | CO | Single bond or CH₂ | Sub-23 |
| 2-2184 | Sub-46 | 3,4-diClPh | CO | Single bond or CH₂ | Sub-24 |
| 2-2185 | Sub-46 | 3,4-diClPh | CO | Single bond or CH₂ | Sub-25 |
| 2-2186 | Sub-46 | 3,4-diClPh | CO | Single bond or CH₂ | Sub-26 |
| 2-2187 | Sub-46 | 3,4-diClPh | CO | Single bond or CH₂ | Sub-27 |
| 2-2188 | Sub-46 | 3,4-diClPh | CO | Single bond or CH₂ | Sub-28 |
| 2-2189 | Sub-46 | 3,4-diClPh | CO | Single bond or CH₂ | Sub-29 |
| 2-2190 | Sub-46 | 3,4-diClPh | CO | Single bond or CH₂ | Sub-30 |
| 2-2191 | Sub-46 | 3,4-diClPh | CO | Single bond or CH₂ | Sub-31 |
| 2-2192 | Sub-46 | 3,4-diClPh | CO | Single bond or CH₂ | Sub-32 |
| 2-2193 | Sub-46 | 3,4-diClPh | CO | Single bond or CH₂ | Sub-65 |
| 2-2194 | Sub-46 | 3,4-diClPh | CO | Single bond or CH₂ | Sub-66 |
| 2-2195 | Sub-46 | 3,4-diClPh | CO | Single bond or CH₂ | Sub-67 |
| 2-2196 | Sub-46 | 3,4-diClPh | CO | Single bond or CH₂ | Sub-68 |
| 2-2197 | Sub-46 | 3,4-diClPh | CO | Single bond or CH₂ | Sub-69 |
| 2-2198 | Sub-46 | 3,4-diClPh | CO | Single bond or CH₂ | Sub-70 |
| 2-2199 | Sub-46 | 3,4-diClPh | CO | Single bond or CH₂ | Sub-71 |
| 2-2200 | Sub-46 | 3,4-diClPh | CO | Single bond or CH₂ | Sub-72 |
| 2-2201 | Sub-46 | 3,4-diClPh | CO | Single bond or CH₂ | Sub-73 |
| 2-2202 | Sub-46 | 3,4-diClPh | CO | Single bond or CH₂ | Sub-74 |
| 2-2203 | Sub-46 | 3,4-diClPh | CO | Single bond or CH₂ | Sub-75 |
| 2-2204 | Sub-46 | 3,4-diClPh | CO | Single bond or CH₂ | Sub-76 |
| 2-2205 | Sub-46 | 3,4-diClPh | CO | Single bond or CH₂ | Sub-77 |
| 2-2206 | Sub-46 | 3,4-diClPh | CO | Single bond or CH₂ | Sub-78 |
| 2-2207 | Sub-46 | 3,4-diClPh | CO | Single bond or CH₂ | Sub-79 |
| 2-2208 | Sub-46 | 3,4-diClPh | CO | Single bond or CH₂ | Sub-80 |
| 2-2209 | Sub-47 | 3,4-diClPh | CO | Single bond or CH₂ | Sub-1 |
| 2-2210 | Sub-47 | 3,4-diClPh | CO | Single bond or CH₂ | Sub-2 |
| 2-2211 | Sub-47 | 3,4-diClPh | CO | Single bond or CH₂ | Sub-3 |
| 2-2212 | Sub-47 | 3,4-diClPh | CO | Single bond or CH₂ | Sub-4 |
| 2-2213 | Sub-47 | 3,4-diClPh | CO | Single bond or CH₂ | Sub-5 |
| 2-2214 | Sub-47 | 3,4-diClPh | CO | Single bond or CH₂ | Sub-6 |
| 2-2215 | Sub-47 | 3,4-diClPh | CO | Single bond or CH₂ | Sub-7 |
| 2-2216 | Sub-47 | 3,4-diClPh | CO | Single bond or CH₂ | Sub-8 |
| 2-2217 | Sub-47 | 3,4-diClPh | CO | Single bond or CH₂ | Sub-9 |
| 2-2218 | Sub-47 | 3,4-diClPh | CO | Single bond or CH₂ | Sub-10 |
| 2-2219 | Sub-47 | 3,4-diClPh | CO | Single bond or CH₂ | Sub-11 |
| 2-2220 | Sub-47 | 3,4-diClPh | CO | Single bond or CH₂ | Sub-12 |
| 2-2221 | Sub-47 | 3,4-diClPh | CO | Single bond or CH₂ | Sub-13 |
| 2-2222 | Sub-47 | 3,4-diClPh | CO | Single bond or CH₂ | Sub-14 |
| 2-2223 | Sub-47 | 3,4-diClPh | CO | Single bond or CH₂ | Sub-15 |
| 2-2224 | Sub-47 | 3,4-diClPh | CO | Single bond or CH₂ | Sub-16 |
| 2-2225 | Sub-47 | 3,4-diClPh | CO | Single bond or CH₂ | Sub-17 |
| 2-2226 | Sub-47 | 3,4-diClPh | CO | Single bond or CH₂ | Sub-18 |
| 2-2227 | Sub-47 | 3,4-diClPh | CO | Single bond or CH₂ | Sub-19 |
| 2-2228 | Sub-47 | 3,4-diClPh | CO | Single bond or CH₂ | Sub-20 |
| 2-2229 | Sub-47 | 3,4-diClPh | CO | Single bond or CH₂ | Sub-21 |
| 2-2230 | Sub-47 | 3,4-diClPh | CO | Single bond or CH₂ | Sub-22 |
| 2-2231 | Sub-47 | 3,4-diClPh | CO | Single bond or CH₂ | Sub-23 |
| 2-2232 | Sub-47 | 3,4-diClPh | CO | Single bond or CH₂ | Sub-24 |
| 2-2233 | Sub-47 | 3,4-diClPh | CO | Single bond or CH₂ | Sub-25 |
| 2-2234 | Sub-47 | 3,4-diClPh | CO | Single bond or CH₂ | Sub-26 |
| 2-2235 | Sub-47 | 3,4-diClPh | CO | Single bond or CH₂ | Sub-27 |
| 2-2236 | Sub-47 | 3,4-diClPh | CO | Single bond or CH₂ | Sub-28 |
| 2-2237 | Sub-47 | 3,4-diClPh | CO | Single bond or CH₂ | Sub-29 |
| 2-2238 | Sub-47 | 3,4-diClPh | CO | Single bond or CH₂ | Sub-30 |
| 2-2239 | Sub-47 | 3,4-diClPh | CO | Single bond or CH₂ | Sub-31 |
| 2-2240 | Sub-47 | 3,4-diClPh | CO | Single bond or CH₂ | Sub-32 |
| 2-2241 | Sub-47 | 3,4-diClPh | CO | Single bond or CH₂ | Sub-65 |
| 2-2242 | Sub-47 | 3,4-diClPh | CO | Single bond or CH₂ | Sub-66 |
| 2-2243 | Sub-47 | 3,4-diClPh | CO | Single bond or CH₂ | Sub-67 |
| 2-2244 | Sub-47 | 3,4-diClPh | CO | Single bond or CH₂ | Sub-68 |
| 2-2245 | Sub-47 | 3,4-diClPh | CO | Single bond or CH₂ | Sub-69 |
| 2-2246 | Sub-47 | 3,4-diClPh | CO | Single bond or CH₂ | Sub-70 |
| 2-2247 | Sub-47 | 3,4-diClPh | CO | Single bond or CH₂ | Sub-71 |
| 2-2248 | Sub-47 | 3,4-diClPh | CO | Single bond or CH₂ | Sub-72 |
| 2-2249 | Sub-47 | 3,4-diClPh | CO | Single bond or CH₂ | Sub-73 |
| 2-2250 | Sub-47 | 3,4-diClPh | CO | Single bond or CH₂ | Sub-74 |
| 2-2251 | Sub-47 | 3,4-diClPh | CO | Single bond or CH₂ | Sub-75 |
| 2-2252 | Sub-47 | 3,4-diClPh | CO | Single bond or CH₂ | Sub-76 |
| 2-2253 | Sub-47 | 3,4-diClPh | CO | Single bond or CH₂ | Sub-77 |
| 2-2254 | Sub-47 | 3,4-diClPh | CO | Single bond or CH₂ | Sub-78 |
| 2-2255 | Sub-47 | 3,4-diClPh | CO | Single bond or CH₂ | Sub-79 |
| 2-2256 | Sub-47 | 3,4-diClPh | CO | Single bond or CH₂ | Sub-80 |
| 2-2257 | Sub-81 | 3,4-diClPh | CO | Single bond or CH₂ | Sub-1 |
| 2-2258 | Sub-81 | 3,4-diClPh | CO | Single bond or CH₂ | Sub-2 |
| 2-2259 | Sub-81 | 3,4-diClPh | CO | Single bond or CH₂ | Sub-3 |
| 2-2260 | Sub-81 | 3,4-diClPh | CO | Single bond or CH₂ | Sub-4 |
| 2-2261 | Sub-81 | 3,4-diClPh | CO | Single bond or CH₂ | Sub-5 |
| 2-2262 | Sub-81 | 3,4-diClPh | CO | Single bond or CH₂ | Sub-6 |
| 2-2263 | Sub-81 | 3,4-diClPh | CO | Single bond or CH₂ | Sub-7 |
| 2-2264 | Sub-81 | 3,4-diClPh | CO | Single bond or CH₂ | Sub-8 |
| 2-2265 | Sub-81 | 3,4-diClPh | CO | Single bond or CH₂ | Sub-9 |
| 2-2266 | Sub-81 | 3,4-diClPh | CO | Single bond or CH₂ | Sub-10 |
| 2-2267 | Sub-81 | 3,4-diClPh | CO | Single bond or CH₂ | Sub-11 |
| 2-2268 | Sub-81 | 3,4-diClPh | CO | Single bond or CH₂ | Sub-12 |
| 2-2269 | Sub-81 | 3,4-diClPh | CO | Single bond or CH₂ | Sub-13 |
| 2-2270 | Sub-81 | 3,4-diClPh | CO | Single bond or CH₂ | Sub-14 |
| 2-2271 | Sub-81 | 3,4-diClPh | CO | Single bond or CH₂ | Sub-15 |
| 2-2272 | Sub-81 | 3,4-diClPh | CO | Single bond or CH₂ | Sub-16 |
| 2-2273 | Sub-81 | 3,4-diClPh | CO | Single bond or CH₂ | Sub-17 |
| 2-2274 | Sub-81 | 3,4-diClPh | CO | Single bond or CH₂ | Sub-18 |
| 2-2275 | Sub-81 | 3,4-diClPh | CO | Single bond or CH₂ | Sub-19 |
| 2-2276 | Sub-81 | 3,4-diClPh | CO | Single bond or CH₂ | Sub-20 |
| 2-2277 | Sub-81 | 3,4-diClPh | CO | Single bond or CH₂ | Sub-21 |
| 2-2278 | Sub-81 | 3,4-diClPh | CO | Single bond or CH₂ | Sub-22 |
| 2-2279 | Sub-81 | 3,4-diClPh | CO | Single bond or CH₂ | Sub-23 |
| 2-2280 | Sub-81 | 3,4-diClPh | CO | Single bond or CH₂ | Sub-24 |
| 2-2281 | Sub-81 | 3,4-diClPh | CO | Single bond or CH₂ | Sub-25 |
| 2-2282 | Sub-81 | 3,4-diClPh | CO | Single bond or CH₂ | Sub-26 |

TABLE 2-continued

| Cpd. No. | R¹ | R² | A | B | Z |
|---|---|---|---|---|---|
| 2-2283 | Sub-81 | 3,4-diClPh | CO | Single bond or CH$_2$ | Sub-27 |
| 2-2284 | Sub-81 | 3,4-diClPh | CO | Single bond or CH$_2$ | Sub-28 |
| 2-2285 | Sub-81 | 3,4-diClPh | CO | Single bond or CH$_2$ | Sub-29 |
| 2-2286 | Sub-81 | 3,4-diClPh | CO | Single bond or CH$_2$ | Sub-30 |
| 2-2287 | Sub-81 | 3,4-diClPh | CO | Single bond or CH$_2$ | Sub-31 |
| 2-2288 | Sub-81 | 3,4-diClPh | CO | Single bond or CH$_2$ | Sub-32 |
| 2-2289 | Sub-81 | 3,4-diClPh | CO | Single bond or CH$_2$ | Sub-65 |
| 2-2290 | Sub-81 | 3,4-diClPh | CO | Single bond or CH$_2$ | Sub-66 |
| 2-2291 | Sub-81 | 3,4-diClPh | CO | Single bond or CH$_2$ | Sub-67 |
| 2-2292 | Sub-81 | 3,4-diClPh | CO | Single bond or CH$_2$ | Sub-68 |
| 2-2293 | Sub-81 | 3,4-diClPh | CO | Single bond or CH$_2$ | Sub-69 |
| 2-2294 | Sub-81 | 3,4-diClPh | CO | Single bond or CH$_2$ | Sub-70 |
| 2-2295 | Sub-81 | 3,4-diClPh | CO | Single bond or CH$_2$ | Sub-71 |
| 2-2296 | Sub-81 | 3,4-diClPh | CO | Single bond or CH$_2$ | Sub-72 |
| 2-2297 | Sub-81 | 3,4-diClPh | CO | Single bond or CH$_2$ | Sub-73 |
| 2-2298 | Sub-81 | 3,4-diClPh | CO | Single bond or CH$_2$ | Sub-74 |
| 2-2299 | Sub-81 | 3,4-diClPh | CO | Single bond or CH$_2$ | Sub-75 |
| 2-2300 | Sub-81 | 3,4-diClPh | CO | Single bond or CH$_2$ | Sub-76 |
| 2-2301 | Sub-81 | 3,4-diClPh | CO | Single bond or CH$_2$ | Sub-77 |
| 2-2302 | Sub-81 | 3,4-diClPh | CO | Single bond or CH$_2$ | Sub-78 |
| 2-2303 | Sub-81 | 3,4-diClPh | CO | Single bond or CH$_2$ | Sub-79 |
| 2-2304 | Sub-81 | 3,4-diClPh | CO | Single bond or CH$_2$ | Sub-80 |
| 2-2305 | Sub-48 | 3,4-diClPh | CO | Single bond or CH$_2$ | Sub-1 |
| 2-2306 | Sub-48 | 3,4-diClPh | CO | Single bond or CH$_2$ | Sub-2 |
| 2-2307 | Sub-48 | 3,4-diClPh | CO | Single bond or CH$_2$ | Sub-3 |
| 2-2308 | Sub-48 | 3,4-diClPh | CO | Single bond or CH$_2$ | Sub-4 |
| 2-2309 | Sub-48 | 3,4-diClPh | CO | Single bond or CH$_2$ | Sub-5 |
| 2-2310 | Sub-48 | 3,4-diClPh | CO | Single bond or CH$_2$ | Sub-6 |
| 2-2311 | Sub-48 | 3,4-diClPh | CO | Single bond or CH$_2$ | Sub-7 |
| 2-2312 | Sub-48 | 3,4-diClPh | CO | Single bond or CH$_2$ | Sub-8 |
| 2-2313 | Sub-48 | 3,4-diClPh | CO | Single bond or CH$_2$ | Sub-9 |
| 2-2314 | Sub-48 | 3,4-diClPh | CO | Single bond or CH$_2$ | Sub-10 |
| 2-2315 | Sub-48 | 3,4-diClPh | CO | Single bond or CH$_2$ | Sub-11 |
| 2-2316 | Sub-48 | 3,4-diClPh | CO | Single bond or CH$_2$ | Sub-12 |
| 2-2317 | Sub-48 | 3,4-diClPh | CO | Single bond or CH$_2$ | Sub-13 |
| 2-2318 | Sub-48 | 3,4-diClPh | CO | Single bond or CH$_2$ | Sub-14 |
| 2-2319 | Sub-48 | 3,4-diClPh | CO | Single bond or CH$_2$ | Sub-15 |
| 2-2320 | Sub-48 | 3,4-diClPh | CO | Single bond or CH$_2$ | Sub-16 |
| 2-2321 | Sub-48 | 3,4-diClPh | CO | Single bond or CH$_2$ | Sub-17 |
| 2-2322 | Sub-48 | 3,4-diClPh | CO | Single bond or CH$_2$ | Sub-18 |
| 2-2323 | Sub-48 | 3,4-diClPh | CO | Single bond or CH$_2$ | Sub-19 |
| 2-2324 | Sub-48 | 3,4-diClPh | CO | Single bond or CH$_2$ | Sub-20 |
| 2-2325 | Sub-48 | 3,4-diClPh | CO | Single bond or CH$_2$ | Sub-21 |
| 2-2326 | Sub-48 | 3,4-diClPh | CO | Single bond or CH$_2$ | Sub-22 |
| 2-2327 | Sub-48 | 3,4-diClPh | CO | Single bond or CH$_2$ | Sub-23 |
| 2-2328 | Sub-48 | 3,4-diClPh | CO | Single bond or CH$_2$ | Sub-24 |
| 2-2329 | Sub-48 | 3,4-diClPh | CO | Single bond or CH$_2$ | Sub-25 |
| 2-2330 | Sub-48 | 3,4-diClPh | CO | Single bond or CH$_2$ | Sub-26 |
| 2-2331 | Sub-48 | 3,4-diClPh | CO | Single bond or CH$_2$ | Sub-27 |
| 2-2332 | Sub-48 | 3,4-diClPh | CO | Single bond or CH$_2$ | Sub-28 |
| 2-2333 | Sub-48 | 3,4-diClPh | CO | Single bond or CH$_2$ | Sub-29 |
| 2-2334 | Sub-48 | 3,4-diClPh | CO | Single bond or CH$_2$ | Sub-30 |
| 2-2335 | Sub-48 | 3,4-diClPh | CO | Single bond or CH$_2$ | Sub-31 |
| 2-2336 | Sub-48 | 3,4-diClPh | CO | Single bond or CH$_2$ | Sub-32 |
| 2-2337 | Sub-48 | 3,4-diClPh | CO | Single bond or CH$_2$ | Sub-65 |
| 2-2338 | Sub-48 | 3,4-diClPh | CO | Single bond or CH$_2$ | Sub-66 |
| 2-2339 | Sub-48 | 3,4-diClPh | CO | Single bond or CH$_2$ | Sub-67 |
| 2-2340 | Sub-48 | 3,4-diClPh | CO | Single bond or CH$_2$ | Sub-68 |
| 2-2341 | Sub-48 | 3,4-diClPh | CO | Single bond or CH$_2$ | Sub-69 |
| 2-2342 | Sub-48 | 3,4-diClPh | CO | Single bond or CH$_2$ | Sub-70 |
| 2-2343 | Sub-48 | 3,4-diClPh | CO | Single bond or CH$_2$ | Sub-71 |
| 2-2344 | Sub-48 | 3,4-diClPh | CO | Single bond or CH$_2$ | Sub-72 |
| 2-2345 | Sub-48 | 3,4-diClPh | CO | Single bond or CH$_2$ | Sub-73 |
| 2-2346 | Sub-48 | 3,4-diClPh | CO | Single bond or CH$_2$ | Sub-74 |
| 2-2347 | Sub-48 | 3,4-diClPh | CO | Single bond or CH$_2$ | Sub-75 |
| 2-2348 | Sub-48 | 3,4-diClPh | CO | Single bond or CH$_2$ | Sub-76 |
| 2-2349 | Sub-48 | 3,4-diClPh | CO | Single bond or CH$_2$ | Sub-77 |
| 2-2350 | Sub-48 | 3,4-diClPh | CO | Single bond or CH$_2$ | Sub-78 |
| 2-2351 | Sub-48 | 3,4-diClPh | CO | Single bond or CH$_2$ | Sub-79 |
| 2-2352 | Sub-48 | 3,4-diClPh | CO | Single bond or CH$_2$ | Sub-80 |
| 2-2353 | Sub-49 | 3,4-diClPh | CO | Single bond or CH$_2$ | Sub-1 |
| 2-2354 | Sub-49 | 3,4-diClPh | CO | Single bond or CH$_2$ | Sub-2 |
| 2-2355 | Sub-49 | 3,4-diClPh | CO | Single bond or CH$_2$ | Sub-3 |
| 2-2356 | Sub-49 | 3,4-diClPh | CO | Single bond or CH$_2$ | Sub-4 |
| 2-2357 | Sub-49 | 3,4-diClPh | CO | Single bond or CH$_2$ | Sub-5 |
| 2-2358 | Sub-49 | 3,4-diClPh | CO | Single bond or CH$_2$ | Sub-6 |
| 2-2359 | Sub-49 | 3,4-diClPh | CO | Single bond or CH$_2$ | Sub-7 |
| 2-2360 | Sub-49 | 3,4-diClPh | CO | Single bond or CH$_2$ | Sub-8 |
| 2-2361 | Sub-49 | 3,4-diClPh | CO | Single bond or CH$_2$ | Sub-9 |
| 2-2362 | Sub-49 | 3,4-diClPh | CO | Single bond or CH$_2$ | Sub-10 |
| 2-2363 | Sub-49 | 3,4-diClPh | CO | Single bond or CH$_2$ | Sub-11 |
| 2-2364 | Sub-49 | 3,4-diClPh | CO | Single bond or CH$_2$ | Sub-12 |
| 2-2365 | Sub-49 | 3,4-diClPh | CO | Single bond or CH$_2$ | Sub-13 |
| 2-2366 | Sub-49 | 3,4-diClPh | CO | Single bond or CH$_2$ | Sub-14 |
| 2-2367 | Sub-49 | 3,4-diClPh | CO | Single bond or CH$_2$ | Sub-15 |
| 2-2368 | Sub-49 | 3,4-diClPh | CO | Single bond or CH$_2$ | Sub-16 |
| 2-2369 | Sub-49 | 3,4-diClPh | CO | Single bond or CH$_2$ | Sub-17 |
| 2-2370 | Sub-49 | 3,4-diClPh | CO | Single bond or CH$_2$ | Sub-18 |
| 2-2371 | Sub-49 | 3,4-diClPh | CO | Single bond or CH$_2$ | Sub-19 |
| 2-2372 | Sub-49 | 3,4-diClPh | CO | Single bond or CH$_2$ | Sub-20 |
| 2-2373 | Sub-49 | 3,4-diClPh | CO | Single bond or CH$_2$ | Sub-21 |
| 2-2374 | Sub-49 | 3,4-diClPh | CO | Single bond or CH$_2$ | Sub-22 |
| 2-2375 | Sub-49 | 3,4-diClPh | CO | Single bond or CH$_2$ | Sub-23 |
| 2-2376 | Sub-49 | 3,4-diClPh | CO | Single bond or CH$_2$ | Sub-24 |
| 2-2377 | Sub-49 | 3,4-diClPh | CO | Single bond or CH$_2$ | Sub-25 |
| 2-2378 | Sub-49 | 3,4-diClPh | CO | Single bond or CH$_2$ | Sub-26 |
| 2-2379 | Sub-49 | 3,4-diClPh | CO | Single bond or CH$_2$ | Sub-27 |
| 2-2380 | Sub-49 | 3,4-diClPh | CO | Single bond or CH$_2$ | Sub-28 |
| 2-2381 | Sub-49 | 3,4-diClPh | CO | Single bond or CH$_2$ | Sub-29 |
| 2-2382 | Sub-49 | 3,4-diClPh | CO | Single bond or CH$_2$ | Sub-30 |
| 2-2383 | Sub-49 | 3,4-diClPh | CO | Single bond or CH$_2$ | Sub-31 |
| 2-2384 | Sub-49 | 3,4-diClPh | CO | Single bond or CH$_2$ | Sub-32 |
| 2-2385 | Sub-49 | 3,4-diClPh | CO | Single bond or CH$_2$ | Sub-65 |
| 2-2386 | Sub-49 | 3,4-diClPh | CO | Single bond or CH$_2$ | Sub-66 |
| 2-2387 | Sub-49 | 3,4-diClPh | CO | Single bond or CH$_2$ | Sub-67 |
| 2-2388 | Sub-49 | 3,4-diClPh | CO | Single bond or CH$_2$ | Sub-68 |
| 2-2389 | Sub-49 | 3,4-diClPh | CO | Single bond or CH$_2$ | Sub-69 |
| 2-2390 | Sub-49 | 3,4-diClPh | CO | Single bond or CH$_2$ | Sub-70 |
| 2-2391 | Sub-49 | 3,4-diClPh | CO | Single bond or CH$_2$ | Sub-71 |
| 2-2392 | Sub-49 | 3,4-diClPh | CO | Single bond or CH$_2$ | Sub-72 |
| 2-2393 | Sub-49 | 3,4-diClPh | CO | Single bond or CH$_2$ | Sub-73 |
| 2-2394 | Sub-49 | 3,4-diClPh | CO | Single bond or CH$_2$ | Sub-74 |
| 2-2395 | Sub-49 | 3,4-diClPh | CO | Single bond or CH$_2$ | Sub-75 |
| 2-2396 | Sub-49 | 3,4-diClPh | CO | Single bond or CH$_2$ | Sub-76 |
| 2-2397 | Sub-49 | 3,4-diClPh | CO | Single bond or CH$_2$ | Sub-77 |
| 2-2398 | Sub-49 | 3,4-diClPh | CO | Single bond or CH$_2$ | Sub-78 |
| 2-2399 | Sub-49 | 3,4-diClPh | CO | Single bond or CH$_2$ | Sub-79 |
| 2-2400 | Sub-49 | 3,4-diClPh | CO | Single bond or CH$_2$ | Sub-80 |
| 2-2401 | Sub-50 | 3,4-diClPh | CO | Single bond or CH$_2$ | Sub-1 |
| 2-2402 | Sub-50 | 3,4-diClPh | CO | Single bond or CH$_2$ | Sub-2 |
| 2-2403 | Sub-50 | 3,4-diClPh | CO | Single bond or CH$_2$ | Sub-3 |
| 2-2404 | Sub-50 | 3,4-diClPh | CO | Single bond or CH$_2$ | Sub-4 |
| 2-2405 | Sub-50 | 3,4-diClPh | CO | Single bond or CH$_2$ | Sub-5 |
| 2-2406 | Sub-50 | 3,4-diClPh | CO | Single bond or CH$_2$ | Sub-6 |
| 2-2407 | Sub-50 | 3,4-diClPh | CO | Single bond or CH$_2$ | Sub-7 |
| 2-2408 | Sub-50 | 3,4-diClPh | CO | Single bond or CH$_2$ | Sub-8 |
| 2-2409 | Sub-50 | 3,4-diClPh | CO | Single bond or CH$_2$ | Sub-9 |
| 2-2410 | Sub-50 | 3,4-diClPh | CO | Single bond or CH$_2$ | Sub-10 |
| 2-2411 | Sub-50 | 3,4-diClPh | CO | Single bond or CH$_2$ | Sub-11 |
| 2-2412 | Sub-50 | 3,4-diClPh | CO | Single bond or CH$_2$ | Sub-12 |
| 2-2413 | Sub-50 | 3,4-diClPh | CO | Single bond or CH$_2$ | Sub-13 |
| 2-2414 | Sub-50 | 3,4-diClPh | CO | Single bond or CH$_2$ | Sub-14 |
| 2-2415 | Sub-50 | 3,4-diClPh | CO | Single bond or CH$_2$ | Sub-15 |
| 2-2416 | Sub-50 | 3,4-diClPh | CO | Single bond or CH$_2$ | Sub-16 |
| 2-2417 | Sub-50 | 3,4-diClPh | CO | Single bond or CH$_2$ | Sub-17 |
| 2-2418 | Sub-50 | 3,4-diClPh | CO | Single bond or CH$_2$ | Sub-18 |
| 2-2419 | Sub-50 | 3,4-diClPh | CO | Single bond or CH$_2$ | Sub-19 |
| 2-2420 | Sub-50 | 3,4-diClPh | CO | Single bond or CH$_2$ | Sub-20 |
| 2-2421 | Sub-50 | 3,4-diClPh | CO | Single bond or CH$_2$ | Sub-21 |
| 2-2422 | Sub-50 | 3,4-diClPh | CO | Single bond or CH$_2$ | Sub-22 |
| 2-2423 | Sub-50 | 3,4-diClPh | CO | Single bond or CH$_2$ | Sub-23 |
| 2-2424 | Sub-50 | 3,4-diClPh | CO | Single bond or CH$_2$ | Sub-24 |
| 2-2425 | Sub-50 | 3,4-diClPh | CO | Single bond or CH$_2$ | Sub-25 |
| 2-2426 | Sub-50 | 3,4-diClPh | CO | Single bond or CH$_2$ | Sub-26 |
| 2-2427 | Sub-50 | 3,4-diClPh | CO | Single bond or CH$_2$ | Sub-27 |
| 2-2428 | Sub-50 | 3,4-diClPh | CO | Single bond or CH$_2$ | Sub-28 |
| 2-2429 | Sub-50 | 3,4-diClPh | CO | Single bond or CH$_2$ | Sub-29 |
| 2-2430 | Sub-50 | 3,4-diClPh | CO | Single bond or CH$_2$ | Sub-30 |
| 2-2431 | Sub-50 | 3,4-diClPh | CO | Single bond or CH$_2$ | Sub-31 |
| 2-2432 | Sub-50 | 3,4-diClPh | CO | Single bond or CH$_2$ | Sub-32 |
| 2-2433 | Sub-50 | 3,4-diClPh | CO | Single bond or CH$_2$ | Sub-65 |
| 2-2434 | Sub-50 | 3,4-diClPh | CO | Single bond or CH$_2$ | Sub-66 |
| 2-2435 | Sub-50 | 3,4-diClPh | CO | Single bond or CH$_2$ | Sub-67 |
| 2-2436 | Sub-50 | 3,4-diClPh | CO | Single bond or CH$_2$ | Sub-68 |

TABLE 2-continued

| Cpd. No. | R¹ | R² | A | B | Z |
|---|---|---|---|---|---|
| 2-2437 | Sub-50 | 3,4-diClPh | CO | Single bond or $CH_2$ | Sub-69 |
| 2-2438 | Sub-50 | 3,4-diClPh | CO | Single bond or $CH_2$ | Sub-70 |
| 2-2439 | Sub-50 | 3,4-diClPh | CO | Single bond or $CH_2$ | Sub-71 |
| 2-2440 | Sub-50 | 3,4-diClPh | CO | Single bond or $CH_2$ | Sub-72 |
| 2-2441 | Sub-50 | 3,4-diClPh | CO | Single bond or $CH_2$ | Sub-73 |
| 2-2442 | Sub-50 | 3,4-diClPh | CO | Single bond or $CH_2$ | Sub-74 |
| 2-2443 | Sub-50 | 3,4-diClPh | CO | Single bond or $CH_2$ | Sub-75 |
| 2-2444 | Sub-50 | 3,4-diClPh | CO | Single bond or $CH_2$ | Sub-76 |
| 2-2445 | Sub-50 | 3,4-diClPh | CO | Single bond or $CH_2$ | Sub-77 |
| 2-2446 | Sub-50 | 3,4-diClPh | CO | Single bond or $CH_2$ | Sub-78 |
| 2-2447 | Sub-50 | 3,4-diClPh | CO | Single bond or $CH_2$ | Sub-79 |
| 2-2448 | Sub-50 | 3,4-diClPh | CO | Single bond or $CH_2$ | Sub-80 |
| 2-2449 | Sub-51 | 3,4-diClPh | CO | Single bond or $CH_2$ | Sub-1 |
| 2-2450 | Sub-51 | 3,4-diClPh | CO | Single bond or $CH_2$ | Sub-2 |
| 2-2451 | Sub-51 | 3,4-diClPh | CO | Single bond or $CH_2$ | Sub-3 |
| 2-2452 | Sub-51 | 3,4-diClPh | CO | Single bond or $CH_2$ | Sub-4 |
| 2-2453 | Sub-51 | 3,4-diClPh | CO | Single bond or $CH_2$ | Sub-5 |
| 2-2454 | Sub-51 | 3,4-diClPh | CO | Single bond or $CH_2$ | Sub-6 |
| 2-2455 | Sub-51 | 3,4-diClPh | CO | Single bond or $CH_2$ | Sub-7 |
| 2-2456 | Sub-51 | 3,4-diClPh | CO | Single bond or $CH_2$ | Sub-8 |
| 2-2457 | Sub-51 | 3,4-diClPh | CO | Single bond or $CH_2$ | Sub-9 |
| 2-2458 | Sub-51 | 3,4-diClPh | CO | Single bond or $CH_2$ | Sub-10 |
| 2-2459 | Sub-51 | 3,4-diClPh | CO | Single bond or $CH_2$ | Sub-11 |
| 2-2460 | Sub-51 | 3,4-diClPh | CO | Single bond or $CH_2$ | Sub-12 |
| 2-2461 | Sub-51 | 3,4-diClPh | CO | Single bond or $CH_2$ | Sub-13 |
| 2-2462 | Sub-51 | 3,4-diClPh | CO | Single bond or $CH_2$ | Sub-14 |
| 2-2463 | Sub-51 | 3,4-diClPh | CO | Single bond or $CH_2$ | Sub-15 |
| 2-2464 | Sub-51 | 3,4-diClPh | CO | Single bond or $CH_2$ | Sub-16 |
| 2-2465 | Sub-51 | 3,4-diClPh | CO | Single bond or $CH_2$ | Sub-17 |
| 2-2466 | Sub-51 | 3,4-diClPh | CO | Single bond or $CH_2$ | Sub-18 |
| 2-2467 | Sub-51 | 3,4-diClPh | CO | Single bond or $CH_2$ | Sub-19 |
| 2-2468 | Sub-51 | 3,4-diClPh | CO | Single bond or $CH_2$ | Sub-20 |
| 2-2469 | Sub-51 | 3,4-diClPh | CO | Single bond or $CH_2$ | Sub-21 |
| 2-2470 | Sub-51 | 3,4-diClPh | CO | Single bond or $CH_2$ | Sub-22 |
| 2-2471 | Sub-51 | 3,4-diClPh | CO | Single bond or $CH_2$ | Sub-23 |
| 2-2472 | Sub-51 | 3,4-diClPh | CO | Single bond or $CH_2$ | Sub-24 |
| 2-2473 | Sub-51 | 3,4-diClPh | CO | Single bond or $CH_2$ | Sub-25 |
| 2-2474 | Sub-51 | 3,4-diClPh | CO | Single bond or $CH_2$ | Sub-26 |
| 2-2475 | Sub-51 | 3,4-diClPh | CO | Single bond or $CH_2$ | Sub-27 |
| 2-2476 | Sub-51 | 3,4-diClPh | CO | Single bond or $CH_2$ | Sub-28 |
| 2-2477 | Sub-51 | 3,4-diClPh | CO | Single bond or $CH_2$ | Sub-29 |
| 2-2478 | Sub-51 | 3,4-diClPh | CO | Single bond or $CH_2$ | Sub-30 |
| 2-2479 | Sub-51 | 3,4-diClPh | CO | Single bond or $CH_2$ | Sub-31 |
| 2-2480 | Sub-51 | 3,4-diClPh | CO | Single bond or $CH_2$ | Sub-32 |
| 2-2481 | Sub-51 | 3,4-diClPh | CO | Single bond or $CH_2$ | Sub-65 |
| 2-2482 | Sub-51 | 3,4-diClPh | CO | Single bond or $CH_2$ | Sub-66 |
| 2-2483 | Sub-51 | 3,4-diClPh | CO | Single bond or $CH_2$ | Sub-67 |
| 2-2484 | Sub-51 | 3,4-diClPh | CO | Single bond or $CH_2$ | Sub-68 |
| 2-2485 | Sub-51 | 3,4-diClPh | CO | Single bond or $CH_2$ | Sub-69 |
| 2-2486 | Sub-51 | 3,4-diClPh | CO | Single bond or $CH_2$ | Sub-70 |
| 2-2487 | Sub-51 | 3,4-diClPh | CO | Single bond or $CH_2$ | Sub-71 |
| 2-2488 | Sub-51 | 3,4-diClPh | CO | Single bond or $CH_2$ | Sub-72 |
| 2-2489 | Sub-51 | 3,4-diClPh | CO | Single bond or $CH_2$ | Sub-73 |
| 2-2490 | Sub-51 | 3,4-diClPh | CO | Single bond or $CH_2$ | Sub-74 |
| 2-2491 | Sub-51 | 3,4-diClPh | CO | Single bond or $CH_2$ | Sub-75 |
| 2-2492 | Sub-51 | 3,4-diClPh | CO | Single bond or $CH_2$ | Sub-76 |
| 2-2493 | Sub-51 | 3,4-diClPh | CO | Single bond or $CH_2$ | Sub-77 |
| 2-2494 | Sub-51 | 3,4-diClPh | CO | Single bond or $CH_2$ | Sub-78 |
| 2-2495 | Sub-51 | 3,4-diClPh | CO | Single bond or $CH_2$ | Sub-79 |
| 2-2496 | Sub-51 | 3,4-diClPh | CO | Single bond or $CH_2$ | Sub-80 |
| 2-2497 | Sub-52 | 3,4-diClPh | CO | Single bond or $CH_2$ | Sub-1 |
| 2-2498 | Sub-52 | 3,4-diClPh | CO | Single bond or $CH_2$ | Sub-2 |
| 2-2499 | Sub-52 | 3,4-diClPh | CO | Single bond or $CH_2$ | Sub-3 |
| 2-2500 | Sub-52 | 3,4-diClPh | CO | Single bond or $CH_2$ | Sub-4 |
| 2-2501 | Sub-52 | 3,4-diClPh | CO | Single bond or $CH_2$ | Sub-5 |
| 2-2502 | Sub-52 | 3,4-diClPh | CO | Single bond or $CH_2$ | Sub-6 |
| 2-2503 | Sub-52 | 3,4-diClPh | CO | Single bond or $CH_2$ | Sub-7 |
| 2-2504 | Sub-52 | 3,4-diClPh | CO | Single bond or $CH_2$ | Sub-8 |
| 2-2505 | Sub-52 | 3,4-diClPh | CO | Single bond or $CH_2$ | Sub-9 |
| 2-2506 | Sub-52 | 3,4-diClPh | CO | Single bond or $CH_2$ | Sub-10 |
| 2-2507 | Sub-52 | 3,4-diClPh | CO | Single bond or $CH_2$ | Sub-11 |
| 2-2508 | Sub-52 | 3,4-diClPh | CO | Single bond or $CH_2$ | Sub-12 |
| 2-2509 | Sub-52 | 3,4-diClPh | CO | Single bond or $CH_2$ | Sub-13 |
| 2-2510 | Sub-52 | 3,4-diClPh | CO | Single bond or $CH_2$ | Sub-14 |
| 2-2511 | Sub-52 | 3,4-diClPh | CO | Single bond or $CH_2$ | Sub-15 |
| 2-2512 | Sub-52 | 3,4-diClPh | CO | Single bond or $CH_2$ | Sub-16 |
| 2-2513 | Sub-52 | 3,4-diClPh | CO | Single bond or $CH_2$ | Sub-17 |
| 2-2514 | Sub-52 | 3,4-diClPh | CO | Single bond or $CH_2$ | Sub-18 |
| 2-2515 | Sub-52 | 3,4-diClPh | CO | Single bond or $CH_2$ | Sub-19 |
| 2-2516 | Sub-52 | 3,4-diClPh | CO | Single bond or $CH_2$ | Sub-20 |
| 2-2517 | Sub-52 | 3,4-diClPh | CO | Single bond or $CH_2$ | Sub-21 |
| 2-2518 | Sub-52 | 3,4-diClPh | CO | Single bond or $CH_2$ | Sub-22 |
| 2-2519 | Sub-52 | 3,4-diClPh | CO | Single bond or $CH_2$ | Sub-23 |
| 2-2520 | Sub-52 | 3,4-diClPh | CO | Single bond or $CH_2$ | Sub-24 |
| 2-2521 | Sub-52 | 3,4-diClPh | CO | Single bond or $CH_2$ | Sub-25 |
| 2-2522 | Sub-52 | 3,4-diClPh | CO | Single bond or $CH_2$ | Sub-26 |
| 2-2523 | Sub-52 | 3,4-diClPh | CO | Single bond or $CH_2$ | Sub-27 |
| 2-2524 | Sub-52 | 3,4-diClPh | CO | Single bond or $CH_2$ | Sub-28 |
| 2-2525 | Sub-52 | 3,4-diClPh | CO | Single bond or $CH_2$ | Sub-29 |
| 2-2526 | Sub-52 | 3,4-diClPh | CO | Single bond or $CH_2$ | Sub-30 |
| 2-2527 | Sub-52 | 3,4-diClPh | CO | Single bond or $CH_2$ | Sub-31 |
| 2-2528 | Sub-52 | 3,4-diClPh | CO | Single bond or $CH_2$ | Sub-32 |
| 2-2529 | Sub-52 | 3,4-diClPh | CO | Single bond or $CH_2$ | Sub-65 |
| 2-2530 | Sub-52 | 3,4-diClPh | CO | Single bond or $CH_2$ | Sub-66 |
| 2-2531 | Sub-52 | 3,4-diClPh | CO | Single bond or $CH_2$ | Sub-67 |
| 2-2532 | Sub-52 | 3,4-diClPh | CO | Single bond or $CH_2$ | Sub-68 |
| 2-2533 | Sub-52 | 3,4-diClPh | CO | Single bond or $CH_2$ | Sub-69 |
| 2-2534 | Sub-52 | 3,4-diClPh | CO | Single bond or $CH_2$ | Sub-70 |
| 2-2535 | Sub-52 | 3,4-diClPh | CO | Single bond or $CH_2$ | Sub-71 |
| 2-2536 | Sub-52 | 3,4-diClPh | CO | Single bond or $CH_2$ | Sub-72 |
| 2-2537 | Sub-52 | 3,4-diClPh | CO | Single bond or $CH_2$ | Sub-73 |
| 2-2538 | Sub-52 | 3,4-diClPh | CO | Single bond or $CH_2$ | Sub-74 |
| 2-2539 | Sub-52 | 3,4-diClPh | CO | Single bond or $CH_2$ | Sub-75 |
| 2-2540 | Sub-52 | 3,4-diClPh | CO | Single bond or $CH_2$ | Sub-76 |
| 2-2541 | Sub-52 | 3,4-diClPh | CO | Single bond or $CH_2$ | Sub-77 |
| 2-2542 | Sub-52 | 3,4-diClPh | CO | Single bond or $CH_2$ | Sub-78 |
| 2-2543 | Sub-52 | 3,4-diClPh | CO | Single bond or $CH_2$ | Sub-79 |
| 2-2544 | Sub-52 | 3,4-diClPh | CO | Single bond or $CH_2$ | Sub-80 |
| 2-2545 | Sub-53 | 3,4-diClPh | CO | Single bond or $CH_2$ | Sub-1 |
| 2-2546 | Sub-53 | 3,4-diClPh | CO | Single bond or $CH_2$ | Sub-2 |
| 2-2547 | Sub-53 | 3,4-diClPh | CO | Single bond or $CH_2$ | Sub-3 |
| 2-2548 | Sub-53 | 3,4-diClPh | CO | Single bond or $CH_2$ | Sub-4 |
| 2-2549 | Sub-53 | 3,4-diClPh | CO | Single bond or $CH_2$ | Sub-5 |
| 2-2550 | Sub-53 | 3,4-diClPh | CO | Single bond or $CH_2$ | Sub-6 |
| 2-2551 | Sub-53 | 3,4-diClPh | CO | Single bond or $CH_2$ | Sub-7 |
| 2-2552 | Sub-53 | 3,4-diClPh | CO | Single bond or $CH_2$ | Sub-8 |
| 2-2553 | Sub-53 | 3,4-diClPh | CO | Single bond or $CH_2$ | Sub-9 |
| 2-2554 | Sub-53 | 3,4-diClPh | CO | Single bond or $CH_2$ | Sub-10 |
| 2-2555 | Sub-53 | 3,4-diClPh | CO | Single bond or $CH_2$ | Sub-11 |
| 2-2556 | Sub-53 | 3,4-diClPh | CO | Single bond or $CH_2$ | Sub-12 |
| 2-2557 | Sub-53 | 3,4-diClPh | CO | Single bond or $CH_2$ | Sub-13 |
| 2-2558 | Sub-53 | 3,4-diClPh | CO | Single bond or $CH_2$ | Sub-14 |
| 2-2559 | Sub-53 | 3,4-diClPh | CO | Single bond or $CH_2$ | Sub-15 |
| 2-2560 | Sub-53 | 3,4-diClPh | CO | Single bond or $CH_2$ | Sub-16 |
| 2-2561 | Sub-53 | 3,4-diClPh | CO | Single bond or $CH_2$ | Sub-17 |
| 2-2562 | Sub-53 | 3,4-diClPh | CO | Single bond or $CH_2$ | Sub-18 |
| 2-2563 | Sub-53 | 3,4-diClPh | CO | Single bond or $CH_2$ | Sub-19 |
| 2-2564 | Sub-53 | 3,4-diClPh | CO | Single bond or $CH_2$ | Sub-20 |
| 2-2565 | Sub-53 | 3,4-diClPh | CO | Single bond or $CH_2$ | Sub-21 |
| 2-2566 | Sub-53 | 3,4-diClPh | CO | Single bond or $CH_2$ | Sub-22 |
| 2-2567 | Sub-53 | 3,4-diClPh | CO | Single bond or $CH_2$ | Sub-23 |
| 2-2568 | Sub-53 | 3,4-diClPh | CO | Single bond or $CH_2$ | Sub-24 |
| 2-2569 | Sub-53 | 3,4-diClPh | CO | Single bond or $CH_2$ | Sub-25 |
| 2-2570 | Sub-53 | 3,4-diClPh | CO | Single bond or $CH_2$ | Sub-26 |
| 2-2571 | Sub-53 | 3,4-diClPh | CO | Single bond or $CH_2$ | Sub-27 |
| 2-2572 | Sub-53 | 3,4-diClPh | CO | Single bond or $CH_2$ | Sub-28 |
| 2-2573 | Sub-53 | 3,4-diClPh | CO | Single bond or $CH_2$ | Sub-29 |
| 2-2574 | Sub-53 | 3,4-diClPh | CO | Single bond or $CH_2$ | Sub-30 |
| 2-2575 | Sub-53 | 3,4-diClPh | CO | Single bond or $CH_2$ | Sub-31 |
| 2-2576 | Sub-53 | 3,4-diClPh | CO | Single bond or $CH_2$ | Sub-32 |
| 2-2577 | Sub-53 | 3,4-diClPh | CO | Single bond or $CH_2$ | Sub-65 |
| 2-2578 | Sub-53 | 3,4-diClPh | CO | Single bond or $CH_2$ | Sub-66 |
| 2-2579 | Sub-53 | 3,4-diClPh | CO | Single bond or $CH_2$ | Sub-67 |
| 2-2580 | Sub-53 | 3,4-diClPh | CO | Single bond or $CH_2$ | Sub-68 |
| 2-2581 | Sub-53 | 3,4-diClPh | CO | Single bond or $CH_2$ | Sub-69 |
| 2-2582 | Sub-53 | 3,4-diClPh | CO | Single bond or $CH_2$ | Sub-70 |
| 2-2583 | Sub-53 | 3,4-diClPh | CO | Single bond or $CH_2$ | Sub-71 |
| 2-2584 | Sub-53 | 3,4-diClPh | CO | Single bond or $CH_2$ | Sub-72 |
| 2-2585 | Sub-53 | 3,4-diClPh | CO | Single bond or $CH_2$ | Sub-73 |
| 2-2586 | Sub-53 | 3,4-diClPh | CO | Single bond or $CH_2$ | Sub-74 |
| 2-2587 | Sub-53 | 3,4-diClPh | CO | Single bond or $CH_2$ | Sub-75 |
| 2-2588 | Sub-53 | 3,4-diClPh | CO | Single bond or $CH_2$ | Sub-76 |
| 2-2589 | Sub-53 | 3,4-diClPh | CO | Single bond or $CH_2$ | Sub-77 |
| 2-2590 | Sub-53 | 3,4-diClPh | CO | Single bond or $CH_2$ | Sub-78 |

TABLE 2-continued

| Cpd. No. | R¹ | R² | A | B | Z |
|---|---|---|---|---|---|
| 2-2591 | Sub-53 | 3,4-diClPh | CO | Single bond or $CH_2$ | Sub-79 |
| 2-2592 | Sub-53 | 3,4-diClPh | CO | Single bond or $CH_2$ | Sub-80 |
| 2-2593 | Sub-54 | 3,4-diClPh | CO | Single bond or $CH_2$ | Sub-1 |
| 2-2594 | Sub-54 | 3,4-diClPh | CO | Single bond or $CH_2$ | Sub-2 |
| 2-2595 | Sub-54 | 3,4-diClPh | CO | Single bond or $CH_2$ | Sub-3 |
| 2-2596 | Sub-54 | 3,4-diClPh | CO | Single bond or $CH_2$ | Sub-4 |
| 2-2597 | Sub-54 | 3,4-diClPh | CO | Single bond or $CH_2$ | Sub-5 |
| 2-2598 | Sub-54 | 3,4-diClPh | CO | Single bond or $CH_2$ | Sub-6 |
| 2-2599 | Sub-54 | 3,4-diClPh | CO | Single bond or $CH_2$ | Sub-7 |
| 2-2600 | Sub-54 | 3,4-diClPh | CO | Single bond or $CH_2$ | Sub-8 |
| 2-2601 | Sub-54 | 3,4-diClPh | CO | Single bond or $CH_2$ | Sub-9 |
| 2-2602 | Sub-54 | 3,4-diClPh | CO | Single bond or $CH_2$ | Sub-10 |
| 2-2603 | Sub-54 | 3,4-diClPh | CO | Single bond or $CH_2$ | Sub-11 |
| 2-2604 | Sub-54 | 3,4-diClPh | CO | Single bond or $CH_2$ | Sub-12 |
| 2-2605 | Sub-54 | 3,4-diClPh | CO | Single bond or $CH_2$ | Sub-13 |
| 2-2606 | Sub-54 | 3,4-diClPh | CO | Single bond or $CH_2$ | Sub-14 |
| 2-2607 | Sub-54 | 3,4-diClPh | CO | Single bond or $CH_2$ | Sub-15 |
| 2-2608 | Sub-54 | 3,4-diClPh | CO | Single bond or $CH_2$ | Sub-16 |
| 2-2609 | Sub-54 | 3,4-diClPh | CO | Single bond or $CH_2$ | Sub-17 |
| 2-2610 | Sub-54 | 3,4-diClPh | CO | Single bond or $CH_2$ | Sub-18 |
| 2-2611 | Sub-54 | 3,4-diClPh | CO | Single bond or $CH_2$ | Sub-19 |
| 2-2612 | Sub-54 | 3,4-diClPh | CO | Single bond or $CH_2$ | Sub-20 |
| 2-2613 | Sub-54 | 3,4-diClPh | CO | Single bond or $CH_2$ | Sub-21 |
| 2-2614 | Sub-54 | 3,4-diClPh | CO | Single bond or $CH_2$ | Sub-22 |
| 2-2615 | Sub-54 | 3,4-diClPh | CO | Single bond or $CH_2$ | Sub-23 |
| 2-2616 | Sub-54 | 3,4-diClPh | CO | Single bond or $CH_2$ | Sub-24 |
| 2-2617 | Sub-54 | 3,4-diClPh | CO | Single bond or $CH_2$ | Sub-25 |
| 2-2618 | Sub-54 | 3,4-diClPh | CO | Single bond or $CH_2$ | Sub-26 |
| 2-2619 | Sub-54 | 3,4-diClPh | CO | Single bond or $CH_2$ | Sub-27 |
| 2-2620 | Sub-54 | 3,4-diClPh | CO | Single bond or $CH_2$ | Sub-28 |
| 2-2621 | Sub-54 | 3,4-diClPh | CO | Single bond or $CH_2$ | Sub-29 |
| 2-2622 | Sub-54 | 3,4-diClPh | CO | Single bond or $CH_2$ | Sub-30 |
| 2-2623 | Sub-54 | 3,4-diClPh | CO | Single bond or $CH_2$ | Sub-31 |
| 2-2624 | Sub-54 | 3,4-diClPh | CO | Single bond or $CH_2$ | Sub-32 |
| 2-2625 | Sub-54 | 3,4-diClPh | CO | Single bond or $CH_2$ | Sub-65 |
| 2-2626 | Sub-54 | 3,4-diClPh | CO | Single bond or $CH_2$ | Sub-66 |
| 2-2627 | Sub-54 | 3,4-diClPh | CO | Single bond or $CH_2$ | Sub-67 |
| 2-2628 | Sub-54 | 3,4-diClPh | CO | Single bond or $CH_2$ | Sub-68 |
| 2-2629 | Sub-54 | 3,4-diClPh | CO | Single bond or $CH_2$ | Sub-69 |
| 2-2630 | Sub-54 | 3,4-diClPh | CO | Single bond or $CH_2$ | Sub-70 |
| 2-2631 | Sub-54 | 3,4-diClPh | CO | Single bond or $CH_2$ | Sub-71 |
| 2-2632 | Sub-54 | 3,4-diClPh | CO | Single bond or $CH_2$ | Sub-72 |
| 2-2633 | Sub-54 | 3,4-diClPh | CO | Single bond or $CH_2$ | Sub-73 |
| 2-2634 | Sub-54 | 3,4-diClPh | CO | Single bond or $CH_2$ | Sub-74 |
| 2-2635 | Sub-54 | 3,4-diClPh | CO | Single bond or $CH_2$ | Sub-75 |
| 2-2636 | Sub-54 | 3,4-diClPh | CO | Single bond or $CH_2$ | Sub-76 |
| 2-2637 | Sub-54 | 3,4-diClPh | CO | Single bond or $CH_2$ | Sub-77 |
| 2-2638 | Sub-54 | 3,4-diClPh | CO | Single bond or $CH_2$ | Sub-78 |
| 2-2639 | Sub-54 | 3,4-diClPh | CO | Single bond or $CH_2$ | Sub-79 |
| 2-2640 | Sub-54 | 3,4-diClPh | CO | Single bond or $CH_2$ | Sub-80 |
| 2-2641 | Sub-55 | 3,4-diClPh | CO | Single bond or $CH_2$ | Sub-1 |
| 2-2642 | Sub-55 | 3,4-diClPh | CO | Single bond or $CH_2$ | Sub-2 |
| 2-2643 | Sub-55 | 3,4-diClPh | CO | Single bond or $CH_2$ | Sub-3 |
| 2-2644 | Sub-55 | 3,4-diClPh | CO | Single bond or $CH_2$ | Sub-4 |
| 2-2645 | Sub-55 | 3,4-diClPh | CO | Single bond or $CH_2$ | Sub-5 |
| 2-2646 | Sub-55 | 3,4-diClPh | CO | Single bond or $CH_2$ | Sub-6 |
| 2-2647 | Sub-55 | 3,4-diClPh | CO | Single bond or $CH_2$ | Sub-7 |
| 2-2648 | Sub-55 | 3,4-diClPh | CO | Single bond or $CH_2$ | Sub-8 |
| 2-2649 | Sub-55 | 3,4-diClPh | CO | Single bond or $CH_2$ | Sub-9 |
| 2-2650 | Sub-55 | 3,4-diClPh | CO | Single bond or $CH_2$ | Sub-10 |
| 2-2651 | Sub-55 | 3,4-diClPh | CO | Single bond or $CH_2$ | Sub-11 |
| 2-2652 | Sub-55 | 3,4-diClPh | CO | Single bond or $CH_2$ | Sub-12 |
| 2-2653 | Sub-55 | 3,4-diClPh | CO | Single bond or $CH_2$ | Sub-13 |
| 2-2654 | Sub-55 | 3,4-diClPh | CO | Single bond or $CH_2$ | Sub-14 |
| 2-2655 | Sub-55 | 3,4-diClPh | CO | Single bond or $CH_2$ | Sub-15 |
| 2-2656 | Sub-55 | 3,4-diClPh | CO | Single bond or $CH_2$ | Sub-16 |
| 2-2657 | Sub-55 | 3,4-diClPh | CO | Single bond or $CH_2$ | Sub-17 |
| 2-2658 | Sub-55 | 3,4-diClPh | CO | Single bond or $CH_2$ | Sub-18 |
| 2-2659 | Sub-55 | 3,4-diClPh | CO | Single bond or $CH_2$ | Sub-19 |
| 2-2660 | Sub-55 | 3,4-diClPh | CO | Single bond or $CH_2$ | Sub-20 |
| 2-2661 | Sub-55 | 3,4-diClPh | CO | Single bond or $CH_2$ | Sub-21 |
| 2-2662 | Sub-55 | 3,4-diClPh | CO | Single bond or $CH_2$ | Sub-22 |
| 2-2663 | Sub-55 | 3,4-diClPh | CO | Single bond or $CH_2$ | Sub-23 |
| 2-2664 | Sub-55 | 3,4-diClPh | CO | Single bond or $CH_2$ | Sub-24 |
| 2-2665 | Sub-55 | 3,4-diClPh | CO | Single bond or $CH_2$ | Sub-25 |
| 2-2666 | Sub-55 | 3,4-diClPh | CO | Single bond or $CH_2$ | Sub-26 |
| 2-2667 | Sub-55 | 3,4-diClPh | CO | Single bond or $CH_2$ | Sub-27 |
| 2-2668 | Sub-55 | 3,4-diClPh | CO | Single bond or $CH_2$ | Sub-28 |
| 2-2669 | Sub-55 | 3,4-diClPh | CO | Single bond or $CH_2$ | Sub-29 |
| 2-2670 | Sub-55 | 3,4-diClPh | CO | Single bond or $CH_2$ | Sub-30 |
| 2-2671 | Sub-55 | 3,4-diClPh | CO | Single bond or $CH_2$ | Sub-31 |
| 2-2672 | Sub-55 | 3,4-diClPh | CO | Single bond or $CH_2$ | Sub-32 |
| 2-2673 | Sub-55 | 3,4-diClPh | CO | Single bond or $CH_2$ | Sub-65 |
| 2-2674 | Sub-55 | 3,4-diClPh | CO | Single bond or $CH_2$ | Sub-66 |
| 2-2675 | Sub-55 | 3,4-diClPh | CO | Single bond or $CH_2$ | Sub-67 |
| 2-2676 | Sub-55 | 3,4-diClPh | CO | Single bond or $CH_2$ | Sub-68 |
| 2-2677 | Sub-55 | 3,4-diClPh | CO | Single bond or $CH_2$ | Sub-69 |
| 2-2678 | Sub-55 | 3,4-diClPh | CO | Single bond or $CH_2$ | Sub-70 |
| 2-2679 | Sub-55 | 3,4-diClPh | CO | Single bond or $CH_2$ | Sub-71 |
| 2-2680 | Sub-55 | 3,4-diClPh | CO | Single bond or $CH_2$ | Sub-72 |
| 2-2681 | Sub-55 | 3,4-diClPh | CO | Single bond or $CH_2$ | Sub-73 |
| 2-2682 | Sub-55 | 3,4-diClPh | CO | Single bond or $CH_2$ | Sub-74 |
| 2-2683 | Sub-55 | 3,4-diClPh | CO | Single bond or $CH_2$ | Sub-75 |
| 2-2684 | Sub-55 | 3,4-diClPh | CO | Single bond or $CH_2$ | Sub-76 |
| 2-2685 | Sub-55 | 3,4-diClPh | CO | Single bond or $CH_2$ | Sub-77 |
| 2-2686 | Sub-55 | 3,4-diClPh | CO | Single bond or $CH_2$ | Sub-78 |
| 2-2687 | Sub-55 | 3,4-diClPh | CO | Single bond or $CH_2$ | Sub-79 |
| 2-2688 | Sub-55 | 3,4-diClPh | CO | Single bond or $CH_2$ | Sub-80 |
| 2-2689 | Sub-56 | 3,4-diClPh | CO | Single bond or $CH_2$ | Sub-1 |
| 2-2690 | Sub-56 | 3,4-diClPh | CO | Single bond or $CH_2$ | Sub-2 |
| 2-2691 | Sub-56 | 3,4-diClPh | CO | Single bond or $CH_2$ | Sub-3 |
| 2-2692 | Sub-56 | 3,4-diClPh | CO | Single bond or $CH_2$ | Sub-4 |
| 2-2693 | Sub-56 | 3,4-diClPh | CO | Single bond or $CH_2$ | Sub-5 |
| 2-2694 | Sub-56 | 3,4-diClPh | CO | Single bond or $CH_2$ | Sub-6 |
| 2-2695 | Sub-56 | 3,4-diClPh | CO | Single bond or $CH_2$ | Sub-7 |
| 2-2696 | Sub-56 | 3,4-diClPh | CO | Single bond or $CH_2$ | Sub-8 |
| 2-2697 | Sub-56 | 3,4-diClPh | CO | Single bond or $CH_2$ | Sub-9 |
| 2-2698 | Sub-56 | 3,4-diClPh | CO | Single bond or $CH_2$ | Sub-10 |
| 2-2699 | Sub-56 | 3,4-diClPh | CO | Single bond or $CH_2$ | Sub-11 |
| 2-2700 | Sub-56 | 3,4-diClPh | CO | Single bond or $CH_2$ | Sub-12 |
| 2-2701 | Sub-56 | 3,4-diClPh | CO | Single bond or $CH_2$ | Sub-13 |
| 2-2702 | Sub-56 | 3,4-diClPh | CO | Single bond or $CH_2$ | Sub-14 |
| 2-2703 | Sub-56 | 3,4-diClPh | CO | Single bond or $CH_2$ | Sub-15 |
| 2-2704 | Sub-56 | 3,4-diClPh | CO | Single bond or $CH_2$ | Sub-16 |
| 2-2705 | Sub-56 | 3,4-diClPh | CO | Single bond or $CH_2$ | Sub-17 |
| 2-2706 | Sub-56 | 3,4-diClPh | CO | Single bond or $CH_2$ | Sub-18 |
| 2-2707 | Sub-56 | 3,4-diClPh | CO | Single bond or $CH_2$ | Sub-19 |
| 2-2708 | Sub-56 | 3,4-diClPh | CO | Single bond or $CH_2$ | Sub-20 |
| 2-2709 | Sub-56 | 3,4-diClPh | CO | Single bond or $CH_2$ | Sub-21 |
| 2-2710 | Sub-56 | 3,4-diClPh | CO | Single bond or $CH_2$ | Sub-22 |
| 2-2711 | Sub-56 | 3,4-diClPh | CO | Single bond or $CH_2$ | Sub-23 |
| 2-2712 | Sub-56 | 3,4-diClPh | CO | Single bond or $CH_2$ | Sub-24 |
| 2-2713 | Sub-56 | 3,4-diClPh | CO | Single bond or $CH_2$ | Sub-25 |
| 2-2714 | Sub-56 | 3,4-diClPh | CO | Single bond or $CH_2$ | Sub-26 |
| 2-2715 | Sub-56 | 3,4-diClPh | CO | Single bond or $CH_2$ | Sub-27 |
| 2-2716 | Sub-56 | 3,4-diClPh | CO | Single bond or $CH_2$ | Sub-28 |
| 2-2717 | Sub-56 | 3,4-diClPh | CO | Single bond or $CH_2$ | Sub-29 |
| 2-2718 | Sub-56 | 3,4-diClPh | CO | Single bond or $CH_2$ | Sub-30 |
| 2-2719 | Sub-56 | 3,4-diClPh | CO | Single bond or $CH_2$ | Sub-31 |
| 2-2720 | Sub-56 | 3,4-diClPh | CO | Single bond or $CH_2$ | Sub-32 |
| 2-2721 | Sub-56 | 3,4-diClPh | CO | Single bond or $CH_2$ | Sub-65 |
| 2-2722 | Sub-56 | 3,4-diClPh | CO | Single bond or $CH_2$ | Sub-66 |
| 2-2723 | Sub-56 | 3,4-diClPh | CO | Single bond or $CH_2$ | Sub-67 |
| 2-2724 | Sub-56 | 3,4-diClPh | CO | Single bond or $CH_2$ | Sub-68 |
| 2-2725 | Sub-56 | 3,4-diClPh | CO | Single bond or $CH_2$ | Sub-69 |
| 2-2726 | Sub-56 | 3,4-diClPh | CO | Single bond or $CH_2$ | Sub-70 |
| 2-2727 | Sub-56 | 3,4-diClPh | CO | Single bond or $CH_2$ | Sub-71 |
| 2-2728 | Sub-56 | 3,4-diClPh | CO | Single bond or $CH_2$ | Sub-72 |
| 2-2729 | Sub-56 | 3,4-diClPh | CO | Single bond or $CH_2$ | Sub-73 |
| 2-2730 | Sub-56 | 3,4-diClPh | CO | Single bond or $CH_2$ | Sub-74 |
| 2-2731 | Sub-56 | 3,4-diClPh | CO | Single bond or $CH_2$ | Sub-75 |
| 2-2732 | Sub-56 | 3,4-diClPh | CO | Single bond or $CH_2$ | Sub-76 |
| 2-2733 | Sub-56 | 3,4-diClPh | CO | Single bond or $CH_2$ | Sub-77 |
| 2-2734 | Sub-56 | 3,4-diClPh | CO | Single bond or $CH_2$ | Sub-78 |
| 2-2735 | Sub-56 | 3,4-diClPh | CO | Single bond or $CH_2$ | Sub-79 |
| 2-2736 | Sub-56 | 3,4-diClPh | CO | Single bond or $CH_2$ | Sub-80 |
| 2-2737 | Sub-57 | 3,4-diClPh | CO | Single bond or $CH_2$ | Sub-1 |
| 2-2738 | Sub-57 | 3,4-diClPh | CO | Single bond or $CH_2$ | Sub-2 |
| 2-2739 | Sub-57 | 3,4-diClPh | CO | Single bond or $CH_2$ | Sub-3 |
| 2-2740 | Sub-57 | 3,4-diClPh | CO | Single bond or $CH_2$ | Sub-4 |
| 2-2741 | Sub-57 | 3,4-diClPh | CO | Single bond or $CH_2$ | Sub-5 |
| 2-2742 | Sub-57 | 3,4-diClPh | CO | Single bond or $CH_2$ | Sub-6 |
| 2-2743 | Sub-57 | 3,4-diClPh | CO | Single bond or $CH_2$ | Sub-7 |
| 2-2744 | Sub-57 | 3,4-diClPh | CO | Single bond or $CH_2$ | Sub-8 |

TABLE 2-continued

| Cpd. No. | R¹ | R² | A | B | Z |
|---|---|---|---|---|---|
| 2-2745 | Sub-57 | 3,4-diClPh | CO | Single bond or CH₂ | Sub-9 |
| 2-2746 | Sub-57 | 3,4-diClPh | CO | Single bond or CH₂ | Sub-10 |
| 2-2747 | Sub-57 | 3,4-diClPh | CO | Single bond or CH₂ | Sub-11 |
| 2-2748 | Sub-57 | 3,4-diClPh | CO | Single bond or CH₂ | Sub-12 |
| 2-2749 | Sub-57 | 3,4-diClPh | CO | Single bond or CH₂ | Sub-13 |
| 2-2750 | Sub-57 | 3,4-diClPh | CO | Single bond or CH₂ | Sub-14 |
| 2-2751 | Sub-57 | 3,4-diClPh | CO | Single bond or CH₂ | Sub-15 |
| 2-2752 | Sub-57 | 3,4-diClPh | CO | Single bond or CH₂ | Sub-16 |
| 2-2753 | Sub-57 | 3,4-diClPh | CO | Single bond or CH₂ | Sub-17 |
| 2-2754 | Sub-57 | 3,4-diClPh | CO | Single bond or CH₂ | Sub-18 |
| 2-2755 | Sub-57 | 3,4-diClPh | CO | Single bond or CH₂ | Sub-19 |
| 2-2756 | Sub-57 | 3,4-diClPh | CO | Single bond or CH₂ | Sub-20 |
| 2-2757 | Sub-57 | 3,4-diClPh | CO | Single bond or CH₂ | Sub-21 |
| 2-2758 | Sub-57 | 3,4-diClPh | CO | Single bond or CH₂ | Sub-22 |
| 2-2759 | Sub-57 | 3,4-diClPh | CO | Single bond or CH₂ | Sub-23 |
| 2-2760 | Sub-57 | 3,4-diClPh | CO | Single bond or CH₂ | Sub-24 |
| 2-2761 | Sub-57 | 3,4-diClPh | CO | Single bond or CH₂ | Sub-25 |
| 2-2762 | Sub-57 | 3,4-diClPh | CO | Single bond or CH₂ | Sub-26 |
| 2-2763 | Sub-57 | 3,4-diClPh | CO | Single bond or CH₂ | Sub-27 |
| 2-2764 | Sub-57 | 3,4-diClPh | CO | Single bond or CH₂ | Sub-28 |
| 2-2765 | Sub-57 | 3,4-diClPh | CO | Single bond or CH₂ | Sub-29 |
| 2-2766 | Sub-57 | 3,4-diClPh | CO | Single bond or CH₂ | Sub-30 |
| 2-2767 | Sub-57 | 3,4-diClPh | CO | Single bond or CH₂ | Sub-31 |
| 2-2768 | Sub-57 | 3,4-diClPh | CO | Single bond or CH₂ | Sub-32 |
| 2-2769 | Sub-57 | 3,4-diClPh | CO | Single bond or CH₂ | Sub-65 |
| 2-2770 | Sub-57 | 3,4-diClPh | CO | Single bond or CH₂ | Sub-66 |
| 2-2771 | Sub-57 | 3,4-diClPh | CO | Single bond or CH₂ | Sub-67 |
| 2-2772 | Sub-57 | 3,4-diClPh | CO | Single bond or CH₂ | Sub-68 |
| 2-2773 | Sub-57 | 3,4-diClPh | CO | Single bond or CH₂ | Sub-69 |
| 2-2774 | Sub-57 | 3,4-diClPh | CO | Single bond or CH₂ | Sub-70 |
| 2-2775 | Sub-57 | 3,4-diClPh | CO | Single bond or CH₂ | Sub-71 |
| 2-2776 | Sub-57 | 3,4-diClPh | CO | Single bond or CH₂ | Sub-72 |
| 2-2777 | Sub-57 | 3,4-diClPh | CO | Single bond or CH₂ | Sub-73 |
| 2-2778 | Sub-57 | 3,4-diClPh | CO | Single bond or CH₂ | Sub-74 |
| 2-2779 | Sub-57 | 3,4-diClPh | CO | Single bond or CH₂ | Sub-75 |
| 2-2780 | Sub-57 | 3,4-diClPh | CO | Single bond or CH₂ | Sub-76 |
| 2-2781 | Sub-57 | 3,4-diClPh | CO | Single bond or CH₂ | Sub-77 |
| 2-2782 | Sub-57 | 3,4-diClPh | CO | Single bond or CH₂ | Sub-78 |
| 2-2783 | Sub-57 | 3,4-diClPh | CO | Single bond or CH₂ | Sub-79 |
| 2-2784 | Sub-57 | 3,4-diClPh | CO | Single bond or CH₂ | Sub-80 |
| 2-2785 | Sub-58 | 3,4-diClPh | CO | Single bond or CH₂ | Sub-1 |
| 2-2786 | Sub-58 | 3,4-diClPh | CO | Single bond or CH₂ | Sub-2 |
| 2-2787 | Sub-58 | 3,4-diClPh | CO | Single bond or CH₂ | Sub-3 |
| 2-2788 | Sub-58 | 3,4-diClPh | CO | Single bond or CH₂ | Sub-4 |
| 2-2789 | Sub-58 | 3,4-diClPh | CO | Single bond or CH₂ | Sub-5 |
| 2-2790 | Sub-58 | 3,4-diClPh | CO | Single bond or CH₂ | Sub-6 |
| 2-2791 | Sub-58 | 3,4-diClPh | CO | Single bond or CH₂ | Sub-7 |
| 2-2792 | Sub-58 | 3,4-diClPh | CO | Single bond or CH₂ | Sub-8 |
| 2-2793 | Sub-58 | 3,4-diClPh | CO | Single bond or CH₂ | Sub-9 |
| 2-2794 | Sub-58 | 3,4-diClPh | CO | Single bond or CH₂ | Sub-10 |
| 2-2795 | Sub-58 | 3,4-diClPh | CO | Single bond or CH₂ | Sub-11 |
| 2-2796 | Sub-58 | 3,4-diClPh | CO | Single bond or CH₂ | Sub-12 |
| 2-2797 | Sub-58 | 3,4-diClPh | CO | Single bond or CH₂ | Sub-13 |
| 2-2798 | Sub-58 | 3,4-diClPh | CO | Single bond or CH₂ | Sub-14 |
| 2-2799 | Sub-58 | 3,4-diClPh | CO | Single bond or CH₂ | Sub-15 |
| 2-2800 | Sub-58 | 3,4-diClPh | CO | Single bond or CH₂ | Sub-16 |
| 2-2801 | Sub-58 | 3,4-diClPh | CO | Single bond or CH₂ | Sub-17 |
| 2-2802 | Sub-58 | 3,4-diClPh | CO | Single bond or CH₂ | Sub-18 |
| 2-2803 | Sub-58 | 3,4-diClPh | CO | Single bond or CH₂ | Sub-19 |
| 2-2804 | Sub-58 | 3,4-diClPh | CO | Single bond or CH₂ | Sub-20 |
| 2-2805 | Sub-58 | 3,4-diClPh | CO | Single bond or CH₂ | Sub-21 |
| 2-2806 | Sub-58 | 3,4-diClPh | CO | Single bond or CH₂ | Sub-22 |
| 2-2807 | Sub-58 | 3,4-diClPh | CO | Single bond or CH₂ | Sub-23 |
| 2-2808 | Sub-58 | 3,4-diClPh | CO | Single bond or CH₂ | Sub-24 |
| 2-2809 | Sub-58 | 3,4-diClPh | CO | Single bond or CH₂ | Sub-25 |
| 2-2810 | Sub-58 | 3,4-diClPh | CO | Single bond or CH₂ | Sub-26 |
| 2-2811 | Sub-58 | 3,4-diClPh | CO | Single bond or CH₂ | Sub-27 |
| 2-2812 | Sub-58 | 3,4-diClPh | CO | Single bond or CH₂ | Sub-28 |
| 2-2813 | Sub-58 | 3,4-diClPh | CO | Single bond or CH₂ | Sub-29 |
| 2-2814 | Sub-58 | 3,4-diClPh | CO | Single bond or CH₂ | Sub-30 |
| 2-2815 | Sub-58 | 3,4-diClPh | CO | Single bond or CH₂ | Sub-31 |
| 2-2816 | Sub-58 | 3,4-diClPh | CO | Single bond or CH₂ | Sub-32 |
| 2-2817 | Sub-58 | 3,4-diClPh | CO | Single bond or CH₂ | Sub-65 |
| 2-2818 | Sub-58 | 3,4-diClPh | CO | Single bond or CH₂ | Sub-66 |
| 2-2819 | Sub-58 | 3,4-diClPh | CO | Single bond or CH₂ | Sub-67 |
| 2-2820 | Sub-58 | 3,4-diClPh | CO | Single bond or CH₂ | Sub-68 |
| 2-2821 | Sub-58 | 3,4-diClPh | CO | Single bond or CH₂ | Sub-69 |
| 2-2822 | Sub-58 | 3,4-diClPh | CO | Single bond or CH₂ | Sub-70 |
| 2-2823 | Sub-58 | 3,4-diClPh | CO | Single bond or CH₂ | Sub-71 |
| 2-2824 | Sub-58 | 3,4-diClPh | CO | Single bond or CH₂ | Sub-72 |
| 2-2825 | Sub-58 | 3,4-diClPh | CO | Single bond or CH₂ | Sub-73 |
| 2-2826 | Sub-58 | 3,4-diClPh | CO | Single bond or CH₂ | Sub-74 |
| 2-2827 | Sub-58 | 3,4-diClPh | CO | Single bond or CH₂ | Sub-75 |
| 2-2828 | Sub-58 | 3,4-diClPh | CO | Single bond or CH₂ | Sub-76 |
| 2-2829 | Sub-58 | 3,4-diClPh | CO | Single bond or CH₂ | Sub-77 |
| 2-2830 | Sub-58 | 3,4-diClPh | CO | Single bond or CH₂ | Sub-78 |
| 2-2831 | Sub-58 | 3,4-diClPh | CO | Single bond or CH₂ | Sub-79 |
| 2-2832 | Sub-58 | 3,4-diClPh | CO | Single bond or CH₂ | Sub-80 |
| 2-2833 | Sub-59 | 3,4-diClPh | CO | Single bond or CH₂ | Sub-1 |
| 2-2834 | Sub-59 | 3,4-diClPh | CO | Single bond or CH₂ | Sub-2 |
| 2-2835 | Sub-59 | 3,4-diClPh | CO | Single bond or CH₂ | Sub-3 |
| 2-2836 | Sub-59 | 3,4-diClPh | CO | Single bond or CH₂ | Sub-4 |
| 2-2837 | Sub-59 | 3,4-diClPh | CO | Single bond or CH₂ | Sub-5 |
| 2-2838 | Sub-59 | 3,4-diClPh | CO | Single bond or CH₂ | Sub-6 |
| 2-2839 | Sub-59 | 3,4-diClPh | CO | Single bond or CH₂ | Sub-7 |
| 2-2840 | Sub-59 | 3,4-diClPh | CO | Single bond or CH₂ | Sub-8 |
| 2-2841 | Sub-59 | 3,4-diClPh | CO | Single bond or CH₂ | Sub-9 |
| 2-2842 | Sub-59 | 3,4-diClPh | CO | Single bond or CH₂ | Sub-10 |
| 2-2843 | Sub-59 | 3,4-diClPh | CO | Single bond or CH₂ | Sub-11 |
| 2-2844 | Sub-59 | 3,4-diClPh | CO | Single bond or CH₂ | Sub-12 |
| 2-2845 | Sub-59 | 3,4-diClPh | CO | Single bond or CH₂ | Sub-13 |
| 2-2846 | Sub-59 | 3,4-diClPh | CO | Single bond or CH₂ | Sub-14 |
| 2-2847 | Sub-59 | 3,4-diClPh | CO | Single bond or CH₂ | Sub-15 |
| 2-2848 | Sub-59 | 3,4-diClPh | CO | Single bond or CH₂ | Sub-16 |
| 2-2849 | Sub-59 | 3,4-diClPh | CO | Single bond or CH₂ | Sub-17 |
| 2-2850 | Sub-59 | 3,4-diClPh | CO | Single bond or CH₂ | Sub-18 |
| 2-2851 | Sub-59 | 3,4-diClPh | CO | Single bond or CH₂ | Sub-19 |
| 2-2852 | Sub-59 | 3,4-diClPh | CO | Single bond or CH₂ | Sub-20 |
| 2-2853 | Sub-59 | 3,4-diClPh | CO | Single bond or CH₂ | Sub-21 |
| 2-2854 | Sub-59 | 3,4-diClPh | CO | Single bond or CH₂ | Sub-22 |
| 2-2855 | Sub-59 | 3,4-diClPh | CO | Single bond or CH₂ | Sub-23 |
| 2-2856 | Sub-59 | 3,4-diClPh | CO | Single bond or CH₂ | Sub-24 |
| 2-2857 | Sub-59 | 3,4-diClPh | CO | Single bond or CH₂ | Sub-25 |
| 2-2858 | Sub-59 | 3,4-diClPh | CO | Single bond or CH₂ | Sub-26 |
| 2-2859 | Sub-59 | 3,4-diClPh | CO | Single bond or CH₂ | Sub-27 |
| 2-2860 | Sub-59 | 3,4-diClPh | CO | Single bond or CH₂ | Sub-28 |
| 2-2861 | Sub-59 | 3,4-diClPh | CO | Single bond or CH₂ | Sub-29 |
| 2-2862 | Sub-59 | 3,4-diClPh | CO | Single bond or CH₂ | Sub-30 |
| 2-2863 | Sub-59 | 3,4-diClPh | CO | Single bond or CH₂ | Sub-31 |
| 2-2864 | Sub-59 | 3,4-diClPh | CO | Single bond or CH₂ | Sub-32 |
| 2-2865 | Sub-59 | 3,4-diClPh | CO | Single bond or CH₂ | Sub-65 |
| 2-2866 | Sub-59 | 3,4-diClPh | CO | Single bond or CH₂ | Sub-66 |
| 2-2867 | Sub-59 | 3,4-diClPh | CO | Single bond or CH₂ | Sub-67 |
| 2-2868 | Sub-59 | 3,4-diClPh | CO | Single bond or CH₂ | Sub-68 |
| 2-2869 | Sub-59 | 3,4-diClPh | CO | Single bond or CH₂ | Sub-69 |
| 2-2870 | Sub-59 | 3,4-diClPh | CO | Single bond or CH₂ | Sub-70 |
| 2-2871 | Sub-59 | 3,4-diClPh | CO | Single bond or CH₂ | Sub-71 |
| 2-2872 | Sub-59 | 3,4-diClPh | CO | Single bond or CH₂ | Sub-72 |
| 2-2873 | Sub-59 | 3,4-diClPh | CO | Single bond or CH₂ | Sub-73 |
| 2-2874 | Sub-59 | 3,4-diClPh | CO | Single bond or CH₂ | Sub-74 |
| 2-2875 | Sub-59 | 3,4-diClPh | CO | Single bond or CH₂ | Sub-75 |
| 2-2876 | Sub-59 | 3,4-diClPh | CO | Single bond or CH₂ | Sub-76 |
| 2-2877 | Sub-59 | 3,4-diClPh | CO | Single bond or CH₂ | Sub-77 |
| 2-2878 | Sub-59 | 3,4-diClPh | CO | Single bond or CH₂ | Sub-78 |
| 2-2879 | Sub-59 | 3,4-diClPh | CO | Single bond or CH₂ | Sub-79 |
| 2-2880 | Sub-59 | 3,4-diClPh | CO | Single bond or CH₂ | Sub-80 |
| 2-2881 | Sub-82 | 3,4-diClPh | CO | Single bond or CH₂ | Sub-1 |
| 2-2882 | Sub-82 | 3,4-diClPh | CO | Single bond or CH₂ | Sub-2 |
| 2-2883 | Sub-82 | 3,4-diClPh | CO | Single bond or CH₂ | Sub-3 |
| 2-2884 | Sub-82 | 3,4-diClPh | CO | Single bond or CH₂ | Sub-4 |
| 2-2885 | Sub-82 | 3,4-diClPh | CO | Single bond or CH₂ | Sub-5 |
| 2-2886 | Sub-82 | 3,4-diClPh | CO | Single bond or CH₂ | Sub-6 |
| 2-2887 | Sub-82 | 3,4-diClPh | CO | Single bond or CH₂ | Sub-7 |
| 2-2888 | Sub-82 | 3,4-diClPh | CO | Single bond or CH₂ | Sub-8 |
| 2-2889 | Sub-82 | 3,4-diClPh | CO | Single bond or CH₂ | Sub-9 |
| 2-2890 | Sub-82 | 3,4-diClPh | CO | Single bond or CH₂ | Sub-10 |
| 2-2891 | Sub-82 | 3,4-diClPh | CO | Single bond or CH₂ | Sub-11 |
| 2-2892 | Sub-82 | 3,4-diClPh | CO | Single bond or CH₂ | Sub-12 |
| 2-2893 | Sub-82 | 3,4-diClPh | CO | Single bond or CH₂ | Sub-13 |
| 2-2894 | Sub-82 | 3,4-diClPh | CO | Single bond or CH₂ | Sub-14 |
| 2-2895 | Sub-82 | 3,4-diClPh | CO | Single bond or CH₂ | Sub-15 |
| 2-2896 | Sub-82 | 3,4-diClPh | CO | Single bond or CH₂ | Sub-16 |
| 2-2897 | Sub-82 | 3,4-diClPh | CO | Single bond or CH₂ | Sub-17 |
| 2-2898 | Sub-82 | 3,4-diClPh | CO | Single bond or CH₂ | Sub-18 |

TABLE 2-continued

| Cpd. No. | R¹ | R² | A | B | Z |
|---|---|---|---|---|---|
| 2-2899 | Sub-82 | 3,4-diClPh | CO | Single bond or CH$_2$ | Sub-19 |
| 2-2900 | Sub-82 | 3,4-diClPh | CO | Single bond or CH$_2$ | Sub-20 |
| 2-2901 | Sub-82 | 3,4-diClPh | CO | Single bond or CH$_2$ | Sub-21 |
| 2-2902 | Sub-82 | 3,4-diClPh | CO | Single bond or CH$_2$ | Sub-22 |
| 2-2903 | Sub-82 | 3,4-diClPh | CO | Single bond or CH$_2$ | Sub-23 |
| 2-2904 | Sub-82 | 3,4-diClPh | CO | Single bond or CH$_2$ | Sub-24 |
| 2-2905 | Sub-82 | 3,4-diClPh | CO | Single bond or CH$_2$ | Sub-25 |
| 2-2906 | Sub-82 | 3,4-diClPh | CO | Single bond or CH$_2$ | Sub-26 |
| 2-2907 | Sub-82 | 3,4-diClPh | CO | Single bond or CH$_2$ | Sub-27 |
| 2-2908 | Sub-82 | 3,4-diClPh | CO | Single bond or CH$_2$ | Sub-28 |
| 2-2909 | Sub-82 | 3,4-diClPh | CO | Single bond or CH$_2$ | Sub-29 |
| 2-2910 | Sub-82 | 3,4-diClPh | CO | Single bond or CH$_2$ | Sub-30 |
| 2-2911 | Sub-82 | 3,4-diClPh | CO | Single bond or CH$_2$ | Sub-31 |
| 2-2912 | Sub-82 | 3,4-diClPh | CO | Single bond or CH$_2$ | Sub-32 |
| 2-2913 | Sub-82 | 3,4-diClPh | CO | Single bond or CH$_2$ | Sub-65 |
| 2-2914 | Sub-82 | 3,4-diClPh | CO | Single bond or CH$_2$ | Sub-66 |
| 2-2915 | Sub-82 | 3,4-diClPh | CO | Single bond or CH$_2$ | Sub-67 |
| 2-2916 | Sub-82 | 3,4-diClPh | CO | Single bond or CH$_2$ | Sub-68 |
| 2-2917 | Sub-82 | 3,4-diClPh | CO | Single bond or CH$_2$ | Sub-69 |
| 2-2918 | Sub-82 | 3,4-diClPh | CO | Single bond or CH$_2$ | Sub-70 |
| 2-2919 | Sub-82 | 3,4-diClPh | CO | Single bond or CH$_2$ | Sub-71 |
| 2-2920 | Sub-82 | 3,4-diClPh | CO | Single bond or CH$_2$ | Sub-72 |
| 2-2921 | Sub-82 | 3,4-diClPh | CO | Single bond or CH$_2$ | Sub-73 |
| 2-2922 | Sub-82 | 3,4-diClPh | CO | Single bond or CH$_2$ | Sub-74 |
| 2-2923 | Sub-82 | 3,4-diClPh | CO | Single bond or CH$_2$ | Sub-75 |
| 2-2924 | Sub-82 | 3,4-diClPh | CO | Single bond or CH$_2$ | Sub-76 |
| 2-2925 | Sub-82 | 3,4-diClPh | CO | Single bond or CH$_2$ | Sub-77 |
| 2-2926 | Sub-82 | 3,4-diClPh | CO | Single bond or CH$_2$ | Sub-78 |
| 2-2927 | Sub-82 | 3,4-diClPh | CO | Single bond or CH$_2$ | Sub-79 |
| 2-2928 | Sub-82 | 3,4-diClPh | CO | Single bond or CH$_2$ | Sub-80 |
| 2-2929 | Sub-83 | 3,4-diClPh | CO | Single bond or CH$_2$ | Sub-1 |
| 2-2930 | Sub-83 | 3,4-diClPh | CO | Single bond or CH$_2$ | Sub-2 |
| 2-2931 | Sub-83 | 3,4-diClPh | CO | Single bond or CH$_2$ | Sub-3 |
| 2-2932 | Sub-83 | 3,4-diClPh | CO | Single bond or CH$_2$ | Sub-4 |
| 2-2933 | Sub-83 | 3,4-diClPh | CO | Single bond or CH$_2$ | Sub-5 |
| 2-2934 | Sub-83 | 3,4-diClPh | CO | Single bond or CH$_2$ | Sub-6 |
| 2-2935 | Sub-83 | 3,4-diClPh | CO | Single bond or CH$_2$ | Sub-7 |
| 2-2936 | Sub-83 | 3,4-diClPh | CO | Single bond or CH$_2$ | Sub-8 |
| 2-2937 | Sub-83 | 3,4-diClPh | CO | Single bond or CH$_2$ | Sub-9 |
| 2-2938 | Sub-83 | 3,4-diClPh | CO | Single bond or CH$_2$ | Sub-10 |
| 2-2939 | Sub-83 | 3,4-diClPh | CO | Single bond or CH$_2$ | Sub-11 |
| 2-2940 | Sub-83 | 3,4-diClPh | CO | Single bond or CH$_2$ | Sub-12 |
| 2-2941 | Sub-83 | 3,4-diClPh | CO | Single bond or CH$_2$ | Sub-13 |
| 2-2942 | Sub-83 | 3,4-diClPh | CO | Single bond or CH$_2$ | Sub-14 |
| 2-2943 | Sub-83 | 3,4-diClPh | CO | Single bond or CH$_2$ | Sub-15 |
| 2-2944 | Sub-83 | 3,4-diClPh | CO | Single bond or CH$_2$ | Sub-16 |
| 2-2945 | Sub-83 | 3,4-diClPh | CO | Single bond or CH$_2$ | Sub-17 |
| 2-2946 | Sub-83 | 3,4-diClPh | CO | Single bond or CH$_2$ | Sub-18 |
| 2-2947 | Sub-83 | 3,4-diClPh | CO | Single bond or CH$_2$ | Sub-19 |
| 2-2948 | Sub-83 | 3,4-diClPh | CO | Single bond or CH$_2$ | Sub-20 |
| 2-2949 | Sub-83 | 3,4-diClPh | CO | Single bond or CH$_2$ | Sub-21 |
| 2-2950 | Sub-83 | 3,4-diClPh | CO | Single bond or CH$_2$ | Sub-22 |
| 2-2951 | Sub-83 | 3,4-diClPh | CO | Single bond or CH$_2$ | Sub-23 |
| 2-2952 | Sub-83 | 3,4-diClPh | CO | Single bond or CH$_2$ | Sub-24 |
| 2-2953 | Sub-83 | 3,4-diClPh | CO | Single bond or CH$_2$ | Sub-25 |
| 2-2954 | Sub-83 | 3,4-diClPh | CO | Single bond or CH$_2$ | Sub-26 |
| 2-2955 | Sub-83 | 3,4-diClPh | CO | Single bond or CH$_2$ | Sub-27 |
| 2-2956 | Sub-83 | 3,4-diClPh | CO | Single bond or CH$_2$ | Sub-28 |
| 2-2957 | Sub-83 | 3,4-diClPh | CO | Single bond or CH$_2$ | Sub-29 |
| 2-2958 | Sub-83 | 3,4-diClPh | CO | Single bond or CH$_2$ | Sub-30 |
| 2-2959 | Sub-83 | 3,4-diClPh | CO | Single bond or CH$_2$ | Sub-31 |
| 2-2960 | Sub-83 | 3,4-diClPh | CO | Single bond or CH$_2$ | Sub-32 |
| 2-2961 | Sub-83 | 3,4-diClPh | CO | Single bond or CH$_2$ | Sub-65 |
| 2-2962 | Sub-83 | 3,4-diClPh | CO | Single bond or CH$_2$ | Sub-66 |
| 2-2963 | Sub-83 | 3,4-diClPh | CO | Single bond or CH$_2$ | Sub-67 |
| 2-2964 | Sub-83 | 3,4-diClPh | CO | Single bond or CH$_2$ | Sub-68 |
| 2-2965 | Sub-83 | 3,4-diClPh | CO | Single bond or CH$_2$ | Sub-69 |
| 2-2966 | Sub-83 | 3,4-diClPh | CO | Single bond or CH$_2$ | Sub-70 |
| 2-2967 | Sub-83 | 3,4-diClPh | CO | Single bond or CH$_2$ | Sub-71 |
| 2-2968 | Sub-83 | 3,4-diClPh | CO | Single bond or CH$_2$ | Sub-72 |
| 2-2969 | Sub-83 | 3,4-diClPh | CO | Single bond or CH$_2$ | Sub-73 |
| 2-2970 | Sub-83 | 3,4-diClPh | CO | Single bond or CH$_2$ | Sub-74 |
| 2-2971 | Sub-83 | 3,4-diClPh | CO | Single bond or CH$_2$ | Sub-75 |
| 2-2972 | Sub-83 | 3,4-diClPh | CO | Single bond or CH$_2$ | Sub-76 |
| 2-2973 | Sub-83 | 3,4-diClPh | CO | Single bond or CH$_2$ | Sub-77 |
| 2-2974 | Sub-83 | 3,4-diClPh | CO | Single bond or CH$_2$ | Sub-78 |
| 2-2975 | Sub-83 | 3,4-diClPh | CO | Single bond or CH$_2$ | Sub-79 |
| 2-2976 | Sub-83 | 3,4-diClPh | CO | Single bond or CH$_2$ | Sub-80 |
| 2-2977 | Sub-61 | 3,4-diClPh | CO | Single bond or CH$_2$ | Sub-1 |
| 2-2978 | Sub-61 | 3,4-diClPh | CO | Single bond or CH$_2$ | Sub-2 |
| 2-2979 | Sub-61 | 3,4-diClPh | CO | Single bond or CH$_2$ | Sub-3 |
| 2-2980 | Sub-61 | 3,4-diClPh | CO | Single bond or CH$_2$ | Sub-4 |
| 2-2981 | Sub-61 | 3,4-diClPh | CO | Single bond or CH$_2$ | Sub-5 |
| 2-2982 | Sub-61 | 3,4-diClPh | CO | Single bond or CH$_2$ | Sub-6 |
| 2-2983 | Sub-61 | 3,4-diClPh | CO | Single bond or CH$_2$ | Sub-7 |
| 2-2984 | Sub-61 | 3,4-diClPh | CO | Single bond or CH$_2$ | Sub-8 |
| 2-2985 | Sub-61 | 3,4-diClPh | CO | Single bond or CH$_2$ | Sub-9 |
| 2-2986 | Sub-61 | 3,4-diClPh | CO | Single bond or CH$_2$ | Sub-10 |
| 2-2987 | Sub-61 | 3,4-diClPh | CO | Single bond or CH$_2$ | Sub-11 |
| 2-2988 | Sub-61 | 3,4-diClPh | CO | Single bond or CH$_2$ | Sub-12 |
| 2-2989 | Sub-61 | 3,4-diClPh | CO | Single bond or CH$_2$ | Sub-13 |
| 2-2990 | Sub-61 | 3,4-diClPh | CO | Single bond or CH$_2$ | Sub-14 |
| 2-2991 | Sub-61 | 3,4-diClPh | CO | Single bond or CH$_2$ | Sub-15 |
| 2-2992 | Sub-61 | 3,4-diClPh | CO | Single bond or CH$_2$ | Sub-16 |
| 2-2993 | Sub-61 | 3,4-diClPh | CO | Single bond or CH$_2$ | Sub-17 |
| 2-2994 | Sub-61 | 3,4-diClPh | CO | Single bond or CH$_2$ | Sub-18 |
| 2-2995 | Sub-61 | 3,4-diClPh | CO | Single bond or CH$_2$ | Sub-19 |
| 2-2996 | Sub-61 | 3,4-diClPh | CO | Single bond or CH$_2$ | Sub-20 |
| 2-2997 | Sub-61 | 3,4-diClPh | CO | Single bond or CH$_2$ | Sub-21 |
| 2-2998 | Sub-61 | 3,4-diClPh | CO | Single bond or CH$_2$ | Sub-22 |
| 2-2999 | Sub-61 | 3,4-diClPh | CO | Single bond or CH$_2$ | Sub-23 |
| 2-3000 | Sub-61 | 3,4-diClPh | CO | Single bond or CH$_2$ | Sub-24 |
| 2-3001 | Sub-61 | 3,4-diClPh | CO | Single bond or CH$_2$ | Sub-25 |
| 2-3002 | Sub-61 | 3,4-diClPh | CO | Single bond or CH$_2$ | Sub-26 |
| 2-3003 | Sub-61 | 3,4-diClPh | CO | Single bond or CH$_2$ | Sub-27 |
| 2-3004 | Sub-61 | 3,4-diClPh | CO | Single bond or CH$_2$ | Sub-28 |
| 2-3005 | Sub-61 | 3,4-diClPh | CO | Single bond or CH$_2$ | Sub-29 |
| 2-3006 | Sub-61 | 3,4-diClPh | CO | Single bond or CH$_2$ | Sub-30 |
| 2-3007 | Sub-61 | 3,4-diClPh | CO | Single bond or CH$_2$ | Sub-31 |
| 2-3008 | Sub-61 | 3,4-diClPh | CO | Single bond or CH$_2$ | Sub-32 |
| 2-3009 | Sub-61 | 3,4-diClPh | CO | Single bond or CH$_2$ | Sub-65 |
| 2-3010 | Sub-61 | 3,4-diClPh | CO | Single bond or CH$_2$ | Sub-66 |
| 2-3011 | Sub-61 | 3,4-diClPh | CO | Single bond or CH$_2$ | Sub-67 |
| 2-3012 | Sub-61 | 3,4-diClPh | CO | Single bond or CH$_2$ | Sub-68 |
| 2-3013 | Sub-61 | 3,4-diClPh | CO | Single bond or CH$_2$ | Sub-69 |
| 2-3014 | Sub-61 | 3,4-diClPh | CO | Single bond or CH$_2$ | Sub-70 |
| 2-3015 | Sub-61 | 3,4-diClPh | CO | Single bond or CH$_2$ | Sub-71 |
| 2-3016 | Sub-61 | 3,4-diClPh | CO | Single bond or CH$_2$ | Sub-72 |
| 2-3017 | Sub-61 | 3,4-diClPh | CO | Single bond or CH$_2$ | Sub-73 |
| 2-3018 | Sub-61 | 3,4-diClPh | CO | Single bond or CH$_2$ | Sub-74 |
| 2-3019 | Sub-61 | 3,4-diClPh | CO | Single bond or CH$_2$ | Sub-75 |
| 2-3020 | Sub-61 | 3,4-diClPh | CO | Single bond or CH$_2$ | Sub-76 |
| 2-3021 | Sub-61 | 3,4-diClPh | CO | Single bond or CH$_2$ | Sub-77 |
| 2-3022 | Sub-61 | 3,4-diClPh | CO | Single bond or CH$_2$ | Sub-78 |
| 2-3023 | Sub-61 | 3,4-diClPh | CO | Single bond or CH$_2$ | Sub-79 |
| 2-3024 | Sub-61 | 3,4-diClPh | CO | Single bond or CH$_2$ | Sub-80 |
| 2-3025 | Sub-60 | 3,4-diClPh | CO | Single bond or CH$_2$ | Sub-1 |
| 2-3026 | Sub-60 | 3,4-diClPh | CO | Single bond or CH$_2$ | Sub-2 |
| 2-3027 | Sub-60 | 3,4-diClPh | CO | Single bond or CH$_2$ | Sub-3 |
| 2-3028 | Sub-60 | 3,4-diClPh | CO | Single bond or CH$_2$ | Sub-4 |
| 2-3029 | Sub-60 | 3,4-diClPh | CO | Single bond or CH$_2$ | Sub-5 |
| 2-3030 | Sub-60 | 3,4-diClPh | CO | Single bond or CH$_2$ | Sub-6 |
| 2-3031 | Sub-60 | 3,4-diClPh | CO | Single bond or CH$_2$ | Sub-7 |
| 2-3032 | Sub-60 | 3,4-diClPh | CO | Single bond or CH$_2$ | Sub-8 |
| 2-3033 | Sub-60 | 3,4-diClPh | CO | Single bond or CH$_2$ | Sub-9 |
| 2-3034 | Sub-60 | 3,4-diClPh | CO | Single bond or CH$_2$ | Sub-10 |
| 2-3035 | Sub-60 | 3,4-diClPh | CO | Single bond or CH$_2$ | Sub-11 |
| 2-3036 | Sub-60 | 3,4-diClPh | CO | Single bond or CH$_2$ | Sub-12 |
| 2-3037 | Sub-60 | 3,4-diClPh | CO | Single bond or CH$_2$ | Sub-13 |
| 2-3038 | Sub-60 | 3,4-diClPh | CO | Single bond or CH$_2$ | Sub-14 |
| 2-3039 | Sub-60 | 3,4-diClPh | CO | Single bond or CH$_2$ | Sub-15 |
| 2-3040 | Sub-60 | 3,4-diClPh | CO | Single bond or CH$_2$ | Sub-16 |
| 2-3041 | Sub-60 | 3,4-diClPh | CO | Single bond or CH$_2$ | Sub-17 |
| 2-3042 | Sub-60 | 3,4-diClPh | CO | Single bond or CH$_2$ | Sub-18 |
| 2-3043 | Sub-60 | 3,4-diClPh | CO | Single bond or CH$_2$ | Sub-19 |
| 2-3044 | Sub-60 | 3,4-diClPh | CO | Single bond or CH$_2$ | Sub-20 |
| 2-3045 | Sub-60 | 3,4-diClPh | CO | Single bond or CH$_2$ | Sub-21 |
| 2-3046 | Sub-60 | 3,4-diClPh | CO | Single bond or CH$_2$ | Sub-22 |
| 2-3047 | Sub-60 | 3,4-diClPh | CO | Single bond or CH$_2$ | Sub-23 |
| 2-3048 | Sub-60 | 3,4-diClPh | CO | Single bond or CH$_2$ | Sub-24 |
| 2-3049 | Sub-60 | 3,4-diClPh | CO | Single bond or CH$_2$ | Sub-25 |
| 2-3050 | Sub-60 | 3,4-diClPh | CO | Single bond or CH$_2$ | Sub-26 |
| 2-3051 | Sub-60 | 3,4-diClPh | CO | Single bond or CH$_2$ | Sub-27 |
| 2-3052 | Sub-60 | 3,4-diClPh | CO | Single bond or CH$_2$ | Sub-28 |

TABLE 2-continued

| Cpd. No. | R¹ | R² | A | B | Z |
|---|---|---|---|---|---|
| 2-3053 | Sub-60 | 3,4-diClPh | CO | Single bond or CH$_2$ | Sub-29 |
| 2-3054 | Sub-60 | 3,4-diClPh | CO | Single bond or CH$_2$ | Sub-30 |
| 2-3055 | Sub-60 | 3,4-diClPh | CO | Single bond or CH$_2$ | Sub-31 |
| 2-3056 | Sub-60 | 3,4-diClPh | CO | Single bond or CH$_2$ | Sub-32 |
| 2-3057 | Sub-60 | 3,4-diClPh | CO | Single bond or CH$_2$ | Sub-65 |
| 2-3058 | Sub-60 | 3,4-diClPh | CO | Single bond or CH$_2$ | Sub-66 |
| 2-3059 | Sub-60 | 3,4-diClPh | CO | Single bond or CH$_2$ | Sub-67 |
| 2-3060 | Sub-60 | 3,4-diClPh | CO | Single bond or CH$_2$ | Sub-68 |
| 2-3061 | Sub-60 | 3,4-diClPh | CO | Single bond or CH$_2$ | Sub-69 |
| 2-3062 | Sub-60 | 3,4-diClPh | CO | Single bond or CH$_2$ | Sub-70 |
| 2-3063 | Sub-60 | 3,4-diClPh | CO | Single bond or CH$_2$ | Sub-71 |
| 2-3064 | Sub-60 | 3,4-diClPh | CO | Single bond or CH$_2$ | Sub-72 |
| 2-3065 | Sub-60 | 3,4-diClPh | CO | Single bond or CH$_2$ | Sub-73 |
| 2-3066 | Sub-60 | 3,4-diClPh | CO | Single bond or CH$_2$ | Sub-74 |
| 2-3067 | Sub-60 | 3,4-diClPh | CO | Single bond or CH$_2$ | Sub-75 |
| 2-3068 | Sub-60 | 3,4-diClPh | CO | Single bond or CH$_2$ | Sub-76 |
| 2-3069 | Sub-60 | 3,4-diClPh | CO | Single bond or CH$_2$ | Sub-77 |
| 2-3070 | Sub-60 | 3,4-diClPh | CO | Single bond or CH$_2$ | Sub-78 |
| 2-3071 | Sub-60 | 3,4-diClPh | CO | Single bond or CH$_2$ | Sub-79 |
| 2-3072 | Sub-60 | 3,4-diClPh | CO | Single bond or CH$_2$ | Sub-80 |
| 2-3073 | Sub-33 | 3,4-diClPh | SO$_2$ | Single bond | Sub-1 |
| 2-3074 | Sub-33 | 3,4-diClPh | SO$_2$ | Single bond | Sub-2 |
| 2-3075 | Sub-33 | 3,4-diClPh | SO$_2$ | Single bond | Sub-3 |
| 2-3076 | Sub-33 | 3,4-diClPh | SO$_2$ | Single bond | Sub-4 |
| 2-3077 | Sub-33 | 3,4-diClPh | SO$_2$ | Single bond | Sub-5 |
| 2-3078 | Sub-33 | 3,4-diClPh | SO$_2$ | Single bond | Sub-6 |
| 2-3079 | Sub-33 | 3,4-diClPh | SO$_2$ | Single bond | Sub-7 |
| 2-3080 | Sub-33 | 3,4-diClPh | SO$_2$ | Single bond | Sub-8 |
| 2-3081 | Sub-33 | 3,4-diClPh | SO$_2$ | Single bond | Sub-9 |
| 2-3082 | Sub-33 | 3,4-diClPh | SO$_2$ | Single bond | Sub-10 |
| 2-3083 | Sub-33 | 3,4-diClPh | SO$_2$ | Single bond | Sub-11 |
| 2-3084 | Sub-33 | 3,4-diClPh | SO$_2$ | Single bond | Sub-12 |
| 2-3085 | Sub-33 | 3,4-diClPh | SO$_2$ | Single bond | Sub-13 |
| 2-3086 | Sub-33 | 3,4-diClPh | SO$_2$ | Single bond | Sub-14 |
| 2-3087 | Sub-33 | 3,4-diClPh | SO$_2$ | Single bond | Sub-15 |
| 2-3088 | Sub-33 | 3,4-diClPh | SO$_2$ | Single bond | Sub-16 |
| 2-3089 | Sub-33 | 3,4-diClPh | SO$_2$ | Single bond | Sub-17 |
| 2-3090 | Sub-33 | 3,4-diClPh | SO$_2$ | Single bond | Sub-18 |
| 2-3091 | Sub-33 | 3,4-diClPh | SO$_2$ | Single bond | Sub-19 |
| 2-3092 | Sub-33 | 3,4-diClPh | SO$_2$ | Single bond | Sub-20 |
| 2-3093 | Sub-33 | 3,4-diClPh | SO$_2$ | Single bond | Sub-21 |
| 2-3094 | Sub-33 | 3,4-diClPh | SO$_2$ | Single bond | Sub-22 |
| 2-3095 | Sub-33 | 3,4-diClPh | SO$_2$ | Single bond | Sub-23 |
| 2-3096 | Sub-33 | 3,4-diClPh | SO$_2$ | Single bond | Sub-24 |
| 2-3097 | Sub-33 | 3,4-diClPh | SO$_2$ | Single bond | Sub-25 |
| 2-3098 | Sub-33 | 3,4-diClPh | SO$_2$ | Single bond | Sub-26 |
| 2-3099 | Sub-33 | 3,4-diClPh | SO$_2$ | Single bond | Sub-27 |
| 2-3100 | Sub-33 | 3,4-diClPh | SO$_2$ | Single bond | Sub-28 |
| 2-3101 | Sub-33 | 3,4-diClPh | SO$_2$ | Single bond | Sub-29 |
| 2-3102 | Sub-33 | 3,4-diClPh | SO$_2$ | Single bond | Sub-30 |
| 2-3103 | Sub-33 | 3,4-diClPh | SO$_2$ | Single bond | Sub-31 |
| 2-3104 | Sub-33 | 3,4-diClPh | SO$_2$ | Single bond | Sub-32 |
| 2-3105 | Sub-33 | 3,4-diClPh | SO$_2$ | Single bond | Sub-65 |
| 2-3106 | Sub-33 | 3,4-diClPh | SO$_2$ | Single bond | Sub-66 |
| 2-3107 | Sub-33 | 3,4-diClPh | SO$_2$ | Single bond | Sub-67 |
| 2-3108 | Sub-33 | 3,4-diClPh | SO$_2$ | Single bond | Sub-68 |
| 2-3109 | Sub-33 | 3,4-diClPh | SO$_2$ | Single bond | Sub-69 |
| 2-3110 | Sub-33 | 3,4-diClPh | SO$_2$ | Single bond | Sub-70 |
| 2-3111 | Sub-33 | 3,4-diClPh | SO$_2$ | Single bond | Sub-71 |
| 2-3112 | Sub-33 | 3,4-diClPh | SO$_2$ | Single bond | Sub-72 |
| 2-3113 | Sub-33 | 3,4-diClPh | SO$_2$ | Single bond | Sub-73 |
| 2-3114 | Sub-33 | 3,4-diClPh | SO$_2$ | Single bond | Sub-74 |
| 2-3115 | Sub-33 | 3,4-diClPh | SO$_2$ | Single bond | Sub-75 |
| 2-3116 | Sub-33 | 3,4-diClPh | SO$_2$ | Single bond | Sub-76 |
| 2-3117 | Sub-33 | 3,4-diClPh | SO$_2$ | Single bond | Sub-77 |
| 2-3118 | Sub-33 | 3,4-diClPh | SO$_2$ | Single bond | Sub-78 |
| 2-3119 | Sub-33 | 3,4-diClPh | SO$_2$ | Single bond | Sub-79 |
| 2-3120 | Sub-33 | 3,4-diClPh | SO$_2$ | Single bond | Sub-80 |
| 2-3121 | Sub-34 | 3,4-diClPh | SO$_2$ | Single bond | Sub-1 |
| 2-3122 | Sub-34 | 3,4-diClPh | SO$_2$ | Single bond | Sub-2 |
| 2-3123 | Sub-34 | 3,4-diClPh | SO$_2$ | Single bond | Sub-3 |
| 2-3124 | Sub-34 | 3,4-diClPh | SO$_2$ | Single bond | Sub-4 |
| 2-3125 | Sub-34 | 3,4-diClPh | SO$_2$ | Single bond | Sub-5 |
| 2-3126 | Sub-34 | 3,4-diClPh | SO$_2$ | Single bond | Sub-6 |
| 2-3127 | Sub-34 | 3,4-diClPh | SO$_2$ | Single bond | Sub-7 |
| 2-3128 | Sub-34 | 3,4-diClPh | SO$_2$ | Single bond | Sub-8 |
| 2-3129 | Sub-34 | 3,4-diClPh | SO$_2$ | Single bond | Sub-9 |
| 2-3130 | Sub-34 | 3,4-diClPh | SO$_2$ | Single bond | Sub-10 |
| 2-3131 | Sub-34 | 3,4-diClPh | SO$_2$ | Single bond | Sub-11 |
| 2-3132 | Sub-34 | 3,4-diClPh | SO$_2$ | Single bond | Sub-12 |
| 2-3133 | Sub-34 | 3,4-diClPh | SO$_2$ | Single bond | Sub-13 |
| 2-3134 | Sub-34 | 3,4-diClPh | SO$_2$ | Single bond | Sub-14 |
| 2-3135 | Sub-34 | 3,4-diClPh | SO$_2$ | Single bond | Sub-15 |
| 2-3136 | Sub-34 | 3,4-diClPh | SO$_2$ | Single bond | Sub-16 |
| 2-3137 | Sub-34 | 3,4-diClPh | SO$_2$ | Single bond | Sub-17 |
| 2-3138 | Sub-34 | 3,4-diClPh | SO$_2$ | Single bond | Sub-18 |
| 2-3139 | Sub-34 | 3,4-diClPh | SO$_2$ | Single bond | Sub-19 |
| 2-3140 | Sub-34 | 3,4-diClPh | SO$_2$ | Single bond | Sub-20 |
| 2-3141 | Sub-34 | 3,4-diClPh | SO$_2$ | Single bond | Sub-21 |
| 2-3142 | Sub-34 | 3,4-diClPh | SO$_2$ | Single bond | Sub-22 |
| 2-3143 | Sub-34 | 3,4-diClPh | SO$_2$ | Single bond | Sub-23 |
| 2-3144 | Sub-34 | 3,4-diClPh | SO$_2$ | Single bond | Sub-24 |
| 2-3145 | Sub-34 | 3,4-diClPh | SO$_2$ | Single bond | Sub-25 |
| 2-3146 | Sub-34 | 3,4-diClPh | SO$_2$ | Single bond | Sub-26 |
| 2-3147 | Sub-34 | 3,4-diClPh | SO$_2$ | Single bond | Sub-27 |
| 2-3148 | Sub-34 | 3,4-diClPh | SO$_2$ | Single bond | Sub-28 |
| 2-3149 | Sub-34 | 3,4-diClPh | SO$_2$ | Single bond | Sub-29 |
| 2-3150 | Sub-34 | 3,4-diClPh | SO$_2$ | Single bond | Sub-30 |
| 2-3151 | Sub-34 | 3,4-diClPh | SO$_2$ | Single bond | Sub-31 |
| 2-3152 | Sub-34 | 3,4-diClPh | SO$_2$ | Single bond | Sub-32 |
| 2-3153 | Sub-34 | 3,4-diClPh | SO$_2$ | Single bond | Sub-65 |
| 2-3154 | Sub-34 | 3,4-diClPh | SO$_2$ | Single bond | Sub-66 |
| 2-3155 | Sub-34 | 3,4-diClPh | SO$_2$ | Single bond | Sub-67 |
| 2-3156 | Sub-34 | 3,4-diClPh | SO$_2$ | Single bond | Sub-68 |
| 2-3157 | Sub-34 | 3,4-diClPh | SO$_2$ | Single bond | Sub-69 |
| 2-3158 | Sub-34 | 3,4-diClPh | SO$_2$ | Single bond | Sub-70 |
| 2-3159 | Sub-34 | 3,4-diClPh | SO$_2$ | Single bond | Sub-71 |
| 2-3160 | Sub-34 | 3,4-diClPh | SO$_2$ | Single bond | Sub-72 |
| 2-3161 | Sub-34 | 3,4-diClPh | SO$_2$ | Single bond | Sub-73 |
| 2-3162 | Sub-34 | 3,4-diClPh | SO$_2$ | Single bond | Sub-74 |
| 2-3163 | Sub-34 | 3,4-diClPh | SO$_2$ | Single bond | Sub-75 |
| 2-3164 | Sub-34 | 3,4-diClPh | SO$_2$ | Single bond | Sub-76 |
| 2-3165 | Sub-34 | 3,4-diClPh | SO$_2$ | Single bond | Sub-77 |
| 2-3166 | Sub-34 | 3,4-diClPh | SO$_2$ | Single bond | Sub-78 |
| 2-3167 | Sub-34 | 3,4-diClPh | SO$_2$ | Single bond | Sub-79 |
| 2-3168 | Sub-34 | 3,4-diClPh | SO$_2$ | Single bond | Sub-80 |
| 2-3169 | Sub-35 | 3,4-diClPh | SO$_2$ | Single bond | Sub-1 |
| 2-3170 | Sub-35 | 3,4-diClPh | SO$_2$ | Single bond | Sub-2 |
| 2-3171 | Sub-35 | 3,4-diClPh | SO$_2$ | Single bond | Sub-3 |
| 2-3172 | Sub-35 | 3,4-diClPh | SO$_2$ | Single bond | Sub-4 |
| 2-3173 | Sub-35 | 3,4-diClPh | SO$_2$ | Single bond | Sub-5 |
| 2-3174 | Sub-35 | 3,4-diClPh | SO$_2$ | Single bond | Sub-6 |
| 2-3175 | Sub-35 | 3,4-diClPh | SO$_2$ | Single bond | Sub-7 |
| 2-3176 | Sub-35 | 3,4-diClPh | SO$_2$ | Single bond | Sub-8 |
| 2-3177 | Sub-35 | 3,4-diClPh | SO$_2$ | Single bond | Sub-9 |
| 2-3178 | Sub-35 | 3,4-diClPh | SO$_2$ | Single bond | Sub-10 |
| 2-3179 | Sub-35 | 3,4-diClPh | SO$_2$ | Single bond | Sub-11 |
| 2-3180 | Sub-35 | 3,4-diClPh | SO$_2$ | Single bond | Sub-12 |
| 2-3181 | Sub-35 | 3,4-diClPh | SO$_2$ | Single bond | Sub-13 |
| 2-3182 | Sub-35 | 3,4-diClPh | SO$_2$ | Single bond | Sub-14 |
| 2-3183 | Sub-35 | 3,4-diClPh | SO$_2$ | Single bond | Sub-15 |
| 2-3184 | Sub-35 | 3,4-diClPh | SO$_2$ | Single bond | Sub-16 |
| 2-3185 | Sub-35 | 3,4-diClPh | SO$_2$ | Single bond | Sub-17 |
| 2-3186 | Sub-35 | 3,4-diClPh | SO$_2$ | Single bond | Sub-18 |
| 2-3187 | Sub-35 | 3,4-diClPh | SO$_2$ | Single bond | Sub-19 |
| 2-3188 | Sub-35 | 3,4-diClPh | SO$_2$ | Single bond | Sub-20 |
| 2-3189 | Sub-35 | 3,4-diClPh | SO$_2$ | Single bond | Sub-21 |
| 2-3190 | Sub-35 | 3,4-diClPh | SO$_2$ | Single bond | Sub-22 |
| 2-3191 | Sub-35 | 3,4-diClPh | SO$_2$ | Single bond | Sub-23 |
| 2-3192 | Sub-35 | 3,4-diClPh | SO$_2$ | Single bond | Sub-24 |
| 2-3193 | Sub-35 | 3,4-diClPh | SO$_2$ | Single bond | Sub-25 |
| 2-3194 | Sub-35 | 3,4-diClPh | SO$_2$ | Single bond | Sub-26 |
| 2-3195 | Sub-35 | 3,4-diClPh | SO$_2$ | Single bond | Sub-27 |
| 2-3196 | Sub-35 | 3,4-diClPh | SO$_2$ | Single bond | Sub-28 |
| 2-3197 | Sub-35 | 3,4-diClPh | SO$_2$ | Single bond | Sub-29 |
| 2-3198 | Sub-35 | 3,4-diClPh | SO$_2$ | Single bond | Sub-30 |
| 2-3199 | Sub-35 | 3,4-diClPh | SO$_2$ | Single bond | Sub-31 |
| 2-3200 | Sub-35 | 3,4-diClPh | SO$_2$ | Single bond | Sub-32 |
| 2-3201 | Sub-35 | 3,4-diClPh | SO$_2$ | Single bond | Sub-65 |
| 2-3202 | Sub-35 | 3,4-diClPh | SO$_2$ | Single bond | Sub-66 |
| 2-3203 | Sub-35 | 3,4-diClPh | SO$_2$ | Single bond | Sub-67 |
| 2-3204 | Sub-35 | 3,4-diClPh | SO$_2$ | Single bond | Sub-68 |
| 2-3205 | Sub-35 | 3,4-diClPh | SO$_2$ | Single bond | Sub-69 |
| 2-3206 | Sub-35 | 3,4-diClPh | SO$_2$ | Single bond | Sub-70 |

TABLE 2-continued

| Cpd. No. | R¹ | R² | A | B | Z |
|---|---|---|---|---|---|
| 2-3207 | Sub-35 | 3,4-diClPh | SO₂ | Single bond | Sub-71 |
| 2-3208 | Sub-35 | 3,4-diClPh | SO₂ | Single bond | Sub-72 |
| 2-3209 | Sub-35 | 3,4-diClPh | SO₂ | Single bond | Sub-73 |
| 2-3210 | Sub-35 | 3,4-diClPh | SO₂ | Single bond | Sub-74 |
| 2-3211 | Sub-35 | 3,4-diClPh | SO₂ | Single bond | Sub-75 |
| 2-3212 | Sub-35 | 3,4-diClPh | SO₂ | Single bond | Sub-76 |
| 2-3213 | Sub-35 | 3,4-diClPh | SO₂ | Single bond | Sub-77 |
| 2-3214 | Sub-35 | 3,4-diClPh | SO₂ | Single bond | Sub-78 |
| 2-3215 | Sub-35 | 3,4-diClPh | SO₂ | Single bond | Sub-79 |
| 2-3216 | Sub-35 | 3,4-diClPh | SO₂ | Single bond | Sub-80 |
| 2-3217 | Sub-36 | 3,4-diClPh | SO₂ | Single bond | Sub-1 |
| 2-3218 | Sub-36 | 3,4-diClPh | SO₂ | Single bond | Sub-2 |
| 2-3219 | Sub-36 | 3,4-diClPh | SO₂ | Single bond | Sub-3 |
| 2-3220 | Sub-36 | 3,4-diClPh | SO₂ | Single bond | Sub-4 |
| 2-3221 | Sub-36 | 3,4-diClPh | SO₂ | Single bond | Sub-5 |
| 2-3222 | Sub-36 | 3,4-diClPh | SO₂ | Single bond | Sub-6 |
| 2-3223 | Sub-36 | 3,4-diClPh | SO₂ | Single bond | Sub-7 |
| 2-3224 | Sub-36 | 3,4-diClPh | SO₂ | Single bond | Sub-8 |
| 2-3225 | Sub-36 | 3,4-diClPh | SO₂ | Single bond | Sub-9 |
| 2-3226 | Sub-36 | 3,4-diClPh | SO₂ | Single bond | Sub-10 |
| 2-3227 | Sub-36 | 3,4-diClPh | SO₂ | Single bond | Sub-11 |
| 2-3228 | Sub-36 | 3,4-diClPh | SO₂ | Single bond | Sub-12 |
| 2-3229 | Sub-36 | 3,4-diClPh | SO₂ | Single bond | Sub-13 |
| 2-3230 | Sub-36 | 3,4-diClPh | SO₂ | Single bond | Sub-14 |
| 2-3231 | Sub-36 | 3,4-diClPh | SO₂ | Single bond | Sub-15 |
| 2-3232 | Sub-36 | 3,4-diClPh | SO₂ | Single bond | Sub-16 |
| 2-3233 | Sub-36 | 3,4-diClPh | SO₂ | Single bond | Sub-17 |
| 2-3234 | Sub-36 | 3,4-diClPh | SO₂ | Single bond | Sub-18 |
| 2-3235 | Sub-36 | 3,4-diClPh | SO₂ | Single bond | Sub-19 |
| 2-3236 | Sub-36 | 3,4-diClPh | SO₂ | Single bond | Sub-20 |
| 2-3237 | Sub-36 | 3,4-diClPh | SO₂ | Single bond | Sub-21 |
| 2-3238 | Sub-36 | 3,4-diClPh | SO₂ | Single bond | Sub-22 |
| 2-3239 | Sub-36 | 3,4-diClPh | SO₂ | Single bond | Sub-23 |
| 2-3240 | Sub-36 | 3,4-diClPh | SO₂ | Single bond | Sub-24 |
| 2-3241 | Sub-36 | 3,4-diClPh | SO₂ | Single bond | Sub-25 |
| 2-3242 | Sub-36 | 3,4-diClPh | SO₂ | Single bond | Sub-26 |
| 2-3243 | Sub-36 | 3,4-diClPh | SO₂ | Single bond | Sub-27 |
| 2-3244 | Sub-36 | 3,4-diClPh | SO₂ | Single bond | Sub-28 |
| 2-3245 | Sub-36 | 3,4-diClPh | SO₂ | Single bond | Sub-29 |
| 2-3246 | Sub-36 | 3,4-diClPh | SO₂ | Single bond | Sub-30 |
| 2-3247 | Sub-36 | 3,4-diClPh | SO₂ | Single bond | Sub-31 |
| 2-3248 | Sub-36 | 3,4-diClPh | SO₂ | Single bond | Sub-32 |
| 2-3249 | Sub-36 | 3,4-diClPh | SO₂ | Single bond | Sub-65 |
| 2-3250 | Sub-36 | 3,4-diClPh | SO₂ | Single bond | Sub-66 |
| 2-3251 | Sub-36 | 3,4-diClPh | SO₂ | Single bond | Sub-67 |
| 2-3252 | Sub-36 | 3,4-diClPh | SO₂ | Single bond | Sub-68 |
| 2-3253 | Sub-36 | 3,4-diClPh | SO₂ | Single bond | Sub-69 |
| 2-3254 | Sub-36 | 3,4-diClPh | SO₂ | Single bond | Sub-70 |
| 2-3255 | Sub-36 | 3,4-diClPh | SO₂ | Single bond | Sub-71 |
| 2-3256 | Sub-36 | 3,4-diClPh | SO₂ | Single bond | Sub-72 |
| 2-3257 | Sub-36 | 3,4-diClPh | SO₂ | Single bond | Sub-73 |
| 2-3258 | Sub-36 | 3,4-diClPh | SO₂ | Single bond | Sub-74 |
| 2-3259 | Sub-36 | 3,4-diClPh | SO₂ | Single bond | Sub-75 |
| 2-3260 | Sub-36 | 3,4-diClPh | SO₂ | Single bond | Sub-76 |
| 2-3261 | Sub-36 | 3,4-diClPh | SO₂ | Single bond | Sub-77 |
| 2-3262 | Sub-36 | 3,4-diClPh | SO₂ | Single bond | Sub-78 |
| 2-3263 | Sub-36 | 3,4-diClPh | SO₂ | Single bond | Sub-79 |
| 2-3264 | Sub-36 | 3,4-diClPh | SO₂ | Single bond | Sub-80 |
| 2-3265 | Sub-37 | 3,4-diClPh | SO₂ | Single bond | Sub-1 |
| 2-3266 | Sub-37 | 3,4-diClPh | SO₂ | Single bond | Sub-2 |
| 2-3267 | Sub-37 | 3,4-diClPh | SO₂ | Single bond | Sub-3 |
| 2-3268 | Sub-37 | 3,4-diClPh | SO₂ | Single bond | Sub-4 |
| 2-3269 | Sub-37 | 3,4-diClPh | SO₂ | Single bond | Sub-5 |
| 2-3270 | Sub-37 | 3,4-diClPh | SO₂ | Single bond | Sub-6 |
| 2-3271 | Sub-37 | 3,4-diClPh | SO₂ | Single bond | Sub-7 |
| 2-3272 | Sub-37 | 3,4-diClPh | SO₂ | Single bond | Sub-8 |
| 2-3273 | Sub-37 | 3,4-diClPh | SO₂ | Single bond | Sub-9 |
| 2-3274 | Sub-37 | 3,4-diClPh | SO₂ | Single bond | Sub-10 |
| 2-3275 | Sub-37 | 3,4-diClPh | SO₂ | Single bond | Sub-11 |
| 2-3276 | Sub-37 | 3,4-diClPh | SO₂ | Single bond | Sub-12 |
| 2-3277 | Sub-37 | 3,4-diClPh | SO₂ | Single bond | Sub-13 |
| 2-3278 | Sub-37 | 3,4-diClPh | SO₂ | Single bond | Sub-14 |
| 2-3279 | Sub-37 | 3,4-diClPh | SO₂ | Single bond | Sub-15 |
| 2-3280 | Sub-37 | 3,4-diClPh | SO₂ | Single bond | Sub-16 |
| 2-3281 | Sub-37 | 3,4-diClPh | SO₂ | Single bond | Sub-17 |
| 2-3282 | Sub-37 | 3,4-diClPh | SO₂ | Single bond | Sub-18 |
| 2-3283 | Sub-37 | 3,4-diClPh | SO₂ | Single bond | Sub-19 |
| 2-3284 | Sub-37 | 3,4-diClPh | SO₂ | Single bond | Sub-20 |
| 2-3285 | Sub-37 | 3,4-diClPh | SO₂ | Single bond | Sub-21 |
| 2-3286 | Sub-37 | 3,4-diClPh | SO₂ | Single bond | Sub-22 |
| 2-3287 | Sub-37 | 3,4-diClPh | SO₂ | Single bond | Sub-23 |
| 2-3288 | Sub-37 | 3,4-diClPh | SO₂ | Single bond | Sub-24 |
| 2-3289 | Sub-37 | 3,4-diClPh | SO₂ | Single bond | Sub-25 |
| 2-3290 | Sub-37 | 3,4-diClPh | SO₂ | Single bond | Sub-26 |
| 2-3291 | Sub-37 | 3,4-diClPh | SO₂ | Single bond | Sub-27 |
| 2-3292 | Sub-37 | 3,4-diClPh | SO₂ | Single bond | Sub-28 |
| 2-3293 | Sub-37 | 3,4-diClPh | SO₂ | Single bond | Sub-29 |
| 2-3294 | Sub-37 | 3,4-diClPh | SO₂ | Single bond | Sub-30 |
| 2-3295 | Sub-37 | 3,4-diClPh | SO₂ | Single bond | Sub-31 |
| 2-3296 | Sub-37 | 3,4-diClPh | SO₂ | Single bond | Sub-32 |
| 2-3297 | Sub-37 | 3,4-diClPh | SO₂ | Single bond | Sub-65 |
| 2-3298 | Sub-37 | 3,4-diClPh | SO₂ | Single bond | Sub-66 |
| 2-3299 | Sub-37 | 3,4-diClPh | SO₂ | Single bond | Sub-67 |
| 2-3300 | Sub-37 | 3,4-diClPh | SO₂ | Single bond | Sub-68 |
| 2-3301 | Sub-37 | 3,4-diClPh | SO₂ | Single bond | Sub-69 |
| 2-3302 | Sub-37 | 3,4-diClPh | SO₂ | Single bond | Sub-70 |
| 2-3303 | Sub-37 | 3,4-diClPh | SO₂ | Single bond | Sub-71 |
| 2-3304 | Sub-37 | 3,4-diClPh | SO₂ | Single bond | Sub-72 |
| 2-3305 | Sub-37 | 3,4-diClPh | SO₂ | Single bond | Sub-73 |
| 2-3306 | Sub-37 | 3,4-diClPh | SO₂ | Single bond | Sub-74 |
| 2-3307 | Sub-37 | 3,4-diClPh | SO₂ | Single bond | Sub-75 |
| 2-3308 | Sub-37 | 3,4-diClPh | SO₂ | Single bond | Sub-76 |
| 2-3309 | Sub-37 | 3,4-diClPh | SO₂ | Single bond | Sub-77 |
| 2-3310 | Sub-37 | 3,4-diClPh | SO₂ | Single bond | Sub-78 |
| 2-3311 | Sub-37 | 3,4-diClPh | SO₂ | Single bond | Sub-79 |
| 2-3312 | Sub-37 | 3,4-diClPh | SO₂ | Single bond | Sub-80 |
| 2-3313 | Sub-38 | 3,4-diClPh | SO₂ | Single bond | Sub-1 |
| 2-3314 | Sub-38 | 3,4-diClPh | SO₂ | Single bond | Sub-2 |
| 2-3315 | Sub-38 | 3,4-diClPh | SO₂ | Single bond | Sub-3 |
| 2-3316 | Sub-38 | 3,4-diClPh | SO₂ | Single bond | Sub-4 |
| 2-3317 | Sub-38 | 3,4-diClPh | SO₂ | Single bond | Sub-5 |
| 2-3318 | Sub-38 | 3,4-diClPh | SO₂ | Single bond | Sub-6 |
| 2-3319 | Sub-38 | 3,4-diClPh | SO₂ | Single bond | Sub-7 |
| 2-3320 | Sub-38 | 3,4-diClPh | SO₂ | Single bond | Sub-8 |
| 2-3321 | Sub-38 | 3,4-diClPh | SO₂ | Single bond | Sub-9 |
| 2-3322 | Sub-38 | 3,4-diClPh | SO₂ | Single bond | Sub-10 |
| 2-3323 | Sub-38 | 3,4-diClPh | SO₂ | Single bond | Sub-11 |
| 2-3324 | Sub-38 | 3,4-diClPh | SO₂ | Single bond | Sub-12 |
| 2-3325 | Sub-38 | 3,4-diClPh | SO₂ | Single bond | Sub-13 |
| 2-3326 | Sub-38 | 3,4-diClPh | SO₂ | Single bond | Sub-14 |
| 2-3327 | Sub-38 | 3,4-diClPh | SO₂ | Single bond | Sub-15 |
| 2-3328 | Sub-38 | 3,4-diClPh | SO₂ | Single bond | Sub-16 |
| 2-3329 | Sub-38 | 3,4-diClPh | SO₂ | Single bond | Sub-17 |
| 2-3330 | Sub-38 | 3,4-diClPh | SO₂ | Single bond | Sub-18 |
| 2-3331 | Sub-38 | 3,4-diClPh | SO₂ | Single bond | Sub-19 |
| 2-3332 | Sub-38 | 3,4-diClPh | SO₂ | Single bond | Sub-20 |
| 2-3333 | Sub-38 | 3,4-diClPh | SO₂ | Single bond | Sub-21 |
| 2-3334 | Sub-38 | 3,4-diClPh | SO₂ | Single bond | Sub-22 |
| 2-3335 | Sub-38 | 3,4-diClPh | SO₂ | Single bond | Sub-23 |
| 2-3336 | Sub-38 | 3,4-diClPh | SO₂ | Single bond | Sub-24 |
| 2-3337 | Sub-38 | 3,4-diClPh | SO₂ | Single bond | Sub-25 |
| 2-3338 | Sub-38 | 3,4-diClPh | SO₂ | Single bond | Sub-26 |
| 2-3339 | Sub-38 | 3,4-diClPh | SO₂ | Single bond | Sub-27 |
| 2-3340 | Sub-38 | 3,4-diClPh | SO₂ | Single bond | Sub-28 |
| 2-3341 | Sub-38 | 3,4-diClPh | SO₂ | Single bond | Sub-29 |
| 2-3342 | Sub-38 | 3,4-diClPh | SO₂ | Single bond | Sub-30 |
| 2-3343 | Sub-38 | 3,4-diClPh | SO₂ | Single bond | Sub-31 |
| 2-3344 | Sub-38 | 3,4-diClPh | SO₂ | Single bond | Sub-32 |
| 2-3345 | Sub-38 | 3,4-diClPh | SO₂ | Single bond | Sub-65 |
| 2-3346 | Sub-38 | 3,4-diClPh | SO₂ | Single bond | Sub-66 |
| 2-3347 | Sub-38 | 3,4-diClPh | SO₂ | Single bond | Sub-67 |
| 2-3348 | Sub-38 | 3,4-diClPh | SO₂ | Single bond | Sub-68 |
| 2-3349 | Sub-38 | 3,4-diClPh | SO₂ | Single bond | Sub-69 |
| 2-3350 | Sub-38 | 3,4-diClPh | SO₂ | Single bond | Sub-70 |
| 2-3351 | Sub-38 | 3,4-diClPh | SO₂ | Single bond | Sub-71 |
| 2-3352 | Sub-38 | 3,4-diClPh | SO₂ | Single bond | Sub-72 |
| 2-3353 | Sub-38 | 3,4-diClPh | SO₂ | Single bond | Sub-73 |
| 2-3354 | Sub-38 | 3,4-diClPh | SO₂ | Single bond | Sub-74 |
| 2-3355 | Sub-38 | 3,4-diClPh | SO₂ | Single bond | Sub-75 |
| 2-3356 | Sub-38 | 3,4-diClPh | SO₂ | Single bond | Sub-76 |
| 2-3357 | Sub-38 | 3,4-diClPh | SO₂ | Single bond | Sub-77 |
| 2-3358 | Sub-38 | 3,4-diClPh | SO₂ | Single bond | Sub-78 |
| 2-3359 | Sub-38 | 3,4-diClPh | SO₂ | Single bond | Sub-79 |
| 2-3360 | Sub-38 | 3,4-diClPh | SO₂ | Single bond | Sub-80 |

TABLE 2-continued

| Cpd. No. | R¹ | R² | A | B | Z |
|---|---|---|---|---|---|
| 2-3361 | Sub-39 | 3,4-diClPh | SO$_2$ | Single bond | Sub-1 |
| 2-3362 | Sub-39 | 3,4-diClPh | SO$_2$ | Single bond | Sub-2 |
| 2-3363 | Sub-39 | 3,4-diClPh | SO$_2$ | Single bond | Sub-3 |
| 2-3364 | Sub-39 | 3,4-diClPh | SO$_2$ | Single bond | Sub-4 |
| 2-3365 | Sub-39 | 3,4-diClPh | SO$_2$ | Single bond | Sub-5 |
| 2-3366 | Sub-39 | 3,4-diClPh | SO$_2$ | Single bond | Sub-6 |
| 2-3367 | Sub-39 | 3,4-diClPh | SO$_2$ | Single bond | Sub-7 |
| 2-3368 | Sub-39 | 3,4-diClPh | SO$_2$ | Single bond | Sub-8 |
| 2-3369 | Sub-39 | 3,4-diClPh | SO$_2$ | Single bond | Sub-9 |
| 2-3370 | Sub-39 | 3,4-diClPh | SO$_2$ | Single bond | Sub-10 |
| 2-3371 | Sub-39 | 3,4-diClPh | SO$_2$ | Single bond | Sub-11 |
| 2-3372 | Sub-39 | 3,4-diClPh | SO$_2$ | Single bond | Sub-12 |
| 2-3373 | Sub-39 | 3,4-diClPh | SO$_2$ | Single bond | Sub-13 |
| 2-3374 | Sub-39 | 3,4-diClPh | SO$_2$ | Single bond | Sub-14 |
| 2-3375 | Sub-39 | 3,4-diClPh | SO$_2$ | Single bond | Sub-15 |
| 2-3376 | Sub-39 | 3,4-diClPh | SO$_2$ | Single bond | Sub-16 |
| 2-3377 | Sub-39 | 3,4-diClPh | SO$_2$ | Single bond | Sub-17 |
| 2-3378 | Sub-39 | 3,4-diClPh | SO$_2$ | Single bond | Sub-18 |
| 2-3379 | Sub-39 | 3,4-diClPh | SO$_2$ | Single bond | Sub-19 |
| 2-3380 | Sub-39 | 3,4-diClPh | SO$_2$ | Single bond | Sub-20 |
| 2-3381 | Sub-39 | 3,4-diClPh | SO$_2$ | Single bond | Sub-21 |
| 2-3382 | Sub-39 | 3,4-diClPh | SO$_2$ | Single bond | Sub-22 |
| 2-3383 | Sub-39 | 3,4-diClPh | SO$_2$ | Single bond | Sub-23 |
| 2-3384 | Sub-39 | 3,4-diClPh | SO$_2$ | Single bond | Sub-24 |
| 2-3385 | Sub-39 | 3,4-diClPh | SO$_2$ | Single bond | Sub-25 |
| 2-3386 | Sub-39 | 3,4-diClPh | SO$_2$ | Single bond | Sub-26 |
| 2-3387 | Sub-39 | 3,4-diClPh | SO$_2$ | Single bond | Sub-27 |
| 2-3388 | Sub-39 | 3,4-diClPh | SO$_2$ | Single bond | Sub-28 |
| 2-3389 | Sub-39 | 3,4-diClPh | SO$_2$ | Single bond | Sub-29 |
| 2-3390 | Sub-39 | 3,4-diClPh | SO$_2$ | Single bond | Sub-30 |
| 2-3391 | Sub-39 | 3,4-diClPh | SO$_2$ | Single bond | Sub-31 |
| 2-3392 | Sub-39 | 3,4-diClPh | SO$_2$ | Single bond | Sub-32 |
| 2-3393 | Sub-39 | 3,4-diClPh | SO$_2$ | Single bond | Sub-65 |
| 2-3394 | Sub-39 | 3,4-diClPh | SO$_2$ | Single bond | Sub-66 |
| 2-3395 | Sub-39 | 3,4-diClPh | SO$_2$ | Single bond | Sub-67 |
| 2-3396 | Sub-39 | 3,4-diClPh | SO$_2$ | Single bond | Sub-68 |
| 2-3397 | Sub-39 | 3,4-diClPh | SO$_2$ | Single bond | Sub-69 |
| 2-3398 | Sub-39 | 3,4-diClPh | SO$_2$ | Single bond | Sub-70 |
| 2-3399 | Sub-39 | 3,4-diClPh | SO$_2$ | Single bond | Sub-71 |
| 2-3400 | Sub-39 | 3,4-diClPh | SO$_2$ | Single bond | Sub-72 |
| 2-3401 | Sub-39 | 3,4-diClPh | SO$_2$ | Single bond | Sub-73 |
| 2-3402 | Sub-39 | 3,4-diClPh | SO$_2$ | Single bond | Sub-74 |
| 2-3403 | Sub-39 | 3,4-diClPh | SO$_2$ | Single bond | Sub-75 |
| 2-3404 | Sub-39 | 3,4-diClPh | SO$_2$ | Single bond | Sub-76 |
| 2-3405 | Sub-39 | 3,4-diClPh | SO$_2$ | Single bond | Sub-77 |
| 2-3406 | Sub-39 | 3,4-diClPh | SO$_2$ | Single bond | Sub-78 |
| 2-3407 | Sub-39 | 3,4-diClPh | SO$_2$ | Single bond | Sub-79 |
| 2-3408 | Sub-39 | 3,4-diClPh | SO$_2$ | Single bond | Sub-80 |
| 2-3409 | Sub-40 | 3,4-diClPh | SO$_2$ | Single bond | Sub-1 |
| 2-3410 | Sub-40 | 3,4-diClPh | SO$_2$ | Single bond | Sub-2 |
| 2-3411 | Sub-40 | 3,4-diClPh | SO$_2$ | Single bond | Sub-3 |
| 2-3412 | Sub-40 | 3,4-diClPh | SO$_2$ | Single bond | Sub-4 |
| 2-3413 | Sub-40 | 3,4-diClPh | SO$_2$ | Single bond | Sub-5 |
| 2-3414 | Sub-40 | 3,4-diClPh | SO$_2$ | Single bond | Sub-6 |
| 2-3415 | Sub-40 | 3,4-diClPh | SO$_2$ | Single bond | Sub-7 |
| 2-3416 | Sub-40 | 3,4-diClPh | SO$_2$ | Single bond | Sub-8 |
| 2-3417 | Sub-40 | 3,4-diClPh | SO$_2$ | Single bond | Sub-9 |
| 2-3418 | Sub-40 | 3,4-diClPh | SO$_2$ | Single bond | Sub-10 |
| 2-3419 | Sub-40 | 3,4-diClPh | SO$_2$ | Single bond | Sub-11 |
| 2-3420 | Sub-40 | 3,4-diClPh | SO$_2$ | Single bond | Sub-12 |
| 2-3421 | Sub-40 | 3,4-diClPh | SO$_2$ | Single bond | Sub-13 |
| 2-3422 | Sub-40 | 3,4-diClPh | SO$_2$ | Single bond | Sub-14 |
| 2-3423 | Sub-40 | 3,4-diClPh | SO$_2$ | Single bond | Sub-15 |
| 2-3424 | Sub-40 | 3,4-diClPh | SO$_2$ | Single bond | Sub-16 |
| 2-3425 | Sub-40 | 3,4-diClPh | SO$_2$ | Single bond | Sub-17 |
| 2-3426 | Sub-40 | 3,4-diClPh | SO$_2$ | Single bond | Sub-18 |
| 2-3427 | Sub-40 | 3,4-diClPh | SO$_2$ | Single bond | Sub-19 |
| 2-3428 | Sub-40 | 3,4-diClPh | SO$_2$ | Single bond | Sub-20 |
| 2-3429 | Sub-40 | 3,4-diClPh | SO$_2$ | Single bond | Sub-21 |
| 2-3430 | Sub-40 | 3,4-diClPh | SO$_2$ | Single bond | Sub-22 |
| 2-3431 | Sub-40 | 3,4-diClPh | SO$_2$ | Single bond | Sub-23 |
| 2-3432 | Sub-40 | 3,4-diClPh | SO$_2$ | Single bond | Sub-24 |
| 2-3433 | Sub-40 | 3,4-diClPh | SO$_2$ | Single bond | Sub-25 |
| 2-3434 | Sub-40 | 3,4-diClPh | SO$_2$ | Single bond | Sub-26 |
| 2-3435 | Sub-40 | 3,4-diClPh | SO$_2$ | Single bond | Sub-27 |
| 2-3436 | Sub-40 | 3,4-diClPh | SO$_2$ | Single bond | Sub-28 |
| 2-3437 | Sub-40 | 3,4-diClPh | SO$_2$ | Single bond | Sub-29 |
| 2-3438 | Sub-40 | 3,4-diClPh | SO$_2$ | Single bond | Sub-30 |
| 2-3439 | Sub-40 | 3,4-diClPh | SO$_2$ | Single bond | Sub-31 |
| 2-3440 | Sub-40 | 3,4-diClPh | SO$_2$ | Single bond | Sub-32 |
| 2-3441 | Sub-40 | 3,4-diClPh | SO$_2$ | Single bond | Sub-65 |
| 2-3442 | Sub-40 | 3,4-diClPh | SO$_2$ | Single bond | Sub-66 |
| 2-3443 | Sub-40 | 3,4-diClPh | SO$_2$ | Single bond | Sub-67 |
| 2-3444 | Sub-40 | 3,4-diClPh | SO$_2$ | Single bond | Sub-68 |
| 2-3445 | Sub-40 | 3,4-diClPh | SO$_2$ | Single bond | Sub-69 |
| 2-3446 | Sub-40 | 3,4-diClPh | SO$_2$ | Single bond | Sub-70 |
| 2-3447 | Sub-40 | 3,4-diClPh | SO$_2$ | Single bond | Sub-71 |
| 2-3448 | Sub-40 | 3,4-diClPh | SO$_2$ | Single bond | Sub-72 |
| 2-3449 | Sub-40 | 3,4-diClPh | SO$_2$ | Single bond | Sub-73 |
| 2-3450 | Sub-40 | 3,4-diClPh | SO$_2$ | Single bond | Sub-74 |
| 2-3451 | Sub-40 | 3,4-diClPh | SO$_2$ | Single bond | Sub-75 |
| 2-3452 | Sub-40 | 3,4-diClPh | SO$_2$ | Single bond | Sub-76 |
| 2-3453 | Sub-40 | 3,4-diClPh | SO$_2$ | Single bond | Sub-77 |
| 2-3454 | Sub-40 | 3,4-diClPh | SO$_2$ | Single bond | Sub-78 |
| 2-3455 | Sub-40 | 3,4-diClPh | SO$_2$ | Single bond | Sub-79 |
| 2-3456 | Sub-40 | 3,4-diClPh | SO$_2$ | Single bond | Sub-80 |
| 2-3457 | Sub-41 | 3,4-diClPh | SO$_2$ | Single bond | Sub-1 |
| 2-3458 | Sub-41 | 3,4-diClPh | SO$_2$ | Single bond | Sub-2 |
| 2-3459 | Sub-41 | 3,4-diClPh | SO$_2$ | Single bond | Sub-3 |
| 2-3460 | Sub-41 | 3,4-diClPh | SO$_2$ | Single bond | Sub-4 |
| 2-3461 | Sub-41 | 3,4-diClPh | SO$_2$ | Single bond | Sub-5 |
| 2-3462 | Sub-41 | 3,4-diClPh | SO$_2$ | Single bond | Sub-6 |
| 2-3463 | Sub-41 | 3,4-diClPh | SO$_2$ | Single bond | Sub-7 |
| 2-3464 | Sub-41 | 3,4-diClPh | SO$_2$ | Single bond | Sub-8 |
| 2-3465 | Sub-41 | 3,4-diClPh | SO$_2$ | Single bond | Sub-9 |
| 2-3466 | Sub-41 | 3,4-diClPh | SO$_2$ | Single bond | Sub-10 |
| 2-3467 | Sub-41 | 3,4-diClPh | SO$_2$ | Single bond | Sub-11 |
| 2-3468 | Sub-41 | 3,4-diClPh | SO$_2$ | Single bond | Sub-12 |
| 2-3469 | Sub-41 | 3,4-diClPh | SO$_2$ | Single bond | Sub-13 |
| 2-3470 | Sub-41 | 3,4-diClPh | SO$_2$ | Single bond | Sub-14 |
| 2-3471 | Sub-41 | 3,4-diClPh | SO$_2$ | Single bond | Sub-15 |
| 2-3472 | Sub-41 | 3,4-diClPh | SO$_2$ | Single bond | Sub-16 |
| 2-3473 | Sub-41 | 3,4-diClPh | SO$_2$ | Single bond | Sub-17 |
| 2-3474 | Sub-41 | 3,4-diClPh | SO$_2$ | Single bond | Sub-18 |
| 2-3475 | Sub-41 | 3,4-diClPh | SO$_2$ | Single bond | Sub-19 |
| 2-3476 | Sub-41 | 3,4-diClPh | SO$_2$ | Single bond | Sub-20 |
| 2-3477 | Sub-41 | 3,4-diClPh | SO$_2$ | Single bond | Sub-21 |
| 2-3478 | Sub-41 | 3,4-diClPh | SO$_2$ | Single bond | Sub-22 |
| 2-3479 | Sub-41 | 3,4-diClPh | SO$_2$ | Single bond | Sub-23 |
| 2-3480 | Sub-41 | 3,4-diClPh | SO$_2$ | Single bond | Sub-24 |
| 2-3481 | Sub-41 | 3,4-diClPh | SO$_2$ | Single bond | Sub-25 |
| 2-3482 | Sub-41 | 3,4-diClPh | SO$_2$ | Single bond | Sub-26 |
| 2-3483 | Sub-41 | 3,4-diClPh | SO$_2$ | Single bond | Sub-27 |
| 2-3484 | Sub-41 | 3,4-diClPh | SO$_2$ | Single bond | Sub-28 |
| 2-3485 | Sub-41 | 3,4-diClPh | SO$_2$ | Single bond | Sub-29 |
| 2-3486 | Sub-41 | 3,4-diClPh | SO$_2$ | Single bond | Sub-30 |
| 2-3487 | Sub-41 | 3,4-diClPh | SO$_2$ | Single bond | Sub-31 |
| 2-3488 | Sub-41 | 3,4-diClPh | SO$_2$ | Single bond | Sub-32 |
| 2-3489 | Sub-41 | 3,4-diClPh | SO$_2$ | Single bond | Sub-65 |
| 2-3490 | Sub-41 | 3,4-diClPh | SO$_2$ | Single bond | Sub-66 |
| 2-3491 | Sub-41 | 3,4-diClPh | SO$_2$ | Single bond | Sub-67 |
| 2-3492 | Sub-41 | 3,4-diClPh | SO$_2$ | Single bond | Sub-68 |
| 2-3493 | Sub-41 | 3,4-diClPh | SO$_2$ | Single bond | Sub-69 |
| 2-3494 | Sub-41 | 3,4-diClPh | SO$_2$ | Single bond | Sub-70 |
| 2-3495 | Sub-41 | 3,4-diClPh | SO$_2$ | Single bond | Sub-71 |
| 2-3496 | Sub-41 | 3,4-diClPh | SO$_2$ | Single bond | Sub-72 |
| 2-3497 | Sub-41 | 3,4-diClPh | SO$_2$ | Single bond | Sub-73 |
| 2-3498 | Sub-41 | 3,4-diClPh | SO$_2$ | Single bond | Sub-74 |
| 2-3499 | Sub-41 | 3,4-diClPh | SO$_2$ | Single bond | Sub-75 |
| 2-3500 | Sub-41 | 3,4-diClPh | SO$_2$ | Single bond | Sub-76 |
| 2-3501 | Sub-41 | 3,4-diClPh | SO$_2$ | Single bond | Sub-77 |
| 2-3502 | Sub-41 | 3,4-diClPh | SO$_2$ | Single bond | Sub-78 |
| 2-3503 | Sub-41 | 3,4-diClPh | SO$_2$ | Single bond | Sub-79 |
| 2-3504 | Sub-41 | 3,4-diClPh | SO$_2$ | Single bond | Sub-80 |
| 2-3505 | Sub-42 | 3,4-diClPh | SO$_2$ | Single bond | Sub-1 |
| 2-3506 | Sub-42 | 3,4-diClPh | SO$_2$ | Single bond | Sub-2 |
| 2-3507 | Sub-42 | 3,4-diClPh | SO$_2$ | Single bond | Sub-3 |
| 2-3508 | Sub-42 | 3,4-diClPh | SO$_2$ | Single bond | Sub-4 |
| 2-3509 | Sub-42 | 3,4-diClPh | SO$_2$ | Single bond | Sub-5 |
| 2-3510 | Sub-42 | 3,4-diClPh | SO$_2$ | Single bond | Sub-6 |
| 2-3511 | Sub-42 | 3,4-diClPh | SO$_2$ | Single bond | Sub-7 |
| 2-3512 | Sub-42 | 3,4-diClPh | SO$_2$ | Single bond | Sub-8 |
| 2-3513 | Sub-42 | 3,4-diClPh | SO$_2$ | Single bond | Sub-9 |
| 2-3514 | Sub-42 | 3,4-diClPh | SO$_2$ | Single bond | Sub-10 |

TABLE 2-continued

| Cpd. No. | R¹ | R² | A | B | Z |
|---|---|---|---|---|---|
| 2-3515 | Sub-42 | 3,4-diClPh | SO₂ | Single bond | Sub-11 |
| 2-3516 | Sub-42 | 3,4-diClPh | SO₂ | Single bond | Sub-12 |
| 2-3517 | Sub-42 | 3,4-diClPh | SO₂ | Single bond | Sub-13 |
| 2-3518 | Sub-42 | 3,4-diClPh | SO₂ | Single bond | Sub-14 |
| 2-3519 | Sub-42 | 3,4-diClPh | SO₂ | Single bond | Sub-15 |
| 2-3520 | Sub-42 | 3,4-diClPh | SO₂ | Single bond | Sub-16 |
| 2-3521 | Sub-42 | 3,4-diClPh | SO₂ | Single bond | Sub-17 |
| 2-3522 | Sub-42 | 3,4-diClPh | SO₂ | Single bond | Sub-18 |
| 2-3523 | Sub-42 | 3,4-diClPh | SO₂ | Single bond | Sub-19 |
| 2-3524 | Sub-42 | 3,4-diClPh | SO₂ | Single bond | Sub-20 |
| 2-3525 | Sub-42 | 3,4-diClPh | SO₂ | Single bond | Sub-21 |
| 2-3526 | Sub-42 | 3,4-diClPh | SO₂ | Single bond | Sub-22 |
| 2-3527 | Sub-42 | 3,4-diClPh | SO₂ | Single bond | Sub-23 |
| 2-3528 | Sub-42 | 3,4-diClPh | SO₂ | Single bond | Sub-24 |
| 2-3529 | Sub-42 | 3,4-diClPh | SO₂ | Single bond | Sub-25 |
| 2-3530 | Sub-42 | 3,4-diClPh | SO₂ | Single bond | Sub-26 |
| 2-3531 | Sub-42 | 3,4-diClPh | SO₂ | Single bond | Sub-27 |
| 2-3532 | Sub-42 | 3,4-diClPh | SO₂ | Single bond | Sub-28 |
| 2-3533 | Sub-42 | 3,4-diClPh | SO₂ | Single bond | Sub-29 |
| 2-3534 | Sub-42 | 3,4-diClPh | SO₂ | Single bond | Sub-30 |
| 2-3535 | Sub-42 | 3,4-diClPh | SO₂ | Single bond | Sub-31 |
| 2-3536 | Sub-42 | 3,4-diClPh | SO₂ | Single bond | Sub-32 |
| 2-3537 | Sub-42 | 3,4-diClPh | SO₂ | Single bond | Sub-65 |
| 2-3538 | Sub-42 | 3,4-diClPh | SO₂ | Single bond | Sub-66 |
| 2-3539 | Sub-42 | 3,4-diClPh | SO₂ | Single bond | Sub-67 |
| 2-3540 | Sub-42 | 3,4-diClPh | SO₂ | Single bond | Sub-68 |
| 2-3541 | Sub-42 | 3,4-diClPh | SO₂ | Single bond | Sub-69 |
| 2-3542 | Sub-42 | 3,4-diClPh | SO₂ | Single bond | Sub-70 |
| 2-3543 | Sub-42 | 3,4-diClPh | SO₂ | Single bond | Sub-71 |
| 2-3544 | Sub-42 | 3,4-diClPh | SO₂ | Single bond | Sub-72 |
| 2-3545 | Sub-42 | 3,4-diClPh | SO₂ | Single bond | Sub-73 |
| 2-3546 | Sub-42 | 3,4-diClPh | SO₂ | Single bond | Sub-74 |
| 2-3547 | Sub-42 | 3,4-diClPh | SO₂ | Single bond | Sub-75 |
| 2-3548 | Sub-42 | 3,4-diClPh | SO₂ | Single bond | Sub-76 |
| 2-3549 | Sub-42 | 3,4-diClPh | SO₂ | Single bond | Sub-77 |
| 2-3550 | Sub-42 | 3,4-diClPh | SO₂ | Single bond | Sub-78 |
| 2-3551 | Sub-42 | 3,4-diClPh | SO₂ | Single bond | Sub-79 |
| 2-3552 | Sub-42 | 3,4-diClPh | SO₂ | Single bond | Sub-80 |
| 2-3553 | Sub-43 | 3,4-diClPh | SO₂ | Single bond | Sub-1 |
| 2-3554 | Sub-43 | 3,4-diClPh | SO₂ | Single bond | Sub-2 |
| 2-3555 | Sub-43 | 3,4-diClPh | SO₂ | Single bond | Sub-3 |
| 2-3556 | Sub-43 | 3,4-diClPh | SO₂ | Single bond | Sub-4 |
| 2-3557 | Sub-43 | 3,4-diClPh | SO₂ | Single bond | Sub-5 |
| 2-3558 | Sub-43 | 3,4-diClPh | SO₂ | Single bond | Sub-6 |
| 2-3559 | Sub-43 | 3,4-diClPh | SO₂ | Single bond | Sub-7 |
| 2-3560 | Sub-43 | 3,4-diClPh | SO₂ | Single bond | Sub-8 |
| 2-3561 | Sub-43 | 3,4-diClPh | SO₂ | Single bond | Sub-9 |
| 2-3562 | Sub-43 | 3,4-diClPh | SO₂ | Single bond | Sub-10 |
| 2-3563 | Sub-43 | 3,4-diClPh | SO₂ | Single bond | Sub-11 |
| 2-3564 | Sub-43 | 3,4-diClPh | SO₂ | Single bond | Sub-12 |
| 2-3565 | Sub-43 | 3,4-diClPh | SO₂ | Single bond | Sub-13 |
| 2-3566 | Sub-43 | 3,4-diClPh | SO₂ | Single bond | Sub-14 |
| 2-3567 | Sub-43 | 3,4-diClPh | SO₂ | Single bond | Sub-15 |
| 2-3568 | Sub-43 | 3,4-diClPh | SO₂ | Single bond | Sub-16 |
| 2-3569 | Sub-43 | 3,4-diClPh | SO₂ | Single bond | Sub-17 |
| 2-3570 | Sub-43 | 3,4-diClPh | SO₂ | Single bond | Sub-18 |
| 2-3571 | Sub-43 | 3,4-diClPh | SO₂ | Single bond | Sub-19 |
| 2-3572 | Sub-43 | 3,4-diClPh | SO₂ | Single bond | Sub-20 |
| 2-3573 | Sub-43 | 3,4-diClPh | SO₂ | Single bond | Sub-21 |
| 2-3574 | Sub-43 | 3,4-diClPh | SO₂ | Single bond | Sub-22 |
| 2-3575 | Sub-43 | 3,4-diClPh | SO₂ | Single bond | Sub-23 |
| 2-3576 | Sub-43 | 3,4-diClPh | SO₂ | Single bond | Sub-24 |
| 2-3577 | Sub-43 | 3,4-diClPh | SO₂ | Single bond | Sub-25 |
| 2-3578 | Sub-43 | 3,4-diClPh | SO₂ | Single bond | Sub-26 |
| 2-3579 | Sub-43 | 3,4-diClPh | SO₂ | Single bond | Sub-27 |
| 2-3580 | Sub-43 | 3,4-diClPh | SO₂ | Single bond | Sub-28 |
| 2-3581 | Sub-43 | 3,4-diClPh | SO₂ | Single bond | Sub-29 |
| 2-3582 | Sub-43 | 3,4-diClPh | SO₂ | Single bond | Sub-30 |
| 2-3583 | Sub-43 | 3,4-diClPh | SO₂ | Single bond | Sub-31 |
| 2-3584 | Sub-43 | 3,4-diClPh | SO₂ | Single bond | Sub-32 |
| 2-3585 | Sub-43 | 3,4-diClPh | SO₂ | Single bond | Sub-65 |
| 2-3586 | Sub-43 | 3,4-diClPh | SO₂ | Single bond | Sub-66 |
| 2-3587 | Sub-43 | 3,4-diClPh | SO₂ | Single bond | Sub-67 |
| 2-3588 | Sub-43 | 3,4-diClPh | SO₂ | Single bond | Sub-68 |
| 2-3589 | Sub-43 | 3,4-diClPh | SO₂ | Single bond | Sub-69 |
| 2-3590 | Sub-43 | 3,4-diClPh | SO₂ | Single bond | Sub-70 |
| 2-3591 | Sub-43 | 3,4-diClPh | SO₂ | Single bond | Sub-71 |
| 2-3592 | Sub-43 | 3,4-diClPh | SO₂ | Single bond | Sub-72 |
| 2-3593 | Sub-43 | 3,4-diClPh | SO₂ | Single bond | Sub-73 |
| 2-3594 | Sub-43 | 3,4-diClPh | SO₂ | Single bond | Sub-74 |
| 2-3595 | Sub-43 | 3,4-diClPh | SO₂ | Single bond | Sub-75 |
| 2-3596 | Sub-43 | 3,4-diClPh | SO₂ | Single bond | Sub-76 |
| 2-3597 | Sub-43 | 3,4-diClPh | SO₂ | Single bond | Sub-77 |
| 2-3598 | Sub-43 | 3,4-diClPh | SO₂ | Single bond | Sub-78 |
| 2-3599 | Sub-43 | 3,4-diClPh | SO₂ | Single bond | Sub-79 |
| 2-3600 | Sub-43 | 3,4-diClPh | SO₂ | Single bond | Sub-80 |
| 2-3601 | Sub-44 | 3,4-diClPh | SO₂ | Single bond | Sub-1 |
| 2-3602 | Sub-44 | 3,4-diClPh | SO₂ | Single bond | Sub-2 |
| 2-3603 | Sub-44 | 3,4-diClPh | SO₂ | Single bond | Sub-3 |
| 2-3604 | Sub-44 | 3,4-diClPh | SO₂ | Single bond | Sub-4 |
| 2-3605 | Sub-44 | 3,4-diClPh | SO₂ | Single bond | Sub-5 |
| 2-3606 | Sub-44 | 3,4-diClPh | SO₂ | Single bond | Sub-6 |
| 2-3607 | Sub-44 | 3,4-diClPh | SO₂ | Single bond | Sub-7 |
| 2-3608 | Sub-44 | 3,4-diClPh | SO₂ | Single bond | Sub-8 |
| 2-3609 | Sub-44 | 3,4-diClPh | SO₂ | Single bond | Sub-9 |
| 2-3610 | Sub-44 | 3,4-diClPh | SO₂ | Single bond | Sub-10 |
| 2-3611 | Sub-44 | 3,4-diClPh | SO₂ | Single bond | Sub-11 |
| 2-3612 | Sub-44 | 3,4-diClPh | SO₂ | Single bond | Sub-12 |
| 2-3613 | Sub-44 | 3,4-diClPh | SO₂ | Single bond | Sub-13 |
| 2-3614 | Sub-44 | 3,4-diClPh | SO₂ | Single bond | Sub-14 |
| 2-3615 | Sub-44 | 3,4-diClPh | SO₂ | Single bond | Sub-15 |
| 2-3616 | Sub-44 | 3,4-diClPh | SO₂ | Single bond | Sub-16 |
| 2-3617 | Sub-44 | 3,4-diClPh | SO₂ | Single bond | Sub-17 |
| 2-3618 | Sub-44 | 3,4-diClPh | SO₂ | Single bond | Sub-18 |
| 2-3619 | Sub-44 | 3,4-diClPh | SO₂ | Single bond | Sub-19 |
| 2-3620 | Sub-44 | 3,4-diClPh | SO₂ | Single bond | Sub-20 |
| 2-3621 | Sub-44 | 3,4-diClPh | SO₂ | Single bond | Sub-21 |
| 2-3622 | Sub-44 | 3,4-diClPh | SO₂ | Single bond | Sub-22 |
| 2-3623 | Sub-44 | 3,4-diClPh | SO₂ | Single bond | Sub-23 |
| 2-3624 | Sub-44 | 3,4-diClPh | SO₂ | Single bond | Sub-24 |
| 2-3625 | Sub-44 | 3,4-diClPh | SO₂ | Single bond | Sub-25 |
| 2-3626 | Sub-44 | 3,4-diClPh | SO₂ | Single bond | Sub-26 |
| 2-3627 | Sub-44 | 3,4-diClPh | SO₂ | Single bond | Sub-27 |
| 2-3628 | Sub-44 | 3,4-diClPh | SO₂ | Single bond | Sub-28 |
| 2-3629 | Sub-44 | 3,4-diClPh | SO₂ | Single bond | Sub-29 |
| 2-3630 | Sub-44 | 3,4-diClPh | SO₂ | Single bond | Sub-30 |
| 2-3631 | Sub-44 | 3,4-diClPh | SO₂ | Single bond | Sub-31 |
| 2-3632 | Sub-44 | 3,4-diClPh | SO₂ | Single bond | Sub-32 |
| 2-3633 | Sub-44 | 3,4-diClPh | SO₂ | Single bond | Sub-65 |
| 2-3634 | Sub-44 | 3,4-diClPh | SO₂ | Single bond | Sub-66 |
| 2-3635 | Sub-44 | 3,4-diClPh | SO₂ | Single bond | Sub-67 |
| 2-3636 | Sub-44 | 3,4-diClPh | SO₂ | Single bond | Sub-68 |
| 2-3637 | Sub-44 | 3,4-diClPh | SO₂ | Single bond | Sub-69 |
| 2-3638 | Sub-44 | 3,4-diClPh | SO₂ | Single bond | Sub-70 |
| 2-3639 | Sub-44 | 3,4-diClPh | SO₂ | Single bond | Sub-71 |
| 2-3640 | Sub-44 | 3,4-diClPh | SO₂ | Single bond | Sub-72 |
| 2-3641 | Sub-44 | 3,4-diClPh | SO₂ | Single bond | Sub-73 |
| 2-3642 | Sub-44 | 3,4-diClPh | SO₂ | Single bond | Sub-74 |
| 2-3643 | Sub-44 | 3,4-diClPh | SO₂ | Single bond | Sub-75 |
| 2-3644 | Sub-44 | 3,4-diClPh | SO₂ | Single bond | Sub-76 |
| 2-3645 | Sub-44 | 3,4-diClPh | SO₂ | Single bond | Sub-77 |
| 2-3646 | Sub-44 | 3,4-diClPh | SO₂ | Single bond | Sub-78 |
| 2-3647 | Sub-44 | 3,4-diClPh | SO₂ | Single bond | Sub-79 |
| 2-3648 | Sub-44 | 3,4-diClPh | SO₂ | Single bond | Sub-80 |
| 2-3649 | Sub-45 | 3,4-diClPh | SO₂ | Single bond | Sub-1 |
| 2-3650 | Sub-45 | 3,4-diClPh | SO₂ | Single bond | Sub-2 |
| 2-3651 | Sub-45 | 3,4-diClPh | SO₂ | Single bond | Sub-3 |
| 2-3652 | Sub-45 | 3,4-diClPh | SO₂ | Single bond | Sub-4 |
| 2-3653 | Sub-45 | 3,4-diClPh | SO₂ | Single bond | Sub-5 |
| 2-3654 | Sub-45 | 3,4-diClPh | SO₂ | Single bond | Sub-6 |
| 2-3655 | Sub-45 | 3,4-diClPh | SO₂ | Single bond | Sub-7 |
| 2-3656 | Sub-45 | 3,4-diClPh | SO₂ | Single bond | Sub-8 |
| 2-3657 | Sub-45 | 3,4-diClPh | SO₂ | Single bond | Sub-9 |
| 2-3658 | Sub-45 | 3,4-diClPh | SO₂ | Single bond | Sub-10 |
| 2-3659 | Sub-45 | 3,4-diClPh | SO₂ | Single bond | Sub-11 |
| 2-3660 | Sub-45 | 3,4-diClPh | SO₂ | Single bond | Sub-12 |
| 2-3661 | Sub-45 | 3,4-diClPh | SO₂ | Single bond | Sub-13 |
| 2-3662 | Sub-45 | 3,4-diClPh | SO₂ | Single bond | Sub-14 |
| 2-3663 | Sub-45 | 3,4-diClPh | SO₂ | Single bond | Sub-15 |
| 2-3664 | Sub-45 | 3,4-diClPh | SO₂ | Single bond | Sub-16 |
| 2-3665 | Sub-45 | 3,4-diClPh | SO₂ | Single bond | Sub-17 |
| 2-3666 | Sub-45 | 3,4-diClPh | SO₂ | Single bond | Sub-18 |
| 2-3667 | Sub-45 | 3,4-diClPh | SO₂ | Single bond | Sub-19 |
| 2-3668 | Sub-45 | 3,4-diClPh | SO₂ | Single bond | Sub-20 |

TABLE 2-continued

| Cpd. No. | R¹ | R² | A | B | Z |
|---|---|---|---|---|---|
| 2-3669 | Sub-45 | 3,4-diClPh | SO$_2$ | Single bond | Sub-21 |
| 2-3670 | Sub-45 | 3,4-diClPh | SO$_2$ | Single bond | Sub-22 |
| 2-3671 | Sub-45 | 3,4-diClPh | SO$_2$ | Single bond | Sub-23 |
| 2-3672 | Sub-45 | 3,4-diClPh | SO$_2$ | Single bond | Sub-24 |
| 2-3673 | Sub-45 | 3,4-diClPh | SO$_2$ | Single bond | Sub-25 |
| 2-3674 | Sub-45 | 3,4-diClPh | SO$_2$ | Single bond | Sub-26 |
| 2-3675 | Sub-45 | 3,4-diClPh | SO$_2$ | Single bond | Sub-27 |
| 2-3676 | Sub-45 | 3,4-diClPh | SO$_2$ | Single bond | Sub-28 |
| 2-3677 | Sub-45 | 3,4-diClPh | SO$_2$ | Single bond | Sub-29 |
| 2-3678 | Sub-45 | 3,4-diClPh | SO$_2$ | Single bond | Sub-30 |
| 2-3679 | Sub-45 | 3,4-diClPh | SO$_2$ | Single bond | Sub-31 |
| 2-3680 | Sub-45 | 3,4-diClPh | SO$_2$ | Single bond | Sub-32 |
| 2-3681 | Sub-45 | 3,4-diClPh | SO$_2$ | Single bond | Sub-65 |
| 2-3682 | Sub-45 | 3,4-diClPh | SO$_2$ | Single bond | Sub-66 |
| 2-3683 | Sub-45 | 3,4-diClPh | SO$_2$ | Single bond | Sub-67 |
| 2-3684 | Sub-45 | 3,4-diClPh | SO$_2$ | Single bond | Sub-68 |
| 2-3685 | Sub-45 | 3,4-diClPh | SO$_2$ | Single bond | Sub-69 |
| 2-3686 | Sub-45 | 3,4-diClPh | SO$_2$ | Single bond | Sub-70 |
| 2-3687 | Sub-45 | 3,4-diClPh | SO$_2$ | Single bond | Sub-71 |
| 2-3688 | Sub-45 | 3,4-diClPh | SO$_2$ | Single bond | Sub-72 |
| 2-3689 | Sub-45 | 3,4-diClPh | SO$_2$ | Single bond | Sub-73 |
| 2-3690 | Sub-45 | 3,4-diClPh | SO$_2$ | Single bond | Sub-74 |
| 2-3691 | Sub-45 | 3,4-diClPh | SO$_2$ | Single bond | Sub-75 |
| 2-3692 | Sub-45 | 3,4-diClPh | SO$_2$ | Single bond | Sub-76 |
| 2-3693 | Sub-45 | 3,4-diClPh | SO$_2$ | Single bond | Sub-77 |
| 2-3694 | Sub-45 | 3,4-diClPh | SO$_2$ | Single bond | Sub-78 |
| 2-3695 | Sub-45 | 3,4-diClPh | SO$_2$ | Single bond | Sub-79 |
| 2-3696 | Sub-45 | 3,4-diClPh | SO$_2$ | Single bond | Sub-80 |
| 2-3697 | Sub-46 | 3,4-diClPh | SO$_2$ | Single bond | Sub-1 |
| 2-3698 | Sub-46 | 3,4-diClPh | SO$_2$ | Single bond | Sub-2 |
| 2-3699 | Sub-46 | 3,4-diClPh | SO$_2$ | Single bond | Sub-3 |
| 2-3700 | Sub-46 | 3,4-diClPh | SO$_2$ | Single bond | Sub-4 |
| 2-3701 | Sub-46 | 3,4-diClPh | SO$_2$ | Single bond | Sub-5 |
| 2-3702 | Sub-46 | 3,4-diClPh | SO$_2$ | Single bond | Sub-6 |
| 2-3703 | Sub-46 | 3,4-diClPh | SO$_2$ | Single bond | Sub-7 |
| 2-3704 | Sub-46 | 3,4-diClPh | SO$_2$ | Single bond | Sub-8 |
| 2-3705 | Sub-46 | 3,4-diClPh | SO$_2$ | Single bond | Sub-9 |
| 2-3706 | Sub-46 | 3,4-diClPh | SO$_2$ | Single bond | Sub-10 |
| 2-3707 | Sub-46 | 3,4-diClPh | SO$_2$ | Single bond | Sub-11 |
| 2-3708 | Sub-46 | 3,4-diClPh | SO$_2$ | Single bond | Sub-12 |
| 2-3709 | Sub-46 | 3,4-diClPh | SO$_2$ | Single bond | Sub-13 |
| 2-3710 | Sub-46 | 3,4-diClPh | SO$_2$ | Single bond | Sub-14 |
| 2-3711 | Sub-46 | 3,4-diClPh | SO$_2$ | Single bond | Sub-15 |
| 2-3712 | Sub-46 | 3,4-diClPh | SO$_2$ | Single bond | Sub-16 |
| 2-3713 | Sub-46 | 3,4-diClPh | SO$_2$ | Single bond | Sub-17 |
| 2-3714 | Sub-46 | 3,4-diClPh | SO$_2$ | Single bond | Sub-18 |
| 2-3715 | Sub-46 | 3,4-diClPh | SO$_2$ | Single bond | Sub-19 |
| 2-3716 | Sub-46 | 3,4-diClPh | SO$_2$ | Single bond | Sub-20 |
| 2-3717 | Sub-46 | 3,4-diClPh | SO$_2$ | Single bond | Sub-21 |
| 2-3718 | Sub-46 | 3,4-diClPh | SO$_2$ | Single bond | Sub-22 |
| 2-3719 | Sub-46 | 3,4-diClPh | SO$_2$ | Single bond | Sub-23 |
| 2-3720 | Sub-46 | 3,4-diClPh | SO$_2$ | Single bond | Sub-24 |
| 2-3721 | Sub-46 | 3,4-diClPh | SO$_2$ | Single bond | Sub-25 |
| 2-3722 | Sub-46 | 3,4-diClPh | SO$_2$ | Single bond | Sub-26 |
| 2-3723 | Sub-46 | 3,4-diClPh | SO$_2$ | Single bond | Sub-27 |
| 2-3724 | Sub-46 | 3,4-diClPh | SO$_2$ | Single bond | Sub-28 |
| 2-3725 | Sub-46 | 3,4-diClPh | SO$_2$ | Single bond | Sub-29 |
| 2-3726 | Sub-46 | 3,4-diClPh | SO$_2$ | Single bond | Sub-30 |
| 2-3727 | Sub-46 | 3,4-diClPh | SO$_2$ | Single bond | Sub-31 |
| 2-3728 | Sub-46 | 3,4-diClPh | SO$_2$ | Single bond | Sub-32 |
| 2-3729 | Sub-46 | 3,4-diClPh | SO$_2$ | Single bond | Sub-65 |
| 2-3730 | Sub-46 | 3,4-diClPh | SO$_2$ | Single bond | Sub-66 |
| 2-3731 | Sub-46 | 3,4-diClPh | SO$_2$ | Single bond | Sub-67 |
| 2-3732 | Sub-46 | 3,4-diClPh | SO$_2$ | Single bond | Sub-68 |
| 2-3733 | Sub-46 | 3,4-diClPh | SO$_2$ | Single bond | Sub-69 |
| 2-3734 | Sub-46 | 3,4-diClPh | SO$_2$ | Single bond | Sub-70 |
| 2-3735 | Sub-46 | 3,4-diClPh | SO$_2$ | Single bond | Sub-71 |
| 2-3736 | Sub-46 | 3,4-diClPh | SO$_2$ | Single bond | Sub-72 |
| 2-3737 | Sub-46 | 3,4-diClPh | SO$_2$ | Single bond | Sub-73 |
| 2-3738 | Sub-46 | 3,4-diClPh | SO$_2$ | Single bond | Sub-74 |
| 2-3739 | Sub-46 | 3,4-diClPh | SO$_2$ | Single bond | Sub-75 |
| 2-3740 | Sub-46 | 3,4-diClPh | SO$_2$ | Single bond | Sub-76 |
| 2-3741 | Sub-46 | 3,4-diClPh | SO$_2$ | Single bond | Sub-77 |
| 2-3742 | Sub-46 | 3,4-diClPh | SO$_2$ | Single bond | Sub-78 |
| 2-3743 | Sub-46 | 3,4-diClPh | SO$_2$ | Single bond | Sub-79 |
| 2-3744 | Sub-46 | 3,4-diClPh | SO$_2$ | Single bond | Sub-80 |
| 2-3745 | Sub-47 | 3,4-diClPh | SO$_2$ | Single bond | Sub-1 |
| 2-3746 | Sub-47 | 3,4-diClPh | SO$_2$ | Single bond | Sub-2 |
| 2-3747 | Sub-47 | 3,4-diClPh | SO$_2$ | Single bond | Sub-3 |
| 2-3748 | Sub-47 | 3,4-diClPh | SO$_2$ | Single bond | Sub-4 |
| 2-3749 | Sub-47 | 3,4-diClPh | SO$_2$ | Single bond | Sub-5 |
| 2-3750 | Sub-47 | 3,4-diClPh | SO$_2$ | Single bond | Sub-6 |
| 2-3751 | Sub-47 | 3,4-diClPh | SO$_2$ | Single bond | Sub-7 |
| 2-3752 | Sub-47 | 3,4-diClPh | SO$_2$ | Single bond | Sub-8 |
| 2-3753 | Sub-47 | 3,4-diClPh | SO$_2$ | Single bond | Sub-9 |
| 2-3754 | Sub-47 | 3,4-diClPh | SO$_2$ | Single bond | Sub-10 |
| 2-3755 | Sub-47 | 3,4-diClPh | SO$_2$ | Single bond | Sub-11 |
| 2-3756 | Sub-47 | 3,4-diClPh | SO$_2$ | Single bond | Sub-12 |
| 2-3757 | Sub-47 | 3,4-diClPh | SO$_2$ | Single bond | Sub-13 |
| 2-3758 | Sub-47 | 3,4-diClPh | SO$_2$ | Single bond | Sub-14 |
| 2-3759 | Sub-47 | 3,4-diClPh | SO$_2$ | Single bond | Sub-15 |
| 2-3760 | Sub-47 | 3,4-diClPh | SO$_2$ | Single bond | Sub-16 |
| 2-3761 | Sub-47 | 3,4-diClPh | SO$_2$ | Single bond | Sub-17 |
| 2-3762 | Sub-47 | 3,4-diClPh | SO$_2$ | Single bond | Sub-18 |
| 2-3763 | Sub-47 | 3,4-diClPh | SO$_2$ | Single bond | Sub-19 |
| 2-3764 | Sub-47 | 3,4-diClPh | SO$_2$ | Single bond | Sub-20 |
| 2-3765 | Sub-47 | 3,4-diClPh | SO$_2$ | Single bond | Sub-21 |
| 2-3766 | Sub-47 | 3,4-diClPh | SO$_2$ | Single bond | Sub-22 |
| 2-3767 | Sub-47 | 3,4-diClPh | SO$_2$ | Single bond | Sub-23 |
| 2-3768 | Sub-47 | 3,4-diClPh | SO$_2$ | Single bond | Sub-24 |
| 2-3769 | Sub-47 | 3,4-diClPh | SO$_2$ | Single bond | Sub-25 |
| 2-3770 | Sub-47 | 3,4-diClPh | SO$_2$ | Single bond | Sub-26 |
| 2-3771 | Sub-47 | 3,4-diClPh | SO$_2$ | Single bond | Sub-27 |
| 2-3772 | Sub-47 | 3,4-diClPh | SO$_2$ | Single bond | Sub-28 |
| 2-3773 | Sub-47 | 3,4-diClPh | SO$_2$ | Single bond | Sub-29 |
| 2-3774 | Sub-47 | 3,4-diClPh | SO$_2$ | Single bond | Sub-30 |
| 2-3775 | Sub-47 | 3,4-diClPh | SO$_2$ | Single bond | Sub-31 |
| 2-3776 | Sub-47 | 3,4-diClPh | SO$_2$ | Single bond | Sub-32 |
| 2-3777 | Sub-47 | 3,4-diClPh | SO$_2$ | Single bond | Sub-65 |
| 2-3778 | Sub-47 | 3,4-diClPh | SO$_2$ | Single bond | Sub-66 |
| 2-3779 | Sub-47 | 3,4-diClPh | SO$_2$ | Single bond | Sub-67 |
| 2-3780 | Sub-47 | 3,4-diClPh | SO$_2$ | Single bond | Sub-68 |
| 2-3781 | Sub-47 | 3,4-diClPh | SO$_2$ | Single bond | Sub-69 |
| 2-3782 | Sub-47 | 3,4-diClPh | SO$_2$ | Single bond | Sub-70 |
| 2-3783 | Sub-47 | 3,4-diClPh | SO$_2$ | Single bond | Sub-71 |
| 2-3784 | Sub-47 | 3,4-diClPh | SO$_2$ | Single bond | Sub-72 |
| 2-3785 | Sub-47 | 3,4-diClPh | SO$_2$ | Single bond | Sub-73 |
| 2-3786 | Sub-47 | 3,4-diClPh | SO$_2$ | Single bond | Sub-74 |
| 2-3787 | Sub-47 | 3,4-diClPh | SO$_2$ | Single bond | Sub-75 |
| 2-3788 | Sub-47 | 3,4-diClPh | SO$_2$ | Single bond | Sub-76 |
| 2-3789 | Sub-47 | 3,4-diClPh | SO$_2$ | Single bond | Sub-77 |
| 2-3790 | Sub-47 | 3,4-diClPh | SO$_2$ | Single bond | Sub-78 |
| 2-3791 | Sub-47 | 3,4-diClPh | SO$_2$ | Single bond | Sub-79 |
| 2-3792 | Sub-47 | 3,4-diClPh | SO$_2$ | Single bond | Sub-80 |
| 2-3793 | Sub-81 | 3,4-diClPh | SO$_2$ | Single bond | Sub-1 |
| 2-3794 | Sub-81 | 3,4-diClPh | SO$_2$ | Single bond | Sub-2 |
| 2-3795 | Sub-81 | 3,4-diClPh | SO$_2$ | Single bond | Sub-3 |
| 2-3796 | Sub-81 | 3,4-diClPh | SO$_2$ | Single bond | Sub-4 |
| 2-3797 | Sub-81 | 3,4-diClPh | SO$_2$ | Single bond | Sub-5 |
| 2-3798 | Sub-81 | 3,4-diClPh | SO$_2$ | Single bond | Sub-6 |
| 2-3799 | Sub-81 | 3,4-diClPh | SO$_2$ | Single bond | Sub-7 |
| 2-3800 | Sub-81 | 3,4-diClPh | SO$_2$ | Single bond | Sub-8 |
| 2-3801 | Sub-81 | 3,4-diClPh | SO$_2$ | Single bond | Sub-9 |
| 2-3802 | Sub-81 | 3,4-diClPh | SO$_2$ | Single bond | Sub-10 |
| 2-3803 | Sub-81 | 3,4-diClPh | SO$_2$ | Single bond | Sub-11 |
| 2-3804 | Sub-81 | 3,4-diClPh | SO$_2$ | Single bond | Sub-12 |
| 2-3805 | Sub-81 | 3,4-diClPh | SO$_2$ | Single bond | Sub-13 |
| 2-3806 | Sub-81 | 3,4-diClPh | SO$_2$ | Single bond | Sub-14 |
| 2-3807 | Sub-81 | 3,4-diClPh | SO$_2$ | Single bond | Sub-15 |
| 2-3808 | Sub-81 | 3,4-diClPh | SO$_2$ | Single bond | Sub-16 |
| 2-3809 | Sub-81 | 3,4-diClPh | SO$_2$ | Single bond | Sub-17 |
| 2-3810 | Sub-81 | 3,4-diClPh | SO$_2$ | Single bond | Sub-18 |
| 2-3811 | Sub-81 | 3,4-diClPh | SO$_2$ | Single bond | Sub-19 |
| 2-3812 | Sub-81 | 3,4-diClPh | SO$_2$ | Single bond | Sub-20 |
| 2-3813 | Sub-81 | 3,4-diClPh | SO$_2$ | Single bond | Sub-21 |
| 2-3814 | Sub-81 | 3,4-diClPh | SO$_2$ | Single bond | Sub-22 |
| 2-3815 | Sub-81 | 3,4-diClPh | SO$_2$ | Single bond | Sub-23 |
| 2-3816 | Sub-81 | 3,4-diClPh | SO$_2$ | Single bond | Sub-24 |
| 2-3817 | Sub-81 | 3,4-diClPh | SO$_2$ | Single bond | Sub-25 |
| 2-3818 | Sub-81 | 3,4-diClPh | SO$_2$ | Single bond | Sub-26 |
| 2-3819 | Sub-81 | 3,4-diClPh | SO$_2$ | Single bond | Sub-27 |
| 2-3820 | Sub-81 | 3,4-diClPh | SO$_2$ | Single bond | Sub-28 |
| 2-3821 | Sub-81 | 3,4-diClPh | SO$_2$ | Single bond | Sub-29 |
| 2-3822 | Sub-81 | 3,4-diClPh | SO$_2$ | Single bond | Sub-30 |

TABLE 2-continued

| Cpd. No. | R¹ | R² | A | B | Z |
|---|---|---|---|---|---|
| 2-3823 | Sub-81 | 3,4-diClPh | SO$_2$ | Single bond | Sub-31 |
| 2-3824 | Sub-81 | 3,4-diClPh | SO$_2$ | Single bond | Sub-32 |
| 2-3825 | Sub-81 | 3,4-diClPh | SO$_2$ | Single bond | Sub-65 |
| 2-3826 | Sub-81 | 3,4-diClPh | SO$_2$ | Single bond | Sub-66 |
| 2-3827 | Sub-81 | 3,4-diClPh | SO$_2$ | Single bond | Sub-67 |
| 2-3828 | Sub-81 | 3,4-diClPh | SO$_2$ | Single bond | Sub-68 |
| 2-3829 | Sub-81 | 3,4-diClPh | SO$_2$ | Single bond | Sub-69 |
| 2-3830 | Sub-81 | 3,4-diClPh | SO$_2$ | Single bond | Sub-70 |
| 2-3831 | Sub-81 | 3,4-diClPh | SO$_2$ | Single bond | Sub-71 |
| 2-3832 | Sub-81 | 3,4-diClPh | SO$_2$ | Single bond | Sub-72 |
| 2-3833 | Sub-81 | 3,4-diClPh | SO$_2$ | Single bond | Sub-73 |
| 2-3834 | Sub-81 | 3,4-diClPh | SO$_2$ | Single bond | Sub-74 |
| 2-3835 | Sub-81 | 3,4-diClPh | SO$_2$ | Single bond | Sub-75 |
| 2-3836 | Sub-81 | 3,4-diClPh | SO$_2$ | Single bond | Sub-76 |
| 2-3837 | Sub-81 | 3,4-diClPh | SO$_2$ | Single bond | Sub-77 |
| 2-3838 | Sub-81 | 3,4-diClPh | SO$_2$ | Single bond | Sub-78 |
| 2-3839 | Sub-81 | 3,4-diClPh | SO$_2$ | Single bond | Sub-79 |
| 2-3840 | Sub-81 | 3,4-diClPh | SO$_2$ | Single bond | Sub-80 |
| 2-3841 | Sub-48 | 3,4-diClPh | SO$_2$ | Single bond | Sub-1 |
| 2-3842 | Sub-48 | 3,4-diClPh | SO$_2$ | Single bond | Sub-2 |
| 2-3843 | Sub-48 | 3,4-diClPh | SO$_2$ | Single bond | Sub-3 |
| 2-3844 | Sub-48 | 3,4-diClPh | SO$_2$ | Single bond | Sub-4 |
| 2-3845 | Sub-48 | 3,4-diClPh | SO$_2$ | Single bond | Sub-5 |
| 2-3846 | Sub-48 | 3,4-diClPh | SO$_2$ | Single bond | Sub-6 |
| 2-3847 | Sub-48 | 3,4-diClPh | SO$_2$ | Single bond | Sub-7 |
| 2-3848 | Sub-48 | 3,4-diClPh | SO$_2$ | Single bond | Sub-8 |
| 2-3849 | Sub-48 | 3,4-diClPh | SO$_2$ | Single bond | Sub-9 |
| 2-3850 | Sub-48 | 3,4-diClPh | SO$_2$ | Single bond | Sub-10 |
| 2-3851 | Sub-48 | 3,4-diClPh | SO$_2$ | Single bond | Sub-11 |
| 2-3852 | Sub-48 | 3,4-diClPh | SO$_2$ | Single bond | Sub-12 |
| 2-3853 | Sub-48 | 3,4-diClPh | SO$_2$ | Single bond | Sub-13 |
| 2-3854 | Sub-48 | 3,4-diClPh | SO$_2$ | Single bond | Sub-14 |
| 2-3855 | Sub-48 | 3,4-diClPh | SO$_2$ | Single bond | Sub-15 |
| 2-3856 | Sub-48 | 3,4-diClPh | SO$_2$ | Single bond | Sub-16 |
| 2-3857 | Sub-48 | 3,4-diClPh | SO$_2$ | Single bond | Sub-17 |
| 2-3858 | Sub-48 | 3,4-diClPh | SO$_2$ | Single bond | Sub-18 |
| 2-3859 | Sub-48 | 3,4-diClPh | SO$_2$ | Single bond | Sub-19 |
| 2-3860 | Sub-48 | 3,4-diClPh | SO$_2$ | Single bond | Sub-20 |
| 2-3861 | Sub-48 | 3,4-diClPh | SO$_2$ | Single bond | Sub-21 |
| 2-3862 | Sub-48 | 3,4-diClPh | SO$_2$ | Single bond | Sub-22 |
| 2-3863 | Sub-48 | 3,4-diClPh | SO$_2$ | Single bond | Sub-23 |
| 2-3864 | Sub-48 | 3,4-diClPh | SO$_2$ | Single bond | Sub-24 |
| 2-3865 | Sub-48 | 3,4-diClPh | SO$_2$ | Single bond | Sub-25 |
| 2-3866 | Sub-48 | 3,4-diClPh | SO$_2$ | Single bond | Sub-26 |
| 2-3867 | Sub-48 | 3,4-diClPh | SO$_2$ | Single bond | Sub-27 |
| 2-3868 | Sub-48 | 3,4-diClPh | SO$_2$ | Single bond | Sub-28 |
| 2-3869 | Sub-48 | 3,4-diClPh | SO$_2$ | Single bond | Sub-29 |
| 2-3870 | Sub-48 | 3,4-diClPh | SO$_2$ | Single bond | Sub-30 |
| 2-3871 | Sub-48 | 3,4-diClPh | SO$_2$ | Single bond | Sub-31 |
| 2-3872 | Sub-48 | 3,4-diClPh | SO$_2$ | Single bond | Sub-32 |
| 2-3873 | Sub-48 | 3,4-diClPh | SO$_2$ | Single bond | Sub-65 |
| 2-3874 | Sub-48 | 3,4-diClPh | SO$_2$ | Single bond | Sub-66 |
| 2-3875 | Sub-48 | 3,4-diClPh | SO$_2$ | Single bond | Sub-67 |
| 2-3876 | Sub-48 | 3,4-diClPh | SO$_2$ | Single bond | Sub-68 |
| 2-3877 | Sub-48 | 3,4-diClPh | SO$_2$ | Single bond | Sub-69 |
| 2-3878 | Sub-48 | 3,4-diClPh | SO$_2$ | Single bond | Sub-70 |
| 2-3879 | Sub-48 | 3,4-diClPh | SO$_2$ | Single bond | Sub-71 |
| 2-3880 | Sub-48 | 3,4-diClPh | SO$_2$ | Single bond | Sub-72 |
| 2-3881 | Sub-48 | 3,4-diClPh | SO$_2$ | Single bond | Sub-73 |
| 2-3882 | Sub-48 | 3,4-diClPh | SO$_2$ | Single bond | Sub-74 |
| 2-3883 | Sub-48 | 3,4-diClPh | SO$_2$ | Single bond | Sub-75 |
| 2-3884 | Sub-48 | 3,4-diClPh | SO$_2$ | Single bond | Sub-76 |
| 2-3885 | Sub-48 | 3,4-diClPh | SO$_2$ | Single bond | Sub-77 |
| 2-3886 | Sub-48 | 3,4-diClPh | SO$_2$ | Single bond | Sub-78 |
| 2-3887 | Sub-48 | 3,4-diClPh | SO$_2$ | Single bond | Sub-79 |
| 2-3888 | Sub-48 | 3,4-diClPh | SO$_2$ | Single bond | Sub-80 |
| 2-3889 | Sub-49 | 3,4-diClPh | SO$_2$ | Single bond | Sub-1 |
| 2-3890 | Sub-49 | 3,4-diClPh | SO$_2$ | Single bond | Sub-2 |
| 2-3891 | Sub-49 | 3,4-diClPh | SO$_2$ | Single bond | Sub-3 |
| 2-3892 | Sub-49 | 3,4-diClPh | SO$_2$ | Single bond | Sub-4 |
| 2-3893 | Sub-49 | 3,4-diClPh | SO$_2$ | Single bond | Sub-5 |
| 2-3894 | Sub-49 | 3,4-diClPh | SO$_2$ | Single bond | Sub-6 |
| 2-3895 | Sub-49 | 3,4-diClPh | SO$_2$ | Single bond | Sub-7 |
| 2-3896 | Sub-49 | 3,4-diClPh | SO$_2$ | Single bond | Sub-8 |
| 2-3897 | Sub-49 | 3,4-diClPh | SO$_2$ | Single bond | Sub-9 |
| 2-3898 | Sub-49 | 3,4-diClPh | SO$_2$ | Single bond | Sub-10 |
| 2-3899 | Sub-49 | 3,4-diClPh | SO$_2$ | Single bond | Sub-11 |
| 2-3900 | Sub-49 | 3,4-diClPh | SO$_2$ | Single bond | Sub-12 |
| 2-3901 | Sub-49 | 3,4-diClPh | SO$_2$ | Single bond | Sub-13 |
| 2-3902 | Sub-49 | 3,4-diClPh | SO$_2$ | Single bond | Sub-14 |
| 2-3903 | Sub-49 | 3,4-diClPh | SO$_2$ | Single bond | Sub-15 |
| 2-3904 | Sub-49 | 3,4-diClPh | SO$_2$ | Single bond | Sub-16 |
| 2-3905 | Sub-49 | 3,4-diClPh | SO$_2$ | Single bond | Sub-17 |
| 2-3906 | Sub-49 | 3,4-diClPh | SO$_2$ | Single bond | Sub-18 |
| 2-3907 | Sub-49 | 3,4-diClPh | SO$_2$ | Single bond | Sub-19 |
| 2-3908 | Sub-49 | 3,4-diClPh | SO$_2$ | Single bond | Sub-20 |
| 2-3909 | Sub-49 | 3,4-diClPh | SO$_2$ | Single bond | Sub-21 |
| 2-3910 | Sub-49 | 3,4-diClPh | SO$_2$ | Single bond | Sub-22 |
| 2-3911 | Sub-49 | 3,4-diClPh | SO$_2$ | Single bond | Sub-23 |
| 2-3912 | Sub-49 | 3,4-diClPh | SO$_2$ | Single bond | Sub-24 |
| 2-3913 | Sub-49 | 3,4-diClPh | SO$_2$ | Single bond | Sub-25 |
| 2-3914 | Sub-49 | 3,4-diClPh | SO$_2$ | Single bond | Sub-26 |
| 2-3915 | Sub-49 | 3,4-diClPh | SO$_2$ | Single bond | Sub-27 |
| 2-3916 | Sub-49 | 3,4-diClPh | SO$_2$ | Single bond | Sub-28 |
| 2-3917 | Sub-49 | 3,4-diClPh | SO$_2$ | Single bond | Sub-29 |
| 2-3918 | Sub-49 | 3,4-diClPh | SO$_2$ | Single bond | Sub-30 |
| 2-3919 | Sub-49 | 3,4-diClPh | SO$_2$ | Single bond | Sub-31 |
| 2-3920 | Sub-49 | 3,4-diClPh | SO$_2$ | Single bond | Sub-32 |
| 2-3921 | Sub-49 | 3,4-diClPh | SO$_2$ | Single bond | Sub-65 |
| 2-3922 | Sub-49 | 3,4-diClPh | SO$_2$ | Single bond | Sub-66 |
| 2-3923 | Sub-49 | 3,4-diClPh | SO$_2$ | Single bond | Sub-67 |
| 2-3924 | Sub-49 | 3,4-diClPh | SO$_2$ | Single bond | Sub-68 |
| 2-3925 | Sub-49 | 3,4-diClPh | SO$_2$ | Single bond | Sub-69 |
| 2-3926 | Sub-49 | 3,4-diClPh | SO$_2$ | Single bond | Sub-70 |
| 2-3927 | Sub-49 | 3,4-diClPh | SO$_2$ | Single bond | Sub-71 |
| 2-3928 | Sub-49 | 3,4-diClPh | SO$_2$ | Single bond | Sub-72 |
| 2-3929 | Sub-49 | 3,4-diClPh | SO$_2$ | Single bond | Sub-73 |
| 2-3930 | Sub-49 | 3,4-diClPh | SO$_2$ | Single bond | Sub-74 |
| 2-3931 | Sub-49 | 3,4-diClPh | SO$_2$ | Single bond | Sub-75 |
| 2-3932 | Sub-49 | 3,4-diClPh | SO$_2$ | Single bond | Sub-76 |
| 2-3933 | Sub-49 | 3,4-diClPh | SO$_2$ | Single bond | Sub-77 |
| 2-3934 | Sub-49 | 3,4-diClPh | SO$_2$ | Single bond | Sub-78 |
| 2-3935 | Sub-49 | 3,4-diClPh | SO$_2$ | Single bond | Sub-79 |
| 2-3936 | Sub-49 | 3,4-diClPh | SO$_2$ | Single bond | Sub-80 |
| 2-3937 | Sub-50 | 3,4-diClPh | SO$_2$ | Single bond | Sub-1 |
| 2-3938 | Sub-50 | 3,4-diClPh | SO$_2$ | Single bond | Sub-2 |
| 2-3939 | Sub-50 | 3,4-diClPh | SO$_2$ | Single bond | Sub-3 |
| 2-3940 | Sub-50 | 3,4-diClPh | SO$_2$ | Single bond | Sub-4 |
| 2-3941 | Sub-50 | 3,4-diClPh | SO$_2$ | Single bond | Sub-5 |
| 2-3942 | Sub-50 | 3,4-diClPh | SO$_2$ | Single bond | Sub-6 |
| 2-3943 | Sub-50 | 3,4-diClPh | SO$_2$ | Single bond | Sub-7 |
| 2-3944 | Sub-50 | 3,4-diClPh | SO$_2$ | Single bond | Sub-8 |
| 2-3945 | Sub-50 | 3,4-diClPh | SO$_2$ | Single bond | Sub-9 |
| 2-3946 | Sub-50 | 3,4-diClPh | SO$_2$ | Single bond | Sub-10 |
| 2-3947 | Sub-50 | 3,4-diClPh | SO$_2$ | Single bond | Sub-11 |
| 2-3948 | Sub-50 | 3,4-diClPh | SO$_2$ | Single bond | Sub-12 |
| 2-3949 | Sub-50 | 3,4-diClPh | SO$_2$ | Single bond | Sub-13 |
| 2-3950 | Sub-50 | 3,4-diClPh | SO$_2$ | Single bond | Sub-14 |
| 2-3951 | Sub-50 | 3,4-diClPh | SO$_2$ | Single bond | Sub-15 |
| 2-3952 | Sub-50 | 3,4-diClPh | SO$_2$ | Single bond | Sub-16 |
| 2-3953 | Sub-50 | 3,4-diClPh | SO$_2$ | Single bond | Sub-17 |
| 2-3954 | Sub-50 | 3,4-diClPh | SO$_2$ | Single bond | Sub-18 |
| 2-3955 | Sub-50 | 3,4-diClPh | SO$_2$ | Single bond | Sub-19 |
| 2-3956 | Sub-50 | 3,4-diClPh | SO$_2$ | Single bond | Sub-20 |
| 2-3957 | Sub-50 | 3,4-diClPh | SO$_2$ | Single bond | Sub-21 |
| 2-3958 | Sub-50 | 3,4-diClPh | SO$_2$ | Single bond | Sub-22 |
| 2-3959 | Sub-50 | 3,4-diClPh | SO$_2$ | Single bond | Sub-23 |
| 2-3960 | Sub-50 | 3,4-diClPh | SO$_2$ | Single bond | Sub-24 |
| 2-3961 | Sub-50 | 3,4-diClPh | SO$_2$ | Single bond | Sub-25 |
| 2-3962 | Sub-50 | 3,4-diClPh | SO$_2$ | Single bond | Sub-26 |
| 2-3963 | Sub-50 | 3,4-diClPh | SO$_2$ | Single bond | Sub-27 |
| 2-3964 | Sub-50 | 3,4-diClPh | SO$_2$ | Single bond | Sub-28 |
| 2-3965 | Sub-50 | 3,4-diClPh | SO$_2$ | Single bond | Sub-29 |
| 2-3966 | Sub-50 | 3,4-diClPh | SO$_2$ | Single bond | Sub-30 |
| 2-3967 | Sub-50 | 3,4-diClPh | SO$_2$ | Single bond | Sub-31 |
| 2-3968 | Sub-50 | 3,4-diClPh | SO$_2$ | Single bond | Sub-32 |
| 2-3969 | Sub-50 | 3,4-diClPh | SO$_2$ | Single bond | Sub-65 |
| 2-3970 | Sub-50 | 3,4-diClPh | SO$_2$ | Single bond | Sub-66 |
| 2-3971 | Sub-50 | 3,4-diClPh | SO$_2$ | Single bond | Sub-67 |
| 2-3972 | Sub-50 | 3,4-diClPh | SO$_2$ | Single bond | Sub-68 |
| 2-3973 | Sub-50 | 3,4-diClPh | SO$_2$ | Single bond | Sub-69 |
| 2-3974 | Sub-50 | 3,4-diClPh | SO$_2$ | Single bond | Sub-70 |
| 2-3975 | Sub-50 | 3,4-diClPh | SO$_2$ | Single bond | Sub-71 |
| 2-3976 | Sub-50 | 3,4-diClPh | SO$_2$ | Single bond | Sub-72 |

TABLE 2-continued

| Cpd. No. | R¹ | R² | A | B | Z |
|---|---|---|---|---|---|
| 2-3977 | Sub-50 | 3,4-diClPh | SO₂ | Single bond | Sub-73 |
| 2-3978 | Sub-50 | 3,4-diClPh | SO₂ | Single bond | Sub-74 |
| 2-3979 | Sub-50 | 3,4-diClPh | SO₂ | Single bond | Sub-75 |
| 2-3980 | Sub-50 | 3,4-diClPh | SO₂ | Single bond | Sub-76 |
| 2-3981 | Sub-50 | 3,4-diClPh | SO₂ | Single bond | Sub-77 |
| 2-3982 | Sub-50 | 3,4-diClPh | SO₂ | Single bond | Sub-78 |
| 2-3983 | Sub-50 | 3,4-diClPh | SO₂ | Single bond | Sub-79 |
| 2-3984 | Sub-50 | 3,4-diClPh | SO₂ | Single bond | Sub-80 |
| 2-3985 | Sub-51 | 3,4-diClPh | SO₂ | Single bond | Sub-1 |
| 2-3986 | Sub-51 | 3,4-diClPh | SO₂ | Single bond | Sub-2 |
| 2-3987 | Sub-51 | 3,4-diClPh | SO₂ | Single bond | Sub-3 |
| 2-3988 | Sub-51 | 3,4-diClPh | SO₂ | Single bond | Sub-4 |
| 2-3989 | Sub-51 | 3,4-diClPh | SO₂ | Single bond | Sub-5 |
| 2-3990 | Sub-51 | 3,4-diClPh | SO₂ | Single bond | Sub-6 |
| 2-3991 | Sub-51 | 3,4-diClPh | SO₂ | Single bond | Sub-7 |
| 2-3992 | Sub-51 | 3,4-diClPh | SO₂ | Single bond | Sub-8 |
| 2-3993 | Sub-51 | 3,4-diClPh | SO₂ | Single bond | Sub-9 |
| 2-3994 | Sub-51 | 3,4-diClPh | SO₂ | Single bond | Sub-10 |
| 2-3995 | Sub-51 | 3,4-diClPh | SO₂ | Single bond | Sub-11 |
| 2-3996 | Sub-51 | 3,4-diClPh | SO₂ | Single bond | Sub-12 |
| 2-3997 | Sub-51 | 3,4-diClPh | SO₂ | Single bond | Sub-13 |
| 2-3998 | Sub-51 | 3,4-diClPh | SO₂ | Single bond | Sub-14 |
| 2-3999 | Sub-51 | 3,4-diClPh | SO₂ | Single bond | Sub-15 |
| 2-4000 | Sub-51 | 3,4-diClPh | SO₂ | Single bond | Sub-16 |
| 2-4001 | Sub-51 | 3,4-diClPh | SO₂ | Single bond | Sub-17 |
| 2-4002 | Sub-51 | 3,4-diClPh | SO₂ | Single bond | Sub-18 |
| 2-4003 | Sub-51 | 3,4-diClPh | SO₂ | Single bond | Sub-19 |
| 2-4004 | Sub-51 | 3,4-diClPh | SO₂ | Single bond | Sub-20 |
| 2-4005 | Sub-51 | 3,4-diClPh | SO₂ | Single bond | Sub-21 |
| 2-4006 | Sub-51 | 3,4-diClPh | SO₂ | Single bond | Sub-22 |
| 2-4007 | Sub-51 | 3,4-diClPh | SO₂ | Single bond | Sub-23 |
| 2-4008 | Sub-51 | 3,4-diClPh | SO₂ | Single bond | Sub-24 |
| 2-4009 | Sub-51 | 3,4-diClPh | SO₂ | Single bond | Sub-25 |
| 2-4010 | Sub-51 | 3,4-diClPh | SO₂ | Single bond | Sub-26 |
| 2-4011 | Sub-51 | 3,4-diClPh | SO₂ | Single bond | Sub-27 |
| 2-4012 | Sub-51 | 3,4-diClPh | SO₂ | Single bond | Sub-28 |
| 2-4013 | Sub-51 | 3,4-diClPh | SO₂ | Single bond | Sub-29 |
| 2-4014 | Sub-51 | 3,4-diClPh | SO₂ | Single bond | Sub-30 |
| 2-4015 | Sub-51 | 3,4-diClPh | SO₂ | Single bond | Sub-31 |
| 2-4016 | Sub-51 | 3,4-diClPh | SO₂ | Single bond | Sub-32 |
| 2-4017 | Sub-51 | 3,4-diClPh | SO₂ | Single bond | Sub-65 |
| 2-4018 | Sub-51 | 3,4-diClPh | SO₂ | Single bond | Sub-66 |
| 2-4019 | Sub-51 | 3,4-diClPh | SO₂ | Single bond | Sub-67 |
| 2-4020 | Sub-51 | 3,4-diClPh | SO₂ | Single bond | Sub-68 |
| 2-4021 | Sub-51 | 3,4-diClPh | SO₂ | Single bond | Sub-69 |
| 2-4022 | Sub-51 | 3,4-diClPh | SO₂ | Single bond | Sub-70 |
| 2-4023 | Sub-51 | 3,4-diClPh | SO₂ | Single bond | Sub-71 |
| 2-4024 | Sub-51 | 3,4-diClPh | SO₂ | Single bond | Sub-72 |
| 2-4025 | Sub-51 | 3,4-diClPh | SO₂ | Single bond | Sub-73 |
| 2-4026 | Sub-51 | 3,4-diClPh | SO₂ | Single bond | Sub-74 |
| 2-4027 | Sub-51 | 3,4-diClPh | SO₂ | Single bond | Sub-75 |
| 2-4028 | Sub-51 | 3,4-diClPh | SO₂ | Single bond | Sub-76 |
| 2-4029 | Sub-51 | 3,4-diClPh | SO₂ | Single bond | Sub-77 |
| 2-4030 | Sub-51 | 3,4-diClPh | SO₂ | Single bond | Sub-78 |
| 2-4031 | Sub-51 | 3,4-diClPh | SO₂ | Single bond | Sub-79 |
| 2-4032 | Sub-51 | 3,4-diClPh | SO₂ | Single bond | Sub-80 |
| 2-4033 | Sub-52 | 3,4-diClPh | SO₂ | Single bond | Sub-1 |
| 2-4034 | Sub-52 | 3,4-diClPh | SO₂ | Single bond | Sub-2 |
| 2-4035 | Sub-52 | 3,4-diClPh | SO₂ | Single bond | Sub-3 |
| 2-4036 | Sub-52 | 3,4-diClPh | SO₂ | Single bond | Sub-4 |
| 2-4037 | Sub-52 | 3,4-diClPh | SO₂ | Single bond | Sub-5 |
| 2-4038 | Sub-52 | 3,4-diClPh | SO₂ | Single bond | Sub-6 |
| 2-4039 | Sub-52 | 3,4-diClPh | SO₂ | Single bond | Sub-7 |
| 2-4040 | Sub-52 | 3,4-diClPh | SO₂ | Single bond | Sub-8 |
| 2-4041 | Sub-52 | 3,4-diClPh | SO₂ | Single bond | Sub-9 |
| 2-4042 | Sub-52 | 3,4-diClPh | SO₂ | Single bond | Sub-10 |
| 2-4043 | Sub-52 | 3,4-diClPh | SO₂ | Single bond | Sub-11 |
| 2-4044 | Sub-52 | 3,4-diClPh | SO₂ | Single bond | Sub-12 |
| 2-4045 | Sub-52 | 3,4-diClPh | SO₂ | Single bond | Sub-13 |
| 2-4046 | Sub-52 | 3,4-diClPh | SO₂ | Single bond | Sub-14 |
| 2-4047 | Sub-52 | 3,4-diClPh | SO₂ | Single bond | Sub-15 |
| 2-4048 | Sub-52 | 3,4-diClPh | SO₂ | Single bond | Sub-16 |
| 2-4049 | Sub-52 | 3,4-diClPh | SO₂ | Single bond | Sub-17 |
| 2-4050 | Sub-52 | 3,4-diClPh | SO₂ | Single bond | Sub-18 |
| 2-4051 | Sub-52 | 3,4-diClPh | SO₂ | Single bond | Sub-19 |
| 2-4052 | Sub-52 | 3,4-diClPh | SO₂ | Single bond | Sub-20 |
| 2-4053 | Sub-52 | 3,4-diClPh | SO₂ | Single bond | Sub-21 |
| 2-4054 | Sub-52 | 3,4-diClPh | SO₂ | Single bond | Sub-22 |
| 2-4055 | Sub-52 | 3,4-diClPh | SO₂ | Single bond | Sub-23 |
| 2-4056 | Sub-52 | 3,4-diClPh | SO₂ | Single bond | Sub-24 |
| 2-4057 | Sub-52 | 3,4-diClPh | SO₂ | Single bond | Sub-25 |
| 2-4058 | Sub-52 | 3,4-diClPh | SO₂ | Single bond | Sub-26 |
| 2-4059 | Sub-52 | 3,4-diClPh | SO₂ | Single bond | Sub-27 |
| 2-4060 | Sub-52 | 3,4-diClPh | SO₂ | Single bond | Sub-28 |
| 2-4061 | Sub-52 | 3,4-diClPh | SO₂ | Single bond | Sub-29 |
| 2-4062 | Sub-52 | 3,4-diClPh | SO₂ | Single bond | Sub-30 |
| 2-4063 | Sub-52 | 3,4-diClPh | SO₂ | Single bond | Sub-31 |
| 2-4064 | Sub-52 | 3,4-diClPh | SO₂ | Single bond | Sub-32 |
| 2-4065 | Sub-52 | 3,4-diClPh | SO₂ | Single bond | Sub-65 |
| 2-4066 | Sub-52 | 3,4-diClPh | SO₂ | Single bond | Sub-66 |
| 2-4067 | Sub-52 | 3,4-diClPh | SO₂ | Single bond | Sub-67 |
| 2-4068 | Sub-52 | 3,4-diClPh | SO₂ | Single bond | Sub-68 |
| 2-4069 | Sub-52 | 3,4-diClPh | SO₂ | Single bond | Sub-69 |
| 2-4070 | Sub-52 | 3,4-diClPh | SO₂ | Single bond | Sub-70 |
| 2-4071 | Sub-52 | 3,4-diClPh | SO₂ | Single bond | Sub-71 |
| 2-4072 | Sub-52 | 3,4-diClPh | SO₂ | Single bond | Sub-72 |
| 2-4073 | Sub-52 | 3,4-diClPh | SO₂ | Single bond | Sub-73 |
| 2-4074 | Sub-52 | 3,4-diClPh | SO₂ | Single bond | Sub-74 |
| 2-4075 | Sub-52 | 3,4-diClPh | SO₂ | Single bond | Sub-75 |
| 2-4076 | Sub-52 | 3,4-diClPh | SO₂ | Single bond | Sub-76 |
| 2-4077 | Sub-52 | 3,4-diClPh | SO₂ | Single bond | Sub-77 |
| 2-4078 | Sub-52 | 3,4-diClPh | SO₂ | Single bond | Sub-78 |
| 2-4079 | Sub-52 | 3,4-diClPh | SO₂ | Single bond | Sub-79 |
| 2-4080 | Sub-52 | 3,4-diClPh | SO₂ | Single bond | Sub-80 |
| 2-4081 | Sub-53 | 3,4-diClPh | SO₂ | Single bond | Sub-1 |
| 2-4082 | Sub-53 | 3,4-diClPh | SO₂ | Single bond | Sub-2 |
| 2-4083 | Sub-53 | 3,4-diClPh | SO₂ | Single bond | Sub-3 |
| 2-4084 | Sub-53 | 3,4-diClPh | SO₂ | Single bond | Sub-4 |
| 2-4085 | Sub-53 | 3,4-diClPh | SO₂ | Single bond | Sub-5 |
| 2-4086 | Sub-53 | 3,4-diClPh | SO₂ | Single bond | Sub-6 |
| 2-4087 | Sub-53 | 3,4-diClPh | SO₂ | Single bond | Sub-7 |
| 2-4088 | Sub-53 | 3,4-diClPh | SO₂ | Single bond | Sub-8 |
| 2-4089 | Sub-53 | 3,4-diClPh | SO₂ | Single bond | Sub-9 |
| 2-4090 | Sub-53 | 3,4-diClPh | SO₂ | Single bond | Sub-10 |
| 2-4091 | Sub-53 | 3,4-diClPh | SO₂ | Single bond | Sub-11 |
| 2-4092 | Sub-53 | 3,4-diClPh | SO₂ | Single bond | Sub-12 |
| 2-4093 | Sub-53 | 3,4-diClPh | SO₂ | Single bond | Sub-13 |
| 2-4094 | Sub-53 | 3,4-diClPh | SO₂ | Single bond | Sub-14 |
| 2-4095 | Sub-53 | 3,4-diClPh | SO₂ | Single bond | Sub-15 |
| 2-4096 | Sub-53 | 3,4-diClPh | SO₂ | Single bond | Sub-16 |
| 2-4097 | Sub-53 | 3,4-diClPh | SO₂ | Single bond | Sub-17 |
| 2-4098 | Sub-53 | 3,4-diClPh | SO₂ | Single bond | Sub-18 |
| 2-4099 | Sub-53 | 3,4-diClPh | SO₂ | Single bond | Sub-19 |
| 2-4100 | Sub-53 | 3,4-diClPh | SO₂ | Single bond | Sub-20 |
| 2-4101 | Sub-53 | 3,4-diClPh | SO₂ | Single bond | Sub-21 |
| 2-4102 | Sub-53 | 3,4-diClPh | SO₂ | Single bond | Sub-22 |
| 2-4103 | Sub-53 | 3,4-diClPh | SO₂ | Single bond | Sub-23 |
| 2-4104 | Sub-53 | 3,4-diClPh | SO₂ | Single bond | Sub-24 |
| 2-4105 | Sub-53 | 3,4-diClPh | SO₂ | Single bond | Sub-25 |
| 2-4106 | Sub-53 | 3,4-diClPh | SO₂ | Single bond | Sub-26 |
| 2-4107 | Sub-53 | 3,4-diClPh | SO₂ | Single bond | Sub-27 |
| 2-4108 | Sub-53 | 3,4-diClPh | SO₂ | Single bond | Sub-28 |
| 2-4109 | Sub-53 | 3,4-diClPh | SO₂ | Single bond | Sub-29 |
| 2-4110 | Sub-53 | 3,4-diClPh | SO₂ | Single bond | Sub-30 |
| 2-4111 | Sub-53 | 3,4-diClPh | SO₂ | Single bond | Sub-31 |
| 2-4112 | Sub-53 | 3,4-diClPh | SO₂ | Single bond | Sub-32 |
| 2-4113 | Sub-53 | 3,4-diClPh | SO₂ | Single bond | Sub-65 |
| 2-4114 | Sub-53 | 3,4-diClPh | SO₂ | Single bond | Sub-66 |
| 2-4115 | Sub-53 | 3,4-diClPh | SO₂ | Single bond | Sub-67 |
| 2-4116 | Sub-53 | 3,4-diClPh | SO₂ | Single bond | Sub-68 |
| 2-4117 | Sub-53 | 3,4-diClPh | SO₂ | Single bond | Sub-69 |
| 2-4118 | Sub-53 | 3,4-diClPh | SO₂ | Single bond | Sub-70 |
| 2-4119 | Sub-53 | 3,4-diClPh | SO₂ | Single bond | Sub-71 |
| 2-4120 | Sub-53 | 3,4-diClPh | SO₂ | Single bond | Sub-72 |
| 2-4121 | Sub-53 | 3,4-diClPh | SO₂ | Single bond | Sub-73 |
| 2-4122 | Sub-53 | 3,4-diClPh | SO₂ | Single bond | Sub-74 |
| 2-4123 | Sub-53 | 3,4-diClPh | SO₂ | Single bond | Sub-75 |
| 2-4124 | Sub-53 | 3,4-diClPh | SO₂ | Single bond | Sub-76 |
| 2-4125 | Sub-53 | 3,4-diClPh | SO₂ | Single bond | Sub-77 |
| 2-4126 | Sub-53 | 3,4-diClPh | SO₂ | Single bond | Sub-78 |
| 2-4127 | Sub-53 | 3,4-diClPh | SO₂ | Single bond | Sub-79 |
| 2-4128 | Sub-53 | 3,4-diClPh | SO₂ | Single bond | Sub-80 |
| 2-4129 | Sub-54 | 3,4-diClPh | SO₂ | Single bond | Sub-1 |
| 2-4130 | Sub-54 | 3,4-diClPh | SO₂ | Single bond | Sub-2 |

TABLE 2-continued

| Cpd. No. | R¹ | R² | A | B | Z |
|---|---|---|---|---|---|
| 2-4131 | Sub-54 | 3,4-diClPh | SO₂ | Single bond | Sub-3 |
| 2-4132 | Sub-54 | 3,4-diClPh | SO₂ | Single bond | Sub-4 |
| 2-4133 | Sub-54 | 3,4-diClPh | SO₂ | Single bond | Sub-5 |
| 2-4134 | Sub-54 | 3,4-diClPh | SO₂ | Single bond | Sub-6 |
| 2-4135 | Sub-54 | 3,4-diClPh | SO₂ | Single bond | Sub-7 |
| 2-4136 | Sub-54 | 3,4-diClPh | SO₂ | Single bond | Sub-8 |
| 2-4137 | Sub-54 | 3,4-diClPh | SO₂ | Single bond | Sub-9 |
| 2-4138 | Sub-54 | 3,4-diClPh | SO₂ | Single bond | Sub-10 |
| 2-4139 | Sub-54 | 3,4-diClPh | SO₂ | Single bond | Sub-11 |
| 2-4140 | Sub-54 | 3,4-diClPh | SO₂ | Single bond | Sub-12 |
| 2-4141 | Sub-54 | 3,4-diClPh | SO₂ | Single bond | Sub-13 |
| 2-4142 | Sub-54 | 3,4-diClPh | SO₂ | Single bond | Sub-14 |
| 2-4143 | Sub-54 | 3,4-diClPh | SO₂ | Single bond | Sub-15 |
| 2-4144 | Sub-54 | 3,4-diClPh | SO₂ | Single bond | Sub-16 |
| 2-4145 | Sub-54 | 3,4-diClPh | SO₂ | Single bond | Sub-17 |
| 2-4146 | Sub-54 | 3,4-diClPh | SO₂ | Single bond | Sub-18 |
| 2-4147 | Sub-54 | 3,4-diClPh | SO₂ | Single bond | Sub-19 |
| 2-4148 | Sub-54 | 3,4-diClPh | SO₂ | Single bond | Sub-20 |
| 2-4149 | Sub-54 | 3,4-diClPh | SO₂ | Single bond | Sub-21 |
| 2-4150 | Sub-54 | 3,4-diClPh | SO₂ | Single bond | Sub-22 |
| 2-4151 | Sub-54 | 3,4-diClPh | SO₂ | Single bond | Sub-23 |
| 2-4152 | Sub-54 | 3,4-diClPh | SO₂ | Single bond | Sub-24 |
| 2-4153 | Sub-54 | 3,4-diClPh | SO₂ | Single bond | Sub-25 |
| 2-4154 | Sub-54 | 3,4-diClPh | SO₂ | Single bond | Sub-26 |
| 2-4155 | Sub-54 | 3,4-diClPh | SO₂ | Single bond | Sub-27 |
| 2-4156 | Sub-54 | 3,4-diClPh | SO₂ | Single bond | Sub-28 |
| 2-4157 | Sub-54 | 3,4-diClPh | SO₂ | Single bond | Sub-29 |
| 2-4158 | Sub-54 | 3,4-diClPh | SO₂ | Single bond | Sub-30 |
| 2-4159 | Sub-54 | 3,4-diClPh | SO₂ | Single bond | Sub-31 |
| 2-4160 | Sub-54 | 3,4-diClPh | SO₂ | Single bond | Sub-32 |
| 2-4161 | Sub-54 | 3,4-diClPh | SO₂ | Single bond | Sub-65 |
| 2-4162 | Sub-54 | 3,4-diClPh | SO₂ | Single bond | Sub-66 |
| 2-4163 | Sub-54 | 3,4-diClPh | SO₂ | Single bond | Sub-67 |
| 2-4164 | Sub-54 | 3,4-diClPh | SO₂ | Single bond | Sub-68 |
| 2-4165 | Sub-54 | 3,4-diClPh | SO₂ | Single bond | Sub-69 |
| 2-4166 | Sub-54 | 3,4-diClPh | SO₂ | Single bond | Sub-70 |
| 2-4167 | Sub-54 | 3,4-diClPh | SO₂ | Single bond | Sub-71 |
| 2-4168 | Sub-54 | 3,4-diClPh | SO₂ | Single bond | Sub-72 |
| 2-4169 | Sub-54 | 3,4-diClPh | SO₂ | Single bond | Sub-73 |
| 2-4170 | Sub-54 | 3,4-diClPh | SO₂ | Single bond | Sub-74 |
| 2-4171 | Sub-54 | 3,4-diClPh | SO₂ | Single bond | Sub-75 |
| 2-4172 | Sub-54 | 3,4-diClPh | SO₂ | Single bond | Sub-76 |
| 2-4173 | Sub-54 | 3,4-diClPh | SO₂ | Single bond | Sub-77 |
| 2-4174 | Sub-54 | 3,4-diClPh | SO₂ | Single bond | Sub-78 |
| 2-4175 | Sub-54 | 3,4-diClPh | SO₂ | Single bond | Sub-79 |
| 2-4176 | Sub-54 | 3,4-diClPh | SO₂ | Single bond | Sub-80 |
| 2-4177 | Sub-55 | 3,4-diClPh | SO₂ | Single bond | Sub-1 |
| 2-4178 | Sub-55 | 3,4-diClPh | SO₂ | Single bond | Sub-2 |
| 2-4179 | Sub-55 | 3,4-diClPh | SO₂ | Single bond | Sub-3 |
| 2-4180 | Sub-55 | 3,4-diClPh | SO₂ | Single bond | Sub-4 |
| 2-4181 | Sub-55 | 3,4-diClPh | SO₂ | Single bond | Sub-5 |
| 2-4182 | Sub-55 | 3,4-diClPh | SO₂ | Single bond | Sub-6 |
| 2-4183 | Sub-55 | 3,4-diClPh | SO₂ | Single bond | Sub-7 |
| 2-4184 | Sub-55 | 3,4-diClPh | SO₂ | Single bond | Sub-8 |
| 2-4185 | Sub-55 | 3,4-diClPh | SO₂ | Single bond | Sub-9 |
| 2-4186 | Sub-55 | 3,4-diClPh | SO₂ | Single bond | Sub-10 |
| 2-4187 | Sub-55 | 3,4-diClPh | SO₂ | Single bond | Sub-11 |
| 2-4188 | Sub-55 | 3,4-diClPh | SO₂ | Single bond | Sub-12 |
| 2-4189 | Sub-55 | 3,4-diClPh | SO₂ | Single bond | Sub-13 |
| 2-4190 | Sub-55 | 3,4-diClPh | SO₂ | Single bond | Sub-14 |
| 2-4191 | Sub-55 | 3,4-diClPh | SO₂ | Single bond | Sub-15 |
| 2-4192 | Sub-55 | 3,4-diClPh | SO₂ | Single bond | Sub-16 |
| 2-4193 | Sub-55 | 3,4-diClPh | SO₂ | Single bond | Sub-17 |
| 2-4194 | Sub-55 | 3,4-diClPh | SO₂ | Single bond | Sub-18 |
| 2-4195 | Sub-55 | 3,4-diClPh | SO₂ | Single bond | Sub-19 |
| 2-4196 | Sub-55 | 3,4-diClPh | SO₂ | Single bond | Sub-20 |
| 2-4197 | Sub-55 | 3,4-diClPh | SO₂ | Single bond | Sub-21 |
| 2-4198 | Sub-55 | 3,4-diClPh | SO₂ | Single bond | Sub-22 |
| 2-4199 | Sub-55 | 3,4-diClPh | SO₂ | Single bond | Sub-23 |
| 2-4200 | Sub-55 | 3,4-diClPh | SO₂ | Single bond | Sub-24 |
| 2-4201 | Sub-55 | 3,4-diClPh | SO₂ | Single bond | Sub-25 |
| 2-4202 | Sub-55 | 3,4-diClPh | SO₂ | Single bond | Sub-26 |
| 2-4203 | Sub-55 | 3,4-diClPh | SO₂ | Single bond | Sub-27 |
| 2-4204 | Sub-55 | 3,4-diClPh | SO₂ | Single bond | Sub-28 |
| 2-4205 | Sub-55 | 3,4-diClPh | SO₂ | Single bond | Sub-29 |
| 2-4206 | Sub-55 | 3,4-diClPh | SO₂ | Single bond | Sub-30 |
| 2-4207 | Sub-55 | 3,4-diClPh | SO₂ | Single bond | Sub-31 |
| 2-4208 | Sub-55 | 3,4-diClPh | SO₂ | Single bond | Sub-32 |
| 2-4209 | Sub-55 | 3,4-diClPh | SO₂ | Single bond | Sub-65 |
| 2-4210 | Sub-55 | 3,4-diClPh | SO₂ | Single bond | Sub-66 |
| 2-4211 | Sub-55 | 3,4-diClPh | SO₂ | Single bond | Sub-67 |
| 2-4212 | Sub-55 | 3,4-diClPh | SO₂ | Single bond | Sub-68 |
| 2-4213 | Sub-55 | 3,4-diClPh | SO₂ | Single bond | Sub-69 |
| 2-4214 | Sub-55 | 3,4-diClPh | SO₂ | Single bond | Sub-70 |
| 2-4215 | Sub-55 | 3,4-diClPh | SO₂ | Single bond | Sub-71 |
| 2-4216 | Sub-55 | 3,4-diClPh | SO₂ | Single bond | Sub-72 |
| 2-4217 | Sub-55 | 3,4-diClPh | SO₂ | Single bond | Sub-73 |
| 2-4218 | Sub-55 | 3,4-diClPh | SO₂ | Single bond | Sub-74 |
| 2-4219 | Sub-55 | 3,4-diClPh | SO₂ | Single bond | Sub-75 |
| 2-4220 | Sub-55 | 3,4-diClPh | SO₂ | Single bond | Sub-76 |
| 2-4221 | Sub-55 | 3,4-diClPh | SO₂ | Single bond | Sub-77 |
| 2-4222 | Sub-55 | 3,4-diClPh | SO₂ | Single bond | Sub-78 |
| 2-4223 | Sub-55 | 3,4-diClPh | SO₂ | Single bond | Sub-79 |
| 2-4224 | Sub-55 | 3,4-diClPh | SO₂ | Single bond | Sub-80 |
| 2-4225 | Sub-56 | 3,4-diClPh | SO₂ | Single bond | Sub-1 |
| 2-4226 | Sub-56 | 3,4-diClPh | SO₂ | Single bond | Sub-2 |
| 2-4227 | Sub-56 | 3,4-diClPh | SO₂ | Single bond | Sub-3 |
| 2-4228 | Sub-56 | 3,4-diClPh | SO₂ | Single bond | Sub-4 |
| 2-4229 | Sub-56 | 3,4-diClPh | SO₂ | Single bond | Sub-5 |
| 2-4230 | Sub-56 | 3,4-diClPh | SO₂ | Single bond | Sub-6 |
| 2-4231 | Sub-56 | 3,4-diClPh | SO₂ | Single bond | Sub-7 |
| 2-4232 | Sub-56 | 3,4-diClPh | SO₂ | Single bond | Sub-8 |
| 2-4233 | Sub-56 | 3,4-diClPh | SO₂ | Single bond | Sub-9 |
| 2-4234 | Sub-56 | 3,4-diClPh | SO₂ | Single bond | Sub-10 |
| 2-4235 | Sub-56 | 3,4-diClPh | SO₂ | Single bond | Sub-11 |
| 2-4236 | Sub-56 | 3,4-diClPh | SO₂ | Single bond | Sub-12 |
| 2-4237 | Sub-56 | 3,4-diClPh | SO₂ | Single bond | Sub-13 |
| 2-4238 | Sub-56 | 3,4-diClPh | SO₂ | Single bond | Sub-14 |
| 2-4239 | Sub-56 | 3,4-diClPh | SO₂ | Single bond | Sub-15 |
| 2-4240 | Sub-56 | 3,4-diClPh | SO₂ | Single bond | Sub-16 |
| 2-4241 | Sub-56 | 3,4-diClPh | SO₂ | Single bond | Sub-17 |
| 2-4242 | Sub-56 | 3,4-diClPh | SO₂ | Single bond | Sub-18 |
| 2-4243 | Sub-56 | 3,4-diClPh | SO₂ | Single bond | Sub-19 |
| 2-4244 | Sub-56 | 3,4-diClPh | SO₂ | Single bond | Sub-20 |
| 2-4245 | Sub-56 | 3,4-diClPh | SO₂ | Single bond | Sub-21 |
| 2-4246 | Sub-56 | 3,4-diClPh | SO₂ | Single bond | Sub-22 |
| 2-4247 | Sub-56 | 3,4-diClPh | SO₂ | Single bond | Sub-23 |
| 2-4248 | Sub-56 | 3,4-diClPh | SO₂ | Single bond | Sub-24 |
| 2-4249 | Sub-56 | 3,4-diClPh | SO₂ | Single bond | Sub-25 |
| 2-4250 | Sub-56 | 3,4-diClPh | SO₂ | Single bond | Sub-26 |
| 2-4251 | Sub-56 | 3,4-diClPh | SO₂ | Single bond | Sub-27 |
| 2-4252 | Sub-56 | 3,4-diClPh | SO₂ | Single bond | Sub-28 |
| 2-4253 | Sub-56 | 3,4-diClPh | SO₂ | Single bond | Sub-29 |
| 2-4254 | Sub-56 | 3,4-diClPh | SO₂ | Single bond | Sub-30 |
| 2-4255 | Sub-56 | 3,4-diClPh | SO₂ | Single bond | Sub-31 |
| 2-4256 | Sub-56 | 3,4-diClPh | SO₂ | Single bond | Sub-32 |
| 2-4257 | Sub-56 | 3,4-diClPh | SO₂ | Single bond | Sub-65 |
| 2-4258 | Sub-56 | 3,4-diClPh | SO₂ | Single bond | Sub-66 |
| 2-4259 | Sub-56 | 3,4-diClPh | SO₂ | Single bond | Sub-67 |
| 2-4260 | Sub-56 | 3,4-diClPh | SO₂ | Single bond | Sub-68 |
| 2-4261 | Sub-56 | 3,4-diClPh | SO₂ | Single bond | Sub-69 |
| 2-4262 | Sub-56 | 3,4-diClPh | SO₂ | Single bond | Sub-70 |
| 2-4263 | Sub-56 | 3,4-diClPh | SO₂ | Single bond | Sub-71 |
| 2-4264 | Sub-56 | 3,4-diClPh | SO₂ | Single bond | Sub-72 |
| 2-4265 | Sub-56 | 3,4-diClPh | SO₂ | Single bond | Sub-73 |
| 2-4266 | Sub-56 | 3,4-diClPh | SO₂ | Single bond | Sub-74 |
| 2-4267 | Sub-56 | 3,4-diClPh | SO₂ | Single bond | Sub-75 |
| 2-4268 | Sub-56 | 3,4-diClPh | SO₂ | Single bond | Sub-76 |
| 2-4269 | Sub-56 | 3,4-diClPh | SO₂ | Single bond | Sub-77 |
| 2-4270 | Sub-56 | 3,4-diClPh | SO₂ | Single bond | Sub-78 |
| 2-4271 | Sub-56 | 3,4-diClPh | SO₂ | Single bond | Sub-79 |
| 2-4272 | Sub-56 | 3,4-diClPh | SO₂ | Single bond | Sub-80 |
| 2-4273 | Sub-57 | 3,4-diClPh | SO₂ | Single bond | Sub-1 |
| 2-4274 | Sub-57 | 3,4-diClPh | SO₂ | Single bond | Sub-2 |
| 2-4275 | Sub-57 | 3,4-diClPh | SO₂ | Single bond | Sub-3 |
| 2-4276 | Sub-57 | 3,4-diClPh | SO₂ | Single bond | Sub-4 |
| 2-4277 | Sub-57 | 3,4-diClPh | SO₂ | Single bond | Sub-5 |
| 2-4278 | Sub-57 | 3,4-diClPh | SO₂ | Single bond | Sub-6 |
| 2-4279 | Sub-57 | 3,4-diClPh | SO₂ | Single bond | Sub-7 |
| 2-4280 | Sub-57 | 3,4-diClPh | SO₂ | Single bond | Sub-8 |
| 2-4281 | Sub-57 | 3,4-diClPh | SO₂ | Single bond | Sub-9 |
| 2-4282 | Sub-57 | 3,4-diClPh | SO₂ | Single bond | Sub-10 |
| 2-4283 | Sub-57 | 3,4-diClPh | SO₂ | Single bond | Sub-11 |
| 2-4284 | Sub-57 | 3,4-diClPh | SO₂ | Single bond | Sub-12 |

TABLE 2-continued

| Cpd. No. | R¹ | R² | A | B | Z |
|---|---|---|---|---|---|
| 2-4285 | Sub-57 | 3,4-diClPh | SO₂ | Single bond | Sub-13 |
| 2-4286 | Sub-57 | 3,4-diClPh | SO₂ | Single bond | Sub-14 |
| 2-4287 | Sub-57 | 3,4-diClPh | SO₂ | Single bond | Sub-15 |
| 2-4288 | Sub-57 | 3,4-diClPh | SO₂ | Single bond | Sub-16 |
| 2-4289 | Sub-57 | 3,4-diClPh | SO₂ | Single bond | Sub-17 |
| 2-4290 | Sub-57 | 3,4-diClPh | SO₂ | Single bond | Sub-18 |
| 2-4291 | Sub-57 | 3,4-diClPh | SO₂ | Single bond | Sub-19 |
| 2-4292 | Sub-57 | 3,4-diClPh | SO₂ | Single bond | Sub-20 |
| 2-4293 | Sub-57 | 3,4-diClPh | SO₂ | Single bond | Sub-21 |
| 2-4294 | Sub-57 | 3,4-diClPh | SO₂ | Single bond | Sub-22 |
| 2-4295 | Sub-57 | 3,4-diClPh | SO₂ | Single bond | Sub-23 |
| 2-4296 | Sub-57 | 3,4-diClPh | SO₂ | Single bond | Sub-24 |
| 2-4297 | Sub-57 | 3,4-diClPh | SO₂ | Single bond | Sub-25 |
| 2-4298 | Sub-57 | 3,4-diClPh | SO₂ | Single bond | Sub-26 |
| 2-4299 | Sub-57 | 3,4-diClPh | SO₂ | Single bond | Sub-27 |
| 2-4300 | Sub-57 | 3,4-diClPh | SO₂ | Single bond | Sub-28 |
| 2-4301 | Sub-57 | 3,4-diClPh | SO₂ | Single bond | Sub-29 |
| 2-4302 | Sub-57 | 3,4-diClPh | SO₂ | Single bond | Sub-30 |
| 2-4303 | Sub-57 | 3,4-diClPh | SO₂ | Single bond | Sub-31 |
| 2-4304 | Sub-57 | 3,4-diClPh | SO₂ | Single bond | Sub-32 |
| 2-4305 | Sub-57 | 3,4-diClPh | SO₂ | Single bond | Sub-65 |
| 2-4306 | Sub-57 | 3,4-diClPh | SO₂ | Single bond | Sub-66 |
| 2-4307 | Sub-57 | 3,4-diClPh | SO₂ | Single bond | Sub-67 |
| 2-4308 | Sub-57 | 3,4-diClPh | SO₂ | Single bond | Sub-68 |
| 2-4309 | Sub-57 | 3,4-diClPh | SO₂ | Single bond | Sub-69 |
| 2-4310 | Sub-57 | 3,4-diClPh | SO₂ | Single bond | Sub-70 |
| 2-4311 | Sub-57 | 3,4-diClPh | SO₂ | Single bond | Sub-71 |
| 2-4312 | Sub-57 | 3,4-diClPh | SO₂ | Single bond | Sub-72 |
| 2-4313 | Sub-57 | 3,4-diClPh | SO₂ | Single bond | Sub-73 |
| 2-4314 | Sub-57 | 3,4-diClPh | SO₂ | Single bond | Sub-74 |
| 2-4315 | Sub-57 | 3,4-diClPh | SO₂ | Single bond | Sub-75 |
| 2-4316 | Sub-57 | 3,4-diClPh | SO₂ | Single bond | Sub-76 |
| 2-4317 | Sub-57 | 3,4-diClPh | SO₂ | Single bond | Sub-77 |
| 2-4318 | Sub-57 | 3,4-diClPh | SO₂ | Single bond | Sub-78 |
| 2-4319 | Sub-57 | 3,4-diClPh | SO₂ | Single bond | Sub-79 |
| 2-4320 | Sub-57 | 3,4-diClPh | SO₂ | Single bond | Sub-80 |
| 2-4321 | Sub-58 | 3,4-diClPh | SO₂ | Single bond | Sub-1 |
| 2-4322 | Sub-58 | 3,4-diClPh | SO₂ | Single bond | Sub-2 |
| 2-4323 | Sub-58 | 3,4-diClPh | SO₂ | Single bond | Sub-3 |
| 2-4324 | Sub-58 | 3,4-diClPh | SO₂ | Single bond | Sub-4 |
| 2-4325 | Sub-58 | 3,4-diClPh | SO₂ | Single bond | Sub-5 |
| 2-4326 | Sub-58 | 3,4-diClPh | SO₂ | Single bond | Sub-6 |
| 2-4327 | Sub-58 | 3,4-diClPh | SO₂ | Single bond | Sub-7 |
| 2-4328 | Sub-58 | 3,4-diClPh | SO₂ | Single bond | Sub-8 |
| 2-4329 | Sub-58 | 3,4-diClPh | SO₂ | Single bond | Sub-9 |
| 2-4330 | Sub-58 | 3,4-diClPh | SO₂ | Single bond | Sub-10 |
| 2-4331 | Sub-58 | 3,4-diClPh | SO₂ | Single bond | Sub-11 |
| 2-4332 | Sub-58 | 3,4-diClPh | SO₂ | Single bond | Sub-12 |
| 2-4333 | Sub-58 | 3,4-diClPh | SO₂ | Single bond | Sub-13 |
| 2-4334 | Sub-58 | 3,4-diClPh | SO₂ | Single bond | Sub-14 |
| 2-4335 | Sub-58 | 3,4-diClPh | SO₂ | Single bond | Sub-15 |
| 2-4336 | Sub-58 | 3,4-diClPh | SO₂ | Single bond | Sub-16 |
| 2-4337 | Sub-58 | 3,4-diClPh | SO₂ | Single bond | Sub-17 |
| 2-4338 | Sub-58 | 3,4-diClPh | SO₂ | Single bond | Sub-18 |
| 2-4339 | Sub-58 | 3,4-diClPh | SO₂ | Single bond | Sub-19 |
| 2-4340 | Sub-58 | 3,4-diClPh | SO₂ | Single bond | Sub-20 |
| 2-4341 | Sub-58 | 3,4-diClPh | SO₂ | Single bond | Sub-21 |
| 2-4342 | Sub-58 | 3,4-diClPh | SO₂ | Single bond | Sub-22 |
| 2-4343 | Sub-58 | 3,4-diClPh | SO₂ | Single bond | Sub-23 |
| 2-4344 | Sub-58 | 3,4-diClPh | SO₂ | Single bond | Sub-24 |
| 2-4345 | Sub-58 | 3,4-diClPh | SO₂ | Single bond | Sub-25 |
| 2-4346 | Sub-58 | 3,4-diClPh | SO₂ | Single bond | Sub-26 |
| 2-4347 | Sub-58 | 3,4-diClPh | SO₂ | Single bond | Sub-27 |
| 2-4348 | Sub-58 | 3,4-diClPh | SO₂ | Single bond | Sub-28 |
| 2-4349 | Sub-58 | 3,4-diClPh | SO₂ | Single bond | Sub-29 |
| 2-4350 | Sub-58 | 3,4-diClPh | SO₂ | Single bond | Sub-30 |
| 2-4351 | Sub-58 | 3,4-diClPh | SO₂ | Single bond | Sub-31 |
| 2-4352 | Sub-58 | 3,4-diClPh | SO₂ | Single bond | Sub-32 |
| 2-4353 | Sub-58 | 3,4-diClPh | SO₂ | Single bond | Sub-65 |
| 2-4354 | Sub-58 | 3,4-diClPh | SO₂ | Single bond | Sub-66 |
| 2-4355 | Sub-58 | 3,4-diClPh | SO₂ | Single bond | Sub-67 |
| 2-4356 | Sub-58 | 3,4-diClPh | SO₂ | Single bond | Sub-68 |
| 2-4357 | Sub-58 | 3,4-diClPh | SO₂ | Single bond | Sub-69 |
| 2-4358 | Sub-58 | 3,4-diClPh | SO₂ | Single bond | Sub-70 |
| 2-4359 | Sub-58 | 3,4-diClPh | SO₂ | Single bond | Sub-71 |
| 2-4360 | Sub-58 | 3,4-diClPh | SO₂ | Single bond | Sub-72 |
| 2-4361 | Sub-58 | 3,4-diClPh | SO₂ | Single bond | Sub-73 |
| 2-4362 | Sub-58 | 3,4-diClPh | SO₂ | Single bond | Sub-74 |
| 2-4363 | Sub-58 | 3,4-diClPh | SO₂ | Single bond | Sub-75 |
| 2-4364 | Sub-58 | 3,4-diClPh | SO₂ | Single bond | Sub-76 |
| 2-4365 | Sub-58 | 3,4-diClPh | SO₂ | Single bond | Sub-77 |
| 2-4366 | Sub-58 | 3,4-diClPh | SO₂ | Single bond | Sub-78 |
| 2-4367 | Sub-58 | 3,4-diClPh | SO₂ | Single bond | Sub-79 |
| 2-4368 | Sub-58 | 3,4-diClPh | SO₂ | Single bond | Sub-80 |
| 2-4369 | Sub-59 | 3,4-diClPh | SO₂ | Single bond | Sub-1 |
| 2-4370 | Sub-59 | 3,4-diClPh | SO₂ | Single bond | Sub-2 |
| 2-4371 | Sub-59 | 3,4-diClPh | SO₂ | Single bond | Sub-3 |
| 2-4372 | Sub-59 | 3,4-diClPh | SO₂ | Single bond | Sub-4 |
| 2-4373 | Sub-59 | 3,4-diClPh | SO₂ | Single bond | Sub-5 |
| 2-4374 | Sub-59 | 3,4-diClPh | SO₂ | Single bond | Sub-6 |
| 2-4375 | Sub-59 | 3,4-diClPh | SO₂ | Single bond | Sub-7 |
| 2-4376 | Sub-59 | 3,4-diClPh | SO₂ | Single bond | Sub-8 |
| 2-4377 | Sub-59 | 3,4-diClPh | SO₂ | Single bond | Sub-9 |
| 2-4378 | Sub-59 | 3,4-diClPh | SO₂ | Single bond | Sub-10 |
| 2-4379 | Sub-59 | 3,4-diClPh | SO₂ | Single bond | Sub-11 |
| 2-4380 | Sub-59 | 3,4-diClPh | SO₂ | Single bond | Sub-12 |
| 2-4381 | Sub-59 | 3,4-diClPh | SO₂ | Single bond | Sub-13 |
| 2-4382 | Sub-59 | 3,4-diClPh | SO₂ | Single bond | Sub-14 |
| 2-4383 | Sub-59 | 3,4-diClPh | SO₂ | Single bond | Sub-15 |
| 2-4384 | Sub-59 | 3,4-diClPh | SO₂ | Single bond | Sub-16 |
| 2-4385 | Sub-59 | 3,4-diClPh | SO₂ | Single bond | Sub-17 |
| 2-4386 | Sub-59 | 3,4-diClPh | SO₂ | Single bond | Sub-18 |
| 2-4387 | Sub-59 | 3,4-diClPh | SO₂ | Single bond | Sub-19 |
| 2-4388 | Sub-59 | 3,4-diClPh | SO₂ | Single bond | Sub-20 |
| 2-4389 | Sub-59 | 3,4-diClPh | SO₂ | Single bond | Sub-21 |
| 2-4390 | Sub-59 | 3,4-diClPh | SO₂ | Single bond | Sub-22 |
| 2-4391 | Sub-59 | 3,4-diClPh | SO₂ | Single bond | Sub-23 |
| 2-4392 | Sub-59 | 3,4-diClPh | SO₂ | Single bond | Sub-24 |
| 2-4393 | Sub-59 | 3,4-diClPh | SO₂ | Single bond | Sub-25 |
| 2-4394 | Sub-59 | 3,4-diClPh | SO₂ | Single bond | Sub-26 |
| 2-4395 | Sub-59 | 3,4-diClPh | SO₂ | Single bond | Sub-27 |
| 2-4396 | Sub-59 | 3,4-diClPh | SO₂ | Single bond | Sub-28 |
| 2-4397 | Sub-59 | 3,4-diClPh | SO₂ | Single bond | Sub-29 |
| 2-4398 | Sub-59 | 3,4-diClPh | SO₂ | Single bond | Sub-30 |
| 2-4399 | Sub-59 | 3,4-diClPh | SO₂ | Single bond | Sub-31 |
| 2-4400 | Sub-59 | 3,4-diClPh | SO₂ | Single bond | Sub-32 |
| 2-4401 | Sub-59 | 3,4-diClPh | SO₂ | Single bond | Sub-65 |
| 2-4402 | Sub-59 | 3,4-diClPh | SO₂ | Single bond | Sub-66 |
| 2-4403 | Sub-59 | 3,4-diClPh | SO₂ | Single bond | Sub-67 |
| 2-4404 | Sub-59 | 3,4-diClPh | SO₂ | Single bond | Sub-68 |
| 2-4405 | Sub-59 | 3,4-diClPh | SO₂ | Single bond | Sub-69 |
| 2-4406 | Sub-59 | 3,4-diClPh | SO₂ | Single bond | Sub-70 |
| 2-4407 | Sub-59 | 3,4-diClPh | SO₂ | Single bond | Sub-71 |
| 2-4408 | Sub-59 | 3,4-diClPh | SO₂ | Single bond | Sub-72 |
| 2-4409 | Sub-59 | 3,4-diClPh | SO₂ | Single bond | Sub-73 |
| 2-4410 | Sub-59 | 3,4-diClPh | SO₂ | Single bond | Sub-74 |
| 2-4411 | Sub-59 | 3,4-diClPh | SO₂ | Single bond | Sub-75 |
| 2-4412 | Sub-59 | 3,4-diClPh | SO₂ | Single bond | Sub-76 |
| 2-4413 | Sub-59 | 3,4-diClPh | SO₂ | Single bond | Sub-77 |
| 2-4414 | Sub-59 | 3,4-diClPh | SO₂ | Single bond | Sub-78 |
| 2-4415 | Sub-59 | 3,4-diClPh | SO₂ | Single bond | Sub-79 |
| 2-4416 | Sub-59 | 3,4-diClPh | SO₂ | Single bond | Sub-80 |
| 2-4417 | Sub-82 | 3,4-diClPh | SO₂ | Single bond | Sub-1 |
| 2-4418 | Sub-82 | 3,4-diClPh | SO₂ | Single bond | Sub-2 |
| 2-4419 | Sub-82 | 3,4-diClPh | SO₂ | Single bond | Sub-3 |
| 2-4420 | Sub-82 | 3,4-diClPh | SO₂ | Single bond | Sub-4 |
| 2-4421 | Sub-82 | 3,4-diClPh | SO₂ | Single bond | Sub-5 |
| 2-4422 | Sub-82 | 3,4-diClPh | SO₂ | Single bond | Sub-6 |
| 2-4423 | Sub-82 | 3,4-diClPh | SO₂ | Single bond | Sub-7 |
| 2-4424 | Sub-82 | 3,4-diClPh | SO₂ | Single bond | Sub-8 |
| 2-4425 | Sub-82 | 3,4-diClPh | SO₂ | Single bond | Sub-9 |
| 2-4426 | Sub-82 | 3,4-diClPh | SO₂ | Single bond | Sub-10 |
| 2-4427 | Sub-82 | 3,4-diClPh | SO₂ | Single bond | Sub-11 |
| 2-4428 | Sub-82 | 3,4-diClPh | SO₂ | Single bond | Sub-12 |
| 2-4429 | Sub-82 | 3,4-diClPh | SO₂ | Single bond | Sub-13 |
| 2-4430 | Sub-82 | 3,4-diClPh | SO₂ | Single bond | Sub-14 |
| 2-4431 | Sub-82 | 3,4-diClPh | SO₂ | Single bond | Sub-15 |
| 2-4432 | Sub-82 | 3,4-diClPh | SO₂ | Single bond | Sub-16 |
| 2-4433 | Sub-82 | 3,4-diClPh | SO₂ | Single bond | Sub-17 |
| 2-4434 | Sub-82 | 3,4-diClPh | SO₂ | Single bond | Sub-18 |
| 2-4435 | Sub-82 | 3,4-diClPh | SO₂ | Single bond | Sub-19 |
| 2-4436 | Sub-82 | 3,4-diClPh | SO₂ | Single bond | Sub-20 |
| 2-4437 | Sub-82 | 3,4-diClPh | SO₂ | Single bond | Sub-21 |
| 2-4438 | Sub-82 | 3,4-diClPh | SO₂ | Single bond | Sub-22 |

TABLE 2-continued

| Cpd. No. | R¹ | R² | A | B | Z |
|---|---|---|---|---|---|
| 2-4439 | Sub-82 | 3,4-diClPh | SO₂ | Single bond | Sub-23 |
| 2-4440 | Sub-82 | 3,4-diClPh | SO₂ | Single bond | Sub-24 |
| 2-4441 | Sub-82 | 3,4-diClPh | SO₂ | Single bond | Sub-25 |
| 2-4442 | Sub-82 | 3,4-diClPh | SO₂ | Single bond | Sub-26 |
| 2-4443 | Sub-82 | 3,4-diClPh | SO₂ | Single bond | Sub-27 |
| 2-4444 | Sub-82 | 3,4-diClPh | SO₂ | Single bond | Sub-28 |
| 2-4445 | Sub-82 | 3,4-diClPh | SO₂ | Single bond | Sub-29 |
| 2-4446 | Sub-82 | 3,4-diClPh | SO₂ | Single bond | Sub-30 |
| 2-4447 | Sub-82 | 3,4-diClPh | SO₂ | Single bond | Sub-31 |
| 2-4448 | Sub-82 | 3,4-diClPh | SO₂ | Single bond | Sub-32 |
| 2-4449 | Sub-82 | 3,4-diClPh | SO₂ | Single bond | Sub-65 |
| 2-4450 | Sub-82 | 3,4-diClPh | SO₂ | Single bond | Sub-66 |
| 2-4451 | Sub-82 | 3,4-diClPh | SO₂ | Single bond | Sub-67 |
| 2-4452 | Sub-82 | 3,4-diClPh | SO₂ | Single bond | Sub-68 |
| 2-4453 | Sub-82 | 3,4-diClPh | SO₂ | Single bond | Sub-69 |
| 2-4454 | Sub-82 | 3,4-diClPh | SO₂ | Single bond | Sub-70 |
| 2-4455 | Sub-82 | 3,4-diClPh | SO₂ | Single bond | Sub-71 |
| 2-4456 | Sub-82 | 3,4-diClPh | SO₂ | Single bond | Sub-72 |
| 2-4457 | Sub-82 | 3,4-diClPh | SO₂ | Single bond | Sub-73 |
| 2-4458 | Sub-82 | 3,4-diClPh | SO₂ | Single bond | Sub-74 |
| 2-4459 | Sub-82 | 3,4-diClPh | SO₂ | Single bond | Sub-75 |
| 2-4460 | Sub-82 | 3,4-diClPh | SO₂ | Single bond | Sub-76 |
| 2-4461 | Sub-82 | 3,4-diClPh | SO₂ | Single bond | Sub-77 |
| 2-4462 | Sub-82 | 3,4-diClPh | SO₂ | Single bond | Sub-78 |
| 2-4463 | Sub-82 | 3,4-diClPh | SO₂ | Single bond | Sub-79 |
| 2-4464 | Sub-82 | 3,4-diClPh | SO₂ | Single bond | Sub-80 |
| 2-4465 | Sub-83 | 3,4-diClPh | SO₂ | Single bond | Sub-1 |
| 2-4466 | Sub-83 | 3,4-diClPh | SO₂ | Single bond | Sub-2 |
| 2-4467 | Sub-83 | 3,4-diClPh | SO₂ | Single bond | Sub-3 |
| 2-4468 | Sub-83 | 3,4-diClPh | SO₂ | Single bond | Sub-4 |
| 2-4469 | Sub-83 | 3,4-diClPh | SO₂ | Single bond | Sub-5 |
| 2-4470 | Sub-83 | 3,4-diClPh | SO₂ | Single bond | Sub-6 |
| 2-4471 | Sub-83 | 3,4-diClPh | SO₂ | Single bond | Sub-7 |
| 2-4472 | Sub-83 | 3,4-diClPh | SO₂ | Single bond | Sub-8 |
| 2-4473 | Sub-83 | 3,4-diClPh | SO₂ | Single bond | Sub-9 |
| 2-4474 | Sub-83 | 3,4-diClPh | SO₂ | Single bond | Sub-10 |
| 2-4475 | Sub-83 | 3,4-diClPh | SO₂ | Single bond | Sub-11 |
| 2-4476 | Sub-83 | 3,4-diClPh | SO₂ | Single bond | Sub-12 |
| 2-4477 | Sub-83 | 3,4-diClPh | SO₂ | Single bond | Sub-13 |
| 2-4478 | Sub-83 | 3,4-diClPh | SO₂ | Single bond | Sub-14 |
| 2-4479 | Sub-83 | 3,4-diClPh | SO₂ | Single bond | Sub-15 |
| 2-4480 | Sub-83 | 3,4-diClPh | SO₂ | Single bond | Sub-16 |
| 2-4481 | Sub-83 | 3,4-diClPh | SO₂ | Single bond | Sub-17 |
| 2-4482 | Sub-83 | 3,4-diClPh | SO₂ | Single bond | Sub-18 |
| 2-4483 | Sub-83 | 3,4-diClPh | SO₂ | Single bond | Sub-19 |
| 2-4484 | Sub-83 | 3,4-diClPh | SO₂ | Single bond | Sub-20 |
| 2-4485 | Sub-83 | 3,4-diClPh | SO₂ | Single bond | Sub-21 |
| 2-4486 | Sub-83 | 3,4-diClPh | SO₂ | Single bond | Sub-22 |
| 2-4487 | Sub-83 | 3,4-diClPh | SO₂ | Single bond | Sub-23 |
| 2-4488 | Sub-83 | 3,4-diClPh | SO₂ | Single bond | Sub-24 |
| 2-4489 | Sub-83 | 3,4-diClPh | SO₂ | Single bond | Sub-25 |
| 2-4490 | Sub-83 | 3,4-diClPh | SO₂ | Single bond | Sub-26 |
| 2-4491 | Sub-83 | 3,4-diClPh | SO₂ | Single bond | Sub-27 |
| 2-4492 | Sub-83 | 3,4-diClPh | SO₂ | Single bond | Sub-28 |
| 2-4493 | Sub-83 | 3,4-diClPh | SO₂ | Single bond | Sub-29 |
| 2-4494 | Sub-83 | 3,4-diClPh | SO₂ | Single bond | Sub-30 |
| 2-4495 | Sub-83 | 3,4-diClPh | SO₂ | Single bond | Sub-31 |
| 2-4496 | Sub-83 | 3,4-diClPh | SO₂ | Single bond | Sub-32 |
| 2-4497 | Sub-83 | 3,4-diClPh | SO₂ | Single bond | Sub-65 |
| 2-4498 | Sub-83 | 3,4-diClPh | SO₂ | Single bond | Sub-66 |
| 2-4499 | Sub-83 | 3,4-diClPh | SO₂ | Single bond | Sub-67 |
| 2-4500 | Sub-83 | 3,4-diClPh | SO₂ | Single bond | Sub-68 |
| 2-4501 | Sub-83 | 3,4-diClPh | SO₂ | Single bond | Sub-69 |
| 2-4502 | Sub-83 | 3,4-diClPh | SO₂ | Single bond | Sub-70 |
| 2-4503 | Sub-83 | 3,4-diClPh | SO₂ | Single bond | Sub-71 |
| 2-4504 | Sub-83 | 3,4-diClPh | SO₂ | Single bond | Sub-72 |
| 2-4505 | Sub-83 | 3,4-diClPh | SO₂ | Single bond | Sub-73 |
| 2-4506 | Sub-83 | 3,4-diClPh | SO₂ | Single bond | Sub-74 |
| 2-4507 | Sub-83 | 3,4-diClPh | SO₂ | Single bond | Sub-75 |
| 2-4508 | Sub-83 | 3,4-diClPh | SO₂ | Single bond | Sub-76 |
| 2-4509 | Sub-83 | 3,4-diClPh | SO₂ | Single bond | Sub-77 |
| 2-4510 | Sub-83 | 3,4-diClPh | SO₂ | Single bond | Sub-78 |
| 2-4511 | Sub-83 | 3,4-diClPh | SO₂ | Single bond | Sub-79 |
| 2-4512 | Sub-83 | 3,4-diClPh | SO₂ | Single bond | Sub-80 |
| 2-4513 | Sub-61 | 3,4-diClPh | SO₂ | Single bond | Sub-1 |
| 2-4514 | Sub-61 | 3,4-diClPh | SO₂ | Single bond | Sub-2 |
| 2-4515 | Sub-61 | 3,4-diClPh | SO₂ | Single bond | Sub-3 |
| 2-4516 | Sub-61 | 3,4-diClPh | SO₂ | Single bond | Sub-4 |
| 2-4517 | Sub-61 | 3,4-diClPh | SO₂ | Single bond | Sub-5 |
| 2-4518 | Sub-61 | 3,4-diClPh | SO₂ | Single bond | Sub-6 |
| 2-4519 | Sub-61 | 3,4-diClPh | SO₂ | Single bond | Sub-7 |
| 2-4520 | Sub-61 | 3,4-diClPh | SO₂ | Single bond | Sub-8 |
| 2-4521 | Sub-61 | 3,4-diClPh | SO₂ | Single bond | Sub-9 |
| 2-4522 | Sub-61 | 3,4-diClPh | SO₂ | Single bond | Sub-10 |
| 2-4523 | Sub-61 | 3,4-diClPh | SO₂ | Single bond | Sub-11 |
| 2-4524 | Sub-61 | 3,4-diClPh | SO₂ | Single bond | Sub-12 |
| 2-4525 | Sub-61 | 3,4-diClPh | SO₂ | Single bond | Sub-13 |
| 2-4526 | Sub-61 | 3,4-diClPh | SO₂ | Single bond | Sub-14 |
| 2-4527 | Sub-61 | 3,4-diClPh | SO₂ | Single bond | Sub-15 |
| 2-4528 | Sub-61 | 3,4-diClPh | SO₂ | Single bond | Sub-16 |
| 2-4529 | Sub-61 | 3,4-diClPh | SO₂ | Single bond | Sub-17 |
| 2-4530 | Sub-61 | 3,4-diClPh | SO₂ | Single bond | Sub-18 |
| 2-4531 | Sub-61 | 3,4-diClPh | SO₂ | Single bond | Sub-19 |
| 2-4532 | Sub-61 | 3,4-diClPh | SO₂ | Single bond | Sub-20 |
| 2-4533 | Sub-61 | 3,4-diClPh | SO₂ | Single bond | Sub-21 |
| 2-4534 | Sub-61 | 3,4-diClPh | SO₂ | Single bond | Sub-22 |
| 2-4535 | Sub-61 | 3,4-diClPh | SO₂ | Single bond | Sub-23 |
| 2-4536 | Sub-61 | 3,4-diClPh | SO₂ | Single bond | Sub-24 |
| 2-4537 | Sub-61 | 3,4-diClPh | SO₂ | Single bond | Sub-25 |
| 2-4538 | Sub-61 | 3,4-diClPh | SO₂ | Single bond | Sub-26 |
| 2-4539 | Sub-61 | 3,4-diClPh | SO₂ | Single bond | Sub-27 |
| 2-4540 | Sub-61 | 3,4-diClPh | SO₂ | Single bond | Sub-28 |
| 2-4541 | Sub-61 | 3,4-diClPh | SO₂ | Single bond | Sub-29 |
| 2-4542 | Sub-61 | 3,4-diClPh | SO₂ | Single bond | Sub-30 |
| 2-4543 | Sub-61 | 3,4-diClPh | SO₂ | Single bond | Sub-31 |
| 2-4544 | Sub-61 | 3,4-diClPh | SO₂ | Single bond | Sub-32 |
| 2-4545 | Sub-61 | 3,4-diClPh | SO₂ | Single bond | Sub-65 |
| 2-4546 | Sub-61 | 3,4-diClPh | SO₂ | Single bond | Sub-66 |
| 2-4547 | Sub-61 | 3,4-diClPh | SO₂ | Single bond | Sub-67 |
| 2-4548 | Sub-61 | 3,4-diClPh | SO₂ | Single bond | Sub-68 |
| 2-4549 | Sub-61 | 3,4-diClPh | SO₂ | Single bond | Sub-69 |
| 2-4550 | Sub-61 | 3,4-diClPh | SO₂ | Single bond | Sub-70 |
| 2-4551 | Sub-61 | 3,4-diClPh | SO₂ | Single bond | Sub-71 |
| 2-4552 | Sub-61 | 3,4-diClPh | SO₂ | Single bond | Sub-72 |
| 2-4553 | Sub-61 | 3,4-diClPh | SO₂ | Single bond | Sub-73 |
| 2-4554 | Sub-61 | 3,4-diClPh | SO₂ | Single bond | Sub-74 |
| 2-4555 | Sub-61 | 3,4-diClPh | SO₂ | Single bond | Sub-75 |
| 2-4556 | Sub-61 | 3,4-diClPh | SO₂ | Single bond | Sub-76 |
| 2-4557 | Sub-61 | 3,4-diClPh | SO₂ | Single bond | Sub-77 |
| 2-4558 | Sub-61 | 3,4-diClPh | SO₂ | Single bond | Sub-78 |
| 2-4559 | Sub-61 | 3,4-diClPh | SO₂ | Single bond | Sub-79 |
| 2-4560 | Sub-61 | 3,4-diClPh | SO₂ | Single bond | Sub-80 |
| 2-4561 | Sub-60 | 3,4-diClPh | SO₂ | Single bond | Sub-1 |
| 2-4562 | Sub-60 | 3,4-diClPh | SO₂ | Single bond | Sub-2 |
| 2-4563 | Sub-60 | 3,4-diClPh | SO₂ | Single bond | Sub-3 |
| 2-4564 | Sub-60 | 3,4-diClPh | SO₂ | Single bond | Sub-4 |
| 2-4565 | Sub-60 | 3,4-diClPh | SO₂ | Single bond | Sub-5 |
| 2-4566 | Sub-60 | 3,4-diClPh | SO₂ | Single bond | Sub-6 |
| 2-4567 | Sub-60 | 3,4-diClPh | SO₂ | Single bond | Sub-7 |
| 2-4568 | Sub-60 | 3,4-diClPh | SO₂ | Single bond | Sub-8 |
| 2-4569 | Sub-60 | 3,4-diClPh | SO₂ | Single bond | Sub-9 |
| 2-4570 | Sub-60 | 3,4-diClPh | SO₂ | Single bond | Sub-10 |
| 2-4571 | Sub-60 | 3,4-diClPh | SO₂ | Single bond | Sub-11 |
| 2-4572 | Sub-60 | 3,4-diClPh | SO₂ | Single bond | Sub-12 |
| 2-4573 | Sub-60 | 3,4-diClPh | SO₂ | Single bond | Sub-13 |
| 2-4574 | Sub-60 | 3,4-diClPh | SO₂ | Single bond | Sub-14 |
| 2-4575 | Sub-60 | 3,4-diClPh | SO₂ | Single bond | Sub-15 |
| 2-4576 | Sub-60 | 3,4-diClPh | SO₂ | Single bond | Sub-16 |
| 2-4577 | Sub-60 | 3,4-diClPh | SO₂ | Single bond | Sub-17 |
| 2-4578 | Sub-60 | 3,4-diClPh | SO₂ | Single bond | Sub-18 |
| 2-4579 | Sub-60 | 3,4-diClPh | SO₂ | Single bond | Sub-19 |
| 2-4580 | Sub-60 | 3,4-diClPh | SO₂ | Single bond | Sub-20 |
| 2-4581 | Sub-60 | 3,4-diClPh | SO₂ | Single bond | Sub-21 |
| 2-4582 | Sub-60 | 3,4-diClPh | SO₂ | Single bond | Sub-22 |
| 2-4583 | Sub-60 | 3,4-diClPh | SO₂ | Single bond | Sub-23 |
| 2-4584 | Sub-60 | 3,4-diClPh | SO₂ | Single bond | Sub-24 |
| 2-4585 | Sub-60 | 3,4-diClPh | SO₂ | Single bond | Sub-25 |
| 2-4586 | Sub-60 | 3,4-diClPh | SO₂ | Single bond | Sub-26 |
| 2-4587 | Sub-60 | 3,4-diClPh | SO₂ | Single bond | Sub-27 |
| 2-4588 | Sub-60 | 3,4-diClPh | SO₂ | Single bond | Sub-28 |
| 2-4589 | Sub-60 | 3,4-diClPh | SO₂ | Single bond | Sub-29 |
| 2-4590 | Sub-60 | 3,4-diClPh | SO₂ | Single bond | Sub-30 |
| 2-4591 | Sub-60 | 3,4-diClPh | SO₂ | Single bond | Sub-31 |
| 2-4592 | Sub-60 | 3,4-diClPh | SO₂ | Single bond | Sub-32 |

TABLE 2-continued

| Cpd. No. | R¹ | R² | A | B | Z |
|---|---|---|---|---|---|
| 2-4593 | Sub-60 | 3,4-diClPh | SO₂ | Single bond | Sub-65 |
| 2-4594 | Sub-60 | 3,4-diClPh | SO₂ | Single bond | Sub-66 |
| 2-4595 | Sub-60 | 3,4-diClPh | SO₂ | Single bond | Sub-67 |
| 2-4596 | Sub-60 | 3,4-diClPh | SO₂ | Single bond | Sub-68 |
| 2-4597 | Sub-60 | 3,4-diClPh | SO₂ | Single bond | Sub-69 |
| 2-4598 | Sub-60 | 3,4-diClPh | SO₂ | Single bond | Sub-70 |
| 2-4599 | Sub-60 | 3,4-diClPh | SO₂ | Single bond | Sub-71 |
| 2-4600 | Sub-60 | 3,4-diClPh | SO₂ | Single bond | Sub-72 |
| 2-4601 | Sub-60 | 3,4-diClPh | SO₂ | Single bond | Sub-73 |
| 2-4602 | Sub-60 | 3,4-diClPh | SO₂ | Single bond | Sub-74 |
| 2-4603 | Sub-60 | 3,4-diClPh | SO₂ | Single bond | Sub-75 |
| 2-4604 | Sub-60 | 3,4-diClPh | SO₂ | Single bond | Sub-76 |
| 2-4605 | Sub-60 | 3,4-diClPh | SO₂ | Single bond | Sub-77 |
| 2-4606 | Sub-60 | 3,4-diClPh | SO₂ | Single bond | Sub-78 |
| 2-4607 | Sub-60 | 3,4-diClPh | SO₂ | Single bond | Sub-79 |
| 2-4608 | Sub-60 | 3,4-diClPh | SO₂ | Single bond | Sub-80 |

TABLE 3

| Cpd. No. | R¹ | R² | A | B | E |
|---|---|---|---|---|---|
| 3-1 | Sub-33 | 3,4-diClPh | —CO— | Single Bond | —CH₂— |
| 3-2 | Sub-34 | 3,4-diClPh | —CO— | Single Bond | —CH₂— |
| 3-3 | Sub-35 | 3,4-diClPh | —CO— | Single Bond | —CH₂— |
| 3-4 | Sub-36 | 3,4-diClPh | —CO— | Single Bond | —CH₂— |
| 3-5 | Sub-37 | 3,4-diClPh | —CO— | Single Bond | —CH₂— |
| 3-6 | Sub-38 | 3,4-diClPh | —CO— | Single Bond | —CH₂— |
| 3-7 | Sub-39 | 3,4-diClPh | —CO— | Single Bond | —CH₂— |
| 3-8 | Sub-40 | 3,4-diClPh | —CO— | Single Bond | —CH₂— |
| 3-9 | Sub-41 | 3,4-diClPh | —CO— | Single Bond | —CH₂— |
| 3-10 | Sub-42 | 3,4-diClPh | —CO— | Single Bond | —CH₂— |
| 3-11 | Sub-84 | 3,4-diClPh | —CO— | Single Bond | —CH₂— |
| 3-12 | Sub-43 | 3,4-diClPh | —CO— | Single Bond | —CH₂— |
| 3-13 | Sub-44 | 3,4-diClPh | —CO— | Single Bond | —CH₂— |
| 3-14 | Sub-45 | 3,4-diClPh | —CO— | Single Bond | —CH₂— |
| 3-15 | Sub-46 | 3,4-diClPh | —CO— | Single Bond | —CH₂— |
| 3-16 | Sub-47 | 3,4-diClPh | —CO— | Single Bond | —CH₂— |
| 3-17 | Sub-81 | 3,4-diClPh | —CO— | Single Bond | —CH₂— |
| 3-18 | Sub-48 | 3,4-diClPh | —CO— | Single Bond | —CH₂— |
| 3-19 | Sub-49 | 3,4-diClPh | —CO— | Single Bond | —CH₂— |
| 3-20 | Sub-50 | 3,4-diClPh | —CO— | Single Bond | —CH₂— |
| 3-21 | Sub-51 | 3,4-diClPh | —CO— | Single Bond | —CH₂— |
| 3-22 | Sub-52 | 3,4-diClPh | —CO— | Single Bond | —CH₂— |
| 3-23 | Sub-53 | 3,4-diClPh | —CO— | Single Bond | —CH₂— |
| 3-24 | Sub-54 | 3,4-diClPh | —CO— | Single Bond | —CH₂— |
| 3-25 | Sub-56 | 3,4-diClPh | —CO— | Single Bond | —CH₂— |
| 3-26 | Sub-57 | 3,4-diClPh | —CO— | Single Bond | —CH₂— |
| 3-27 | Sub-58 | 3,4-diClPh | —CO— | Single Bond | —CH₂— |
| 3-28 | Sub-59 | 3,4-diClPh | —CO— | Single Bond | —CH₂— |
| 3-29 | Sub-82 | 3,4-diClPh | —CO— | Single Bond | —CH₂— |
| 3-30 | Sub-83 | 3,4-diClPh | —CO— | Single Bond | —CH₂— |
| 3-31 | Sub-61 | 3,4-diClPh | —CO— | Single Bond | —CH₂— |
| 3-32 | Sub-55 | 3,4-diClPh | —CO— | Single Bond | —CH₂— |
| 3-33 | Sub-33 | 3,4-diClPh | —CO— | Single Bond | —CH₂CH₂— |
| 3-34 | Sub-34 | 3,4-diClPh | —CO— | Single Bond | —CH₂CH₂— |
| 3-35 | Sub-35 | 3,4-diClPh | —CO— | Single Bond | —CH₂CH₂— |
| 3-36 | Sub-36 | 3,4-diClPh | —CO— | Single Bond | —CH₂CH₂— |
| 3-37 | Sub-37 | 3,4-diClPh | —CO— | Single Bond | —CH₂CH₂— |
| 3-38 | Sub-38 | 3,4-diClPh | —CO— | Single Bond | —CH₂CH₂— |
| 3-39 | Sub-39 | 3,4-diClPh | —CO— | Single Bond | —CH₂CH₂— |
| 3-40 | Sub-40 | 3,4-diClPh | —CO— | Single Bond | —CH₂CH₂— |
| 3-41 | Sub-41 | 3,4-diClPh | —CO— | Single Bond | —CH₂CH₂— |
| 3-42 | Sub-42 | 3,4-diClPh | —CO— | Single Bond | —CH₂CH₂— |
| 3-43 | Sub-84 | 3,4-diClPh | —CO— | Single Bond | —CH₂CH₂— |
| 3-44 | Sub-43 | 3,4-diClPh | —CO— | Single Bond | —CH₂CH₂— |
| 3-45 | Sub-44 | 3,4-diClPh | —CO— | Single Bond | —CH₂CH₂— |
| 3-46 | Sub-45 | 3,4-diClPh | —CO— | Single Bond | —CH₂CH₂— |
| 3-47 | Sub-46 | 3,4-diClPh | —CO— | Single Bond | —CH₂CH₂— |
| 3-48 | Sub-47 | 3,4-diClPh | —CO— | Single Bond | —CH₂CH₂— |
| 3-49 | Sub-81 | 3,4-diClPh | —CO— | Single Bond | —CH₂CH₂— |
| 3-50 | Sub-48 | 3,4-diClPh | —CO— | Single Bond | —CH₂CH₂— |
| 3-51 | Sub-49 | 3,4-diClPh | —CO— | Single Bond | —CH₂CH₂— |
| 3-52 | Sub-50 | 3,4-diClPh | —CO— | Single Bond | —CH₂CH₂— |
| 3-53 | Sub-51 | 3,4-diClPh | —CO— | Single Bond | —CH₂CH₂— |
| 3-54 | Sub-52 | 3,4-diClPh | —CO— | Single Bond | —CH₂CH₂— |
| 3-55 | Sub-53 | 3,4-diClPh | —CO— | Single Bond | —CH₂CH₂— |
| 3-56 | Sub-54 | 3,4-diClPh | —CO— | Single Bond | —CH₂CH₂— |
| 3-57 | Sub-56 | 3,4-diClPh | —CO— | Single Bond | —CH₂CH₂— |
| 3-58 | Sub-57 | 3,4-diClPh | —CO— | Single Bond | —CH₂CH₂— |

TABLE 3-continued

| Cpd. No. | R¹ | R² | A | B | E |
|---|---|---|---|---|---|
| 3-59 | Sub-58 | 3,4-diClPh | —CO— | Single Bond | —CH₂CH₂— |
| 3-60 | Sub-59 | 3,4-diClPh | —CO— | Single Bond | —CH₂CH₂— |
| 3-61 | Sub-82 | 3,4-diClPh | —CO— | Single Bond | —CH₂CH₂— |
| 3-62 | Sub-83 | 3,4-diClPh | —CO— | Single Bond | —CH₂CH₂— |
| 3-63 | Sub-61 | 3,4-diClPh | —CO— | Single Bond | —CH₂CH₂— |
| 3-64 | Sub-55 | 3,4-diClPh | —CO— | Single Bond | —CH₂CH₂— |
| 3-65 | Sub-33 | 3,4-diClPh | —CO— | Single Bond | —(CH₂)₃— |
| 3-66 | Sub-34 | 3,4-diClPh | —CO— | Single Bond | —(CH₂)₃— |
| 3-67 | Sub-35 | 3,4-diClPh | —CO— | Single Bond | —(CH₂)₃— |
| 3-68 | Sub-36 | 3,4-diClPh | —CO— | Single Bond | —(CH₂)₃— |
| 3-69 | Sub-37 | 3,4-diClPh | —CO— | Single Bond | —(CH₂)₃— |
| 3-70 | Sub-38 | 3,4-diClPh | —CO— | Single Bond | —(CH₂)₃— |
| 3-71 | Sub-39 | 3,4-diClPh | —CO— | Single Bond | —(CH₂)₃— |
| 3-72 | Sub-40 | 3,4-diClPh | —CO— | Single Bond | —(CH₂)₃— |
| 3-73 | Sub-41 | 3,4-diClPh | —CO— | Single Bond | —(CH₂)₃— |
| 3-74 | Sub-42 | 3,4-diClPh | —CO— | Single Bond | —(CH₂)₃— |
| 3-75 | Sub-84 | 3,4-diClPh | —CO— | Single Bond | —(CH₂)₃— |
| 3-76 | Sub-43 | 3,4-diClPh | —CO— | Single Bond | —(CH₂)₃— |
| 3-77 | Sub-44 | 3,4-diClPh | —CO— | Single Bond | —(CH₂)₃— |
| 3-78 | Sub-45 | 3,4-diClPh | —CO— | Single Bond | —(CH₂)₃— |
| 3-79 | Sub-46 | 3,4-diClPh | —CO— | Single Borid | —(CH₂)₃— |
| 3-80 | Sub-47 | 3,4-diClPh | —CO— | Single Bond | —(CH₂)₃— |
| 3-81 | Sub-81 | 3,4-diClPh | —CO— | Single Bond | —(CH₂)₃— |
| 3-82 | Sub-48 | 3,4-diClPh | —CO— | Single Bond | —(CH₂)₃— |
| 3-83 | Sub-49 | 3,4-diClPh | —CO— | Single Bond | —(CH₂)₃— |
| 3-84 | Sub-50 | 3,4-diClPh | —CO— | Single Bond | —(CH₂)₃— |
| 3-85 | Sub-51 | 3,4-diClPh | —CO— | Single Bond | —(CH₂)₃— |
| 3-86 | Sub-52 | 3,4-diClPh | —CO— | Single Bond | —(CH₂)₃— |
| 3-87 | Sub-53 | 3,4-diClPh | —CO— | Single Bond | —(CH₂)₃— |
| 3-88 | Sub-54 | 3,4-diClPh | —CO— | Single Bond | —(CH₂)₃— |
| 3-89 | Sub-56 | 3,4-diClPh | —CO— | Single Bond | —(CH₂)₃— |
| 3-90 | Sub-57 | 3,4-diClPh | —CO— | Single Bond | —(CH₂)₃— |
| 3-91 | Sub-58 | 3,4-diClPh | —CO— | Single Bond | —(CH₂)₃— |
| 3-92 | Sub-59 | 3,4-diClPh | —CO— | Single Bond | —(CH₂)₃— |
| 3-93 | Sub-82 | 3,4-diClPh | —CO— | Single Bond | —(CH₂)₃— |
| 3-94 | Sub-83 | 3,4-diClPh | —CO— | Single Bond | —(CH₂)₃— |
| 3-95 | Sub-61 | 3,4-diClPh | —CO— | Single Borid | —(CH₂)₃— |
| 3-96 | Sub-55 | 3,4-diClPh | —CO— | Single Bond | —(CH₂)₃— |
| 3-97 | Sub-33 | 3,4-diClPh | —CO— | Single Bond | —CH₂C(Me)₂— |
| 3-98 | Sub-34 | 3,4-diClPh | —CO— | Single Bond | —CH₂C(Me)₂— |
| 3-99 | Sub-35 | 3,4-diClPh | —CO— | Single Bond | —CH₂C(Me)₂— |
| 3-100 | Sub-36 | 3,4-diClPh | —CO— | Single Bond | —CH₂C(Me)₂— |
| 3-101 | Sub-37 | 3,4-diClPh | —CO— | Single Bond | —CH₂C(Me)₂— |
| 3-102 | Sub-38 | 3,4-diClPh | —CO— | Single Bond | —CH₂C(Me)₂— |
| 3-103 | Sub-39 | 3,4-diClPh | —CO— | Single Bond | —CH₂C(Me)₂— |
| 3-104 | Sub-40 | 3,4-diClPh | —CO— | Single Bond | —CH₂C(Me)₂— |
| 3-105 | Sub-41 | 3,4-diClPh | —CO— | Single Bond | —CH₂C(Me)₂— |
| 3-106 | Sub-42 | 3,4-diClPh | —CO— | Single Bond | —CH₂C(Me)₂— |
| 3-107 | Sub-84 | 3,4-diClPh | —CO— | Single Bond | —CH₂C(Me)₂— |
| 3-108 | Sub-43 | 3,4-diClPh | —CO— | Single Bond | —CH₂C(Me)₂— |
| 3-109 | Sub-44 | 3,4-diClPh | —CO— | Single Bond | —CH₂C(Me)₂— |
| 3-110 | Sub-45 | 3,4-diClPh | —CO— | Single Bond | —CH₂C(Me)₂— |
| 3-111 | Sub-46 | 3,4-diClPh | —CO— | Single Bond | —CH₂C(Me)₂— |
| 3-112 | Sub-47 | 3,4-diClPh | —CO— | Single Bond | —CH₂C(Me)₂— |
| 3-113 | Sub-81 | 3,4-diClPh | —CO— | Single Bond | —CH₂C(Me)₂— |
| 3-114 | Sub-48 | 3,4-diClPh | —CO— | Single Bond | —CH₂C(Me)₂— |
| 3-115 | Sub-49 | 3,4-diClPh | —CO— | Single Bond | —CH₂C(Me)₂— |
| 3-116 | Sub-50 | 3,4-diClPh | —CO— | Single Bond | —CH₂C(Me)₂— |
| 3-117 | Sub-51 | 3,4-diClPh | —CO— | Single Bond | —CH₂C(Me)₂— |
| 3-118 | Sub-52 | 3,4-diClPh | —CO— | Single Bond | —CH₂C(Me)₂— |
| 3-119 | Sub-53 | 3,4-diClPh | —CO— | Single Bond | —CH₂C(Me)₂— |
| 3-120 | Sub-54 | 3,4-diClPh | —CO— | Single Bond | —CH₂C(Me)₂— |
| 3-121 | Sub-56 | 3,4-diClPh | —CO— | Single Bond | —CH₂C(Me)₂— |
| 3-122 | Sub-57 | 3,4-diClPh | —CO— | Single Bond | —CH₂C(Me)₂— |
| 3-123 | Sub-58 | 3,4-diClPh | —CO— | Single Bond | —CH₂C(Me)₂— |
| 3-124 | Sub-59 | 3,4-diClPh | —CO— | Single Bond | —CH₂C(Me)₂— |
| 3-125 | Sub-82 | 3,4-diClPh | —CO— | Single Bond | —CH₂C(Me)₂— |
| 3-126 | Sub-83 | 3,4-diClPh | —CO— | Single Bond | —CH₂C)Me)₂— |
| 3-127 | Sub-61 | 3,4-diClPh | —CO— | Single Bond | —CH₂C(Me)₂— |
| 3-128 | Sub-55 | 3,4-diClPh | —CO— | Single Bond | —CH₂C(Me)₂— |
| 3-129 | Sub-33 | 3,4-diClPh | —CO— | Single Bond | —CH₂-cPr— |
| 3-130 | Sub-34 | 3,4-diClPh | —CO— | Single Bond | —CH₂-cPr— |
| 3-131 | Sub-35 | 3,4-diClPh | —CO— | Single Bond | —CH₂-cPr— |
| 3-132 | Sub-36 | 3,4-diClPh | —CO— | Single Bond | —CH₂-cPr— |
| 3-133 | Sub-37 | 3,4-diClPh | —CO— | Single Bond | —CH₂-cPr— |
| 3-134 | Sub-38 | 3,4-diClPh | —CO— | Single Bond | —CH₂-cPr— |

TABLE 3-continued

| Cpd. No. | R¹ | R² | A | B | E |
|---|---|---|---|---|---|
| 3-135 | Sub-39 | 3,4-diClPh | —CO— | Single Bond | —CH$_2$-cPr— |
| 3-136 | Sub-40 | 3,4-diClPh | —CO— | Single Bond | —CH$_2$-cPr— |
| 3-137 | Sub-41 | 3,4-diClPh | —CO— | Single Bond | —CH$_2$-cPr— |
| 3-138 | Sub-42 | 3,4-diClPh | —CO— | Single Bond | —CH$_2$-cPr— |
| 3-139 | Sub-84 | 3,4-diClPh | —CO— | Single Bond | —CH$_2$-cPr— |
| 3-140 | Sub-43 | 3,4-diClPh | —CO— | Single Bond | —CH$_2$-cPr— |
| 3-141 | Sub-44 | 3,4-diClPh | —CO— | Single Bond | —CH$_2$-cPr— |
| 3-142 | Sub-45 | 3,4-diClPh | —CO— | Single Bond | —CH$_2$-cPr— |
| 3-143 | Sub-46 | 3,4-diClPh | —CO— | Single Bond | —CH$_2$-cPr— |
| 3-144 | Sub-47 | 3,4-diClPh | —CO— | Single Bond | —CH$_2$-cPr— |
| 3-145 | Sub-81 | 3,4-diClPh | —CO— | Single Bond | —CH$_2$-cPr— |
| 3-146 | Sub-48 | 3,4-diClPh | —CO— | Single Bond | —CH$_2$-cPr— |
| 3-147 | Sub-49 | 3,4-diClPh | —CO— | Single Bond | —CH$_2$-cPr— |
| 3-148 | Sub-50 | 3,4-diClPh | —CO— | Single Bond | —CH$_2$-cPr— |
| 3-149 | Sub-51 | 3,4-diClPh | —CO— | Single Bond | —CH$_2$-cPr— |
| 3-150 | Sub-52 | 3,4-diClPh | —CO— | Single Bond | —CH$_2$-cPr— |
| 3-151 | Sub-53 | 3,4-diClPh | —CO— | Single Bond | —CH$_2$-cPr— |
| 3-152 | Sub-54 | 3,4-diClPh | —CO— | Single Bond | —CH$_2$-cPr— |
| 3-153 | Sub-56 | 3,4-diClPh | —CO— | Single Bond | —CH$_2$-cPr— |
| 3-154 | Sub-57 | 3,4-diClPh | —CO— | Single Bond | —CH$_2$-cPr— |
| 3-155 | Sub-58 | 3,4-diClPh | —CO— | Single Bond | —CH$_2$-cPr— |
| 3-156 | Sub-59 | 3,4-diClPh | —CO— | Single Bond | —CH$_2$-cPr— |
| 3-157 | Sub-82 | 3,4-diClPh | —CO— | Single Bond | —CH$_2$-cPr— |
| 3-158 | Sub-83 | 3,4-diClPh | —CO— | Single Bond | —CH$_2$-cPr— |
| 3-159 | Sub-61 | 3,4-diClPh | —CO— | Single Bond | —CH$_2$-cPr— |
| 3-160 | Sub-55 | 3,4-diClPh | —CO— | Single Bond | —CH$_2$-cPr— |
| 3-161 | Sub-33 | 3,4-diClPh | —CO— | Sihgle Bond | —CH$_2$-cBu— |
| 3-162 | Sub-34 | 3,4-diClPh | —CO— | Single Bond | —CH$_2$-cBu— |
| 3-163 | Sub-35 | 3,4-diClPh | —CO— | Single Bond | —CH$_2$-cBu— |
| 3-164 | Sub-36 | 3,4-diClPh | —CO— | Single Bond | —CH$_2$-cBu— |
| 3-165 | Sub-37 | 3,4-diClPh | —CO— | Single Bond | —CH$_2$-cBu— |
| 3-166 | Sub-38 | 3,4-diClPh | —CO— | Single Bond | —CH$_2$-cBu— |
| 3-167 | Sub-39 | 3,4-diClPh | —CO— | Single Bond | —CH$_2$-cBu— |
| 3-168 | Sub-40 | 3,4-diClPh | —CO— | Single Bond | —CH$_2$-cBu— |
| 3-169 | Sub-41 | 3,4-diClPh | —CO— | Single Bond | —CH$_2$-cBu— |
| 3-170 | Sub-42 | 3,4-diClPh | —CO— | Single Bond | —CH$_2$-cBu— |
| 3-171 | Sub-84 | 3,4-diClPh | —CO— | Single Bond | —CH$_2$-cBu— |
| 3-172 | Sub-43 | 3,4-diClPh | —CO— | Single Bond | —CH$_2$-cBu— |
| 3-173 | Sub-44 | 3,4-diClPh | —CO— | Single Bond | —CH$_2$-cBu— |
| 3-174 | Sub-45 | 3,4-diClPh | —CO— | Single Bond | —CH$_2$-cBu— |
| 3-175 | Sub-46 | 3,4-diClPh | —CO— | Single Bond | —CH$_2$-cBu— |
| 3-176 | Sub-47 | 3,4-diClPh | —CO— | Single Bond | —CH$_2$-cBu— |
| 3-177 | Sub-81 | 3,4-diClPh | —CO— | Single Bond | —CH$_2$-cBu— |
| 3-178 | Sub-48 | 3,4-diClPh | —CO— | Single Bond | —CH$_2$-cBu— |
| 3-179 | Sub-49 | 3,4-diClPh | —CO— | Single Bond | —CH$_2$-cBu— |
| 3-180 | Sub-50 | 3,4-diClPh | —CO— | Single Bond | —CH$_2$-cBu— |
| 3-181 | Sub-51 | 3,4-diClPh | —CO— | Single Bond | —CH$_2$-cBu— |
| 3-182 | Sub-52 | 3,4-diClPh | —CO— | Single Bond | —CH$_2$-cBu— |
| 3-183 | Sub-53 | 3,4-diClPh | —CO— | Single Bond | —CH$_2$-cBu— |
| 3-184 | Sub-54 | 3,4-diClPh | —CO— | Single Bond | —CH$_2$-cBu— |
| 3-185 | Sub-56 | 3,4-diClPh | —CO— | Single Bond | —CH$_2$-cBu— |
| 3-186 | Sub-57 | 3,4-diClPh | —CO— | Single Bond | —CH$_2$-cBu— |
| 3-187 | Sub-58 | 3,4-diClPh | —CO— | Single Bond | —CH$_2$-cBu— |
| 3-188 | Sub-59 | 3,4-diClPh | —CO— | Single Bond | —CH$_2$-cBu— |
| 3-189 | Sub-82 | 3,4-diClPh | —CO— | Single Bond | —CH$_2$-cBu— |
| 3-190 | Sub-83 | 3,4-diClPh | —CO— | Single Bond | —CH$_2$-cBu— |
| 3-191 | Sub-61 | 3,4-diClPh | —CO— | Single Bond | —CH$_2$-cBu— |
| 3-192 | Sub-55 | 3,4-diClPh | —CO— | Single Bond | —CH$_2$-cBu— |
| 3-193 | Sub-33 | 3,4-diClPh | —CO— | Single Bond | —CH$_2$-cPn— |
| 3-194 | Sub-34 | 3,4-diClPh | —CO— | Single Bond | —CH$_2$-cPn— |
| 3-195 | Sub-35 | 3,4-diClPh | —CO— | Single Bond | —CH$_2$-cPn— |
| 3-196 | Sub-36 | 3,4-diClPh | —CO— | Single Bond | —CH$_2$-cPn— |
| 3-197 | Sub-37 | 3,4-diClPh | —CO— | Single Bond | —CH$_2$-cPn— |
| 3-198 | Sub-38 | 3,4-diClPh | —CO— | Single Bond | —CH$_2$-cPn— |
| 3-199 | Sub-39 | 3,4-diClPh | —CO— | Single Bond | —CH$_2$-cPn— |
| 3-200 | Sub-40 | 3,4-diClPh | —CO— | Single Bond | —CH$_2$-cPn— |
| 3-201 | Sub-41 | 3,4-diClPh | —CO— | Single Bond | —CH$_2$-cPn— |
| 3-202 | Sub-42 | 3,4-diClPh | —CO— | Single Bond | —CH$_2$-cPn— |
| 3-203 | Sub-84 | 3,4-diClPh | —CO— | Single Bond | —CH$_2$-cPn— |
| 3-204 | Sub-43 | 3,4-diClPh | —CO— | Single Bond | —CH$_2$-cPn— |
| 3-205 | Sub-44 | 3,4-diClPh | —CO— | Single Bond | —CH$_2$-cPn— |
| 3-206 | Sub-45 | 3,4-diClPh | —CO— | Single Bond | —CH$_2$-cPn— |
| 3-207 | Sub-46 | 3,4-diClPh | —CO— | Single Bond | —CH$_2$-cPn— |
| 3-208 | Sub-47 | 3,4-diClPh | —CO— | Single Bond | —CH$_2$-cPn— |
| 3-209 | Sub-81 | 3,4-diClPh | —CO— | Single Bond | —CH$_2$-cPn— |
| 3-210 | Sub-48 | 3,4-diClPh | —CO— | Single Bond | —CH$_2$-cPn— |

TABLE 3-continued

| Cpd. No. | R¹ | R² | A | B | E |
|---|---|---|---|---|---|
| 3-211 | Sub-49 | 3,4-diClPh | —CO— | Single Bond | —CH₂-cPn— |
| 3-212 | Sub-50 | 3,4-diClPh | —CO— | Single Bond | —CH₂-cPn— |
| 3-213 | Sub-51 | 3,4-diClPh | —CO— | Single Bond | —CH₂-cPn— |
| 3-214 | Sub-52 | 3,4-diClPh | —CO— | Single Bond | —CH₂-cPn— |
| 3-215 | Sub-53 | 3,4-diClPh | —CO— | Single Bond | —CH₂-cPn— |
| 3-216 | Sub-54 | 3,4-diClPh | —CO— | Single Bond | —CH₂-cPn— |
| 3-217 | Sub-56 | 3,4-diClPh | —CO— | Single Bond | —CH₂-cPn— |
| 3-218 | Sub-57 | 3,4-diClPh | —CO— | Single Bond | —CH₂-cPn— |
| 3-219 | Sub-58 | 3,4-diClPh | —CO— | Single Bond | —CH₂-cPn— |
| 3-220 | Sub-59 | 3,4-diClPh | —CO— | Single Bond | —CH₂-cPn— |
| 3-221 | Sub-82 | 3,4-diClPh | —CO— | Single Bond | —CH₂-cPn— |
| 3-222 | Sub-83 | 3,4-diClPh | —CO— | Single Bond | —CH₂-cPn— |
| 3-223 | Sub-61 | 3,4-diClPh | —CO— | Single Bond | —CH₂-cPn— |
| 3-224 | Sub-55 | 3,4-diClPh | —CO— | Single Bond | —CH₂-cPn— |
| 3-225 | Sub-33 | 3,4-diClPh | —CO— | Single Bond | —CH₂-cHx— |
| 3-226 | Sub-34 | 3,4-diClPh | —CO— | Single Bond | —CH₂-cHx— |
| 3-227 | Sub-35 | 3,4-diClPh | —CO— | Single Bond | —CH₂-cHx— |
| 3-228 | Sub-36 | 3,4-diClPh | —CO— | Single Bond | —CH₂-cHx— |
| 3-229 | Sub-37 | 3,4-diClPh | —CO— | Single Bond | —CH₂-cHx— |
| 3-230 | Sub-38 | 3,4-diClPh | —CO— | Single Bond | —CH₂-cHx— |
| 3-231 | Sub-39 | 3,4-diClPh | —CO— | Single Bond | —CH₂-cHx— |
| 3-232 | Sub-40 | 3,4-diClPh | —CO— | Single Bond | —CH₂-cHx— |
| 3-233 | Sub-41 | 3,4-diClPh | —CO— | Single Bond | —CH₂-cHx— |
| 3-234 | Sub-42 | 3,4-diClPh | —CO— | Single Bond | —CH₂-cHx— |
| 3-235 | Sub-84 | 3,4-diClPh | —CO— | Single Bond | —CH₂-cHx— |
| 3-236 | Sub-43 | 3,4-diClPh | —CO— | Single Bond | —CH₂-cHx— |
| 3-237 | Sub-44 | 3,4-diClPh | —CO— | Single Bond | —CH₂-cHx— |
| 3-238 | Sub-45 | 3,4-diClPh | —CO— | Single Bond | —CH₂-cHx— |
| 3-239 | Sub-46 | 3,4-diClPh | —CO— | Single Bond | —CH₂-cHx— |
| 3-240 | Sub-47 | 3,4-diClPh | —CO— | Single Bond | —CH₂-cHx— |
| 3-241 | Sub-81 | 3,4-diClPh | —CO— | Single Bond | —CH₂-cHx— |
| 3-242 | Sub-48 | 3,4-diClPh | —CO— | Single Bond | —CH₂-cHx— |
| 3-243 | Sub-49 | 3,4-diClPh | —CO— | Single Bond | —CH₂-cHx— |
| 3-244 | Sub-50 | 3,4-diClPh | —CO— | Single Bond | —CH₂-cHx— |
| 3-245 | Sub-51 | 3,4-diClPh | —CO— | Single Bond | —CH₂-cHx— |
| 3-246 | Sub-52 | 3,4-diClPh | —CO— | Single Bond | —CH₂-cHx— |
| 3-247 | Sub-53 | 3,4-diClPh | —CO— | Single Bond | —CH₂-cHx— |
| 3-248 | Sub-54 | 3,4-diClPh | —CO— | Single Bond | —CH₂-cHx— |
| 3-249 | Sub-56 | 3,4-diClPh | —CO— | Single Bond | —CH₂-cHx— |
| 3-250 | Sub-57 | 3,4-diClPh | —CO— | Single Bond | —CH₂-cHx— |
| 3-251 | Sub-58 | 3,4-diClPh | —CO— | Single Bond | —CH₂-cHx— |
| 3-252 | Sub-59 | 3,4-diClPh | —CO— | Single Bond | —CH₂-cHx— |
| 3-253 | Sub-82 | 3,4-diClPh | —CO— | Single Bond | —CH₂-cHx— |
| 3-254 | Sub-83 | 3,4-diClPh | —CO— | Single Bond | —CH₂-cHx— |
| 3-255 | Sub-61 | 3,4-diClPh | —CO— | Single Bond | —CH₂-cHx— |
| 3-256 | Sub-55 | 3,4-diClPh | —CO— | Single Bond | —CH₂-cHx— |
| 3-257 | Sub-33 | 4-ClPh | —CO— | Single Bond | —CH₂— |
| 3-258 | Sub-34 | 4-ClPh | —CO— | Single Bond | —CH₂— |
| 3-259 | Sub-35 | 4-ClPh | —CO— | Single Bond | —CH₂— |
| 3-260 | Sub-36 | 4-ClPh | —CO— | Single Bond | —CH₂— |
| 3-261 | Sub-37 | 4-ClPh | —CO— | Single Bond | —CH₂— |
| 3-262 | Sub-38 | 4-ClPh | —CO— | Single Bond | —CH₂— |
| 3-263 | Sub-39 | 4-ClPh | —CO— | Single Bond | —CH₂— |
| 3-264 | Sub-40 | 4-ClPh | —CO— | Single Bond | —CH₂— |
| 3-265 | Sub-41 | 4-ClPh | —CO— | Single Bond | —CH₂— |
| 3-266 | Sub-42 | 4-ClPh | —CO— | Single Bond | —CH₂— |
| 3-267 | Sub-84 | 4-ClPh | —CO— | Single Bond | —CH₂— |
| 3-268 | Sub-43 | 4-ClPh | —CO— | Single Bond | —CH₂— |
| 3-269 | Sub-44 | 4-ClPh | —CO— | Single Bond | —CH₂— |
| 3-270 | Sub-45 | 4-ClPh | —CO— | Single Bond | —CH₂— |
| 3-271 | Sub-46 | 4-ClPh | —CO— | Single Bond | —CH₂— |
| 3-272 | Sub-47 | 4-ClPh | —CO— | Single Bond | —CH₂— |
| 3-273 | Sub-81 | 4-ClPh | —CO— | Single Bond | —CH₂— |
| 3-274 | Sub-48 | 4-ClPh | —CO— | Single Bond | —CH₂— |
| 3-275 | Sub-49 | 4-ClPh | —CO— | Single Bond | —CH₂— |
| 3-276 | Sub-50 | 4-ClPh | —CO— | Single Bond | —CH₂— |
| 3-277 | Sub-51 | 4-ClPh | —CO— | Single Bond | —CH₂— |
| 3-278 | Sub-52 | 4-ClPh | —CO— | Single Bond | —CH₂— |
| 3-279 | Sub-53 | 4-ClPh | —CO— | Single Bond | —CH₂— |
| 3-280 | Sub-54 | 4-ClPh | —CO— | Single Bond | —CH₂— |
| 3-281 | Sub-56 | 4-ClPh | —CO— | Single Bond | —CH₂— |
| 3-282 | Sub-57 | 4-ClPh | —CO— | Single Bond | —CH₂— |
| 3-283 | Sub-58 | 4-ClPh | —CO— | Single Bond | —CH₂— |
| 3-284 | Sub-59 | 4-ClPh | —CO— | Single Bond | —CH₂— |
| 3-285 | Sub-82 | 4-ClPh | —CO— | Single Bond | —CH₂— |
| 3-286 | Sub-83 | 4-ClPh | —CO— | Single Bond | —CH₂— |

TABLE 3-continued

| Cpd. No. | R¹ | R² | A | B | E |
|---|---|---|---|---|---|
| 3-287 | Sub-61 | 4-ClPh | —CO— | Single Bond | —CH₂— |
| 3-288 | Sub-55 | 4-ClPh | —CO— | Single Bond | —CH₂— |
| 3-289 | Sub-33 | 4-ClPh | —CO— | Single Bond | —CH₂CH₂— |
| 3-290 | Sub-34 | 4-ClPh | —CO— | Single Bond | —CH₂CH₂— |
| 3-291 | Sub-35 | 4-ClPh | —CO— | Single Bond | —CH₂CH₂— |
| 3-292 | Sub-36 | 4-ClPh | —CO— | Single Bond | —CH₂CH₂— |
| 3-293 | Sub-37 | 4-ClPh | —CO— | Single Bond | —CH₂CH₂— |
| 3-294 | Sub-38 | 4-ClPh | —CO— | Single Bond | —CH₂CH₂— |
| 3-295 | Sub-39 | 4-ClPh | —CO— | Single Bond | —CH₂CH₂— |
| 3-296 | Sub-40 | 4-ClPh | —CO— | Single Bond | —CH₂CH₂— |
| 3-297 | Sub-41 | 4-ClPh | —CO— | Single Bond | —CH₂CH₂— |
| 3-298 | Sub-42 | 4-ClPh | —CO— | Single Bond | —CH₂CH₂— |
| 3-299 | Sub-84 | 4-ClPh | —CO— | Single Bond | —CH₂CH₂— |
| 3-300 | Sub-43 | 4-ClPh | —CO— | Single Bond | —CH₂CH₂— |
| 3-301 | Sub-44 | 4-ClPh | —CO— | Single Bond | —CH₂CH₂— |
| 3-302 | Sub-45 | 4-ClPh | —CO— | Single Bond | —CH₂CH₂— |
| 3-303 | Sub-46 | 4-ClPh | —CO— | Single Bond | —CH₂CH₂— |
| 3-304 | Sub-47 | 4-ClPh | —CO— | Single Bond | —CH₂CH₂— |
| 3-305 | Sub-81 | 4-ClPh | —CO— | Single Bond | —CH₂CH₂— |
| 3-306 | Sub-48 | 4-ClPh | —CO— | Single Bond | —CH₂CH₂— |
| 3-307 | Sub-49 | 4-ClPh | —CO— | Single Bond | —CH₂CH₂— |
| 3-308 | Sub-50 | 4-ClPh | —CO— | Single Bond | —CH₂CH₂— |
| 3-309 | Sub-51 | 4-ClPh | —CO— | Single Bond | —CH₂CH₂— |
| 3-310 | Sub-52 | 4-ClPh | —CO— | Single Bond | —CH₂CH₂— |
| 3-311 | Sub-53 | 4-ClPh | —CO— | Single Bond | —CH₂CH₂— |
| 3-312 | Sub-54 | 4-ClPh | —CO— | Single Bond | —CH₂CH₂— |
| 3-313 | Sub-56 | 4-ClPh | —CO— | Single Bond | —CH₂CH₂— |
| 3-314 | Sub-57 | 4-ClPh | —CO— | Single Bond | —CH₂CH₂— |
| 3-315 | Sub-58 | 4-ClPh | —CO— | Single Bond | —CH₂CH₂— |
| 3-316 | Sub-59 | 4-ClPh | —CO— | Single Bond | —CH₂CH₂— |
| 3-317 | Sub-82 | 4-ClPh | —CO— | Single Bond | —CH₂CH₂— |
| 3-318 | Sub-83 | 4-ClPh | —CO— | Single Bond | —CH₂CH₂— |
| 3-319 | Sub-61 | 4-ClPh | —CO— | Single Bond | —CH₂CH₂— |
| 3-320 | Sub-55 | 4-ClPh | —CO— | Single Bond | —CH₂CH₂— |
| 3-321 | Sub-33 | 4-ClPh | —CO— | Single Bond | —(CH₂)₃— |
| 3-322 | Sub-34 | 4-ClPh | —CO— | Single Bond | —(CH₂)₃— |
| 3-323 | Sub-35 | 4-ClPh | —CO— | Single Bond | —(CH₂)₃— |
| 3-324 | Sub-36 | 4-ClPh | —CO— | Single Bond | —(CH₂)₃— |
| 3-325 | Sub-37 | 4-ClPh | —CO— | Single Bond | —(CH₂)₃— |
| 3-326 | Sub-38 | 4-ClPh | —CO— | Single Bond | —(CH₂)₃— |
| 3-327 | Sub-39 | 4-ClPh | —CO— | Single Bond | —(CH₂)₃— |
| 3-328 | Sub-40 | 4-ClPh | —CO— | Single Bond | —(CH₂)₃— |
| 3-329 | Sub-41 | 4-ClPh | —CO— | Single Bond | —(CH₂)₃— |
| 3-330 | Sub-42 | 4-ClPh | —CO— | Single Bond | —(CH₂)₃— |
| 3-331 | Sub-84 | 4-ClPh | —CO— | Single Bond | —(CH₂)₃— |
| 3-332 | Sub-43 | 4-ClPh | —CO— | Single Bond | —(CH₂)₃— |
| 3-333 | Sub-44 | 4-ClPh | —CO— | Single Bond | —(CH₂)₃— |
| 3-334 | Sub-45 | 4-ClPh | —CO— | Single Bond | —(CH₂)₃— |
| 3-335 | Sub-46 | 4-ClPh | —CO— | Single Bond | —(CH₂)₃— |
| 3-336 | Sub-47 | 4-ClPh | —CO— | Single Bond | —(CH₂)₃— |
| 3-337 | Sub-81 | 4-ClPh | —CO— | Single Bond | —(CH₂)₃— |
| 3-338 | Sub-48 | 4-ClPh | —CO— | Single Bond | —(CH₂)₃— |
| 3-339 | Sub-49 | 4-ClPh | —CO— | Single Bond | —(CH₂)₃— |
| 3-340 | Sub-50 | 4-ClPh | —CO— | Single Bond | —(CH₂)₃— |
| 3-341 | Sub-51 | 4-ClPh | —CO— | Single Bond | —(CH₂)₃— |
| 3-342 | Sub-52 | 4-ClPh | —CO— | Single Bond | —(CH₂)₃— |
| 3-343 | Sub-53 | 4-ClPh | —CO— | Single Bond | —(CH₂)₃— |
| 3-344 | Sub-54 | 4-ClPh | —CO— | Single Bond | —(CH₂)₃— |
| 3-345 | Sub-56 | 4-ClPh | —CO— | Single Bond | —(CH₂)₃— |
| 3-346 | Sub-57 | 4-ClPh | —CO— | Single Bond | —(CH₂)₃— |
| 3-347 | Sub-58 | 4-ClPh | —CO— | Single Bond | —(CH₂)₃— |
| 3-348 | Sub-59 | 4-ClPh | —CO— | Single Bond | —(CH₂)₃— |
| 3-349 | Sub-82 | 4-ClPh | —CO— | Single Bond | —(CH₂)₃— |
| 3-350 | Sub-83 | 4-ClPh | —CO— | Single Bond | —(CH₂)₃— |
| 3-351 | Sub-61 | 4-ClPh | —CO— | Single Bond | —(CH₂)₃— |
| 3-352 | Sub-55 | 4-ClPh | —CO— | Single Bond | —(CH₂)₃— |
| 3-353 | Sub-33 | 4-ClPh | —CO— | Single Bond | —CH₂C(Me)₂— |
| 3-354 | Sub-34 | 4-ClPh | —CO— | Single Bond | —CH₂C(Me)₂— |
| 3-355 | Sub-35 | 4-ClPh | —CO— | Single Bond | —CH₂C(Me)₂— |
| 3-356 | Sub-36 | 4-ClPh | —CO— | Single Bond | —CH₂C(Me)₂— |
| 3-357 | Sub-37 | 4-ClPh | —CO— | Single Bond | —CH₂C(Me)₂— |
| 3-358 | Sub-38 | 4-ClPh | —CO— | Single Bond | —CH₂C(Me)₂— |
| 3-359 | Sub-39 | 4-ClPh | —CO— | Single Bond | —CH₂C(Me)₂— |
| 3-360 | Sub-40 | 4-ClPh | —CO— | Single Bond | —CH₂C(Me)₂— |
| 3-361 | Sub-41 | 4-ClPh | —CO— | Single Bond | —CH₂C(Me)₂— |
| 3-362 | Sub-42 | 4-ClPh | —CO— | Single Bond | —CH₂C(Me)₂— |

TABLE 3-continued

| Cpd. No. | R¹ | R² | A | B | E |
|---|---|---|---|---|---|
| 3-363 | Sub-84 | 4-ClPh | —CO— | Single Bond | —CH$_2$C(Me)$_2$— |
| 3-364 | Sub-43 | 4-ClPh | —CO— | Single Bond | —CH$_2$C(Me)$_2$— |
| 3-365 | Sub-44 | 4-ClPh | —CO— | Single Bond | —CH$_2$C(Me)$_2$— |
| 3-366 | Sub-45 | 4-ClPh | —CO— | Single Bond | —CH$_2$C(Me)$_2$— |
| 3-367 | Sub-46 | 4-ClPh | —CO— | Single Bond | —CH$_2$C(Me)$_2$— |
| 3-368 | Sub-47 | 4-ClPh | —CO— | Single Bond | —CH$_2$C(Me)$_2$— |
| 3-369 | Sub-81 | 4-ClPh | —CO— | Single Bond | —CH$_2$C(Me)$_2$— |
| 3-370 | Sub-48 | 4-ClPh | —CO— | Single Bond | —CH$_2$C(Me)$_2$— |
| 3-371 | Sub-49 | 4-ClPh | —CO— | Single Bond | —CH$_2$C(Me)$_2$— |
| 3-372 | Sub-50 | 4-ClPh | —CO— | Single Bond | —CH$_2$C(Me)$_2$— |
| 3-373 | Sub-51 | 4-ClPh | —CO— | Single Bond | —CH$_2$C(Me)$_2$— |
| 3-374 | Sub-52 | 4-ClPh | —CO— | Single Bond | —CH$_2$C(Me)$_2$— |
| 3-375 | Sub-53 | 4-ClPh | —CO— | Single Bond | —CH$_2$C(Me)$_2$— |
| 3-376 | Sub-54 | 4-ClPh | —CO— | Single Bond | —CH$_2$C(Me)$_2$— |
| 3-377 | Sub-56 | 4-ClPh | —CO— | Single Bond | —CH$_2$C(Me)$_2$— |
| 3-378 | Sub-57 | 4-ClPh | —CO— | Single Bond | —CH$_2$C(Me)$_2$— |
| 3-379 | Sub-58 | 4-ClPh | —CO— | Single Bond | —CH$_2$C(Me)$_2$— |
| 3-380 | Sub-59 | 4-ClPh | —CO— | Single Bond | —CH$_2$C(Me)$_2$— |
| 3-381 | Sub-82 | 4-ClPh | —CO— | Single Bond | —CH$_2$C(Me)$_2$— |
| 3-382 | Sub-83 | 4-ClPh | —CO— | Single Bond | —CH$_2$C(Me)$_2$— |
| 3-383 | Sub-61 | 4-ClPh | —CO— | Single Bond | —CH$_2$C(Me)$_2$— |
| 3-384 | Sub-55 | 4-ClPh | —CO— | Single Bond | —CH$_2$C(Me)$_2$— |
| 3-385 | Sub-33 | 4-ClPh | —CO— | Single Bond | —CH$_2$-cPr— |
| 3-386 | Sub-34 | 4-ClPh | —CO— | Single Bond | —CH$_2$-cPr— |
| 3-387 | Sub-35 | 4-ClPh | —CO— | Single Bond | —CH$_2$-cPr— |
| 3-388 | Sub-36 | 4-ClPh | —CO— | Single Bond | —CH$_2$-cPr— |
| 3-389 | Sub-37 | 4-ClPh | —CO— | Single Bond | —CH$_2$-cPr— |
| 3-390 | Sub-38 | 4-ClPh | —CO— | Single Bond | —CH$_2$-cPr— |
| 3-391 | Sub-39 | 4-ClPh | —CO— | Single Bond | —CH$_2$-cPr— |
| 3-392 | Sub-40 | 4-ClPh | —CO— | Single Bond | —CH$_2$-cPr— |
| 3-393 | Sub-41 | 4-ClPh | —CO— | Single Bond | —CH$_2$-cPr— |
| 3-394 | Sub-42 | 4-ClPh | —CO— | Single Bond | —CH$_2$-cPr— |
| 3-395 | Sub-84 | 4-ClPh | —CO— | Single Bond | —CH$_2$-cPr— |
| 3-396 | Sub-43 | 4-ClPh | —CO— | Single Bond | —CH$_2$-cPr— |
| 3-397 | Sub-44 | 4-ClPh | —CO— | Single Bond | —CH$_2$-cPr— |
| 3-398 | Sub-45 | 4-ClPh | —CO— | Single Bond | —CH$_2$-cPr— |
| 3-399 | Sub-46 | 4-ClPh | —CO— | Single Bond | —CH$_2$-cPr— |
| 3-400 | Sub-47 | 4-ClPh | —CO— | Single Bond | —CH$_2$-cPr— |
| 3-401 | Sub-81 | 4-ClPh | —CO— | Single Bond | —CH$_2$-cPr— |
| 3-402 | Sub-48 | 4-ClPh | —CO— | Single Bond | —CH$_2$-cPr— |
| 3-403 | Sub-49 | 4-ClPh | —CO— | Single Bond | —CH$_2$-cPr— |
| 3-404 | Sub-50 | 4-ClPh | —CO— | Single Bond | —CH$_2$-cPr— |
| 3-405 | Sub-51 | 4-ClPh | —CO— | Single Bond | —CH$_2$-cPr— |
| 3-406 | Sub-52 | 4-ClPh | —CO— | Single Bond | —CH$_2$-cPr— |
| 3-407 | Sub-53 | 4-ClPh | —CO— | Single Bond | —CH$_2$-cPr— |
| 3-408 | Sub-54 | 4-ClPh | —CO— | Single Bond | —CH$_2$-cPr— |
| 3-409 | Sub-56 | 4-ClPh | —CO— | Single Bond | —CH$_2$-cPr— |
| 3-410 | Sub-57 | 4-ClPh | —CO— | Single Bond | —CH$_2$-cPr— |
| 3-411 | Sub-58 | 4-ClPh | —CO— | Single Bond | —CH$_2$-cPr— |
| 3-412 | Sub-59 | 4-ClPh | —CO— | Single Bond | —CH$_2$-cPr— |
| 3-413 | Sub-82 | 4-ClPh | —CO— | Single Bond | —CH$_2$-cPr— |
| 3-414 | Sub-83 | 4-ClPh | —CO— | Single Bond | —CH$_2$-cPr— |
| 3-415 | Sub-61 | 4-ClPh | —CO— | Single Bond | —CH$_2$-cPr— |
| 3-416 | Sub-55 | 4-ClPh | —CO— | Single Bond | —CH$_2$-cPr— |
| 3-417 | Sub-33 | 4-ClPh | —CO— | Single Bond | —CH$_2$-cBu— |
| 3-418 | Sub-34 | 4-ClPh | —CO— | Single Bond | —CH$_2$-cBu— |
| 3-419 | Sub-35 | 4-ClPh | —CO— | Single Bond | —CH$_2$-cBu— |
| 3-420 | Sub-36 | 4-ClPh | —CO— | Single Bond | —CH$_2$-cBu— |
| 3-421 | Sub-37 | 4-ClPh | —CO— | Single Bond | —CH$_2$-cBu— |
| 3-422 | Sub-38 | 4-ClPh | —CO— | Single Bond | —CH$_2$-cBu— |
| 3-423 | Sub-39 | 4-ClPh | —CO— | Single Bond | —CH$_2$-cBu— |
| 3-424 | Sub-40 | 4-ClPh | —CO— | Single Bond | —CH$_2$-cBu— |
| 3-425 | Sub-41 | 4-ClPh | —CO— | Single Bond | —CH$_2$-cBu— |
| 3-426 | Sub-42 | 4-ClPh | —CO— | Single Bond | —CH$_2$-cBu— |
| 3-427 | Sub-84 | 4-ClPh | —CO— | Single Bond | —CH$_2$-cBu— |
| 3-428 | Sub-43 | 4-ClPh | —CO— | Single Bond | —CH$_2$-cBu— |
| 3-429 | Sub-44 | 4-ClPh | —CO— | Single Bond | —CH$_2$-cBu— |
| 3-430 | Sub-45 | 4-ClPh | —CO— | Single Bond | —CH$_2$-cBu— |
| 3-431 | Sub-46 | 4-ClPh | —CO— | Single Bond | —CH$_2$-cBu— |
| 3-432 | Sub-47 | 4-ClPh | —CO— | Single Bond | —CH$_2$-cBu— |
| 3-433 | Sub-81 | 4-ClPh | —CO— | Single Bond | —CH$_2$-cBu— |
| 3-434 | Sub-48 | 4-ClPh | —CO— | Single Bond | —CH$_2$-cBu— |
| 3-435 | Sub-49 | 4-ClPh | —CO— | Single Bond | —CH$_2$-cBu— |
| 3-436 | Sub-50 | 4-ClPh | —CO— | Single Bond | —CH$_2$-cBu— |
| 3-437 | Sub-51 | 4-ClPh | —CO— | Single Bond | —CH$_2$-cBu— |
| 3-438 | Sub-52 | 4-ClPh | —CO— | Single.Bond | —CH$_2$-cBu— |

TABLE 3-continued

| Cpd. No. | R¹ | R² | A | B | E |
|---|---|---|---|---|---|
| 3-439 | Sub-53 | 4-ClPh | —CO— | Single Bond | —CH₂-cBu— |
| 3-440 | Sub-54 | 4-ClPh | —CO— | Single Bond | —CH₂-cBu— |
| 3-441 | Sub-56 | 4-ClPh | —CO— | Single Bond | —CH₂-cBu— |
| 3-442 | Sub-57 | 4-ClPh | —CO— | Single Bond | —CH₂-cBu— |
| 3-443 | Sub-58 | 4-ClPh | —CO— | Single Bond | —CH₂-cBu— |
| 3-444 | Sub-59 | 4-ClPh | —CO— | Single Bond | —CH₂-cBu— |
| 3-445 | Sub-82 | 4-ClPh | —CO— | Single Bond | —CH₂-cBu— |
| 3-446 | Sub-83 | 4-ClPh | —CO— | Single Bond | —CH₂-cBu— |
| 3-447 | Sub-61 | 4-ClPh | —CO— | Single Bond | —CH₂-cBu— |
| 3-448 | Sub-55 | 4-ClPh | —CO— | Single Bond | —CH₂-cBu— |
| 3-449 | Sub-33 | 4-ClPh | —CO— | Single Bond | —CH₂-cPn— |
| 3-450 | Sub-34 | 4-ClPh | —CO— | Single Bond | —CH₂-cPn— |
| 3-451 | Sub-35 | 4-ClPh | —CO— | Single Bond | —CH₂-cPn— |
| 3-452 | Sub-36 | 4-ClPh | —CO— | Single Bond | —CH₂-cPn— |
| 3-453 | Sub-37 | 4-ClPh | —CO— | Single Bond | —CH₂-cPn— |
| 3-454 | Sub-38 | 4-ClPh | —CO— | Single Bond | —CH₂-cPn— |
| 3-455 | Sub-39 | 4-ClPh | —CO— | Single Bond | —CH₂-cPn— |
| 3-456 | Sub-40 | 4-ClPh | —CO— | Single Bond | —CH₂-cPn— |
| 3-457 | Sub-41 | 4-ClPh | —CO— | Single Bond | —CH₂-cPn— |
| 3-458 | Sub-42 | 4-ClPh | —CO— | Single Bond | —CH₂-cPn— |
| 3-459 | Sub-84 | 4-ClPh | —CO— | Single Bond | —CH₂-cPn— |
| 3-460 | Sub-43 | 4-ClPh | —CO— | Single Bond | —CH₂-cPn— |
| 3-461 | Sub-44 | 4-ClPh | —CO— | Single Bond | —CH₂-cPn— |
| 3-462 | Sub-45 | 4-ClPh | —CO— | Single Bond | —CH₂-cPn— |
| 3-463 | Sub-46 | 4-ClPh | —CO— | Single Bond | —CH₂-cPn— |
| 3-464 | Sub-47 | 4-ClPh | —CO— | Single Bond | —CH₂-cPn— |
| 3-465 | Sub-81 | 4-ClPh | —CO— | Single Bond | —CH₂-cPn— |
| 3-466 | Sub-48 | 4-ClPh | —CO— | Single Bond | —CH₂-cPn— |
| 3-467 | Sub-49 | 4-ClPh | —CO— | Single Bond | —CH₂-cPn— |
| 3-468 | Sub-50 | 4-ClPh | —CO— | Single Bond | —CH₂-cPn— |
| 3-469 | Sub-51 | 4-ClPh | —CO— | Single Bond | —CH₂-cPn— |
| 3-470 | Sub-52 | 4-ClPh | —CO— | Single Bond | —CH₂-cPn— |
| 3-471 | Sub-53 | 4-ClPh | —CO— | Single Bond | —CH₂-cPn— |
| 3-472 | Sub-54 | 4-ClPh | —CO— | Single Bond | —CH₂-cPn— |
| 3-473 | Sub-56 | 4-ClPh | —CO— | Single Bond | —CH₂-cPn— |
| 3-474 | Sub-57 | 4-ClPh | —CO— | Single Bond | —CH₂-cPn— |
| 3-475 | Sub-58 | 4-ClPh | —CO— | Single Bond | —CH₂-cPn— |
| 3-476 | Sub-59 | 4-ClPh | —CO— | Single Bond | —CH₂-cPn— |
| 3-477 | Sub-82 | 4-ClPh | —CO— | Single Bond | —CH₂-cPn— |
| 3-478 | Sub-83 | 4-ClPh | —CO— | Single Bond | —CH₂-cPn— |
| 3-479 | Sub-61 | 4-ClPh | —CO— | Single Bond | —CH₂-cPn— |
| 3-480 | Sub-55 | 4-ClPh | —CO— | Single Bond | —CH₂-cPn— |
| 3-481 | Sub-33 | 4-ClPh | —CO— | Single Bond | —CH₂-cHx— |
| 3-482 | Sub-34 | 4-ClPh | —CO— | Single Bond | —CH₂-cHx— |
| 3-483 | Sub-35 | 4-ClPh | —CO— | Single Bond | —CH₂-cHx— |
| 3-484 | Sub-36 | 4-ClPh | —CO— | Single Bond | —CH₂-cHx— |
| 3-485 | Sub-37 | 4-ClPh | —CO— | Single Bond | —CH₂-cHx— |
| 3-486 | Sub-38 | 4-ClPh | —CO— | Single Bond | —CH₂-cHx— |
| 3-487 | Sub-39 | 4-ClPh | —CO— | Single Bond | —CH₂-cHx— |
| 3-488 | Sub-40 | 4-ClPh | —CO— | Single Bond | —CH₂-cHx— |
| 3-489 | Sub-41 | 4-ClPh | —CO— | Single Bond | —CH₂-cHx— |
| 3-490 | Sub-42 | 4-ClPh | —CO— | Single Bond | —CH₂-cHx— |
| 3-491 | Sub-84 | 4-ClPh | —CO— | Single Bond | —CH₂-cHx— |
| 3-492 | Sub-43 | 4-ClPh | —CO— | Single Bond | —CH₂-cHx— |
| 3-493 | Sub-44 | 4-ClPh | —CO— | Single Bond | —CH₂-cHx— |
| 3-494 | Sub-45 | 4-ClPh | —CO— | Single Bond | —CH₂-cHx— |
| 3-495 | Sub-46 | 4-ClPh | —CO— | Single Bond | —CH₂-cHx— |
| 3-496 | Sub-47 | 4-ClPh | —CO— | Single Bond | —CH₂-cHx— |
| 3-497 | Sub-81 | 4-ClPh | —CO— | Single Bond | —CH₂-cHx— |
| 3-498 | Sub-48 | 4-ClPh | —CO— | Single Bond | —CH₂-cHx— |
| 3-499 | Sub-49 | 4-ClPh | —CO— | Single Bond | —CH₂-cHx— |
| 3-500 | Sub-50 | 4-ClPh | —CO— | Single Bond | —CH₂-cHx— |
| 3-501 | Sub-51 | 4-ClPh | —CO— | Single Bond | —CH₂-cHx— |
| 3-502 | Sub-52 | 4-ClPh | —CO— | Single Bond | —CH₂-cHx— |
| 3-503 | Sub-53 | 4-ClPh | —CO— | Single Bond | —CH₂-cHx— |
| 3-504 | Sub-54 | 4-ClPh | —CO— | Single Bond | —CH₂-cHx— |
| 3-505 | Sub-56 | 4-ClPh | —CO— | Single Bond | —CH₂-cHx— |
| 3-506 | Sub-57 | 4-ClPh | —CO— | Single Bond | —CH₂-cHx— |
| 3-507 | Sub-58 | 4-ClPh | —CO— | Single Bond | —CH₂-cHx— |
| 3-508 | Sub-59 | 4-ClPh | —CO— | Single Bond | —CH₂-cHx— |
| 3-509 | Sub-82 | 4-ClPh | —CO— | Single Bond | —CH₂-cHx— |
| 3-510 | Sub-83 | 4-ClPh | —CO— | Single Bond | —CH₂-cHx— |
| 3-511 | Sub-61 | 4-ClPh | —CO— | Single Bond | —CH₂-cHx— |
| 3-512 | Sub-55 | 4-ClPh | —CO— | Single Bond | —CH₂-cHx— |
| 3-513 | Sub-33 | 4-FPh | —CO— | Single Bond | —CH₂— |
| 3-514 | Sub-34 | 4-FPh | —CO— | Single Bond | —CH₂— |

TABLE 3-continued

| Cpd. No. | R¹ | R² | A | B | E |
|---|---|---|---|---|---|
| 3-515 | Sub-35 | 4-FPh | —CO— | Single Bond | —CH₂— |
| 3-516 | Sub-36 | 4-FPh | —CO— | Single Bond | —CH₂— |
| 3-517 | Sub-37 | 4-FPh | —CO— | Single Bond | —CH₂— |
| 3-518 | Sub-38 | 4-FPh | —CO— | Single Bond | —CH₂— |
| 3-519 | Sub-39 | 4-FPh | —CO— | Single Bond | —CH₂— |
| 3-520 | Sub-40 | 4-FPh | —CO— | Single Bond | —CH₂— |
| 3-521 | Sub-41 | 4-FPh | —CO— | Single Bond | —CH₂— |
| 3-522 | Sub-42 | 4-FPh | —CO— | Single Bond | —CH₂— |
| 3-523 | Sub-84 | 4-FPh | —CO— | Single Bond | —CH₂— |
| 3-524 | Sub-43 | 4-FPh | —CO— | Single Bond | —CH₂— |
| 3-525 | Sub-44 | 4-FPh | —CO— | Single Bond | —CH₂— |
| 3-526 | Sub-45 | 4-FPh | —CO— | Single Bond | —CH₂— |
| 3-527 | Sub-46 | 4-FPh | —CO— | Single Bond | —CH₂— |
| 3-528 | Sub-47 | 4-FPh | —CO— | Single Bond | —CH₂— |
| 3-529 | Sub-81 | 4-FPh | —CO— | Single Bond | —CH₂— |
| 3-530 | Sub-48 | 4-FPh | —CO— | Single Bond | —CH₂— |
| 3-531 | Sub-49 | 4-FPh | —CO— | Single Bond | —CH₂— |
| 3-532 | Sub-50 | 4-FPh | —CO— | Single Bond | —CH₂— |
| 3-533 | Sub-51 | 4-FPh | —CO— | Single Bond | —CH₂— |
| 3-534 | Sub-52 | 4-FPh | —CO— | Single Bond | —CH₂— |
| 3-535 | Sub-53 | 4-FPh | —CO— | Single Bond | —CH₂— |
| 3-536 | Sub-54 | 4-FPh | —CO— | Single Bond | —CH₂— |
| 3-537 | Sub-56 | 4-FPh | —CO— | Single Bond | —CH₂— |
| 3-538 | Sub-57 | 4-FPh | —CO— | Single Bond | —CH₂— |
| 3-539 | Sub-58 | 4-FPh | —CO— | Single Bond | —CH₂— |
| 3-540 | Sub-59 | 4-FPh | —CO— | Single Bond | —CH₂— |
| 3-541 | Sub-82 | 4-FPh | —CO— | Single Bond | —CH₂— |
| 3-542 | Sub-83 | 4-FPh | —CO— | Single Bond | —CH₂— |
| 3-543 | Sub-61 | 4-FPh | —CO— | Single Bond | —CH₂— |
| 3-544 | Sub-55 | 4-FPh | —CO— | Single Bond | —CH₂— |
| 3-545 | Sub-33 | 4-FPh | —CO— | Single Bond | —CH₂CH₂— |
| 3-546 | Sub-34 | 4-FPh | —CO— | Single Bond | —CH₂CH₂— |
| 3-547 | Sub-35 | 4-FPh | —CO— | Single Bond | —CH₂CH₂— |
| 3-548 | Sub-36 | 4-FPh | —CO— | Single Bond | —CH₂CH₂— |
| 3-549 | Sub-37 | 4-FPh | —CO— | Single Bond | —CH₂CH₂— |
| 3-550 | Sub-38 | 4-FPh | —CO— | Single Bond | —CH₂CH₂— |
| 3-551 | Sub-39 | 4-FPh | —CO— | Single Bond | —CH₂CH₂— |
| 3-552 | Sub-40 | 4-FPh | —CO— | Single Bond | —CH₂CH₂— |
| 3-553 | Sub-41 | 4-FPh | —CO— | Single Bond | —CH₂CH₂— |
| 3-554 | Sub-42 | 4-FPh | —CO— | Single Bond | —CH₂CH₂— |
| 3-555 | Sub-84 | 4-FPh | —CO— | Single Bond | —CH₂CH₂— |
| 3-556 | Sub-43 | 4-FPh | —CO— | Single Bond | —CH₂CH₂— |
| 3-557 | Sub-44 | 4-FPh | —CO— | Single Bond | —CH₂CH₂— |
| 3-558 | Sub-45 | 4-FPh | —CO— | Single Bond | —CH₂CH₂— |
| 3-559 | Sub-46 | 4-FPh | —CO— | Single Bond | —CH₂CH₂— |
| 3-560 | Sub-47 | 4-FPh | —CO— | Single Bond | —CH₂CH₂— |
| 3-561 | Sub-81 | 4-FPh | —CO— | Single Bond | —CH₂CH₂— |
| 3-562 | Sub-48 | 4-FPh | —CO— | Single Bond | —CH₂CH₂— |
| 3-563 | Sub-49 | 4-FPh | —CO— | Single Bond | —CH₂CH₂— |
| 3-564 | Sub-50 | 4-FPh | —CO— | Single Bond | —CH₂CH₂— |
| 3-565 | Sub-51 | 4-FPh | —CO— | Single Bond | —CH₂CH₂— |
| 3-566 | Sub-52 | 4-FPh | —CO— | Single Bond | —CH₂CH₂— |
| 3-567 | Sub-53 | 4-FPh | —CO— | Single Bond | —CH₂CH₂— |
| 3-568 | Sub-54 | 4-FPh | —CO— | Single Bond | —CH₂CH₂— |
| 3-569 | Sub-56 | 4-FPh | —CO— | Single Bond | —CH₂CH₂— |
| 3-570 | Sub-57 | 4-FPh | —CO— | Single Bond | —CH₂CH₂— |
| 3-571 | Sub-58 | 4-FPh | —CO— | Single Bond | —CH₂CH₂— |
| 3-572 | Sub-59 | 4-FPh | —CO— | Single Bond | —CH₂CH₂— |
| 3-573 | Sub-82 | 4-FPh | —CO— | Single Bond | —CH₂CH₂— |
| 3-574 | Sub-83 | 4-FPh | —CO— | Single Bond | —CH₂CH₂— |
| 3-575 | Sub-61 | 4-FPh | —CO— | Single Bond | —CH₂CH₂— |
| 3-576 | Sub-55 | 4-FPh | —CO— | Single Bond | —CH₂CH₂— |
| 3-577 | Sub-33 | 4-FPh | —CO— | Single Bond | —(CH₂)₃— |
| 3-578 | Sub-34 | 4-FPh | —CO— | Single Bond | —(CH₂)₃— |
| 3-579 | Sub-35 | 4-FPh | —CO— | Single Bond | —(CH₂)₃— |
| 3-580 | Sub-36 | 4-FPh | —CO— | Single Bond | —(CH₂)₃— |
| 3-581 | Sub-37 | 4-FPh | —CO— | Single Bond | —(CH₂)₃— |
| 3-582 | Sub-38 | 4-FPh | —CO— | Single Bond | —(CH₂)₃— |
| 3-583 | Sub-39 | 4-FPh | —CO— | Single Bond | —(CH₂)₃— |
| 3-584 | Sub-40 | 4-FPh | —CO— | Single Bond | —(CH₂)₃— |
| 3-585 | Sub-41 | 4-FPh | —CO— | Single Bond | —(CH₂)₃— |
| 3-586 | Sub-42 | 4-FPh | —CO— | Single Bond | —(CH₂)₃— |
| 3-587 | Sub-84 | 4-FPh | —CO— | Single Bond | —(CH₂)₃— |
| 3-588 | Sub-43 | 4-FPh | —CO— | Single Bond | —(CH₂)₃— |
| 3-589 | Sub-44 | 4-FPh | —CO— | Single Bond | —(CH₂)₃— |
| 3-590 | Sub-45 | 4-FPh | —CO— | Single Bond | —(CH₂)₃— |

TABLE 3-continued

| Cpd. No. | R¹ | R² | A | B | E |
|---|---|---|---|---|---|
| 3-591 | Sub-46 | 4-FPh | —CO— | Single Bond | —(CH$_2$)$_3$— |
| 3-592 | Sub-47 | 4-FPh | —CO— | Single Bond | —(CH$_2$)$_3$— |
| 3-593 | Sub-81 | 4-FPh | —CO— | Single Bond | —(CH$_2$)$_3$— |
| 3-594 | Sub-48 | 4-FPh | —CO— | Single Bond | —(CH$_2$)$_3$— |
| 3-595 | Sub-49 | 4-FPh | —CO— | Single Bond | —(CH$_2$)$_3$— |
| 3-596 | Sub-50 | 4-FPh | —CO— | Single Bond | —(CH$_2$)$_3$— |
| 3-597 | Sub-51 | 4-FPh | —CO— | Single Bond | —(CH$_2$)$_3$— |
| 3-598 | Sub-52 | 4-FPh | —CO— | Single Bond | —(CH$_2$)$_3$— |
| 3-599 | Sub-53 | 4-FPh | —CO— | Single Bond | —(CH$_2$)$_3$— |
| 3-600 | Sub-54 | 4-FPh | —CO— | Single Bond | —(CH$_2$)$_3$— |
| 3-601 | Sub-56 | 4-FPh | —CO— | Single Bond | —(CH$_2$)$_3$— |
| 3-602 | Sub-57 | 4-FPh | —CO— | Single Bond | —(CH$_2$)$_3$— |
| 3-603 | Sub-58 | 4-FPh | —CO— | Single Bond | —(CH$_2$)$_3$— |
| 3-604 | Sub-59 | 4-FPh | —CO— | Single Bond | —(CH$_2$)$_3$— |
| 3-605 | Sub-82 | 4-FPh | —CO— | Single Bond | —(CH$_2$)$_3$— |
| 3-606 | Sub-83 | 4-FPh | —CO— | Single Bond | —(CH$_2$)$_3$— |
| 3-607 | Sub-61 | 4-FPh | —CO— | Single Bond | —(CH$_2$)$_3$— |
| 3-608 | Sub-55 | 4-FPh | —CO— | Single Bond | —(CH$_2$)$_3$— |
| 3-609 | Sub-33 | 4-FPh | —CO— | Single Bond | —CH$_2$C(Me)$_2$— |
| 3-610 | Sub-34 | 4-FPh | —CO— | Single Bond | —CH$_2$C(Me)$_2$— |
| 3-611 | Sub-35 | 4-FPh | —CO— | Single Bond | —CH$_2$C(Me)$_2$— |
| 3-612 | Sub-36 | 4-FPh | —CO— | Single Bond | —CH$_2$C(Me)$_2$— |
| 3-613 | Sub-37 | 4-FPh | —CO— | Single Bond | —CH$_2$C(Me)$_2$— |
| 3-614 | Sub-38 | 4-FPh | —CO— | Single Bond | —CH$_2$C(Me)$_2$— |
| 3-615 | Sub-39 | 4-FPh | —CO— | Single Bond | —CH$_2$C(Me)$_2$— |
| 3-616 | Sub-40 | 4-FPh | —CO— | Single Bond | —CH$_2$C(Me)$_2$— |
| 3-617 | Sub-41 | 4-FPh | —CO— | Single Bond | —CH$_2$C(Me)$_2$— |
| 3-618 | Sub-42 | 4-FPh | —CO— | Single Bond | —CH$_2$C(Me)$_2$— |
| 3-619 | Sub-84 | 4-FPh | —CO— | Single Bond | —CH$_2$C(Me)$_2$— |
| 3-620 | Sub-43 | 4-FPh | —CO— | Single Bond | —CH$_2$C(Me)$_2$— |
| 3-621 | Sub-44 | 4-FPh | —CO— | Single Bond | —CH$_2$C(Me)$_2$— |
| 3-622 | Sub-45 | 4-FPh | —CO— | Single Bond | —CH$_2$C(Me)$_2$— |
| 3-623 | Sub-46 | 4-FPh | —CO— | Single Bond | —CH$_2$C(Me)$_2$— |
| 3-624 | Sub-47 | 4-FPh | —CO— | Single Bond | —CH$_2$C(Me)$_2$— |
| 3-625 | Sub-81 | 4-FPh | —CO— | Single Bond | —CH$_2$C(Me)$_2$— |
| 3-626 | Sub-48 | 4-FPh | —CO— | Single Bond | —CH$_2$C(Me)$_2$— |
| 3-627 | Sub-49 | 4-FPh | —CO— | Single Bond | —CH$_2$C(Me)$_2$— |
| 3-628 | Sub-50 | 4-FPh | —CO— | Single Bond | —CH$_2$C(Me)$_2$— |
| 3-629 | Sub-51 | 4-FPh | —CO— | Single Bond | —CH$_2$C(Me)$_2$— |
| 3-630 | Sub-52 | 4-FPh | —CO— | Single Bond | —CH$_2$C(Me)$_2$— |
| 3-631 | Sub-53 | 4-FPh | —CO— | Single Bond | —CH$_2$C(Me)$_2$— |
| 3-632 | Sub-54 | 4-FPh | —CO— | Single Bond | —CH$_2$C(Me)$_2$— |
| 3-633 | Sub-56 | 4-FPh | —CO— | Single Bond | —CH$_2$C(Me)$_2$— |
| 3-634 | Sub-57 | 4-FPh | —CO— | Single Bond | —CH$_2$C(Me)$_2$— |
| 3-635 | Sub-58 | 4-FPh | —CO— | Single Bond | —CH$_2$C(Me)$_2$— |
| 3-636 | Sub-59 | 4-FPh | —CO— | Single Bond | —CH$_2$C(Me)$_2$— |
| 3-637 | Sub-82 | 4-FPh | —CO— | Single Bond | —CH$_2$C(Me)$_2$— |
| 3-638 | Sub-83 | 4-FPh | —CO— | Single Bond | —CH$_2$C(Me)$_2$— |
| 3-639 | Sub-61 | 4-FPh | —CO— | Single Bond | —CH$_2$C(Me)$_2$— |
| 3-640 | Sub-55 | 4-FPh | —CO— | Single Bond | —CH$_2$C(Me)$_2$— |
| 3-641 | Sub-33 | 4-FPh | —CO— | Single Bond | —CH$_2$-cPr— |
| 3-642 | Sub-34 | 4-FPh | —CO— | Single Bond | —CH$_2$-cPr— |
| 3-643 | Sub-35 | 4-FPh | —CO— | Single Bond | —CH$_2$-cPr— |
| 3-644 | Sub-36 | 4-FPh | —CO— | Single Bond | —CH$_2$-cPr— |
| 3-645 | Sub-37 | 4-FPh | —CO— | Single Bond | —CH$_2$-cPr— |
| 3-646 | Sub-38 | 4-FPh | —CO— | Single Bond | —CH$_2$-cPr— |
| 3-647 | Sub-39 | 4-FPh | —CO— | Single Bond | —CH$_2$-cPr— |
| 3-648 | Sub-40 | 4-FPh | —CO— | Single Bond | —CH$_2$-cPr— |
| 3-649 | Sub-41 | 4-FPh | —CO— | Single Bond | —CH$_2$-cPr— |
| 3-650 | Sub-42 | 4-FPh | —CO— | Single Bond | —CH$_2$-cPr— |
| 3-651 | Sub-84 | 4-FPh | —CO— | Single Bond | —CH$_2$-cPr— |
| 3-652 | Sub-43 | 4-FPh | —CO— | Single Bond | —CH$_2$-cPr— |
| 3-653 | Sub-44 | 4-FPh | —CO— | Single Bond | —CH$_2$-cPr— |
| 3-654 | Sub-45 | 4-FPh | —CO— | Single Bond | —CH$_2$-cPr— |
| 3-655 | Sub-46 | 4-FPh | —CO— | Single Bond | —CH$_2$-cPr— |
| 3-656 | Sub-47 | 4-FPh | —CO— | Single Bond | —CH$_2$-cPr— |
| 3-657 | Sub-81 | 4-FPh | —CO— | Single Bond | —CH$_2$-cPr— |
| 3-658 | Sub-48 | 4-FPh | —CO— | Single Bond | —CH$_2$-cPr— |
| 3-659 | Sub-49 | 4-FPh | —CO— | Single Bond | —CH$_2$-cPr— |
| 3-660 | Sub-50 | 4-FPh | —CO— | Single Bond | —CH$_2$-cPr— |
| 3-661 | Sub-51 | 4-FPh | —CO— | Single Bond | —CH$_2$-cPr— |
| 3-662 | Sub-52 | 4-FPh | —CO— | Single Bond | —CH$_2$-cPr- |
| 3-663 | Sub-53 | 4-FPh | —CO— | Single Bond | —CH$_2$-cPr— |
| 3-664 | Sub-54 | 4-FPh | —CO— | Single Bond | —CH$_2$-cPr— |
| 3-665 | Sub-56 | 4-FPh | —CO— | Single Bond | —CH$_2$-cPr— |
| 3-666 | Sub-57 | 4-FPh | —CO— | Single Bond | —CH$_2$-cPr— |

TABLE 3-continued

| Cpd. No. | R¹ | R² | A | B | E |
|---|---|---|---|---|---|
| 3-667 | Sub-58 | 4-FPh | —CO— | Single Bond | —CH$_2$-cPr— |
| 3-668 | Sub-59 | 4-FPh | —CO— | Single Bond | —CH$_2$-cPr— |
| 3-669 | Sub-82 | 4-FPh | —CO— | Single Bond | —CH$_2$-cPr— |
| 3-670 | Sub-83 | 4-FPh | —CO— | Single Bond | —CH$_2$-cPr— |
| 3-671 | Sub-61 | 4-FPh | —CO— | Single Bond | —CH$_2$-cPr— |
| 3-672 | Sub-55 | 4-FPh | —CO— | Single Bond | —CH$_2$-cPr— |
| 3-673 | Sub-33 | 4-FPh | —CO— | Single Bond | —CH$_2$-cBu— |
| 3-674 | Sub-34 | 4-FPh | —CO— | Single Bond | —CH$_2$-cBu— |
| 3-675 | Sub-35 | 4-FPh | —CO— | Single Bond | —CH$_2$-cBu— |
| 3-676 | Sub-36 | 4-FPh | —CO— | Single Bond | —CH$_2$-cBu— |
| 3-677 | Sub-37 | 4-FPh | —CO— | Single Bond | —CH$_2$-cBu— |
| 3-678 | Sub-38 | 4-FPh | —CO— | Single Bond | —CH$_2$-cBu— |
| 3-679 | Sub-39 | 4-FPh | —CO— | Single Bond | —CH$_2$-cBu— |
| 3-680 | Sub-40 | 4-FPh | —CO— | Single Bond | —CH$_2$-cBu— |
| 3-681 | Sub-41 | 4-FPh | —CO— | Single Bond | —CH$_2$-cBu— |
| 3-682 | Sub-42 | 4-FPh | —CO— | Single Bond | —CH$_2$-cBu— |
| 3-683 | Sub-84 | 4-FPh | —CO— | Single Bond | —CH$_2$-cBu— |
| 3-684 | Sub-43 | 4-FPh | —CO— | Single Bond | —CH$_2$-cBu— |
| 3-685 | Sub-44 | 4-FPh | —CO— | Single Bond | —CH$_2$-cBu— |
| 3-686 | Sub-45 | 4-FPh | —CO— | Single Bond | —CH$_2$-cBu— |
| 3-687 | Sub-46 | 4-FPh | —CO— | Single Bond | —CH$_2$-cBu— |
| 3-688 | Sub-47 | 4-FPh | —CO— | Single Bond | —CH$_2$-cBu— |
| 3-689 | Sub-81 | 4-FPh | —CO— | Single Bond | —CH$_2$-cBu— |
| 3-690 | Sub-48 | 4-FPh | —CO— | Single Bond | —CH$_2$-cBu— |
| 3-691 | Sub-49 | 4-FPh | —CO— | Single Bond | —CH$_2$-cBu— |
| 3-692 | Sub-50 | 4-FPh | —CO— | Single Bond | —CH$_2$-cBu— |
| 3-693 | Sub-51 | 4-FPh | —CO— | Single Bond | —CH$_2$-cBu— |
| 3-694 | Sub-52 | 4-FPh | —CO— | Single Bond | —CH$_2$-cBu— |
| 3-695 | Sub-53 | 4-FPh | —CO— | Single Bond | —CH$_2$-cBu— |
| 3-696 | Sub-54 | 4-FPh | —CO— | Single Bond | —CH$_2$-cBu— |
| 3-697 | Sub-56 | 4-FPh | —CO— | Single Bond | —CH$_2$-cBu— |
| 3-698 | Sub-57 | 4-FPh | —CO— | Single Bond | —CH$_2$-cBu— |
| 3-699 | Sub-58 | 4-FPh | —CO— | Single Bond | —CH$_2$-cBu— |
| 3-700 | Sub-59 | 4-FPh | —CO— | Single Bond | —CH$_2$-cBu— |
| 3-701 | Sub-82 | 4-FPh | —CO— | Single Bond | —CH$_2$-cBu— |
| 3-702 | Sub-83 | 4-FPh | —CO— | Single Bond | —CH$_2$-cBu— |
| 3-703 | Sub-61 | 4-FPh | —CO— | Single Bond | —CH$_2$-cBu— |
| 3-704 | Sub-55 | 4-FPh | —CO— | Single Bond | —CH$_2$-cBu— |
| 3-705 | Sub-33 | 4-FPh | —CO— | Single Bond | —CH$_2$-cPn— |
| 3-706 | Sub-34 | 4-FPh | —CO— | Single Bond | —CH$_2$-cPn— |
| 3-707 | Sub-35 | 4-FPh | —CO— | Single Bond | —CH$_2$-cPn— |
| 3-708 | Sub-36 | 4-FPh | —CO— | Single Bond | —CH$_2$-cPn— |
| 3-709 | Sub-37 | 4-FPh | —CO— | Single Bond | —CH$_2$-cPn— |
| 3-710 | Sub-38 | 4-FPh | —CO— | Single Bond | —CH$_2$-cPn— |
| 3-711 | Sub-39 | 4-FPh | —CO— | Single Bond | —CH$_2$-cPn— |
| 3-712 | Sub-40 | 4-FPh | —CO— | Single Bond | —CH$_2$-cPn— |
| 3-713 | Sub-41 | 4-FPh | —CO— | Single Bond | —CH$_2$-cPn— |
| 3-714 | Sub-42 | 4-FPh | —CO— | Single Bond | —CH$_2$-cPn— |
| 3-715 | Sub-84 | 4-FPh | —CO— | Single Bond | —CH$_2$-cPn— |
| 3-716 | Sub-43 | 4-FPh | —CO— | Single Bond | —CH$_2$-cPn— |
| 3-717 | Sub-44 | 4-FPh | —CO— | Single Bond | —CH$_2$-cPn— |
| 3-718 | Sub-45 | 4-FPh | —CO— | Single Bond | —CH$_2$-cPn— |
| 3-719 | Sub-46 | 4-FPh | —CO— | Single Bond | —CH$_2$-cPn— |
| 3-720 | Sub-47 | 4-FPh | —CO— | Single Bond | —CH$_2$-cPn— |
| 3-721 | Sub-81 | 4-FPh | —CO— | Single Bond | —CH$_2$-cPn— |
| 3-722 | Sub-48 | 4-FPh | —CO— | Single Bond | —CH$_2$-cPn— |
| 3-723 | Sub-49 | 4-FPh | —CO— | Single Bond | —CH$_2$-cPn— |
| 3-724 | Sub-50 | 4-FPh | —CO— | Single Bond | —CH$_2$-cPn— |
| 3-725 | Sub-51 | 4-FPh | —CO— | Single Bond | —CH$_2$-cPn— |
| 3-726 | Sub-52 | 4-FPk | —CO— | Single Bond | —CH$_2$-cPn— |
| 3-727 | Sub-53 | 4-FPh | —CO— | Single Bond | —CH$_2$-cPn— |
| 3-728 | Sub-54 | 4-FPh | —CO— | Single Bond | —CH$_2$-cPn— |
| 3-729 | Sub-56 | 4-FPh | —CO— | Single Bond | —CH$_2$-cPn— |
| 3-730 | Sub-57 | 4-FPh | —CO— | Single Bond | —CH$_2$-cPn— |
| 3-731 | Sub-58 | 4-FPh | —CO— | Single Bond | —CH$_2$-cPn— |
| 3-732 | Sub-59 | 4-FPh | —CO— | Single Bond | —CH$_2$-cPn— |
| 3-733 | Sub-82 | 4-FPh | —CO— | Single Bond | —CH$_2$-cPn— |
| 3-734 | Sub-83 | 4-FPh | —CO— | Single Bond | —CH$_2$-cPn— |
| 3-735 | Sub-61 | 4-FPh | —CO— | Single Bond | —CH$_2$-cPn— |
| 3-736 | Sub-55 | 4-FPh | —CO— | Single Bond | —CH$_2$-cPn— |
| 3-737 | Sub-33 | 4-FPh | —CO— | Single Bond | —CH$_2$-cHx— |
| 3-738 | Sub-34 | 4-FPh | —CO— | Single Bond | —CH$_2$-cHx— |
| 3-739 | Sub-35 | 4-FPh | —CO— | Single Bond | —CH$_2$-cHx— |
| 3-740 | Sub-36 | 4-FPh | —CO— | Single Bond | —CH$_2$-cHx— |
| 3-741 | Sub-37 | 4-FPh | —CO— | Single Bond | —CH$_2$-cHx— |
| 3-742 | Sub-38 | 4-FPh | —CO— | Single Bond | —CH$_2$-cHx— |

TABLE 3-continued

| Cpd. No. | R¹ | R² | A | B | E |
|---|---|---|---|---|---|
| 3-743 | Sub-39 | 4-FPh | —CO— | Single Bond | —CH₂-cHx— |
| 3-744 | Sub-40 | 4-FPh | —CO— | Single Bond | —CH₂-cHx— |
| 3-745 | Sub-41 | 4-FPh | —CO— | Single Bond | —CH₂-cHx— |
| 3-746 | Sub-42 | 4-FPh | —CO— | Single Bond | —CH₂-cHx— |
| 3-747 | Sub-84 | 4-FPh | —CO— | Single Bond | —CH₂-cHx— |
| 3-748 | Sub-43 | 4-FPh | —CO— | Single Bond | —CH₂-cHx— |
| 3-749 | Sub-44 | 4-FPh | —CO— | Single Bond | —CH₂-cHx— |
| 3-750 | Sub-45 | 4-FPh | —CO— | Single Bond | —CH₂-cHx— |
| 3-751 | Sub-46 | 4-FPh | —CO— | Single Bond | —CH₂-cHx— |
| 3-752 | Sub-47 | 4-FPh | —CO— | Single Bond | —CH₂-cHx— |
| 3-753 | Sub-81 | 4-FPh | —CO— | Single Bond | —CH₂-cHx— |
| 3-754 | Sub-48 | 4-FPh | —CO— | Single Bond | —CH₂-cHx— |
| 3-755 | Sub-49 | 4-FPh | —CO— | Single Bond | —CH₂-cHx— |
| 3-756 | Sub-50 | 4-FPh | —CO— | Single Bond | —CH₂-cHx— |
| 3-757 | Sub-51 | 4-FPh | —CO— | Single Bond | —CH₂-cHx— |
| 3-758 | Sub-52 | 4-FPh | —CO— | Single Bond | —CH₂-cHx— |
| 3-759 | Sub-53 | 4-FPh | —CO— | Single Bond | —CH₂-cHx— |
| 3-760 | Sub-54 | 4-FPh | —CO— | Single Bond | —CH₂-cHx— |
| 3-761 | Sub-56 | 4-FPh | —CO— | Single Bond | —CH₂-cHx— |
| 3-762 | Sub-57 | 4-FPh | —CO— | Single Bond | —CH₂-cHx— |
| 3-763 | Sub-58 | 4-FPh | —CO— | Single Bond | —CH₂-cHx— |
| 3-764 | Sub-59 | 4-FPh | —CO— | Single Bond | —CH₂-cHx— |
| 3-765 | Sub-82 | 4-FPh | —CO— | Single Bond | —CH₂-cHx— |
| 3-766 | Sub-83 | 4-FPh | —CO— | Single Bond | —CH₂-cHx— |
| 3-767 | Sub-61 | 4-FPh | —CO— | Single Bond | —CH₂-cHx— |
| 3-768 | Sub-55 | 4-FPh | —CO— | Single Bond | —CH₂-cHx— |
| 3-769 | Sub-33 | 3,4-diClPh | —CO— | —CH₂— | —CH₂— |
| 3-770 | Sub-34 | 3,4-diClPh | —CO— | —CH₂— | —CH₂— |
| 3-771 | Sub-35 | 3,4-diClPh | —CO— | —CH₂— | —CH₂— |
| 3-772 | Sub-36 | 3,4-diClPh | —CO— | —CH₂— | —CH₂— |
| 3-773 | Sub-37 | 3,4-diClPh | —CO— | —CH₂— | —CH₂— |
| 3-774 | Sub-38 | 3,4-diClPh | —CO— | —CH₂— | —CH₂— |
| 3-775 | Sub-39 | 3,4-diClPh | —CO— | —CH₂— | —CH₂— |
| 3-776 | Sub-40 | 3,4-diClPh | —CO— | —CH₂— | —CH₂— |
| 3-777 | Sub-41 | 3,4-diClPh | —CO— | —CH₂— | —CH₂— |
| 3-778 | Sub-42 | 3,4-diClPh | —CO— | —CH₂— | —CH₂— |
| 3-779 | Sub-84 | 3,4-diClPh | —CO— | —CH₂— | —CH₂— |
| 3-780 | Sub-43 | 3,4-diClPh | —CO— | —CH₂— | —CH₂— |
| 3-781 | Sub-44 | 3,4-diClPh | —CO— | —CH₂— | —CH₂— |
| 3-782 | Sub-45 | 3,4-diClPh | —CO— | —CH₂— | —CH₂— |
| 3-783 | Sub-46 | 3,4-diClPh | —CO— | —CH₂— | —CH₂— |
| 3-784 | Sub-47 | 3,4-diClPh | —CO— | —CH₂— | —CH₂— |
| 3-785 | Sub-81 | 3,4-diClPh | —CO— | —CH₂— | —CH₂— |
| 3-786 | Sub-48 | 3,4-diClPh | —CO— | —CH₂— | —CH₂— |
| 3-787 | Sub-49 | 3,4-diClPh | —CO— | —CH₂— | —CH₂— |
| 3-788 | Sub-50 | 3,4-diClPh | —CO— | —CH₂— | —CH₂— |
| 3-789 | Sub-51 | 3,4-diClPh | —CO— | —CH₂— | —CH₂— |
| 3-790 | Sub-52 | 3,4-diClPh | —CO— | —CH₂— | —CH₂— |
| 3-791 | Sub-53 | 3,4-diClPh | —CO— | —CH₂— | —CH₂— |
| 3-792 | Sub-54 | 3,4-diClPh | —CO— | —CH₂— | —CH₂— |
| 3-793 | Sub-56 | 3,4-diClPh | —CO— | —CH₂— | —CH₂— |
| 3-794 | Sub-57 | 3,4-diClPh | —CO— | —CH₂— | —CH₂— |
| 3-795 | Sub-58 | 3,4-diClPh | —CO— | —CH₂— | —CH₂— |
| 3-796 | Sub-59 | 3,4-diClPh | —CO— | —CH₂— | —CH₂— |
| 3-797 | Sub-82 | 3,4-diClPh | —CO— | —CH₂— | —CH₂— |
| 3-798 | Sub-83 | 3,4-diClPh | —CO— | —CH₂— | —CH₂— |
| 3-799 | Sub-61 | 3,4-diClPh | —CO— | —CH₂— | —CH₂— |
| 3-800 | Sub-55 | 3,4-diClPh | —CO— | —CH₂— | —CH₂— |
| 3-801 | Sub-33 | 3,4-diClPh | —CO— | —CH₂— | —CH₂CH₂— |
| 3-802 | Sub-34 | 3,4-diClPh | —CO— | —CH₂— | —CH₂CH₂— |
| 3-803 | Sub-35 | 3,4-diClPh | —CO— | —CH₂— | —CH₂CH₂— |
| 3-804 | Sub-36 | 3,4-diClPh | —CO— | —CH₂— | —CH₂CH₂— |
| 3-805 | Sub-37 | 3,4-diClPh | —CO— | —CH₂— | —CH₂CH₂— |
| 3-806 | Sub-38 | 3,4-diClPh | —CO— | —CH₂— | —CH₂CH₂— |
| 3-807 | Sub-39 | 3,4-diClPh | —CO— | —CH₂— | —CH₂CH₂— |
| 3-808 | Sub-40 | 3,4-diClPh | —CO— | —CH₂— | —CH₂CH₂— |
| 3-809 | Sub-41 | 3,4-diClPh | —CO— | —CH₂— | —CH₂CH₂— |
| 3-810 | Sub-42 | 3,4-diClPh | —CO— | —CH₂— | —CH₂CH₂— |
| 3-811 | Sub-84 | 3,4-diClh | —CO— | —CH₂— | —CH₂CH₂— |
| 3-812 | Sub-43 | 3,4-diClPh | —CO— | —CH₂— | —CH₂CH₂— |
| 3-813 | Sub-44 | 3,4-diClPh | —CO— | —CH₂— | —CH₂CH₂— |
| 3-814 | Sub-45 | 3,4-diClPh | —CO— | —CH₂— | —CH₂CH₂— |
| 3-815 | Sub-46 | 3,4-diClPh | —CO— | —CH₂— | —CH₂CH₂— |
| 3-816 | Sub-47 | 3,4-diClPh | —CO— | —CH₂— | —CH₂CH₂— |
| 3-817 | Sub-81 | 3,4-diClPh | —CO— | —CH₂— | —CH₂CH₂— |
| 3-818 | Sub-48 | 3,4-diClPh | —CO— | —CH₂— | —CH₂CH₂— |

TABLE 3-continued

| Cpd. No. | R$^1$ | R$^2$ | A | B | E |
|---|---|---|---|---|---|
| 3-819 | Sub-49 | 3,4-diClPh | —CO— | —CH$_2$— | —CH$_2$CH$_2$— |
| 3-820 | Sub-50 | 3,4-diClPh | —CO— | —CH$_2$— | —CH$_2$CH$_2$— |
| 3-821 | Sub-51 | 3,4-diClPh | —CO— | —CH$_2$— | —CH$_2$CH$_2$— |
| 3-822 | Sub-52 | 3,4-diClPh | —CO— | —CH$_2$— | —CH$_2$CH$_2$— |
| 3-823 | Sub-53 | 3,4-diClPh | —CO— | —CH$_2$— | —CH$_2$CH$_2$— |
| 3-824 | Sub-54 | 3,4-diClPh | —CO— | —CH$_2$— | —CH$_2$CH$_2$— |
| 3-825 | Sub-56 | 3,4-diClPh | —CO— | —CH$_2$— | —CH$_2$CH$_2$— |
| 3-826 | Sub-57 | 3,4-diClPh | —CO— | —CH$_2$— | —CH$_2$CH$_2$— |
| 3-827 | Sub-58 | 3,4-diClPh | —CO— | —CH$_2$— | —CH$_2$CH$_2$— |
| 3-828 | Sub-59 | 3,4-diClPh | —CO— | —CH$_2$— | —CH$_2$CH$_2$— |
| 3-829 | Sub-82 | 3,4-diClPh | —CO— | —CH$_2$— | —CH$_2$CH$_2$— |
| 3-830 | Sub-83 | 3,4-diClPh | —CO— | —CH$_2$— | —CH$_2$CH$_2$— |
| 3-831 | Sub-61 | 3,4-diClPh | —CO— | —CH$_2$— | —CH$_2$CH$_2$— |
| 3-832 | Sub-55 | 3,4-diClPh | —CO— | —CH$_2$— | —CH$_2$CH$_2$— |
| 3-833 | Sub-33 | 3,4-diClPh | —CO— | —CH$_2$— | —(CH$_2$)$_3$— |
| 3-834 | Sub-34 | 3,4-diClPh | —CO— | —CH$_2$— | —(CH$_2$)$_3$— |
| 3-835 | Sub-35 | 3,4-diClPh | —CO— | —CH$_2$— | —(CH$_2$)$_3$— |
| 3-836 | Sub-36 | 3,4-diClPh | —CO— | —CH$_2$— | —(CH$_2$)$_3$— |
| 3-837 | Sub-37 | 3,4-diClPh | —CO— | —CH$_2$— | —(CH$_2$)$_3$— |
| 3-838 | Sub-38 | 3,4-diClPh | —CO— | —CH$_2$— | —(CH$_2$)$_3$— |
| 3-839 | Sub-39 | 3,4-diClPh | —CO— | —CH$_2$— | —(CH$_2$)$_3$— |
| 3-840 | Sub-40 | 3,4-diClPh | —CO— | —CH$_2$— | —(CH$_2$)$_3$— |
| 3-841 | Sub-41 | 3,4-diClPh | —CO— | —CH$_2$— | —(CH$_2$)$_3$— |
| 3-842 | Sub-42 | 3,4-diClPh | —CO— | —CH$_2$— | —(CH$_2$)$_3$— |
| 3-843 | Sub-84 | 3,4-diClPh | —CO— | —CH$_2$— | —(CH$_2$)$_3$— |
| 3-844 | Sub-43 | 3,4-diClPh | —CO— | —CH$_2$— | —(CH$_2$)$_3$— |
| 3-845 | Sub-44 | 3,4-diClPh | —CO— | —CH$_2$— | —(CH$_2$)$_3$— |
| 3-846 | Sub-45 | 3,4-diClPh | —CO— | —CH$_2$— | —(CH$_2$)$_3$— |
| 3-847 | Sub-46 | 3,4-diClPh | —CO— | —CH$_2$— | —(CH$_2$)$_3$— |
| 3-848 | Sub-47 | 3,4-diClPh | —CO— | —CH$_2$— | —(CH$_2$)$_3$— |
| 3-849 | Sub-81 | 3,4-diClPh | —CO— | —CH$_2$— | —(CH$_2$)$_3$— |
| 3-850 | Sub-48 | 3,4-diClPh | —CO— | —CH$_2$— | —(CH$_2$)$_3$— |
| 3-851 | Sub-49 | 3,4-diClPh | —CO— | —CH$_2$— | —(CH$_2$)$_3$— |
| 3-852 | Sub-50 | 3,4-diClPh | —CO— | —CH$_2$— | —(CH$_2$)$_3$— |
| 3-853 | Sub-51 | 3,4-diClPh | —CO— | —CH$_2$— | —(CH$_2$)$_3$— |
| 3-854 | Sub-52 | 3,4-diClPh | —CO— | —CH$_2$— | —(CH$_2$)$_3$— |
| 3-855 | Sub-53 | 3,4-diClPh | —CO— | —CH$_2$— | —(CH$_2$)$_3$— |
| 3-856 | Sub-54 | 3,4-diClPh | —CO— | —CH$_2$— | —(CH$_2$)$_3$— |
| 3-857 | Sub-56 | 3,4-diClPh | —CO— | —CH$_2$— | —(CH$_2$)$_3$— |
| 3-858 | Sub-57 | 3,4-diClPh | —CO— | —CH$_2$— | —(CH$_2$)$_3$— |
| 3-859 | Sub-58 | 3,4-diClPh | —CO— | —CH$_2$— | —(CH$_2$)$_3$— |
| 3-860 | Sub-59 | 3,4-diClPh | —CO— | —CH$_2$— | —(CH$_2$)$_3$— |
| 3-861 | Sub-82 | 3,4-diClPh | —CO— | —CH$_2$— | —(CH$_2$)$_3$— |
| 3-862 | Sub-83 | 3,4-diClPh | —CO— | —CH$_2$— | —(CH$_2$)$_3$— |
| 3-863 | Sub-61 | 3,4-diClPh | —CO— | —CH$_2$— | —(CH$_2$)$_3$— |
| 3-864 | Sub-55 | 3,4-diClPh | —CO— | —CH$_2$— | —(CH$_2$)$_3$— |
| 3-865 | Sub-33 | 3,4-diClPh | —CO— | —CH$_2$— | —CH$_2$C(Me)$_2$— |
| 3-866 | Sub-34 | 3,4-diClPh | —CO— | —CH$_2$— | —CH$_2$C(Me)$_2$— |
| 3-867 | Sub-35 | 3,4-diClPh | —CO— | —CH$_2$— | —CH$_2$C(Me)$_2$— |
| 3-868 | Sub-36 | 3,4-diClPh | —CO— | —CH$_2$— | —CH$_2$C(Me)$_2$— |
| 3-869 | Sub-37 | 3,4-diClPh | —CO— | —CH$_2$— | —CH$_2$C(Me)$_2$— |
| 3-870 | Sub-38 | 3,4-diClPh | —CO— | —CH$_2$— | —CH$_2$C(Me)$_2$— |
| 3-871 | Sub-39 | 3,4-diClPh | —CO— | —CH$_2$— | —CH$_2$C(Me)$_2$— |
| 3-872 | Sub-40 | 3,4-diClPh | —CO— | —CH$_2$— | —CH$_2$C(Me)$_2$— |
| 3-873 | Sub-41 | 3,4-diClPh | —CO— | —CH$_2$— | —CH$_2$C(Me)$_2$— |
| 3-874 | Sub-42 | 3,4-diClPh | —CO— | —CH$_2$— | —CH$_2$C(Me)$_2$— |
| 3-875 | Sub-84 | 3,4-diClPh | —CO— | —CH$_2$— | —CH$_2$C(Me)$_2$— |
| 3-876 | Sub-43 | 3,4-diClPh | —CO— | —CH$_2$— | —CH$_2$C(Me)$_2$— |
| 3-877 | Sub-44 | 3,4-diClPh | —CO— | —CH$_2$— | —CH$_2$C(Me)$_2$— |
| 3-878 | Sub-45 | 3,4-diClPh | —CO— | —CH$_2$— | —CH$_2$C(Me)$_2$— |
| 3-879 | Sub-46 | 3,4-diClPh | —CO— | —CH$_2$— | —CH$_2$C(Me)$_2$— |
| 3-880 | Sub-47 | 3,4-diClPh | —CO— | —CH$_2$— | —CH$_2$C(Me)$_2$— |
| 3-881 | Sub-81 | 3,4-diClPh | —CO— | —CH$_2$— | —CH$_2$C(Me)$_2$— |
| 3-882 | Sub-48 | 3,4-diClPh | —CO— | —CH$_2$— | —CH$_2$C(Me)$_2$— |
| 3-883 | Sub-49 | 3,4-diClPh | —CO— | —CH$_2$— | —CH$_2$C(Me)$_2$— |
| 3-884 | Sub-50 | 3,4-diClPh | —CO— | —CH$_2$— | —CH$_2$C(Me)$_2$— |
| 3-885 | Sub-51 | 3,4-diClPh | —CO— | —CH$_2$— | —CH$_2$C(Me)$_2$— |
| 3-886 | Sub-52 | 3,4-diClPh | —CO— | —CH$_2$— | —CH$_2$C(Me)$_2$— |
| 3-887 | Sub-53 | 3,4-diClPh | —CO— | —CH$_2$— | —CH$_2$C(Me)$_2$— |
| 3-888 | Sub-54 | 3,4-diClPh | —CO— | —CH$_2$— | —CH$_2$C(Me)$_2$— |
| 3-889 | Sub-56 | 3,4-diClPh | —CO— | —CH$_2$— | —CH$_2$C(Me)$_2$— |
| 3-890 | Sub-57 | 3,4-diClPh | —CO— | —CH$_2$— | —CH$_2$C(Me)$_2$— |
| 3-891 | Sub-58 | 3,4-diClPh | —CO— | —CH$_2$— | —CH$_2$C(Me)$_2$— |
| 3-892 | Sub-59 | 3,4-diClPh | —CO— | —CH$_2$— | —CH$_2$C(Me)$_2$— |
| 3-893 | Sub-82 | 3,4-diClPh | —CO— | —CH$_2$— | —CH$_2$C(Me)$_2$— |
| 3-894 | Sub-83 | 3,4-diClPh | —CO— | —CH$_2$— | —CH$_2$C(Me)$_2$— |

TABLE 3-continued

| Cpd. No. | R¹ | R² | A | B | E |
|---|---|---|---|---|---|
| 3-895 | Sub-61 | 3,4-diClPh | —CO— | —CH$_2$— | —CH$_2$C(Me)$_2$— |
| 3-896 | Sub-55 | 3,4-diClPh | —CO— | —CH$_2$— | —CH$_2$C(Me)$_2$— |
| 3-897 | Sub-33 | 3,4-diClPh | —CO— | —CH$_2$— | —CH$_2$-cPr— |
| 3-898 | Sub-34 | 3,4-diClPh | —CO— | —CH$_2$— | —CH$_2$-cPr— |
| 3-899 | Sub-35 | 3,4-diClPh | —CO— | —CH$_2$— | —CH$_2$-cPr— |
| 3-900 | Sub-36 | 3,4-diClPh | —CO— | —CH$_2$— | —CH$_2$-cPr— |
| 3-901 | Sub-37 | 3,4-diClPh | —CO— | —CH$_2$— | —CH$_2$-cPr— |
| 3-902 | Sub-38 | 3,4-diClPh | —CO— | —CH$_2$— | —CH$_2$-cPr— |
| 3-903 | Sub-39 | 3,4-diClPh | —CO— | —CH$_2$— | —CH$_2$-cPr— |
| 3-904 | Sub-40 | 3,4-diClPh | —CO— | —CH$_2$— | —CH$_2$-cPr— |
| 3-905 | Sub-41 | 3,4-diClPh | —CO— | —CH$_2$— | —CH$_2$-cPr— |
| 3-906 | Sub-42 | 3,4-diClPh | —CO— | —CH$_2$— | —CH$_2$-cPr— |
| 3-907 | Sub-84 | 3,4-diClPh | —CO— | —CH$_2$— | —CH$_2$-cPr— |
| 3-908 | Sub-43 | 3,4-diClPh | —CO— | —CH$_2$— | —CH$_2$-cPr— |
| 3-909 | Sub-44 | 3,4-diClPh | —CO— | —CH$_2$— | —CH$_2$-cPr— |
| 3-910 | Sub-45 | 3,4-diClPh | —CO— | —CH$_2$— | —CH$_2$-cPr— |
| 3-911 | Sub-46 | 3,4-diClPh | —CO— | —CH$_2$— | —CH$_2$-cPr— |
| 3-912 | Sub-47 | 3,4-diClPh | —CO— | —CH$_2$— | —CH$_2$-cPr- |
| 3-913 | Sub-81 | 3,4-diClPh | —CO— | —CH$_2$— | —CH$_2$-cPr— |
| 3-914 | Sub-48 | 3,4-diClPh | —CO— | —CH$_2$— | —CH$_2$-cPr— |
| 3-915 | Sub-49 | 3,4-diClPh | —CO— | —CH$_2$— | —CH$_2$-cPr— |
| 3-916 | Sub-50 | 3,4-diClPh | —CO— | —CH$_2$— | —CH$_2$-cPr— |
| 3-917 | Sub-51 | 3,4-diClPh | —CO— | —CH$_2$— | —CH$_2$-cPr— |
| 3-918 | Sub-52 | 3,4-diClPh | —CO— | —CH$_2$— | —CH$_2$-cPr— |
| 3-919 | Sub-53 | 3,4-diClPh | —CO— | —CH$_2$— | —CH$_2$-cPr— |
| 3-920 | Sub-54 | 3,4-diClPh | —CO— | —CH$_2$— | —CH$_2$-cPr— |
| 3-921 | Sub-56 | 3,4-diClPh | —CO— | —CH$_2$— | —CH$_2$-cPr— |
| 3-922 | Sub-57 | 3,4-diClPh | —CO— | —CH$_2$— | —CH$_2$-cPr— |
| 3-923 | Sub-58 | 3,4-diClPh | —CO— | —CH$_2$— | —CH$_2$-cPr— |
| 3-924 | Sub-59 | 3,4-diClPh | —CO— | —CH$_2$— | —CH$_2$-cPr— |
| 3-925 | Sub-82 | 3,4-diClPh | —CO— | —CH$_2$— | —CH$_2$-cPr— |
| 3-926 | Sub-83 | 3,4-diClPh | —CO— | —CH$_2$— | —CH$_2$-cPr- |
| 3-927 | Sub-61 | 3,4-diClPh | —CO— | —CH$_2$— | —CH$_2$-cPr— |
| 3-928 | Sub-55 | 3,4-diClPh | —CO— | —CH$_2$— | —CH$_2$-cPr— |
| 3-929 | Sub-33 | 3,4-diClPh | —CO— | —CH$_2$— | —CH$_2$-cBu— |
| 3-930 | Sub-34 | 3,4-diClPh | —CO— | —CH$_2$— | —CH$_2$-cBu— |
| 3-931 | Sub-35 | 3,4-diClPh | —CO— | —CH$_2$— | —CH$_2$-cBu— |
| 3-932 | Sub-36 | 3,4-diClPh | —CO— | —CH$_2$— | —CH$_2$-cBu— |
| 3-933 | Sub-37 | 3,4-diClPh | —CO— | —CH$_2$— | —CH$_2$-cBu— |
| 3-934 | Sub-38 | 3,4-diClPh | —CO— | —CH$_2$— | —CH$_2$-cBu— |
| 3-935 | Sub-39 | 3,4-diClPh | —CO— | —CH$_2$— | —CH$_2$-cBu— |
| 3-936 | Sub-40 | 3,4-diClPh | —CO— | —CH$_2$— | —CH$_2$-cBu— |
| 3-937 | Sub-41 | 3,4-diClPh | —CO— | —CH$_2$— | —CH$_2$-cBu— |
| 3-938 | Sub-42 | 3,4-diClPh | —CO— | —CH$_2$— | —CH$_2$-cBu— |
| 3-939 | Sub-84 | 3,4-diClPh | —CO— | —CH$_2$— | —CH$_2$-cBu— |
| 3-940 | Sub-43 | 3,4-diClPh | —CO— | —CH$_2$— | —CH$_2$-cBu— |
| 3-941 | Sub-44 | 3,4-diClPh | —CO— | —CH$_2$— | —CH$_2$-cBu— |
| 3-942 | Sub-45 | 3,4-diClPh | —CO— | —CH$_2$— | —CH$_2$-cBu— |
| 3-943 | Sub-46 | 3,4-diClPh | —CO— | —CH$_2$— | —CH$_2$-cBu— |
| 3-944 | Sub-47 | 3,4-diClPh | —CO— | —CH$_2$— | —CH$_2$-cBu— |
| 3-945 | Sub-81 | 3,4-diClPh | —CO— | —CH$_2$— | —CH$_2$-cBu— |
| 3-946 | Sub-48 | 3,4-diClPh | —CO— | —CH$_2$— | —CH$_2$-cBu— |
| 3-947 | Sub-49 | 3,4-diClPh | —CO— | —CH$_2$— | —CH$_2$-cBu— |
| 3-948 | Sub-50 | 3,4-diClPh | —CO— | —CH$_2$— | —CH$_2$-cBu— |
| 3-949 | Sub-51 | 3,4-diClPh | —CO— | —CH$_2$— | —CH$_2$-cBu— |
| 3-950 | Sub-52 | 3,4-diClPh | —CO— | —CH$_2$— | —CH$_2$-cBu— |
| 3-951 | Sub-53 | 3,4-diClPh | —CO— | —CH$_2$— | —CH$_2$-cBu— |
| 3-952 | Sub-54 | 3,4-diClPh | —CO— | —CH$_2$— | —CH$_2$-cBu— |
| 3-953 | Sub-56 | 3,4-diClPh | —CO— | —CH$_2$— | —CH$_2$-cBu— |
| 3-954 | Sub-57 | 3,4-diClPh | —CO— | —CH$_2$— | —CH$_2$-cBu— |
| 3-955 | Sub-58 | 3,4-diClPh | —CO— | —CH$_2$— | —CH$_2$-cBu— |
| 3-956 | Sub-59 | 3,4-diClPh | —CO— | —CH$_2$— | —CH$_2$-cBu— |
| 3-957 | Sub-82 | 3,4-diClPh | —CO— | —CH$_2$— | —CH$_2$-cBu— |
| 3-958 | Sub-83 | 3,4-diClPh | —CO— | —CH$_2$— | —CH$_2$-cBu— |
| 3-959 | Sub-61 | 3,4-diClPh | —CO— | —CH$_2$— | —CH$_2$-cBu— |
| 3-960 | Sub-55 | 3,4-diClPh | —CO— | —CH$_2$— | —CH$_2$-cBu— |
| 3-961 | Sub-33 | 3,4-diClPh | —CO— | —CH$_2$— | —CH$_2$-cPn— |
| 3-962 | Sub-34 | 3,4-diClPh | —CO— | —CH$_2$— | —CH$_2$-cPn— |
| 3-963 | Sub-35 | 3,4-diClPh | —CO— | —CH$_2$— | —CH$_2$-cPn— |
| 3-964 | Sub-36 | 3,4-diClPh | —CO— | —CH$_2$— | —CH$_2$-cPn— |
| 3-965 | Sub-37 | 3,4-diClPh | —CO— | —CH$_2$— | —CH$_2$-cPn— |
| 3-966 | Sub-38 | 3,4-diClPh | —CO— | —CH$_2$— | —CH$_2$-cPn— |
| 3-967 | Sub-39 | 3,4-diClPh | —CO— | —CH$_2$— | —CH$_2$-cPn— |
| 3-968 | Sub-40 | 3,4-diClPh | —CO— | —CH$_2$— | —CH$_2$-cPn— |
| 3-969 | Sub-41 | 3,4-diClPh | —CO— | —CH$_2$— | —CH$_2$-cPn— |
| 3-970 | Sub-42 | 3,4-diClPh | —CO— | —CH$_2$— | —CH$_2$-cPn— |

TABLE 3-continued

| Cpd. No. | R¹ | R² | A | B | E |
|---|---|---|---|---|---|
| 3-971 | Sub-84 | 3,4-diClPh | —CO— | —CH$_2$— | —CH$_2$-cPn— |
| 3-972 | Sub-43 | 3,4-diClPh | —CO— | —CH$_2$— | —CH$_2$-cPn— |
| 3-973 | Sub-44 | 3,4-diClPh | —CO— | —CH$_2$— | —CH$_2$-cPn— |
| 3-974 | Sub-45 | 3,4-diClPh | —CO— | —CH$_2$— | —CH$_2$-cPn— |
| 3-975 | Sub-46 | 3,4-diClPh | —CO— | —CH$_2$— | —CH$_2$-cPn— |
| 3-976 | Sub-47 | 3,4-diClPh | —CO— | —CH$_2$— | —CH$_2$-cPn— |
| 3-977 | Sub-81 | 3,4-diClPh | —CO— | —CH$_2$— | —CH$_2$-cPn— |
| 3-978 | Sub-48 | 3,4-diClPh | —CO— | —CH$_2$— | —CH$_2$-cPn— |
| 3-979 | Sub-49 | 3,4-diClPh | —CO— | —CH$_2$— | —CH$_2$-cPn— |
| 3-980 | Sub-50 | 3,4-diClPh | —CO— | —CH$_2$— | —CH$_2$-cPn— |
| 3-981 | Sub-51 | 3,4-diClPh | —CO— | —CH$_2$— | —CH$_2$-cPn— |
| 3-982 | Sub-52 | 3,4-diClPh | —CO— | —CH$_2$— | —CH$_2$-cPn— |
| 3-983 | Sub-53 | 3,4-diClPh | —CO— | —CH$_2$— | —CH$_2$-cPn— |
| 3-984 | Sub-54 | 3,4-diClPh | —CO— | —CH$_2$— | —CH$_2$-cPn— |
| 3-985 | Sub-56 | 3,4-diClPh | —CO— | —CH$_2$— | —CH$_2$-cPn— |
| 3-986 | Sub-57 | 3,4-diClPh | —CO— | —CH$_2$— | —CH$_2$-cPn— |
| 3-987 | Sub-58 | 3,4-diClPh | —CO— | —CH$_2$— | —CH$_2$-cPn— |
| 3-988 | Sub-59 | 3,4-diClPh | —CO— | —CH$_2$— | —CH$_2$-cPn— |
| 3-989 | Sub-82 | 3,4-diClPh | —CO— | —CH$_2$— | —CH$_2$-cPn— |
| 3-990 | Sub-83 | 3,4-diClPh | —CO— | —CH$_2$— | —CH$_2$-cPn— |
| 3-991 | Sub-61 | 3,4-diClPh | —CO— | —CH$_2$— | —CH$_2$-cPn— |
| 3-992 | Sub-55 | 3,4-diClPh | —CO— | —CH$_2$— | —CH$_2$-cPn— |
| 3-993 | Sub-33 | 3,4-diClPh | —CO— | —CH$_2$— | —CH$_2$-cHx— |
| 3-994 | Sub-34 | 3,4-diClPh | —CO— | —CH$_2$— | —CH$_2$-cHx— |
| 3-995 | Sub-35 | 3,4-diClPh | —CO— | —CH$_2$— | —CH$_2$-cHx— |
| 3-996 | Sub-36 | 3,4-diClPh | —CO— | —CH$_2$— | —CH$_2$-cHx— |
| 3-997 | Sub-37 | 3,4-diClPh | —CO— | —CH$_2$— | —CH$_2$-cHx— |
| 3-998 | Sub-38 | 3,4-diClPh | —CO— | —CH$_2$— | —CH$_2$-cHx— |
| 3-999 | Sub-39 | 3,4-diClPh | —CO— | —CH$_2$— | —CH$_2$-cHx— |
| 3-1000 | Sub-40 | 3,4-diClPh | —CO— | —CH$_2$— | —CH$_2$-cHx— |
| 3-1001 | Sub-41 | 3,4-diClPh | —CO— | —CH$_2$— | —CH$_2$-cHx— |
| 3-1002 | Sub-42 | 3,4-diClPh | —CO— | —CH$_2$— | —CH$_2$-cHx— |
| 3-1003 | Sub-84 | 3,4-diClPh | —CO— | —CH$_2$— | —CH$_2$-cHx— |
| 3-1004 | Sub-43 | 3,4-diClPh | —CO— | —CH$_2$— | —CH$_2$-cHx— |
| 3-1005 | Sub-44 | 3,4-diClPh | —CO— | —CH$_2$— | —CH$_2$-cHx— |
| 3-1006 | Sub-45 | 3,4-diClPh | —CO— | —CH$_2$— | —CH$_2$-cHx— |
| 3-1007 | Sub-46 | 3,4-diClPh | —CO— | —CH$_2$— | —CH$_2$-cHx— |
| 3-1008 | Sub-47 | 3,4-diClPh | —CO— | —CH$_2$— | —CH$_2$-cHx— |
| 3-1009 | Sub-81 | 3,4-diClPh | —CO— | —CH$_2$— | —CH$_2$-cHx— |
| 3-1010 | Sub-48 | 3,4-diClPh | —CO— | —CH$_2$— | —CH$_2$-cHx— |
| 3-1011 | Sub-49 | 3,4-diClPh | —CO— | —CH$_2$— | —CH$_2$-cHx— |
| 3-1012 | Sub-50 | 3,4-diClPh | —CO— | —CH$_2$— | —CH$_2$-cHx— |
| 3-1013 | Sub-51 | 3,4-diClPh | —CO— | —CH$_2$— | —CH$_2$-cHx— |
| 3-1014 | Sub-52 | 3,4-diClPh | —CO— | —CH$_2$— | —CH$_2$-cHx— |
| 3-1015 | Sub-53 | 3,4-diClPh | —CO— | —CH$_2$— | —CH$_2$-cHx— |
| 3-1016 | Sub-54 | 3,4-diClPh | —CO— | —CH$_2$— | —CH$_2$-cHx— |
| 3-1017 | Sub-56 | 3,4-diClPh | —CO— | —CH$_2$— | —CH$_2$-cHx— |
| 3-1018 | Sub-57 | 3,4-diClPh | —CO— | —CH$_2$— | —CH$_2$-cHx— |
| 3-1019 | Sub-58 | 3,4-diClPh | —CO— | —CH$_2$— | —CH$_2$-cHx— |
| 3-1020 | Sub-59 | 3,4-diClPh | —CO— | —CH$_2$— | —CH$_2$-cHx— |
| 3-1021 | Sub-82 | 3,4-diClPh | —CO— | —CH$_2$— | —CH$_2$-cHx— |
| 3-1022 | Sub-83 | 3,4-diClPh | —CO— | —CH$_2$— | —CH$_2$-cHx— |
| 3-1023 | Sub-61 | 3,4-diClPh | —CO— | —CH$_2$— | —CH$_2$-cHx— |
| 3-1024 | Sub-55 | 3,4-diClPh | —CO— | —CH$_2$— | —CH$_2$-cHx— |
| 3-1025 | Sub-33 | 4-ClPh | —CO— | —CH$_2$— | —CH$_2$— |
| 3-1026 | Sub-34 | 4-ClPh | —CO— | —CH$_2$— | —CH$_2$— |
| 3-1027 | Sub-35 | 4-ClPh | —CO— | —CH$_2$— | —CH$_2$— |
| 3-1028 | Sub-36 | 4-ClPh | —CO— | —CH$_2$— | —CH$_2$— |
| 3-1029 | Sub-37 | 4-ClPh | —CO— | —CH$_2$— | —CH$_2$— |
| 3-1030 | Sub-38 | 4-ClPh | —CO— | —CH$_2$— | —CH$_2$— |
| 3-1031 | Sub-39 | 4-ClPh | —CO— | —CH$_2$— | —CH$_2$— |
| 3-1032 | Sub-40 | 4-ClPh | —CO— | —CH$_2$— | —CH$_2$— |
| 3-1033 | Sub-41 | 4-ClPh | —CO— | —CH$_2$— | —CH$_2$— |
| 3-1034 | Sub-42 | 4-ClPh | —CO— | —CH$_2$— | —CH$_2$— |
| 3-1035 | Sub-84 | 4-ClPh | —CO— | —CH$_2$— | —CH$_2$— |
| 3-1036 | Sub-43 | 4-ClPh | —CO— | —CH$_2$— | —CH$_2$— |
| 3-1037 | Sub-44 | 4-ClPh | —CO— | —CH$_2$— | —CH$_2$— |
| 3-1038 | Sub-45 | 4-ClPh | —CO— | —CH$_2$— | —CH$_2$— |
| 3-1039 | Sub-46 | 4-ClPh | —CO— | —CH$_2$— | —CH$_2$— |
| 3-1040 | Sub-47 | 4-ClPh | —CO— | —CH$_2$— | —CH$_2$— |
| 3-1041 | Sub-81 | 4-ClPh | —CO— | —CH$_2$— | —CH$_2$— |
| 3-1042 | Sub-48 | 4-ClPh | —CO— | —CH$_2$— | —CH$_2$— |
| 3-1043 | Sub-49 | 4-ClPh | —CO— | —CH$_2$— | —CH$_2$— |
| 3-1044 | Sub-50 | 4-ClPh | —CO— | —CH$_2$— | —CH$_2$— |
| 3-1045 | Sub-51 | 4-ClPh | —CO— | —CH$_2$— | —CH$_2$— |
| 3-1046 | Sub-52 | 4-ClPh | —CO— | —CH$_2$— | —CH$_2$— |

TABLE 3-continued

| Cpd. No. | R¹ | R² | A | B | E |
|---|---|---|---|---|---|
| 3-1047 | Sub-53 | 4-ClPh | —CO— | —CH₂— | —CH₂— |
| 3-1048 | Sub-54 | 4-ClPh | —CO— | —CH₂— | —CH₂— |
| 3-1049 | Sub-56 | 4-ClPh | —CO— | —CH₂— | —CH₂— |
| 3-1050 | Sub-57 | 4-ClPh | —CO— | —CH₂— | —CH₂— |
| 3-1051 | Sub-58 | 4-ClPh | —CO— | —CH₂— | —CH₂— |
| 3-1052 | Sub-59 | 4-ClPh | —CO— | —CH₂— | —CH₂— |
| 3-1053 | Sub-82 | 4-ClPh | —CO— | —CH₂— | —CH₂— |
| 3-1054 | Sub-83 | 4-ClPh | —CO— | —CH₂— | —CH₂— |
| 3-1055 | Sub-61 | 4-ClPh | —CO— | —CH₂— | —CH₂— |
| 3-1056 | Sub-55 | 4-ClPh | —CO— | —CH₂— | —CH₂— |
| 3-1057 | Sub-33 | 4-ClPh | —CO— | —CH₂— | —CH₂CH₂— |
| 3-1058 | Sub-34 | 4-ClPh | —CO— | —CH₂— | —CH₂CH₂— |
| 3-1059 | Sub-35 | 4-ClPh | —CO— | —CH₂— | —CH₂CH₂— |
| 3-1060 | Sub-36 | 4-ClPh | —CO— | —CH₂— | —CH₂CH₂— |
| 3-1061 | Sub-37 | 4-ClPh | —CO— | —CH₂— | —CH₂CH₂— |
| 3-1062 | Sub-38 | 4-ClPh | —CO— | —CH₂— | —CH₂CH₂— |
| 3-1063 | Sub-39 | 4-ClPh | —CO— | —CH₂— | —CH₂CH₂— |
| 3-1064 | Sub-40 | 4-ClPh | —CO— | —CH₂— | —CH₂CH₂— |
| 3-1065 | Sub-41 | 4-ClPh | —CO— | —CH₂— | —CH₂CH₂— |
| 3-1066 | Sub-42 | 4-ClPh | —CO— | —CH₂— | —CH₂CH₂— |
| 3-1067 | Sub-84 | 4-ClPh | —CO— | —CH₂— | —CH₂CH₂— |
| 3-1068 | Sub-43 | 4-ClPh | —CO— | —CH₂— | —CH₂CH₂— |
| 3-1069 | Sub-44 | 4-ClPh | —CO— | —CH₂— | —CH₂CH₂— |
| 3-1070 | Sub-45 | 4-ClPh | —CO— | —CH₂— | —CH₂CH₂— |
| 3-1071 | Sub-46 | 4-ClPh | —CO— | —CH₂— | —CH₂CH₂— |
| 3-1072 | Sub-47 | 4-ClPh | —CO— | —CH₂— | —CH₂CH₂— |
| 3-1073 | Sub-81 | 4-ClPh | —CO— | —CH₂— | —CH₂CH₂— |
| 3-1074 | Sub-48 | 4-ClPh | —CO— | —CH₂— | —CH₂CH₂— |
| 3-1075 | Sub-49 | 4-ClPh | —CO— | —CH₂— | —CH₂CH₂— |
| 3-1076 | Sub-50 | 4-ClPh | —CO— | —CH₂— | —CH₂CH₂— |
| 3-1077 | Sub-51 | 4-ClPh | —CO— | —CH₂— | —CH₂CH₂— |
| 3-1078 | Sub-52 | 4-ClPh | —CO— | —CH₂— | —CH₂CH₂— |
| 3-1079 | Sub-53 | 4-ClPh | —CO— | —CH₂— | —CH₂CH₂— |
| 3-1080 | Sub-54 | 4-ClPh | —CO— | —CH₂— | —CH₂CH₂— |
| 3-1081 | Sub-56 | 4-ClPh | —CO— | —CH₂— | —CH₂CH₂— |
| 3-1082 | Sub-57 | 4-ClPh | —CO— | —CH₂— | —CH₂CH₂— |
| 3-1083 | Sub-58 | 4-ClPh | —CO— | —CH₂— | —CH₂CH₂— |
| 3-1084 | Sub-59 | 4-ClPh | —CO— | —CH₂— | —CH₂CH₂— |
| 3-1085 | Sub-82 | 4-ClPh | —CO— | —CH₂— | —CH₂CH₂— |
| 3-1086 | Sub-83 | 4-ClPh | —CO— | —CH₂— | —CH₂CH₂— |
| 3-1087 | Sub-61 | 4-ClPh | —CO— | —CH₂— | —CH₂CH₂— |
| 3-1088 | Sub-55 | 4-ClPh | —CO— | —CH₂— | —CH₂CH₂— |
| 3-1089 | Sub-33 | 4-ClPh | —CO— | —CH₂— | —(CH₂)₃— |
| 3-1090 | Sub-34 | 4-ClPh | —CO— | —CH₂— | —(CH₂)₃— |
| 3-1091 | Sub-35 | 4-ClPh | —CO— | —CH₂— | —(CH₂)₃— |
| 3-1092 | Sub-36 | 4-ClPh | —CO— | —CH₂— | —(CH₂)₃— |
| 3-1093 | Sub-37 | 4-ClPh | —CO— | —CH₂— | —(CH₂)₃— |
| 3-1094 | Sub-38 | 4-ClPh | —CO— | —CH₂— | —(CH₂)₃— |
| 3-1095 | Sub-39 | 4-ClPh | —CO— | —CH₂— | —(CH₂)₃— |
| 3-1096 | Sub-40 | 4-ClPh | —CO— | —CH₂— | —(CH₂)₃— |
| 3-1097 | Sub-41 | 4-ClPh | —CO— | —CH₂— | —(CH₂)₃— |
| 3-1098 | Sub-42 | 4-ClPh | —CO— | —CH₂— | —(CH₂)₃— |
| 3-1099 | Sub-84 | 4-ClPh | —CO— | —CH₂— | —(CH₂)₃— |
| 3-1100 | Sub-43 | 4-ClPh | —CO— | —CH₂— | —(CH₂)₃— |
| 3-1101 | Sub-44 | 4-ClPh | —CO— | —CH₂— | —(CH₂)₃— |
| 3-1102 | Sub-45 | 4-ClPh | —CO— | —CH₂— | —(CH₂)₃— |
| 3-1103 | Sub-46 | 4-ClPh | —CO— | —CH₂— | —(CH₂)₃— |
| 3-1104 | Sub-47 | 4-ClPh | —CO— | —CH₂— | —(CH₂)₃— |
| 3-1105 | Sub-81 | 4-ClPh | —CO— | —CH₂— | —(CH₂)₃— |
| 3-1106 | Sub-48 | 4-ClPh | —CO— | —CH₂— | —(CH₂)₃— |
| 3-1107 | Sub-49 | 4-ClPh | —CO— | —CH₂— | —(CH₂)₃— |
| 3-1108 | Sub-50 | 4-ClPh | —CO— | —CH₂— | —(CH₂)₃— |
| 3-1109 | Sub-51 | 4-ClPh | —CO— | —CH₂— | —(CH₂)₃— |
| 3-1110 | Sub-52 | 4-ClPh | —CO— | —CH₂— | —(CH₂)₃— |
| 3-1111 | Sub-53 | 4-ClPh | —CO— | —CH₂— | —(CH₂)₃— |
| 3-1112 | Sub-54 | 4-ClPh | —CO— | —CH₂— | —(CH₂)₃— |
| 3-1113 | Sub-56 | 4-ClPh | —CO— | —CH₂— | —(CH₂)₃— |
| 3-1114 | Sub-57 | 4-ClPh | —CO— | —CH₂— | —(CH₂)₃— |
| 3-1115 | Sub-58 | 4-ClPh | —CO— | —CH₂— | —(CH₂)₃— |
| 3-1116 | Sub-59 | 4-ClPh | —CO— | —CH₂— | —(CH₂)₃— |
| 3-1117 | Sub-82 | 4-ClPh | —CO— | —CH₂— | —(CH₂)₃— |
| 3-1118 | Sub-83 | 4-ClPh | —CO— | —CH₂— | —(CH₂)₃— |
| 3-1119 | Sub-61 | 4-ClPh | —CO— | —CH₂— | —(CH₂)₃— |
| 3-1120 | Sub-55 | 4-ClPh | —CO— | —CH₂— | —(CH₂)₃— |
| 3-1121 | Sub-33 | 4-ClPh | —CO— | —CH₂— | —CH₂C(Me)₂— |
| 3-1122 | Sub-34 | 4-ClPh | —CO— | —CH₂— | —CH₂C(Me)₂— |

TABLE 3-continued

| Cpd. No. | R¹ | R² | A | B | E |
|---|---|---|---|---|---|
| 3-1123 | Sub-35 | 4-CPh | —CO— | —CH$_2$— | —CH$_2$C(Me)$_2$— |
| 3-1124 | Sub-36 | 4-ClPh | —CO— | —CH$_2$— | —CH$_2$C(Me)$_2$— |
| 3-1125 | Sub-37 | 4-ClPh | —CO— | —CH$_2$— | —CH$_2$C(Me)$_2$— |
| 3-1126 | Sub-38 | 4-ClPh | —CO— | —CH$_2$— | —CH$_2$C(Me)$_2$— |
| 3-1127 | Sub-39 | 4-ClPh | —CO— | —CH$_2$— | —CH$_2$C(Me)$_2$— |
| 3-1128 | Sub-40 | 4-ClPh | —CO— | —CH$_2$— | —CH$_2$C(Me)$_2$— |
| 3-1129 | Sub-41 | 4-ClPh | —CO— | —CH$_2$— | —CH$_2$C(Me)$_2$— |
| 3-1130 | Sub-42 | 4-ClPh | —CO— | —CH$_2$— | —CH$_2$C(Me)$_2$— |
| 3-1131 | Sub-84 | 4-ClPh | —CO— | —CH$_2$— | —CH$_2$C(Me)$_2$— |
| 3-1132 | Sub-43 | 4-ClPh | —CO— | —CH$_2$— | —CH$_2$C(Me)$_2$— |
| 3-1133 | Sub-44 | 4-ClPh | —CO— | —CH$_2$— | —CH$_2$C(Me)$_2$— |
| 3-1134 | Sub-45 | 4-ClPh | —CO— | —CH$_2$— | —CH$_2$C(Me)$_2$— |
| 3-1135 | Sub-46 | 4-ClPh | —CO— | —CH$_2$— | —CH$_2$C(Me)$_2$— |
| 3-1136 | Sub-47 | 4-ClPh | —CO— | —CH$_2$— | —CH$_2$C(Me)$_2$— |
| 3-1137 | Sub-81 | 4-ClPh | —CO— | —CH$_2$— | —CH$_2$C(Me)$_2$— |
| 3-1138 | Sub-48 | 4-ClPh | —CO— | —CH$_2$— | —CH$_2$C(Me)$_2$— |
| 3-1139 | Sub-49 | 4-ClPh | —CO— | —CH$_2$— | —CH$_2$C(Me)$_2$— |
| 3-1140 | Sub-50 | 4-ClPh | —CO— | —CH$_2$— | —CH$_2$C(Me)$_2$— |
| 3-1141 | Sub-51 | 4-ClPh | —CO— | —CH$_2$— | —CH$_2$C(Me)$_2$— |
| 3-1142 | Sub-52 | 4-ClPh | —CO— | —CH$_2$— | —CH$_2$C(Me)$_2$— |
| 3-1143 | Sub-53 | 4-ClPh | —CO— | —CH$_2$— | —CH$_2$C(Me)$_2$— |
| 3-1144 | Sub-54 | 4-ClPh | —CO— | —CH$_2$— | —CH$_2$C(Me)$_2$— |
| 3-1145 | Sub-56 | 4-ClPh | —CO— | —CH$_2$— | —CH$_2$C(Me)$_2$— |
| 3-1146 | Sub-57 | 4-ClPh | —CO— | —CH$_2$— | —CH$_2$C(Me)$_2$— |
| 3-1147 | Sub-58 | 4-ClPh | —CO— | —CH$_2$— | —CH$_2$C(Me)$_2$— |
| 3-1148 | Sub-59 | 4-ClPh | —CO— | —CH$_2$— | —CH$_2$C(Me)$_2$— |
| 3-1149 | Sub-82 | 4-ClPh | —CO— | —CH$_2$— | —CH$_2$C(Me)$_2$— |
| 3-1150 | Sub-83 | 4-ClPh | —CO— | —CH$_2$— | —CH$_2$C(Me)$_2$— |
| 3-1151 | Sub-61 | 4-ClPh | —CO— | —CH$_2$— | —CH$_2$C(Me)$_2$— |
| 3-1152 | Sub-55 | 4-ClPh | —CO— | —CH$_2$— | —CH$_2$C(Me)$_2$— |
| 3-1153 | Sub-33 | 4-ClPh | —CO— | —CH$_2$— | —CH$_2$-cPr— |
| 3-1154 | Sub-34 | 4-ClPh | —CO— | —CH$_2$— | —CH$_2$-cPr— |
| 3-1155 | Sub-35 | 4-ClPh | —CO— | —CH$_2$— | —CH$_2$-cPr— |
| 3-1156 | Sub-36 | 4-ClPh | —CO— | —CH$_2$— | —CH$_2$-cPr— |
| 3-1157 | Sub-37 | 4-ClPh | —CO— | —CH$_2$— | —CH$_2$-cPr— |
| 3-1158 | Sub-38 | 4-ClPh | —CO— | —CH$_2$— | —CH$_2$-cPr— |
| 3-1159 | Sub-39 | 4-ClPh | —CO— | —CH$_2$— | —CH$_2$-cPr— |
| 3-1160 | Sub-40 | 4-ClPh | —CO— | —CH$_2$— | —CH$_2$-cPr— |
| 3-1161 | Sub-41 | 4-ClPh | —CO— | —CH$_2$— | —CH$_2$-cPr— |
| 3-1162 | Sub-42 | 4-ClPh | —CO— | —CH$_2$— | —CH$_2$-cPr— |
| 3-1163 | Sub-84 | 4-ClPh | —CO— | —CH$_2$— | —CH$_2$-cPr— |
| 3-1164 | Sub-43 | 4-ClPh | —CO— | —CH$_2$— | —CH$_2$-cPr— |
| 3-1165 | Sub-44 | 4-ClPh | —CO— | —CH$_2$— | —CH$_2$-cPr— |
| 3-1166 | Sub-45 | 4-ClPh | —CO— | —CH$_2$— | —CH$_2$-cPr— |
| 3-1167 | Sub-46 | 4-ClPh | —CO— | —CH$_2$— | —CH$_2$-cPr— |
| 3-1168 | Sub-47 | 4-ClPh | —CO— | —CH$_2$— | —CH$_2$-cPr— |
| 3-1169 | Sub-81 | 4-ClPh | —CO— | —CH$_2$— | —CH$_2$-cPr— |
| 3-1170 | Sub-48 | 4-ClPh | —CO— | —CH$_2$— | —CH$_2$-cPr— |
| 3-1171 | Sub-49 | 4-ClPh | —CO— | —CH$_2$— | —CH$_2$-cPr— |
| 3-1172 | Sub-50 | 4-ClPh | —CO— | —CH$_2$— | —CH$_2$-cPr— |
| 3-1173 | Sub-51 | 4-ClPh | —CO— | —CH$_2$— | —CH$_2$-cPr— |
| 3-1174 | Sub-52 | 4-ClPh | —CO— | —CH$_2$— | —CH$_2$-cPr— |
| 3-1175 | Sub-53 | 4-ClPh | —CO— | —CH$_2$— | —CH$_2$-cPr— |
| 3-1176 | Sub-54 | 4-ClPh | —CO— | —CH$_2$— | —CH$_2$-cPr— |
| 3-1177 | Sub-56 | 4-ClPh | —CO— | —CH$_2$— | —CH$_2$-cPr— |
| 3-1178 | Sub-57 | 4-ClPh | —CO— | —CH$_2$— | —CH$_2$-cPr— |
| 3-1179 | Sub-58 | 4-ClPh | —CO— | —CH$_2$— | —CH$_2$-cPr— |
| 3-1180 | Sub-59 | 4-ClPh | —CO— | —CH$_2$— | —CH$_2$-cPr— |
| 3-1181 | Sub-82 | 4-ClPh | —CO— | —CH$_2$— | —CH$_2$-cPr— |
| 3-1182 | Sub-83 | 4-ClPh | —CO— | —CH$_2$— | —CH$_2$-cPr— |
| 3-1183 | Sub-61 | 4-ClPh | —CO— | —CH$_2$— | —CH$_2$-cPr— |
| 3-1184 | Sub-55 | 4-ClPh | —CO— | —CH$_2$— | —CH$_2$-cPr— |
| 3-1185 | Sub-33 | 4-ClPh | —CO— | —CH$_2$— | —CH$_2$-cBu— |
| 3-1186 | Sub-34 | 4-ClPh | —CO— | —CH$_2$— | —CH$_2$-cBu— |
| 3-1187 | Sub-35 | 4-ClPh | —CO— | —CH$_2$— | —CH$_2$-cBu— |
| 3-1188 | Sub-36 | 4-ClPh | —CO— | —CH$_2$— | —CH$_2$-cBu— |
| 3-1189 | Sub-37 | 4-ClPh | —CO— | —CH$_2$— | —CH$_2$-cBu— |
| 3-1190 | Sub-38 | 4-ClPh | —CO— | —CH$_2$— | —CH$_2$-cBu— |
| 3-1191 | Sub-39 | 4-ClPh | —CO— | —CH$_2$— | —CH$_2$-cBu— |
| 3-1192 | Sub-40 | 4-ClPh | —CO— | —CH$_2$— | —CH$_2$-cBu— |
| 3-1193 | Sub-41 | 4-ClPh | —CO— | —CH$_2$— | —CH$_2$-cBu— |
| 3-1194 | Sub-42 | 4-ClPh | —CO— | —CH$_2$— | —CH$_2$-cBu— |
| 3-1195 | Sub-84 | 4-ClPh | —CO— | —CH$_2$— | —CH$_2$-cBu— |
| 3-1196 | Sub-43 | 4-ClPh | —CO— | —CH$_2$— | —CH$_2$-cBu— |
| 3-1197 | Sub-44 | 4-ClPh | —CO— | —CH$_2$— | —CH$_2$-cBu— |
| 3-1198 | Sub-45 | 4-ClPh | —CO— | —CH$_2$— | —CH$_2$-cBu— |

TABLE 3-continued

| Cpd. No. | R¹ | R² | A | B | E |
|---|---|---|---|---|---|
| 3-1199 | Sub-46 | 4-ClPh | —CO— | —CH₂— | —CH₂-cBu— |
| 3-1200 | Sub-47 | 4-ClPh | —CO— | —CH₂— | —CH₂-cBu— |
| 3-1201 | Sub-81 | 4-ClPh | —CO— | —CH₂— | —CH₂-cBu— |
| 3-1202 | Sub-48 | 4-ClPh | —CO— | —CH₂— | —CH₂-cBu— |
| 3-1203 | Sub-49 | 4-ClPh | —CO— | —CH₂— | —CH₂-cBu— |
| 3-1204 | Sub-50 | 4-ClPh | —CO— | —CH₂— | —CH₂-cBu— |
| 3-1205 | Sub-51 | 4-ClPh | —CO— | —CH₂— | —CH₂-cBu— |
| 3-1206 | Sub-52 | 4-ClPh | —CO— | —CH₂— | —CH₂-cBu— |
| 3-1207 | Sub-53 | 4-ClPh | —CO— | —CH₂— | —CH₂-cBu— |
| 3-1208 | Sub-54 | 4-ClPh | —CO— | —CH₂— | —CH₂-cBu— |
| 3-1209 | Sub-56 | 4-ClPh | —CO— | —CH₂— | —CH₂-cBu— |
| 3-1210 | Sub-57 | 4-ClPh | —CO— | —CH₂— | —CH₂-cBu— |
| 3-1211 | Sub-58 | 4-ClPh | —CO— | —CH₂— | —CH₂-cBu— |
| 3-1212 | Sub-59 | 4-ClPh | —CO— | —CH₂— | —CH₂-cBu— |
| 3-1213 | Sub-82 | 4-ClPh | —CO— | —CH₂— | —CH₂-cBu— |
| 3-1214 | Sub-83 | 4-ClPh | —CO— | —CH₂— | —CH₂-cBu— |
| 3-1215 | Sub-61 | 4-ClPh | —CO— | —CH₂— | —CH₂-cBu— |
| 3-1216 | Sub-55 | 4-ClPh | —CO— | —CH₂— | —CH₂-cBu— |
| 3-1217 | Sub-33 | 4-ClPh | —CO— | —CH₂— | —CH₂-cPn— |
| 3-1218 | Sub-34 | 4-ClPh | —CO— | —CH₂— | —CH₂-cPn— |
| 3-1219 | Sub-35 | 4-ClPh | —CO— | —CH₂— | —CH₂-cPn— |
| 3-1220 | Sub-36 | 4-ClPh | —CO— | —CH₂— | —CH₂-cPn— |
| 3-1221 | Sub-37 | 4-ClPh | —CO— | —CH₂— | —CH₂-cPn— |
| 3-1222 | Sub-38 | 4-ClPh | —CO— | —CH₂— | —CH₂-cPn— |
| 3-1223 | Sub-39 | 4-ClPh | —CO— | —CH₂— | —CH₂-cPn— |
| 3-1224 | Sub-40 | 4-ClPh | —CO— | —CH₂— | —CH₂-cPn— |
| 3-1225 | Sub-41 | 4-ClPh | —CO— | —CH₂— | —CH₂-cPn— |
| 3-1226 | Sub-42 | 4-ClPh | —CO— | —CH₂— | —CH₂-cPn— |
| 3-1227 | Sub-84 | 4-ClPh | —CO— | —CH₂— | —CH₂-cPn— |
| 3-1228 | Sub-43 | 4-ClPh | —CO— | —CH₂— | —CH₂-cPn— |
| 3-1229 | Sub-44 | 4-ClPh | —CO— | —CH₂— | —CH₂-cPn— |
| 3-1230 | Sub-45 | 4-ClPh | —CO— | —CH₂— | —CH₂-cPn— |
| 3-1231 | Sub-46 | 4-ClPh | —CO— | —CH₂— | —CH₂-cPn— |
| 3-1232 | Sub-47 | 4-ClPh | —CO— | —CH₂— | —CH₂-cPn— |
| 3-1233 | Sub-81 | 4-ClPh | —CO— | —CH₂— | —CH₂-cPn— |
| 3-1234 | Sub-48 | 4-ClPh | —CO— | —CH₂— | —CH₂-cPn— |
| 3-1235 | Sub-49 | 4-ClPh | —CO— | —CH₂— | —CH₂-cPn— |
| 3-1236 | Sub-50 | 4-ClPh | —CO— | —CH₂— | —CH₂-cPn— |
| 3-1237 | Sub-51 | 4-ClPh | —CO— | —CH₂— | —CH₂-cPn— |
| 3-1238 | Sub-52 | 4-ClPh | —CO— | —CH₂— | —CH₂-cPn— |
| 3-1239 | Sub-53 | 4-ClPh | —CO— | —CH₂— | —CH₂-cPn— |
| 3-1240 | Sub-54 | 4-ClPh | —CO— | —CH₂— | —CH₂-cPn— |
| 3-1241 | Sub-56 | 4-ClPh | —CO— | —CH₂— | —CH₂-cPn— |
| 3-1242 | Sub-57 | 4-ClPh | —CO— | —CH₂— | —CH₂-cPn— |
| 3-1243 | Sub-58 | 4-ClPh | —CO— | —CH₂— | —CH₂-cPn— |
| 3-1244 | Sub-59 | 4-ClPh | —CO— | —CH₂— | —CH₂-cPn— |
| 3-1245 | Sub-82 | 4-ClPh | —CO— | —CH₂— | —CH₂-cPn— |
| 3-1246 | Sub-83 | 4-ClPh | —CO— | —CH₂— | —CH₂-cPn— |
| 3-1247 | Sub-61 | 4-ClPh | —CO— | —CH₂— | —CH₂-cPn— |
| 3-1248 | Sub-55 | 4-ClPh | —CO— | —CH₂— | —CH₂-cPn— |
| 3-1249 | Sub-33 | 4-ClPh | —CO— | —CH₂— | —CH₂-cHx— |
| 3-1250 | Sub-34 | 4-ClPh | —CO— | —CH₂— | —CH₂-cHx— |
| 3-1251 | Sub-35 | 4-ClPh | —CO— | —CH₂— | —CH₂-cHx— |
| 3-1252 | Sub-36 | 4-ClPh | —CO— | —CH₂— | —CH₂-cHx— |
| 3-1253 | Sub-37 | 4-ClPh | —CO— | —CH₂— | —CH₂-cHx— |
| 3-1254 | Sub-38 | 4-ClPh | —CO— | —CH₂— | —CH₂-cHx— |
| 3-1255 | Sub-39 | 4-ClPh | —CO— | —CH₂— | —CH₂-cHx— |
| 3-1256 | Sub-40 | 4-ClPh | —CO— | —CH₂— | —CH₂-cHx— |
| 3-1257 | Sub-41 | 4-ClPh | —CO— | —CH₂— | —CH₂-cHx— |
| 3-1258 | Sub-42 | 4-ClPh | —CO— | —CH₂— | —CH₂-cHx— |
| 3-1259 | Sub-84 | 4-ClPh | —CO— | —CH₂— | —CH₂-cHx— |
| 3-1260 | Sub-43 | 4-ClPh | —CO— | —CH₂— | —CH₂-cHx— |
| 3-1261 | Sub-44 | 4-ClPh | —CO— | —CH₂— | —CH₂-cHx— |
| 3-1262 | Sub-45 | 4-ClPh | —CO— | —CH₂— | —CH₂-cHx— |
| 3-1263 | Sub-46 | 4-ClPh | —CO— | —CH₂— | —CH₂-cHx— |
| 3-1264 | Sub-47 | 4-ClPh | —CO— | —CH₂— | —CH₂-cHx— |
| 3-1265 | Sub-81 | 4-ClPh | —CO— | —CH₂— | —CH₂-cHx— |
| 3-1266 | Sub-48 | 4-ClPh | —CO— | —CH₂— | —CH₂-cHx— |
| 3-1267 | Sub-49 | 4-ClPh | —CO— | —CH₂— | —CH₂-cHx— |
| 3-1268 | Sub-50 | 4-ClPh | —CO— | —CH₂— | —CH₂-cHx— |
| 3-1269 | Sub-51 | 4-ClPh | —CO— | —CH₂— | —CH₂-cHx— |
| 3-1270 | Sub-52 | 4-ClPh | —CO— | —CH₂— | —CH₂-cHx— |
| 3-1271 | Sub-53 | 4-ClPh | —CO— | —CH₂— | —CH₂-cHx— |
| 3-1272 | Sub-54 | 4-ClPh | —CO— | —CH₂— | —CH₂-cHx— |
| 3-1273 | Sub-56 | 4-ClPh | —CO— | —CH₂— | —CH₂-cHx— |
| 3-1274 | Sub-57 | 4-ClPh | —CO— | —CH₂— | —CH₂-cHx— |

TABLE 3-continued

| Cpd. No. | R¹ | R² | A | B | E |
|---|---|---|---|---|---|
| 3-1275 | Sub-58 | 4-ClPh | —CO— | —CH₂— | —CH₂-cHx— |
| 3-1276 | Sub-59 | 4-ClPh | —CO— | —CH₂— | —CH₂-cHx— |
| 3-1277 | Sub-82 | 4-ClPh | —CO— | —CH₂— | —CH₂-cHx— |
| 3-1278 | Sub-83 | 4-ClPh | —CO— | —CH₂— | —CH₂-cHx— |
| 3-1279 | Sub-61 | 4-ClPh | —CO— | —CH₂— | —CH₂-cHx— |
| 3-1280 | Sub-55 | 4-ClPh | —CO— | —CH₂— | —CH₂-cHx— |
| 3-1281 | Sub-33 | 4-FPh | —CO— | —CH₂— | —CH₂— |
| 3-1282 | Sub-34 | 4-FPh | —CO— | —CH₂— | —CH₂— |
| 3-1283 | Sub-35 | 4-FPh | —CO— | —CH₂— | —CH₂— |
| 3-1284 | Sub-36 | 4-FPh | —CO— | —CH₂— | —CH₂— |
| 3-1285 | Sub-37 | 4-FPh | —CO— | —CH₂— | —CH₂— |
| 3-1286 | Sub-38 | 4-FPh | —CO— | —CH₂— | —CH₂— |
| 3-1287 | Sub-39 | 4-FPh | —CO— | —CH₂— | —CH₂— |
| 3-1288 | Sub-40 | 4-FPh | —CO— | —CH₂— | —CH₂— |
| 3-1289 | Sub-41 | 4-FPh | —CO— | —CH₂— | —CH₂— |
| 3-1290 | Sub-42 | 4-FPh | —CO— | —CH₂— | —CH₂— |
| 3-1291 | Sub-84 | 4-FPh | —CO— | —CH₂— | —CH₂— |
| 3-1292 | Sub-43 | 4-FPh | —CO— | —CH₂— | —CH₂— |
| 3-1293 | Sub-44 | 4-FPh | —CO— | —CH₂— | —CH₂— |
| 3-1294 | Sub-45 | 4-FPh | —CO— | —CH₂— | —CH₂— |
| 3-1295 | Sub-46 | 4-FPh | —CO— | —CH₂— | —CH₂— |
| 3-1296 | Sub-47 | 4-FPh | —CO— | —CH₂— | —CH₂— |
| 3-1297 | Sub-81 | 4-FPh | —CO— | —CH₂— | —CH₂— |
| 3-1298 | Sub-48 | 4-FPh | —CO— | —CH₂— | —CH₂— |
| 3-1299 | Sub-49 | 4-FPh | —CO— | —CH₂— | —CH₂— |
| 3-1300 | Sub-50 | 4-FPh | —CO— | —CH₂— | —CH₂— |
| 3-1301 | Sub-51 | 4-FPh | —CO— | —CH₂— | —CH₂— |
| 3-1302 | Sub-52 | 4-FPh | —CO— | —CH₂— | —CH₂— |
| 3-1303 | Sub-53 | 4-FPh | —CO— | —CH₂— | —CH₂— |
| 3-1304 | Sub-54 | 4-FPh | —CO— | —CH₂— | —CH₂— |
| 3-1305 | Sub-56 | 4-FPh | —CO— | —CH₂— | —CH₂— |
| 3-1306 | Sub-57 | 4-FPh | —CO— | —CH₂— | —CH₂— |
| 3-1307 | Sub-58 | 4-FPh | —CO— | —CH₂— | —CH₂— |
| 3-1308 | Sub-59 | 4-FPh | —CO— | —CH₂— | —CH₂— |
| 3-1309 | Sub-82 | 4-FPh | —CO— | —CH₂— | —CH₂— |
| 3-1310 | Sub-83 | 4-FPh | —CO— | —CH₂— | —CH₂— |
| 3-1311 | Sub-61 | 4-FPh | —CO— | —CH₂— | —CH₂— |
| 3-1312 | Sub-55 | 4-FPh | —CO— | —CH₂— | —CH₂— |
| 3-1313 | Sub-33 | 4-FPh | —CO— | —CH₂— | —CH₂CH₂— |
| 3-1314 | Sub-34 | 4-FPh | —CO— | —CH₂— | —CH₂CH₂— |
| 3-1315 | Sub-35 | 4-FPh | —CO— | —CH₂— | —CH₂CH₂— |
| 3-1316 | Sub-36 | 4-FPh | —CO— | —CH₂— | —CH₂CH₂— |
| 3-1317 | Sub-37 | 4-FPh | —CO— | —CH₂— | —CH₂CH₂— |
| 3-1318 | Sub-38 | 4-FPh | —CO— | —CH₂— | —CH₂CH₂— |
| 3-1319 | Sub-39 | 4-FPh | —CO— | —CH₂— | —CH₂CH₂— |
| 3-1320 | Sub-40 | 4-FPh | —CO— | —CH₂— | —CH₂CH₂— |
| 3-1321 | Sub-41 | 4-FPh | —CO— | —CH₂— | —CH₂CH₂— |
| 3-1322 | Sub-42 | 4-FPh | —CO— | —CH₂— | —CH₂CH₂— |
| 3-1323 | Sub-84 | 4-FPh | —CO— | —CH₂— | —CH₂CH₂— |
| 3-1324 | Sub-43 | 4-FPh | —CO— | —CH₂— | —CH₂CH₂— |
| 3-1325 | Sub-44 | 4-FPh | —CO— | —CH₂— | —CH₂CH₂— |
| 3-1326 | Sub-45 | 4-FPh | —CO— | —CH₂— | —CH₂CH₂— |
| 3-1327 | Sub-46 | 4-FPh | —CO— | —CH₂— | —CH₂CH₂— |
| 3-1328 | Sub-47 | 4-FPh | —CO— | —CH₂— | —CH₂CH₂— |
| 3-1329 | Sub-81 | 4-FPh | —CO— | —CH₂— | —CH₂CH₂— |
| 3-1330 | Sub-48 | 4-FPh | —CO— | —CH₂— | —CH₂CH₂— |
| 3-1331 | Sub-49 | 4-FPh | —CO— | —CH₂— | —CH₂CH₂— |
| 3-1332 | Sub-50 | 4-FPh | —CO— | —CH₂— | —CH₂CH₂— |
| 3-1333 | Sub-51 | 4-FPh | —CO— | —CH₂— | —CH₂CH₂— |
| 3-1334 | Sub-52 | 4-FPh | —CO— | —CH₂— | —CH₂CH₂— |
| 3-1335 | Sub-53 | 4-FPh | —CO— | —CH₂— | —CH₂CH₂— |
| 3-1336 | Sub-54 | 4-FPh | —CO— | —CH₂— | —CH₂CH₂— |
| 3-1337 | Sub-56 | 4-FPh | —CO— | —CH₂— | —CH₂CH₂— |
| 3-1338 | Sub-57 | 4-FPh | —CO— | —CH₂— | —CH₂CH₂— |
| 3-1339 | Sub-58 | 4-FPh | —CO— | —CH₂— | —CH₂CH₂— |
| 3-1340 | Sub-59 | 4-FPh | —CO— | —CH₂— | —CH₂CH₂— |
| 3-1341 | Sub-82 | 4-FPh | —CO— | —CH₂— | —CH₂CH₂— |
| 3-1342 | Sub-83 | 4-FPh | —CO— | —CH₂— | —CH₂CH₂— |
| 3-1343 | Sub-61 | 4-FPh | —CO— | —CH₂— | —CH₂CH₂— |
| 3-1344 | Sub-55 | 4-FPh | —CO— | —CH₂— | —CH₂CH₂— |
| 3-1345 | Sub-33 | 4-FPh | —CO— | —CH₂— | —(CH₂)₃— |
| 3-1346 | Sub-34 | 4-FPh | —CO— | —CH₂— | —(CH₂)₃— |
| 3-1347 | Sub-35 | 4-FPh | —CO— | —CH₂— | —(CH₂)₃— |
| 3-1348 | Sub-36 | 4-FPh | —CO— | —CH₂— | —(CH₂)₃— |
| 3-1349 | Sub-37 | 4-FPh | —CO— | —CH₂— | —(CH₂)₃— |
| 3-1350 | Sub-38 | 4-FPh | —CO— | —CH₂— | —(CH₂)₃— |

TABLE 3-continued

| Cpd. No. | R¹ | R² | A | B | E |
|---|---|---|---|---|---|
| 3-1351 | Sub-39 | 4-FPh | —CO— | —CH₂— | —(CH₂)₃— |
| 3-1352 | Sub-40 | 4-FPh | —CO— | —CH₂— | —(CH₂)₃— |
| 3-1353 | Sub-41 | 4-FPh | —CO— | —CH₂— | —(CH₂)₃— |
| 3-1354 | Sub-42 | 4-FPh | —CO— | —CH₂— | —(CH₂)₃— |
| 3-1355 | Sub-84 | 4-FPh | —CO— | —CH₂— | —(CH₂)₃— |
| 3-1356 | Sub-43 | 4-FPh | —CO— | —CH₂— | —(CH₂)₃— |
| 3-1357 | Sub-44 | 4-FPh | —CO— | —CH₂— | —(CH₂)₃— |
| 3-1358 | Sub-45 | 4-FPh | —CO— | —CH₂— | —(CH₂)₃— |
| 3-1359 | Sub-46 | 4-FPh | —CO— | —CH₂— | —(CH₂)₃— |
| 3-1360 | Sub-47 | 4-FPh | —CO— | —CH₂— | —(CH₂)₃— |
| 3-1361 | Sub-81 | 4-FPh | —CO— | —CH₂— | —(CH₂)₃— |
| 3-1362 | Sub-48 | 4-FPh | —CO— | —CH₂— | —(CH₂)₃— |
| 3-1363 | Sub-49 | 4-FPh | —CO— | —CH₂— | —(CH₂)₃— |
| 3-1364 | Sub-50 | 4-FPh | —CO— | —CH₂— | —(CH₂)₃— |
| 3-1365 | Sub-51 | 4-FPh | —CO— | —CH₂— | —(CH₂)₃— |
| 3-1366 | Sub-52 | 4-FPh | —CO— | —CH₂— | —(CH₂)₃— |
| 3-1367 | Sub-53 | 4-FPh | —CO— | —CH₂— | —(CH₂)₃— |
| 3-1368 | Sub-54 | 4-FPh | —CO— | —CH₂— | —(CH₂)₃— |
| 3-1369 | Sub-56 | 4-FPh | —CO— | —CH₂— | —(CH₂)₃— |
| 3-1370 | Sub-57 | 4-FPh | —CO— | —CH₂— | —(CH₂)₃— |
| 3-1371 | Sub-58 | 4-FPh | —CO— | —CH₂— | —(CH₂)₃— |
| 3-1372 | Sub-59 | 4-FPh | —CO— | —CH₂— | —(CH₂)₃— |
| 3-1373 | Sub-82 | 4-FPh | —CO— | —CH₂— | —(CH₂)₃— |
| 3-1374 | Sub-83 | 4-FPh | —CO— | —CH₂— | —(CH₂)₃— |
| 3-1375 | Sub-61 | 4-FPh | —CO— | —CH₂— | —(CH₂)₃— |
| 3-1376 | Sub-55 | 4-FPh | —CO— | —CH₂— | —(CH₂)₃— |
| 3-1377 | Sub-33 | 4-FPh | —CO— | —CH₂— | —CH₂C(Me)₂— |
| 3-1378 | Sub-34 | 4-FPh | —CO— | —CH₂— | —CH₂C(Me)₂— |
| 3-1379 | Sub-35 | 4-FPh | —CO— | —CH₂— | —CH₂C(Me)₂— |
| 3-1380 | Sub-36 | 4-FPh | —CO— | —CH₂— | —CH₂C(Me)₂— |
| 3-1381 | Sub-37 | 4-FPh | —CO— | —CH₂— | —CH₂C(Me)₂— |
| 3-1382 | Sub-38 | 4-FPh | —CO— | —CH₂— | —CH₂C(Me)₂— |
| 3-1383 | Sub-39 | 4-FPh | —CO— | —CH₂— | —CH₂C(Me)₂— |
| 3-1384 | Sub-40 | 4-FPh | —CO— | —CH₂— | —CH₂C(Me)₂— |
| 3-1385 | Sub-41 | 4-FPh | —CO— | —CH₂— | —CH₂C(Me)₂— |
| 3-1386 | Sub-42 | 4-FPh | —CO— | —CH₂— | —CH₂C(Me)₂— |
| 3-1387 | Sub-84 | 4-FPh | —CO— | —CH₂— | —CH₂C(Me)₂— |
| 3-1388 | Sub-43 | 4-FPh | —CO— | —CH₂— | —CH₂C(Me)₂— |
| 3-1389 | Sub-44 | 4-FPh | —CO— | —CH₂— | —CH₂C(Me)₂— |
| 3-1390 | Sub-45 | 4-FPh | —CO— | —CH₂— | —CH₂C(Me)₂— |
| 3-1391 | Sub-46 | 4-FPh | —CO— | —CH₂— | —CH₂C(Me)₂— |
| 3-1392 | Sub-47 | 4-FPh | —CO— | —CH₂— | —CH₂C(Me)₂— |
| 3-1393 | Sub-81 | 4-FPh | —CO— | —CH₂— | —CH₂C(Me)₂— |
| 3-1394 | Sub-48 | 4-FPh | —CO— | —CH₂— | —CH₂C(Me)₂— |
| 3-1395 | Sub-49 | 4-FPh | —CO— | —CH₂— | —CH₂C(Me)₂— |
| 3-1396 | Sub-50 | 4-FPh | —CO— | —CH₂— | —CH₂C(Me)₂— |
| 3-1397 | Sub-51 | 4-FPh | —CO— | —CH₂— | —CH₂C(Me)₂— |
| 3-1398 | Sub-52 | 4-FPh | —CO— | —CH₂— | —CH₂C(Me)₂— |
| 3-1399 | Sub-53 | 4-FPh | —CO— | —CH₂— | —CH₂C(Me)₂— |
| 3-1400 | Sub-54 | 4-FPh | —CO— | —CH₂— | —CH₂C(Me)₂— |
| 3-1401 | Sub-56 | 4-FPh | —CO— | —CH₂— | —CH₂C(Me)₂— |
| 3-1402 | Sub-57 | 4-FPh | —CO— | —CH₂— | —CH₂C(Me)₂— |
| 3-1403 | Sub-58 | 4-FPh | —CO— | —CH₂— | —CH₂C(Me)₂— |
| 3-1404 | Sub-59 | 4-FPh | —CO— | —CH₂— | —CH₂C(Me)₂— |
| 3-1405 | Sub-82 | 4-FPh | —CO— | —CH₂— | —CH₂C(Me)₂— |
| 3-1406 | Sub-83 | 4-FPh | —CO— | —CH₂— | —CH₂C(Me)₂— |
| 3-1407 | Sub-61 | 4-FPh | —CO— | —CH₂— | —CH₂C(Me)₂— |
| 3-1408 | Sub-55 | 4-FPh | —CO— | —CH₂— | —CH₂C(Me)₂— |
| 3-1409 | Sub-33 | 4-FPh | —CO— | —CH₂— | —CH₂-cPr— |
| 3-1410 | Sub-34 | 4-FPh | —CO— | —CH₂— | —CH₂-cPr— |
| 3-1411 | Sub-35 | 4-FPh | —CO— | —CH₂— | —CH₂-cPr— |
| 3-1412 | Sub-36 | 4-FPh | —CO— | —CH₂— | —CH₂-cPr— |
| 3-1413 | Sub-37 | 4-FPh | —CO— | —CH₂— | —CH₂-cPr— |
| 3-1414 | Sub-38 | 4-FPh | —CO— | —CH₂— | —CH₂-cPr— |
| 3-1415 | Sub-39 | 4-FPh | —CO— | —CH₂— | —CH₂-cPr— |
| 3-1416 | Sub-40 | 4-FPh | —CO— | —CH₂— | —CH₂-cPr— |
| 3-1417 | Sub-41 | 4-FPh | —CO— | —CH₂— | —CH₂-cPr— |
| 3-1418 | Sub-42 | 4-FPh | —CO— | —CH₂— | —CH₂-cPr— |
| 3-1419 | Sub-84 | 4-FPh | —CO— | —CH₂— | —CH₂-cPr— |
| 3-1420 | Sub-43 | 4-FPh | —CO— | —CH₂— | —CH₂-cPr— |
| 3-1421 | Sub-44 | 4-FPh | —CO— | —CH₂— | —CH₂-cPr— |
| 3-1422 | Sub-45 | 4-FPh | —CO— | —CH₂— | —CH₂-cPr— |
| 3-1423 | Sub-46 | 4-FPh | —CO— | —CH₂— | —CH₂-cPr— |
| 3-1424 | Sub-47 | 4-FPh | —CO— | —CH₂— | —CH₂-cPr— |
| 3-1425 | Sub-81 | 4-FPh | —CO— | —CH₂— | —CH₂-cPr— |
| 3-1426 | Sub-48 | 4-FPh | —CO— | —CH₂— | —CH₂-cPr— |

TABLE 3-continued

| Cpd. No. | R¹ | R² | A | B | E |
|---|---|---|---|---|---|
| 3-1427 | Sub-49 | 4-FPh | —CO— | —CH₂— | —CH₂-cPr— |
| 3-1428 | Sub-50 | 4-FPh | —CO— | —CH₂— | —CH₂-cPr— |
| 3-1429 | Sub-51 | 4-FPh | —CO— | —CH₂— | —CH₂-cPr— |
| 3-1430 | Sub-52 | 4-FPh | —CO— | —CH₂— | —CH₂-cPr— |
| 3-1431 | Sub-53 | 4-FPh | —CO— | —CH₂— | —CH₂-cPr— |
| 3-1432 | Sub-54 | 4-FPh | —CO— | —CH₂— | —CH₂-cPr— |
| 3-1433 | Sub-56 | 4-FPh | —CO— | —CH₂— | —CH₂-cPr— |
| 3-1434 | Sub-57 | 4-FPh | —CO— | —CH₂— | —CH₂-cPr— |
| 3-1435 | Sub-58 | 4-FPh | —CO— | —CH₂— | —CH₂-cPr— |
| 3-1436 | Sub-59 | 4-FPh | —CO— | —CH₂— | —CH₂-cPr— |
| 3-1437 | Sub-82 | 4-FPh | —CO— | —CH₂— | —CH₂-cPr— |
| 3-1438 | Sub-83 | 4-FPh | —CO— | —CH₂— | —CH₂-cPr— |
| 3-1439 | Sub-61 | 4-FPh | —CO— | —CH₂— | —CH₂-cPr— |
| 3-1440 | Sub-55 | 4-FPh | —CO— | —CH₂— | —CH₂-cPr— |
| 3-1441 | Sub-33 | 4-FPh | —CO— | —CH₂— | —CH₂-cBu— |
| 3-1442 | Sub-34 | 4-FPh | —CO— | —CH₂— | —CH₂-cBu— |
| 3-1443 | Sub-35 | 4-FPh | —CO— | —CH₂— | —CH₂-cBu— |
| 3-1444 | Sub-36 | 4-FPh | —CO— | —CH₂— | —CH₂-cBu— |
| 3-1445 | Sub-37 | 4-FPh | —CO— | —CH₂— | —CH₂-cBu— |
| 3-1446 | Sub-38 | 4-FPh | —CO— | —CH₂— | —CH₂-cBu— |
| 3-1447 | Sub-39 | 4-FPh | —CO— | —CH₂— | —CH₂-cBu— |
| 3-1448 | Sub-40 | 4-FPh | —CO— | —CH₂— | —CH₂-cBu— |
| 3-1449 | Sub-41 | 4-FPh | —CO— | —CH₂— | —CH₂-cBu— |
| 3-1450 | Sub-42 | 4-FPh | —CO— | —CH₂— | —CH₂-cBu— |
| 3-1451 | Sub-84 | 4-FPh | —CO— | —CH₂— | —CH₂-cBu— |
| 3-1452 | Sub-43 | 4-FPh | —CO— | —CH₂— | —CH₂-cBu— |
| 3-1453 | Sub-44 | 4-FPh | —CO— | —CH₂— | —CH₂-cBu— |
| 3-1454 | Sub-45 | 4-FPh | —CO— | —CH₂— | —CH₂-cBu— |
| 3-1455 | Sub-46 | 4-FPh | —CO— | —CH₂— | —CH₂-cBu— |
| 3-1456 | Sub-47 | 4-FPh | —CO— | —CH₂— | —CH₂-cBu— |
| 3-1457 | Sub-81 | 4-FPh | —CO— | —CH₂— | —CH₂-cBu— |
| 3-1458 | Sub-48 | 4-FPh | —CO— | —CH₂— | —CH₂-cBu— |
| 3-1459 | Sub-49 | 4-FPh | —CO— | —CH₂— | —CH₂-cBu— |
| 3-1460 | Sub-50 | 4-FPh | —CO— | —CH₂— | —CH₂-cBu— |
| 3-1461 | Sub-51 | 4-FPh | —CO— | —CH₂— | —CH₂-cBu— |
| 3-1462 | Sub-52 | 4-FPh | —CO— | —CH₂— | —CH₂-cBu— |
| 3-1463 | Sub-53 | 4-FPh | —CO— | —CH₂— | —CH₂-cBu— |
| 3-1464 | Sub-54 | 4-FPh | —CO— | —CH₂— | —CH₂-cBu— |
| 3-1465 | Sub-56 | 4-FPh | —CO— | —CH₂— | —CH₂-cBu— |
| 3-1466 | Sub-57 | 4-FPh | —CO— | —CH₂— | —CH₂-cBu— |
| 3-1467 | Sub-58 | 4-FPh | —CO— | —CH₂— | —CH₂cBu— |
| 3-1468 | Sub-59 | 4-FPh | —CO— | —CH₂— | —CH₂-cBu— |
| 3-1469 | Sub-82 | 4-FPh | —CO— | —CH₂— | —CH₂-cBu— |
| 3-1470 | Sub-83 | 4-FPh | —CO— | —CH₂— | —CH₂-cBu— |
| 3-1471 | Sub-61 | 4-FPh | —CO— | —CH₂— | —CH₂-cBu— |
| 3-1472 | Sub-55 | 4-FPh | —CO— | —CH₂— | —CH₂-cBu— |
| 3-1473 | Sub-33 | 4-FPh | —CO— | —CH₂— | —CH₂-cPn— |
| 3-1474 | Sub-34 | 4-FPh | —CO— | —CH₂— | —CH₂-cPn— |
| 3-1475 | Sub-35 | 4-FPh | —CO— | —CH₂— | —CH₂-cPn— |
| 3-1476 | Sub-36 | 4-FPh | —CO— | —CH₂— | —CH₂-cPn— |
| 3-1477 | Sub-37 | 4-FPh | —CO— | —CH₂— | —CH₂-cPn— |
| 3-1478 | Sub-38 | 4-FPh | —CO— | —CH₂— | —CH₂-cPn— |
| 3-1479 | Sub-39 | 4-FPh | —CO— | —CH₂— | —CH₂-cPn— |
| 3-1480 | Sub-40 | 4-FPh | —CO— | —CH₂— | —CH₂-cPn— |
| 3-1481 | Sub-41 | 4-FPh | —CO— | —CH₂— | —CH₂-cPn— |
| 3-1482 | Sub-42 | 4-FPh | —CO— | —CH₂— | —CH₂-cPn— |
| 3-1483 | Sub-84 | 4-FPh | —CO— | —CH₂— | —CH₂-cPn— |
| 3-1484 | Sub-43 | 4-FPh | —CO— | —CH₂— | —CH₂-cPn— |
| 3-1485 | Sub-44 | 4-FPh | —CO— | —CH₂— | —CH₂-cPn— |
| 3-1486 | Sub-45 | 4-FPh | —CO— | —CH₂— | —CH₂-cPn— |
| 3-1487 | Sub-46 | 4-FPh | —CO— | —CH₂— | —CH₂-cPn— |
| 3-1488 | Sub-47 | 4-FPh | —CO— | —CH₂— | —CH₂-cPn— |
| 3-1489 | Sub-81 | 4-FPh | —CO— | —CH₂— | —CH₂-cPn— |
| 3-1490 | Sub-48 | 4-FPh | —CO— | —CH₂— | —CH₂-cPn— |
| 3-1491 | Sub-49 | 4-FPh | —CO— | —CH₂— | —CH₂-cPn— |
| 3-1492 | Sub-50 | 4-FPh | —CO— | —CH₂— | —CH₂-cPn— |
| 3-1493 | Sub-51 | 4-FPh | —CO— | —CH₂— | —CH₂-cPn— |
| 3-1494 | Sub-52 | 4-FPh | —CO— | —CH₂— | —CH₂-cPn— |
| 3-1495 | Sub-53 | 4-FPh | —CO— | —CH₂— | —CH₂-cPn— |
| 3-1496 | Sub-54 | 4-FPh | —CO— | —CH₂— | —CH₂-cPn— |
| 3-1497 | Sub-56 | 4-FPh | —CO— | —CH₂— | —CH₂-cPn— |
| 3-1498 | Sub-57 | 4-FPh | —CO— | —CH₂— | —CH₂-cPn— |
| 3-1499 | Sub-58 | 4-FPh | —CO— | —CH₂— | —CH₂-cPn— |
| 3-1500 | Sub-59 | 4-FPh | —CO— | —CH₂— | —CH₂-cPn— |
| 3-1501 | Sub-82 | 4-FPh | —CO— | —CH₂— | —CH₂-cPn— |
| 3-1502 | Sub-83 | 4-FPh | —CO— | —CH₂— | —CH₂-cPn— |

TABLE 3-continued

| Cpd. No. | R¹ | R² | A | B | E |
|---|---|---|---|---|---|
| 3-1503 | Sub-61 | 4-FPh | —CO— | —CH$_2$— | —CH$_2$-cPn— |
| 3-1504 | Sub-55 | 4-FPh | —CO— | —CH$_2$— | —CH$_2$-cPn— |
| 3-1505 | Sub-33 | 4-FPh | —CO— | —CH$_2$— | —CH$_2$-cHx— |
| 3-1506 | Sub-34 | 4-FPh | —CO— | —CH$_2$— | —CH$_2$-cHx— |
| 3-1507 | Sub-35 | 4-FPh | —CO— | —CH$_2$— | —CH$_2$-cHx— |
| 3-1508 | Sub-36 | 4-FPh | —CO— | —CH$_2$— | —CH$_2$-cHx— |
| 3-1509 | Sub-37 | 4-FPh | —CO— | —CH$_2$— | —CH$_2$-cHx— |
| 3-1510 | Sub-38 | 4-FPh | —CO— | —CH$_2$— | —CH$_2$-cHx— |
| 3-1511 | Sub-39 | 4-FPh | —CO— | —CH$_2$— | —CH$_2$-cHx— |
| 3-1512 | Sub-40 | 4-FPh | —CO— | —CH$_2$— | —CH$_2$-cHx— |
| 3-1513 | Sub-41 | 4-FPh | —CO— | —CH$_2$— | —CH$_2$-cHx— |
| 3-1514 | Sub-42 | 4-FPh | —CO— | —CH$_2$— | —CH$_2$-cHx— |
| 3-1515 | Sub-84 | 4-FPh | —CO— | —CH$_2$— | —CH$_2$-cHx— |
| 3-1516 | Sub-43 | 4-FPh | —CO— | —CH$_2$— | —CH$_2$-cHx— |
| 3-1517 | Sub-44 | 4-FPh | —CO— | —CH$_2$— | —CH$_2$-cHx— |
| 3-1518 | Sub-45 | 4-FPh | —CO— | —CH$_2$— | —CH$_2$-cHx— |
| 3-1519 | Sub-46 | 4-FPh | —CO— | —CH$_2$— | —CH$_2$-cHx— |
| 3-1520 | Sub-47 | 4-FPh | —CO— | —CH$_2$— | —CH$_2$-cHx— |
| 3-1521 | Sub-81 | 4-FPh | —CO— | —CH$_2$— | —CH$_2$-cHx— |
| 3-1522 | Sub-48 | 4-FPh | —CO— | —CH$_2$— | —CH$_2$-cHx— |
| 3-1523 | Sub-49 | 4-FPh | —CO— | —CH$_2$— | —CH$_2$-cHx— |
| 3-1524 | Sub-50 | 4-FPh | —CO— | —CH$_2$— | —CH$_2$-cHx— |
| 3-1525 | Sub-51 | 4-FPh | —CO— | —CH$_2$— | —CH$_2$-cHx— |
| 3-1526 | Sub-52 | 4-FPh | —CO— | —CH$_2$— | —CH$_2$-cHx— |
| 3-1527 | Sub-53 | 4-FPh | —CO— | —CH$_2$— | —CH$_2$-cHx— |
| 3-1528 | Sub-54 | 4-FPh | —CO— | —CH$_2$— | —CH$_2$-cHx— |
| 3-1529 | Sub-56 | 4-FPh | —CO— | —CH$_2$— | —CH$_2$-cHx— |
| 3-1530 | Sub-57 | 4-FPh | —CO— | —CH$_2$— | —CH$_2$-cHx— |
| 3-1531 | Sub-58 | 4-FPh | —CO— | —CH$_2$— | —CH$_2$-cHx— |
| 3-1532 | Sub-59 | 4-FPh | —CO— | —CH$_2$— | —CH$_2$-cHx— |
| 3-1533 | Sub-82 | 4-FPh | —CO— | —CH$_2$— | —CH$_2$-cHx— |
| 3-1534 | Sub-83 | 4-FPh | —CO— | —CH$_2$— | —CH$_2$-cHx— |
| 3-1535 | Sub-61 | 4-FPh | —CO— | —CH$_2$— | —CH$_2$-cHx— |
| 3-1536 | Sub-55 | 4-FPh | —CO— | —CH$_2$— | —CH$_2$-cHx— |
| 3-1537 | Sub-33 | 3,4-diClPh | —CO— | Single Bond | —C(Me)$_2$— |
| 3-1538 | Sub-34 | 3,4-diClPh | —CO— | Single Bond | —C(Me)$_2$— |
| 3-1539 | Sub-35 | 3,4-diClPh | —CO— | Single Bond | —C(Me)$_2$— |
| 3-1540 | Sub-36 | 3,4-diClPh | —CO— | Single Bond | —C(Me)$_2$— |
| 3-1541 | Sub-37 | 3,4-diClPh | —CO— | Single Bond | —C(Me)$_2$— |
| 3-1542 | Sub-38 | 3,4-diClPh | —CO— | Single Bond | —C(Me)$_2$— |
| 3-1543 | Sub-39 | 3,4-diClPh | —CO— | Single Bond | —C(Me)$_2$— |
| 3-1544 | Sub-40 | 3,4-diClPh | —CO— | Single Bond | —C(Me)$_2$— |
| 3-1545 | Sub-41 | 3,4-diClPh | —CO— | Single Bond | —C(Me)$_2$— |
| 3-1546 | Sub-42 | 3,4-diClPh | —CO— | Single Bond | —C(Me)$_2$— |
| 3-1547 | Sub-84 | 3,4-diClPh | —CO— | Single Bond | —C(Me)$_2$— |
| 3-1548 | Sub-43 | 3,4-diClPh | —CO— | Single Bond | —C(Me)$_2$— |
| 3-1549 | Sub-44 | 3,4-diClPh | —CO— | Single Bond | —C(Me)$_2$— |
| 3-1550 | Sub-45 | 3,4-diClPh | —CO— | Single Bond | —C(Me)$_2$— |
| 3-1551 | Sub-46 | 3,4-diClPh | —CO— | Single Bond | —C(Me)$_2$— |
| 3-1552 | Sub-47 | 3,4-diClPh | —CO— | Single Bond | —C(Me)$_2$— |
| 3-1553 | Sub-81 | 3,4-diClPh | —CO— | Single Bond | —C(Me)$_2$— |
| 3-1554 | Sub-48 | 3,4-diClPh | —CO— | Single Bond | —C(Me)$_2$— |
| 3-1555 | Sub-49 | 3,4-diClPh | —CO— | Single Bond | —C(Me)$_2$— |
| 3-1556 | Sub-50 | 3,4-diClPh | —CO— | Single Bond | —C(Me)$_2$— |
| 3-1557 | Sub-51 | 3,4-diClPh | —CO— | Single Bond | —C(Me)$_2$— |
| 3-1558 | Sub-52 | 3,4-diClPh | —CO— | Single Bond | —C(Me)$_2$— |
| 3-1559 | Sub-53 | 3,4-diClPh | —CO— | Single Bond | —C(Me)$_2$— |
| 3-1560 | Sub-54 | 3,4-diClPh | —CO— | Single Bond | —C(Me)$_2$— |
| 3-1561 | Sub-56 | 3,4-diClPh | —CO— | Single Bond | —C(Me)$_2$— |
| 3-1562 | Sub-57 | 3,4-diClPh | —CO— | Single Bond | —C(Me)$_2$— |
| 3-1563 | Sub-58 | 3,4-diClPh | —CO— | Single Bond | —C(Me)$_2$— |
| 3-1564 | Sub-59 | 3,4-diClPh | —CO— | Single Bond | —C(Me)$_2$— |
| 3-1565 | Sub-82 | 3,4-diClPh | —CO— | Single Bond | —C(Me)$_2$— |
| 3-1566 | Sub-83 | 3,4-diClPh | —CO— | Single Bond | —C(Me)$_2$— |
| 3-1567 | Sub-61 | 3,4-diClPh | —CO— | Single Bond | —C(Me)$_2$— |
| 3-1568 | Sub-55 | 3,4-diClPh | —CO— | Single Bond | —C(Me)$_2$— |
| 3-1569 | Sub-33 | 3,4-diClPh | —CO— | —CH$_2$— | —C(Me)$_2$— |
| 3-1570 | Sub-34 | 3,4-diClPh | —CO— | —CH$_2$— | —C(Me)$_2$— |
| 3-1571 | Sub-35 | 3,4-diClPh | —CO— | —CH$_2$— | —C(Me)$_2$— |
| 3-1572 | Sub-36 | 3,4-diClPh | —CO— | —CH$_2$— | —C(Me)$_2$— |
| 3-1573 | Sub-37 | 3,4-diClPh | —CO— | —CH$_2$— | —C(Me)$_2$— |
| 3-1574 | Sub-38 | 3,4-diClPh | —CO— | —CH$_2$— | —C(Me)$_2$— |
| 3-1575 | Sub-39 | 3,4-diClPh | —CO— | —CH$_2$— | —C(Me)$_2$— |
| 3-1576 | Sub-40 | 3,4-diClPh | —CO— | —CH$_2$— | —C(Me)$_2$— |
| 3-1577 | Sub-41 | 3,4-diClPh | —CO— | —CH$_2$— | —C(Me)$_2$— |
| 3-1578 | Sub-42 | 3,4-diClPh | —CO— | —CH$_2$— | —C(Me)$_2$— |

TABLE 3-continued

| Cpd. No. | R¹ | R² | A | B | E |
|---|---|---|---|---|---|
| 3-1579 | Sub-84 | 3,4-diClPh | —CO— | —CH₂— | —C(Me)₂— |
| 3-1580 | Sub-43 | 3,4-diClPh | —CO— | —CH₂— | —C(Me)₂— |
| 3-1581 | Sub-44 | 3,4-diClPh | —CO— | —CH₂— | —C(Me)₂— |
| 3-1582 | Sub-45 | 3,4-diClPh | —CO— | —CH₂— | —C(Me)₂— |
| 3-1583 | Sub-46 | 3,4-diClPh | —CO— | —CH₂— | —C(Me)₂— |
| 3-1584 | Sub-47 | 3,4-diClPh | —CO— | —CH₂— | —C(Me)₂— |
| 3-1585 | Sub-81 | 3,4-diClPh | —CO— | —CH₂— | —C(Me)₂— |
| 3-1586 | Sub-48 | 3,4-diClPh | —CO— | —CH₂— | —C(Me)₂— |
| 3-1587 | Sub-49 | 3,4-diClPh | —CO— | —CH₂— | —C(Me)₂— |
| 3-1588 | Sub-50 | 3,4-diClPh | —CO— | —CH₂— | —C(Me)₂— |
| 3-1589 | Sub-51 | 3,4-diClPh | —CO— | —CH₂— | —C(Me)₂— |
| 3-1590 | Sub-52 | 3,4-diClPh | —CO— | —CH₂— | —C(Me)₂— |
| 3-1591 | Sub-53 | 3,4-diClPh | —CO— | —CH₂— | —C(Me)₂— |
| 3-1592 | Sub-54 | 3,4-diClPh | —CO— | —CH₂— | —C(Me)₂— |
| 3-1593 | Sub-56 | 3,4-diClPh | —CO— | —CH₂— | —C(Me)₂— |
| 3-1594 | Sub-57 | 3,4-diClPh | —CO— | —CH₂— | —C(Me)₂— |
| 3-1595 | Sub-58 | 3,4-diClPh | —CO— | —CH₂— | —C(Me)₂— |
| 3-1596 | Sub-59 | 3,4-diClPh | —CO— | —CH₂— | —C(Me)₂— |
| 3-1597 | Sub-82 | 3,4-diClPh | —CO— | —CH₂— | —C(Me)₂— |
| 3-1598 | Sub-83 | 3,4-diClPh | —CO— | —CH₂— | —C(Me)₂— |
| 3-1599 | Sub-61 | 3,4-diClPh | —CO— | —CH₂— | —C(Me)₂— |
| 3-1600 | Sub-55 | 3,4-diClPh | —CO— | —CH₂— | —C(Me)₂— |
| 3-1601 | Sub-33 | 4-ClPh | —CO— | Single Bond | —C(Me)₂— |
| 3-1602 | Sub-34 | 4-ClPh | —CO— | Single Bond | —C(Me)₂— |
| 3-1603 | Sub-35 | 4-ClPh | —CO— | Single Bond | —C(Me)₂— |
| 3-1604 | Sub-36 | 4-ClPh | —CO— | Single Bond | —C(Me)₂— |
| 3-1605 | Sub-37 | 4-ClPh | —CO— | Single Bond | —C(Me)₂— |
| 3-1606 | Sub-38 | 4-ClPh | —CO— | Single Bond | —C(Me)₂— |
| 3-1607 | Sub-39 | 4-ClPh | —CO— | Single Bond | —C(Me)₂— |
| 3-1608 | Sub-40 | 4-ClPh | —CO— | Single Bond | —C(Me)₂— |
| 3-1609 | Sub-41 | 4-ClPh | —CO— | Single Bond | —C(Me)₂— |
| 3-1610 | Sub-42 | 4-ClPh | —CO— | Single Bond | —C(Me)₂— |
| 3-1611 | Sub-84 | 4-ClPh | —CO— | Single Bond | —C(Me)₂— |
| 3-1612 | Sub-43 | 4-ClPh | —CO— | Single Bond | —C(Me)₂— |
| 3-1613 | Sub-44 | 4-ClPh | —CO— | Single Bond | —C(Me)₂— |
| 3-1614 | Sub-45 | 4-ClPh | —CO— | Single Bond | —C(Me)₂— |
| 3-1615 | Sub-46 | 4-ClPh | —CO— | Single Bond | —C(Me)₂— |
| 3-1616 | Sub-47 | 4-ClPh | —CO— | Single Bond | —C(Me)₂— |
| 3-1617 | Sub-81 | 4-ClPh | —CO— | Single Bond | —C(Me)₂— |
| 3-1618 | Sub-48 | 4-ClPh | —CO— | Single Bond | —C(Me)₂— |
| 3-1619 | Sub-49 | 4-ClPh | —CO— | Single Bond | —C(Me)₂— |
| 3-1620 | Sub-50 | 4-ClPh | —CO— | Single Bond | —C(Me)₂— |
| 3-1621 | Sub-51 | 4-ClPh | —CO— | Single Bond | —C(Me)₂— |
| 3-1622 | Sub-52 | 4-ClPh | —CO— | Single Bond | —C(Me)₂— |
| 3-1623 | Sub-53 | 4-ClPh | —CO— | Single Bond | —C(Me)₂— |
| 3-1624 | Sub-54 | 4-ClPh | —CO— | Single Bond | —C(Me)₂— |
| 3-1625 | Sub-56 | 4-ClPh | —CO— | Single Bond | —C(Me)₂— |
| 3-1626 | Sub-57 | 4-ClPh | —CO— | Single Bond | —C(Me)₂— |
| 3-1627 | Sub-58 | 4-ClPh | —CO— | Single Bond | —C(Me)₂— |
| 3-1628 | Sub-59 | 4-ClPh | —CO— | Single Bond | —C(Me)₂— |
| 3-1629 | Sub-82 | 4-ClPh | —CO— | Single Bond | —C(Me)₂— |
| 3-1630 | Sub-83 | 4-ClPh | —CO— | Single Bond | —C(Me)₂— |
| 3-1631 | Sub-61 | 4-ClPh | —CO— | Single Bond | —C(Me)₂— |
| 3-1632 | Sub-55 | 4-ClPh | —CO— | Single Bond | —C(Me)₂— |
| 3-1633 | Sub-33 | 4-ClPh | —CO— | —CH₂— | —C(Me)₂— |
| 3-1634 | Sub-34 | 4-ClPh | —CO— | —CH₂— | —C(Me)₂— |
| 3-1635 | Sub-35 | 4-ClPh | —CO— | —CH₂— | —C(Me)₂— |
| 3-1636 | Sub-36 | 4-ClPh | —CO— | —CH₂— | —C(Me)₂— |
| 3-1637 | Sub-37 | 4-ClPh | —CO— | —CH₂— | —C(Me)₂— |
| 3-1638 | Sub-38 | 4-ClPh | —CO— | —CH₂— | —C(Me)₂— |
| 3-1639 | Sub-39 | 4-ClPh | —CO— | —CH₂— | —C(Me)₂— |
| 3-1640 | Sub-40 | 4-ClPh | —CO— | —CH₂— | —C(Me)₂— |
| 3-1641 | Sub-41 | 4-ClPh | —CO— | —CH₂— | —C(Me)₂— |
| 3-1642 | Sub-42 | 4-ClPh | —CO— | —CH₂— | —C(Me)₂— |
| 3-1643 | Sub-84 | 4-ClPh | —CO— | —CH₂— | —C(Me)₂— |
| 3-1644 | Sub-43 | 4-ClPh | —CO— | —CH₂— | —Cl(Me)₂— |
| 3-1645 | Sub-44 | 4-ClPh | —CO— | —CH₂— | —C(Me)₂— |
| 3-1646 | Sub-45 | 4-ClPh | —CO— | —CH₂— | —C(Me)₂— |
| 3-1647 | Sub-46 | 4-ClPh | —CO— | —CH₂— | —C(Me)₂— |
| 3-1648 | Sub-47 | 4-ClPh | —CO— | —CH₂— | —C(Me)₂— |
| 3-1649 | Sub-81 | 4-ClPh | —CO— | —CH₂— | —C(Me)₂— |
| 3-1650 | Sub-48 | 4-ClPh | —CO— | —CH₂— | —C(Me)₂— |
| 3-1651 | Sub-49 | 4-ClPh | —CO— | —CH₂— | —C(Me)₂— |
| 3-1652 | Sub-50 | 4-ClPh | —CO— | —CH₂— | —C(Me)₂— |
| 3-1653 | Sub-51 | 4-ClPh | —CO— | —CH₂— | —C(Me)₂— |
| 3-1654 | Sub-52 | 4-ClPh | —CO— | —CH₂— | —C(Me)₂— |

TABLE 3-continued

| Cpd. No. | R¹ | R² | A | B | E |
|---|---|---|---|---|---|
| 3-1655 | Sub-53 | 4-ClPh | —CO— | —CH₂— | —C(Me)₂— |
| 3-1656 | Sub-54 | 4-ClPh | —CO— | —CH₂— | —C(Me)₂— |
| 3-1657 | Sub-56 | 4-ClPh | —CO— | —CH₂— | —C(Me)₂— |
| 3-1658 | Sub-57 | 4-ClPh | —CO— | —CH₂— | —C(Me)₂— |
| 3-1659 | Sub-58 | 4-ClPh | —CO— | —CH₂— | —C(Me)₂— |
| 3-1660 | Sub-59 | 4-ClPh | —CO— | —CH₂— | —C(Me)₂— |
| 3-1661 | Sub-82 | 4-ClPh | —CO— | —CH₂— | —C(Me)₂— |
| 3-1662 | Sub-83 | 4-ClPh | —CO— | —CH₂— | —C(Me)₂— |
| 3-1663 | Sub-61 | 4-ClPh | —CO— | —CH₂— | —C(Me)₂— |
| 3-1664 | Sub-55 | 4-ClPh | —CO— | —CH₂— | —C(Me)₂— |
| 3-1665 | Sub-33 | 4-FPh | —CO— | Single Bond | —C(Me)₂— |
| 3-1666 | Sub-34 | 4-FPh | —CO— | Single Bond | —C(Me)₂— |
| 3-1667 | Sub-35 | 4-FPh | —CO— | Single Bond | —C(Me)₂— |
| 3-1668 | Sub-36 | 4-FPh | —CO— | Single Bond | —C(Me)₂— |
| 3-1669 | Sub-37 | 4-FPh | —CO— | Single Bond | —C(Me)₂— |
| 3-1670 | Sub-38 | 4-FPh | —CO— | Single Bond | —C(Me)₂— |
| 3-1671 | Suh-39 | 4-FPh | —CO— | Single Bond | —C(Me)₂— |
| 3-1672 | Sub-40 | 4-FPh | —CO— | Single Bond | —C(Me)₂— |
| 3-1673 | Sub-41 | 4-FPh | —CO— | Single Bond | —C(Me)₂— |
| 3-1674 | Sub-42 | 4-FPh | —CO— | Single Bond | —C(Me)₂— |
| 3-1675 | Sub-84 | 4-FPh | —CO— | Single Bond | —C(Me)₂— |
| 3-1676 | Sub-43 | 4-FPh | —CO— | Single Bond | —C(Me)₂— |
| 3-1677 | Sub-44 | 4-FPh | —CO— | Single Bond | —C(Me)₂— |
| 3-1678 | Sub-45 | 4-FPh | —CO— | Single Bond | —C(Me)₂— |
| 3-1679 | Sub-46 | 4-FPh | —CO— | Single Bond | —C(Me)₂— |
| 3-1680 | Sub-47 | 4-FPh | —CO— | Single Bond | —C(Me)₂— |
| 3-1681 | Sub-81 | 4-FPh | —CO— | Single Bond | —C(Me)₂— |
| 3-1682 | Sub-48 | 4-FPh | —CO— | Single Bond | —C(Me)₂— |
| 3-1683 | Sub-49 | 4-FPh | —CO— | Single Bond | —C(Me)₂— |
| 3-1684 | Sub-50 | 4-FPh | —CO— | Single Bond | —C(Me)₂— |
| 3-1685 | Sub-51 | 4-FPh | —CO— | Single Bond | —C(Me)₂— |
| 3-1686 | Sub-52 | 4-FPh | —CO— | Single Bond | —C(Me)₂— |
| 3-1687 | Sub-53 | 4-FPh | —CO— | Single Bond | —C(Me)₂— |
| 3-1688 | Sub-54 | 4-FPh | —CO— | Single Bond | —C(Me)₂— |
| 3-1689 | Sub-56 | 4-FPh | —CO— | Single Bond | —C(Me)₂— |
| 3-1690 | Sub-57 | 4-FPh | —CO— | Single Bond | —C(Me)₂— |
| 3-1691 | Sub-58 | 4-FPh | —CO— | Single Bond | —C(Me)₂— |
| 3-1692 | Sub-59 | 4-FPh | —CO— | Single Bond | —C(Me)₂— |
| 3-1693 | Sub-82 | 4-FPh | —CO— | Single Bond | —C(Me)₂— |
| 3-1694 | Sub-83 | 4-FPh | —CO— | Single Bond | —C(Me)₂— |
| 3-1695 | Sub-61 | 4-FPh | —CO— | Single Bond | —C(Me)₂— |
| 3-1696 | Sub-55 | 4-FPh | —CO— | Single Bond | —C(Me)₂— |
| 3-1697 | Sub-33 | 4-FPh | —CO— | —CH₂— | —C(Me)₂— |
| 3-1698 | Sub-34 | 4-FPh | —CO— | —CH₂— | —C(Me)₂— |
| 3-1699 | Sub-35 | 4-FPh | —CO— | —CH₂— | —C(Me)₂— |
| 3-1700 | Sub-36 | 4-FPh | —CO— | —CH₂— | —C(Me)₂— |
| 3-1701 | Sub-37 | 4-FPh | —CO— | —CH₂— | —C(Me)₂— |
| 3-1702 | Sub-38 | 4-FPh | —CO— | —CH₂— | —C(Me)₂— |
| 3-1703 | Sub-39 | 4-FPh | —CO— | —CH₂— | —C(Me)₂— |
| 3-1704 | Sub-40 | 4-FPh | —CO— | —CH₂— | —C(Me)₂— |
| 3-1705 | Sub-41 | 4-FPh | —CO— | —CH₂— | —C(Me)₂— |
| 3-1706 | Sub-42 | 4-FPh | —CO— | —CH₂— | —C(Me)₂— |
| 3-1707 | Sub-84 | 4-FPh | —CO— | —CH₂— | —C(Me)₂— |
| 3-1708 | Sub-43 | 4-FPh | —CO— | —CH₂— | —C(Me)₂— |
| 3-1709 | Sub-44 | 4-FPh | —CO— | —CH₂— | —C(Me)₂— |
| 3-1710 | Sub-45 | 4-FPh | —CO— | —CH₂— | —C(Me)₂— |
| 3-1711 | Sub-46 | 4-FPh | —CO— | —CH₂— | —C(Me)₂— |
| 3-1712 | Sub-47 | 4-FPh | —CO— | —CH₂— | —C(Me)₂— |
| 3-1713 | Sub-81 | 4-FPh | —CO— | —CH₂— | —C(Me)₂— |
| 3-1714 | Sub-48 | 4-FPh | —CO— | —CH₂— | —C(Me)₂— |
| 3-1715 | Sub-49 | 4-FPh | —CO— | —CH₂— | —C(Me)₂— |
| 3-1716 | Sub-50 | 4-FPh | —CO— | —CH₂— | —C(Me)₂— |
| 3-1717 | Sub-51 | 4-FPh | —CO— | —CH₂— | —C(Me)₂— |
| 3-1718 | Sub-52 | 4-FPh | —CO— | —CH₂— | —C(Me)₂— |
| 3-1719 | Sub-53 | 4-FPh | —CO— | —CH₂— | —C(Me)₂— |
| 3-1720 | Sub-54 | 4-FPh | —CO— | —CH₂— | —C(Me)₂— |
| 3-1721 | Sub-56 | 4-FPh | —CO— | —CH₂— | —C(Me)₂— |
| 3-1722 | Sub-57 | 4-FPh | —CO— | —CH₂— | —C(Me)₂— |
| 3-1723 | Sub-58 | 4-FPh | —CO— | —CH₂— | —C(Me)₂— |
| 3-1724 | Sub-59 | 4-FPh | —CO— | —CH₂— | —C(Me)₂— |
| 3-1725 | Sub-82 | 4-FPh | —CO— | —CH₂— | —C(Me)₂— |
| 3-1726 | Sub-83 | 4-FPh | —CO— | —CH₂— | —C(Me)₂— |
| 3-1727 | Sub-61 | 4-FPh | —CO— | —CH₂— | —C(Me)₂— |
| 3-1728 | Sub-55 | 4-FPh | —CO— | —CH₂— | —C(Me)₂— |
| 3-1729 | Sub-37 | 3,4-diClPh | —CH₂— | Single Bond | —CH₂— |
| 3-1730 | Sub-38 | 3,4-diClPh | —CH₂— | Single Bond | —CH₂— |

TABLE 3-continued

| Cpd. No. | R¹ | R² | A | B | E |
|---|---|---|---|---|---|
| 3-1731 | Sub-39 | 3,4-diClPh | —CH₂— | Single Bond | —CH₂— |
| 3-1732 | Sub-40 | 3,4-diClPh | —CH₂— | Single Bond | —CH₂— |
| 3-1733 | Sub-41 | 3,4-diClPh | —CH₂— | Single Bond | —CH₂— |
| 3-1734 | Sub-42 | 3,4-diClPh | —CH₂— | Single Bond | —CH₂— |
| 3-1735 | Sub-84 | 3,4-diClPh | —CH₂— | Single Bond | —CH₂— |
| 3-1736 | Sub-81 | 3,4-diClPh | —CH₂— | Single Bond | —CH₂— |
| 3-1737 | Sub-48 | 3,4-diClPh | —CH₂— | Single Bond | —CH₂— |
| 3-1738 | Sub-37 | 4-ClPh | —CH₂— | Single Bond | —CH₂— |
| 3-1739 | Sub-38 | 4-ClPh | —CH₂— | Single Bond | —CH₂— |
| 3-1740 | Sub-39 | 4-ClPh | —CH₂— | Single Bond | —CH₂— |
| 3-1741 | Sub-40 | 4-ClPh | —CH₂— | Single Bond | —CH₂— |
| 3-1742 | Sub-41 | 4-ClPh | —CH₂— | Single Bond | —CH₂— |
| 3-1743 | Sub-42 | 4-ClPh | —CH₂— | Single Bond | —CH₂— |
| 3-1744 | Sub-84 | 4-ClPh | —CH₂— | Single Bond | —CH₂— |
| 3-1745 | Sub-81 | 4-ClPh | —CH₂— | Single Bond | —CH₂— |
| 3-1746 | Sub-48 | 4-ClPh | —CH₂— | Single Bond | —CH₂— |
| 3-1747 | Sub-37 | 4-FPh | —CH₂— | Single Bond | —CH₂— |
| 3-1748 | Sub-38 | 4-FPh | —CH₂— | Single Bond | —CH₂— |
| 3-1749 | Sub-39 | 4-FPh | —CH₂— | Single Bond | —CH₂— |
| 3-1750 | Sub-40 | 4-FPh | —CH₂— | Single Bond | —CH₂— |
| 3-1751 | Sub-41 | 4-FPh | —CH₂— | Single Bond | —CH₂— |
| 3-1752 | Sub-42 | 4-FPh | —CH₂— | Single Bond | —CH₂— |
| 3-1753 | Sub-84 | 4-FPh | —CH₂— | Single Bond | —CH₂— |
| 3-1754 | Sub-81 | 4-FPh | —CH₂— | Single Bond | —CH₂— |
| 3-1755 | Sub-48 | 4-FPh | —CH₂— | Single Bond | —CH₂— |
| 3-1756 | Sub-37 | 3,4-diClPh | —CH₂— | Single Bond | —CH₂CH₂— |
| 3-1757 | Sub-38 | 3,4-diClPh | —CH₂— | Single Bond | —CH₂CH₂— |
| 3-1758 | Sub-39 | 3,4-diClPh | —CH₂— | Single Bond | —CH₂CH₂— |
| 3-1759 | Sub-40 | 3,4-diClPh | —CH₂— | Single Bond | —CH₂CH₂— |
| 3-1760 | Sub-41 | 3,4-diClPh | —CH₂— | Single Bond | —CH₂CH₂— |
| 3-1761 | Sub-42 | 3,4-diClPh | —CH₂— | Single Bond | —CH₂CH₂— |
| 3-1762 | Sub-84 | 3,4-diClPh | —CH₂— | Single Bond | —CH₂CH₂— |
| 3-1763 | Sub-81 | 3,4-diClPh | —CH₂— | Single Bond | —CH₂CH₂— |
| 3-1764 | Sub-48 | 3,4-diClPh | —CH₂— | Single Bond | —CH₂CH₂— |
| 3-1765 | Sub-37 | 4-ClPh | —CH₂— | Single Bond | —CH₂CH₂— |
| 3-1766 | Sub-38 | 4-ClPh | —CH₂— | Single Bond | —CH₂CH₂— |
| 3-1767 | Sub-39 | 4-ClPh | —CH₂— | Single Bond | —CH₂CH₂— |
| 3-1768 | Sub-40 | 4-ClPh | —CH₂— | Single Bond | —CH₂CH₂— |
| 3-1769 | Sub-41 | 4-ClPh | —CH₂— | Single Bond | —CH₂CH₂— |
| 3-1770 | Sub-42 | 4-ClPh | —CH₂— | Single Bond | —CH₂CH₂— |
| 3-1771 | Sub-84 | 4-ClPh | —CH₂— | Single Bond | —CH₂CH₂— |
| 3-1772 | Sub-81 | 4-ClPh | —CH₂— | Single Bond | —CH₂CH₂— |
| 3-1773 | Sub-48 | 4-ClPh | —CH₂— | Single Bond | —CH₂CH₂— |
| 3-1774 | Sub-37 | 4-FPh | —CH₂— | Single Bond | —CH₂CH₂— |
| 3-1775 | Sub-38 | 4-FPh | —CH₂— | Single Bond | —CH₂CH₂— |
| 3-1776 | Sub-39 | 4-FPh | —CH₂— | Single Bond | —CH₂CH₂— |
| 3-1777 | Sub-40 | 4-FPh | —CH₂— | Single Bond | —CH₂CH₂— |
| 3-1778 | Sub-41 | 4-FPh | —CH₂— | Single Bond | —CH₂CH₂— |
| 3-1779 | Sub-42 | 4-FPh | —CH₂— | Single Bond | —CH₂CH₂— |
| 3-1780 | Sub-84 | 4-FPh | —CH₂— | Single Bond | —CH₂CH₂— |
| 3-1781 | Sub-81 | 4-FPh | —CH₂— | Single Bond | —CH₂CH₂— |
| 3-1782 | Sub-48 | 4-FPh | —CH₂— | Single Bond | —CH₂CH₂— |
| 3-1783 | Sub-37 | 3,4-diClPh | —CH₂— | Single Bond | —(CH₂)₃— |
| 3-1784 | Sub-38 | 3,4-diClPh | —CH₂— | Single Bond | —(CH₂)₃— |
| 3-1785 | Sub-39 | 3,4-diClPh | —CH₂— | Single Bond | —(CH₂)₃— |
| 3-1786 | Sub-40 | 3,4-diClPh | —CH₂— | Single Bond | —(CH₂)₃— |
| 3-1787 | Sub-41 | 3,4-diClPh | —CH₂— | Single Bond | —(CH₂)₃— |
| 3-1788 | Sub-42 | 3,4-diClPh | —CH₂— | Single Bond | —(CH₂)₃— |
| 3-1789 | Sub-84 | 3,4-diClPh | —CH₂— | Single Bond | —(CH₂)₃— |
| 3-1790 | Sub-81 | 3,4-diClPh | —CH₂— | Single Bond | —(CH₂)₃— |
| 3-1791 | Sub-48 | 3,4-diClPh | —CH₂— | Single Bond | —(CH₂)₃— |
| 3-1792 | Sub-37 | 4-ClPh | —CH₂— | Single Bond | —(CH₂)₃— |
| 3-1793 | Sub-38 | 4-ClPh | —CH₂— | Single Bond | —(CH₂)₃— |
| 3-1794 | Sub-39 | 4-ClPh | —CH₂— | Single Bond | —(CH₂)₃— |
| 3-1795 | Sub-40 | 4-ClPh | —CH₂— | Single Bond | —(CH₂)₃— |
| 3-1796 | Sub-41 | 4-ClPh | —CH₂— | Single Bond | —(CH₂)₃— |
| 3-1797 | Sub-42 | 4-ClPh | —CH₂— | Single Bond | —(CH₂)₃— |
| 3-1798 | Sub-84 | 4-ClPh | —CH₂— | Single Bond | —(CH₂)₃— |
| 3-1799 | Sub-81 | 4-ClPh | —CH₂— | Single Bond | —(CH₂)₃— |
| 3-1800 | Sub-48 | 4-ClPh | —CH₂— | Single Bond | —(CH₂)₃— |
| 3-1801 | Sub-37 | 4-FPh | —CH₂— | Single Bond | —(CH₂)₃— |
| 3-1802 | Sub-38 | 4-FPh | —CH₂— | Single Bond | —(CH₂)₃— |
| 3-1803 | Sub-39 | 4-FPh | —CH₂— | Single Bond | —(CH₂)₃— |
| 3-1804 | Sub-40 | 4-FPh | —CH₂— | Single Bond | —(CH₂)₃— |
| 3-1805 | Sub-41 | 4-FPh | —CH₂— | Single Bond | —(CH₂)₃— |
| 3-1806 | Sub-42 | 4-FPh | —CH₂— | Single Bond | —(CH₂)₃— |

TABLE 3-continued

| Cpd. No. | R¹ | R² | A | B | E |
|---|---|---|---|---|---|
| 3-1807 | Sub-84 | 4-FPh | —CH₂— | Single Bond | —(CH₂)₃— |
| 3-1808 | Sub-81 | 4-FPh | —CH₂— | Single Bond | —(CH₂)₃— |
| 3-1809 | Sub-48 | 4-FPh | —CH₂— | Single Bond | —(CH₂)₃— |
| 3-1810 | Sub-37 | 3,4-diClPh | —CH₂— | Single Bond | —CH₂C(Me)₂— |
| 3-1811 | Sub-38 | 3,4-diClPh | —CH₂— | Single Bond | —CH₂C(Me)₂— |
| 3-1812 | Sub-39 | 3,4-diClPh | —CH₂— | Single Bond | —CH₂C(Me)₂— |
| 3-1813 | Sub-40 | 3,4-diClPh | —CH₂— | Single Bond | —CH₂C(Me)₂— |
| 3-1814 | Sub-41 | 3,4-diClPh | —CH₂— | Single Bond | —CH₂C(Me)₂— |
| 3-1815 | Sub-42 | 3,4-diClPh | —CH₂— | Single Bond | —CH₂C(Me)₂— |
| 3-1816 | Sub-84 | 3,4-diClPh | —CH₂— | Single Bond | —CH₂C(Me)₂— |
| 3-1817 | Sub-81 | 3,4-diClPh | —CH₂— | Single Bond | —CH₂C(Me)₂— |
| 3-1818 | Sub-48 | 3,4-diClPh | —CH₂— | Single Bond | —CH₂C(Me)₂— |
| 3-1819 | Sub-37 | 4-ClPh | —CH₂— | Single Bond | —CH₂C(Me)₂— |
| 3-1820 | Sub-38 | 4-ClPh | —CH₂— | Single Bond | —CH₂C(Me)₂— |
| 3-1821 | Sub-39 | 4-ClPh | —CH₂— | Single Bond | —CH₂C(Me)₂— |
| 3-1822 | Sub-40 | 4-ClPh | —CH₂— | Single Bond | —CH₂C(Me)₂— |
| 3-1823 | Sub-41 | 4-ClPh | —CH₂— | Single Bond | —CH₂C(Me)₂— |
| 3-1824 | Sub-42 | 4-ClPh | —CH₂— | Single Bond | —CH₂C(Me)₂— |
| 3-1825 | Sub-84 | 4-ClPh | —CH₂— | Single Bond | —CH₂C(Me)₂— |
| 3-1826 | Sub-81 | 4-ClPh | —CH₂— | Single Bond | —CH₂C(Me)₂— |
| 3-1827 | Sub-48 | 4-ClPh | —CH₂— | Single Bond | —CH₂C(Me)₂— |
| 3-1828 | Sub-37 | 4-FPh | —CH₂— | Single Bond | —CH₂C(Me)₂— |
| 3-1829 | Sub-38 | 4-FPh | —CH₂— | Single Bond | —CH₂C(Me)₂— |
| 3-1830 | Sub-39 | 4-FPh | —CH₂— | Single Bond | —CH₂C(Me)₂— |
| 3-1831 | Sub-40 | 4-FPh | —CH₂— | Single Bond | —CH₂C(Me)₂— |
| 3-1832 | Sub-41 | 4-FPh | —CH₂— | Single Bond | —CH₂C(Me)₂— |
| 3-1833 | Sub-42 | 4-FPh | —CH₂— | Single Bond | —CH₂C(Me)₂— |
| 3-1834 | Sub-84 | 4-FPh | —CH₂— | Single Bond | —CH₂C(Me)₂— |
| 3-1835 | Sub-81 | 4-FPh | —CH₂— | Single Bond | —CH₂C(Me)₂— |
| 3-1836 | Sub-48 | 4-FPh | —CH₂— | Single Bond | —CH₂C(Me)₂— |
| 3-1837 | Sub-37 | 3,4-diClPh | —CH₂— | Single Bond | —CH₂-cPr— |
| 3-1838 | Sub-38 | 3,4-diClPh | —CH₂— | Single Bond | —CH₂-cPr— |
| 3-1839 | Sub-39 | 3,4-diClPh | —CH₂— | Single Bond | —CH₂-cPr— |
| 3-1840 | Sub-40 | 3,4-diClPh | —CH₂— | Single Bond | —CH₂-cPr— |
| 3-1841 | Sub-41 | 3,4-diClPh | —CH₂— | Single Bond | —CH₂-cPr— |
| 3-1842 | Sub-42 | 3,4-diClPh | —CH₂— | Single Bond | —CH₂-cPr— |
| 3-1843 | Sub-84 | 3,4-diClPh | —CH₂— | Single Bond | —CH₂-cPr— |
| 3-1844 | Sub-81 | 3,4-diClPh | —CH₂— | Single Bond | —CH₂-cPr— |
| 3-1845 | Sub-48 | 3,4-diClPh | —CH₂— | Single Bond | —CH₂-cPr— |
| 3-1846 | Sub-37 | 4-ClPh | —CH₂— | Single Bond | —CH₂-cPr— |
| 3-1847 | Sub-38 | 4-ClPh | —CH₂— | Single Bond | —CH₂-cPr— |
| 3-1848 | Sub-39 | 4-ClPh | —CH₂— | Single Bond | —CH₂-cPr— |
| 3-1849 | Sub-40 | 4-ClPh | —CH₂— | Single Bond | —CH₂-cPr— |
| 3-1850 | Sub-41 | 4-ClPh | —CH₂— | Single Bond | —CH₂-cPr— |
| 3-1851 | Sub-42 | 4-ClPh | —CH₂— | Single Bond | —CH₂-cPr— |
| 3-1852 | Sub-84 | 4-ClPh | —CH₂— | Single Bond | —CH₂-cPr— |
| 3-1853 | Sub-81 | 4-ClPh | —CH₂— | Single Bond | —CH₂-cPr— |
| 3-1854 | Sub-48 | 4-ClPh | —CH₂— | Single Bond | —CH₂-cPr— |
| 3-1855 | Sub-37 | 4-FPh | —CH₂— | Single Bond | —CH₂-cPr— |
| 3-1856 | Sub-38 | 4-FPh | —CH₂— | Single Bond | —CH₂-cPr— |
| 3-1857 | Sub-39 | 4-FPh | —CH₂— | Single Bond | —CH₂-cPr— |
| 3-1858 | Sub-40 | 4-FPh | —CH₂— | Single Bond | —CH₂-cPr— |
| 3-1859 | Sub-41 | 4-FPh | —CH₂— | Single Bond | —CH₂-cPr— |
| 3-1860 | Sub-42 | 4-FPh | —CH₂— | Single Bond | —CH₂-cPr— |
| 3-1861 | Sub-84 | 4-FPh | —CH₂— | Single Bond | —CH₂-cPr— |
| 3-1862 | Sub-81 | 4-FPh | —CH₂— | Single Bond | —CH₂-cPr— |
| 3-1863 | Sub-48 | 4-FPh | —CH₂— | Single Bond | —CH₂-cPr— |
| 3-1864 | Sub-37 | 3,4-diClPh | —CH₂— | Single Bond | —C(Me)₂— |
| 3-1865 | Sub-38 | 3,4-diClPh | —CH₂— | Single Bond | —C(Me)₂— |
| 3-1866 | Sub-39 | 3,4-diClPh | —CH₂— | Single Bond | —C(Me)₂— |
| 3-1867 | Sub-40 | 3,4-diClPh | —CH₂— | Single Bond | —C(Me)₂— |
| 3-1868 | Sub-41 | 3,4-diClPh | —CH₂— | Single Bond | —C(Me)₂— |
| 3-1869 | Sub-42 | 3,4-diClPh | —CH₂— | Single Bond | —C(Me)₂— |
| 3-1870 | Sub-84 | 3,4-diClPh | —CH₂— | Single Bond | —C(Me)₂— |
| 3-1871 | Sub-81 | 3,4-diClPh | —CH₂— | Single Bond | —C(Me)₂— |
| 3-1872 | Sub-48 | 3,4-diClPh | —CH₂— | Single Bond | —C(Me)₂— |
| 3-1873 | Sub-37 | 4-ClPh | —CH₂— | Single Bond | —C(Me)₂— |
| 3-1874 | Sub-38 | 4-ClPh | —CH₂— | Single Bond | —C(Me)₂— |
| 3-1875 | Sub-39 | 4-ClPh | —CH₂— | Single Bond | —C(Me)₂— |
| 3-1876 | Sub-40 | 4-ClPh | —CH₂— | Single Bond | —C(Me)₂— |
| 3-1877 | Sub-41 | 4-ClPh | —CH₂— | Single Bond | —C(Me)₂— |
| 3-1878 | Sub-42 | 4-ClPh | —CH₂— | Single Bond | —C(Me)₂— |
| 3-1879 | Sub-84 | 4-ClPh | —CH₂— | Single Bond | —C(Me)₂— |
| 3-1880 | Sub-81 | 4-ClPh | —CH₂— | Single Bond | —C(Me)₂— |
| 3-1881 | Sub-48 | 4-ClPh | —CH₂— | Single Bond | —C(Me)₂— |
| 3-1882 | Sub-37 | 4-FPh | —CH₂— | Single Bond | —C(Me)₂— |

TABLE 3-continued

| Cpd. No. | R¹ | R² | A | B | E |
|---|---|---|---|---|---|
| 3-1883 | Sub-38 | 4-FPh | —CH₂— | Single Bond | —C(Me)₂— |
| 3-1884 | Sub-39 | 4-FPh | —CH₂— | Single Bond | —C(Me)₂— |
| 3-1885 | Sub-40 | 4-FPh | —CH₂— | Single Bond | —C(Me)₂— |
| 3-1886 | Sub-41 | 4-FPh | —CH₂— | Single Bond | —C(Me)₂— |
| 3-1887 | Sub-42 | 4-FPh | —CH₂— | Single Bond | —C(Me)₂— |
| 3-1888 | Sub-84 | 4-FPh | —CH₂— | Single Bond | —C(Me)₂— |
| 3-1889 | Sub-81 | 4-FPh | —CH₂— | Single Bond | —C(Me)₂— |
| 3-1890 | Sub-48 | 4-FPh | —CH₂— | Single Bond | —C(Me)₂— |
| 3-1891 | Sub-37 | 3,4-diClPh | —CH₂— | —CH₂— | —CH₂— |
| 3-1892 | Sub-38 | 3,4-diClPh | —CH₂— | —CH₂— | —CH₂— |
| 3-1893 | Sub-39 | 3,4-diClPh | —CH₂— | —CH₂— | —CH₂— |
| 3-1894 | Sub-40 | 3,4-diClPh | —CH₂— | —CH₂— | —CH₂— |
| 3-1895 | Sub-41 | 3,4-diClPh | —CH₂— | —CH₂— | —CH₂— |
| 3-1896 | Sub-42 | 3,4-diClPh | —CH₂— | —CH₂— | —CH₂— |
| 3-1897 | Sub-84 | 3,4-diClPh | —CH₂— | —CH₂— | —CH₂— |
| 3-1898 | Sub-81 | 3,4-diClPh | —CH₂— | —CH₂— | —CH₂— |
| 3-1899 | Sub-48 | 3,4-diClPh | —CH₂— | —CH₂— | —CH₂— |
| 3-1900 | Sub-37 | 4-ClPh | —CH₂— | —CH₂— | —CH₂— |
| 3-1901 | Sub-38 | 4-ClPh | —CH₂— | —CH₂— | —CH₂— |
| 3-1902 | Sub-39 | 4-ClPh | —CH₂— | —CH₂— | —CH₂— |
| 3-1903 | Sub-40 | 4-ClPh | —CH₂— | —CH₂— | —CH₂— |
| 3-1904 | Sub-41 | 4-ClPh | —CH₂— | —CH₂— | —CH₂— |
| 3-1905 | Sub-42 | 4-ClPh | —CH₂— | —CH₂— | —CH₂— |
| 3-1906 | Sub-84 | 4-ClPh | —CH₂— | —CH₂— | —CH₂— |
| 3-1907 | Sub-81 | 4-ClPh | —CH₂— | —CH₂— | —CH₂— |
| 3-1908 | Sub-48 | 4-ClPh | —CH₂— | —CH₂— | —CH₂— |
| 3-1909 | Sub-37 | 4-FPh | —CH₂— | —CH₂— | —CH₂— |
| 3-1910 | Sub-38 | 4-FPh | —CH₂— | —CH₂— | —CH₂— |
| 3-1911 | Sub-39 | 4-FPh | —CH₂— | —CH₂— | —CH₂— |
| 3-1912 | Sub-40 | 4-FPh | —CH₂— | —CH₂— | —CH₂— |
| 3-1913 | Sub-41 | 4-FPh | —CH₂— | —CH₂— | —CH₂— |
| 3-1914 | Sub-42 | 4-FPh | —CH₂— | —CH₂— | —CH₂— |
| 3-1915 | Sub-84 | 4-FPh | —CH₂— | —CH₂— | —CH₂— |
| 3-1916 | Sub-81 | 4-FPh | —CH₂— | —CH₂— | —CH₂— |
| 3-1917 | Sub-48 | 4-FPh | —CH₂— | —CH₂— | —CH₂— |
| 3-1918 | Sub-37 | 3,4-diClPh | —CH₂— | —CH₂— | —CH₂CH₂— |
| 3-1919 | Sub-38 | 3,4-diClPh | —CH₂— | —CH₂— | —CH₂CH₂— |
| 3-1920 | Sub-39 | 3,4-diClPh | —CH₂— | —CH₂— | —CH₂CH₂— |
| 3-1921 | Sub-40 | 3,4-diClPh | —CH₂— | —CH₂— | —CH₂CH₂— |
| 3-1922 | Sub-41 | 3,4-diClPh | —CH₂— | —CH₂— | —CH₂CH₂— |
| 3-1923 | Sub-42 | 3,4-diClPh | —CH₂— | —CH₂— | —CH₂CH₂— |
| 3-1924 | Sub-84 | 3,4-diClPh | —CH₂— | —CH₂— | —CH₂CH₂— |
| 3-1925 | Sub-81 | 3,4-diClPh | —CH₂— | —CH₂— | —CH₂CH₂— |
| 3-1926 | Sub-48 | 3,4-diClPh | —CH₂— | —CH₂— | —CH₂CH₂— |
| 3-1927 | Sub-37 | 4-ClPh | —CH₂— | —CH₂— | —CH₂CH₂— |
| 3-1928 | Sub-38 | 4-ClPh | —CH₂— | —CH₂— | —CH₂CH₂— |
| 3-1929 | Sub-39 | 4-ClPh | —CH₂— | —CH₂— | —CH₂CH₂— |
| 3-1930 | Sub-40 | 4-ClPh | —CH₂— | —CH₂— | —CH₂CH₂— |
| 3-1931 | Sub-41 | 4-ClPh | —CH₂— | —CH₂— | —CH₂CH₂— |
| 3-1932 | Sub-42 | 4-ClPh | —CH₂— | —CH₂— | —CH₂CH₂— |
| 3-1933 | Sub-84 | 4-ClPh | —CH₂— | —CH₂— | —CH₂CH₂— |
| 3-1934 | Sub-81 | 4-ClPh | —CH₂— | —CH₂— | —CH₂CH₂— |
| 3-1935 | Sub-48 | 4-ClPh | —CH₂— | —CH₂— | —CH₂CH₂— |
| 3-1936 | Sub-37 | 4-FPh | —CH₂— | —CH₂— | —CH₂CH₂— |
| 3-1937 | Sub-38 | 4-FPh | —CH₂— | —CH₂— | —CH₂CH₂— |
| 3-1938 | Sub-39 | 4-FPh | —CH₂— | —CH₂— | —CH₂CH₂— |
| 3-1939 | Sub-40 | 4-FPh | —CH₂— | —CH₂— | —CH₂CH₂— |
| 3-1940 | Sub-41 | 4-FPh | —CH₂— | —CH₂— | —CH₂CH₂— |
| 3-1941 | Sub-42 | 4-FPh | —CH₂— | —CH₂— | —CH₂CH₂— |
| 3-1942 | Sub-84 | 4-FPh | —CH₂— | —CH₂— | —CH₂CH₂— |
| 3-1943 | Sub-81 | 4-FPh | —CH₂— | —CH₂— | —CH₂CH₂— |
| 3-1944 | Sub-48 | 4-FPh | —CH₂— | —CH₂— | —CH₂CH₂— |
| 3-1945 | Sub-37 | 3,4-diClPh | —CH₂— | —CH₂— | —(CH₂)₃— |
| 3-1946 | Sub-38 | 3,4-diClPh | —CH₂— | —CH₂— | —(CH₂)₃— |
| 3-1947 | Sub-39 | 3,4-diClPh | —CH₂— | —CH₂— | —(CH₂)₃— |
| 3-1948 | Sub-40 | 3,4-diClPh | —CH₂— | —CH₂— | —(CH₂)₃— |
| 3-1949 | Sub-41 | 3,4-diClPh | —CH₂— | —CH₂— | —(CH₂)₃— |
| 3-1950 | Sub-42 | 3,4-diClPh | —CH₂— | —CH₂— | —(CH₂)₃— |
| 3-1951 | Sub-84 | 3,4-diClPh | —CH₂— | —CH₂— | —(CH₂)₃— |
| 3-1952 | Sub-81 | 3,4-diClPh | —CH₂— | —CH₂— | —(CH₂)₃— |
| 3-1953 | Sub-48 | 3,4-diClPh | —CH₂— | —CH₂— | —(CH₂)₃— |
| 3-1954 | Sub-37 | 4-ClPh | —CH₂— | —CH₂— | —(CH₂)₃— |
| 3-1955 | Sub-38 | 4-ClPh | —CH₂— | —CH₂— | —(CH₂)₃— |
| 3-1956 | Sub-39 | 4-ClPh | —CH₂— | —CH₂— | —(CH₂)₃— |
| 3-1957 | Sub-40 | 4-ClPh | —CH₂— | —CH₂— | —(CH₂)₃— |
| 3-1958 | Sub-41 | 4-ClPh | —CH₂— | —CH₂— | —(CH₂)₃— |

TABLE 3-continued

| Cpd. No. | R¹ | R² | A | B | E |
|---|---|---|---|---|---|
| 3-1959 | Sub-42 | 4-ClPh | —CH₂— | —CH₂— | —(CH₂)₃— |
| 3-1960 | Sub-84 | 4-ClPh | —CH₂— | —CH₂— | —(CH₂)₃— |
| 3-1961 | Sub-81 | 4-ClPh | —CH₂— | —CH₂— | —(CH₂)₃— |
| 3-1962 | Sub-48 | 4-ClPh | —CH₂— | —CH₂— | —(CH₂)₃— |
| 3-1963 | Sub-37 | 4-FPh | —CH₂— | —CH₂— | —(CH₂)₃— |
| 3-1964 | Sub-38 | 4-FPh | —CH₂— | —CH₂— | —(CH₂)₃— |
| 3-1965 | Sub-39 | 4-FPh | —CH₂— | —CH₂— | —(CH₂)₃— |
| 3-1966 | Sub-40 | 4-FPh | —CH₂— | —CH₂— | —(CH₂)₃— |
| 3-1967 | Sub-41 | 4-FPh | —CH₂— | —CH₂— | —(CH₂)₃— |
| 3-1968 | Sub-42 | 4-FPh | —CH₂— | —CH₂— | —(CH₂)₃— |
| 3-1969 | Sub-84 | 4-FPh | —CH₂— | —CH₂— | —(CH₂)₃— |
| 3-1970 | Sub-81 | 4-FPh | —CH₂— | —CH₂— | —(CH₂)₃— |
| 3-1971 | Sub-48 | 4-FPh | —CH₂— | —CH₂— | —(CH₂)₃— |
| 3-1972 | Sub-37 | 3,4-diClPh | —CH₂— | —CH₂— | —CH₂C(Me)₂— |
| 3-1973 | Sub-38 | 3,4-diClPh | —CH₂— | —CH₂— | —CH₂C(Me)₂— |
| 3-1974 | Sub-39 | 3,4-diClPh | —CH₂— | —CH₂— | —CH₂C(Me)₂— |
| 3-1975 | Sub-40 | 3,4-diClPh | —CH₂— | —CH₂— | —CH₂C(Me)₂— |
| 3-1976 | Sub-41 | 3,4-diClPh | —CH₂— | —CH₂— | —CH₂C(Me)₂— |
| 3-1977 | Sub-42 | 3,4-diClPh | —CH₂— | —CH₂— | —CH₂C(Me)₂— |
| 3-1978 | Sub-84 | 3,4-diClPh | —CH₂— | —CH₂— | —CH₂C(Me)₂— |
| 3-1979 | Sub-81 | 3,4-diClPh | —CH₂— | —CH₂— | —CH₂C(Me)₂— |
| 3-1980 | Sub-48 | 3,4-diClPh | —CH₂— | —CH₂— | —CH₂C(Me)₂— |
| 3-1981 | Sub-37 | 4-ClPh | —CH₂— | —CH₂— | —CH₂C(Me)₂— |
| 3-1982 | Sub-38 | 4-ClPh | —CH₂— | —CH₂— | —CH₂C(Me)₂— |
| 3-1983 | Sub-39 | 4-ClPh | —CH₂— | —CH₂— | —CH₂C(Me)₂— |
| 3-1984 | Sub-40 | 4-ClPh | —CH₂— | —CH₂— | —CH₂C(Me)₂— |
| 3-1985 | Sub-41 | 4-ClPh | —CH₂— | —CH₂— | —CH₂C(Me)₂— |
| 3-1986 | Sub-42 | 4-ClPh | —CH₂— | —CH₂— | —CH₂C(Me)₂— |
| 3-1987 | Sub-84 | 4-ClPh | —CH₂— | —CH₂— | —CH₂C(Me)₂— |
| 3-1988 | Sub-81 | 4-ClPh | —CH₂— | —CH₂— | —CH₂C(Me)₂— |
| 3-1989 | Sub-48 | 4-ClPh | —CH₂— | —CH₂— | —CH₂C(Me)₂— |
| 3-1990 | Sub-37 | 4-FPh | —CH₂— | —CH₂— | —CH₂C(Me)₂— |
| 3-1991 | Sub-38 | 4-FPh | —CH₂— | —CH₂— | —CH₂C(Me)₂— |
| 3-1992 | Sub-39 | 4-FPh | —CH₂— | —CH₂— | —CH₂C(Me)₂— |
| 3-1993 | Sub-40 | 4-FPh | —CH₂— | —CH₂— | —CH₂C(Me)₂— |
| 3-1994 | Sub-41 | 4-FPh | —CH₂— | —CH₂— | —CH₂C(Me)₂— |
| 3-1995 | Sub-42 | 4-FPh | —CH₂— | —CH₂— | —CH₂C(Me)₂— |
| 3-1996 | Sub-84 | 4-FPh | —CH₂— | —CH₂— | —CH₂C(Me)₂— |
| 3-1997 | Sub-81 | 4-FPh | —CH₂— | —CH₂— | —CH₂C(Me)₂— |
| 3-1998 | Sub-48 | 4-FPh | —CH₂— | —CH₂— | —CH₂C(Me)₂— |
| 3-1999 | Sub-37 | 3,4-diClPh | —CH₂— | —CH₂— | —CH₂-cPr— |
| 3-2000 | Sub-38 | 3,4-diClPh | —CH₂— | —CH₂— | —CH₂-cPr— |
| 3-2001 | Sub-39 | 3,4-diClPh | —CH₂— | —CH₂— | —CH₂-cPr— |
| 3-2002 | Sub-40 | 3,4-diClPh | —CH₂— | —CH₂— | —CH₂-cPr— |
| 3-2003 | Sub-41 | 3,4-diClPh | —CH₂— | —CH₂— | —CH₂-cPr— |
| 3-2004 | Sub-42 | 3,4-diClPh | —CH₂— | —CH₂— | —CH₂-cPr— |
| 3-2005 | Sub-84 | 3,4-diClPh | —CH₂— | —CH₂— | —CH₂-cPr— |
| 3-2006 | Sub-81 | 3,4-diClPh | —CH₂— | —CH₂— | —CH₂-cPr— |
| 3-2007 | Sub-48 | 3,4-diClPh | —CH₂— | —CH₂— | —CH₂-cPr— |
| 3-2008 | Sub-37 | 4-ClPh | —CH₂— | —CH₂— | —CH₂-cPr— |
| 3-2009 | Sub-38 | 4-ClPh | —CH₂— | —CH₂— | —CH₂-cPr— |
| 3-2010 | Sub-39 | 4-ClPh | —CH₂— | —CH₂— | —CH₂-cPr— |
| 3-2011 | Sub-40 | 4-ClPh | —CH₂— | —CH₂— | —CH₂-cPr— |
| 3-2012 | Sub-41 | 4-ClPh | —CH₂— | —CH₂— | —CH₂-cPr— |
| 3-2013 | Sub-42 | 4-ClPh | —CH₂— | —CH₂— | —CH₂-cPr— |
| 3-2014 | Sub-84 | 4-ClPh | —CH₂— | —CH₂— | —CH₂-cPr— |
| 3-2015 | Sub-81 | 4-ClPh | —CH₂— | —CH₂— | —CH₂-cPr— |
| 3-2016 | Sub-48 | 4-ClPh | —CH₂— | —CH₂— | —CH₂-cPr— |
| 3-2017 | Sub-37 | 4-FPh | —CH₂— | —CH₂— | —CH₂-cPr— |
| 3-2018 | Sub-38 | 4-FPh | —CH₂— | —CH₂— | —CH₂-cPr— |
| 3-2019 | Sub-39 | 4-FPh | —CH₂— | —CH₂— | —CH₂-cPr— |
| 3-2020 | Sub-40 | 4-FPh | —CH₂— | —CH₂— | —CH₂-cPr— |
| 3-2021 | Sub-41 | 4-FPh | —CH₂— | —CH₂— | —CH₂-cPr- |
| 3-2022 | Sub-42 | 4-FPh | —CH₂— | —CH₂— | —CH₂-cPr- |
| 3-2023 | Sub-84 | 4-FPh | —CH₂— | —CH₂— | —CH₂-cPr— |
| 3-2024 | Sub-81 | 4-FPh | —CH₂— | —CH₂— | —CH₂-cPr— |
| 3-2025 | Sub-48 | 4-FPh | —CH₂— | —CH₂— | —CH₂-cPr— |
| 3-2026 | Sub-37 | 3,4-diClPh | —CH₂— | —CH₂— | —C(Me)₂— |
| 3-2027 | Sub-38 | 3,4-diClPh | —CH₂— | —CH₂— | —C(Me)₂— |
| 3-2028 | Sub-39 | 3,4-diClPh | —CH₂— | —CH₂— | —C(Me)₂— |
| 3-2029 | Sub-40 | 3,4-diClPh | —CH₂— | —CH₂— | —C(Me)₂— |
| 3-2030 | Sub-41 | 3,4-diClPh | —CH₂— | —CH₂— | —C(Me)₂— |
| 3-2031 | Sub-42 | 3,4-diClPh | —CH₂— | —CH₂— | —C(Me)₂— |
| 3-2032 | Sub-84 | 3,4-diClPh | —CH₂— | —CH₂— | —C(Me)₂— |
| 3-2033 | Sub-81 | 3,4-diClPh | —CH₂— | —CH₂— | —C(Me)₂— |
| 3-2034 | Sub-48 | 3,4-diClPh | —CH₂— | —CH₂— | —C(Me)₂— |

TABLE 3-continued

| Cpd. No. | R¹ | R² | A | B | E |
|---|---|---|---|---|---|
| 3-2035 | Sub-37 | 4-ClPh | —CH₂— | —CH₂— | —C(Me)₂— |
| 3-2036 | Sub-38 | 4-ClPh | —CH₂— | —CH₂— | —C(Me)₂— |
| 3-2037 | Sub-39 | 4-ClPh | —CH₂— | —CH₂— | —C(Me)₂— |
| 3-2038 | Sub-40 | 4-ClPh | —CH₂— | —CH₂— | —C(Me)₂— |
| 3-2039 | Sub-41 | 4-ClPh | —CH₂— | —CH₂— | —C(Me)₂— |
| 3-2040 | Sub-42 | 4-ClPh | —CH₂— | —CH₂— | —C(Me)₂— |
| 3-2041 | Sub-84 | 4-ClPh | —CH₂— | —CH₂— | —C(Me)₂— |
| 3-2042 | Sub-81 | 4-ClPh | —CH₂— | —CH₂— | —C(Me)₂— |
| 3-2043 | Sub-48 | 4-ClPh | —CH₂— | —CH₂— | —C(Me)₂— |
| 3-2044 | Sub-37 | 4-FPh | —CH₂— | —CH₂— | —C(Me)₂— |
| 3-2045 | Sub-38 | 4-FPh | —CH₂— | —CH₂— | —C(Me)₂— |
| 3-2046 | Sub-39 | 4-FPh | —CH₂— | —CH₂— | —C(Me)₂— |
| 3-2047 | Sub-40 | 4-FPh | —CH₂— | —CH₂— | —C(Me)₂— |
| 3-2048 | Sub-41 | 4-FPh | —CH₂— | —CH₂— | —C(Me)₂— |
| 3-2049 | Sub-42 | 4-FPh | —CH₂— | —CH₂— | —C(Me)₂— |
| 3-2050 | Sub-84 | 4-FPh | —CH₂— | —CH₂— | —C(Me)₂— |
| 3-2051 | Sub-81 | 4-FPh | —CH₂— | —CH₂— | —C(Me)₂— |
| 3-2052 | Sub-48 | 4-FPh | —CH₂— | —CH₂— | —C(Me)₂— |
| 3-2053 | Sub-37 | 3,4-diClPh | —SO₂— | Single Bond | —CH₂— |
| 3-2054 | Sub-38 | 3,4-diClPh | —SO₂— | Single Bond | —CH₂— |
| 3-2055 | Sub-39 | 3,4-diClPh | —SO₂— | Single Bond | —CH₂— |
| 3-2056 | Sub-40 | 3,4-diClPh | —SO₂— | Single Bond | —CH₂— |
| 3-2057 | Sub-41 | 3,4-diClPh | —SO₂— | Single Bond | —CH₂— |
| 3-2058 | Sub-42 | 3,4-diClPh | —SO₂— | Single Bond | —CH₂— |
| 3-2059 | Sub-84 | 3,4-diClPh | —SO₂— | Single Bond | —CH₂— |
| 3-2060 | Sub-81 | 3,4-diClPh | —SO₂— | Single Bond | —CH₂— |
| 3-2061 | Sub-48 | 3,4-diClPh | —SO₂— | Single Bond | —CH₂— |
| 3-2062 | Sub-37 | 4-ClPh | —SO₂— | Single Bond | —CH₂— |
| 3-2063 | Sub-38 | 4-ClPh | —SO₂— | Single Bond | —CH₂— |
| 3-2064 | Sub-39 | 4-ClPh | —SO₂— | Single Bond | —CH₂— |
| 3-2065 | Sub-40 | 4-ClPh | —SO₂— | Single Bond | —CH₂— |
| 3-2066 | Sub-41 | 4-ClPh | —SO₂— | Single Bond | —CH₂— |
| 3-2067 | Sub-42 | 4-ClPh | —SO₂— | Single Bond | —CH₂— |
| 3-2068 | Sub-84 | 4-ClPh | —SO₂— | Single Bond | —CH₂— |
| 3-2069 | Sub-81 | 4-ClPh | —SO₂— | Single Bond | —CH₂— |
| 3-2070 | Sub-48 | 4-ClPh | —SO₂— | Single Bond | —CH₂— |
| 3-2071 | Sub-37 | 4-FPh | —SO₂— | Single Bond | —CH₂— |
| 3-2072 | Sub-38 | 4-FPh | —SO₂— | Single Bond | —CH₂— |
| 3-2073 | Sub-39 | 4-FPh | —SO₂— | Single Bond | —CH₂— |
| 3-2074 | Sub-40 | 4-FPh | —SO₂— | Single Bond | —CH₂— |
| 3-2075 | Sub-41 | 4-FPh | —SO₂— | Single Bond | —CH₂— |
| 3-2076 | Sub-42 | 4-FPh | —SO₂— | Single Bond | —CH₂— |
| 3-2077 | Sub-84 | 4-FPh | —SO₂— | Single Bond | —CH₂— |
| 3-2078 | Sub-81 | 4-FPh | —SO₂— | Single Bond | —CH₂— |
| 3-2079 | Sub-48 | 4-FPh | —SO₂— | Single Bond | —CH₂— |
| 3-2080 | Sub-37 | 3,4-diClPh | —SO₂— | Single Bond | —CH₂CH₂— |
| 3-2081 | Sub-38 | 3,4-diClPh | —SO₂— | Single Bond | —CH₂CH₂— |
| 3-2082 | Sub-39 | 3,4-diClPh | —SO₂— | Single Bond | —CH₂CH₂— |
| 3-2083 | Sub-40 | 3,4-diClPh | —SO₂— | Single Bond | —CH₂CH₂— |
| 3-2084 | Sub-41 | 3,4-diClPh | —SO₂— | Single Bond | —CH₂CH₂— |
| 3-2085 | Sub-42 | 3,4-diClPh | —SO₂— | Single Bond | —CH₂CH₂— |
| 3-2086 | Sub-84 | 3,4-diClPh | —SO₂— | Single Bond | —CH₂CH₂— |
| 3-2087 | Sub-81 | 3,4-diClPh | —SO₂— | Single Bond | —CH₂CH₂— |
| 3-2088 | Sub-48 | 3,4-diClPh | —SO₂— | Single Bond | —CH₂CH₂— |
| 3-2089 | Sub-37 | 4-ClPh | —SO₂— | Single Bond | —CH₂CH₂— |
| 3-2090 | Sub-38 | 4-ClPh | —SO₂— | Single Bond | —CH₂CH₂— |
| 3-2091 | Sub-39 | 4-ClPh | —SO₂— | Single Bond | —CH₂CH₂— |
| 3-2092 | Sub-40 | 4-ClPh | —SO₂— | Single Bond | —CH₂CH₂— |
| 3-2093 | Sub-41 | 4-ClPh | —SO₂— | Single Bond | —CH₂CH₂— |
| 3-2094 | Sub-42 | 4-ClPh | —SO₂— | Single Bond | —CH₂CH₂— |
| 3-2095 | Sub-84 | 4-ClPh | —SO₂— | Single Bond | —CH₂CH₂— |
| 3-2096 | Sub-81 | 4-ClPh | —SO₂— | Single Bond | —CH₂CH₂— |
| 3-2097 | SubA8 | 4-ClPh | —SO₂— | Single Bond | —CH₂CH₂— |
| 3-2098 | Sub-37 | 4-FPh | —SO₂— | Single Bond | —CH₂CH₂— |
| 3-2099 | Sub-38 | 4-FPh | —SO₂— | Single Bond | —CH₂CH₂— |
| 3-2100 | Sub-39 | 4-FPh | —SO₂— | Single Bond | —CH₂CH₂— |
| 3-2101 | Sub-40 | 4-FPh | —SO₂— | Single Bond | —CH₂CH₂— |
| 3-2102 | Sub-41 | 4-FPh | —SO₂— | Single Bond | —CH₂CH₂— |
| 3-2103 | Sub-42 | 4-FPh | —SO₂— | Single Bond | —CH₂CH₂— |
| 3-2104 | Sub-84 | 4-FPh | —SO₂— | Single Bond | —CH₂CH₂— |
| 3-2105 | Sub-81 | 4-FPh | —SO₂— | Single Bond | —CH₂CH₂— |
| 3-2106 | Sub-48 | 4-FPh | —SO₂— | Single Bond | —CH₂CH₂— |
| 3-2107 | Sub-37 | 3,4-diClPh | —SO₂— | Single Bond | —(CH₂)₃— |
| 3-2108 | Sub-38 | 3,4-diClPh | —SO₂— | Single Bond | —(CH₂)₃— |
| 3-2109 | Sub-39 | 3,4-diClPh | —SO₂— | Single Bond | —(CH₂)₃— |
| 3-2110 | Sub-40 | 3,4-diClPh | —SO₂— | Single Bond | —(CH₂)₃— |

TABLE 3-continued

| Cpd. No. | R¹ | R² | A | B | E |
|---|---|---|---|---|---|
| 3-2111 | Sub-41 | 3,4-diClPh | —SO₂— | Single Bond | —(CH₂)₃— |
| 3-2112 | Sub-42 | 3,4-diClPh | —SO₂— | Single Bond | —(CH₂)₃— |
| 3-2113 | Sub-84 | 3,4-diClPh | —SO₂— | Single Bond | —(CH₂)₃— |
| 3-2114 | Sub-81 | 3,4-diClPh | —SO₂— | Single Bond | —(CH₂)₃— |
| 3-2115 | Sub-48 | 3,4-diClPh | —SO₂— | Single Bond | —(CH₂)₃— |
| 3-2116 | Sub-37 | 4-ClPh | —SO₂— | Single Bond | —(CH₂)₃— |
| 3-2117 | Sub-38 | 4-ClPh | —SO₂— | Single Bond | —(CH₂)₃— |
| 3-2118 | Sub-39 | 4-ClPh | —SO₂— | Single Bond | —(CH₂)₃— |
| 3-2119 | Sub-40 | 4-ClPh | —SO₂— | Single Bond | —(CH₂)₃— |
| 3-2120 | Sub-41 | 4-ClPh | —SO₂— | Single Bond | —(CH₂)₃— |
| 3-2121 | Sub-42 | 4-ClPh | —SO₂— | Single Bond | —(CH₂)₃— |
| 3-2122 | Sub-84 | 4-ClPh | —SO₂— | Single Bond | —(CH₂)₃— |
| 3-2123 | Sub-81 | 4-ClPh | —SO₂— | Single Bond | —(CH₂)₃— |
| 3-2124 | Sub-48 | 4-ClPh | —SO₂— | Single Bond | —(CH₂)₃— |
| 3-2125 | Sub-37 | 4-FPh | —SO₂— | Single Bond | —(CH₂)₃— |
| 3-2126 | Sub-38 | 4-FPh | —SO₂— | Single Bond | —(CH₂)₃— |
| 3-2127 | Sub-39 | 4-FPh | —SO₂— | Single Bond | —(CH₂)₃— |
| 3-2128 | Sub-40 | 4-FPh | —SO₂— | Single Bond | —(CH₂)₃— |
| 3-2129 | Sub-41 | 4-FPh | —SO₂— | Single Bond | —(CH₂)₃— |
| 3-2130 | Sub-42 | 4-FPh | —SO₂— | Single Bond | —(CH₂)₃— |
| 3-2131 | Sub-84 | 4-FPh | —SO₂— | Single Bond | —(CH₂)₃— |
| 3-2132 | Sub-81 | 4-FPh | —SO₂— | Single Bond | —(CH₂)₃— |
| 3-2133 | Sub-48 | 4-FPh | —SO₂— | Single Bond | —(CH₂)₃— |
| 3-2134 | Sub-37 | 3,4-diClPh | —SO₂— | Single Bond | —CH₂C(Me)₂— |
| 3-2135 | Sub-38 | 3,4-diClPh | —SO₂— | Single Bond | —CH₂C(Me)₂— |
| 3-2136 | Sub-39 | 3,4-diClPh | —SO₂— | Single Bond | —CH₂C(Me)₂— |
| 3-2137 | Sub-40 | 3,4-diClPh | —SO₂— | Single Bond | —CH₂C(Me)₂— |
| 3-2138 | Sub-41 | 3,4-diClPh | —SO₂— | Single Bond | —CH₂C(Me)₂— |
| 3-2139 | Sub-42 | 3,4-diClPh | —SO₂— | Single Bond | —CH₂C(Me)₂— |
| 3-2140 | Sub-84 | 3,4-diClPh | —SO₂— | Single Bond | —CH₂C(Me)₂— |
| 3-2141 | Sub-81 | 3,4-diClPh | —SO₂— | Single Bond | —CH₂C(Me)₂— |
| 3-2142 | Sub-48 | 3,4-diClPh | —SO₂— | Single Bond | —CH₂C(Me)₂— |
| 3-2143 | Sub-37 | 4-ClPh | —SO₂— | Single Bond | —CH₂C(Me)₂— |
| 3-2144 | Sub-38 | 4-ClPh | —SO₂— | Single Bond | —CH₂C(Me)₂— |
| 3-2145 | Sub-39 | 4-ClPh | —SO₂— | Single Bond | —CH₂C(Me)₂— |
| 3-2146 | Sub-40 | 4-ClPh | —SO₂— | Single Bond | —CH₂C(Me)₂— |
| 3-2147 | Sub-41 | 4-ClPh | —SO₂— | Single Bond | —CH₂C(Me)₂— |
| 3-2148 | Sub-42 | 4-ClPh | —SO₂— | Single Bond | —CH₂C(Me)₂— |
| 3-2149 | Sub-84 | 4-ClPh | —SO₂— | Single Bond | —CH₂C(Me)₂— |
| 3-2150 | Sub-81 | 4-ClPh | —SO₂— | Single Bond | —CH₂C(Me)₂— |
| 3-2151 | Sub-48 | 4-ClPh | —SO₂— | Single Bond | —CH₂C(Me)₂— |
| 3-2152 | Sub-37 | 4-FPh | —SO₂— | Single Bond | —CH₂C(Me)₂— |
| 3-2153 | Sub-38 | 4-FPh | —SO₂— | Single Bond | —CH₂C(Me)₂— |
| 3-2154 | Sub-39 | 4-FPh | —SO₂— | Single Bond | —CH₂C(Me)₂— |
| 3-2155 | Sub-40 | 4-FPh | —SO₂— | Single Bond | —CH₂C(Me)₂— |
| 3-2156 | Sub-41 | 4-FPh | —SO₂— | Single Bond | —CH₂C(Me)₂— |
| 3-2157 | Sub-42 | 4-FPh | —SO₂— | Single Bond | —CH₂C(Me)₂— |
| 3-2158 | Sub-84 | 4-FPh | —SO₂— | Single Bond | —CH₂C(Me)₂— |
| 3-2159 | Sub-81 | 4-FPh | —SO₂— | Single Bond | —CH₂C(Me)₂— |
| 3-2160 | Sub-48 | 4-FPh | —SO₂— | Single Bond | —CH₂C(Me)₂— |
| 3-2161 | Sub-37 | 3,4-diClPh | —SO₂— | Single Bond | —CH₂-cPr— |
| 3-2162 | Sub-38 | 3,4-diClPh | —SO₂— | Single Bond | —CH₂-cPr— |
| 3-2163 | Sub-39 | 3,4-diClPh | —SO₂— | Single Bond | —CH₂-cPr— |
| 3-2164 | Sub-40 | 3,4-diClPh | —SO₂— | Single Bond | —CH₂-cPr— |
| 3-2165 | Sub-41 | 3,4-diClPh | —SO₂— | Single Bond | —CH₂-cPr— |
| 3-2166 | Sub-42 | 3,4-diClPh | —SO₂— | Single Bond | —CH₂-cPr— |
| 3-2167 | Sub-84 | 3,4-diClPh | —SO₂— | Single Bond | —CH₂-cPr— |
| 3-2168 | Sub-81 | 3,4-diClPh | —SO₂— | Single Bond | —CH₂-cPr— |
| 3-2169 | Sub-48 | 3,4-diClPh | —SO₂— | Single Bond | —CH₂-cPr— |
| 3-2170 | Sub-37 | 4-ClPh | —SO₂— | Single Bond | —CH₂-cPr— |
| 3-2171 | Sub-38 | 4-ClPh | —SO₂— | Single Bond | —CH₂-cPr— |
| 3-2172 | Sub-39 | 4-ClPh | —SO₂— | Single Bond | —CH₂-cPr— |
| 3-2173 | Sub-40 | 4-ClPh | —SO₂— | Single Bond | —CH₂-cPr— |
| 3-2174 | Sub-41 | 4-ClPh | —SO₂— | Single Bond | —CH₂-cPr— |
| 3-2175 | Sub-42 | 4-ClPh | —SO₂— | Single Bond | —CH₂-cPr— |
| 3-2176 | Sub-84 | 4-ClPh | —SO₂— | Single Bond | —CH₂-cPr— |
| 3-2177 | Sub-81 | 4-ClPh | —SO₂— | Single Bond | —CH₂-cPr— |
| 3-2178 | Sub-48 | 4-ClPh | —SO₂— | Single Bond | —CH₂-cPr— |
| 3-2179 | Sub-37 | 4-FPh | —SO₂— | Single Bond | —CH₂-cPr— |
| 3-2180 | Sub-38 | 4-FPh | —SO₂— | Single Bond | —CH₂-cPr— |
| 3-2181 | Sub-39 | 4-FPh | —SO₂— | Single Bond | —CH₂-cPr— |
| 3-2182 | Sub-40 | 4-FPh | —SO₂— | Single Bond | —CH₂-cPr— |
| 3-2183 | Sub-41 | 4-FPh | —SO₂— | Single Bond | —CH₂-cPr— |
| 3-2184 | Sub-42 | 4-FPh | —SO₂— | Single Bond | —CH₂-cPr— |
| 3-2185 | Sub-84 | 4-FPh | —SO₂— | Single Bond | —CH₂-cPr— |
| 3-2186 | Sub-81 | 4-FPh | —SO₂— | Single Bond | —CH₂-cPr— |

TABLE 3-continued

| Cpd. No. | R¹ | R² | A | B | E |
|---|---|---|---|---|---|
| 3-2187 | Sub-48 | 4-FPh | —SO$_2$— | Single Bond | —CH$_2$-cPr— |
| 3-2188 | Sub-37 | 3,4-diClPh | —SO$_2$— | Single Bond | —C(Me)$_2$— |
| 3-2189 | Sub-38 | 3,4-diClPh | —SO$_2$— | Single Bond | —C(Me)$_2$— |
| 3-2190 | Sub-39 | 3,4-diClPh | —SO$_2$— | Single Bond | —C(Me)$_2$— |
| 3-2191 | Sub-40 | 3,4-diClPh | —SO$_2$— | Single Bond | —C(Me)$_2$— |
| 3-2192 | Sub-41 | 3,4-diClPh | —SO$_2$— | Single Bond | —C(Me)$_2$— |
| 3-2193 | Sub-42 | 3,4-diClPh | —SO$_2$— | Single Bond | —C(Me)$_2$— |
| 3-2194 | Sub-84 | 3,4-diClPh | —SO$_2$— | Single Bond | —C(Me)$_2$— |
| 3-2195 | Sub-81 | 3,4-diClPh | —SO$_2$— | Single Bond | —C(Me)$_2$— |
| 3-2196 | Sub-48 | 3,4-diClPh | —SO$_2$— | Single Bond | —C(Me)$_2$— |
| 3-2197 | Sub-37 | 4-ClPh | —SO$_2$— | Single Bond | —C(Me)$_2$— |
| 3-2198 | Sub-38 | 4-ClPh | —SO$_2$— | Single Bond | —C(Me)$_2$— |
| 3-2199 | Sub-39 | 4-ClPh | —SO$_2$— | Single Bond | —C(Me)$_2$— |
| 3-2200 | Sub-40 | 4-ClPh | —SO$_2$— | Single Bond | —C(Me)$_2$— |
| 3-2201 | Sub-41 | 4-ClPh | —SO$_2$— | Single Bond | —C(Me)$_2$— |
| 3-2202 | Sub-42 | 4-ClPh | —SO$_2$— | Single Bond | —C(Me)$_2$— |
| 3-2203 | Sub-84 | 4-ClPh | —SO$_2$— | Single Bond | —C(Me)$_2$— |
| 3-2204 | Sub-81 | 4-ClPh | —SO$_2$— | Single Bond | —C(Me)$_2$— |
| 3-2205 | Sub-48 | 4-ClPh | —SO$_2$— | Single Bond | —C(Me)$_2$— |
| 3-2206 | Sub-37 | 4-FPh | —SO$_2$— | Single Bond | —C(Me)$_2$— |
| 3-2207 | Sub-38 | 4-FPh | —SO$_2$— | Single Bond | —C(Me)$_2$— |
| 3-2208 | Sub-39 | 4-FPh | —SO$_2$— | Single Bond | —C(Me)$_2$— |
| 3-2209 | Sub-40 | 4-FPh | —SO$_2$— | Single Bond | —C(Me)$_2$— |
| 3-2210 | Sub-41 | 4-FPh | —SO$_2$— | Single Bond | —C(Me)$_2$— |
| 3-2211 | Sub-42 | 4-FPh | —SO$_2$— | Single Bond | —C(Me)$_2$— |
| 3-2212 | Sub-84 | 4-FPh | —SO$_2$— | Single Bond | —C(Me)$_2$— |
| 3-2213 | Sub-81 | 4-FPh | —SO$_2$— | Single Bond | —C(Me)$_2$— |
| 3-2214 | Sub-48 | 4-FPh | —SO$_2$— | Single Bond | —C(Me)$_2$— |
| 3-2215 | Sub-37 | 3,4-diClPh | —SO$_2$— | —CH$_2$— | —CH$_2$— |
| 3-2216 | Sub-38 | 3,4-diClPh | —SO$_2$— | —CH$_2$— | —CH$_2$— |
| 3-2217 | Sub-39 | 3,4-diClPh | —SO$_2$— | —CH$_2$— | —CH$_2$— |
| 3-2218 | Sub-40 | 3,4-diClPh | —SO$_2$— | —CH$_2$— | —CH$_2$— |
| 3-2219 | Sub-41 | 3,4-diClPh | —SO$_2$— | —CH$_2$— | —CH$_2$— |
| 3-2220 | Sub-42 | 3,4-diClPh | —SO$_2$— | —CH$_2$— | —CH$_2$— |
| 3-2221 | Sub-84 | 3,4-diClPh | —SO$_2$— | —CH$_2$— | —CH$_2$— |
| 3-2222 | Sub-81 | 3,4-diClPh | —SO$_2$— | —CH$_2$— | —CH$_2$— |
| 3-2223 | Sub-48 | 3,4-diClPh | —SO$_2$— | —CH$_2$— | —CH$_2$— |
| 3-2224 | Sub-37 | 4-ClPh | —SO$_2$— | —CH$_2$— | —CH$_2$— |
| 3-2225 | Sub-38 | 4-ClPh | —SO$_2$— | —CH$_2$— | —CH$_2$— |
| 3-2226 | Sub-39 | 4-ClPh | —SO$_2$— | —CH$_2$— | —CH$_2$— |
| 3-2227 | Sub-40 | 4-ClPh | —SO$_2$— | —CH$_2$— | —CH$_2$— |
| 3-2228 | Sub-41 | 4-ClPh | —SO$_2$— | —CH$_2$— | —CH$_2$— |
| 3-2229 | Sub-42 | 4-ClPh | —SO$_2$— | —CH$_2$— | —CH$_2$— |
| 3-2230 | Sub-84 | 4-ClPh | —SO$_2$— | —CH$_2$— | —CH$_2$— |
| 3-2231 | Sub-81 | 4-ClPh | —SO$_2$— | —CH$_2$— | —CH$_2$— |
| 3-2232 | Sub-48 | 4-ClPh | —SO$_2$— | —CH$_2$— | —CH$_2$— |
| 3-2233 | Sub-37 | 4-FPh | —SO$_2$— | —CH$_2$— | —CH$_2$— |
| 3-2234 | Sub-38 | 4-FPh | —SO$_2$— | —CH$_2$— | —CH$_2$— |
| 3-2235 | Sub-39 | 4-FPh | —SO$_2$— | —CH$_2$— | —CH$_2$— |
| 3-2236 | Sub-40 | 4-FPh | —SO$_2$— | —CH$_2$— | —CH$_2$— |
| 3-2237 | Sub-41 | 4-FPh | —SO$_2$— | —CH$_2$— | —CH$_2$— |
| 3-2238 | Sub-42 | 4-FPh | —SO$_2$— | —CH$_2$— | —CH$_2$— |
| 3-2239 | Sub-84 | 4-FPh | —SO$_2$— | —CH$_2$— | —CH$_2$— |
| 3-2240 | Sub-81 | 4-FPh | —SO$_2$— | —CH$_2$— | —CH$_2$— |
| 3-2241 | Sub-48 | 4-FPh | —SO$_2$— | —CH$_2$— | —CH$_2$— |
| 3-2242 | Sub-37 | 3,4-diClPh | —SO$_2$— | —CH$_2$— | —CH$_2$CH$_2$— |
| 3-2243 | Sub-38 | 3,4-diClPh | —SO$_2$— | —CH$_2$— | —CH$_2$CH$_2$— |
| 3-2244 | Sub-39 | 3,4-diClPh | —SO$_2$— | —CH$_2$— | —CH$_2$CH$_2$— |
| 3-2245 | Sub-40 | 3,4-diClPh | —SO$_2$— | —CH$_2$— | —CH$_2$CH$_2$— |
| 3-2246 | Sub-41 | 3,4-diClPh | —SO$_2$— | —CH$_2$— | —CH$_2$CH$_2$— |
| 3-2247 | Sub-42 | 3,4-diClPh | —SO$_2$— | —CH$_2$— | —CH$_2$CH$_2$— |
| 3-2248 | Sub-84 | 3,4-diClPh | —SO$_2$— | —CH$_2$— | —CH$_2$CH$_2$— |
| 3-2249 | Sub-81 | 3,4-diClPh | —SO$_2$— | —CH$_2$— | —CH$_2$CH$_2$— |
| 3-2250 | Sub-48 | 3,4-diClPh | —SO$_2$— | —CH$_2$— | —CH$_2$CH$_2$— |
| 3-2251 | Sub-37 | 4-ClPh | —SO$_2$— | —CH$_2$— | —CH$_2$CH$_2$— |
| 3-2252 | Sub-38 | 4-ClPh | —SO$_2$— | —CH$_2$— | —CH$_2$CH$_2$— |
| 3-2253 | Sub-39 | 4-ClPh | —SO$_2$— | —CH$_2$— | —CH$_2$CH$_2$— |
| 3-2254 | Sub-40 | 4-ClPh | —SO$_2$— | —CH$_2$— | —CH$_2$CH$_2$— |
| 3-2255 | Sub-41 | 4-ClPh | —SO$_2$— | —CH$_2$— | —CH$_2$CH$_2$— |
| 3-2256 | Sub-42 | 4-ClPh | —SO$_2$— | —CH$_2$— | —CH$_2$CH$_2$— |
| 3-2257 | Sub-84 | 4-ClPh | —SO$_2$— | —CH$_2$— | —CH$_2$CH$_2$— |
| 3-2258 | Sub-81 | 4-ClPh | —SO$_2$— | —CH$_2$— | —CH$_2$CH$_2$— |
| 3-2259 | Sub-48 | 4-ClPh | —SO$_2$— | —CH$_2$— | —CH$_2$CH$_2$— |
| 3-2260 | Sub-37 | 4-FPh | —SO$_2$— | —CH$_2$— | —CH$_2$CH$_2$— |
| 3-2261 | Sub-38 | 4-FPh | —SO$_2$— | —CH$_2$— | —CH$_2$CH$_2$— |
| 3-2262 | Sub-39 | 4-FPh | —SO$_2$— | —CH$_2$— | —CH$_2$CH$_2$— |

TABLE 3-continued

| Cpd. No. | R¹ | R² | A | B | E |
|---|---|---|---|---|---|
| 3-2263 | Sub-40 | 4-FPh | —SO$_2$— | —CH$_2$— | —CH$_2$CH$_2$— |
| 3-2264 | Sub-41 | 4-FPh | —SO$_2$— | —CH$_2$— | —CH$_2$CH$_2$— |
| 3-2265 | Sub-42 | 4-FPh | —SO$_2$— | —CH$_2$— | —CH$_2$CH$_2$— |
| 3-2266 | Sub-84 | 4-FPh | —SO$_2$— | —CH$_2$— | —CH$_2$CH$_2$— |
| 3-2267 | Sub-81 | 4-FPh | —SO$_2$— | —CH$_2$— | —CH$_2$CH$_2$— |
| 3-2268 | Sub-48 | 4-FPh | —SO$_2$— | —CH$_2$— | —CH$_2$CH$_2$— |
| 3-2269 | Sub-37 | 3,4-diClPh | —SO$_2$— | —CH$_2$— | —(CH$_2$)$_3$— |
| 3-2270 | Sub-38 | 3,4-diClPh | —SO$_2$— | —CH$_2$— | —(CH$_2$)$_3$— |
| 3-2271 | Sub-39 | 3,4-diClPh | —SO$_2$— | —CH$_2$— | —(CH$_2$)$_3$— |
| 3-2272 | Sub-40 | 3,4-diClPh | —SO$_2$— | —CH$_2$— | —(CH$_2$)$_3$— |
| 3-2273 | Sub-41 | 3,4-diClPh | —SO$_2$— | —CH$_2$— | —(CH$_2$)$_3$— |
| 3-2274 | Sub-42 | 3,4-diClPh | —SO$_2$— | —CH$_2$— | —(CH$_2$)$_3$— |
| 3-2275 | Sub-84 | 3,4-diClPh | —SO$_2$— | —CH$_2$— | —(CH$_2$)$_3$— |
| 3-2276 | Sub-81 | 3,4-diClPh | —SO$_2$— | —CH$_2$— | —(CH$_2$)$_3$— |
| 3-2277 | Sub-48 | 3,4-diClPh | —SO$_2$— | —CH$_2$— | —(CH$_2$)$_3$— |
| 3-2278 | Sub-37 | 4-ClPh | —SO$_2$— | —CH$_2$— | —(CH$_2$)$_3$— |
| 3-2279 | Sub-38 | 4-ClPh | —SO$_2$— | —CH$_2$— | —(CH$_2$)$_3$— |
| 3-2280 | Sub-39 | 4-ClPh | —SO$_2$— | —CH$_2$— | —(CH$_2$)$_3$— |
| 3-2281 | Sub-40 | 4-ClPh | —SO$_2$— | —CH$_2$— | —(CH$_2$)$_3$— |
| 3-2282 | Sub-41 | 4-ClPh | —SO$_2$— | —CH$_2$— | —(CH$_2$)$_3$— |
| 3-2283 | Sub-42 | 4-ClPh | —SO$_2$— | —CH$_2$— | —(CH$_2$)$_3$— |
| 3-2284 | Sub-84 | 4-ClPh | —SO$_2$— | —CH$_2$— | —(CH$_2$)$_3$— |
| 3-2285 | Sub-81 | 4-ClPh | —SO$_2$— | —CH$_2$— | —(CH$_2$)$_3$— |
| 3-2286 | Sub-48 | 4-ClPh | —SO$_2$— | —CH$_2$— | —(CH$_2$)$_3$— |
| 3-2287 | Sub-37 | 4-FPh | —SO$_2$— | —CH$_2$— | —(CH$_2$)$_3$— |
| 3-2288 | Sub-38 | 4-FPh | —SO$_2$— | —CH$_2$— | —(CH$_2$)$_3$— |
| 3-2289 | Sub-39 | 4-FPh | —SO$_2$— | —CH$_2$— | —(CH$_2$)$_3$— |
| 3-2290 | Sub-40 | 4-FPh | —SO$_2$— | —CH$_2$— | —(CH$_2$)$_3$— |
| 3-2291 | Sub-41 | 4-FPh | —SO$_2$— | —CH$_2$— | —(CH$_2$)$_3$— |
| 3-2292 | Sub-42 | 4-FPh | —SO$_2$— | —CH$_2$— | —(CH$_2$)$_3$— |
| 3-2293 | Sub-84 | 4-FPh | —SO$_2$— | —CH$_2$— | —(CH$_2$)$_3$— |
| 3-2294 | Sub-81 | 4-FPh | —SO$_2$— | —CH$_2$— | —(CH$_2$)$_3$— |
| 3-2295 | Sub-48 | 4-FPh | —SO$_2$— | —CH$_2$— | —(CH$_2$)$_3$— |
| 3-2296 | Sub-37 | 3,4-diClPh | —SO$_2$— | —CH$_2$— | —CH$_2$C(Me)$_2$— |
| 3-2297 | Sub-38 | 3,4-diClPh | —SO$_2$— | —CH$_2$— | —CH$_2$C(Me)$_2$— |
| 3-2298 | Sub-39 | 3,4-diClPh | —SO$_2$— | —CH$_2$— | —CH$_2$C(Me)$_2$— |
| 3-2299 | Sub-40 | 3,4-diClPh | —SO$_2$— | —CH$_2$— | —CH$_2$C(Me)$_2$— |
| 3-2300 | Sub-41 | 3,4-diClPh | —SO$_2$— | —CH$_2$— | —CH$_2$C(Me)$_2$— |
| 3-2301 | Sub-42 | 3,4-diClPh | —SO$_2$— | —CH$_2$— | —CH$_2$C(Me)$_2$— |
| 3-2302 | Sub-84 | 3,4-diClPh | —SO$_2$— | —CH$_2$— | —CH$_2$C(Me)$_2$— |
| 3-2303 | Sub-81 | 3,4-diClPh | —SO$_2$— | —CH$_2$— | —CH$_2$C(Me)$_2$— |
| 3-2304 | Sub-48 | 3,4-diClPh | —SO$_2$— | —CH$_2$— | —CH$_2$C(Me)$_2$— |
| 3-2305 | Sub-37 | 4-ClPh | —SO$_2$— | —CH$_2$— | —CH$_2$C(Me)$_2$— |
| 3-2306 | Sub-38 | 4-ClPh | —SO$_2$— | —CH$_2$— | —CH$_2$C(Me)$_2$— |
| 3-2307 | Sub-39 | 4-ClPh | —SO$_2$— | —CH$_2$— | —CH$_2$C(Me)$_2$— |
| 3-2308 | Sub-40 | 4-ClPh | —SO$_2$— | —CH$_2$— | —CH$_2$C(Me)$_2$— |
| 3-2309 | Sub-41 | 4-ClPh | —SO$_2$— | —CH$_2$— | —CH$_2$C(Me)$_2$— |
| 3-2310 | Sub-42 | 4-ClPh | —SO$_2$— | —CH$_2$— | —CH$_2$C(Me)$_2$— |
| 3-2311 | Sub-84 | 4-ClPh | —SO$_2$— | —CH$_2$— | —CH$_2$C(Me)$_2$— |
| 3-2312 | Sub-81 | 4-ClPh | —SO$_2$— | —CH$_2$— | —CH$_2$C(Me)$_2$— |
| 3-2313 | Sub-48 | 4-ClPh | —SO$_2$— | —CH$_2$— | —CH$_2$C(Me)$_2$— |
| 3-2314 | Sub-37 | 4-FPh | —SO$_2$— | —CH$_2$— | —CH$_2$C(Me)$_2$— |
| 3-2315 | Sub-38 | 4-FPh | —SO$_2$— | —CH$_2$— | —CH$_2$C(Me)$_2$— |
| 3-2316 | Sub-39 | 4-FPh | —SO$_2$— | —CH$_2$— | —CH$_2$C(Me)$_2$— |
| 3-2317 | Sub-40 | 4-FPh | —SO$_2$— | —CH$_2$— | —CH$_2$C(Me)$_2$— |
| 3-2318 | Sub-41 | 4-FPh | —SO$_2$— | —CH$_2$— | —CH$_2$C(Me)$_2$— |
| 3-2319 | Sub-42 | 4-FPh | —SO$_2$— | —CH$_2$— | —CH$_2$C(Me)$_2$— |
| 3-2320 | Sub-84 | 4-FPh | —SO$_2$— | —CH$_2$— | —CH$_2$C(Me)$_2$— |
| 3-2321 | Sub-81 | 4-FPh | —SO$_2$— | —CH$_2$— | —CH$_2$C(Me)$_2$— |
| 3-2322 | Sub-48 | 4-FPh | —SO$_2$— | —CH$_2$— | —CH$_2$C(Me)$_2$— |
| 3-2323 | Sub-37 | 3,4-diClPh | —SO$_2$— | —CH$_2$— | —CH$_2$-cPr— |
| 3-2324 | Sub-38 | 3,4-diClPh | —SO$_2$— | —CH$_2$— | —CH$_2$-cPr— |
| 3-2325 | Sub-39 | 3,4-diClPh | —SO$_2$— | —CH$_2$— | —CH$_2$-cPr— |
| 3-2326 | Sub-40 | 3,4-diClPh | —SO$_2$— | —CH$_2$— | —CH$_2$-cPr— |
| 3-2327 | Sub-41 | 3,4-diClPh | —SO$_2$— | —CH$_2$— | —CH$_2$-cPr— |
| 3-2328 | Sub-42 | 3,4-diClPh | —SO$_2$— | —CH$_2$— | —CH$_2$-cPr— |
| 3-2329 | Sub-84 | 3,4-diClPh | —SO$_2$— | —CH$_2$— | —CH$_2$-cPr— |
| 3-2330 | Sub-81 | 3,4-diClPh | —SO$_2$— | —CH$_2$— | —CH$_2$-cPr— |
| 3-2331 | Sub-48 | 3,4-diClPh | —SO$_2$— | —CH$_2$— | —CH$_2$-cPr— |
| 3-2332 | Sub-37 | 4-ClPh | —SO$_2$— | —CH$_2$— | —CH$_2$-cPr— |
| 3-2333 | Sub-38 | 4-ClPh | —SO$_2$— | —CH$_2$— | —CH$_2$-cPr— |
| 3-2334 | Sub-39 | 4-ClPh | —SO$_2$— | —CH$_2$— | —CH$_2$-cPr— |
| 3-2335 | Sub-40 | 4-ClPh | —SO$_2$— | —CH$_2$— | —CH$_2$-cPr— |
| 3-2336 | Sub-41 | 4-ClPh | —SO$_2$— | —CH$_2$— | —CH$_2$cPr— |
| 3-2337 | Sub-42 | 4-ClPh | —SO$_2$— | —CH$_2$— | —CH$_2$-cPr— |
| 3-2338 | Sub-84 | 4-ClPh | —SO$_2$— | —CH$_2$— | —CH$_2$-cPr— |

TABLE 3-continued

| Cpd. No. | R¹ | R² | A | B | E |
|---|---|---|---|---|---|
| 3-2339 | Sub-81 | 4-ClPh | —SO₂— | —CH₂— | —CH₂-cPr— |
| 3-2340 | Sub-48 | 4-ClPh | —SO₂— | —CH₂— | —CH₂-cPr— |
| 3-2341 | Sub-37 | 4-FPh | —SO₂— | —CH₂— | —CH₂-cPr— |
| 3-2342 | Sub-38 | 4-FPh | —SO₂— | —CH₂— | —CH₂-cPr— |
| 3-2343 | Sub-39 | 4-FPh | —SO₂— | —CH₂— | —CH₂-cPr— |
| 3-2344 | Sub-40 | 4-FPh | —SO₂— | —CH₂— | —CH₂-cPr— |
| 3-2345 | Sub-41 | 4-FPh | —SO₂— | —CH₂— | —CH₂-cPr— |
| 3-2346 | Sub-42 | 4-FPh | —SO₂— | —CH₂— | —CH₂-cPr— |
| 3-2347 | Sub-84 | 4-FPh | —SO₂— | —CH₂— | —CH₂-cPr— |
| 3-2348 | Sub-81 | 4-FPh | —SO₂— | —CH₂— | —CH₂-cPr— |
| 3-2349 | Sub-48 | 4-FPh | —SO₂— | —CH₂— | —CH₂-cPr— |
| 3-2350 | Sub-37 | 3,4-diClPh | —SO₂— | —CH₂— | —C(Me)₂— |
| 3-2351 | Sub-38 | 3,4-diClPh | —SO₂— | —CH₂— | —C(Me)₂— |
| 3-2352 | Sub-39 | 3,4-diClPh | —SO₂— | —CH₂— | —C(Me)₂— |
| 3-2353 | Sub-40 | 3,4-diClPh | —SO₂— | —CH₂— | —C(Me)₂— |
| 3-2354 | Sub-41 | 3,4-diClPh | —SO₂— | —CH₂— | —C(Me)₂— |
| 3-2355 | Sub-42 | 3,4-diClPh | —SO₂— | —CH₂— | —C(Me)₂— |
| 3-2356 | Sub-84 | 3,4-diClPh | —SO₂— | —CH₂— | —C(Me)₂— |
| 3-2357 | Sub-81 | 3,4-diClPh | —SO₂— | —CH₂— | —C(Me)₂— |
| 3-2358 | Sub-48 | 3,4-diClPh | —SO₂— | —CH₂— | —C(Me)₂— |
| 3-2359 | Sub-37 | 4-ClPh | —SO₂— | —CH₂— | —C(Me)₂— |
| 3-2360 | Sub-38 | 4-ClPh | —SO₂— | —CH₂— | —C(Me)₂— |
| 3-2361 | Sub-39 | 4-ClPh | —SO₂— | —CH₂— | —C(Me)₂— |
| 3-2362 | Sub-40 | 4-ClPh | —SO₂— | —CH₂— | —C(Me)₂— |
| 3-2363 | Sub-41 | 4-ClPh | —SO₂— | —CH₂— | —C(Me)₂— |
| 3-2364 | Sub-42 | 4-ClPh | —SO₂— | —CH₂— | —C(Me)₂— |
| 3-2365 | Sub-84 | 4-ClPh | —SO₂— | —CH₂— | —C(Me)₂— |
| 3-2366 | Sub-81 | 4-ClPh | —SO₂— | —CH₂— | —C(Me)₂— |
| 3-2367 | Sub-48 | 4-ClPh | —SO₂— | —CH₂— | —C(Me)₂— |
| 3-2368 | Sub-37 | 4-FPh | —SO₂— | —CH₂— | —C(Me)₂— |
| 3-2369 | Sub-38 | 4-FPh | —SO₂— | —CH₂— | —C(Me)₂— |
| 3-2370 | Sub-39 | 4-FPh | —SO₂— | —CH₂— | —C(Me)₂— |
| 3-2371 | Sub-40 | 4-FPh | —SO₂— | —CH₂— | —C(Me)₂— |
| 3-2372 | Sub-41 | 4-FPh | —SO₂— | —CH₂— | —C(Me)₂— |
| 3-2373 | Sub-42 | 4-FPh | —SO₂— | —CH₂— | —C(Me)₂— |
| 3-2374 | Sub-84 | 4-FPh | —SO₂— | —CH₂— | —C(Me)₂— |
| 3-2375 | Sub-81 | 4-FPh | —SO₂— | —CH₂— | —C(Me)₂— |
| 3-2376 | Sub-48 | 4-FPh | —SO₂— | —CH₂— | —C(Me)₂— |

Of the compounds listed above, the following are preferred, that is to say Compounds No. 1-1025 to 1-1536, 2-1537 to 2-1728, 2-1825 to 2-1920, 2-1969 to 2-2016, 2-2113 to 2-2160, 2-2257 to 2-2352, 3-1 to 3-64, and 3-97 to 3-160.

More preferred compounds are Compounds No. 1-1089 to 1-1120, 1-1217 to 1-1280, 1-1313 to 1-1344, 1-1505 to 1-1536, 2-1825 to 2-1920, 2-1969 to 2-2016, 2-2257 to 2-2352, 3-5 to 3-11, 3-17, 3-18, 3-37 to 3-43, 3-49, 3-50, 3-101, to 3-107, 3-113, 3-114, 3-133 to 3-139, 3-145 and 3-146.

Still more preferred compounds 1-1089 to 1-1120, 1-1313 to 1-1344, 2-1969 to 2-2016, 3-7, 3-8, 3-10, 3-11, 3-39, 3-40, 3-42, 3-43, 3-103, 3-104, 3-106, 3-107, 3-135, 3-136, 3-138, and 3-139.

The most preferred compounds of the present invention are as follows:

1-{2-[5-(3,4-dichlorophenyl)-3-(3,4,5-trimethoxybenzoyl)oxazolidin-5-yl]ethyl}-4-phenylpiperidine-4-carboxamide;

1-{2-[5-(3,4-dichlorophenyl)-3-(3,4,5-trimethoxybenzoyl)oxazolidin-5-yl]ethyl}-4-phenylpiperidine-4-(N,N-dimethylcarboxamide);

1-{2-[5-(3,4-dichlorophenyl)-3-(3,4,5-trimethoxybenzoyl)oxazolidin-5-yl]ethyl}-4-(2-pyridyl)piperidine-4-carboxamide;

1-{2-[5-(3,4-dichlorophenyl)-3-(3,4,5-trimethoxybenzoyl)oxazolidin-5-yl]ethyl}-4-(3-pyridyl)piperidine-4-carboxamide;

1-{2-[5-(3,4-dichlorophenyl)-3-(3,4,5-trimethoxybenzoyl)oxazolidin-5-yl]ethyl}-4-(4-pyridyl)piperidine-4-carboxamide;

1-{2-[5-(4-chlorophenyl)-3-(3,4,5-trimethoxybenzoyl)oxazolidin-5-yl]ethyl}-4-phenylpiperidine-4-carboxamide;

1-{2-[5-(4-chlorophenyl)-3-(3,4,5-trimethoxybenzoyl)oxazolidin-5-yl]ethyl}-4-phenylpiperidine-4-(N,N-dimethylcarboxamide);

1-{2-[5-(4-chlorophenyl)-3-(3,4,5-trimethoxybenzoyl)oxazolidin-5-yl]ethyl}-4-(2-pyridyl)piperidine-4-carboxamide;

1-{2-[5-(4-chlorophenyl)-3-(3,4,5-trimethoxybenzoyl)oxazolidin-5-yl]ethyl}-4-(3-pyridyl)piperidine-4-carboxamide;

1-{2-[5-(4-chlorophenyl)-3-(3,4,5-trimethoxybenzoyl)oxazolidin-5-yl]ethyl}-4-(4-pyridyl)piperidine-4-carboxamide;

1-{2-[5-(4-fluorophenyl)-3-(3,4,5-trimethoxybenzoyl)oxazolidin-5-yl]ethyl}-4-phenylpiperidine-4-carboxamide;

1-{2-[5-(4-fluorophenyl)-3-(3,4,5-triethoxybenzoyl)oxazolidin-5-yl]ethyl}-4-phenylpiperidine-4-(N,N-dimethylcarboxamide);

1-{2-[5-(4-fluorophenyl)-3-(3,4,5-trimethoxybenzoyl)oxazolidin-5-yl]ethyl}-4-(2-pyridyl)piperidine-4-carboxamide;

1-{2-[5-(4-fluorophenyl)-3-(3,4,5-triethoxybenzoyl)oxazolidin-5-yl]ethyl}-4-(3-pyridyl)piperidine-4-carboxamide;

1-{2-[5-(4-fluorophenyl)-3-(3,4,5-trimethoxybenzoyl) oxazolidin-5-yl]ethyl}-4-(4-pyridyl)piperidine-4-carboxamide;

1-{2-[2-(3,4-dichlorophenyl)-4-(3,4,5-trimethoxybenzoyl)morpholin-2-yl]ethyl}-4-phenylpiperidine-4-carboxamide;

1-{2-[2-(3,4-dichlorophenyl)-4-(3,4,5-trimethoxybenzoyl)morpholin-2-yl]ethyl}-4-phenylpiperidine-4-(N,N-dimethylcarboxamide);

1-{2-[2-(3,4-dichlorophenyl)-4-(3,4,5-trimethoxybenzoyl)morpholin-2-yl]ethyl}-4-phenyl-4-(pyrrolidin-1-ylcarbonyl)piperidine;

1-{2-[2-(3,4-dichlorophenyl)-4-(3,4,5-trimethoxybenzoyl)morpholin-2-yl]ethyl}-4-morpholinocarbonyl-4-phenylpiperidine;

1-{2-[2-(4-chlorophenyl)-4-(3,4,5-trimethoxybenzoyl)morpholin-2-yl]ethyl}-4-phenylpiperidine-4-carboxamide;

1-{2-[2-(4-chlorophenyl)-4-(3,4,5-triethoxybenzoyl)morpholin-2-yl]ethyl[-4-phenylpiperidine-4-(N,N-dimethylcarboxamide);

1-{2-[2-(4-fluorophenyl)-4-(3,4,5-trimethoxybenzoyl)morpholin-2-yl]ethyl[-4-phenylpiperidine-4-carboxamide;

1-{2-[2-(4-fluorophenyl)-4-(3,4,5-trimethoxybenzoyl)morpholin-2-yl]ethyl}-4-phenylpiperidine-4-(N,N-dimethylcarboxamide);

1-{2-[2-(3,4-dichlorophenyl)-4-(3-methoxybenzoyl)morpholin-2-yl]ethyl}-4-phenylpiperidine-4-carboxamide;

1-{2-[2-(3,4-dichlorophenyl)-4-(3-methoxybenzoyl)morpholin-2-yl]ethyl}-4-phenylpiperidine-4-(N,N-dimethylcarboxamide);

1-{2-[2-(3,4-dichlorophenyl)-4-(3,4,5-trimethoxybenzoyl)morpholin-2-yl]ethyl}spiro[isobenzofuran-1(3H),4'-piperidine];

1-{2-[2-(3,4-dichlorophenyl)-4-(3,4,5-trimethoxybenzoyl)morphoin-2-yl]ethyl}spiro[benzo[c]thiophene-1(3H),4'-piperidine];

1-{2-[2-(3,4-dichlorophenyl)-4-(3,4,5-trimethoxybenzoyl)morpholin-2-yl]ethyl}spiro[benzo[c]thiophene-1(3H),4'-piperidine]-2-oxide;

1-{2-[2-(3,4-dichlorophenyl)-4-(3,4,5-triethoxybenzoyl)morpholin-2-yl]ethyl}spiro[isoquinoline-1(2H),4'-piperidine]-3-(4H)-one;

1-{2-[2-(3,4-dichlorophenyl)-4-(3-methoxybenzoyl)morpholin-2-yl]ethyl}spiro[isobenzofuran-1(3H),4'-piperidine];

1-{2-[2-(3,4-dichlorophenyl)-4-(3-methoxybenzoyl)morpholin-2-yl]ethyl}spiro[benzo[c]thiophene-1(3H),4'-piperidine];

1-{2-[2-(3,4-dichlorophenyl)-4-(3-methoxybenzoyl)morpholin-2-yl]ethyl}spiro[benzo[c]thiophene-1(3H),4'-piperidine]-2-oxide;

1-{2-[2-(3,4-dichlorophenyl)-4-(3-methoxybenzoyl)morpholin-2-yl]ethyl}spiro[isoquinoline-1(2H),4'-piperidin]-3-(4H)-one;

1-{2-[(5R)-(3,4-dichlorophenyl)-3-(3,4,5-trimethoxybenzoyl)oxazolidin-5-yl]ethyl}spiro[benzo[c]thiophene-1(3H),4'-piperidine]-(2S)-oxide;

1-{2-[(5R)-(4-chlorophenyl)-3-(3,4,5-trimethoxybenzoyl)oxazolidin-5-yl]ethyl}spiro[benzo[c]thiophene-1(3H),4'-piperidine]-(2S)-oxide;

1-{2-[(5R)-(4-fluorophenyl)-3-(3,4,5-trimethoxybenzoyl)oxazolidin-5-yl]ethyl}spiro[benzo[c]thiophene-1(3H),4'-piperidine]-(2S)-oxide;

1-{2-[(2R)-(3,4-dichlorophenyl)-4-(3,4,5-trimethoxybenzoyl)morphoin-2-yl]ethyl}spiro[benzo[c]thiophene-1(3H),4'-piperidine]-(2S)-oxide;

1-{2-[(2R)-(4-chlorophenyl)-4-(3,4,5-trimethoxybenzoyl)morpholin-2-yl]ethyl}spiro[benzo[c]thiophene-1-(3H),4'-piperidine]-(2S)-oxide;

1-{2-[(2R)-(4-florophenyl)-4-(3,4,5-trimethoxybenzoyl)morpholin-2-yl]ehtyl}spiro[benzo[c]thiophene-1(3H),4'-piperidine]-(2S)-oxide;

1-{2-[(2R)-(3,4-dichlorophenyl)-4-(3,4,5-trimethoxybenzoyl)hexahydro-1,4-oxazepin-2-yl]ethyl}spiro[benzo[c]thiophene-1(3H),4'-piperidine]-(2)-oxide;

1-{2-[(2R)-(4-chlorophenyl)-4-(3,4,5-trimethoxybenzoyl)hexahydro-1,4-oxazepin-2-yl]ethyl}spiro[benzo[c]thiophene-1(3H),4'-piperidine]-(2S)-oxide;

1-{2-[(2R)-(4-fluorophenyl)-4-(3,4,5-trimethoxybenzoyl)hexahydro-1,4-oxazepin-2-yl]ethyl}spiro[benzo[c]thiophene-1-(3H),4'-piperidine]-(2S)-oxide;

1-{2-[(2R)-(3,4-dichlorophenyl)-4-(3-isopropoxyphenyacetyl)morpholin-2-yl]ethyl}spiro[benzo[c]thiophene-1(3H),4'-piperidine]-(2S)-oxide;

1-{2-[(2R)-(4-chlorophenyl)-4-(3-isopropoxyphenylacetyl)morpholin-2-yl]ethyl}spiro[benzo[c]thiophene-1(3H),4'-piperidine]-(2S)-oxide;

1-{2-[(2R)-(4-fluorophenyl)-4-(3-isopropoxyphenylacetyl)morpholin-2-yl]ethyl}spiro[benzo[c]thiophene-1(3H),4'-piperidine]-(2S)-oxide; and 1-{2-[(2R)-(3,4-dichlorophenyl)-5,5-dimethyl-4-(3,4,5-trimethoxybenzoyl)morpholin-2-yl]ethyl}spiro[benzo[c]thiophene-1-(3H),4'-piperidine]-(2S)-oxide.

The compounds of the present invention may be prepared by a variety of processes well known for the preparation of compounds of this type, for example as illustrated by the following Reaction Schemes A to J.

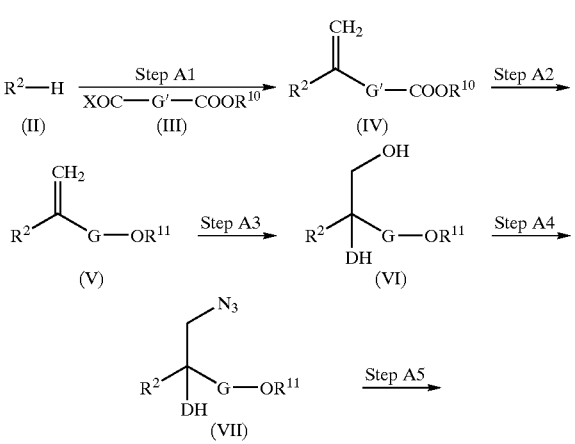

Reaction Scheme A:

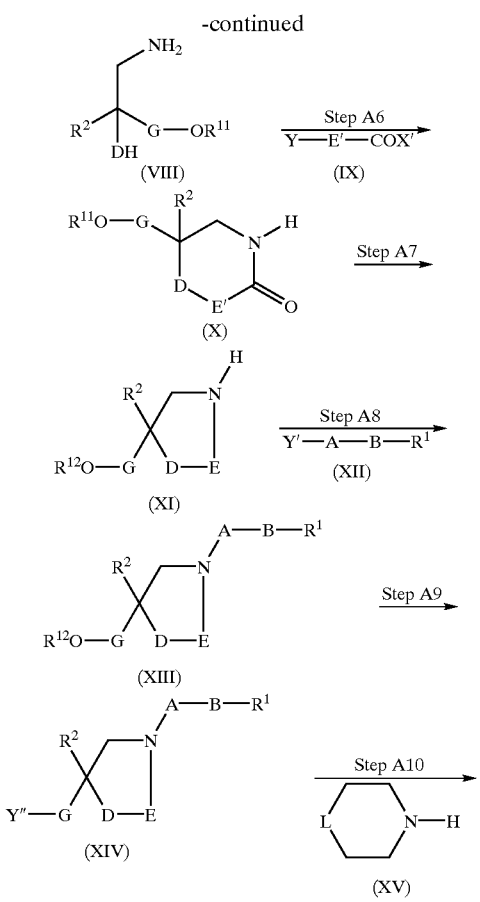

wherein R¹, R², A, B, D, E, G and L are as defined above.

X, X', Y, Y' and Y" may be any group or atom which is capable of being eliminated as a nucleophilic residue and are not specifically limited. Preferred examples of such groups and atoms include: halogen atoms, such as the chlorine, bromine and iodine atoms; trihalomethoxy groups, such as the trichloromethoxy group; alkanesulfonyloxy groups having from 1 to 6 carbon atoms, such as the methanesulfonyloxy and ethanesulfonyloxy groups; haloalkanesulfonyloxy groups having from 1 to 6 carbon atoms, such as the trifluoromethanesulfonyloxy and pentafluoroethanesulfonyloxy groups; and arylsulfonyloxy groups, such as the benzenesulfonyloxy, p-toluenesulfonyloxy and p-nitrobenzenesulfonyloxy groups. Of these, we prefer the halogen atoms and the alkanesulfonyloxy groups.

X may bond with $R^{10}$ to represent a single bond. In this case, the compound of formula (III) becomes an acid anhydride.

E' represents a group corresponding to the group represented by E, but in which the number of carbon atoms is one less than that of the alkylene group having from 1 to 4 carbon atoms or of the cycloalkane-1,1-diylmethyl group or of the cycloalkane-1,1-di(ylmethyl) group.

G' represents a group corresponding to the group represented by G, but in which the number of carbon atoms is one less than that of the alkylene group having from 1 to 4 carbon atoms or of the alkenylene group having from 2 to 4 carbon atoms.

$R^{10}$ represents a carboxy-protecting group which can be cleaved by a chemical process, such as hydrogenolysis, hydrolysis, electrolysis, or photolysis. Preferred examples of such protecting groups used in the reaction include:

alkyl groups having from 1 to 6 carbon atoms, such as those exemplified above in relation to $R^5$ etc.;

alkenyl groups having from 2 to 6 carbon atoms, such as the vinyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, and 5-hexenyl groups;

alkynyl groups having from 2 to 6 carbon atoms, such as the ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 4-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl, and 5-hexynyl groups;

haloalkyl groups having from 1 to 6 carbon atoms, such as those exemplified above in relation to substituents α;

hydroxyalkyl groups, such as the hydroxymethyl, 2-hydroxyethyl, 2,3-dihydroxypropyl, 3-hydroxypropyl, 3,4-dihydroxybutyl, and 4-hydroxybutyl groups;

aliphatic acyl-substituted alkyl groups, such as the acetylmethyl group;

aralkyl groups, such as those exemplified above in relation to $R^5$ etc.; and silyl groups, such as those exemplified above in relation to ester groups.

$R^{11}$ represents a hydroxy-protecting group which can be cleaved by a chemical process, such as hydrogenolysis, hydrolysis, electrolysis, or photolysis. Preferred examples of such protecting groups include:

acyl groups (including alkanoyl, haloalkanoyl, alkoxyalkanoyl, alkenoyl and alkynoyl groups), such as those exemplified above in relation to $R^5$ etc.;

aromatic acyl groups (including halogen-substituted, alkyl-substituted, alkoxy-substituted, nitro-substituted, alkoxycarbonyl-substituted and aryl-substituted aromatic acyl groups), such as those exemplified above in relation to $R^5$;

tetrahydropyranyl or tetrahydrothiopyranyl groups, such as those exemplified above in relation to ester groups;

tetrahydrofuranyl or tetrahydrothiofuranyl groups, such as those exemplified above in relation to ester groups;

silyl groups, such as those exemplified above in relation to ester groups;

alkoxymethyl groups, such as those exemplified above in relation to ester groups;

substituted ethyl groups, such as those exemplified above in relation to ester groups;

aralkyl groups, such as those exemplified above in relation to $R^5$ etc.;

alkoxycarbonyl groups, such as those exemplified above in relation to substituents α;

alkenyloxycarbonyl groups, such as those exemplified above in relation to ester groups; and aralkyloxycarbonyl groups, such as those exemplified above in relation to ester groups.

$R^{12}$ represents a hydrogen atom or a hydroxy-protecting group, as exemplified above in relation to $R^{11}$.

Step A1

In this Step, a compound of formula (IV) is prepared by reacting a compound of formula (II) according to the Friedel-Crafts reaction with an acid derivative of formula (III) in the presence of a Lewis acid and in a solvent (Step A1a), optionally esterifying the resultant free carboxylic acid with a group of formula $R^{10}$ when the acid derivative of formula (III) is an acid anhydride (Step A1b), and then converting a carbonyl group into an exo-methylene group according to the Wittig reaction in a solvent in the presence of a base (Step A1c).

Step A1a

There is no particular restriction on the nature of the Lewis acids used in the Friedel-Crafts reaction, and any Lewis acid commonly used in reactions of this type may equally be used here. Examples of such Lewis acids include: tri($C_1$-$C_6$ alkyl)silyl trifluoromethanesulfonates, such as trimethylsilyl trifluoromethanesulfonate; aluminum salts, such as aluminum chloride; tin salts, such as tin tetrachloride; zinc salts, such as zinc bromide; titanium salts, such as titanium tetrachloride; perchlorates, such as trimethylsilyl perchlorate or triphenylmethyl perchlorate. Of these, we prefer the aluminum salts and the titanium salts, aluminum chloride being particularly preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; nitro compounds, such as nitroethane and nitrobenzene. Of these, we particularly prefer the halogenated hydrocarbons.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 150° C., more preferably from 0 to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 12 hours, will usually suffice.

Step A1b

When the esterification of this Step is alkylation, the reaction may be accomplished by any one of the following processes.

Step A1b(i)

Alkylation may be accomplished by reacting the resulting carboxylic acid with a compound of formula $R^{10}$—X', wherein:

$R^{10}$ is as defined above; and

X' represents a group capable of being eliminated as a nucleophilic residue, such as a halogen atom (e.g. a chlorine, bromine or iodine atom); an alkanesulfonyloxy group having from 1 to 6 carbon atoms (e.g. a methanesulfonyloxy or ethanesulfonyloxy group); a haloalkanesulfonyloxy group having from 1 to 6 carbon atoms (e.g. a trifluoromethanesulfonyloxy or pentafluoroethanesulfonyloxy group); an arylsulfonyloxy group (e.g. a benzenesulfonyloxy, p-toluenesulfonyloxy or p-nitrobenzenesulfonyloxy group).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitriles, such as acetonitrile or isobutyronitrile; amides, such as formamide, dimethylformamide, dimethylacetamide, N-methyl-2-pyrrolidone, N-methylpyrrolidinone and hexamethylphosphoric triamide.

The reaction is also normally and preferably carried out in the presence of a base. There is likewise no particular restriction on the nature of the bases used, and any base commonly used in reactions of this type may equally be used here. Examples of such bases include: alkali metal carbonates, such as sodium carbonate, potassium carbonate and lithium carbonate; alkali metal hydrogencarbonates, such as sodium hydrogencarbonate, potassium hydrogencarbonate and lithium hydrogencarbonate; alkali metal hydrides, such as lithium hydride, sodium hydride, and potassium hydride; alkali metal hydroxides, such as sodium hydroxide, potassium hydroxide, barium hydroxide and lithium hydroxide; alkali metal fluorides, such as, lithium fluoride, sodium fluoride, and potassium fluoride; alkali metal alkoxides, such as sodium methoxide, sodium ethoxide, potassium methoxide, potassium ethoxide, potassium t-butoxide and lithium methoxide; alkali metal mercaptans, such as sodium methylmercaptan and sodium ethylmercaptan; organic bases, such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU); and organic metal bases, such as butyllithium, lithium diisopropylamide and lithium bis(trimethylsilyl)amide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 120° C., more preferably from 0 to 80° C. The time required for the reaction may also vary widely, depending on many factors, notably the reaction temperature and the nature of the reagents and solvent employed. However, provided that the reaction is effected under the preferred conditions outlined above, a period of from 0.5 to 10 hours will usually suffice.

Step A1b(ii)

Alkylation may be accomplished by reacting the resulting carboxylic acid with a compound of formula $R^{10}$—OH [wherein $R^{10}$ is as defined above], using a condensing agent.

There is no particular restriction on the nature of the condensing agents used, and any condensing agent commonly used in reactions of this type may equally be used here. Examples of such condensing agents include:

(1) a combination of a phosphonate (e.g. diphenylphosphoryl azide or diethyl cyanophosphonate) and one or more of the bases described below;

(2) a carbodiimide (e.g. 1,3-dicyclohexylcarbodiimide, 1,3-diisopropylcarbodiimide or 1-ethyl-3-(3-dimethylaminopropyl)carbodiimide); a combination of one or more of the above carbodiimides and one or more of the bases described below; or a combination of one or more of the above carbodiimides and an N-hydroxy compound (e.g. N-hydroxysuccinimide, 1-hydroxybenzotriazole or N-hydroxy-5-norbornene-2,3-dicarboxyimide);

(3) combination of a disulfide (e.g. 2,2'-dipyridyl disulfide or 2,2'-dibenzothiazolyl disulfide, etc.) and a phosphine (e.g. triphenylphosphine or tributylphosphine);

(4) a carbonate [e.g. N,N'-disuccinimidyl carbonate, di-2-pyridyl carbonate or S,S'-bis(1-phenyl-1H-tetrazol-5-yl)dithiocarbonate];

(5) a phosphinic chloride [e.g. N,N'-bis(2-oxo-3-oxazolidinyl)phosphinic chloride];

(6) an oxalate [e.g. N,N'-disuccinimidyl oxalate, N,N'-diphthalimide oxalate, N,N'-bis(5-norbornene-2,3-dicarboxyimidyl)oxalate, 1,1'-bis(benzotriazolyl)oxalate, 1,1'-bis(6-chlorobenzotriazolyl)oxalate or 1,1'-bis(6-trifluoromethylbenzotriazolyl)oxalate];

(7) a combination of one or more of the above phosphines and one or more azodicarboxylates or azodicarboxyamides [e.g. diethyl azodicarboxylate, 1,1'-(azodicarbonyl)dipiperidine]; or a combination of one or more of the above phosphines and one or more of the bases described below;

(8) an N-alkyl-5-arylisoxazolium-3'-sulfonate, in which the alkyl part has from 1 to 6 carbon atoms and the aryl part is as defined and exemplified above in relation to $R^1$ etc. (e.g. N-ethyl-5-phenylisoxazolium-3'-sulfonate);

(9) a diheteroaryldiselenide (e.g. di-2-pyridyldiselenide);

(10) an arylsulfonyltriazolide in which the aryl part is as defined and exemplified above in relation to $R^1$ etc. (e.g. p-nitrobenzenesulfonyltriazolide);

(11) a 2-halo-1-alkylpyridinium halide, in which the alkyl part has from 1 to 6 carbon atoms (e.g. 2-chloro-1-methylpyridinium iodide);

(12) an imidazole (e.g. 1,1'-oxalyldiimidazole, N,N'-carbonyldiimidazole);

(13) a 3-alkyl-2-halogen-benzothiazolium fluoroborate, in which the alkyl part has from 1 to 6 carbon atoms (e.g. 3-ethyl-2-chloro-benzothiazolium fluoroborate);

(14) a 3-alkyl-benzothiazole-2-serone, in which the alkyl part has from 1 to 6 carbon atoms (e.g. 3-methyl-benzothiazol-2-serone);

(15) a phosphate (e.g. phenyldichlorophosphate or polyphosphate);

(16) a halosulfonyl isocyanate (e.g. chlorosulfonyl isocyanate);

(17) a halosilane (e.g. trimethylsilyl chloride or triethylsilyl chloride);

(18) a combination of an alkanesulfonyl halide having from 1 to 6 carbon atoms (e.g. methanesulfonyl chloride) and one or more of the bases described below; and

(19) an N,N,N',N'-tetraalkyl haloformamidium chlorides, in which each alkyl group has from 1 to 6 carbon atoms (e.g. N,N,N',N'-tetramethylchloroformamidium chloride).

Of these, we prefer the carbodiimides or a combination of a phosphine and an azodicarboxylate or azodicarboxyamide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide There is likewise no particular restriction on the nature of the bases used, and any base commonly used in reactions of this type may equally be used here. Examples of such bases include: organic bases, such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, quinoline, N,N-dimethylaniline and N,N-diethylaniline.

If desired, 4-(N,N-dimethylamino)pyridine or 4-pyrrolidinopyridine can be used in a catalytic amount in combination with one or more of the other bases. The efficiency of the reaction may also, if desired, be improved by conducting it in the presence of one or more of the following: dehydrating agents (e.g. molecular sieves), quatemary ammonium salts (e.g. benzyltriethylammonium chloride or tetrabutylammonium chloride), crown ethers (e.g. dibenzo-18-crown-6) and acid scavengers (e.g. 3,4-dihydro-2H-pyrido[1,2-a]pyrimidin-2-one).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Step A1b(iii)

Introduction of a lower alkyl protecting group by alkylation may be accomplished by reacting the resulting carboxylic acid with a corresponding alcohol (e.g. methanol, ethanol, propanol or butanol).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: the same alcohols as those of the reagent; aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitriles, such as acetonitrile or isobutyronitrile; amides, such as formamide, dimethylformamide, dimethylacetamide, N-methyl-2-pyrrolidone, N-methylpyrrolidinone or hexamethylphosphoric triamide. Of these, we particularly prefer the same alcohols as those of the reagent.

The reaction is carried out in the presence of an acid catalyst. There is likewise no particular restriction on the nature of the acid catalysts used, and any acid catalyst commonly used in reactions of this type may equally be used here. Examples of such acid catalysts include: Brønsted acids, such as inorganic acids (e.g. hydrogen chloride, hydrogen bromide, sulfuric acid, perchloric acid or phosphoric acid) and organic acids (e.g. acetic acid, formic acid, oxalic acid, methanesulfonic acid, p-toluenesulfonic acid, trifluoroacetic acid or trifluoromethanesulfonic acid); and Lewis acids (e.g. boron trichloride, boron trifluoride or boron tribromide) or acidic ion-exchange resins.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 150° C., more preferably from 50 to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 5 hours, will usually suffice.

Step A1c

In the Wittig reaction, there is likewise no particular restriction on the nature of the Wittig reagents used, and any Wittig reagent commonly used in reactions of this type may equally be used here. Examples of such Wittig reagents include: methyltriphenylphosphonium halides, such as methyltriphenylphosphonium bromide and methyltriphenylphosphonium iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diusopropyl ether and tetrahydrofuran; nitrites, such as acetonitrile and isobutyronitrile; amides, such as formamide, dimethylformamide, dimethylacetamide and hexamethylphosphoric triamide; and sulfoxides, such as dimethyl sulfoxide and sulfolane. Of these, we particularly prefer the aromatic hydrocarbons, most preferably benzene.

There is likewise no particular restriction on the nature of the bases used, and any base commonly used in reactions of this type may equally be used here. Examples of such bases include: alkali metal carbonates, such as sodium carbonate, potassium carbonate and lithium carbonate; alkali metal hydrogencarbonates, such as sodium hydrogencarbonate, potassium hydrogencarbonate and lithium hydrogencarbonate; alkali metal hydrides, such as lithium hydride, sodium hydride and potassium hydride; alkali metal and alkaline earth metal hydroxides, such as sodium hydroxide, potassium hydroxide, barium hydroxide and lithium hydroxide; alkali metal fluorides, such as sodium fluoride and potassium fluoride; and alkali metal alkoxides, such as sodium methoxide, sodium ethoxide, potassium methoxide, potassium ethoxide, potassium t-butoxide and lithium methoxide. Of these, we particularly prefer the alkali metal hydrides and alkali metal alkoxides, most preferably the alkali metal alkoxides.

The reaction can take place over a wide range of termperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 100° C., more preferably from 0 to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 12 hours, will usually suffice.

Step A2

In this Step a compound of formula (V) is prepared by reducing the ester compound of formula (IV) (which may have been prepared as described in Step A1) in a solvent using a reducing agent to convert the ester group into a primary hydroxy group and then protecting this hydroxy group with a group $R^{11}$.

There is no particular restriction on the nature of the reducing agents used, and any reducing agent commonly used in reactions of this type may equally be used here. Examples of such reducing agents include: hydride reagents, such as alkali metal borohydrides (e.g. sodium borohydride or lithium borohydride), aluminum hydride compounds (e.g. lithium aluminum hydride or lithium tri-t-butoxyaluminohydride), sodium tellurium hydride and organic aluminum hydride reducing agents [e.g. diisobutylaluminum hydride or sodium bis(methoxyethoxy) aluminum hydride]. Of these, we particularly prefer the aluminum hydride compounds and organic aluminum hydride reducing agents, most preferably the aluminum hydride compounds.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; and ethers, such as diethyl ether, diisopropyl ether, tetrahydrofiran, dioxane, dimethoxyethane and diethylene glycol dimethyl ether. Of these, we particularly prefer the ethers, most preferably diethyl ether and tetrahydrofuran.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78 to 50° C., more preferably from −20 to 20° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 10 minutes to 2 hours, will usually suffice.

Introduction of the protecting group $R^{11}$ may be accomplished by any one of the following processes.

Step A2(i)

The protecting group $R^{11}$ may be introduced by reacting the unprotected compound with a suitable amount, preferably from 1 to 4 equivalents (more preferably from 2 to 3 equivalents) of a compound of formula $R^{11}$—X" or $R^{11}$—O—$R^{11}$ ($R^{11}$ in the latter compound should be a group of the acyl type)

wherein $R^{11}$ is as defined above, preferably a silyl group, of which, we particularly prefer the t-butyldimethylsilyl group;

X" represents any group capable of being eliminated as a nucleophilic residue, for example: a halogen atom, such as a chlorine, bromine or iodine atom; an alkoxycarbonyloxy group having from 1 to 6 carbon atoms in the alkoxy part, such as a methoxycarbonyloxy or ethoxycarbonyloxy group; a haloalkanoyloxy group having from 2 to 6 carbon atoms, such as a chloroacetoxy, dichloroacetoxy, trichloroacetoxy or trifluoroacetoxy group; an alkanesulfonyloxy group having from 1 to 6 carbon atoms, such as a methanesulfonyloxy or ethanesulfonyloxy group; a haloalkanesulfonyloxy group having from 1 to 6 carbon atoms, such as a trifluoromethanesulfonyloxy or pentafluoroethanesulfonyloxy group; an arylsulfonyloxy group in which the aryl part is as defined and exemplified above in relation to $R^1$ etc., such as a benzenesulfonyloxy, p-toluenesulfonyloxy or P-nitrobenzenesulfonyloxy group. Of these, we particularly prefer the halogen atoms, the alkanesulfonyloxy groups and the arylsulfonyloxy groups.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetarnide, N-methyl-2-pyrrolidone, N-methylpyrrolidinone and hexamethylphosphoric triamide. Of these, we particularly prefer the amides.

The reaction may be carried out in the presence of a base. There is likewise no particular restriction on the nature of the bases used, and any base commonly used in reactions of this type may equally be used here. Examples of such bases include: organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, imidazole, quinoline, N,N-dimethylaniline and N,N-diethylaniline. Of these, we particularly prefer triethylamine and 4-(N,N-dimethylarnino)pyridine.

Furthermore, 4-N,N-dimethylamino)pyridine or 4-pyrrolidinopyridine can be used in a catalytic amount in combination with one or more of the other bases. The efficiency of the reaction may, if desired, be further improved by carrying it out in the presence of one or more of the following: quatemary ammonium salts (e.g. benzyltriethylammonium chloride or tetrabutylammonium chloride) and crown ethers (e.g. dibenzo-18-crown-6).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 100° C., more preferably from −10 to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 1 day, more preferably from 30 minutes to 10 hours., will usually suffice.

Specific examples of the compound of formula $R^{11}$—X include: acyl halides, such as aliphatic acyl halides (e.g. acetyl chloride, propionyl chloride, butyryl bromide, valeryl chloride and hexanoyl chloride); alkoxycarbonyl halides having from 1 to 6 carbon atoms in the alkoxy part (e.g. methoxycarbonyl chloride, methoxycarbonyl bromide, ethoxycarbonyl chloride, propoxycarbonyl chloride, butoxycarbonyl chloride and hexyloxycarbonyl chloride); arylcarbonyl halides (e.g. benzoyl chloride, benzoyl bromide and naphthoyl chloride); and silyl halides, such as t-butyldimnethylsilyl chloride, trirnethylsilyl chloride, triethylsilyl chloride, triethylsilyl bromide, triisopropylsilyl chloride, dimethylisopropylsilyl chloride, diethylisopropylsilyl chloride, t-butyldiphenylsilyl chloride, diphenylmethylsilyl chloride, triphenylsilyl chloride or corresponding silyl trifluoromethanesulfonates; aralkyl halides, such as benzyl chloride and benzyl bromide; carbonyloxyalkyl halides having from 1 to 6 carbon atoms in the alkyl part, such as pivaloyloxymethyl chloride and ethoxycarbonyloxymethyl chloride.

Specific examples of the compound of formula $R^{11}$—O—$R^{11}$: include aliphatic carboxylic anhydrides, such as acetic anhydride, propionic anhydride, valeric anhydride and hexanoic anhydride. An mixed acid anhydride (e.g. a mixed anhydride of formic acid and acetic acid) can also be used.

Step A2(ii)

The protecting group $R^{11}$ may be introduced by reacting the unprotected compound with a compound of formula $R^{11}$—OH [wherein $R^{11}$ is one of the groups of the acyl type included in those defined above] in a solvent in the presence of a condensing agent, as exemplified above in relation to Step A1b(ii), and in the presence or absence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide.

The base used in Step A2(ii) may be any of those exemplified above in relation to Step A2(i).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Step A2(iii)

The protecting group $R^{11}$ may be introduced by reacting the unprotected compound with a compound of formula $R^{11}$—OH [wherein $R^{11}$ is one of the groups of the acyl type included in those defined above] in a solvent and in the presence of a dialkyl halophosphate (e.g. diethyl chlorophosphate) and a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide.

The base used in Step A2(iii) may be any of those exemplified above in relation to Step A2(i).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to the reflux temperature of the solvent used, more preferably from room temperature to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Step A3

In this Step, a compound of formula (VI) is prepared by oxidizing the exo-methylene group of a compound of formula (V) in a solvent using an oxidizing agent to convert the compound into a diol form.

There is likewise no particular restriction on the nature of the oxidizing agents used, and any oxidizing agent commonly used in reactions of this type may equally be used here. Examples of such oxidizing agents include: manganese oxides, such as potassium permanganate and manganese dioxide; ruthenium oxides, such as ruthenium (IV) oxide; selenium compounds, such as selenium dioxide; and osmium compounds, such as osmium tetroxide and potassium osmate dihydrate ($K_2OsO_4 2H_2O$). We particularly prefer to use a catalytic amount of osmium tetroxide and a reoxidizing agent for osmium compounds. Examples of such reoxidizing agents include: metal ferricyanides, such as potassium ferricyanide (III); oxides of amines, such as 4-methylmorpholine oxide; inorganic oxidizing agents, such as persulfate compounds (e.g. potassium persulfate or sodium persulfate); peroxides, such as t-butyl hydroperoxide; hypochlorite compounds, such as t-butyl hypochlorite; and nitrites, such as methyl nitrite. Of these, we particularly prefer the metal ferricyanides and oxides of amines.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, especially halogenated aliphatic hydrocarbons, such as methylene chloride and chloroform; ethers, such as diethyl ether, tetrahydrofuran, dioxane and dimethoxyethane; amides, such as dimethylformamide, dimethylacetamide and hexamethylphosphoric triamide; sulfoxides, such as dimethyl sulfoxide; alcohols, such as methanol, ethanol, propanol, isopropanol, butanol, isobutanol, t-butanol and isoamyl alcohol; esters, such as ethyl acetate, propyl acetate, butyl acetate and diethyl carbonate; dilute acids, such as aqueous sulfuric acid; dilute bases, such as an aqueous solution of sodium hydroxide; water; ketones, such as acetone and methyl ethyl ketone; organic bases, such as pyridine; nitriles, such as acetonitrile; or a mixture of any two or more of the above solvents. Of these, we particularly prefer acetone or a mixture of acetone and water.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 80° C., more preferably from −5 to 50° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 12 hours, will usually suffice.

An optically active diol derivative having a specific absolute configuration can be produced by optionally conducting an asymmetric dihydroxylation reaction using a chiral ligand. The asymmetric dihydroxylation reaction can be accomplished, for example, by the process of Sharpless et al. (Chemical Review, Vol. 94, page 2483 (1994)).

Examples of the oxidizing agent used for this reaction include from 0.0001 to 0.1 equivalents (more preferably from 0.001 to 0.005 equivalents) of osmium tetroxide. Examples of the chiral ligand include hydroquinidines, such as hydroquinidine 1,4-phthalazinediyl diether ((DHQD)$_2$-PHAL) and hydroquinidine 2,5-diphenyl-4,6-pyrimidinediyl diether ((DHQD)$_2$-PYR) (preferably (DHQD)$_2$-PHAL). Examples of the oxidizing agent for reoxidizing osmium compounds include potassium ferricyanide (III) and potassium carbonate.

Examples of the solvent used include a mixture of water and one or more of the following organic solvents: halogenated hydrocarbons, especially halogenated aliphatic hydrocarbons, such as methylene chloride or chloroform; ethers, such as diethyl ether, tetrahydrofuran, dioxane or dimethoxyethane; amides, such as dimethylformamide, dimethylacetamide or hexamethylphosphoric triamide; sulfoxides, such as dimethyl sulfoxide; alcohols, such as methanol, ethanol, propanol, isopropanol, butanol, isobutanol, t-butanol or isoamyl alcohol; ketones, such as acetone or methyl ethyl ketone; esters, such as ethyl acetate, propyl acetate, butyl acetate or diethyl carbonate; and nitriles, such as acetonitrile, preferably a mixture of water and an alcohol. Of these, we particularly prefer a mixture of water and t-butanol.

A compound of formula (VI) wherein D is a sulfur atom can be produced by converting the exo-methylene group of the compound of formula (V) into thiirane according to a conventional process, followed by ring-opening with a hydroxy ion.

Step A4

In this Step, a compound of formula (VII) is prepared by: (a) converting a primary hydroxy group of a compound of formula (VI) into a group that can be eliminated (this reaction takes place in the presence of a base in the presence or absence of a solvent); and (b) then reacting the resulting compound with an azidation reagent in a solvent in the presence or absence of a catalyst to convert it into an azide group.

The reactions are normally and preferably effected in the presence of a solvent. There is no particular restriction on the nature of the solvent to be employed, provided that it has no adverse effect on the reactions or on the reagents involved and that it can dissolve the reagents, at least to some extent. Examples of suitable solvents include: aromatic hydrocarbons, such as benzene, toluene and xylene; halogenated hydrocarbons, especially halogenated aliphatic hydrocarbons, such as methylene chloride and chloroform; ethers, such as diethyl ether, tetrahydrofuran, dioxane and dimethoxyethane; nitriles, such as acetonitrile; and amides, such as formamide, dimethylformamide, dimethylacetamide, N-methyl-2-pyrrolidone, N-methylpyrrolidinone and hexamethylphosphoric triamide; more preferably a halogenated hydrocarbon or an ether in the first stage reaction or an amide in the second stage reaction.

There is no particular restriction on the nature of the bases used in the first stage reaction, and any base commonly used in reactions of this type may equally be used here. Examples of such bases include: organic bases such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Of these, we particularly prefer triethylamine, pyridine and 4-(N,N-dimethylamino)pyridine.

The reaction is most preferably accomplished using pyridine as a solvent and adding a catalytic amount of 4-(N,N-dimethylamino)pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 50° C., more preferably from −10 to 20° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 6 hours, will usually suffice.

The group capable of being eliminated is the same group as that defined above for X. The reagent for forming the elimination group, is preferably a corresponding halide, and examples of such a reagent include sulfonyl halides, such as methanesulfonyl chloride and p-toluenesulfonyl chloride. The reaction may be conducted in the same manner as that employed to introduce the protecting group $R^{11}$.

There is likewise no particular restriction on the nature of the azidation reagents used in the second stage reaction, and any azidation reagent commonly used in reactions of this type may equally be used here. Examples of such azidation reagents include: diarylphosphoryl azides, such as diphenylphosphoryl azide; trialkylsilyl azides, such as trimethylsilyl azide and triethylsilyl azide; and alkali metal azides, such as sodium azide, potassium azide and lithium azide. Of these, we particularly prefer the alkali metal azides.

Examples of the catalyst which may be used include trialkylsilyl triflates, such as trimethylsilyl triflate and triethylsilyl triflate; Lewis acids, such as boron trifluoride etherate, aluminum chloride and zinc chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 20 to 180° C., more preferably from 50 to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 8 hours, will usually suffice.

Step A5

In this Step, an amino compound of formula (VIII) is prepared by reducing the azide group of a compound of formula (VII) in a solvent.

The reduction process may be carried out using any reagent capable of reducing an azide group to form an amino group, and is not specifically limited. Preferably, the reaction is conducted at a temperature of from 20 to 150° C. (more preferably from 50 to 100° C.) for a period of from 15 minutes to 1 day (more preferably from 1 to 12 hours) in a water-containing solvent (preferably an ether, such as tetrahydrofuran) using triphenylphosphine as the reducing agent.

Alternatively, the reaction may be accomplished by conducting a catalytic hydrogenation reaction at a temperature of from −10 to 100° C. (more preferably from 0 to 50° C.) for a period of from 1 hour to 4 days (more preferably from 2 hours to 2 days) in an organic solvents, such as an alcohol (e.g. methanol or ethanol), an ester (e.g. ethyl acetate, propyl acetate, butyl acetate or diethyl acetate), an ether (e.g. tetrahydrofuran or dioxane) or a fatty acid (e.g. acetic acid) or a mixture of any one or more of these organic solvent and water (preferably alcohols) using a catalyst, such as palladium-on-carbon, platinum or Raney nickel.

Step A6

In this Step, a compound of formula (X) is prepared by the acylation reaction of the amino group of a compound of formula (VIII) with a compound of formula (IX) in a solvent in the presence of a base (Step A6a), followed by ring-closing alkylation on a group of formula DH, to form a cyclic amide (Step A6b).

Step A6a

The acylation reaction in this stage is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide.

There is likewise no particular restriction on the nature of the bases used, and any base commonly used in reactions of this type may equally be used here. Examples of such bases include: organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline and N,N-diethylaniline.

If desired, 4-(N,N-dimethylamino)pyridine or 4-pyrrolidinopyridine can be used in a catalytic amount in combination with one or more of the other bases. The efficiency of the reaction may, if desired, be improved by carrying it out in the presence of one or more of the following: dehydrating agents (e.g. molecular sieves), quaternary ammonium salts (e.g. benzyltriethylammonium chloride or tetrabutylammonium chloride), crown ethers (e.g. dibenzo-18-crown-6) and acid scavengers (e.g. 3,4-dihydro-2H-pyrido[1,2-a]pyrimidin-2-one).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

In case of the carboxylic acid derivative wherein the group X' of the compound of formula (IX) represents a hydroxy group, this reaction can also be accomplished by reacting the compounds of formulae (VIII) and (IX) with the condensing agent described in Step A1b(ii) in the above solvent in the presence or absence of the above base.

Step A6b

The ring-closing alkylation reaction in this stage is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; nitriles, such as acetonitrile, propionitrile and isobutyronitrile; amides, such as formamide, dimethylformamide, dimethylacetamide, N-methyl-2-pyrrolidone, N-methylpyrrolidinone and hexamethylphosphoric triamide; and sulfoxides, such as dimethyl sulfoxide and sulfolane. Of these, we particularly prefer the ethers and amides, most preferably tetrahydrofuran or dimethylformamide.

There is likewise no particular restriction on the nature of the bases used, and any base cormmonly used in reactions of this type may equally be used here. Examples of such bases include: alkali metal carbonates, such as sodium carbonate, potassium carbonate and lithium carbonate; alkali metal hydrogencarbonates, such as sodium hydrogencarbonate, potassium hydrogencarbonate and lithium hydrogencarbonate; alkali metal hydrides, such as lithium hydride, sodium hydride and potassium hydride; alkali metal hydroxides, such as sodium hydroxide, potassium hydroxide, barium hydroxide and lithium hydroxide; alkali metal fluorides, such as sodium fluoride and potassium fluoride; and alkali metal alkoxides, such as sodium methoxide, sodium ethoxide, potassium methoxide, potassium ethoxide, potassium t-butoxide and lithium methoxide. Of these, we particularly prefer the alkali metal hydrides and alkali metal alkoxides.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 100° C., more preferably from 0 to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 12 hours, will usually suffice.

Step A7

In this Step, a compound of formula (XI) is prepared by reducing the amide group of a compound of formula (X) in a solvent using a reducing agent to convert into an imino group; it is then optionally reprotected with a group $R^{12}$.

The reaction in the main step is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; and ethers, such as diethyl ether, diisopropyl ether, tetrahydrofuran, dioxane, dimethoxyethane and diethylene glycol dimethyl ether. Of these, we particularly prefer the ethers, most preferably diethyl ether or tetrahydrofuran.

There is likewise no particular restriction on the nature of the reducing agents used, and any reducing agent commonly used in reactions of this type may equally be used here. Examples of such reducing agents include: hydride reagents, such as alkali metal borohydrides (e.g. sodium borohydride or lithium borohydride), aluminum hydride compounds (e.g. lithium aluminum hydride or lithium tri-t-butoxyaluminohydride), sodium tellurium hydride, and organic aluminum hydride reducing agents [e.g. diisobutylaluminum hydride or sodium bis(methoxyethoxy) aluminum hydride] and borane reducing agents (e.g. borane-dimethyl sulfide complex or borane-tetrahydrofiran complex, etc.). Of these, we particularly prefer the aluminum hydride compounds and borane reducing agents, further still more prefer the borane reducing agents, most preferably borane-dimethyl sulfide complex.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78 to 150° C., more preferably from −20 to 100° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 10 minutes to 2 hours, will usually suffice.

Step A8

In this Step, a compound of formula (XIII) in which an imino group of the compound of formula (XI) is modified with a group of formula —A—B—$R^1$ (A, B and $R^1$ are as defined above) is prepared by reacting the compound of formula (XI) with a compound of formula (XII) in a solvent and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, such as nitroethane and nitrobenzene; and nitrites, such as acetonitrile and isobutyronitrile. Of these, we particularly prefer the halogenated hydrocarbons and ethers, most preferably methylene chloride or tetrahydrofuran.

There is likewise no particular restriction on the nature of the bases used, and any base commonly used in reactions of this type may equally be used here. Examples of such bases include: organic bases such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo-[5.4.0]undec-7-ene (DBU). Of these, we particularly prefer triethylamine or diisopropylethylamine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 100° C., more preferably from 0 to 20° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 10 minutes to 12 hours, will usually suffice.

When A represents a carbonyl group, this Step may also be accomplished by reacting the compound of formula (XI) with a compound of formula $R^1$—B—A—OH (in which A, B and $R^1$ are as defined above) and a condensing agent in a solvent in the presence or absence of a base.

Examples of the condensing agent which may be used include those described above in relation to Step A1b(ii). Of these, we prefer a combination of a phosphonate and one or more of the bases described below.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide.

There is likewise no particular restriction on the nature of the bases used, and any base commonly used in reactions of this type may equally be used here. Examples of such bases include: organic bases such as N-methylmorpholine, triethylamine, tributylamine, diisopropylethylamine, dicyclohexylamine, N-methylpiperidine, pyridine, 4-pyrrolidinopyridine, picoline, 4-N,N-dimethylamino) pyridine, 2,6-di(t-butyl)-4-methylpyridine, quinoline, N,N-dimethylaniline and N,N-diethylaniline.

If desired, 4-(dimethylamino)pyridine or 4-pyrrolidinopyridine can be used in a catalytic amount in combination with one or more of the other bases. The efficiency of the reaction may, if desired, be improved by carrying it out in the presence of one or more of the following: dehydrating agents (e.g. molecular sieves), quaternary ammonium salts (e.g. benzyltriethylammonium chloride or tetrabutylammonium chloride), crown ethers (e.g. dibenzo-18-crown-6) and acid scavengers (e.g. 3,4-dihydro-2H-pyrido[1,2-a]pyrimidin-2-one).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Step A9

In this Step, a compound of formula (XIV) is prepared by removing the group $R^{12}$ (where $R^{12}$ is a group other than a hydrogen atom) from the compound of formula (XIII) and converting the resulting hydroxy group into an elimination group Y", which may be effected by the procedure described in the first stage of Step A4.

The method used to remove the group $R^{12}$ will vary depending on the nature of that group. However, methods of removing such groups are well known in this technical field.

For example, when the group $R^{12}$ is a silyl group, it can normally be removed by treatment with a compound forming a fluorine anion (e.g. tetrabutylammonium fluoride, hydrogen fluoride, hydrogen fluoride-pyridine or potassium fluoride) or by treatment with an organic acid (e.g. acetic acid, methanesulfonic acid, p-toluenesulfonic acid, trifluoromethanesulfonic acid or B-bromocatechol borane) or an inorganic acid (e.g. hydrochloric acid).

When the group $R^{12}$ is removed by the fluorine anion, the reaction may sometimes be promoted by adding an organic acid, such as formic acid, acetic acid or proplonic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethoxyethane and diethylene glycol dimethyl ether; nitrites, such as acetonitrile and isobutyronitrile; water; and organic acids, such as acetic acid; or a mixture of any two or more thereof.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 150° C., more preferably from 10 to 150° C. The time required for the reaction may also vary widely, depending on many factors, notably the reaction temperature and the nature of the reagents and solvent employed. However, provided that the reaction is effected under the preferred conditions outlined above, a period of from 1 to 48 hours, more preferably from 2 to 12 hours, will usually suffice.

When the group $R^{12}$ is an aralkyl or aralkyloxycarbonyl group, it may preferably be removed by contacting it with a reducing agent (preferably by a catalytic hydrogenation reaction at ambient temperature in the presence of a catalyst) in a solvent or by using an oxidizing agent.

The catalytic hydrogenation reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol and isopropanol; ethers, such as diethyl ether, diisopropyl ether, tetrahydrofuran and dioxane; aromatic hydrocarbons, such as benzene, toluene and xylene; aliphatic hydrocarbons, such as hexane and cyclohexane; esters, such as ethyl acetate and propyl acetate; amides, such as formamide, dimethylformamide, dimethylacetamide, N-methyl-2-pyrrolidone and hexamethylphosphoric triamide; fatty acids, such as formic acid and acetic acid; water; or a mixture of any two or more thereof. Of these, we particularly prefer the alcohols, fatty acids and a mixture of an alcohol and an ether, a mixture of an alcohol and water or a mixture of a fatty acid and water.

There is likewise no particular restriction on the nature of the catalysts used, and any catalyst commonly used in catalytic, hydrogenation reactions of this type may equally be used here. Examples of such catalysts include: palladium-on-carbon, palladium black, Raney nickel, platinum oxide, platinum black, rhodium-aluminum oxide, triphenylphosphine-rhodium chloride and palladium-barium sulfate.

There is no particular restriction on the pressure employed, and the reaction is normally conducted under a pressure within the range of from 1 to 10 atmospheres.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 100° C., more preferably from 20 to 70° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 1 to 24 hours, will usually suffice.

If the protecting group is to be removed by oxidation, the reaction is normally and preferably effected in the presence of a solvent. There is no particular restriction on the nature of the solvent to be employed, provided that it has no adverse effect on the reaction or on the reagents involved and that it can dissolve the reagents, at least to some extent.

A water-containing organic solvent is preferred. Examples of suitable organic solvents include: ketones, such as acetone; halogenated hydrocarbons, especially halogenated aliphatic hydrocarbons, such as methylene chloride, chloroform and carbon tetrachloride; nitrites, such as acetonitrile; ethers, such as diethyl ether, tetrahydrofuran and dioxane; amides, such as dimethylformamide, dimethylacetamide and hexamethylphosphoric triamide; and sulfoxides, such as dimethyl sulfoxide.

There is likewise no particular restriction on the nature of the oxidizing agents used, and any oxidizing agent commonly used in reactions of this type may equally be used here. Examples of such oxidizing agents include: potassium persulfate, sodium persulfate, cerium ammonium nitrate (CAN) and 2,3-dichloro-5,6-dicyano-p-benzoquinone (DDQ).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

It is also possible to remove the protecting group by reaction with an alkali metal (e.g. metallic lithium or metallic sodium) in liquid ammonia or an alcohol (e.g. methanol or ethanol) at a temperature of from −78 to −20° C.

It is also possible to remove the protecting group by reaction with aluminum chloride-sodium iodide or an alkylsilyl halide (e.g. trimethylsilyl iodide) in a solvent. There is no particular restriction on the nature of the solvent to be employed, provided that it has no adverse effect on the reaction or on the reagents involved and that it can dissolve the reagents, at least to some extent. Examples of suitable solvents include: nitrites, such as acetonitrile; halogenated hydrocarbons, especially halogenated aliphatic hydrocarbons, such as methylene chloride and chloroform; or a mixture of any two or more thereof.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 3 days will usually suffice.

When the reaction substrate has a sulfur atom, aluminum chloride-sodium iodide is preferably used.

When the group $R^{12}$ is an aliphatic acyl group, an aromatic acyl group or an alkoxycarbonyl group, it is preferably removed by treating it with a base in a solvent.

There is no particular restriction on the nature of the bases used provided that it has no adverse effect on any other part of the compound, and any base commonly used in reactions of this type may equally be used here. Examples of such bases include: metal alkoxides, such as sodium methoxide; alkali metal carbonates, such as sodium carbonate, potassium carbonate or lithium carbonate; alkali metal hydroxides, such as sodium hydroxide, potassium hydroxide, lithium hydroxide or barium hydroxide; or various forms of ammonia, such as aqueous ammonia or concentrated ammonia-methanol.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent and any solvent commonly used for hydrolysis reactions may equally be employed here. Examples of suitable solvents include: water; organic solvents, such as alcohols (e.g. methanol, ethanol or propanol) and ethers (e.g. tetrahydrofuran or dioxane); or a mixture of water and one or more of the above organic solvents are preferred.

The reaction can take place over a wide range of temperatures, and the precise reaction temperature is not critical to the invention. The preferred reaction temperature will depend upon such factors as the nature of the solvent, and the starting material or reagent used. However, in general, in order to inhibit secondary reactions, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

When the group $R^{12}$ is an alkoxymethyl group, a tetrahydropyranyl group, a tetrahydrothiopyranyl group, a tetrahydrofuranyl group, a tetrahydrothiofuranyl group or a substituted ethyl group, it is normally removed by treatment with an acid in a solvent.

There is likewise no particular restriction on the nature of the acids used, and any acid commonly used in reactions of this type may equally be used here. Examples of such acids include: Bronsted acids, such as inorganic acids (e.g. hydrochloric acid, sulfuric acid or nitric acid); organic acids (e.g. acetic acid, trifluoroacetic acid, methanesulfonic acid or p-toluenesulfonic acid); and Lewis acids, such as boron trifluoride. A strong acidic cation exchange resins, such as Dowex (trade mark) 50W, can also be used.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and methylcellosolve; ketones, such as acetone, methyl ethyl ketone, methyl isobutyl ketone, isophorone and cyclohexanone; water; or a of any two or more mixture thereof. Of these, we particularly prefer the halogenated hydrocarbons, esters and ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 100° C., more preferably from −5 to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 30 minutes to 10 hours, will usually suffice.

When the group $R^{12}$ is an alkenyloxycarbonyl group, it is preferably removed by treatment with a base under the same condition as are used to remove the group $R^{12}$ when that group is an aliphatic acyl group, an aromatic acyl group or an alkoxycarbonyl group.

In case of an allyloxycarbonyl group, it may be removed by using palladium and triphenylphosphine or bis (methyldiphenylphosphine)(1,5-cyclooctadiene)iridium(I) hexafluorophosphate, which is simple and can be conducted with little side reactions.

Step A10

In this Step, a compound of formula (I), which is a compound of the present invention, is prepared by reacting a compound of formula (XIV) with a compound of formula (XV) in a solvent and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether, aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, such as nitroethane and nitrobenzene; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide; sulfoxides, such as dimethyl sulfoxide and sulfolane. Of these, we prefer the amides, ethers and nitriles, most preferably the amides.

There is likewise no particular restriction on the nature of the bases used, and any base commonly used in reactions of this type may equally be used here. Examples of such bases include: a combination of a metal iodide (e.g. potassium iodide) and an inorganic base, such as an alkali metal carbonate (e.g. sodium carbonate, potassium carbonate or lithium carbonate), an alkali metal hydrogencarbonate (e.g. sodium hydrogencarbonate, potassium hydrogencarbonate or lithium hydrogencarbonate), an alkali metal hydride (e.g. lithium hydride, sodium hydride or potassium hydride), an alkali metal hydroxide (e.g. sodium hydroxide, potassium hydroxide, barium hydroxide or lithium hydroxide) or an alkali metal fluoride (e.g. sodium fluoride or potassium fluoride); or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Of the various bases, we particularly prefer the combination of a metal iodide and an inorganic base, most preferably a combination of a metal iodide and an alkali metal hydrogencarbonate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 150° C., more preferably from 20 to 120° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 12 hours, will usually suffice.

After the completion of the respective reactions described above, the compounds produced by these reactions may be collected from the reaction mixture by a conventional process.

For example, in one suitable isolation procedure, the reaction mixture is appropriately neutralized and, after insoluble matter, if any, has been removed by filtration, a water-immiscible solvent (e.g. ethyl acetate) is added. The organic layer is separated, and washed with, for example, water, and the desired compound is dried, for example over anhydrous magnesium sulfate or anhydrous sodium sulfate. Then, the solvent is distilled off to give the desired compound.

The desired compound can, if desired, be isolated and purified by any one or more of the following procedures: recrystallization; reprecipitation; or another process which is normally used for isolation and purification of organic compounds, for example an adsorption column chromatography process using a carrier, such as silica gel, alumina or magnesium-silica gel, Florisil; a process using a synthetic adsorbent, for example, partition column chromatography using Sephadex (trade mark) LH-20 (manufactured by Pharmacia Co.), Amberlite (trade mark) XAD-11 (manufactured by Rohm & Haas Co.), Diaion (trade mark) HP-20 (manufactured by Mitsubishi Kasei Co., Ltd.); a process using ion-exchange chromatography; or a normal/reverse phase liquid chromatography process (preferably high performance liquid chromatography) using silica gel or alkylated silica gel.

When isomers must be isolated, the isolation can be conducted by the above isolation and purification means after the completion of the reactions of the above respective steps or at the suitable time after the completion of the desired steps.

Reaction Scheme B

This provides an alternative method of preparing the compound of formula (IV), which may thereafter be used as shown in Reaction Scheme A to prepare the compound of the present invention.

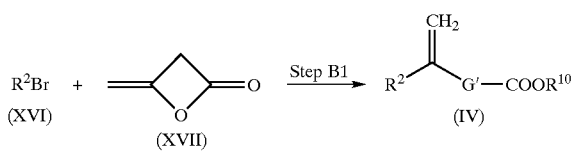

In the above formulae, $R^2$ is as defined above.

Step B1

In this Step, a compound of formula (IV) is prepared by: reacting a compound of formula (XVI) with metallic magnesium according to the process of Ito et al. [described in Bull. Chem. Soc. Jpn., Vol. 64, page 3746 (1991)], to give a Grignard reagent; coupling this Grignard reagent with diketene of formula (XVII) in a solvent in the presence or absence of a Lewis acid and in the presence of a catalytic amount (preferably from 0.1 to 0.5 equivalents) of a palladium catalyst; and reacting the resulting carboxylic acid according to the optional step described in Step A1 to esterify it.

The reaction can be accomplished in a good yield with few by-products when conducted in the presence of the Lewis acid, which is, accordingly, preferred. There is no particular restriction on the nature of the Lewis acid, if used, and any Lewis acid commonly used in reactions of this type may equally be used here. Examples of such Lewis acids include: trialkylsilyl trifluoromethanesulfonates having from 1 to 6 carbon atoms in the alkyl part, such as trimethylsilyl trifluoromethanesulfonate; aluminum salts, such as aluminum chloride; tin salts, such as tin tetrachloride; zinc salts, such as zinc bromide or zinc chloride; titanium salts, such as titanium tetrachloride; or perchlorates, such as trimethylsilyl perchlorate or triphenylmethyl perchlorate. Of these, we particularly prefer the zinc salts, most preferably zinc chloride.

The palladium catalyst used may be any one which contains palladium, and is not particularly limited. Preferred examples include organophosphine palladium compounds, such as dichloro bis(triphenylphosphine)palladium(II).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethoxyethane and diethylene glycol dimethyl ether. Of these, we particularly prefer diethyl ether.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 50° C., more preferably from 0 to 20° C. The time required for the reaction may also vary widely, depending on many factors, notably the reaction temperature and the nature of the reagents and solvent employed. However, provided that the reaction is effected under the preferred conditions outlined above, a period of from 15 minutes to 8 hours, more preferably from 30 minutes to 2 hours, will usually suffice.

After the completion of the above reaction, the desired compound of formula (IV) may be isolated from the reaction mixture by conventional means.

For example, in one suitable isolation procedure, the reaction mixture is appropriately neutralized and, after insoluble matter, if any, has been removed by filtration, a water-immiscible solvent (e.g. ethyl acetate) is added. The organic layer is separated and washed with, for example, water. The desired compound is then dried, for example over anhydrous magnesium sulfate or anhydrous sodium sulfate. Then, the solvent is distilled off to give the desired compound.

The desired compound can, if desired, be isolated and purified by any one or more of the following procedures: recrystallization; reprecipitation; or another process which is normally used for isolation and purification of organic compounds, for example an adsorption column chromatography process using a carrier, such as silica gel, alumina or magnesium-silica gel, Florisil; a process using a synthetic adsorbent, for example, partition column chromatography using Sephadex (trade mark) LH-20 (manufactured by Pharmacia Co.), Amberlite (trade mark) XAD-11 (manufactured by Rohm & Haas Co.), Diaion (trade mark) HP-20 (manufactured by Mitsubishi Kasei Co., Ltd.); a process using ion-exchange chromatography; or a normal/reverse phase liquid chromatography process (preferably high performance liquid chromatography) using silica gel or alkylated silica gel.

Reaction Scheme C

This provides an alternative method of preparing the compound of formula (XI), which may thereafter be used as shown in Reaction Scheme A to prepare the compound of the present invention.

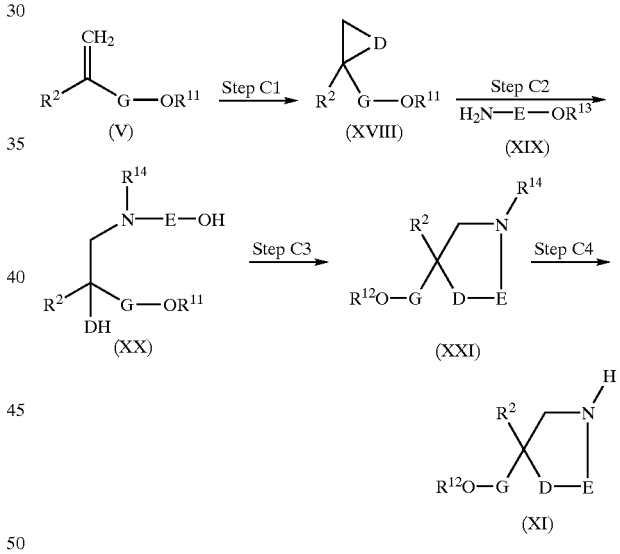

In the above formulae, $R^2$, $R^{11}$, $R^{12}$, D, E and G are as defined above.

$R^{13}$ represents a hydrogen atom or a hydroxy-protecting group and may be any of the same groups defined and exemplified above for the group $R^{11}$.

$R^{14}$ represents an amino-protecting group, and examples thereof include the aliphatic acyl groups, the aromatic acyl groups, the alkoxycarbonyl groups, the alkenyloxycarbonyl groups, the aralkyloxycarbonyl groups and the silyl groups as defined and exemplified above, preferably an alkoxycarbonyl group. Of these, we particularly prefer the t-butoxycarbonyl group.

Step C1

In this Step, an epoxy compound of formula (XVIII) is prepared by reacting the exo-methylene group of a compound of formula (V) with an oxidizing agent in a solvent.

There is likewise no particular restriction on the nature of the oxidizing agents used, and any oxidizing agent commonly used in epoxidation reactions of olefins may equally be used here. Examples of such oxidizing agents include: peracids, such as m-chloroperbenzoic acid, 3,5-dinitroperbenzoic acid, o-carboxyperbenzoic acid, peracetic acid, pertrifluoroacetic acid and perphthalic acid; hydrogen peroxide; peroxides, such as t-butyl hydroperoxide (which may be used in combination with vanadium or a molybdenum complex); and a combination of a succinimide (e.g. N-bromosuccinimide) and an alkali. Of these, we particularly prefer the peracids, most preferably m-chloroperbenzoic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, especially halogenated aliphatic hydrocarbons, such as methylene chloride and chloroform; ethers, such as diethyl ether, tetrahydrofuran, dioxane and dimethoxyethane; amides, such as dimethylformamide, dimethylacetamide and hexamethylphosphoric triamide; sulfoxides, such as dimethyl sulfoxide; alcohols, such as methanol, ethanol, propanol, isopropanol, butanol, isobutanol, t-butanol and isoamyl alcohol; dilute acids, such as aqueous sulfuric acid; dilute bases, such as an aqueous solution of sodium hydroxide; water; ketones, such as acetone and methyl ethyl ketone; organic bases, such as pyridine; nitriles, such as acetonitrile; or a mixture of any two or more of the above solvents. Of these, we particularly prefer methylene chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 80° C., more preferably from −5 to 50° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 12 hours, will usually suffice.

An optically active epoxy compound having a specific absolute configuration can be produced by conducting an asymmetric epoxidation reaction using a chiral ligand, for example, according to the process of Sharpless et al. or the process of Jacobsen et al. [see Catalytic Asymmetric Synthesis, VCH Publishers Inc. (1993)].

Step C2

In this Step, a compound of formula (XX) is prepared by ring-opening the epoxy group of the epoxy compound of formula (XVM) using an amino alcohol compound of formula (XIX) in the presence or absence of a base (Step C2a) and then protecting the secondary amino group thus formed with a group $R^{14}$ (Step C2b).

Step C2a

The ring opening reaction in the first stage is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; nitriles, such as acetonitrile, propionitrile and isobutyronitrile; amides, such as formamide, dimethylformamide, dimethylacetamide, N-methyl-2-pyrrolidone, N-methylpyrrolidinone and hexamethylphosphoric triamide; sulfoxides, such as dimethyl sulfoxide and sulfolane. Of these, we particularly prefer the nitriles.

There is likewise no particular restriction on the nature of the bases used, and any base commonly used in reactions of this type may equally be used here. Examples of such bases include: alkali metal perchlorates, such as lithium perchlorate and sodium perchlorate; alkali metal carbonates, such as sodium carbonate, potassium carbonate and lithium carbonate; alkali metal hydrogencarbonates, such as sodium hydrogencarbonate, potassium hydrogencarbonate and lithium hydrogencarbonate; alkali metal hydrides, such as lithium hydride, sodium hydride and potassium hydride; alkali metal hydroxides, such as sodium hydroxide, potassium hydroxide, barium hydroxide and lithium hydroxide; alkali metal fluorides, such as sodium fluoride and potassium fluoride; alkali metal alkoxides, such as sodium methoxide, sodium ethoxide, potassium methoxide, potassium ethoxide, potassium t-butoxide and lithium methoxide; alkali metal mercaptans, such as sodium methylmercaptan, sodium ethylmercaptan; and organic bases such as N-methylmorpholine, triethylamine, tripropylamine, tributylamine, diisopropylethylamine, dicyclohexylamine, N-methylpiperidine, pyridine, 4pyrrolidinopyridine, picoline, 4-(N,N-dimethylamino)pyridine, 2,6-di(t-butyl) 4methylpyridine, quinoline, N,N-dimethylaniline, N,-diethylaniline, 1,5-diazabicyclo[4.3.0]non-5-ene(DBN), 1,4-diazabicyclo[2.2.2]octane (DABCO) and 1,8-diazabicyclo-[5.4.0]undec-7-ene (DBU).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 150° C., more preferably from room temperature to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Step C2b

Protection of the secondary amino group with a group $R^{14}$ in this stage may be carried out as follows.

Step C2b(i)

The unprotected compound is reacted with a suitable amount, for example from 1 to 4 equivalents (preferably from 2 to 3 equivalents) of a compound of formula $R^{14}$—X" (in which $R^{14}$ is as defined above and in which X" represents an elimination group capable of being eliminated as a nucleophilic residue, and is not specifically limited), or with a compound of formula $R^{14}$—O—$R^{14}$ (in which $R^{14}$ is a group of the acyl type selected from those defined above for $R^{14}$), in a solvent in the presence or absence of a base. Preferred examples of such elimination groups include:

halogen atoms, such as the chlorine, bromine and iodine atoms; alkoxycarbonyloxy groups having from 1 to 6 carbon atoms in the alkoxy part, such as the methoxycarbonyloxy and ethoxycarbonyloxy groups; haloalkylcarbonyloxy groups having from 1 to 6 carbon atoms in the alkyl part, such as the chloroacetoxy, dichloroacetoxy, trichloroacetoxy and trifluoroacetoxy groups; alkanesulfonyloxy groups having from 1 to 6 carbon atoms, such as the methanesulfonyloxy and ethanesulfonyloxy groups; haloalkanesulfonyloxy groups having from 1 to 6 carbon atoms, such as the trifiuoromethanesulfonyloxy and pentafluoroethanesulfonyloxy groups; arylsulfonyloxy groups in which the aryl part is as defined and exemplified above in relation to $R^1$ etc., such as the benzenesulfonyloxy, p-toluenesulfonyloxy and p-nitrobenzenesulfonyloxy groups. Of these, we particularly prefer the halogen atoms, the haloalkanesulfonyloxy groups and the arylsulfonyloxy groups.

Specific examples of such compounds of formula $R^{14}$—X" include: acyl halides, such as aliphatic acyl halides (e.g. acetyl chloride, propionyl chloride, butyryl chloride, valeryl chloride and hexanoyl chloride), alkoxycarbonyl halides having from 1 to 6 carbon atoms in the alkoxy part (e.g. methoxycarbonyl chloride, methoxycarbonyl bromide, ethoxycarbonyl chloride, propoxycarbonyl chloride, butoxycarbonyl chloride and hexyloxycarbonyl chloride), and arylcarbonyl halides, (e.g. benzoyl chloride, benzoyl bromide and naphthoyl chloride); silyl halides, such as t-butyldimethylsilyl chloride, trimethylsilyl chloride, triethylsilyl chloride, triethylsilyl bromide, triisopropylsilyl chloride, dimethylisopropylsilyl chloride, diethylisopropylsilyl chloride, t-butyldiphenylsilyl chloride, diphenylmethylsilyl chloride and triphenylsilyl chloride or the corresponding silyl trifluoromethane-sulfonates; aralkyl halides, such as benzyl chloride and benzyl bromide; or carbonyloxyalkyl halides, such as pivaloyloxymethyl chloride or ethoxycarbonyl-oxymethyl chloride.

Specific examples of such compounds of formula $R^{14}$—O—$R^{14}$ include aliphatic carboxylic anhydrides, such as acetic anhydride, propionic anhydride, valeric anhydride and hexanoic anhydride, and carbonates, such as di-t-butyl dicarbonate. A mixed acid anhydride (e.g. the mixed anhydride of forrric and acetic acids) can also be used.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

There is likewise no particular restriction on the nature of the bases used, and any base commonly used in reactions of this type may equally be used here. Examples of such bases include: organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)4methylpyridine, quinoline, N,N-dimethylaniline and N,N-diethylaniline.

If desired, 4(N,N-dimethylamino)pyridine or 4-pyrrolidinopyridine can be used in a catalytic amount in combination with one or more of the other bases. The efficiency of the reaction may, if desired, be improved by effecting it in the presence of one or more of the following: quatemary ammonium salts (e.g. benzyltriethylammonium chloride or tetrabutylammonium chloride) and crown ethers (e.g. dibenzo-18-crown-6).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to the reflux temperature of the solvent employed, more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 1 hour to 1 day, will usually suffice.

Step C2b(ii)

The unprotected compound is reacted with a compound of formula $R^{14}$—OH (in which $R^{14}$ is a group of the acyl type selected from those defined above for $R^{14}$) in a solvent in the presence of a condensing agent and in the presence or absence of a base.

Examples of condensing agents which may be used include those given above in Step A1b(ii).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofiran, dioxane, dimethoxyethane and diethylene glycol dimethyl ether, nitrites, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

Examples of bases which may be used in this step are as given above in relation to Step C2b(i).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Step C2b(iii)

Particularly, when $R^{14}$ is a t-butoxycarbonyl group or a benzyloxycarbonyl group, the compound formed in Step C1b is reacted with a t-butoxycarbonylating agent or a benzyloxycarbonylating agent in a solvent in the presence of a base, and thus the secondary amino group can be protected with the $R^{14}$ group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide; water; and mixtures of water with any one or more of the above organic solvents.

The bases employed in this Step may be any of those suggested above in Step C1c(i).

There is likewise no particular restriction on the nature of the t-butoxy-carbonylating agents used, and any t-butoxycarbonylating agent commonly used in reactions of this type may equally be used here. Examples of such t-butoxy-carbonylating agents include: di-t-butyl dicarbonate, 2-(t-butoxycarbonyloxy-imino)-2-phenyl acetonitrile, t-butyl S-(4,6-dimethylpyrimidin-2-yl) thiolcarboxylate and 1,2,2,2-tetrachloroethyl t-butyl carbonate, more preferably di-t-butyl dicarbonate.

There is likewise no particular restriction on the nature of the benzyloxycarbonylating agents used, and any benzyloxycarbonylating agent commonly used in reactions of this type may equally be used here. Examples of such benzyloxycarbonylating agents include: benzyloxycarbonyl chloride, benzyloxycarbonyl cyanide and dibenzyl dicarbonate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to three days, more preferably from 30 minutes to 24 hours, will usually suffice.

Step C3

In this Step, a compound of formula (XXI) is prepared by dehydrating a compound of formula (XX) using the Mitsunobu reaction There is no particular restriction on the nature of the reagents used in the Mitsunobu reaction, and any reagent commonly used in reactions of this type may equally be used here. Examples of such reagents include: combination of azo compounds, such as dialkyl azodicarboxylates having from 1 to 6 carbon atoms in the alkyl part (e.g. diethyl azodicarboxylate or diisopropyl azodicarboxylate) or azodicarbonyls [e.g. 1,1'-(azodicarbonyl)dipiperidine]; and phosphines, such as triarylphosphines in which the aryl part is as defined and exemplified above in relation to $R^1$ etc. (e.g. triphenylphosphine) or trialkylphosphines having from 1 to 6 carbon atoms in each alkyl part (e.g. tributylphosphine). Of these, we particularly prefer the combination of a dialkyl azodicarboxylate and a triarylphosphine, most preferably a combination of diethyl azodicarboxylate and triphenylphosphine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide; and sulfoxides, such as dimethyl sulfoxide and sulfolane. Of these, we prefer the aromatic hydrocarbons and the ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20 to 100° C., more preferably from 0 to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 12 hours, will usually suffice.

In the course of carrying out the present step, a group $R^{11}$ is sometimes removed. In that case, the hydroxy group can be protected again according to the second part of Step A2.

Step C4

In this Step, a compound of formula (XI) is prepared by simultaneously or separately conducting the following:

(i) removal of the amino-protecting group $R^{14}$ to leave an amino group, and (ii) optional removal of a group $R^{12}$ when the group $R^{12}$ is a hydroxy-protecting group.

Step C4(i)

The reaction employed to remove the group $R^{14}$ will vary, depending on the nature of the group, but reactions which may be employed to remove such groups are well known in this technical field.

Step C4(i)a

For example, if the amino-protecting group is a silyl group, it is normally removed by treatment with a compound which forms fluorine anions, such as tetrabutylammonium fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran or dioxane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 18 hours will usually suffice.

Step C4(i)b

When the amino-protecting group is an aliphatic acyl group, an aromatic acyl group, an alkoxycarbonyl group or a substituted methylene group which forms a Schiff base, it can be removed by treatment with an acid or a base in the presence of an aqueous solvent.

There is no particular restriction on the nature of the acids used, and any acid commonly used in reactions of this type may equally be used here. Examples of such acids include: inorganic acids, such as hydrochloric acid, sulfuric acid, phosphoric acid and hydrogen bromide; and Lewis acids, such as B-bromocatechol borane. Of these, we prefer B-bromocatechol borane or hydrochloric acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; nitro compounds, such as nitroethane and nitrobenzene. Of these, we particularly prefer the halogenated hydrocarbons.

There is likewise no particular restriction on the nature of the bases used, provided that it has no adverse effect on any other part of the compound, and any base commonly used in reactions of this type may equally be used here. Examples of such bases include: metal alkoxides, such as sodium methoxide; alkali metal carbonates, such as sodium carbonate, potassium carbonate and lithium carbonate; alkali metal hydroxides, such as sodium hydroxide, potassium hydroxide and lithium hydroxide; and ammonia in various forms, such as aqueous ammonia or concentrated methanolic ammonia.

In the hydrolysis using a base, isomerization sometimes occurs.

The reaction is normally and preferably effected in the presence of a solvent. There is no particular restriction on the nature of the solvent to be employed, and any solvent commonly used for hydrolysis reactions may be used, provided that it has no adverse effect on the reaction or on the reagents involved and that it can dissolve the reagents, at least to some extent. Examples of suitable solvents include: water, organic solvents, such as alcohols (e.g. methanol, ethanol or propanol) and ethers (e.g. tetrahydrofuran or dioxane); or a mixture of water and one or more of the above organic solvents.

The reaction can take place over a wide range of temperatures, and the precise reaction temperature is not critical to the invention. The preferred reaction temperature will depend upon such factors as the nature of the solvent, and the starting material or reagent used. However, in general, in order to inhibit side reactions, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

Step C4(i)c

When the amino-protecting group is an aralkyl or aralkyloxycarbonyl group, we prefer to remove it by contacting it with a reducing agent in a solvent (preferably by catalytic hydrogenation at ambient temperature in the presence of catalyst) or by using an oxidizing agent.

The catalytic hydrogenation reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: organic solvents, such as alcohols (e.g. methanol, ethanol or isopropanol), ethers (e.g. diethyl ether, tetrahydrofuran or dioxane), aromatic hydrocarbons (e.g. toluene, benzene or xylene), esters (e.g. ethyl acetate or propyl acetate) and aliphatic acids (e.g. acetic acid) or a mixture of one or more of these organic solvents and water.

There is likewise no particular restriction on the nature of the catalysts used in the catalytic hydrogenation reaction, and any catalyst commonly used in reactions of this type may equally be used here. Examples of such catalysts include: palladium-on-carbon, palladium black, Raney nickel, platinum oxide, platinum black, rhodium-aluminum oxide, triphenylphosphine-rhodium chloride and palladium-barium sulfate.

There is no particular restriction on the pressure employed, and the reaction is normally conducted under a pressure within the range of from 1 to 10 atmospheres.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 100° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

The oxidation reaction is normally and preferably effected in the presence of a solvent. There is no particular restriction on the nature of the solvent to be employed, provided that it has no adverse effect on the reaction or on the reagents involved and that it can dissolve the reagents, at least to some extent. A mixture of water and an organic solvent is preferred. Examples of suitable organic solvents include: ketones, such as acetone; halogenated hydrocarbons, especially halogenated aliphatic hydrocarbons, such as methylene chloride, chloroform and carbon tetrachloride; nitriles, such as acetonitrile; ethers, such as diethyl ether, tetrahydrofuran and dioxane; and amides, such as dimethylformamide, dimethylacetamide and hexamethylphosphoric triamide.

There is likewise no particular restriction on the nature of the oxidizing agents used, and any oxidizing agent commonly used in oxidation reactions of this type may equally be used here. Examples of such oxidizing agents include: potassium persulfate, sodium persulfate, cerium ammonium nitrate (CAN) and 2,3-dichloro-5,6-dicyano-p-benzoquinone (DDQ).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

Step C4(i)d

When the amino-protecting group is an alkenyloxycarbonyl group, it is preferably removed by treating the protected compound with a base under the same conditions as are employed when the amino-protecting group is an aliphatic acyl group, an aromatic acyl group, an alkoxycarbonyl group or a substituted methylene group which forms a Schiff base.

In case of an allyloxycarbonyl group, it may be removed by using palladium and triphenylphosphine or nickel tetracarbonyl, which is a simple process that can be conducted with few side reactions.

Step C4(ii)

The removal of the group $R^{12}$ may be carried out according to the same procedure as that described in Step A9.

After the completion of any of the above reactions, the desired compound may be isolated from the reaction mixture by conventional means.

For example, in one suitable isolation procedure, the reaction mixture is appropriately neutralized and, after insoluble matter, if any, is removed by filtration, a water-immiscible organic solvent (e.g. ethyl acetate) is added. The organic layer is then separated and washed with, for example, water. The desired compound is then dried over, for example, anhydrous magnesium sulfate or anhydrous sodium sulfate. The solvent is then removed by distillation to give the desired compound.

The desired compound can, if desired, be isolated and purified by any one or more of the following procedures: recrystallization; reprecipitation; or another process which is normally used for isolation and purification of organic compounds, for example an adsorption column chromatography process using a carrier, such as silica gel, alumina or magnesium-silica gel, Florisil; a process using a synthetic adsorbent, for example, partition column chromatography using Sephadex (trade mark) LH-20 (manufactured by Pharmacia Co.), Amberlite (trade mark) XAD-11 (manufactured by Rohm & Haas Co.), Diaion (trade mark) HP-20 (manufactured by Mitsubishi Kasei Co., Ltd.); a process using ion-exchange chromatography; or a normal/reverse phase liquid chromatography process (preferably high performance liquid chromatography) using silica gel or an alkylated silica gel.

Reaction Scheme D

In this Reaction Scheme, a compound of formula (I) in which E represents a methylene group, that is to say a compound of formula (Ia), is prepared from a compound of formula (VIII), which may have been prepared as described in Reaction Scheme A, above.

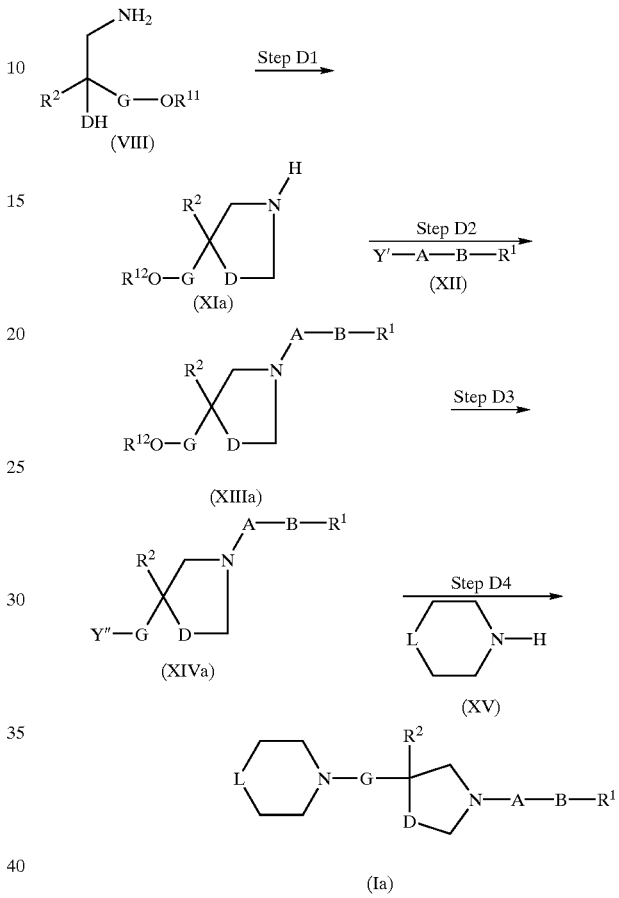

Step D1

In this Step, a compound of formula (XIa) is prepared by reacting the amino group and the group of formula DH of a compound of formula (VIII) with paraformaldehyde in the presence or absence of an acid catalyst and in the presence or absence of a solvent to form an oxazolidine or thiazolidine ring.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, such as nitroethane and nitrobenzene; nitriles, such as acetonitrile, isobutyronitrile;

amides, such as formamide, dimethylformamide, dimethylacetamide, N-methyl-2-pyrrolidone, N-methylpyrrolidinone and hexamethylphosphoric triamide; and sulfoxides, such as dimethyl sulfoxide and sulfolane. Of these, we prefer the aromatic hydrocarbons, most preferably benzene and toluene.

There is likewise no particular restriction on the nature of the acid catalysts used, and any acid catalyst commonly used in reactions of this type may equally be used here. Examples of such acid catalysts include: Bronsted acids, such as inorganic acids (e.g. hydrochloric acid, hydrobrornic acid, sulfuric acid, perchloric acid or phosphoric acid) or organic acids (e.g. acetic acid, formic acid, oxalic acid, methanesulfonic acid, p-toluenesulfonic acid, camphorsulfonic acid, trifluoroacetic acid or trifluoromethanesulfonic acid). Of these, we prefer the organic acids, most preferably p-toluenesulfonic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50 to 200° C., more preferably from 80 to 150° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 12 hours, will usually suffice.

Steps D2, D3 & D4

These Steps correspond to Steps A8, A9 and A10, respectively, and may be carried out using the same reagents and reaction conditions, ultimately to give a compound of formula (Ia).

The desired compound can, if desired, be isolated and purified by any one or more of the following procedures: recrystallization; reprecipitation; or another process which is normally used for isolation and purification of organic compounds, for example an adsorption column chromatography process using a carrier, such as silica gel, alumina or magnesium-silica gel, Florisil; a process using a synthetic adsorbent, for example, partition column chromatography using Sephadex (trade mark) LH-20 (manufactured by Pharmacia Co.), Amberlite (trade mark) XAD-1 I (manufactured by Rohm & Haas Co.), Diaion (trade mark) HP-20 (manufactured by Mitsubishi Kasei Co., Ltd.); a process using ion-exchange chromatography; or a normal/reverse phase liquid chromatography process (preferably high performance liquid chromatography) using silica gel or an alkylated silica gel.

Reaction Scheme E

In this Reaction Scheme, a highly preferred compound of formula (I) in which L represents a fused ring system having a sulfoxide group in which the sulfur atom is in the S-configuration, that is to say the optically active sulfoxide compound of formula (Ib), is prepared.

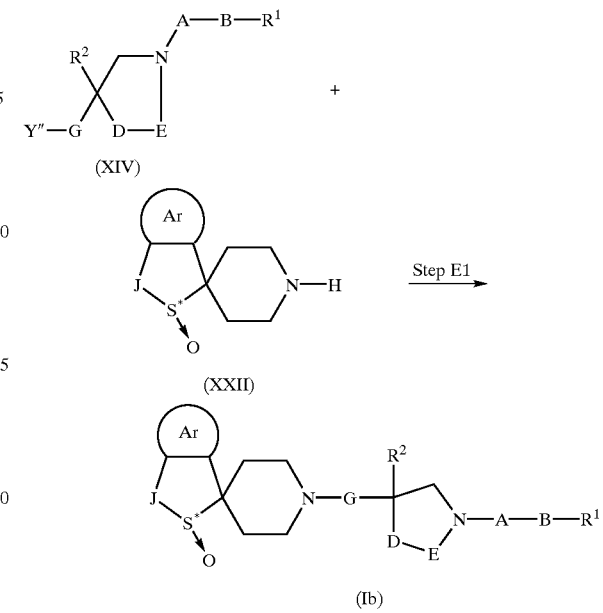

In the above formulae:

Ar, $R^1$, $R^2$, A, B, D, E, J and Y'' are as defined above;

S*→O represents a sulfoxide group in which the sulfur atom is in the S-configuration.

This reaction corresponds to Step A10 and may be carried out using the same reagents and reaction conditions, to give a compound of formula (Ib).

Reaction Scheme F

This Reaction Scheme provides an alternative method of preparing the optically active sulfoxide compound of formula (Ib).

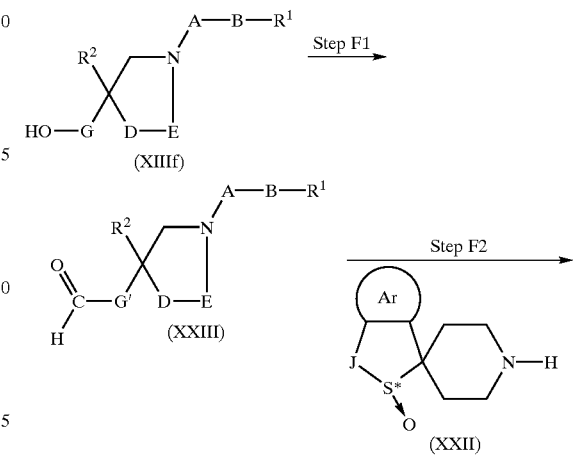

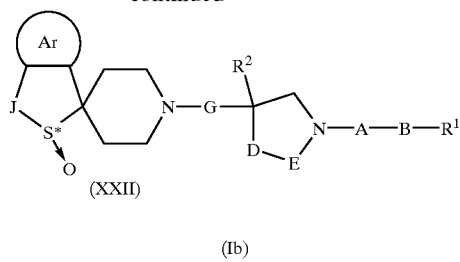

(Ib)

In the above formulae:

$R^1$, $R^2$, A, B, D, E, G', J, Ar and $S^* \rightarrow O$ are as defined above; and Step F1

In this Step, an aldehyde derivative of formula (XXII) is prepared by oxidizing an alcohol derivative of formula (XIIIf). This reaction is usually carried out in a solvent in the presence of an oxidizing agent.

There is no particular restriction on the nature of the oxidation reactions used, and any oxidation reaction commonly used for forming an aldehyde from a primary alcohol may equally be used here. Examples of such oxidation reactions include: Collins oxidation which is carried out in methylene chloride using pyridine and chromic acid; PCC oxidation which is carried out in methylene chloride using pyridinium chlorochromate (PCC); PDC oxidation which is carried out in methylene chloride using pyridinium dichromate (PDC); DMSO oxidation such as Swern oxidation which is carried out in methylene chloride using an electrophilic agent (e.g., acetic anhydride, trifluoroacetic anhydride, thionyl chloride, sulfuryl chloride, oxalyl chloride, dicyclohexylcarbodiimide, diphenylketene-1-tolylimine, N,N-diethylaminoacetylene, N,N-Dimethylamino-phenylacetylene, sulfur trioxide and pyridine complex) and dimethyl sulfoxide (DMSO); and manganese dioxide oxidation which is carried out in methylene chloride or benzene using manganese dioxide.

Preferably, Swern oxidation which is carried out in methylene chloride using oxalyl chloride and DMSO is employed.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to room temperature, more preferably from −78° C. to −20° C. The time required for the reaction may also vary widely, depending on many factors, notably the reaction temperature and the nature of the reagents and solvent employed. However, provided that the reaction is effected under the preferred conditions outlined above, a period of from 10 minutes to two days, more preferably from 10 minutes to 6 hours, will usually suffice.

Step F2

In this Step, an optically active sulfoxide derivative of formula (Ib) is prepared by reacting a compound of formula (XXIII) with the compound of formula (XXII) by means of a reductive amination reaction.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols such as methanol, ethanol and propanol; and ethers such as diethyl ether, tetrahydrofuran and dioxane. Of these, we prefer the alcohols, most preferably methanol or ethanol.

There is likewise no particular restriction on the nature of the reducing agents used, and any reducing agent commonly used in reactions of this type may equally be used here. Examples of such reducing agents include: hydride reagents such as alkali metal borohydrides such as sodium cyanoborohydride, sodium borohydride and lithium borohydride; aluminum hydride compounds such as lithium aluminum hydride and lithium tri-t-butoxyaluminohydride; sodium tellurium hydride; and organoaluminum hydride reducing agents such as diisobutylaluminum hydride and sodium bibs(methoxyethoxy)aluminum hydride. Of these, we prefer the alkali metal borohydrides, most preferably sodium cyanoborohydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 100° C., more preferably from room temperature to 80° C. The time required for the reaction may also vary widely, depending on many factors, notably the reaction temperature and the nature of the reagents and solvent employed. However, provided that the reaction is effected under the preferred conditions outlined above, a period of from 10 minutes to two days, more preferably from one hour to 6 hours, will usually suffice.

Reaction Scheme G

This provides an alternative method of preparing a compound of formula (XI), which may then be used to prepare a compound of the present invention.

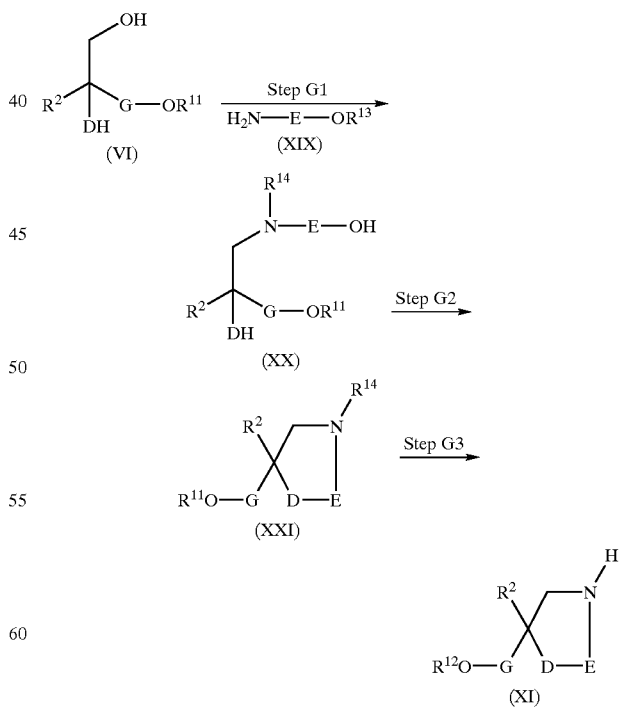

In the above formulae:

$R^2$, $R^{11}$, $R^{12}$, $R^{13}$, $R^{14}$, D, E and G are as defined above; and This Reaction Scheme describes the preparation of compounds of formula (XI) wherein the ring has from 6 to 8-members.

Step G1

In this Step, a compound of formula (XX) is prepared by converting the primary hydroxy group of the diol compound of formula (VI) into a group to be eliminated (Step G1a), which is then replaced by the amino group of an amino alcohol compound of formula (XIX) to form a secondary amino group (Step G1b), which is then protected with an $R^{14}$ group (Step G1c).

Step G1a

The conversion of the primary hydroxy group of the diol compound of formula (VI) into a group to be eliminated may be effected by the procedure described in the first stage of Step A4.

Step G1b

The reaction of replacing the group to be eliminated in the resulting compound by an amino group of the amino alcohol compound of formula (XIX) is usually carried out in a solvent using a metal salt.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile, propionitrile and isobutyronitrile; and amides, such as formamide, dimethylformamide, dimethylacetamide, N-methyl-2-pyrrolidone, N-methylpyrrolidone and hexamethylphosphoric triamide. Of these, we prefer the nitriles, more preferably acetonitrile.

There is likewise no particular restriction on the nature of the metal salts used, and any metal salt commonly used in reactions of this type may equally be used here. Examples of such metal salts include: metal perchlorates, such as lithium perchlorate, magnesium perchlorate and sodium perchlorate; metal chlorides, such as calcium chloride, zinc chloride and cobalt chloride; metal tetrafluoroborates, such as lithium tetrafluoroborate and potassium tetrafluoroborate; and zinc trifluoromethanesulfonate, preferably metal perchlorates, more preferably lithium perchlorate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from room temperature to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 2 days, more preferably from 2 hours to 24 hours, will usually suffice.

Step G1c

The final step of protecting the secondary amino group with the $R^{14}$ group may be carried out as described in Step C2b.

Step G2

In this Step, a compound of formula (XXI) is prepared by subjecting the compound of formula (XX) to a Mitsunobu reaction so as to effect dehydration and ring closure.

This reaction is essentially the same as that described in Step C3, and may be carried out using the same reagents and reaction conditions.

It should be noted that the $R^{11}$ and $R^{14}$ groups may be eliminated during the process of this step. In such cases, the imino group can, if necessary, be protected again with the $R^{14}$ group according to the procedures of Step G1c; while the hydroxy group can be protected again with the $R^{11}$ group, according to the procedures of Steps A2(i) to (iii).

Step G3

In this Step, a compound of formula (XI) is prepared by removing the $R^{11}$ and $R^{14}$ groups of the compound of formula (XXI). This reaction is essentially the same as that described in Step C4(i), and may be carried out using the same reagents and reaction conditions.

Reaction Scheme H

This Reaction Scheme illustrates the preparation of a compound of formula (XXXII), which corresponds to the compound of formula (V) wherein the group represented by G has two carbon atoms.

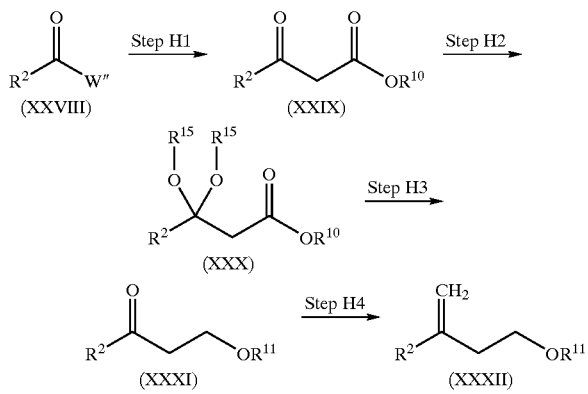

In the above formulae $R^2$, $R^{10}$, and $R^{11}$ are as defined above;

$R^{15}$ represents an alkyl group having from 1 to 6 carbon atoms, as defined and exemplified above in relation to $R^5$, preferably a methyl, ethyl, propyl or isopropyl group, or two groups $R^{15}$ may together represent an alkylene group having from 1 to 6 carbon atoms, preferably a methylene, ethylene or trimethylene group; and W" represents a halogen atom, more preferably a chlorine atom.

Step H1

In this Step, a β-ketoester derivative of formula (XXIX) is prepared from a compound of formula (XXVIII). This reaction may be effected by conventional procedures according to, for example, the method of J. Wemple et al. [Synthesis, 290 (1993)].

Step H2

In this Step, a ketal is prepared by reacting the β-ketoester derivative of formula (XXIX) with an alcohol having the formula $R^{15}$—OH (wherein $R^{15}$ is as defined above), with an alkanediol having the formula HO—$R^{15'}$—OH (wherein $R^{15'}$ represents an alkylene group to be formed by the two $R^{15}$ groups together) or with an orthoformic acid ester having the formula $(R^{15}—O)_3CH$ (wherein $R^{15}$ is as defined above). This reaction may be carried out, for example, in the alcohol or the alkanediol in the presence or absence of an acid catalyst with heating.

Examples of alcohols having the formula $R^{15}$—OH include methanol, ethanol, propanol and isopropanol, preferably ethanol.

Examples of alkanediols having the formula HO—$R^{15'}$—OH include ethylene glycol and propylene glycol.

Examples of orthoformic acid esters having the formula $(R^{15}—O)_3CH$ include trimethoxymethane and triethoxymethane, preferably triethoxymethane.

This step is preferably carried out with heating in ethanol in the presence of ethyl orthoformate using p-toluenesulfonic acid as the catalyst.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 40° C. to 150° C., more preferably from 50° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to two days, more preferably from two hours to 12 hours, will usually suffice.

Step H3

In this Step, the ester of formula (XXX) is reduced to form a primary hydroxy group, the ketal group is then deprotected, and then the primary hydroxy group is protected with a group $R^{11}$, to prepare a compound of formula (XXXI).

The reaction to reduce the ester is essentially the same as that in the first stage of Step A2, and may be carried out using the same reagents and reaction conditions.

The deprotection of the ketal group is usually carried out in a solvent in the presence of an acid, preferably in chloroform using trifluoroacetic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from −10° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 2 hours, will usually suffice.

The reaction protecting the primary hydroxy group may be carried out according to any of Steps A2(i) to (iii), preferably according to Step A2(i).

Step H4

In this Step, a compound of formula (XXXII) is prepared by converting the carbonyl group of the compound of formula (XXXI) into an exo-methylene group by the Wittig reaction in a solvent in the presence of a base. The reaction in this step is essentially the same as that in Step A1c, and may be carried out using the same reagents and reaction conditions.

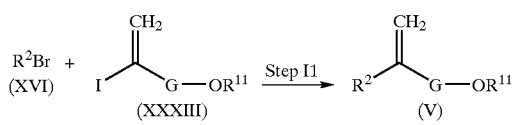

In the above formulae, G, $R^2$ and $R^{11}$ are as defined above.

This is another process for preparing the compound of formula (V), which may then be used in Reaction Scheme A or C.

Step I1

In this Step, a compound of formula (V) is prepared by reacting a compound of formula (XVI) with metallic magnesium by any conventional method to prepare a Grignard reagent and thereafter carrying out a cross coupling reaction of the above-mentioned Grignard reagent with a compound of formula (XXXIII) using a palladium catalyst or a nickel catalyst.

There is no particular restriction on the nature of the palladium catalysts used, and any palladium catalyst commonly used in reactions of this type may equally be used here. Examples of such palladium catalysts include: tetrakis (triphenylphosphine)palladium(0), bis(acetonitrile) palladium(II) chloride, bis(triphenylphosphine)palladium(II) chloride, [1,1'-bis(diphenylphosphino)-ferrocene] palladium(II) chloride, tris(dibenzylideneacetone) dipalladium(0), [1,2-bis(diphenylphosphino)ethane]dichloropalladium(II) and palladium(II) acetate.

There is likewise no particular restriction on the nature of the nickel catalysts used, and any nickel catalyst commonly used in reactions of this type may equally be used here. Examples of such nickel catalysts include: bis(triphenylphosphine)-nickel(II) chloride, [1,3-bis(diphenylphosphino)propane]nickel(II) chloride and nickel (II) acetylacetonate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers such as diethyl ether, diisopropyl ether, tetrahydrofuran, dioxane, and dimethoxyethane diethylene glycol dimethyl ether, more preferably diethyl ether or tetrahydrofuran.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 120° C., more preferably from at room temperature to 80° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 5 hours, will usually suffice.

Reaction Scheme J

This Reaction Scheme illustrates the preparation of the optically active sulfoxide compound of formula (XXII) used as a starting material in Reaction Scheme E.

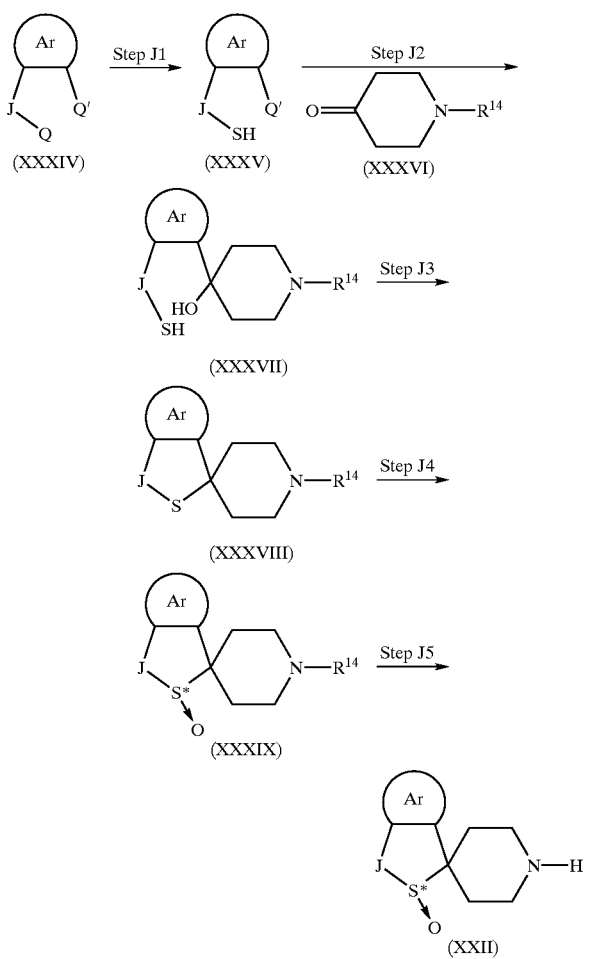

In the above formulae:

$R^{14}$, J, the ring Ar and the formula S*→O are as defined above.

Q represents a hydroxy group or a halogen atom such as a chlorine, bromine, iodine or fluorine atom; and.

Q' represents a halogen atom, preferably a bromine atom.

Step J1

In this Step, a compound of formula (XXXV) is prepared from a compound of formula (XXXIV)

Step J1a

When Q represents a hydroxy group, this step can be achieved by converting the hydroxy group of the compound of formula (XXXIV) into an acetylthio group, followed by hydrolysis of the acetylthio group using a base so as to remove the acetyl group.

The first stage of these reactions may be achieved:

(a) by converting the hydroxy group of the compound of formula (XXXIV) into a group to be eliminated, followed by reaction of the group to be eliminated with a salt of thioacetic acid; or (b) by carrying out a Mitsunobu reaction using thioacetic acid.

The reaction converting the hydroxy group into a group to be eliminated in (a) may be carried out according to the latter substep in Step A9; whereas the thioacetyl group substitution reaction is usually achieved by reaction with a salt of thioacetic acid in a solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile, propionitrile and isobutyronitrile; and amides, such as formamide, dimethylformamide, dimethylacetamide, N-methyl-2-pyrrolidone, N-methylpyrrolidinone and hexamethylphosphoric triamide. Of these, we prefer the amides, more preferably dimethylformamide.

Examples of salts of thioacetic acid which may be employed in this reaction include metal salts of thioacetic acid such as lithium thioacetate, sodium thioacetate and potassium thioacetate.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from room temperature to 100° C. The time required for the reaction may also vary widely, depending on many factors, notably the reaction temperature and the nature of the reagents and solvent employed. However, provided that the reaction is effected under the preferred conditions outlined above, a period of from 30 minutes to two days, more preferably from 2 hours to 24 hours, will usually suffice.

The Mitsunobu reaction in (b) described above may be carried out in the same manner as in Step C3 except that the compound of formula (XXXIV) and thioacetic acid are employed.

The reaction eliminating the acetyl moiety in the acetylthio group can be achieved by treating it with a base in a solvent.

There is likewise no particular restriction on the nature of the bases used, and any base commonly used in reactions of this type may equally be used here. Examples of such bases include: metal alkoxides, such as sodium methoxide; alkali metal carbonates, such as sodium carbonate, potassium carbonate and lithium carbonate; alkali metal and alkaline earth metal hydroxides, such as sodium hydroxide, potassium hydroxide, lithium hydroxide and barium hydroxide; and various forms of ammonia such as aqueous ammonia water or concentrated methanolic ammonia The reaction is normally and preferably effected in the presence of a solvent. There is no particular restriction on the nature of the solvent to be employed, and any solvent commonly employed in hydrolysis reactions may be used, provided that it has no adverse effect on the reaction or on the reagents involved and that it can dissolve the reagents, at least to some extent. Examples of suitable solvents include: water; organic solvents, for example, alcohols (such as methanol, ethanol or propanol), ethers (such as tetrahydrofuran or dioxane) or a mixture of water with any one or more of these organic solvents.

The reaction can take place over a wide range of temperatures, and the precise reaction temperature is not critical to the invention. The preferred reaction temperature will depend upon such factors as the nature of the solvent, and the starting material or reagent used. However, in general, in order to control side reactions, we find it convenient to carry out the reaction at a temperature of from 0 to 150° C. The time required for the reaction may also vary widely, depending on many factors, notably the reaction temperature and the nature of the reagents and solvent employed. However, provided that the reaction is effected under the preferred conditions outlined above, a period of from one to 10 hours will usually suffice.

Step J1b

Where Q is a halogen atom, this step can be achieved by heating the compound of formula (XXXIV) and thiourea in a solvent to effect reaction therebetween, followed by hydrolysis.

The first stage of this reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include alcohols, such as methanol, ethanol and isopropanol.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to 150° C., more preferably from 50° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to four days, more preferably from 12 hours to 24 hours, will usually suffice.

The hydrolysis in the latter substep is usually carried out in a mixture of water with one or more of the alcohols described above.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to 150° C., more preferably from 50° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 6 hours, more preferably from 30 minutes to 2 hours, will usually suffice.

Step J2

In this Step, a compound of formula (XXXV) is reacted with a compound of formula (XXXVI) in a solvent in the presence of a base to provide a compound of formula (XXXVII).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, dimethylacetamide, N-methyl-2-pyrrolidone, N-methylpyrrolidinone and hexamethylphosphoric triamide. Of these, we prefer the ethers, most preferably tetrahydrofuran.

There is likewise no particular restriction on the nature of the bases used, and any base commonly used in reactions of this type may equally be used here. Examples of such bases include: alkali metal hydrides, such as lithium hydride, sodium hydride and potassium hydride; and organometallic bases, such as butyllithium, sec-butyllithium, t-butyllithium, lithium diisopropylamide and lithium bis(trimethylsilyl) amide. Of these, we prefer the organometallic bases, most preferably butyllithium.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 100° C., more preferably from −78° C. to 0° C. The time required for the reaction may also vary widely, depending on many factors, notably the reaction temperature and the nature of the reagents and solvent employed. However, provided that the reaction is effected under the preferred conditions outlined above, a period of from 0.5 hour to 10 hours, more preferably from 1 hour to 6 hours, will usually suffice.

Step J3

In this Step, a compound of formula (XXXVII) is dehydrated in the presence or absence of a solvent and in the presence of an acid to close a ring and to prepare a compound of formula (XXXVII).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile and isobutyronitrile; amides, such as formamide, dimethylformamide, dimethylacetamide, N-methyl-2-pyrrolidone, N-methyl pyrrolidinone and hexamethylphosphoric triamide. Of these, we prefer methanol or ethanol.

There is likewise no particular restriction on the nature of the acids used, and any acid commonly used in reactions of this type may equally be used here. Examples of such acids include: Brønsted acids, such as inorganic acids (e.g. hydrogen chloride, hydrobromic acid, sulfuric acid, perchloric acid or phosphoric acid) and organic acids (e.g. acetic acid, formic acid, oxalic acid, methanesulfonic acid, p-toluenesulfonic acid, trifluoroacetic acid and trifluoromethanesulfonic acid), and Lewis acids, such as boron trichloride, boron trifluoride and boron tribromide, or acidic ion exchange resins. Of these, we prefer the inorganic acids, most preferably sulfuric acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 150° C., more preferably from 50° C. to 120° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 5 hours to 24 hours, will usually suffice.

Step J4

In this Step, an optically active sulfoxide derivative of formula (XXXIX) from a compound of formula (XXXVIII) and is achieved by (a) directly carrying out an asymmetric oxidation of the compound of formula (XXXVIII) or (b) oxidizing the compound of formula (XXXVIII) and thereafter optically resolving the compound by a diastereomeric method.

(a) The asymmetric oxidation in which a sulfoxide is obtained from a sulfide may be a chemical method using an optically active oxidizing agent, a chemical method using a combination of an chiral ligand and an oxidizing agent or a biological method using baker's yeasts and microorganisms. Such an asymmetric oxidation is, for example, described in the following references:

1) G. Solladie, Synthesis 185 (1981):
2) K. K. Andersen, The Chemistry of Sulfones and Sulfoxides: S. Patai, Z. Rappoport, C. J. M. Stirling., Eds. Wiley & Sons, Ltd.; Chichester, England, 1988, Chapter 3, pp 55–94: G. H. Posner., ibid. Chapter 16, pp 823–849:
3) H. B. Kagan et al., Synlett 643 (1990):
4) H. B. Kagan, Asymmetric Oxidation of Sulfides in Catalytic Asymmetric Synthesis 1, Ojima Ed. VCH, pp 203–226 (1993):
5) F. A. Davis et al., J.Am.Chem.Soc., 114, 1428 (1992).

Of these, the asymmetric oxidation is preferable, in which (3'S, 2R)-(–)-N-(phenylsulfonyl) (3,3-dichlorocamphoryl) oxazolidine or (+)-[(8,8-dimethoxycamphoryl) sulfonyl] oxazolidine as reported by F. A. Davis et al. is used.

Where the asymmetric oxidation is carried out according to the method of F. A. Davis et al., the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; alcohols, such as methanol, ethanol, propanol, isopropanol, butanol, isobutanol and isoamyl alcohol; aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, propyl acetate, butyl acetate and diethyl carbonate; ethers, such as diethyl ether, diisopropyl ether, tetrahydrofuran, dioxane, dimethoxyethane and diethylene glycol dimethyl ether; nitrites, such as acetonitrile and isobutyronitrile; and pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –50° C. to 50° C., more preferably from –20° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 2 hours to 1 day, will usually suffice.

(b) When carrying out optical resolution by a diastereomeric method, a compound of formula (XXXVIII) is first oxidized by a conventional method to synthesize a racemate of the sulfoxide derivative. Then, an optically active sulfoxide derivative (XXXIX) can be obtained by removing the protecting group, as described in Step C4(i), and thereafter by forming a salt using an appropriate optically active carboxylic acid as an optical resolving reagent, and by carrying out fractional recrystallization.

The oxidation reaction of the former step is ordinarily carried out in the presence or absence of a solvent and using an oxidizing agent.

There is likewise no particular restriction on the nature of the oxidizing agents used, and any oxidizing agent commonly used in reactions of this type in which a sulfide is oxidized to produce a sulfoxide may equally be used here. Examples of such oxidizing agents include: peracids, such as m-chloroperbenzoic acid, 3,5-dinitroperbenzoic acid, o-carboxyperbenzoic acid, peracetic acid, pertrifluoroacetic acid and perphthalic acid; and a combination of a succinimide, such as N-bromosuccinimide and an alkali, more preferably a peracids, most preferably m-chloroperbenzoic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride and chloroform; ethers, such as diethyl ether, tetrahydrofuran, dioxane and dimethoxyethane; amides, such as dimethylformamide, dimethylacetamide and hexamethylphosphoric triamide; sulfoxides, such as dimethyl sulfoxide; alcohols, such as methanol, ethanol, propanol, isopropanol, butanol, isobutanol and isoamyl alcohol; dilute acids, such as aqueous sulfuric acid; dilute bases, such as aqueous sodium hydroxide; water; ketones, such as acetone and methyl ethyl ketone; organic bases, such as pyridine; nitrites, such as acetonitrile; or a mixture of any two or more of these solvents, more preferably a halogenated hydrocarbon, and most preferably methylene chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –20° C. to 80° C., more preferably from –5° C. to 50° C. The time required for the reaction may also vary widely, depending on many factors, notably the reaction temperature and the nature of the reagents and solvent employed. However, provided that the reaction is effected under the preferred conditions outlined above, a period of from 1 hour to 24 hours, more preferably from 2 hours to 12 hours, will usually suffice.

The optical resolving agent employed for carrying out optical resolution is not particularly limited and examples include tartaric acid, camphor-10-sulfonic acid and mandelic acid, particularly preferably mandelic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. A suitable solvent is acetonitrile.

The salt thus obtained by the resolution is converted to a corresponding amine by using an aqueous alkali, such as aqueous sodium hydroxide, followed by extraction with a solvent which is not dissolved in water (for example, an aromatic hydrocarbon, such as benzene, toluene or xylene; a halogenated hydrocarbon, such as methylene chloride or chloroform; or an ether, such as diethyl ether) to isolate an optically active sulfoxide derivative of formula (XXXIX).

Step J5

In this Step, a compound of formula (XXII) is prepared by removing the protective group $R^{14}$ group from the compound of formula (XXXIX). The reaction may be carried out using any of the procedures described in Step C4(i).

After the completion of any of the above reactions, the desired compound may be isolated from the reaction mixture by conventional means.

For example, in one suitable isolation procedure, the reaction mixture is appropriately neutralized and, after insoluble matter, if any, has been removed by filtration, a water-immiscible solvent (e.g. ethyl acetate) is added. The organic layer is separated and washed with, for example, water. The desired compound is then dried, for example over anhydrous magnesium sulfate or anhydrous sodium sulfate. Then, the solvent is distilled off to give the desired compound.

The desired compound can, if desired, be isolated and purified by any one or more of the following procedures: recrystallization; reprecipitation; or another process which is normally used for isolation and purification of organic compounds, for example an adsorption column chromatography process using a carrier, such as silica gel, alumina or magnesium-silica gel, Florisil; a process using a synthetic adsorbent, for example, partition column chromatography using Sephadex (trade mark) LH-20 (manufactured by Pharmacia Co.), Amberlite (trade mark) XAD-11 (manufactured by Rohm & Haas Co.), Diaion (trade mark) HP-20 (manufactured by Mitsubishi Kasei Co., Ltd.); a process using ion-exchange chromatography; or a normal/reverse phase liquid chromatography process (preferably high performance liquid chromatography) using silica gel or alkylated silica gel.

The starting materials [for example, the compound of formula (XXXIV), etc.] can be purchased commercially or the materials can be easily synthesized according to well known preparation methods.

BIOLOGICAL ACTIVITY

The novel compounds of the present invention have a superior antagonistic effect on substance P and neurokinin A receptors. Moreover, since they have low toxicity, they are useful for the prevention and therapy of tachykinin-mediated diseases, examples of which include diseases of the central nervous system including anxiety, depression, psychosis and schizophrenia; neurodegenerative diseases including dementia of AIDS, Alzheimer's senile dementia, Alzheimer's disease, Down's syndrome, demyelinating disease, amyotrophic lateral sclerosis, neuropathy, peripheral neuropathy and neuralgia; respiratory diseases including chronic obstructive lung disease, bronchitis, pneumonia, bronchoconstriction, asthma and cough; inflammatory diseases, such as inflammatory bowel diseases (IBD), psoriasis, fibrosis, arthrosteitis, degenerative arthritis and rheumatoid arthritis; allergic diseases including eczema and rhinitis; hypersensitivity diseases including hypersensitivity to vines; ophthalmological diseases including conjunctivitis, vernal conjunctivitis, vernal catarrh, destruction of the blood-aqueous humor barrier caused by various inflammatory eye diseases, elevated intraocular pressure and miosis; skin diseases including contact dermatitis, atopic dermatitis, urticaria and other eczematoid dermatitis; addictions including alcohol dependency; somatic diseases caused by stress; sympathetic reflex dystrophy including hand and shoulder syndrome; dysthymia; undesirable immune reactions including rejection of grafts, diseases relating to immunopotentiation including systemic lupus erythematosus or immunosuppression; digestive diseases including diseases caused by abnormalities in nerves regulating the organs, colitis, ulcerative colitis and Crohn's disease; emesis including emesis induced by adverse effects of X-ray irradiation and chemotherapy, poisons, toxins, pregnancy, vestibular disorders, postoperative illness, gastrointestinal occlusion, reduced gastrointestinal movement, visceral pain, migraine headache, increased intracranial pressure, reduced intracranial pressure or administration of various drugs; urinary bladder functional diseases including cystitis and urinary incontinence; eosinophilia caused by collagen diseases, scleriasis and Fasciola hepatica infection; diseases caused by abnormal blood flow due to vasodilation or vasoconstriction including angina pectoris, migraine headache and Reynauds's disease; and, pain of pain nociceptive reception including migraine headache, headache and toothache.

The compounds of the present invention can be administered orally, for example in the form of tablets, capsules, granules, powders or syrups, or administered parenterally, for example in the form of injection preparations or suppositories. These preparations may be produced using additives, such as excipients [e.g. sugar derivatives, such as lactose, sucrose, glucose, mannitol or sorbitol; starch derivatives, such as corn starch, potato starch, α-starch, dextrin or carboxymethyl starch; cellulose derivatives, such as crystalline cellulose, low substitution degree hydroxypropylcellulose, hydroxypropylmethylcellulose, carboxymethylcellulose, carboxymethylcellulose calcium or internally cross-linked carboxymethylcellulose sodium; gum arabic; dextran; organic excipients, such as pullulan; silicate derivatives, such as light anhydrous silicic acid, synthetic aluminum silicate or magnesium aluminate metasilicate; phosphates, such as calcium phosphate; carbonates, such as calcium carbonate; inorganic excipients, such as sulfates (e.g. calcium sulfate), ]; lubricants [e.g. stearic acid and metal stearates, such as calcium stearate, and magnesium stearate; talc; colloidal silica; waxes, such as bee gum, and spermaceti; boric acid; adipic acid; sulfates, such as sodium sulfate; glycol; fumaric acid; sodium benzoate; L leucine; fatty acid sodium salts; laurylsulfates, such as sodium laurylsulfate, and magnesium laurylsulfate; silicic acids, such as anhydrous silicic acid, and silicate hydrate; and the above starch derivatives]; binders [e.g. polyvinyl pyrrolidone, macrogol and the same compounds as those of the above excipients]; disintegrators [e.g. the same compounds as those of the above excipients and chemically modified starchcelluloses, such as croscarmellose sodium, carboxymethylstarch sodium, and cross-linked polyvinylpyrrolidone]; stabilizers [e.g. paraoxybenzoates, such as methylparaben, and propylparaben; alcohols, such as chlorobutanol, benzyl alcohol, and phenethyl alcohol; benzalkonium chloride; phenols, such as phenol, cresol; thimerosal; dehydroacetic acid; and sorbic acid]; corrigents [e.g. normally used sweetening agents, sour agents, and perfumes]; and diluents according to a per se known process.

The dose varies depending on the severity of the disease, as well as the age and body weight of the patient, and the administration route. For example, in the case of oral administration, it is advantageous that the compound of the present invention should be administered one to several times per day with a dose of from 0.01 mg/kg body weight (preferably 0.1 mg/kg body weight, lower limit) to 100 mg/kg body weight (preferably 50 mg/kg body weight, upper limit) according to the severity of diseases. In case of intravenous administration, it is advantageous that the compound of the present invention is administered one to several times per day with a dose of 0.01 mg/kg body weight (preferably 0.05 mg/kg body weight, lower limit) to 100 mg/kg body weight (preferably 50 mg/kg body weight, upper limit) according to the severity of the disease.

The biological activity of the compounds of the present invention may be assessed by the following tests.

NK$_1$ Receptor Binding Test (a) Preparation of Crude Lung Membrane Fraction

A crude membrane fraction was prepared from the lung of male Hartley guinea pigs. The guinea pigs were bled from the cava abdominalis under chloroform anaesthesia and the pulmonary airway tissue was extracted immediately.

The extracted lung was perfused with a buffer (1) (50 mM Tris-HCl, pH 7.4), thinly cut in the buffer, and then homogenised in a buffer (2) [buffer (1) containing 120 mM sodium chloride and 5 mM potassium chloride] using a Polytron homogenizer. The tissue mass was removed from the homogenate by filtration with a nylon mesh (50 µm) and the supernatant was centrifuged (30,000×g, 30 minutes, 4° C.). The resultant pellet was resuspended in an ice-cooled buffer (3) [buffer (1) containing 10 mM EDTA and 300 mM potassium chloride], allowed to stand at 4° C. for 60 minutes and then washed centrifugally twice (30,000×g, 15 minutes, 4° C.).

The crude membrane fraction was preserved at −80° C. before use.

(b) Receptor Binding Test

To a mixed solution (250 µl) of the test drug and [$^3$H]-substance P (final concentration: 1 nM) (50 mM Tris-HCl, pH 7.4; 6 mM manganese chloride, 800 µg/ml BSA, 8 µg/ml chymostatin, 8 µg/ml leupeptin, 80 µg/ml bacitracin, 20 µg/ml phosphoramidon) was added a crude lung membrane fraction solution (250 µl), followed by incubation at room temperature for 30 minutes.

At the end of this time, a lung membrane ingredient was recovered on a GF/B glass fiber filter (manufactured by Whatman Co.) using an automatic filtering device (manufactured by Brandel Co.).

The glass filter was used after being pre-treated with a 0.1% polyethyleneimine solution for about 4 hours so as to inhibit non-specific binding as little as possible. The membrane ingredient-recovered filter was transferred to a mini-plastic vial containing a pico flow (4 ml) and the radioactivity was measured using a liquid scintillation counter (LSC3000, manufactured by Beckman Co.).

The results are shown in Table 4:

TABLE 4

| Test Compound | IC$_{50}$ (ng/ml) |
| --- | --- |
| Compound of Example 75 | 5.9 |
| Compound A | 38 |
| Compound B | >1000 |
| Compound C | 6.5 |

As can be seen from the above results, the compound of the present invention exhibited an activity against NK$_1$ receptors which is at least equal to that of Compound C, which exhibited the strongest activity of the closest compounds of the prior art.

NK$_2$ Receptor Binding Test (a) Preparation of Crude Ileum Membrane Fraction

A crude membrane fraction was prepared from the ileum of male Hartley guinea pigs. The guinea pigs were bled from the cava abdominalis under chloroform anaesthesia and the ileum was extracted immediately.

After the contents, secreta and epithelium of the lumen had been scraped off using a glass slide, the extracted ileum was thinly cut in a buffer (1) (50 mM Tris-HCl, pH 7.4) and then homogenised in a buffer (2) [buffer (1) containing 120 mM sodium chloride and 5 mM potassium chloride] using a Polytron homogenizer.

The tissue mass was removed from the homogenate by filtration with a nylon mesh (50 µm) and the supernatant was centrifuged (30,000×g, 30 minutes, 4° C.). The resultant pellet was resuspended in an ice-cooled buffer (3) [buffer (1) containing 10 mM EDTA and 30 mM potassium chloride], allowed to stand at 4° C. for 60 minutes and then washed centrifugally twice (30,000×g, 15 minutes, 4° C.).

The crude membrane fraction was preserved at −80° C. before use.

(b) Receptor Binding Test

To a mixed solution (250 µl) of the test drug and [$^3$H]-SR-48968 (manufactured by Amasham Co., final concentration: 1 nM) (50 mM Tris-HCl, pH 7.4; 4.6 mM manganese chloride, 800 µg/ml BSA, 8 µg/ml chymostatin, 8 µg/ml leupeptin, 80 µg/ml bacitracin, 20 g/ml phosphoramidon) was added a crude ileum membrane fraction solution (250 µl), followed by incubation at room temperature for 30 minutes.

At the end of this time, a membrane ingredient was recovered on a GF/B glass fiber filter (manufactured by Whatman Co.) using an automatic filtering device (manufactured by Brandel Co.). The glass filter was used after pre-treatment with a 0.1% polyethyleneimine solution for about 4 hours so as to inhibit non-specific binding as little as possible.

The membrane ingredient-recovered filter was transferred to a mini-plastic vial containing a pico flow (4 ml) and the radioactivity was measured using a liquid scintillation counter (LSC3000, manufactured by Beckman Co.).

The compound of the present invention showed a good activity to NK$_1$ and NK$_2$ receptors in comparison with the compounds of the prior art.

The results are shown in Table 5:

TABLE 5

| Test Compound | IC$_{50}$ (ng/ml) |
| --- | --- |
| Compound of Example 75 | 0.85 |
| Compound A | 18 |
| Compound B | 2.2 |
| Compound C | 31 |

As can be seen from the above results, the compound of the present invention exhibited an activity against NK$_2$ receptors which is greater than that of any of the closest compounds of the prior art. Moreover, Compound C, which exhibited the strongest activity in the NK$_1$ binding test, here exhibited very weak activity.

Inhibitory Effect on SP-Induced Increased Vascular Permeability

The inhibitory effect on increased vascular permeability induced by substance P (SP), an NK$_1$ receptor agonist, was assessed based on the amount of pigment leakage as an index using guinea pigs (body weight: approx. 400 g, male Hartley guinea pigs). Immediately after administering pigment (Evans blue: 20 mg/kg, i.v.) and the test drug in that order into the femoral vein of the guinea pigs under pentobarbital anaesthesia (25 mg/kg, i.p.), increased vascular permeability was induced by administration of SP (1 mg/kg, i.v.). Fifteen minutes later, the guinea pigs were sacrificed by chloroform anaesthesia and the amount of pigment that leaked into the primary bronchus was measured according to the method of Harada (J. Pharm. Pharmacol., 23, 218, 1971). Inhibitory effect was determined based on the amount of pigment leakage found in guinea pigs not treated with the test drug, and expressed as the percent of inhibition (%) and the dose level that caused inhibition of 50% (ID$_{50}$).

The results are shown in Table 6:

TABLE 6

| Test Compound | ID$_{50}$ (mg/kg, i.v.) |
| --- | --- |
| Compound of Example 75 | 0.025 |
| Compound of Example 76 | 0.047 |
| Compound A | 5.8 |
| Compound B | >10 |
| Compound C | 0.019 |

As can be seen from the above results, the compounds of the present invention exhibited an inhibitory effect on Substance P-induced increased vascular permeability which is at least equal to that of Compound C, which exhibited the strongest activity of the closest compounds of the prior art.

Inhibitory Effect on NKA-Induced Bronchoconstriction

The inhibitory effect on bronchoconstriction induced with [Nle$^{10}$]-NKA[4-10], an NK$_2$ receptor agonist having higher specificity than neurokinin A (NKA), was assessed based on airway pressure as an index according to the modified method of Konzett-Rössler [Naunyn-Schmiedebergs Arch.Exp.Pathol.Pharmakol., 195, 71, (1940)] using guinea pigs (body weight: approximately 500 g, male Hartley guinea pigs).

After canulating the trachea of the guinea pigs under pentobarbital anaesthesia (30 mg/kg, s.c.) and treatment with gallamine (20 mg/kg, i.v.), the animals were ventilated artificially with a constant volume respiration pump (UgoBasile, 7025) at a frequency of 60 per minute and a tidal volume of 8 ml/kg. Airway pressure during artificial respiration was amplified by means of a pressure transducer (Nihon Koden, TP-200T) installed in a branch of the trachea cannula, detected (Nihon Koden, AP-610G), and recorded with a recorder (Nihon Koden, WT-685G). Following pretreatment with atropine (1 mg/kg, i.v.) and propranolol (1 mg/kg, i.v.), the test drug was administered intravenously. Five minutes later, bronchoconstriction was induced with [Nle$^{10}$]-NKA[4-10] at 4 mg/kg, i.v., and then airway pressure was measured for 10 minutes. The inhibitory effect was determined based on the intensity of bronchoconstriction of guinea pigs not treated with the test drug, and expressed as the percent of inhibition (%) and the dose level that caused inhibition of 50% (ID50).

The results are shown in Table 7:

TABLE 7

| Test Compound | ID$_{50}$ (mg/kg, i.v.) |
| --- | --- |
| Compound of Example 75 | 0.074 |
| Compound of Example 76 | 0.047 |
| Compound A | >10 |
| Compound B | 0.37 |
| Compound C | 1.7 |

As can be seen from the above results, the compounds of the present invention exhibited an activity against NK$_2$ receptors which is greater than that of any of the closest compounds of the prior art.

It is apparent from the above data that the compounds of the present invention exhibited strong activity against both NK$_1$ and NK$_2$ receptors. Moreover, the compounds of the present invention have an activity against the NK$_1$ receptors which is at least equal to that of the closest prior art compounds, and has a stronger activity against the NK$_2$ receptors than that of the closest prior art compounds.

PREPARATION 1

N,N-Dimethyl-1-t-butoxycarbonyl-4-phenylpiperidine-4-carboxamide 1.0 g (3.27 mmole) of t-butoxycarbonyl-4-phenylpiperidine-4-carboxylic acid was dissolved in 20 ml of anhydrous methylene chloride, and 690 mg (3.6 mmole) of 1-ethyl-3-(3-dimethylaminopropyl)carbodiimide hydrochloride, 490 mg (3.6 mmole) of 1-hydroxybenzotriazole, 1.3 ml (7.53 mmole) of diisopropylethylamine and 295 mg (3.93 mmole) of dimethylamine hydrochloride were added to the resulting solution, which was then stirred under a nitrogen atmosphere at room temperature for 15 hours. At the end of this time, the reaction mixture was diluted with methylene chloride, washed with water and with a saturated aqueous solution of sodium chloride, in that order, and then dried over anhydrous sodium sulfate.

The solvent was then removed by distillation under reduced pressure, and the resulting residue was purified by silica gel column chromatography using a gradient elution method, with mixtures of ethyl acetate and hexane ranging from 10:1 to 7:1 by volume as the eluent, to give 925 mg (yield 85%) of the title compound as white crystals.

Nuclear Magnetic Resonance Spectrum (400 MHz, CDCl$_3$) δ ppm: 7.34 (2H, doublet of triplets, J=6.7 & 1.9 Hz); 7.26–7.21 (3H, multiplet); 3.96 (2H, broad singlet);

3.21 (2H, broad singlet); 2.85 (3H, broad singlet); 2.60 (3H, broad singlet); 2.31 (2H, doublet, J=12.05 Hz); 1.87 (2H, broad singlet); 1.45 (9H, singlet). Mass spectrometric analysis (EI) m/z: 332 (M+). "EI" represents "Electron Ionization".

PREPARATION 2

N,N-Dimethyl-4-phenylpiperidine-4-carboxamide Hydrochloride 900 mg (2.7 mmole) of N,N-dimethyl-1-t-butoxycarbonyl-4-phenylpiperidine-4-carboxamide (prepared as described in Preparation 1) were dissolved in 10 ml of ethyl acetate, and 5 ml of a 4 N solution of hydrogen chloride in dioxane were added, whilst ice-cooling. The mixture was then stirred at 0° C. for 1 hour. At the end of this time, the crystals which had deposited were collected by filtration, to give 690 mg (yield 95%) of the title compound as white crystals.

Nuclear Magnetic Resonance Spectrum (400 MHz, hexadeuterated dimethyl sulfoxide) δ ppm: 9.02 (1H, broad singlet); 7.43 (2H, triplet, J=7.6 Hz); 7.31 (1H, doublet, J=7.2 Hz); 7.23 (2H, doublet, J=7.1 Hz); 3.25 (2H, doublet, J=13.1 Hz); 3.03 (2H, triplet, J=12.1 Hz); 2.79 (3H, broad singlet); 2.54 (3H, broad singlet); 2.37 (2H, doublet, J=12.9 Hz); 2.11 (2H, doublet of triplets, J=13.4 & 3.3 Hz). Mass spectrometric analysis (EI) m/z: 232 (free form, M+).

PREPARATION 3

Spiro[Benzo[c]thiophene-1(3H),4'-piperidine] hydrochloride

3(a) 1'-Cyanospiro[benzo[c]thiophene-1(3H),4'-piperidine]

2.34 g (22.1 mmole) of bromine cyanide were dissolved in 20 ml of anhydrous chloroform, and an anhydrous chloroform solution of 2.2 g (10 mmole) of 1'-methylspiro[benzo[c]thiophene-1(3H),4'-piperidine] [synthesised according to the process described in J. Org. Chem., Vol. 41, page 2628 (1976)] was added dropwise under reflux under a nitrogen atmosphere over a period of 20 minutes. The mixture was then heated under reflux for 9 hours, after which the reaction mixture was cooled and poured into ice-cooled aqueous 1 N aqueous hydrochloric acid. The chloroform layer was then separated, washed with water and dried over anhydrous sodium sulfate.

The solvent was then removed by distillation under reduced pressure, and the resulting residue was purified by silica gel column chromatography, using a 1:9 by volume mixture of ethyl acetate and hexane as the eluent, to obtain 1.3 g (yield 56%) of the title compound as white crystals.

Nuclear Magnetic Resonance Spectrum (400 MHz, CDCl$_3$) δ ppm: 7.38–7.27 (3H, multiplet); 7.21 (1H, doublet of doublets, J=1.9 & 6.4 Hz); 4.20 (2H, singlet); 3.51 (2H, multiplet); 3.37 (2H, doublet of triplets, J=2.2 & 12.9 Hz); 2.29 (2H, doublet of triplets, J=4.6 & 12.9 Hz); 1.91 (2H, multiplet). Mass spectrometric analysis (FAB) m/z: 231 (M+H)+ FAB is "Fast Atom Bombardment".

3(b) 1'-t-Butoxycarbonylspiro[benzo[c]thiophene-1(3H),4'-piperidine]

1.3 g (5.64 mmole) of 1'-cyanospiro[benzo[c]thiophene-1(3H),4'-piperidine] [prepared as described in step (a) above] were dissolved in 20% w/v aqueous hydrochloric acid, and the solution was heated under reflux for 20 hours. At the end of this time, the reaction mixture was cooled and washed with ethyl acetate. The aqueous layer was separated and made basic by the addition of a 10% w/v aqueous solution of sodium hydroxide; it was then extracted three times with chloroform. The solvent was then removed from the combined extracts by distillation under reduced pressure, and the resulting residue was dissolved in anhydrous methylene chloride. 1.15 ml (8.18 mmole) of triethylamine were then added, and 1.45 g (6.64 mmole) of di-t-butyl dicarbonate were added, whilst ice-cooling. The mixture was then stirred at room temperature for 2 hours. At the end of this time, the reaction mixture was diluted with methylene chloride and washed, in turn, with water and with a saturated aqueous solution of sodium chloride. The organic layer was separated and dried over anhydrous sodium sulfate, after which the solvent was removed by distillation under reduced pressure. The resulting residue was purified by silica gel column chromatography, using a 3:97 by volume mixture of ethyl acetate and hexane as the eluent, to obtain 1.65 g (yield 96%) of the title compound as white crystals.

Nuclear Magnetic Resonance Spectrum (400 MHz, CDCl$_3$) δ ppm: 7.28–7.24 (3H, multiplet); 7.17–7.15 (1H, multiplet); 4.23 (2H, broad singlet); 4.19 (2H, singlet); 3.02 (2H, broad singlet); 2.07 (2H, doublet of triplets, J=4.4 & 13 Hz); 1.88 (2H, multiplet); 1.49 (9H, singlet). Mass spectrometric analysis (EI) m/z: 305 (M+).

3(c) Spiro[Benzo[c]thiophene-1(3H),4'-piperidine] hydrochloride 150 mg (0.49 mmole) of 1'-t-butoxycarbonylspiro[benzo[c]thiophene-1(3H),4'-piperidine] [prepared as described in step (b) above] were dissolved in 3 ml of anhydrous methylene chloride, and 1 ml of a 4 N solution of hydrogen chloride in dioxane was added. The mixture was then stirred at room temperature for 1 hour. At the end of this time, the crystals which deposited were collected by filtration, to give 108 mg (yield 91%) of the title compound as white crystals.

Nuclear Magnetic Resonance Spectrum (400 MHz, hexadeuterated dimethyl sulfoxide) δ ppm: 9.77 (2H, broad singlet); 7.37–7.25 (4H, multiplet); 4.24 (2H, singlet); 3.67 (2H, doublet, J=12.6 Hz); 3.26 (2H, doublet of triplets, J=12.6 & 2.5 Hz); 2.74 (2H, doublet of triplets, J=3.8 & 14.0 Hz); 2.09 (2H, doublet, J=14.0 Hz). Mass spectrometric analysis (FAB) m/z: 206 (M+H)+ (free form).

PREPARATION 4

Spiro[Benzo[c]thiophene-1(3H),4'-piperidine]-2-oxide Hydrochloride

4(a) 1'-t-Butoxycarbonylspiro[benzo[c]thiophene-1(3H)4'-piperidine]-2-oxide 485 mg (1.59 mmole) of 1'-t-butoxycarbonylspiro[benzo[c]thiophene-1(3H),4'-piperidine] [prepared as described in Preparation 3(b)] were dissolved in 5 ml of anhydrous methylene chloride, and 148 mg (1.76 mmole) of sodium hydrogencarbonate were added, followed by 325 mg (1.88 mmole, content: 85%) of m-chloroperbenzoic acid, whilst ice-cooling. The reaction mixture was stirred, whilst ice-cooling, for 30 minutes, after which it was diluted with methylene chloride and then washed, in turn, with water and with a saturated aqueous solution of sodium chloride. The solution was dried over anhydrous sodium sulfate, and then the solvent was removed by distillation under reduced pressure, and the resulting residue was purified by thin-layer chromatography, using a 2:1 by volume mixture of ethyl acetate and hexane as the developing solvent, to give 498 mg (yield 98%) of the title compound as white crystals.

Nuclear Magnetic Resonance Spectrum (400 MHz, CDCl$_3$) δ ppm: 7.37–7.32 (3H, multiplet); 7.25–7.23 (1H, multiplet); 4.37 (1H, doublet, J=16.7 Hz); 4.13 (2H, broad singlet); 4.05 (2H, doublet, J=16.7 Hz); 3.21 (2H, broad singlet); 2.43 (1H, multiplet); 2.21 (1H, multiplet); 1.70 (1H, multiplet); 1.61 (1H, multiplet); 1.50 (9H, singlet). Mass spectrometric analysis (FAB) m/z: 322 (M+H)+.

4(b) Spiro[Benzo[c]thiophene-1(3H),4'-piperidine]-2-oxide Hydrochloride 295 mg (0.92 mmole) of 1'-t-butoxycarbonylspiro[benzo[c]thiophene-1(3H),4'-piperidine]-2-oxide [prepared as described in step (a) above] were dissolved in 3 ml of methylene chloride, and 1 ml of a 4 N solution of hydrogen chloride in dioxane was added, whilst ice-cooling. The mixture was stirred, whilst ice-cooling, for 1 hour, and then the crystals which deposited were collected by filtration, to give 173 mg (yield 75%) of the title compound as white crystals.

Nuclear Magnetic Resonance Spectrum (400 MHz, hexadeuterated dimethyl sulfoxide) δ ppm: 9.13 (2H, broad singlet); 7.44–7.36 (3H, multiplet); 7.33–7.31 (1H, multiplet); 4.66 (1H, doublet, J=17 Hz); 4.08 (1H, doublet, J=17 Hz); 3.49–3.37 (2H, multiplet); 3.15–3.00 (2H, multiplet); 2.66–2.57 (1H, multiplet); 2.27–2.23 (1H, multiplet); 2.18–2.10 (1H, multiplet); 1.97–1.93 (1H, multiplet). Mass spectrometric analysis (FAB) m/z: 222 $(M+H)^+$ (free form).

PREPARATION 5

Spiro[Benzo[c]thiophene-1(3H),4'-piperidine]-2,2-dioxide Hydrochloride

5(a) 1'-t-butoxycarbonylspiro[benzo[c]thiophene-1(3H),4'-piperidine]-2,2-dioxide 190 g (0.59 mmole) of 1'-t-butoxycarbonylspiro[benzo[c]thiophene-1(3H),4'-piperidine]-2-oxide [prepared as described in Preparation 4(a)] were dissolved in 30 ml of methanol, and 10 ml of an aqueous solution containing 270 mg (1.77 mmole) of Oxone (trade mark) were added. The reaction mixture was stirred at room temperature for 5 days, after which it was poured into water and then extracted twice with chloroform. The organic extract was separated and then dried over anhydrous sodium sulfate, after which the solvent was removed by distillation under reduced pressure. The resulting residue was purified by thin-layer chromatography, using a 1:1 by volume mixture of ethyl acetate and hexane as the developing solvent, to give 175 mg (yield 88%) of the title compound as white crystals.

Nuclear Magnetic Resonance Spectrum (400 MHz, $CDCl_3$) δ ppm: 7.52–7.27 (3H, multiplet); 7.23–7.20 (1H, multiplet); 4.36 (2H, singlet); 4.10 (2H, broad singlet); 3.44 (2H, broad singlet); 2.38 (2H, multiplet); 2.00 (2H, multiplet); 1.50 (9H, singlet). Mass spectrometric analysis (FAB) m/z: 337 $(M^+)$.

5(b) Spiro[benzo[c]thiophene-1(3H),4'-piperidine]-2,2-dioxide Hydrochloride 170 mg (0.5 mmole) of 1'-t-butoxycarbonylspiro[benzo[c]thiophene-1(3H),4'-piperidine]-2,2-dioxide [prepared as described in step (a) above] were dissolved in 3 ml of methylene chloride, and 1 ml of a 4 N solution of hydrogen chloride in dioxane was added, whilst ice-cooling. The mixture was then stirred, whilst ice-cooling, for 1 hour, after which the crystals which deposited were collected by filtration, to give 131 mg (yield 95%) of the title compound as white crystals.

Nuclear Magnetic Resonance Spectrum (400 MHz, hexadeuterated dimethyl sulfoxide) δ ppm: 9.32 (2H, broad singlet) 7.51–7.35 (4H, multiplet). 4.74 (2H, singlet). 3.45–3.67 (2H, multiplet). 3.24–3.12 (2H, multiplet). 2.47–2.43 (4H, multiplet). Mass spectrometric analysis (FAB) m/z: 238 $(M+H)^+$ (free form).

PREPARATION 6

Spiro[Benzo[c]thiophene-1(3H),4'-piperidine]-(2S)-oxide Hydrochloride

6(a) 1'-t-Butoxycarbonylspiro[benzo[c]thiophene-1(3H),4'-piperidine]

81.0 g (0.40 mole) of 2-bromobenzylthiol were dissolved in 800 ml of tetrahydrofuran, and 516 ml of a solution containing 0.84 mole of butyllithium (as a 1.6 M solution in hexane) were added dropwise thereto over a period of 6 hours at a temperature of −78° C. The mixture was then stirred for 1.5 hours at the same temperature, after which 800 ml of a tetrahydrofuran solution containing 79.5 g (0.40 mole) of 1-t-butoxycarbonyl-4-piperidone was added dropwise thereto over a period of 3 hours. The solution was then stirred for a further 1 hour, and then a saturated aqueous solution of ammonium chloride was added, and the mixture was extracted with ethyl acetate. The organic extract was washed with a saturated aqueous solution of sodium chloride and then dried over anhydrous sodium sulfate. The solvent was then removed by distillation under reduced pressure. 2 liters of 4 N aqueous sulfuric acid were added to the residue, and then the mixture was heated under reflux for 14 hours. At the end of this time, the solution was made basic by the addition of 350 g (8.75 mole) of sodium hydroxide, whilst ice-cooling, and then 102 g (0.47 mole) of di-t-butyl dicarbonate were added thereto. The mixture was then stirred for 1 hour. At the end of this time, the product was extracted with methylene chloride, and the organic extract was washed with a saturated aqueous solution of sodium chloride and then dried over anhydrous sodium sulfate. The solvent was removed by distillation under reduced pressure, and the resulting residue was purified by silica gel column chromatography, using a 97:3 by volume mixture of hexane and ethyl acetate as the eluent, to give 56 g of the title compound as white crystals, melting at 131.0–132.5° C. (after crystallisation from hexane/ethyl acetate).

Nuclear Magnetic Resonance Spectrum (400 MHz, $CDCl_3$) δ ppm: 7.28–7.24 (3H, multiplet); 7.17–7.15 (1H, multiplet); 4.23 (2H, broad singlet); 4.19 (2H, singlet); 3.02 (2H, broad singlet); 2.07 (2H, doublet of triplets, J=4.4 & 13 Hz); 1.88 (2H, multiplet); 1.49 (9H, singlet). Infrared absorption spectrum $v_{max}$ $cm^{-1}$ (KBr): 2970, 1680, 1428, 1234, 1163. Mass spectrometric analysis (FAB) m/z: 306 $(M+H)^+$.

6(b) 1'-t-Butoxycarbonylspiro[benzo[c]thiophene-1(3H),4'-piperidine]-2-oxide 42.0 g (0.14 mole) of 1'-t-butoxycarbonylspiro[benzo[c]thiophene-1(3H),4'-piperidine] [prepared as described in step (a) above] were dissolved in 420 ml of chloroform, and 12.7 g (0.15 mole) of sodium hydrogencarbonate were added thereto. 28.0 g (0.14 mole) of m-chloroperbenzoic acid (purity 85%) were then added little by little, whilst ice-cooling. The Mixture was then stirred for 30 minutes, whilst ice-cooling, after which 10 g of potassium iodide were added, and the mixture was stirred for a further 30 minutes at room temperature. The reaction mixture was washed with water and then with a saturated aqueous solution of sodium chloride and dried over anhydrous magnesium sulfate. At the end of this time, the solvent was removed by distillation under reduced pressure, and the resulting residue was purified by silica gel column chromatography, using a 1:1 by volume mixture of hexane and ethyl acetate as the eluent, to give 42 g of the title compound as white crystals, melting at 103–107° C. (after crystallisation from diisopropyl ether).

Nuclear Magnetic Resonance Spectrum (400 MHz, $CDCl_3$) δ ppm: 7.37–7.32 (3H, multiplet); 7.25–7.23 (1H, multiplet); 4.37 (1H, doublet, J=16.7 Hz); 4.13 (2H, broad singlet); 4.05 (2H, doublet, J=16.7 Hz); 3.21 (2H, broad singlet); 2.43 (1H, multiplet); 2.21 (1H, multiplet); 1.70 (1H, multiplet); 1.61 (1H, multiplet); 1.50 (9H, singlet). Infrared absorption spectrum $v_{max}$ cm$^{-1}$ (KBr): 2985, 1686, 1429, 1368, 1286, 1167. Mass spectrometric analysis (FAB) m/z: 322 (M+H)$^+$.

6(c) Spiro[benzo[c]thiophene-1(3H),4'-piperidine]-2-oxide 42.0 g (0.13 mole) of 1'-t-butoxycarbonylspiro[benzo[c]thiophene-1(3H),4'-piperidine]-2-oxide [prepared as described in step (b) above] were dissolved in 420 ml of 2-propanol, and 150 ml of a 4 N solution of hydrogen chloride in dioxane was added thereto, whilst ice-cooling. The mixture was then stirred for 4 hours. At the end of this time, 200 ml of diethyl ether were added to the mixture, and the mixture was allowed to stand for 1 hour, whilst ice-cooling. The precipitated crystals were then collected by filtration. The crystals were dissolved in 200 ml of a 5% w/v aqueous solution of sodium hydroxide. The product was extracted with methylene chloride, and the organic extract was dried over anhydrous sodium sulfate. The solvent was then removed by distillation under reduced pressure, to give 21.7 g of the title compound as a white amorphous product.

6(d) Spiro[benzo[c]thiophene-1(3H),4'-piperidine]-(2S)-oxide (S)-(+)W-mandelate 33.51 g (0.15 mole) of spiro[benzo[c]thiophene-1(3H),4'-piperidine]-2-oxide [prepared as described in step (c) above] were dissolved in 3350 ml of acetonitrile whilst heating, and then 11.52 g (75.7 mmole) of (S)-(+)-mandelic acid was dissolved in the resulting solution. The mixture was allowed to stand overnight at room temperature, and the crystals which precipitated were collected by filtration to give 19.62 g of the title compound as white crystals. The mother liquor was concentrated by evaporation under reduced pressure, and the resulting residue was dissolved in a 5% w/v aqueous solution of sodium hydroxide; it was then extracted with methylene chloride. The organic extract was dried over anhydrous sodium sulfate, and the solvent was removed by distillation under reduced pressure, to give 22.01 g (99.5 mmole) of a residue. This residue was dissolved in 2200 ml of acetonitrile with heating, and then 7.22 g (47.5 mmole) of (R)-(−)-mandelic acid were dissolved therein. The mixture was allowed to stand overnight at room temperature, and the crystals which precipitated were collected by filtration to give 15.91 g of spiro[benzo[c]thiophene-1(3H),4'-piperidine]-(2R)-oxide (R)-(−)-mandelate as white crystals. The mother liquor was concentrated by evaporation under reduced pressure, and the resulting residue was dissolved in a 5% w/v aqueous solution of sodium hydroxide and extracted with methylene chloride. The organic extract was dried over anhydrous sodium sulfate, and the solvent was removed by distillation under reduced pressure, to give 11.51 g (52.0 mmole) of a residue. This residue was dissolved in 1100 ml of acetonitrile with heating, and then 3.95 g (26.0 mmole) of (S)-(+)-mandelic acid were dissolved therein. The mixture was allowed to stand overnight at room temperature. The crystals which precipitated were collected by filtration to give 4.73 g of the title compound as white crystals.

The whole of the title compound thus obtained was combined, and 24.00 g of the compound was dissolved again in 9.6 liters of acetonitrile with heating and the solution was allowed to stand overnight at room temperature. 20.13 g of precipitated crystals, melting at 197–200° C., were obtained. This product was converted into 1'-t-butoxycarbonylspiro[benzo[c]thiophene-1(3H),4'-piperidine]-(2S)-oxide, and HPLC (High Performance Liquid Chromatography) analysis indicated that its optical purity is 99.8% ee.

$[\alpha]_D^{24}$+78.3 (c=1, methanol); Infrared absorption spectrum $v_{max}$ cm$^{-1}$ (KBr): 3388, 3029, 1629, 1332, 1017. Mass spectrometric analysis(EI) m/z: 221 (free form, M$^+$).

6(e) 1'-t-Butoxycarbonylspiro[benzo[c]thiophene-1(3H),4'-piperidine]-(2S)-oxide 19.88 g (53.2 mmole) of spiro[benzo[c]thiophene-1(3H), 4'-piperidine]-(2S)-oxide (S)-(+)-mandelate [prepared as described in step (d) above] were dissolved in 200 ml of a 5% w/v aqueous solution of sodium hydroxide and extracted three times, each time with 200 ml of methylene chloride. The combined organic extracts were dried over anhydrous magnesium sulfate, and then the solvent was removed by distillation under reduced pressure. 11.80 g of the resulting residue were dissolved in 300 ml of methylene chloride, and 11.2 ml (79.8 mmole) of triethylamine and 17.4 g (79.8 mmole) of di-t-butyl dicarbonate were added to the resulting solution, in that order, whilst ice-cooling. The mixture was then stirred overnight at room temperature. At the end of this time, the reaction mixture was diluted with 200 ml of methylene chloride and washed with a 10% w/v aqueous solution of citric acid and then with a saturated aqueous solution of sodium hydrogencarbonate. It was then dried over anhydrous magnesium sulfate. The solvent was removed by distillation under reduced pressure, and the resulting residue was purified by silica gel column chromatography, using a gradient elution method, with mixtures of hexane and ethyl acetate ranging from 4:6 to 3:7 by volume as the eluent; it was then recrystallized from diisopropyl ether, to give 13.1 g of the title compound as white crystals, melting at 129.0–130.5° C.

$[\alpha]_D^{24}$+57.1 (c=1, methanol); HPLC Analysis Column: ChiralCel OD (250×4.6 mmφ) Eluent: hexane:2-propanol= 80:20 by volume Flow rate: 0.8 ml/min Retention time: 18.1 min.

The Nuclear Magnetic Resonance spectrum, Infrared absorption spectrum and Mass spectrometric analysis of this isomer agreed with those of the racemate produced as described in Preparation 6(b).

6(f) Spiro[benzo[c]thiophene-1(3H),4'-piperidine]-(2S)-oxide Hydrochloride 13.0 g (40.4 mmole) of 1'-t-butoxycarbonylspiro[benzo[c]thiophene-1(3H),4'-piperidine]-(2S)-oxide [prepared as described in step (e) above] were dissolved in 130 ml of 2-propanol, and 50 ml of a 4 N solution of hydrogen chloride in dioxane were added thereto, whilst ice-cooling. The mixture was stirred for 1 hour at the same temperature, after which it was stirred for a further 6 hours at room temperature. The reaction mixture was then concentrated by evaporation under reduced pressure. 200 ml of diethyl ether were then added to the residue, and the solvent was removed by distillation under reduced pressure; this procedure was repeated 3 times in all. The resulting residue was recrystallized from 300 ml of a 1:2 by volume mixture of methanol and diethyl ether, to give 9.10 g of the title compound as white crystals, melting at 209.5–210.5° C.

$[\alpha]_D^{24}$+63.8 (c=1, methanol); Nuclear Magnetic Resonance Spectrum (400 MHz, CD$_3$OD) δ ppm: 7.38–7.46 (4H, multiplet); 4.69 (1H, doublet, J=17.2 Hz); 4.17 (1H, doublet, J=17.2 Hz); 3.52–3.63 (2H, multiplet); 3.25–3.40 (2H, multiplet); 2.62 (1H, multiplet); 2.51 (1H, multiplet); 2.22 (1H, multiplet); 2.06 (1H, multiplet).

6(g) 1'-t-Butoxycarbonylspiro[benzo[c]thiophene-1(3H),4'-piperidine]-2(S)-oxide 250 mg (0.82 mmole) of 1'-t-butoxycarbonylspiro[benzo[c]thiophene-1(3H),4'-piperidine] were dissolved in 5 ml of methylene chloride, and 308 mg (0.82 mmol) of (3'S,2R)-(−)-N-(phenylsulfonyl)(3,3-dichlorocamphoryl)oxaziridine synthesized according to the method of F. A. Davis et al. [J. Am. Chem. Soc., 114, 1428 (1992)] were added to the resulting solution. The resulting mixture was then stirred overnight at room temperature. 500 mg of potassium iodide were added to the mixture, and the mixture was stirred for 30 minutes. It was then washed with water and with a saturated aqueous solution of sodium chloride and dried over anhydrous sodium sulfate. The solvent was removed by distillation under reduced pressure, and the residue was purified by silica gel column chromatography, using a 1:2 by volume mixture of hexane and ethyl acetate as the eluent, to give 245 mg of the title compound.

Optical purity: 94% ee.

PREPARATION 7

3-(3,4-Dichlorophenyl)-3-butenol t-butyldimethylsilyl Ether

7(a) 3-(3,4-Dichlorophenyl)-3-oxo-1-propanol 119 g (0.46 mole) of ethyl 3-(3,4-dichlorophenyl)-3-oxopropionate were dissolved in 2.4 liters of ethanol, and 115 ml (0.68 mole) of ethyl orthoformate and 4.4 g (22.8 mmole) of p-toluenesulfonic acid were added thereto. The mixture was then heated under reflux for 8 hours. At the end of this time, the reaction solution was poured into 1 liter of a saturated aqueous solution of sodium hydrogen-carbonate and extracted three times, each time with 700 ml of ethyl acetate. The organic extracts were combined, washed with a saturated aqueous solution of sodium chloride and then dried over anhydrous sodium sulfate. The solvent was then removed by distillation under reduced pressure, and the resulting residue was dissolved in 800 ml of tetrahydrofuran and then added dropwise to 4 liters of a suspension of 25.9 g (0.68 mole) of lithium aluminum hydride in tetrahydrofuran over a period of 1 hour, whilst ice-cooling. The mixture was stirred at 0° C. for 2 hours, and then 250 ml of water and 125 ml of a 10% w/v aqueous solution of sodium hydroxide were added thereto, and the mixture was stirred for a further 1 hour at room temperature. It was then filtered through a Celite (trade mark) filter aid, and the filtrate was poured into 1 liter of a saturated aqueous solution of sodium chloride and then extracted with ethyl acetate. The organic extract was dried over anhydrous sodium sulfate and concentrated by evaporation under reduced pressure. The resulting residue was dissolved in 500 ml of chloroform. 500 ml of 50% v/v aqueous trifluoroacetic acid were added to the resulting solution over a period of 30 minutes, whilst ice-cooling, and the mixture was stirred for a further 30 minutes at the same temperature. At the end of this time, the reaction solution was diluted with 300 ml of methylene chloride, and the organic layer was washed with water and then with a saturated aqueous solution of sodium hydrogencarbonate, after which it was dried over anhydrous sodium sulfate. The solvent was removed by distillation under reduced pressure, and the resulting residue was purified by silica gel column chromatography, using a 9:1 by volume mixture of hexane and ethyl acetate as the eluent, to give 46 g of the title compound as white crystals.

Nuclear Magnetic Resonance Spectrum (270 MHz, CDCl$_3$) δ ppm: 8.05 (1H, doublet, J=2.0 Hz); 7.79 (1H, doublet of doublets, J=2.0 & 8.1 Hz); 7.57 (1H, doublet, J=8.1 Hz); 4.04 (2H, multiplet); 3.19 (2H, triplet, J=5.3 Hz); 2.44 (1H, triplet, J=6.6 Hz, which disappeared on the addition of D$_2$O).

7(b) 3-(3,4-Dichlorophenyl)-3-oxo-1-propanol t-butyldimethylsilyl Ether 46.0 g (0.21 mole) of 3-(3,4-dichlorophenyl)-3-oxo-1-propanol [prepared as described in step (a) above] were dissolved in 460 ml of dimethylformamide, and 35 ml (0.25 mole) of triethylamine and 38.0 g (0.25 mole) of t-butyldimethyl-chlorosilane were added to the resulting solution. The mixture was then stirred for 2 hours at 0° C. At the end of this time, the reaction mixture was poured into water and extracted with ethyl acetate. The organic extract was washed with a saturated aqueous solution of sodium chloride and then dried over anhydrous sodium sulfate. The solvent was removed by distillation under reduced pressure, and the resulting residue was purified by silica gel column chromatography, using a 96:4 by volume mixture of hexane and ethyl acetate as the eluent, to give 66.1 g of the title compound as white crystals.

Nuclear Magnetic Resonance Spectrum (270 MHz, CDCl$_3$) δ ppm: 8.06 (1H, doublet, J=2.0 Hz); 7.80 (1H, doublet of doublets, J=2.0 & 8.3 Hz); 7.55 (1H, doublet, J=8.3 Hz); 4.04 (2H, triplet, J=6.3 Hz); 3.13 (2H, triplet, J=6.3 Hz); 0.85 (9H, singlet); 0.04 (6H, singlet).

7(c) 3-(3,4-Dichlorophenyl)-3-butenol t-butyldimethylsilyl Ether 215 g (0.60 mole) of methyltriphenylphosphonium bromide and 54 g (0.48 mole) of potassium t-butoxide were added to 2 liters of dried benzene, and the mixture was stirred for 9 hours at room temperature. At the end of this time, 40 g (0.12 mole) of 3-(3,4-dichlorophenyl)-3-oxo-1-propanol t-butyldimethylsilyl ether [prepared as described in step (b) above] were dissolved in 800 ml of benzene and the resulting solution was slowly added dropwise to the mixture over a period of 2.5 hours. 1 liter of water was then added to the reaction mixture, and the mixture was stirred for 30 minutes, whilst ice-cooling. The organic layer was separated, and then washed with water and with a saturated aqueous solution of sodium chloride, after which it was dried over anhydrous sodium sulfate. The solvent was removed by distillation under reduced pressure, and the resulting residue was purified by silica gel column chromatography, using hexane as the eluent, to give 23.5 g of the title compound. The physicochemical properties of this product were the same as those of the product produced as described in Example 1(b).

PREPARATION 8

3-(3,4-Dichlorophenyl)-3-butenol t-butyldimethylsilyl Ether 129 mg (5.31 mmole) of magnesium flakes were added to 2 ml of diethyl ether, and a small amount of iodine was added to the mixture. 1 ml of a diethyl ether solution containing 1.01 g (4.47 mmole) of 3,4-dichlorobromobenzene was then added dropwise to the mixture, and the mixture was stirred for 1 hour at room temperature under a nitrogen atmosphere to give a Grignard reagent.

500 mg (1.60 mmole) of 3-iodo-3-butenol t-butyldimethylsilyl ether and 34 mg (0.048 mmole) of dichlorobis(triphenylphosphine)palladium (II) were dissolved in 5 ml of anhydrous tetrahydrofuran, and the previously prepared Grignard reagent was added dropwise thereto at room temperature under a nitrogen atmosphere. While the reaction temperature was raised, the diethyl ether was distilled off, and then the reaction mixture was heated at 60° C. for 1 hour. At the end of this time, the reaction mixture was poured into an aqueous solution of ammonium chloride and extracted with ethyl acetate. The organic layer was washed with a saturated aqueous solution of sodium chloride and then dried over anhydrous sodium sulfate. The solvent was removed by distillation under reduced pressure, and the resulting residue was purified by silica gel column chromatography, using hexane as the eluent, to give 422 mg of the title compound. The physicochemical properties of this product were the same as those of the product produced as described in Example 1(b).

EXAMPLE 1

1-{2-[(5R)-(3,4-Dichlorophenyl)-3-(3,4,5-trimethoxybenzoyl)oxazolidin-5-yl]ethyl}-4-phenylpiperidine-4-carboxamide 1(a) Methyl 3-(3,4-dichlorophenyl)-3-butenoate 11.31 g (0.47 mole) of magnesium flakes were added to 300 ml of diethyl ether, followed by a small amount of iodine. The mixture was then allowed to stand for 1 hour, after which a solution of 102.87 g (0.46 mole) of 1-bromo-3,4-dichlorobenzene in 150 ml of diethyl ether was slowly added dropwise. A further 150 ml of diethyl ether was added, and then 60.33 g (44.3 mmole) of anhydrous zinc chloride was slowly added and the mixture was stirred for 1 hour. 3.10 g (4.42 mmole) of dichlorobis(triphenylphosphine)palladium (II) were then added, and a solution of 34.15 ml (42.8 mmole) of diketene in 600 ml of diethyl ether was added dropwise. The reaction mixture was then stirred at room temperature for 30 minutes, after which it was poured into 1 liter of ice-cooled 1 N aqueous hydrochloric acid and extracted three times, each time with 500 ml of diethyl ether. The combined organic extracts were extracted three times, each time with 700 ml of a 1 N aqueous solution of sodium hydroxide. The combined aqueous extracts were acidified with concentrated aqueous hydrochloric acid, whilst ice-cooling, and extracted three times, each time with 500 ml of diethyl ether, and then the combined organic extracts were dried over anhydrous magnesium sulfate. The solvent was removed by distillation under reduced pressure, and the resulting residue was dissolved in 350 ml of methanol. 10 ml of concentrated aqueous sulfuric acid were added, and the solution was heated under reflux for 30 minutes. At the end of this time, the reaction mixture was cooled in air and neutralised with a saturated aqueous solution of sodium hydrogencarbonate. The methanol was then removed by distillation under reduced pressure, and the resulting residue was extracted with three times, each time with 200 ml of methylene chloride. The combined organic extracts were dried over anhydrous magnesium sulfate, and then the solvent was removed by distillation under reduced pressure. The resulting residue was distilled under reduced pressure to obtain 69.13 g (yield 62%) of the title compound as a pale yellow oil, boiling at 144–146° C. (5 mm Hg).

Nuclear Magnetic Resonance Spectrum (400 MHz, CDCl$_3$) δ ppm: 7.51 (1H, doublet, J=2.2 Hz); 7.40 (1H, doublet, J=8.2 Hz); 7.25 (1H, doublet of doublets, J=8.2 & 2.2 Hz); 5.55 (1H, singlet); 5.30 (1H, singlet); 3.67 (3H, singlet); 3.49 (2H, singlet).

1(b) 3-(3,4-Dichlorophenyl)-3-butenol t-butyldimethylsilyl Ether 11.76 g (0.28 mole) of lithium aluminum hydride were suspended in 500 ml of anhydrous tetrahydrofuran, and a solution of 69.06 g (0.28 mole) of methyl 3-(3,4-dichlorophenyl)-3-butenoate [prepared as described in step (a) above] in 500 ml of anhydrous tetrahydrofuran was slowly added dropwise under a nitrogen atmosphere at 0° C. over a period of 15 minutes. The reaction mixture was then stirred at the same temperature for 30 minutes, after which 500 ml of water and 500 ml of a 10% w/v aqueous solution of sodium hydroxide were slowly added. The mixture was then stirred at room temperature for 1 hour. It was then filtered through a Celite (trade mark) filter aid, and the filtrate was extracted three times, each time with 500 ml of ethyl acetate. The combined organic extracts were then dried over anhydrous magnesium sulfate. The solvent was removed from the extract by distillation under reduced pressure, and the resulting residue was dried under reduced pressure. The residue was then dissolved in 250 ml of anhydrous dimethylformamide, and then 47.12 ml (0.34 mole) of triethylamine, 6.88 g (0.06 mole) of 4-dimethylaminopyridine and 50.96 g (0.34 mole) of t-butyldimethylsilyl chloride were added, in that order, whilst ice-cooling. The mixture was then stirred, whilst ice-cooling, for 2 hours. At the end of this time, 1 liter of ethyl acetate was added to the reaction mixture, and the mixture was washed, in turn, with ice-cooled 10% w/v aqueous hydrochloric acid and with a saturated aqueous solution of sodium chloride. It was then dried over anhydrous magnesium sulfate. The solvent was removed by distillation under reduced pressure, and the resulting residue was purified by silica gel flash column chromatography, using a gradient elution method, with mixtures of hexane and ethyl acetate ranging from 50:1 to 20:1 by volume as the eluent, to obtain 43.52 g (yield 47%) of the title compound as a colorless oil.

Nuclear Magnetic Resonance Spectrum (400 MHz, CDCl$_3$) δ ppm: 7.50 (1H, doublet, J=2.1 Hz); 7.38 (1H, doublet, J=8.1 Hz); 7.24 (1H, doublet of doublets, J=8.1 & 2.1 Hz); 5.35 (1H, singlet); 5.16 (1H, singlet); 3.70 (2H, triplet, J=6.9 Hz); 2.67 (2H, triplet, J=6.9 Hz); 0.86 (9H, singlet); 0.00 (6H, singlet).

1(c) 4-t-Butyldimethylsilyloxy-(2R)-(3,4-dichlorophenyl)butane-1,2-diol 790 mg (1.01 mmole) of hydroquinidine 1,4-phthalazinediyl diether, 100.19 g (0.30 mole) of potassium ferricyanide (III), 42.06 g (0.30 mole) of potassium carbonate and 0.516 ml (0.20 mmole) of osmium tetraoxide (as a 0.393 M solution in toluene) were dissolved in 500 ml of t-butanol and 500 ml of water, and 33.61 g (0.10 mole) of 3-(3,4-dichlorophenyl)-3-butenol t-butyldimethylsilyl ether [prepared as described in step (b) above] were added, whilst cooling, at 0° C. The mixture was then stirred at 0° C. for 5 hours. At the end of this time, 150 g of sodium sulfite were added and the reaction mixture was stirred at room temperature for 1 hour. It was then extracted three times, each time with 800 ml of ethyl acetate, and the combined organic extracts were dried over anhydrous magnesium sulfate. The solvent was then removed by distillation under reduced pressure, and the resulting residue was purified by silica gel flash column chromatography, using a gradient elution method, with mixtures of hexane and ethyl acetate ranging from 5:1 to 1:1 by volume as the eluent to obtain 32.3 g (yield 87%) of the title compound as a colorless oil of optical purity 97% ee.

$[\alpha]_D^{24}$+11.39 (c=1.01, methanol); Nuclear Magnetic Resonance Spectrum (400 MHz, CDCl$_3$) δ ppm: 7.57 (1H, doublet, J=2.1 Hz); 7.43 (1H, doublet, J=8.1 Hz); 7.24 (1H, doublet of doublets, J=8.1 & 2.1 Hz); 5.00 (1H, singlet); 3.80 (1H, doubled doublet of doublets, J=10.4, 3.8 & 3.8 Hz); 3.5–3.7 (3H, multiplet); 2.51 (1H, doublet of doublets, J=8.0 & 5.2 Hz); 2.37 (1H, doubled doublet of doublets, J=15.0, 11.1 & 4.0 Hz); 1.86 (1H, doubled doublet of doublets, J=15.0, 2.9 & 2.9 Hz); 0.89 (9H, singlet); 0.04 (3H, singlet); −0.01 (3H, singlet).

1(d) 1-Azido-4-t-butyldimethylsilyloxy-(2R)-(3,4-dichlorophenyl)-2-butanol 32.07 g (87.8 mmole) of 4-t-butyldimethylsilyloxy-(2R)-(3,4-dichlorophenyl)butane-1,2-diol [prepared as described in step (c) above] and 1.07 g (8.76 mmole) of 4-dimethylaminopyridine were dissolved in 320 ml of pyridine, and 10.19 ml (0.132 mole) of methanesulfonyl chloride was slowly added dropwise, whilst ice-cooling. The mixture was then stirred under a nitrogen atmosphere at the same temperature for 2 hours. The reaction mixture was then poured into 1500 ml of ice-cooled 10% w/v aqueous hydrochloric acid and then extracted three times, each time with 200 ml of ethyl acetate. The combined organic extracts were washed with a saturated aqueous solution of sodium chloride and then dried over anhydrous magnesium sulfate. The solvent was removed by distillation under reduced pressure, and the resulting residue was dried under reduced pressure. The residue was then dissolved in 300 ml of anhydrous dimethylformamide, and 11.41 g (0.18 mole) of sodium azide were added. The mixture was then heated under a nitrogen atmosphere at 120° C. for 4 hours. At the end of this time, the reaction mixture was cooled to room temperature, poured into 1000 ml of a saturated aqueous solution of sodium chloride and then extracted three times, each time with 500 ml of ethyl acetate. The combined organic extracts were dried over anhydrous magnesium sulfate, and the solvent was removed by distillation under reduced pressure. The resulting residue was purified by silica gel flash column chromatography, using a gradient elution method, with mixtures of hexane and ethyl acetate ranging from 10:1 to 5:1 by volume as the eluent, to obtain 29.3 g (yield 85%) of the title compound as a colorless oil.

$[\alpha]_D^{24}$–48.56 (c=1.04, methanol); Nuclear Magnetic Resonance Spectrum (400 MHz, CDCl$_3$) δ ppm: 7.59 (1H, doublet, J=2.2 Hz); 7.44 (1H, doublet, J=8.3 Hz); 7.24 (1H, doublet of doublets, J=8.3 & 2.2 Hz); 5.12 (1H, singlet); 3.81 (1H, doubled doublet of doublets, J=10.6, 4.1 & 3.0 Hz); 3.51 (1H, doubled doublet of doublets, J=10.6, 10.6 & 2.8 Hz); 3.40 (1H, doublet, J=12.5 Hz); 3.31 (1H, doublet, J=12.5 Hz); 2.35 (1H, doubled doublet of doublets, J=15.8, 10.6 & 4.1 Hz); 1.91 (1H, doubled doublet of doublets, J=15.8, 3.0 & 2.8 Hz); 0.88 (9H, singlet); 0.02 (3H, singlet); –0.04 (3H, singlet).

1(e) 1-Amino-4-t-butyldimethylsilyloxy-(2R)-(3,4-dichlorophenyl)-2-butanol 10.00 g (25.6 mmole) of 1-azido-4-t-butyldimethylsilyloxy-(2R)-(3,4-dichlorophenyl)-2-butanol [prepared as described in step (d) above] were dissolved in 100 ml of tetrahydrofuran and 0.6 ml of water, and 7.39 g (28.2 mmole) of triphenylphosphine were added to the resulting solution. The mixture was then stirred under a nitrogen atmosphere at 80° C. for 4 hours. At the end of this time, the solvent was removed by distillation under reduced pressure, hexane was added to the resulting residue and the deposited crystals were removed by filtration. The filtrate was concentrated by evaporation under reduced pressure, and the resulting residue was purified by silica gel flash column chromatography, using a gradient elution method, with mixtures of methylene chloride and methanol ranging from 30:1 to 10:1 by volume as the eluent, to obtain 3.83 g (yield 41%) of the title compound as a colorless oil.

$[\alpha]_D^{24}$+3.94 (c=0.71, methanol); Nuclear Magnetic Resonance Spectrum (400 MHz, CDCl$_3$) δ ppm: 7.56 (1H, doublet, J=2.2 Hz); 7.42 (1H, doublet, J=8.6 Hz); 7.22 (1H, doublet of doublets, J=8.6 & 2.2 Hz); 4.91 (1H, broad singlet); 3.73 (1H, doubled doublet of doublets, J=10.3, 4.6 & 3.7 Hz); 3.53 (1H, doubled doublet of doublets, J=10.3, 10.2 & 3.7 Hz); 2.91 (1H, doublet, J=13.1 Hz); 2.86 (1H, doublet, J=13.1 Hz); 2.16 (1H, doubled doublet of doublets, J=14.6, 10.2 & 4.6 Hz); 1.88 (1H, doubled doublet of doublets, J=14.6, 3.7 & 3.7 Hz); 1.44 (2H, broad singlet); 0.87 (9H, singlet); 0.01 (3H, singlet); –0.04 (3H, singlet).

1(f) 2-[(5R)-(3,4-Dichlorophenyl)-3-(3,4,5-trimethoxybenzoyl)oxazolidin-5-yl]ethanol t-butyldimethylsilyl Ether 1.35 g (3.71 mmole) of 1-amino-4-t-butyldimethylsilyloxy-(2R)-(3,4-dichlorophenyl)-2-butanol [prepared as described in step (e) above] were dissolved in 50 ml of benzene, and 167 mg (5.57 mmole) of paraformaldehyde and 13 mg of p-toluenesulfonyl chloride were added to the resulting solution. The mixture was then heated under reflux under a nitrogen atmosphere at 100° C. for 3 hours, using a Dean-Stark apparatus. At the end of this time, the solvent was removed by distillation under reduced pressure, and 100 ml of ethyl acetate were added to the residue. The resulting solution was washed with a saturated aqueous solution of sodium hydrogencarbonate and then dried over anhydrous magnesium sulfate. The solvent was removed by distillation under reduced pressure to yield 2-[(5R)-(3,4-dichlorophenyl)oxazolidin-5-yl]ethanol t-butyldimethylsilyl ether. This compound was dissolved in 50 ml of methylene chloride, and 0.62 ml (4.45 mmole) of triethylamine and 45 mg (0.37 mmole) of 4-dimethylaminopyridine were added to the resulting solution. 1.03 g (4.47 mmole) of 3,4,5-trimethoxybenzoyl chloride were then added, whilst ice-cooling, and the mixture was stirred at 0° C. for 1 hour. 100 ml of methylene chloride were added to the reaction mixture, and the mixture was washed with 10% w/v aqueous hydrochloric acid, with a saturated aqueous solution of sodium hydrogencarbonate and with a saturated aqueous solution of sodium chloride, in that order. It was then dried over anhydrous magnesium sulfate. The solvent was removed by distillation under reduced pressure, and the resulting residue was purified by silica gel flash column chromatography, using a gradient elution method, with mixtures of ethyl acetate and hexane ranging from 1:5 to 2:1 by volume as the eluent, to obtain 1.27 g (yield 60%) of the title compound as a white amorphous substance.

$[\alpha]_D^{24}$+61.73 (c=1.39, methanol).

1(g) 2-[(5R)-(3,4-Dichlorophenyl)-3-(3,4,5-trimethoxybenzoyl)oxazolidin-5-yl]ethanol Methanesulfonate 3.95 g (6.92 mmole) of 2-[(5R)-(3,4-dichlorophenyl)-3-(3,4,5-trimethoxybenzoyl)oxazolidin-5-yl]ethanol t-butyldimethylsilyl ether [prepared as described in step (f) above] were dissolved in 70 ml of a 3:3:1 by volume mixture of acetic acid, tetrahydrofuran and water. The mixture was then heated under a nitrogen atmosphere at 80° C. for 8 hours. At the end of this time, the solution was neutralised by the addition of a saturated aqueous solution of sodium hydrogencarbonate and extracted with ethyl acetate. The organic layer was then dried over anhydrous magnesium sulfate. The solvent was removed by distillation under reduced pressure, and the resulting residue was dissolved in 30 ml of pyridine. 70 mg (0.57 mmole) of dimethylaminopyridine and 0.66 ml (8.53 mmole) of methanesulfonyl chloride were added, whilst ice-cooling, to the resulting solution, and the mixture was then stirred under a nitrogen atmosphere at 0° C. for 2 hours. At the end of this time, the reaction mixture was poured into 200 ml of ice-cooled 10% w/v aqueous hydrochloric acid and then extracted three times, each time with 100 ml of ethyl acetate. The combined organic extracts were washed with a saturated aqueous solution of sodium chloride and then dried over anhydrous magnesium sulfate. The solvent was removed by distillation under reduced pressure, and the resulting residue was purified by silica gel flash column chromatography, using a gradient elution method, with mixtures of hexane and ethyl acetate ranging from 5:1 to 1:1 by volume as the eluent, to obtain 3.02 g (yield 82%) of the title compound as a white amorphous substance.

$[\alpha]_D^{24}$+53.1 (c=1.0, methanol).

1(h) 1-{2-[(5R)-(3,4-Dichlorophenyl)-3-(3,4,5-trimethoxybenzoyl)oxazolidin-5-yl]ethyl}-4-phenylpiperidine-4-carboxamide 150 mg (0.28 mmole) of 2-[(5R)-(3,4-dichlorophenyl)-3-(3,4,5-trimethoxybenzoyl)oxazolidin-5-yl]ethanol methanesulfonate [prepared as described in step (g) above] and 75 mg (0.31 mmole) of 4-phenylpiperidine-4-carboxamide hydrochloride were dissolved in 3 ml of anhydrous dimethylformamide, and 71 mg (0.85 mmole) of sodium hydrogencarbonate and 70 mg (0.42 mmole) of potassium iodide were added to the resulting solution. The mixture was then heated under a nitrogen atmosphere at 80° C. for 6 hours. At the end of this time, 50 ml of a saturated aqueous solution of sodium chloride were added to the reaction mixture, which was then extracted three times, each time with 50 ml of ethyl acetate. The combined organic extracts were then dried over anhydrous magnesium sulfate. The solvent was removed by distillation under reduced pressure, and the resulting residue was purified by silica gel thin-layer chromatography, using a 10:1 by volume mixture of methylene chloride and methanol as the developing solvent, to give 127 mg (yield 71%) of the title compound as a white amorphous substance.

$[\alpha]_D^{24}$+25.2 (c=0.48, methanol); Nuclear Magnetic Resonance Spectrum (400 MHz, CDCl$_3$) δ ppm: 7.50–7.10 (8H, multiplet); 6.67 (2H, singlet); 5.30–4.85 (2H, multiplet); 5.18 (2H, singlet); 4.13–3.70 (2H, multiplet); 3.87 (3H, singlet); 3.85 (6H, singlet); 2.67–1.93 (12H, multiplet). Infrared absorption spectrum $\nu_{max}$ (KBr) cm$^{-1}$: 2940, 1678, 1640, 1584, 1456, 1416, 1236, 1128. Elemental analysis: Calculated for C$_{33}$H$_{37}$N$_3$O$_6$Cl$_2$.½H$_2$O: C: 60.77%; H: 5.83%; N: 6.45%; Cl: 10.89%; Found: C: 60.63%; H: 5.94%; N: 6.39%; Cl: 10.93%. Mass spectrometric analysis (FAB) m/z: 642 (M+H)$^+$.

The compounds of the following Examples 2–4 were produced following the same procedure as described in Example 1 above.

EXAMPLE 2

1-{2-[(5R)-(3,4-Dichlorophenyl)-3-(3,4,5-trimethoxybenzoyl)oxazolidin-5-yl]ethyl}-4-phenylpiperidine-4-(N,N-dimethylcarboxamide)

Yield: 76%; $[\alpha]_D^{24}$+19.2 (c=1.05, methanol); Nuclear Magnetic Resonance Spectrum (400 MHz, CDCl$_3$) δ ppm: 7.60–7.10 (8H, multiplet); 6.71 (2H, broad singlet); 5.50–4.90 (2H, multiplet); 3.88 (9H, singlet); 3.40–1.40 (20H, multiplet). Infrared absorption spectrum $\nu_{max}$ (KBr) cm$^{-1}$: 2938, 1633, 1584, 1464, 1416, 1236, 1128. Elemental analysis: Calculated for C$_{35}$H$_{41}$N$_3$O$_6$Cl$_2$.H$_2$O: C: 61.05%; H: 6.29%; N: 6.10%; Cl: 10.30%; Found: C: 60.66%; H: 6.25%; N: 5.80%; Cl: 10.65%.

EXAMPLE 3

1-{2-[(5R)-(3,4-Dichlorophenyl)-3-(3,4,5-trimethoxybenzoyl)oxazolidin-5-yl]ethyl}-4-(pyrrolidin-1-ylcarbonyl)-phenylpiperidine Yield: 82%; $[\alpha]_D^{24}$+23.2 (c=0.49, methanol); Nuclear Magnetic Resonance Spectrum (400 MHz, CDCl$_3$) δ ppm: 7.52–7.40 (2H, multiplet); 7.33–7.00 (6H, multiplet); 6.68 (2H, singlet); 5.30–4.85 (2H, multiplet); 4.09–3.65 (2H, multiplet); 3.87 (3H, singlet); 3.86 (6H, singlet); 3.56–3.41 (2H, broad singlet); 2.89–2.60 (4H, multiplet); 2.48–2.29 (4H, multiplet); 2.20–1.98 (10H, multiplet). Infrared absorption spectrum $\nu_{max}$ (KBr) cm$^{-1}$: 2948, 1625, 1584, 1464, 1415, 1235, 1128. Elemental analysis: Calculated for C$_{37}$H$_{43}$N$_3$O$_6$Cl$_2$.½H$_2$O: C: 62.98%; H: 6.28%; N: 5.95%; Cl: 10.04%; Found: C: 63.01%; H: 6.43%; N: 5.97%; Cl: 9.71%. Mass spectrometric analysis (FAB) m/z: 696 (M+H)$^+$.

EXAMPLE 4

1-{2-[(5R)-(3,4-Dichlorophenyl)-3-(3,4,5-trimethoxybenzoyl)oxazolidin-5-yl]ethyl}-4-morpholinocarbonyl-4-phenylpiperidine Yield: 63%; $[\alpha]_D^{24}$+20.5 (c=1.04, methanol); Nuclear Magnetic Resonance Spectrum (400 MHz, CDCl$_3$) δ ppm: 7.60–7.10 (8H, multiplet); 6.70 (2H, singlet); 5.40–4.90 (2H, multiplet); 3.87 (9H, singlet); 4.10–1.40 (22H, multiplet). Infrared absorption spectrum $\nu_{max}$ (KBr) cm$^{-1}$: 2966, 1637, 1584, 1455, 1416, 1233, 1128. Elemental analysis: Calculated for C$_{37}$H$_{43}$N$_3$O$_7$Cl$_2$.½H$_2$O: C: 61.58%; H: 6.15%; N: 5.82%; Cl: 9.83%; Found: C: 61.47%; H: 6.62%; N: 5.45%; Cl: 9.67%. Mass spectrometric analysis (FAB) m/z: 712 (M+H)$^+$.

EXAMPLES 5 TO 40

The compounds shown in the following formulae (A-1) and (A-2) were also prepared by the same procedure as described above. The meanings of the various substituent groups shown in these formulae are summarised in the corresponding one of Tables A-1 and A-2. For convenience, the products of Examples 1 to 4 are also summarised in these Tables.

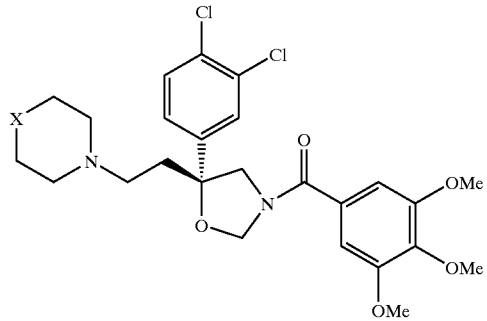

(A-1)

TABLE A-1
| Example No. | X (structure) | $[\alpha]_D^{24}$ (methanol) | FAB Mass spectrometry $[M + H]^+$ |
|---|---|---|---|
| 1 | 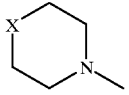 | +25.2 (c = 0.48) | 642 |
| 2 | 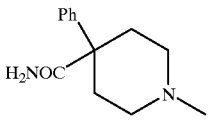 | +19.2 (c = 1.05) | 670 |
| 3 | 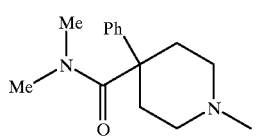 | +23.2 (c = 0.49) | 696 |
| 4 | 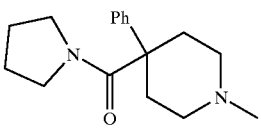 | +20.5 (c = 1.04) | 712 |
| 5 | 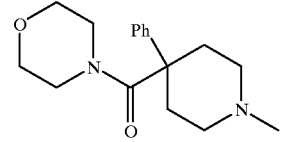 | +23.3 (c = 0.49) | 656 |
| 6 | 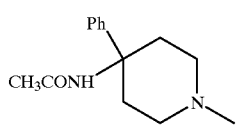 | +26.7 (c = 0.48) | 641 |
| 7 | 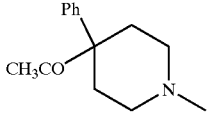 | +21.1 (c = 0.50) | 615 |
| 8 | 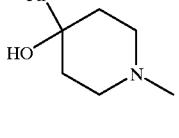 | +21.8 (c = 1.06) | 855 |
| 9 | 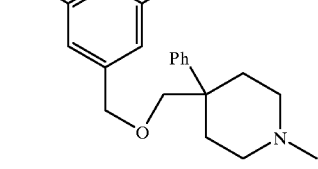 | +18.7 (c = 1.03) | 642 |

TABLE A-1-continued
| Example No. | Structure | $[\alpha]_D^{24}$ (methanol) | FAB Mass spectrometry $[M + H]^+$ |
|---|---|---|---|
| 10 | 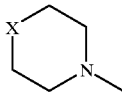 | +33.1 (c = 0.95) | 656 |
| 11 | 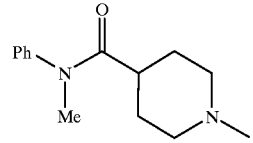 | +28.7 (c = 0.44) | 656 |
| 12 | 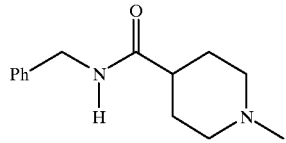 | +29.9 (c = 0.41) | 670 |
| 13 | 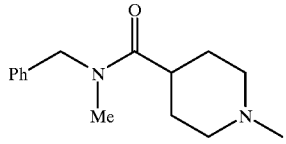 | +27.9 (c = 1.04) | 642 |
| 14 | 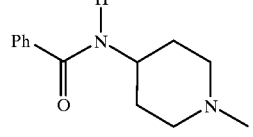 | +35.8 (c = 1.07) | 656 |
| 15 | 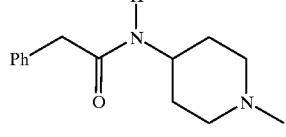 | +25.6 (c = 0.85) | 661 |
| 16 | 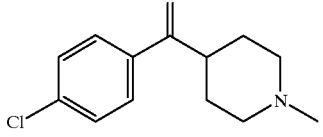 | +1.6 (c = 0.54) | 642 |
| 17 | 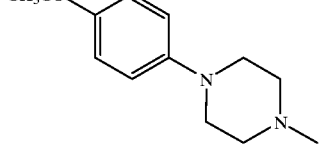 | +17.0 (c = 0.50) | 669 |

TABLE A-1-continued
| Example No. | 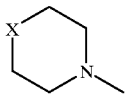 | $[\alpha]_D^{24}$ (methanol) | FAB Mass spectrometry $[M + H]^+$ |
|---|---|---|---|
| 18 | 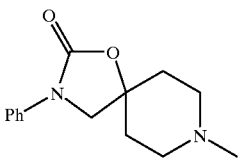 | +19.9 (c = 0.43) | 670 |
| 19 | 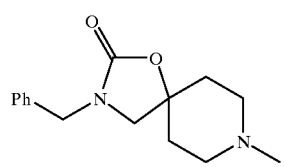 | +27.4 (c = 1.02) | 684 |
| 20 | 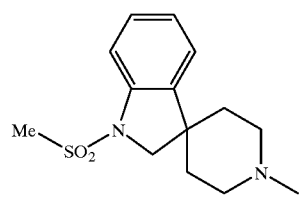 | +10.8 (c = 1.04) | 704 |
| 21 | 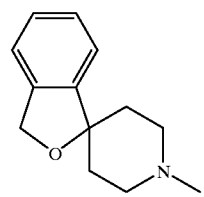 | +26.5 (c = 0.60) | 626 |
| 22 | 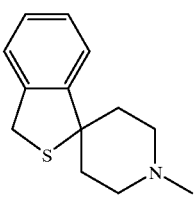 | +19.8 (c = 0.55) | 643 |
| 23 | 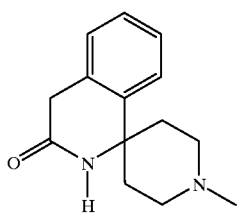 | +24.0 (c = 1.07) | 654 |
| 24 | 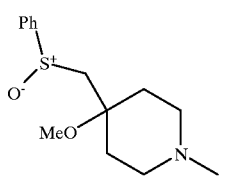 | +71.8 (c = 1.02) | 691 |

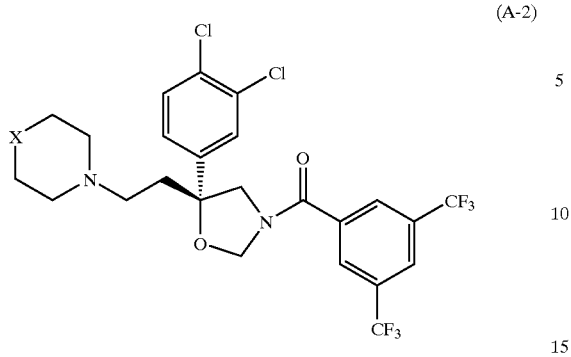
(A-2)
TABLE A-2
| Example No. | X-N structure | $[\alpha]_D^{24}$ (methanol) | FAB Mass spectrometry $[M + H]^+$ |
|---|---|---|---|
| 25 | 4-Ph, 4-CONH$_2$, N-Me piperidine | +25.2 (c = 0.46) | 688 |
| 26 | 4-Ph, 4-NHCOCH$_3$, N-Me piperidine | +21.6 (c = 0.48) | 702 |
| 27 | 4-Ph, 4-OCH$_3$, N-Me piperidine | +22.6 (c = 0.48) | 687 |
| 28 | 4-Ph, 4-OH, N-Me piperidine | +20.7 (c = 0.48) | 661 |
| 29 | 3,5-bis(CF$_3$)benzyl-OCH$_2$-, 4-Ph, N-Me piperidine | +17.5 (c = 0.12) | 901 |
| 30 | 4-CONHPh, N-Me piperidine | +17.2 (c = 1.05) | 688 |

TABLE A-2-continued
| Example No. | [structure with X-N-Me piperazine/piperidine] | $[\alpha]_D^{24}$ (methanol) | FAB Mass spectrometry $[M + H]^+$ |
|---|---|---|---|
| 31 | 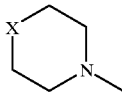 | +33.6 (c = 1.03) | 702 |
| 32 | 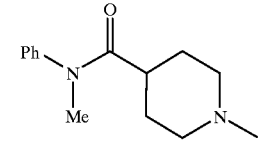 | +23.1 (c = 0.50) | 702 |
| 33 | 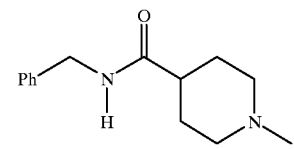 | +26.8 (c = 0.42) | 716 |
| 34 | 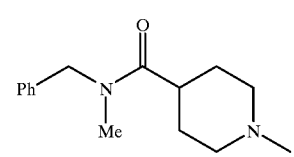 | +17.0 (c = 1.03) | 688 |
| 35 | 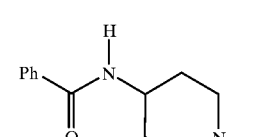 | +24.6 (c = 1.08) | 702 |
| 36 | 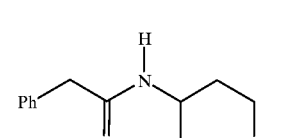 | +19.5 (c = 0.99) | 707 |
| 37 | 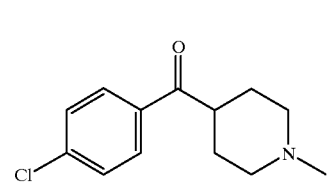 | +3.3 (c = 0.57) | 688 |
| 38 | 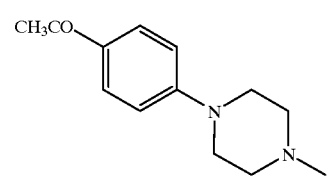 | +18.6 (c = 0.51) | 715 |

TABLE A-2-continued

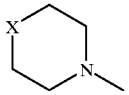

| Example No. | | $[\alpha]_D^{24}$ (methanol) | FAB Mass spectrometry $[M + H]^+$ |
|---|---|---|---|
| 39 | (structure with Ph-N, oxazolidinone spiro piperidine N-Me) | +28.8 (c = 0.48) | 716 |
| 40 | (structure with Ph-CH2-N, oxazolidinone spiro piperidine N-Me) | +23.8 (c = 0.73) | 730 |

EXAMPLE 41

1-{3-[(5R)-(3,4-Dichlorophenyl)-3-(3,4,5-trimethoxybenzoyl)oxazolidin-5-yl]propyl}-4-phenylpiperidine-4-carboxamide 41(a) Methyl 4-(3,4-dichlorophenyl)-4-oxobutanoate 1.00 (6.80 mmole) of dichlorobenzene and 0.72 g (7.14 mmole) of succinic anhydride were suspended in 3 ml of dichloroethane and 1.36 g (10.2 mmole) of aluminum chloride powder were added. The mixture was then stirred at 60° C. for 3 hours. At the end of this time, the reaction mixture was ice-cooled and 1 N aqueous hydrochloric acid was added. The mixture was then extracted with methylene chloride. The organic extract was washed with a saturated aqueous solution of sodium chloride and then dried over anhydrous sodium sulfate. The solvent was then removed by distillation under reduced pressure. The resulting residue was dissolved in 30 ml of methanol, and 0.20 ml of an aqueous solution of sulfuric acid was added. The solution was then heated under reflux for 2 hours, after which the reaction mixture was cooled to room temperature, poured into water and then extracted with diethyl ether. The organic extract was washed with a saturated aqueous solution of sodium hydrogencarbonate and with a saturated aqueous solution of sodium chloride, in that order, and dried over anhydrous sodium sulfate. The solvent was then removed by distillation under reduced pressure. The resulting residue was purified by silica gel column chromatography, using a gradient elution method, with mixtures of hexane and diethyl ether ranging from 17:3 to 7:3 by volume as the eluent, to obtain 0.25 g (yield 14%) of the title compound as pale orange crystals.

Nuclear Magnetic Resonance Spectrum (400 MHz, CDCl$_3$) δ ppm: 8.07 (1H, doublet, J=2 Hz); 7.81 (1H, doublet of doublets, J=2 & 8 Hz); 7.56 (1H, doublet, J=8 Hz); 3.71 (3H, singlet); 3.27 (2H, triplet, J=7 Hz); 2.78 (2H, triplet, J=7 Hz).

41(b) Methyl 4-(3,4-dichlorophenyl)-4-pentenoate 330 mg (0.92 mmole) of methyltriphenylphosphonium bromide and 105 mg (0.94 mmole) of potassium t-butoxide were suspended in 4 ml of dried benzene, and the mixture was stirred under a stream of nitrogen at room temperature for 4 hours. A solution prepared by dissolving 200 mg of methyl 4-(3,4-dichlorophenyl)-4-oxobutanoate [prepared as described in step (a) above] in 1 ml of benzene was added to the reaction mixture, and the mixture was then stirred for 18 hours. At the end of this time, the reaction mixture was filtered through a Celite (trade mark) filter aid and washed with diethyl ether. The filtrate was then concentrated by evaporation under reduced pressure. The resulting residue was purified by silica gel column chromatography, using a 23:2 by volume mixture of hexane and diethyl ether as the eluent, to give 95 mg (yield 64%) of the title compound as a pale yellow oil.

Nuclear Magnetic Resonance Spectrum (400 MHz, CDCl$_3$) δ ppm: 7.48 (1H, doublet, J=2 Hz); 7.40 (1H, doublet, J=8 Hz); 7.23 (1H, doublet of doublets, J=2 & 8 Hz); 5.32 (1H, singlet); 5.14 (1H, singlet); 3.67 (3H, singlet); 2.79 (2H, triplet, J=8 Hz); 2.48 (2H, triplet, J=8 Hz).

41(c) 4-(3,4-Dichlorophenyl-4-penten-1-ol t-butyldimethylsilyl Ether

Following a procedure similar to that described in Example 1(b), but using methyl 4-(3,4-dichlorophenyl)-4-pentenoate [prepared as described in step (b) above], the title compound was obtained in a yield of 93%.

Nuclear Magnetic Resonance Spectrum (400 MHz, CDCl$_3$) δ ppm: 7.49 (1H, doublet, J=2 Hz); 7.38 (1H, doublet, J=9 Hz); 7.24 (1H, doublet of doublets, J=2 & 9 Hz); 5.30 (1H, singlet); 5.13 (1H, doublet, J=1 Hz); 3.62 (2H, triplet, J=6 Hz); 2.52 (2H, triplet, J=8 Hz); 1.60–1.68 (2H, multiplet); 0.90 (9H, singlet); 0.04 (6H, singlet).

41(d) (2R)-5-(t-Butyldimethylsilyloxy)-2-(3,4-dichlorophenyl)pentane-1,2-diol

Following a procedure similar to that described in Example 1(c), but using 4-(3,4-dichlorophenyl)-4-penten-1-ol t-butyldimethylsilyl ether [prepared as described in step (c) above], the title compound was obtained in a yield of 90%.

Optical purity: 98% ee; $[\alpha]_D^{24}$ −2.08 (c=0.48, methanol); Nuclear Magnetic Resonance Spectrum (400 MHz, CDCl$_3$) δ ppm: 7.56 (1H, doublet, J=2 Hz); 7.41 (1H, doublet, J=8 Hz); 7.23 (1H, doublet of doublets, J=2 & 8 Hz); 4.96 (1H, singlet); 3.53–3.70 (4H, multiplet); 1.98–2.14 (3H, multiplet); 1.35–1.57 (2H, multiplet); 0.91 (9H, singlet); 0.082 (3H, singlet); 0.078 (3H, singlet).

41(e) (2R)-1-Azido-5-(t-butyldimethylsilyloxy)-2-(3,4-dichlorophenyl)-2-pentanol Following a procedure similar to that described in Example 1 (d), but using (2R)-5-(t-butyldimethylsilyloxy)-2-(3,4-dichlorophenyl)pentane-1,2-diol [prepared as described in step (d) above], the title compound was obtained in a yield of 86%.

$[\alpha]_D^{24}$ −48.2 (c=0.61, methanol); Nuclear Magnetic Resonance Spectrum (400 MHz, CDCl3) δ ppm: 7.58 (1H, doublet, J=2 Hz); 7.42 (1H, doublet, J=9 Hz); 7.23 (1H, doublet of doublets, J=2 & 9 Hz); 4.93 (1H, singlet); 3.67 (1H, multiplet); 3.58 (1H, multiplet); 3.43 (1H, doublet, J=12 Hz); 3.31 (1H, doublet, J=12 Hz); 2.13 (1H, multiplet); 2.04 (1H, multiplet); 1.54 (1H, multiplet); 1.40 (1H, multiplet); 0.91 (9H, singlet); 0.09 (3H, singlet); 0.08 (3H, singlet).

41(f) (2R)-1-Amino-5-(t-butyldimethylsilyloxy)-2-(3,4-dichlorophenyl)-2-pentanol Following a procedure similar to that described in Example 1(e), but using (2R)-1-azido-5-(t-butyldimethylsilyloxy)-2-(3,4-dichlorophenyl)-2-pentanol [prepared as described in step (e) above], the title compound was obtained in a yield of 76%.

$[\alpha]_D^{24}$ −8.13 (c=0.48, methanol); Nuclear Magnetic Resonance Spectrum (400 MHz, CDCl$_3$) δ ppm: 7.54 (1H, doublet, J=2 Hz); 7.40 (1H, doublet, J=9 Hz); 7.21 (1H, doublet of doublets, J=2 & 9 Hz); 4.57 (1H, broad singlet); 3.50–3.62 (2H, multiplet); 2.96 (1H, doublet, J=13 Hz); 2.82 (1H, doublet, J=13 Hz); 1.93 (1H, multiplet); 1.80 (1H, multiplet); 1.33–1.60 (2H, multiplet); 0.89 (9H, singlet); 0.04 (6H, singlet).

41(g) 3-[(5R)-(3,4-Dichlorophenyl)-3-(3,4,5-trimethoxybenzoyl)oxazolidin-5-yl]-1-propanol t-butyldimethylsilyl Ether Following a procedure similar to that described in Example 1(f), but using (2R)-1-amino-5-(t-butyldimethylsilyloxy)-2-(3,4-dichlorophenyl)-2-pentanol [prepared as described in step (f) above], the title compound was obtained in a yield of 48%.

$[\alpha]_D^{24}$ +37.73 (c=0.44, methanol).

41(h) 3-[(5R)-(3,4-Dichlorophenyl)-3-(3,4,5-trimethoxybenzoyl)oxazolidin-5-yl]-1-propanol Methanesulfonate Following a procedure similar to that described in Example 1(g), but, using 3-[(5R)(3,4-dichlorophenyl)-3-(3,4,5-trimethoxybenzoyl)oxazolidin-5-yl]-1-propanol t-butyldimethylsilyl ether [prepared as described in step (g) above], the title compound was obtained in a yield of 93%.

$[\alpha]_D^{24}$ +52.90 (c=0.62, methanol).

41(i) 1-{3-[(5R)-(3,4-Dichlorophenyl)-3-(3,4,5-trimethoxybenzoyl)oxazolidin-5-yl]propyl}-4-phenylpiperidine-4-carboxamide Following a procedure similar to that described in Example 1(h), but using 3-[(5R)-(3,4-dichlorophenyl)-3-(3,4,5-trimethoxybenzoyl)oxazolidin-5-yl]-1-propanol methanesulfonate [prepared as described in step (h) above] the title compound was obtained in a yield of 66%.

$[\alpha]_D^{24}$ +35.9 (c=0.48, methanol); Nuclear Magnetic Resonance Spectrum (400 MHz, CDCl$_3$) δ ppm: 7.60–7.10 (8H, multiplet); 6.68 (2H, broad singlet); 5.40–4.90 (4H, multiplet); 3.88 (9H, singlet); 3.87 (9H, singlet); 4.10–1.10 (16H, multiplet). Infrared absorption spectrum $\nu_{max}$ (KBr) cm$^{-1}$: 3440, 3353, 2940, 1676, 1641, 1585; Elemental analysis: Calculated for $C_{34}H_{39}N_3O_6Cl_2 \cdot \frac{1}{2}H_2O$: C: 61.35%; H: 6.06%; N: 6.31%; Cl: 10.65%; Found: C: 61.81%; H: 6.22%; N: 6.50%; Cl: 10.26%. Mass spectrometric analysis (FAB) m/z: 656 (M+H)$^+$.

EXAMPLES 42 TO 50

The compounds shown in the following formula (A-3) were also prepared by the same procedure as described in Example 41 above. The meanings of the various substituent groups shown in these formulae are summarised in Table A-3. For convenience, the product of Example 41 is also summarised in this Table.

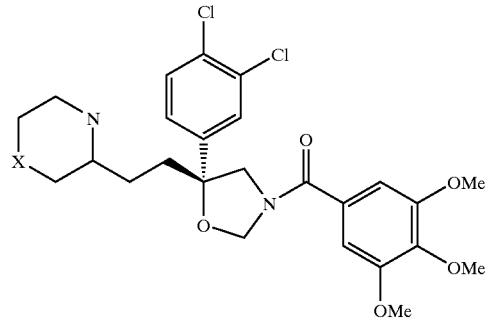

(A-3)

TABLE A-3

| Example No. | X group structure | $[\alpha]_D^{24}$ (methanol) | FAB Mass spectrometry [M + H]$^+$ |
|---|---|---|---|
| 41 | Ph, H$_2$NOC-piperidinyl-N-methyl | +35.9 (c = 0.48) | 656 |
| 42 | pyrrolidinyl-C(O)-Ph-piperidinyl-N-methyl | +36.4 (c = 0.50) | 710 |

TABLE A-3-continued
| Example No. | X-[structure]-N-CH3 | [α]$_D^{24}$ (methanol) | FAB Mass spectrometry [M + H]$^+$ |
|---|---|---|---|
| 43 | 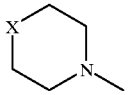 | +36.0 (c = 0.45) | 670 |
| 44 | 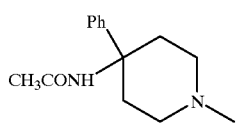 | +38.3 (c = 0.57) | 655 |
| 45 | 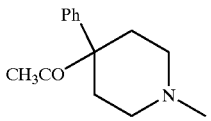 | +41.8 (c = 0.49) | 629 |
| 46 | 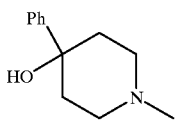 | +34.6 (c = 0.46) | 670 |
| 47 | 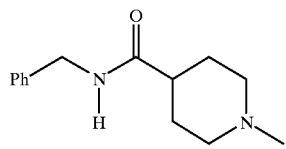 | +50.3 (c = 0.50) | 675 |
| 48 | 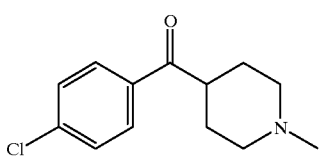 | +32.5 (c = 0.54) | 656 |
| 49 | 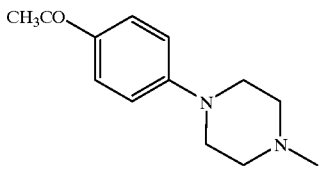 | +37.9 (c = 0.46) | 683 |
| 50 | 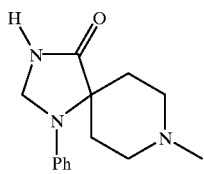 | +41.3 (c = 0.44) | 684 |

EXAMPLE 51

1-{2-[2-(3,4-Dichlorophenyl)-4-(3,4,5-trimethoxybenzoyl)morpholin-2-yl]ethyl}-4-phenylpiperidine-4-carboxamide (Compound 2-1969)

51(a) 3-(3,4-Dichlorophenyl)-3,4-epoxy-1-butanol t-Butyldimethylsilyl Ether 3.00 g (9.05 mmole) of 3-(3,4-dichlorophenyl)-3-butenol t-butyldimethylsilyl ether [prepared as described in Example 1(b)] were dissolved in 60 ml of methylene chloride, and 2.52 g (30.0 mmole) of sodium hydrogencarbonate and 3.88 g (15.7 mmole) of 3-chloroperbenzoic acid (content: 70%) were added to the resulting solution. The mixture was then stirred at room temperature for 3 hours. At the end of this time, the reaction mixture was diluted with methylene chloride and then washed with a 1 N aqueous solution of sodium hydroxide and with a saturated aqueous solution of sodium chloride. The organic layer was then dried over anhydrous sodium sulfate, and the solvent was removed by evaporation under reduced pressure. The resulting residue was then purified by silica gel column chromatography, using a gradient elution method, with mixtures of hexane and diethyl ether ranging from 24:1 to 19:1 by volume as the eluent, to obtain 2.70 g of the title compound.

Nuclear Magnetic Resonance Spectrum (400 MHz, $CDCl_3$) δ ppm: 7.47 (1H, doublet, J=2 Hz); 7.38 (1H, doublet, J=8 Hz); 7.21 (1H, doublet of doublets, J=2 & 8 Hz); 3.57–3.72 (2H, multiplet); 3.01 (1H, doublet, J=5 Hz); 2.68 (1H, doublet, J=5 Hz); 2.27 (1H, multiplet); 2.01 (1H, multiplet); 0.84 (9H, singlet); −0.016 (3H, singlet); −0.024 (3H, singlet).

51(b) 4-(t-Butyldimethylsilyloxyy-2-(3,4-dichlorophenyl)-1-[N-(t-butoxycarbonyl)-N-(2-hydroxyethyl)amino]-2-butanol 1.50 g (4.32 mmole) of 3-(3,4-dichlorophenyl)-3,4-epoxy-1-butanol t-butyldimethylsilyl ether [prepared as described in step (a) above] and 1.84 g (17.3 mmole) of lithium perchlorate were dissolved in 30 ml of acetonitrile. The mixture was then stirred under a nitrogen atmosphere at room temperature for 10 minutes. 2.11 g (34.5 mmole) of 2-aminoethanol were added to the reaction mixture, and the mixture was heated under reflux for 5 hours. At the end of this time, the reaction mixture was cooled to room temperature, diluted with ethyl acetate and then washed with a saturated aqueous solution of sodium chloride. The organic layer was separated and dried over anhydrous sodium sulfate, and then the solvent was removed by distillation under reduced pressure.

The resulting residue was dissolved in 30 ml of methylene chloride, and 0.89 ml (6.42 mmole) of triethylamine and 943 mg (4.32 mmole) of di-t-butyl dicarbonate were added to the resulting solution. The mixture was then stirred at room temperature for 16 hours. At the end of this time, the reaction mixture was poured into water and extracted with methylene chloride. The extract was then washed with a saturated aqueous solution of sodium chloride and dried over anhydrous sodium sulfate. The solvent was then removed by distillation under reduced pressure. The resulting residue was purified by silica gel column chromatography, using a 3:2 by volume mixture of hexane and ethyl acetate as the eluent, to give 1.94 g of the title compound.

Nuclear Magnetic Resonance Spectrum (400 MHz, $CDCl_3$) δ ppm: 7.30–7.75 (3H, multiplet); 5.30 and 5.57 (total 1H, each broad singlet); 3.05–4.00 (9H, multiplet); 2.00–2.40 (2H, multiplet); 1.53 (9H, singlet); 0.94 (9H, singlet); 0.09 (3H, singlet); 0.07 (3H, singlet). Infrared absorption spectrum $v_{max}$ (KBr) $cm^{-1}$: 3298, 2955, 2936, 2885, 2857, 1659. Mass spectrometric analysis (FAB) m/z: 508 $(M+H)^+$.

51(c) 2-[4-t-Butoxycarbonyl-2-(3,4-dichlorophenyl)morpholin-2-yl]ethanol t-Butyldimethylsilyl Ether 10.4 g (20.5 mmole) of 4-(t-butyldimethylsilyloxy)-2-(3,4-dichlorophenyl)-1-[N-(t-butoxycarbonyl)-N-(2-hydroxyethyl)amino]-2-butanol [prepared as described in step (b) above] and 8.03 g (30.6 mmole) of triphenylphosphine were dissolved in 180 ml of anhydrous toluene and a solution of 5.33 g (30.6 mmole) of diethyl azodicarboxylate in 20 ml of toluene was added dropwise under a nitrogen atmosphere at room temperature. The mixture was then stirred for 2 hours. At the end of this time, the reaction mixture was poured into an aqueous solution of ammonium chloride and extracted with ethyl acetate. The mixture was then washed with a saturated aqueous solution of sodium chloride. The organic extract was dried over anhydrous sodium sulfate, and then the solvent was removed by distillation under reduced pressure. The resulting residue was purified by silica gel column chromatography, using a gradient elution method, with mixtures of hexane and ethyl acetate ranging from 23:2 to 9:1 by volume as the eluent, to obtain 8.85 g of the title compound.

Nuclear Magnetic Resonance Spectrum (400 MHz, $CDCl_3$) δ ppm: 7.56 (1H, broad singlet); 7.43 (1H, doublet, J=9 Hz); 7.28 (1H, doublet of doublets, J=2 & 9 Hz); 4.20–4.55 (1H, broad singlet); 3.00–3.80 (8H, multiplet); 1.80–2.10 (2H, multiplet); 1.35–1.60 (9H, broad singlet); 0.85 (9H, multiplet); −0.01 (6H, singlet). Infrared absorption spectrum $v_{max}cm^{-1}$ ($CHCl_3$): 2957, 2931, 2859, 1730, 1687. Mass spectrometric analysis (FAB) m/z: 490 $(M+H)^+$.

51(d) 2-[2-(3,4-Dichlorophenyl)morpholin-2-yl]ethanol 7.80 g (15.9 mmole) of 2-[4-t-butoxycarbonyl-2-(3,4-dichlorophenyl)morpholin-2-yl]ethanol t-butyldimethylsilyl ether [prepared as described in step (c) above] were dissolved in 150 ml of methylene chloride and 7.05 g (35.5 mmole) of B-bromocatecholborane were added. The mixture was then stirred under a stream of nitrogen at room temperature for 2 hours. At the end of this time, 150 ml of water were added to the reaction mixture, and the mixture was then stirred for a further 2 hours. The reaction mixture was made basic by adding a 1 N aqueous solution of sodium hydroxide. It was then extracted with methylene chloride and the extract was washed with a saturated aqueous solution of sodium chloride. The organic extract was then dried over anhydrous sodium sulfate, and the solvent was removed by distillation under reduced pressure. The resulting residue was purified by silica gel column chromatography, using a gradient elution method, with mixtures of methylene chloride and methanol ranging from 19:1 to 17:3 by volume as the eluent, to obtain 4.40 g of the title compound.

Nuclear Magnetic Resonance Spectrum (400 MHz, $CDCl_3$) δ ppm: 7.51 (1H, doublet, J=2 Hz); 7.48 (1H, doublet, J=8 Hz); 7.24 (1H, doublet of doublets, J=2 & 8 Hz); 3.76 (1H, doublet of triplets, J=3 & 12 Hz); 3.66 (1H, multiplet); 3.58 (2H, triplet, J=6 Hz); 3.36 (1H, doublet, J=13 Hz); 3.11 (1H, doublet, J=13 Hz); 2.97 (1H, multiplet); 2.79 (1H, doublet of triplets, J=3 & 13 Hz); 2.14 (1H, doublet of triplets, J=6 & 15 Hz); 1.79 (1H, doublet of triplets, J=6 & 15 Hz).

51(e) 2-[2-(3,4-Dichlorophenyl)-4-(3,4,5-trimethoxybenzoyl)morpholin-2-yl]ethanol 1.28 g (4.63 mmole) of 2-[2-(3,4-dichlorophenyl)morpholin-2-yl]ethanol [prepared as described in step (d) above] were dissolved in 30 ml of methylene chloride, and 2.66 g (26.3 mmole) of triethylamine, 1.28 g (5.55 mmole) of 3,4,5-trimethoxybenzoyl chloride and 5 mg of 4-dimethylaminopyridine were added to the resulting solution. The mixture was then stirred at room temperature for 6 hours. At the end of this time, the reaction solution was poured into an aqueous solution of sodium hydrogencarbonate and extracted with methylene chloride. The extract was then washed with a saturated aqueous solution of sodium chloride. The organic extract was dried over anhydrous sodium sulfate, and the solvent was removed by distillation under reduced pressure. The resulting residue was purified by silica gel column chromatography, using a gradient elution method, with mixtures of methylene chloride and acetone ranging from 4:1 to 7:3 by volume as the eluent, to obtain 1.72 g of the title compound.

Nuclear Magnetic Resonance Spectrum (400 MHz, CDCl$_3$) δ ppm: 6.80–7.80 (3H, multiplet); 6.47 (2H, singlet); 3.40–4.80 (8H, multiplet); 3.84 and 3.86 (total 9H, each singlet); 1.75–2.25 (2H, multiplet). Infrared absorption spectrum $v_{max}$cm$^{-1}$ (KBr): 3429, 2940, 2838, 1630, 1585. Mass spectrometric analysis (EI) m/z: 469 (M)$^+$.

51(f) 2-[2-(3,4-Dichlorophenyl)-4-(3,4,5-trimethoxybenzoyl)morpholin-2-yl]ethanol Methanesulfonate 388 mg (0.83 mmole) of 2-[2-(3,4-dichlorophenyl)-4-(3,4,5-trimethoxybenzoyl)morpholin-2-yl]ethanol [prepared as described in step (e) above] were dissolved in 5 ml of methylene chloride, and 126 mg (1.25 mmole) of triethylamine and 0.078 ml (1.01 mmole) of methanesulfonyl chloride were added to the resulting solution. The mixture was then stirred at room temperature for 2 hours. The reaction mixture was then diluted with methylene chloride, after which it was washed with 1 N aqueous hydrochloric acid and with a saturated aqueous solution of sodium chloride, in that order. The organic extract was dried over anhydrous sodium sulfate, and then the solvent was removed by distillation under reduced pressure. The resulting residue was purified by silica gel column chromatography, using a gradient elution method, with mixtures of hexane and ethyl acetate ranging from 1:4 to 0:1 by volume as the eluent, to obtain 424 mg of the title compound.

Nuclear Magnetic Resonance Spectrum (400 MHz, CDCl$_3$) δ ppm: 6.90–7.80 (3H, multiplet); 6.52 (2H, singlet); 3.40–4.35 (8H, multiplet); 3.86 and 3.87 (total 9H, each singlet); 2.93 (3H, singlet); 2.10–2.55 (2H, multiplet). Infrared absorption spectrum $v_{max}$cm$^{-1}$ (KBr): 2999, 2966, 2939, 2875, 1634, 1585. Mass spectrometric analysis (FAB) m/z: 548 (M+H)$^+$.

51(g) 1-{2-[2-(3,4-Dichlorophenyl)-4-(3,4,5-trimethoxybenzoyl)morpholin-2-yl]ethyl}phenylpiperidine-4-carboxamide 200 mg (0.36 mmole) of 2-[2-(3,4-dichlorophenyl)-4-(3,4,5-trimethoxybenzoyl)morpholin-2-yl]ethanol methanesulfonate [prepared as described in step (f) above], 105 mg (0.44 mmole) of 4-phenylpiperidine-4-carboxamide hydrochloride, 100 mg (1.19 mmole) of sodium hydrogencarbonate and 100 mg (0.60 mmole) of potassium iodide were suspended in 2 ml of dimethylformamide, and the mixture was then stirred under a stream of nitrogen at 80° C. for 6 hours. The reaction mixture was then poured into water and extracted with ethyl acetate. The extract was then washed with an aqueous solution of sodium thiosulfate, with water and with a saturated aqueous solution of sodium chloride, in that order. The organic extract was then dried over anhydrous sodium sulfate, and the solvent was removed by distillation under reduced pressure. The resulting residue was purified by thin-layer chromatography, using a 9:1 by volume mixture of methylene chloride and methanol as the developing solvent and then crystallized from hexane, to give 205 mg (yield 86%) of the title compound.

Nuclear Magnetic Resonance Spectrum (400 MHz, CDCl$_3$) δ ppm: 6.80–7.75 (8H, multiplet); 6.48 (2H, singlet); 5.18 (2H, singlet); 1.80–4.70 (18H, multiplet); 3.83 and 3.85 (total 9H, each singlet). Infrared absorption spectrum $v_{max}$cm$^{-1}$ (KBr): 3440, 3356, 2937, 2831, 1679, 1631, 1584. Mass spectrometric analysis (FAB) m/z: 656 (M+H)$^+$; Elemental analysis: Calculated for C$_{34}$H$_{39}$N$_3$O$_6$Cl$_2$.1/10H$_2$O: C: 62.02%; H: 6.00%; N: 6.38%; Cl: 10.76% Found: C: 61.54%; H: 6.07%; N: 6.25%; Cl: 11.35%.

The compounds of the following Examples 52–69 were produced following the same procedure as described in Example 1 above.

EXAMPLE 52

1-{2-[2-(3,4-Dichlorophenyl)-4-(3,4,5-trimethoxybenzoyl)morpholin-2-yl]ethyl}-4-phenylpiperidine-4-(N,N-dimethylcarboxamide) (Compound No. 2-19712)

Yield: 84%; Mass spectrometric analysis (FAB) m/z: 684 (M+H)$^+$; Elemental analysis: Calculated for C$_{36}$H$_{43}$N$_3$O$_6$Cl$_2$: C: 63.16%; H: 6.33%; N: 6.14%; Cl: 10.36%; Found: C: 63.28%; H: 6.64%; N: 5.79%; Cl: 9.96%.

EXAMPLE 53

1-{2-[2-(3,4-Dichlorophenyl)-4-(3,4,5-trimethoxybenzoyl)morpholin-2-yl]ethyl}-4-phenyl-4-(pyrrolidin-1-ylcarbonyl)piperidine (Compound No. 2-1972)

Yield: 76%; Mass spectrometric analysis (FAB) m/z: 710 (M+H)$^+$; Elemental analysis: Calculated for C$_{38}$H$_{45}$N$_3$O$_6$Cl$_2$.1/10H$_2$O: C: 64.06%; H: 6.39%; N: 5.90%; Cl: 9.95%; Found: C: 63.62%; H: 6.37%; N: 5.75%; Cl: 9.96%.

EXAMPLE 54

1-{2-[2-(3,4-Dichlorophenyl)-4-(3,4,5-trimethoxybenzoyl)morpholin-2-yl]ethyl}-4-morpholinocarbonyl-4-phenylpiperidine (Compound No. 2-1973)

Yield: 68%; Mass spectrometric analysis (FAB) m/z: 726 (M+H)$^+$; Elemental analysis: Calculated for C$_{38}$H$_{45}$N$_3$O$_7$Cl$_2$.1/10H$_2$O: C: 62.65%; H: 6.25%; N: 5.77%; Cl: 9.73%; Found: C: 62.26%; H: 6.18%; N: 5.66%; Cl: 9.87%.

EXAMPLE 55

1-{2-[2-(3,4-Dichlorophenyl)-4-(3,4,5-trimethoxybenzoyl)morpholin-2-yl]ethyl}spiro[isobenzofuran-1(3H),4'-piperidine] (Compound No. 2-2006)

Yield: 63%; Mass spectrometric analysis (FAB) m/z: 641 (M+H)$^+$; Elemental analysis: Calculated for C$_{34}$H$_{38}$N$_2$O$_6$Cl$_2$.1/10H$_2$O: C: 63.47%; H: 5.98%; N: 4.35%; Cl: 11.02%; Found: C: 63.04%; H: 6.10%; N: 4.24%; Cl: 11.10%.

EXAMPLE 56

1-{2-[2-(3,4-Dichlorophenyl-4-(3,4,5-trimethoxybenzoyl)morpholin-2-yl]ethyl}-1-methanesulfonylspiro(indoline-3,4'-piperidine) (Compound No. 2-2014)

Yield: 85%; Mass spectrometric analysis (FAB) m/z: 718 (M+H)$^+$; Elemental analysis: Calculated for $C_{35}H_{41}N_3O_7SCl_2$: C: 58.49%; H: 5.75%; N: 5.85%; Cl: 9.87%; S: 4.46%. Found: C: 58.26%; H: 5.80%; N: 5.74%; Cl: 10.02%; S: 4.33%.

EXAMPLE 57

1-{2-[2-(3,4-Dichlorophenyl)-4-(3,4,5-trimethoxybenzoyl)morpholin-2-yl]ethyl}spiro[benzo[c]thiophene-1(3H),4'-piperidine] (Compound No. 2-2008)

Yield: 78%; Mass spectrometric analysis (FAB) m/z: 657 $(M+H)^+$; Elemental analysis: Calculated for $C_{34}H_{38}N_2O_5SCl_2H_2O$: C: 60.44%; H: 5.97%; N: 4.15%; Cl: 10.49%; S: 4.74%; Found: C: 60.68%; H: 5.95%; N: 3.92%; Cl: 10.60%; S: 4.85%.

EXAMPLE 58

1-{2-[2-(3,4-Dichlorophenyl)-4-(3,4,5-trimethoxybenzoyl)morpholin-2-yl]ethyl}spiro[benzo[c]thiophene-1(3H),4'-piperidine]-2-oxide (compound 2-2010)

Yield: 60%; Mass spectrometric analysis (FAB) m/z: 673 $(M+H)^+$; Elemental analysis: Calculated for $C_{34}H_{38}N_2O_6SCl_2$: C: 60.62%; H: 5.69%; N: 4.16%; Cl: 10.53%; S: 4.76%; Found: C: 60.50%; H: 5.94%; N: 4.09%; Cl: 10.35%; S: 4.71%.

EXAMPLE 59

1-{2-[2-(3,4-Dichlorophenyl)-4-(3,4,5-trimethoxybenzoyl)morpholin-2-yl]ethyl}spiro[isoquinoline-1(2H),4'-piperidine]-3(4H-one (Compound No. 2-2015)

Yield: 80%; Mass spectrometric analysis (FAB) m/z: 668 $(M+H)^+$; Elemental analysis: Calculated for $C_{35}H_{39}N_3O_6Cl_2$: C: 62.87%; H: 5.88%; N: 6.29%; Cl: 10.61%; Found: C: 62.95%; H: 5.98%; N: 6.07%; Cl: 10.77%.

EXAMPLE 60

1-{2-[2-(3,4-Dichlorophenyl)-4-(2-pyridylcarbonyl)morpholin-2-yl]ethyl}-4-phenylpiperidine-4-carboxamide (Compound No. 2-2353)

Yield: 73%; Mass spectrometric analysis (FAB) m/z: 567 $(M+H)^+$; Elemental analysis: Calculated for $C_{30}H_{32}N_4O_3Cl_2 \cdot 1/2H_2O$: C: 62.50%; H: 5.77%; N: 9.72%; Cl: 12.30%; Found: C: 62.19%; H: 5.88%; N: 9.39%; Cl: 13.12%.

EXAMPLE 61

1-{2-[2-(3,4-Dichlorophenyl)-4-(2-pyridylcarbonyl)morpholin-2-yl]ethyl}-4-phenylpiperidine-4-(N,N-dimethylcarboxamide) (Compound No. 2-2355)

Yield: 70%; Mass spectrometric analysis (FAB) m/z: 595 $(M+H)^+$; Elemental analysis: Calculated for $C_{32}H_{36}N_4O_3Cl_2 \cdot 1/2H_2O$: C: 63.57%; H: 6.17%; N: 9.27%; Cl: 11.73%; Found: C: 63.34%; H: 6.26%; N: 9.23%; Cl: 11.97%.

EXAMPLE 62

1-{2-[2-(3,4-Dichlorophenyl)-4-(2-methoxybenzoyl)morpholin-2-yl]ethyl}-4-phenylpiperidine-4-carboxamide (Compound No. 2-1585)

Yield: 75%; Mass spectrometric analysis (FAB) m/z: 596 $(M+H)^+$; Elemental analysis: Calculated for $C_{32}H_{35}N_3O_4Cl_2 \cdot 1/2H_2O$: C: 63.47%; H: 5.99%; N: 6.94%; Cl: 11.71%; Found: C: 63.02%; H: 6.12%; N: 6.74%; Cl: 12.97%.

EXAMPLE 63

1-{2-[2-(3,4-Dichlorophenyl-4-(2-methoxybenzoyl)morpholin-2-yl]ethyl}-4-phenylpiperidine-4-(N,N-dimethylcarboxamide) (Compound No. 2-1586)

Yield: 77%; Mass spectrometric analysis (FAB) m/z: 624 $(M+H)^+$; Elemental analysis: Calculated for $C_{34}H_{39}N_3O_4Cl_2 \cdot 1/2H_2O$: C: 64.45%; H: 6.36%; N: 6.63%; Cl: 11.19%; Found: C: 64.29%; H: 6.42%; N: 6.68%; Cl: 11.57%.

EXAMPLE 64

1-{2-[2-(3,4-Dichlorophenyl)-4-(3-methoxybenzoyl)morpholin-2-yl]ethyl}-4-phenylpiperidine-4-carboxamide (Compound No. 2-1633)

Yield: 80%; Mass spectrometric analysis (FAB) m/z: 596 $(M+H)^+$; Elemental analysis: Calculated for $C_{32}H_{35}N_3O_4Cl_2 \cdot 1/2H_2O$: C: 63.47%; H: 5.99%; N: 6.94%; Cl: 11.71%; Found: C: 63.44%; H: 5.79%; N: 6.79%; Cl: 11.47%.

EXAMPLE 65

1-{2-[2-(3,4-Dichlorophenyl)-4-(3-methoxybenzoyl)morpholin-2-yl]ethyl}-4-phenylpiperidine-4-(N,N-dimethylcarboxamide) (Compound No. 2-1635)

Yield: 80%; Mass spectrometric analysis (FAB) m/z: 624 $(M+H)^+$; Elemental analysis: Calculated for $C_{34}H_{39}N_3O_4Cl_2 \cdot 1/5H_2O$: C: 65.01%; H: 6.32%; N: 6.69%; Cl: 11.29%; Found: C: 64.79%; H: 6.47%; N: 6.42%; Cl: 10.93%.

EXAMPLE 66

1-{2-[2-(3,4-Dichlorophenyl)-4-(4-methoxybenzoyl)morpholin-2-yl]ethyl}-4-phenylpiperidine-4-carboxamide (Compound No. 2-1681)

Yield: 94%; Mass spectrometric analysis (FAB) m/z: 596 $(M+H)^+$; Elemental analysis: Calculated for $C_{32}H_{35}N_3O_4Cl_2 \cdot 1/5H_2O$: C: 64.04%; H: 5.95%; N: 7.00%; Cl: 11.82%; Found: C: 63.67%; H: 5.97%; N: 6.70%; Cl: 12.20%.

EXAMPLE 67

1-{2-[2-(3,4-Dichlorophenyl)-4-(4-methoxybenzoyl)morpholin-2-yl]ethyl}-4-phenylpiperidine-4-(N,N-dimethylcarboxamide) (Compound No. 2-1683)

Yield: 78%; Mass spectrometric analysis (FAB) m/z: 624 $(M+H)^+$; Elemental analysis: Calculated for $C_{34}H_{39}N_3O_4Cl_2$: C: 65.38%; H: 6.29%; N: 6.73%; Cl: 11.35%; Found: C: 65.32%; H: 6.94%; N: 6.61%; Cl: 10.97%.

EXAMPLE 68

1-{2-[2-(3,4-Dichlorophenyl)-4-(2-pyrazinylcarbonyl)morpholin-2-yl]ethyl}-4-phenylpiperidine-4-carboxamide (Compound No. 2-2497)

Yield: 31%; Mass spectrometric analysis (FAB) m/z: 568 $(M+H)^+$; Elemental analysis: Calculated for $C_{29}H_{31}N_5O_3Cl_2.H_2O$: C: 59.39%; H: 5.67%; N: 11.87%; Cl: 12.09%;. Found: C: 59.58%; H: 5.82%; N: 11.30%; Cl: 12.56%.

EXAMPLE 69

1-{2-[2-(3,4-Dichlorophenyl)-4-(2-pyrazinylcarbonyl)morpholin-2-yl]ethyl}-4-phenylpiperidine-4-(N,N-dimethylcarboxamide) (Compound No. 2-2499)

Yield: 33%; Mass spectrometric analysis (FAB) m/z: 596 $(M+H)^+$; Elemental analysis: Calculated for $C_{31}H_{35}N_5O_3Cl_2.H_2O$: C: 60.58%; H: 6.07%; N: 11.40%; Cl: 11.54%; Found: C: 60.57%; H: 5.95%; N: 9.97%; Cl: 12.88%.

EXAMPLE 70

1-{2-[(2R)-(3,4-Dichlorophenyl)-4-(3,4,5-trimethoxybenzoyl)morpholin-2-yl]ethyl}-4-phenylpiperidine-4-carboxamide (Compound No. 2-1969)

70(a) 1-(Chloroacetyl)amino-4-t-butyldimethylsilyloxy-(2R)-(3,4-dichlorophenyl)-2-butanol 3.60 g (9.88 mmole) of 1-amino-4-t-butyldimethylsilyloxy-(2R)-(3,4-dichlorophenyl)-2-butanol [prepared as described in Example 1(e)], 1.64 ml (11.8 mmole) of triethylamine and 121 mg (0.99 mmole) of 4-dimethylaminopyridine were dissolved in 100 ml of methylene chloride, and 0.94 ml (11.8 mmole) of chloroacetyl chloride were added dropwise, whilst ice-cooling. The mixture was then stirred at the same temperature for 2 hours. At the end of this time, 100 ml of methylene chloride were added to the reaction mixture, and the resulting mixture was washed with ice-cooled 10% w/v aqueous hydrochloric acid, with a saturated aqueous solution of sodium hydrogencarbonate and with a saturated aqueous solution of sodium chloride, in that order. It was then dried over anhydrous magnesium sulfate. The solvent was then removed by distillation under reduced pressure, and the resulting residue was purified by silica gel flash column chromatography, using a gradient elution method, with mixtures of ethyl acetate and hexane ranging from 1:5 to 1:2 by volume as the eluent, to obtain 3.32 g (yield 76%) of the title compound as a colorless oil.

Nuclear Magnetic Resonance Spectrum (270 MHz, $CDCl_3$) δ ppm: 7.64 (1H, doublet, J=2.1 Hz); 7.47 (1H, doublet, J=8.4 Hz); 7.28 (1H, doublet of doublets, J=8.4 & 2.1 Hz); 7.03 (1H, broad triplet), 5.27 (1H, singlet); 4.04 (2H, AB-quartet, J=15.1 Hz, Δδ=0.08 ppm); 3.81 (1H, doublet of triplets, J=10.5 & 3.7 Hz); 3.72 (1H, doublet of doublets, J=13.5 & 6.2 Hz); 3.53 (1H, doublet of doublets, J=10.9 & 2.3 Hz); 3.45 (1H, doublet of doublets, J=13.5 & 5.4 Hz); 2.24 (1H, doubled doublet of doublets, J=14.8, 10.9 & 4.1 Hz); 1.93 (1H, doublet of triplets, J=14.8 & 2.8 Hz); 0.92 (9H, singlet); 0.06 (3H, singlet); 0.00 (3H, singlet).

70(b) 2-[(2R)-(3,4-Dichlorophenyl)-5-oxomorpholin-2-yl]ethanol t-Butyldimethylsilyl Ether 219 mg (5.48 mmole) of sodium hydride (as a 60% w/v suspension in mineral oil) were suspended in 30 ml of anhydrous tetrahydrofuran, and a solution prepared by dissolving 1.61 g (3.65 mmole) of 1-(chloroacetyl)amino-4-t-butyldimethylsilyloxy-(2R)-(3,4-dichlorophenyl)-2-butanol [prepared as described in step (a) above] in 30 ml of anhydrous tetrahydrofuran was slowly added dropwise, whilst ice-cooling, over 30 minutes. The mixture was then stirred at the same temperature for 4 hours. At the end of this time, the reaction mixture was poured into ice-cooled 10% w/v aqueous hydrochloric acid and extracted three times, each time with 100 ml of ethyl acetate. The combined organic extracts were washed with a saturated aqueous solution of sodium chloride and dried over anhydrous magnesium sulfate. The solvent was then removed by distillation under reduced pressure, and the resulting residue was purified by silica gel flash column chromatography, using a gradient elution method, with mixtures of ethyl acetate and hexane ranging from 1:4 to 2:1 by volume as the eluent, to obtain 700 mg (yield 47%) of the title compound.

$[\alpha]_D^{24}$=+67.65 (c=0.81, methanol). Nuclear Magnetic Resonance Spectrum (270 MHz, $CDCl_3$) δ ppm: 7.532 (1H, doublet, J=2.2 Hz); 7.526 (1H, doublet, J=8.1 Hz); 7.27 (1H, doublet of doublets, J=8.1 & 2.2 Hz); 6.76 (1H, broad singlet); 4.17 (2H, AB-quartet, J=17.3 Hz, Δδ=0.24 ppm); 3.98 (1H, doublet of doublets, J=13.0 & 3.9 Hz); 3.76 (1H, doublet of doublets, J=13.0 & 2.0 Hz); 3.63 (1H, multiplet); 3.29 (1H, multiplet); 2.12 (2H, multiplet); 0.91 (9H, singlet); 0.04 (3H, singlet); 0.03 (3H, singlet).

70(c) 2-[(2R)-(3,4-Dichlorophenyl)morpholin-2-yl]ethanol 580 mg (1.43 mmole) of 2-[(2R)-(3,4-dichlorophenyl)-5-oxomorpholin-2-yl]ethanol t-butyldimethylsilyl ether [prepared as described in step (b) above] were dissolved in 6 ml of anhydrous tetrahydrofuran. The solution was then heated under reflux under a stream of nitrogen and 0.60 ml (6.0 mmole) of a 10 M boranedimethyl sulfide complex was added dropwise. The mixture was then stirred for 2 hours. At the end of this time, the solvent was removed by distillation under reduced pressure, and 5 ml of 1 N aqueous hydrochloric acid were added. The mixture was then stirred at 100° C. for 1 hour. The reaction mixture was air-cooled, made basic by the addition of a 1 N aqueous solution of sodium hydroxide, diluted with a saturated aqueous solution of sodium chloride and then extracted with ethyl acetate. The organic extract was washed with a saturated aqueous solution of sodium chloride and dried over anhydrous sodium sulfate. The solvent was then removed by distillation under reduced pressure. The resulting residue was purified by silica gel column chromatography, using a gradient elution method, with mixtures of methylene chloride and methanol ranging from 9:1 to 17:3 by volume as the eluent, to obtain 360 mg of the title compound.

$[\alpha]_D^{24}$=+16.22 (c=0.45, methanol).

The nuclear magnetic resonance spectrum, infrared spectrum and mass spectrometric analysis agreed with those of the racemate produced as described in Example 51(d).

70(d) 2-[(2R)-(3,4-Dichlorophenyl)-4-(3,4,5-trimethoxybenzoyl)morpholin-2-yl]ethanol Following a procedure similar to that described in Example 51(e), but using 2-[(2R)-(3,4-dichlorophenyl)morpholin-2-yl]ethanol [prepared as described in step (c) above], the title compound was obtained in a yield of 92%.

$[\alpha]_D^{24}$=+30.65 (c=0.56, methanol).

The nuclear magnetic resonance spectrum, infrared spectrum and mass spectrometric analysis agreed with those of the racemate produced as described in Example 51(e).

70(e) 2-[(2R)-(3,4-Dichlorophenyl)-4-(3,4,5-trimethoxybenzoyl)morpholin-2-yl]ethanol Methanesulfonate 30.0 g (63.8 mmole) of 2-[(2R)-(3,4-dichlorophenyl)-4-(3,4,5-trimethoxybenzoyl)morpholin-2-yl]ethanol [prepared as described in step (d) above] were dissolved in 500 ml of methylene chloride. 11.5 ml (83.0 mmole) of triethylamine and 5.93 ml (76.6 mmole) of methanesulfonyl chloride were then added, in that order, to the mixture, whilst ice-cooling, and the mixture was stirred at room temperature for 2 hours under a nitrogen atmosphere. The reaction mixture was then diluted with methylene chloride and washed with 1 N aqueous hydrochloric acid, and then with a saturated aqueous solution of sodium chloride, after which it was dried over anhydrous sodium sulfate. The solvent was removed by distillation under reduced pressure, and the resulting residue was purified by silica gel column chromatography, using a gradient elution method, with mixtures of hexane and ethyl acetate ranging from 1:4 to 1:9 by volume as the eluent, to give 34.8 g of the title compound.

$[\alpha]_D^{24}$+26.36 (c=0.66, methanol). Nuclear Magnetic Resonance Spectrum (400 MHz, CDCl$_3$) δ ppm: 6.90–7.80 (3H, multiplet); 6.52 (2H, singlet); 3.40–4.35 (8H, multiplet); 3.86 & 3.87 (total 9H, each singlet); 2.93 (3H, singlet); 2.10–2.55 (2H, multiplet). Infrared absorption spectrum $v_{max}$cm$^{-1}$ (KBr): 2999, 2966, 2939, 2875, 1634, 1585; Mass spectrometric analysis (FAB) m/z: 548 (M+H)$^+$.

70(f) 1-{2-[(2R)-(3,4-Dichlorophenyl)-4-(3,4,5-trimethoxybenzoyl)morpholin-2-yl]ethyl}-4-phenylpiperidine-4-carboxamide Following a procedure similar to that described in Example 51(g), but using 2-[(2R)-(3,4-dichlorophenyl)-4-(3,4,5-trimethoxybenzoyl)morpholin-2-yl]ethanol methanesulfonate [prepared as described in step (e) above], the title compound was obtained in a yield of 79%.

$[\alpha]_D^{24}$=+7.53 (c=0.50, methanol). Elemental analysis: Calculated for C$_{34}$H$_{39}$N$_3$O$_6$Cl$_2$.1/5H$_2$O: C: 61.85%; H: 6.01%; N: 6.36%; Cl: 10.74%; Found: C: 61.51%; H: 6.18%; N: 6.13%; Cl: 10.72%.

The nuclear magnetic resonance spectrum, infrared spectrum and mass spectrometric analysis agreed with those of the racemate produced as described in Example 51(g).

The compounds of the following Examples 71–74 were produced following the same procedure as described in Example 70 above.

EXAMPLE 71

1-{2-[(2R)-(3,4-Dichlorophenyl)-4-(3,4,5-trimethoxybenzoyl)morpholin-2-yl]-ethyl}-4-phenylpiperidine-4-(N,N-dimethylcarboxamide) (Compound No. 2-1971)

Yield: 84%; $[\alpha]_D^{24}$=+7.04 (c=0.45, methanol). Elemental analysis: Calculated for C$_{36}$H$_{48}$N$_3$O$_6$Cl$_2$: C: 62.69%; H: 7.02%; N: 6.09%; Cl: 10.28%; Found: C: 62.37%; H: 6.42%; N: 5.94%; Cl: 10.72%.

EXAMPLE 72

1-{2-[(2R)-(3,4-Dichlorophenyl)-4-(3,4,5-trimethoxybenzoyl)morpholin-2-yl]ethyl}spiro[benzo[c]thiophene-1(3H),4'-piperidine]-2-oxide (Compound No. 2-2010)

Yield: 66%; $[\alpha]_D^{24}$=−2.50 (c=0.50, methanol). Elemental analysis: Calculated for C$_{34}$H$_{38}$N$_2$O$_6$SCl$_2$: C: 60.62%; H: 5.69%; N: 4.16%; Cl: 10.53%; S: 4.76%; Found: C: 60.17%; H: 5.68%; N: 4.00%; Cl: 10.47%; S: 4.55%.

EXAMPLE 73

1-{2-[(2R)-(3,4-Dichlorophenyl)-4-(3,4,5-trimethoxybenzoyl)morpholin-2-yl]ethyl}spiro[isoquinoline-1(2H),4'-piperidin]-3(4H)-one (Compound No. 2-2015)

Yield: 75%; $[\alpha]_D^{24}$=+2.58 (c=0.40, methanol). Elemental analysis: Calculated for C$_{35}$H$_{39}$N$_3$O$_6$Cl$_2$: C: 62.87%; H: 5.88%; N: 6.29%; Cl: 10.61%; Found: C: 62.46%; H: 6.01%; N: 6.08%; Cl: 9.63%.

EXAMPLE 74

1-{2-[(2R)-(3,4-Dichlorophenyl-4-(3-methoxybenzoyl)morpholin-2-yl]ethyl}-4-phenylpiperidine-4-(N,N-dimethylcarboxamide) (Compound No. 2-1635)

Yield: 78%; $[\alpha]_D^{24}$=+9.67 (c=0.50, methanol). Elemental analysis: Calculated for C$_{34}$H$_{39}$N$_3$O$_4$Cl$_2$.1/5H$_2$O: C: 65.01%; H: 6.32%; N: 6.69%; Cl: 11.29%; Found: C: 64.84%; H: 6.46%; N: 6.52%; Cl: 11.58%.

EXAMPLE 75

1-{2-[(5R)-(3,4-Dichlorophenyl)-3-(3,4,5-trimethoxybenzoyl)oxazolidine-5-yl]ethyl}spiro[benzo[c]thiophene-1(3H),4'-piperidine]-(2S)-oxide (Compound No. 3-10)

600 mg (1.12 mmole) of 2-[(5R)-(3,4-dichlorophenyl)-3-(3,4,5-trimethoxybenzoyl)oxazolidin-5-yl]ethanol methanesulfonate [prepared as described in Example 1(g)], 318 mg (1.23 mmole) of spiro[benzo[c]thiophene-1(3H),4'-piperidine]-(2S)-oxide hydrochloride (prepared as described in Preparation 6), 283 mg (3.37 mmole) of sodium hydrogencarbonate, and 280 mg (1.69 mmole) of sodium iodide were suspended in 10 ml of anhydrous dimethylformamide, and the mixture was heated at 80° C. for 8 hours under a nitrogen atmosphere. The reaction mixture was then poured into 100 ml of a saturated aqueous solution of sodium chloride and then extracted with ethyl acetate. The organic extract was dried over anhydrous magnesium sulfate, and then the solvent was removed by distillation under reduced pressure. The resulting residue was purified by silica gel column chromatography, using a gradient elution method, with mixtures of methylene chloride and methanol ranging from 40:1 to 20:1 by volume as the eluent, and then crystallized from diisopropyl ether, to give 496 mg of the title compound as white crystals.

$[\alpha]_D^{24}$+41.0 (c=1, methanol). HPLC analysis; Column: YMC-Pack ODS-A (250×4.6 mmφ); Eluent: CH$_3$CN:H$_2$O= 40:60, 0.1% AcONH$_4$; Flow rate: 1.0 ml/min; Retention time: 28.6 min; Nuclear Magnetic Resonance Spectrum (400 MHz, CDCl$_3$) δ ppm: 7.1–7.6 (7H, multiplet); 6.70 (2H, singlet); 4.9–5.3 (total 2H, broad singlet); 4.32 (1H, doublet, J=16.7 Hz); 4.00 (1H, doublet, J=16.7 Hz); 3.7–4.2 (2H, multiplet); 3.87 & 3.89 (total 9H, each singlet); 1.5–3.1 (12H, multiplet). Infrared absorption spectrum $v_{max}$cm$^{-1}$ (KBr): 2940, 1642, 1584, 1416, 1237, 1128. Mass spectrometric analysis (FAB) m/z 659 (M+H)$^+$; Elemental analysis; Calculated for C$_{33}$H$_{36}$N$_2$O$_6$SCl$_2$.1/2H$_2$O: C: 59.28%; H: 5.58%; N: 4.19%; S: 4.79%; Cl: 10.60%; Found: C: 59.36%; H: 5.58%; N: 4.12%; S: 4.73%; Cl: 10.60%.

EXAMPLE 76

1-{2-[(2R)-(3,4-Dichlorophenyl)-4-(3,4,5-trimethoxybenzoyl)morpholin-2-yl]ethyl}spiro[benzo[c]thiophene-1(3H),4'-piperidine]-(2S)-oxide (Compound No. 3-42)

76(a) 4-(t-Butyldimethylsilyloxy)-(2R)-(3,4-dichlorophenyl)-1-[N-(t-butoxycarbonyl)-N-(2-hydroxyethyl)amino]-2-butanol 39.9 g (109 mmole) of 4-t-butyldimethylsilyloxy-(2R)-(3,4-dichlorophenyl)butane-1,2-diol [prepared as described in Example 1(c)] were dissolved in 80 ml of pyridine, and 31.3 g (164 mmole) of p-toluenesulfonyl chloride were added to the resulting solution. The mixture was then stirred at room temperature for 2 days under a nitrogen atmosphere. At the end of this time, the reaction mixture was diluted with water and extracted with ethyl acetate. The organic extract was washed with water and with a saturated aqueous solution of sodium chloride, in that order, after which it was dried over anhydrous sodium sulfate. The solvent was then removed by distillation under reduced pressure. The resulting residue was dissolved in 600 ml of acetonitrile, and 35.0 g (329 mmole) of lithium perchlorate and 33.4 g (547 mmole) of 2-aminoethanol were added to the resulting solution. The mixture was then heated under reflux for 16 hours. At the end of this time, the reaction mixture was cooled to room temperature, diluted with ethyl acetate, and washed with a saturated aqueous solution of sodium chloride. The organic layer was then separated and dried over anhydrous sodium sulfate. The solvent was removed by distillation under reduced pressure, and the resulting residue was dissolved in 700 ml of methylene chloride. 22.8 ml (164 mmole) of triethylamine and 26.3 g (120 mmole) of di-t-butyl dicarbonate were added to the resulting solution, and the mixture was stirred at room temperature for 12 hours. The reaction mixture was then poured into water and extracted with methylene chloride. The organic extract was washed with a saturated aqueous solution of sodium chloride and then dried over anhydrous sodium sulfate. The solvent was then removed by distillation under reduced pressure. The resulting residue was purified by silica gel column chromatography, using a gradient elution method, with mixtures of hexane and ethyl acetate ranging from 4:1 to 7:3 by volume as the eluent, to give 49.9 g of the title compound.

$[\alpha]_D^{24}$+3.92 (c=0.72, methanol). Nuclear Magnetic Resonance Spectrum (400 MHz, CDCl$_3$) δ ppm: 7.30–7.75 (3H, multiplet); 5.30 & 5.57 (total 1H, each broad singlet); 3.05–4.00 (9H, multiplet); 2.00–2.40 (2H, multiplet); 1.53 (9H, singlet); 0.94 (9H, singlet); 0.09 (3H, singlet); 0.07 (3H, singlet). Infrared absorption spectrum $v_{max}$cm$^{-1}$ (KBr): 3420, 2957, 2933, 2885, 2861, 1687. Mass spectrometric analysis (FAB) m/z: 508 (M+H)$^+$.

76(b) 2-[4-t-Butoxycarbonyl-(2R)-(3,4-dichlorophenyl)morpholin-2-yl]ethanol t-Butyldimethylsilyl Ether 49.9 g (98.1 mmole) of 4-t-butyldimethylsilyloxy-(2R)-(3,4-dichlorophenyl)-1-[N-(t-butoxycarbonyl)-N-(2-hydroxyethyl)amino]-2-butanol [prepared as described in step (a) above] and 30.9 g (118 mmole) of triphenylphosphine were dissolved in 600 ml of dried toluene. 51.3 g of a 40% w/v toluene solution containing 118 mmole of diethyl azodicarboxylate were added dropwise to the resulting solution at room temperature under a nitrogen atmosphere, and the mixture was stirred for 2 hours. At the end of this time, the solvent was removed by distillation under reduced pressure, and the resulting residue was purified by silica gel column chromatography, using a gradient elution method, with mixtures of hexane and ethyl acetate ranging from 47:3 to 23:2 by volume as the eluent, to give 43.2 g of the title compound.

$[\alpha]_D^{24}$+32.67 (c=0.60, methanol). Nuclear Magnetic Resonance Spectrum (400 MHz, CDCl$_3$) δ ppm: 7.56 (1H, broad singlet); 7.43 (1H, doublet, J=9 Hz); 7.28 (1H, doublet of doublets, J=2 & 9 Hz); 3.00–4.55 (8H, multiplet); 1.80–2.10 (2H, multiplet); 1.35–1.60 (9H, broad singlet); 0.85 (9H, singlet); −0.01 (6H, singlet). Infrared absorption spectrum $v_{max}$cm$^{-1}$ (CHCl$_3$): 2957, 2931, 2859, 1687. Mass spectrometric analysis (FAB) m/z: 490 (M+H)$^+$.

76(c) (2R)-(3,4-Dichlorophenyl)-2-(2-hydroxyethyl)morpholine Hydrochloride 43.1 g (87.9 mmole) of 2-[4-t-butoxycarbonyl-(2R)-(3,4-dichlorophenyl)morpholin-2-yl]ethanol t-butyldimethylsilyl ether [prepared as described in step (b) above] were dissolved in 600 ml of a 4 N solution of hydrogen chloride in dioxane, and the mixture was stirred at 60° C. for 4 hours. At the end of this time, the solvent was removed by distillation under reduced pressure, and diethyl ether was added to the resulting residue. The solvent was then removed by distillation under reduced pressure. The resulting residue was recrystallized from ethanol/ethyl acetate, to give 24.1 g of the title compound.

$[\alpha]_D^{24}$+48.07 (c=0.57, methanol). Nuclear Magnetic Resonance Spectrum (400 MHz, hexadeuterated dimethyl sulfoxide) δ ppm: 8.60–9.80 (2H, broad singlet); 7.72 (1H, singlet); 7.70 (1H, doublet, J=9 Hz); 7.44 (1H, doublet of doublets, J=2 & 9 Hz); 4.53 (1H, broad singlet); 3.89 (1H, doublet of triplets, J=4 & 13 Hz); 3.75 (1H, doublet, J=14 Hz); 3.68 (1H, multiplet); 3.30–3.45 (2H, multiplet); 2.93–3.13 (3H, multiplet); 2.09 (1H, multiplet); 1.90 (1H, multiplet). Infrared absorption spectrum $v_{max}$cm$^{-1}$ (KBr): 3378, 2966, 2893, 2812, 2783, 2724, 2656, 2530, 1598. Mass spectrometric analysis (FAB) m/z: 276 (M+H)$^+$ (free form).

76(d) 2-[(2R)-(3,4-Dichlorophenyl)-4-(3,4,5-trimethoxybenzoyl)morpholin-2-yl]ethanol 22.9 g (82.9 mmole) of (2R)-(3,4-dichlorophenyl)-2-(2-hydroxyethyl)morpholine hydrochloride [prepared as described in step (c) above] were suspended in 500 ml of methylene chloride. 27.6 ml (199 mmole) of triethylamine, 21.0 g (91.0 mmole) of 3,4,5-trimethoxybenzoyl chloride, and 100 mg of 4-dimethylaminopyridine were then added to the resulting suspension, and the mixture was stirred at room temperature for 12 hours. At the end of this time, the reaction mixture was poured into water and extracted with methylene chloride. The organic extract was washed with a saturated aqueous solution of sodium chloride and dried over anhydrous sodium sulfate. The solvent was removed by distillation under reduced pressure, and the resulting residue was purified by silica gel column chromatography, using a gradient elution method, with mixtures of methylene chloride and acetone ranging from 4:1 to 7:3 by volume as the eluent, to give 30.0 g of the title compound.

$[\alpha]_D^{24}$+30.65 (c=0.56, methanol). Nuclear Magnetic Resonance Spectrum (400 MHz, CDCl$_3$) δ ppm: 6.80–7.80 (3H, multiplet); 6.47 (2H, singlet); 3.40–4.80 (8H, multiplet); 3.84 & 3.86 (total 9H, each singlet); 1.75–2.25 (2H, multiplet). Infrared absorption spectrum $v_{max}$cm$^{-1}$ (KBr): 3429, 2940, 2838, 1630, 1585. Mass spectrometric analysis (EI) m/z: 469 (M$^+$).

76(e) [(2R)-(3,4-Dichlorophenyl)-4-(3,4,5-trimethoxybenzoyl)morpholin-2-yl]ethanal 0.88 ml (10.1 mmole) of oxalyl chloride was dissolved in 10 ml of methylene chloride, and 5 ml of a methylene chloride solution containing 0.79 ml (11.1 mmole) of dimethyl sulfoxide were added dropwise to the resulting solution at −78° C. under a nitrogen atmosphere. The mixture was then stirred for 30 minutes. 10 ml of a methylene chloride solution containing 950 mg (2.02 mmole) of 2-[(2R)-(3,4-dichlorophenyl)-4-(3,4,5-trimethoxybenzoyl)morpholin-2-yl]ethanol [prepared as described in step (d) above] were added dropwise to the resulting mixture, and the mixture was stirred for 4 hours. At the end of this time, a further 2.24 ml (16.2 mmole) of triethylamine was added, and the mixture was stirred at room temperature for 2 hours. The reaction mixture was then poured into water and extracted with methylene chloride. The organic extract was washed with water, and then with a saturated aqueous solution of sodium chloride, after which it was dried over anhydrous sodium sulfate. The solvent was removed by distillation under reduced pressure, and the resulting residue was purified by silica gel column chromatography, using a gradient elution method, with mixtures of methylene chloride and acetone ranging from 23:2 to 21:4 by volume as the eluent, to give 878 mg of the title compound.

$[\alpha]_D^{24}$+36.15 (c=0.65, methanol). Nuclear Magnetic Resonance Spectrum (400 MHz, CDCl$_3$) δ ppm: 9.56 (1H, singlet); 6.90–7.80 (3H, multiplet); 6.50 (2H, singlet); 3.40–4.60 (6H, multiplet); 3.85–3.87 (total 9H, each singlet); 2.70–3.05 (2H, multiplet). Infrared absorption spectrum $v_{max}$cm$^{-1}$ (KBr): 2962, 2930, 2838, 1723, 1636, 1585. Mass spectrometric analysis (FAB) m/z: 468 (M+H)$^+$.

76(f) 1-{2-[(2R)-(3,4-Dichlorophenyl)-4-(3,4,5-trimethoxybenzoyl)morpholin-2-yl]ethyl}spiro[benzo[c]thiophene-1(3H),4'-piperidine]-(2S)-oxide 15.00 g (27.4 mmole) of 2-[(2R)-(3,4-dichlorophenyl)-4-(3,4,5-trimethoxybenzoyl)morpholin-2-yl]ethanol methanesulfonate [prepared as described in Example 70(e)], 7.76 g (30.1 mmole) of spiro[benzo[c]thiophene-1(3H),4'-piperidine]-(2S)-oxide hydrochloride (prepared as described in Preparation 6), 6.89 g (82.0 mmole) of sodium hydrogencarbonate, and 6.81 g (41.0 mmole) of potassium iodide were suspended in 150 ml of anhydrous dimethylformamide. The mixture was then heated at 80° C. for 8 hours under a nitrogen atmosphere. The reaction mixture was then poured into 400 ml of a saturated aqueous solution of sodium chloride and extracted with ethyl acetate. The organic extract was dried over anhydrous magnesium sulfate, and the solvent was removed by distillation under reduced pressure. The resulting residue was purified by silica gel column chromatography, using a gradient elution method, with mixtures of methylene chloride and methanol ranging from 40:1 to 20:1 by volume as the eluent, and then crystallized from hexane, to give 15.5 g of the title compound as white crystals.

$[\alpha]_D^{24}$+14.0 (c=1, methanol). HPLC analysis; Column: YMC-Pack ODS-A (250×4.6 mmφ); Eluent: CH$_3$CN:H$_2$O= 40:60, 0.1% AcONH$_4$; Flow rate: 1.0 ml/min; Retention time: 23.7 min; Nuclear Magnetic Resonance Spectrum (400 MHz, CDCl$_3$) δ ppm: 7.1–7.8 (7H, multiplet); 6.49 (2H, broad singlet); 4.31 (1H, doublet, J=16.8 Hz); 3.99 (1H, doublet, J=16.8 Hz); 3.86 & 3.84 (total 9H, each singlet); 3.3–4.0 (6H, multiplet); 1.5–3.1 (12H, multiplet). Infrared absorption spectrum $v_{max}$cm$^{-1}$ (KBr): 2939, 1636, 1584, 1464, 1426, 1329, 1237, 1128. Mass spectrometric analysis (FAB) m/z: 673 (M+H)$^+$. Elemental analysis: Calculated for C$_{34}$H$_{38}$N$_2$O$_6$SCl$_2$.1/2H$_2$O: C: 59.82%; H: 5.76%; N: 4.10%; S: 4.70%; Cl, 10.39%; Found: C: 60.20%; H: 6.14%; N: 4.04%; S: 4.54%; Cl, 10.38%.

76(g) 1-{2-[(2R)-(3,4-Dichlorophenyl)-4-(3,4,5-trimethoxybenzoyl)morpholin-2-yl]ethyl}spiro[benzo[c]thiophene-1(3H),4'-piperidine]-(2S)-oxide 150 mg (0.32 mmole) of [(2R)-(3,4-dichlorophenyl)-4-(3,4,5-trimethoxybenzoyl)morpholine-2-yl]ethanal [prepared as described in step (e) above] and 99 mg (0.38 mmole) of spiro[benzo[c]thiophene-1(3H),4'-piperidine]-(2)-oxide hydrochloride (prepared as described in Preparation 6) were dissolved in 1 ml of methanol. 100 mg of molecular sieves 3A (powder) and 209 mg (3.33 mmole) of sodium cyanoborohydride were added to the resulting solution, and the mixture was heated under reflux for 8 hours under a nitrogen atmosphere. The reaction mixture was filtered through a Celite (trade mark) filter aid. The filtrate was poured into water and extracted with ethyl acetate. The organic extract was washed with a saturated aqueous solution of sodium chloride and then dried over anhydrous sodium sulfate. The solvent was removed by distillation under reduced pressure, and the resulting residue was purified by silica gel column chromatography, using a gradient elution method, with mixtures of methylene chloride and methanol ranging from 97:3 to 19:1 by volume as the eluent, to give 184 mg of the title compound. Various physicochemical properties of this product agreed with those of the product synthesised as described in Example 76(f).

EXAMPLE 77

1-{2-[(2R)-(3,4-Dichlorophenyl)-4-[(3-isopropoxyphenyl)acetyl]morpholin-2-yl]ethyl}spiro[benzo[c]thiophene-1(3H),4'-piperidine]-(2S)-oxide (Compound No. 3-811)

77(a) 2-{(2R)-(3,4-Dichlorophenyl)-4-[(3-isopropoxyphenyl)acetyl]morpholin-2-yl}ethanol 1.03 g (5.28 mmole) of 3-isopropoxyphenylacetic acid were dissolved in 50 ml of methylene chloride, and 1.10 g (5.76 mmole) of WSC.HCl (Water Soluble Carbodiimide.HCl), 780 mg (5.76 mmole) of 1-hydroxybenzotriazol.H$_2$O, 1.61 ml (11.5 mmole) of triethylamine, and 1.50 g (4.80 mmole) of (2R)-(3,4-dichlorophenyl)-2-(2-hydroxyethyl)morpholine hydrochloride [prepared as described in Example 76(c)] were added to the resulting solution, in that order. The mixture was then stirred at room temperature for 15 hours under a nitrogen atmosphere. At the end of this time, a saturated aqueous solution of ammonium chloride was added to the reaction mixture, which was then extracted with ethyl acetate. The organic extract was washed with a saturated aqueous solution of sodium hydrogencarbonate and with a saturated aqueous solution of sodium chloride, in that order, after which it was dried over anhydrous magnesium sulfate. The solvent was removed by distillation under reduced pressure, and the resulting residue was purified by silica gel column chromatography, using a gradient elution method, with mixtures of hexane and ethyl acetate ranging from 3:1 to 2:1 by volume as the eluent, to give 1.81 g of the title compound.

$[\alpha]_D^{24}$−8.2 (c=0.60, methanol). Nuclear Magnetic Resonance Spectrum (270 MHz, CDCl$_3$) δ ppm: 6.45–7.57 (7H, multiplet); 4.74 (1H, doublet, J=13.9 Hz); 4.37–4.52 (1H, multiplet); 3.22–3.90 (9H, multiplet); 2.10–2.21 (1H, broad singlet); 1.87–2.09 (2H, multiplet); 1.30 (3H, singlet); 1.28 (3H, singlet). Infrared absorption spectrum $v_{max}$cm$^{-1}$ (KBr): 3693, 3622, 3589, 2981, 2934, 1645, 1608, 1583. Mass spectrometric analysis (FAB) m/z: 452 (M+H)$^+$.

77(b) 2-{(2R)-(3,4-Dichlorophenyl)-4-[(3-isopropoxyphenyl)acetyl]morpholin-2-yl}ethanol Methanesulfonate 1.81 g (4.00 mmole) of 2-{(2R)-(3,4-dichlorophenyl)-4-[(3-isopropoxyphenyl)acetyl]morpholin-2-yl}ethanol [prepared as described in step (a) above] were dissolved in 5 ml of pyridine, and 45 mg (0.40 mmole) of 4-dimethylaminopyridine and 0.46 ml (6.00 mmole) of methanesulfonyl chloride were added to the resulting solution, whilst ice-cooling. The mixture was then stirred at 0° C. for 2 hours under a nitrogen atmosphere. At the end of this time, the reaction mixture was poured into ice-cooled 10% w/v aqueous hydrochloric acid, and then extracted with ethyl acetate. The organic extract was washed with a saturated aqueous solution of sodium chloride and then dried over anhydrous magnesium sulfate. The solvent was removed by distillation under reduced pressure, and the resulting residue was purified by silica gel column chromatography, using a gradient elution method, with mixtures of hexane and ethyl acetate ranging from 1:1 to 1:2 by volume as the eluent, to give 2.00 g of the title compound as a colorless oil.

$[\alpha]_D^{24}$ −6.3 (c=0.70, methanol). Nuclear Magnetic Resonance Spectrum (270 MHz, CDCl$_3$) δ ppm: 6.51–7.59 (7H, multiplet); 4.40–4.63 (2H, multiplet); 3.17–4.26 (9H, multiplet); 2.93 (3H, singlet); 2.08–2.32 (2H, multiplet); 1.31 (3H, singlet); 1.29 (3H, singlet). Infrared absorption spectrum $v_{max}$cm$^{-1}$ (KBr): 2981, 2934, 1645, 1608, 1583. Mass spectrometric analysis (FAB) m/z: 530 (M+H)$^+$.

77(c) 1-{2-[(2R)-(3,4-Dichlorophenyl)-4-[(3-isopropoxyphenyl)acetyl]morpholin-2-yl]ethyl}spiro[benzo[c]thiophene-1(3H),4'-piperidine]-(2S)-oxide 630 mg (1.19 mmole) of 2-{(2R)-(3,4-dichlorophenyl)-4-[(3-isopropoxyphenyl)acetyl]morpholin-2-yl}ethanol methanesulfonate [prepared as described in step (b) above], 367 mg (1.43 mmole) of spiro[benzo[c]thiophene-1(3H),4'-piperidine]-(2S)-oxide hydrochloride (prepared as described in Preparation 6), 299 mg (3.56 mmole) of sodium hydrogencarbonate, and 296 mg (1.78 mmole) of potassium iodide were suspended in 6 ml of anhydrous dimethylformamide, and the suspension was heated at 80° C. for 6 hours under a nitrogen atmosphere. At the end of this time, the reaction mixture was poured into a saturated aqueous solution of sodium chloride and extracted with ethyl acetate. The organic extract was dried over anhydrous magnesium sulfate, and the solvent was removed by distillation under reduced pressure. The resulting residue was purified by silica gel column chromatography, using a 25:1 by volume mixture of methylene chloride and methanol as the eluent, and then crystallized from hexane, to give 400 mg of the title compound as white crystals, melting at 85–88° C.

$[\alpha]_D^{24}$ +2.5 (c=0.51, methanol). HPLC analysis; Column: YMC-Pack ODS-A (250×4.6 mmφ); Eluent: CH$_3$CN:H$_2$O=60:40, 0.1% AcONH$_4$; Flow rate: 1.0 ml/min; Retention time: 23.7 min; Nuclear Magnetic Resonance Spectrum (400 MHz, CDCl$_3$) δ ppm: 6.55–7.61 (11H, multiplet); 4.71 (1H, doublet, J=13.8 Hz); 4.40–4.51 (1H, multiplet); 4.31 (3H, doublet, J=16.8 Hz); 3.99 (1H, doublet, J=16.8 Hz); 3.25–3.85 (8H, multiplet); 2.56–2.97 (2H, multiplet); 2.01–2.45 (6H, multiplet); 1.88–2.45 (2H, multiplet); 1.48–1.59 (1H, multiplet); 1.30 (3H, singlet); 1.29 (3H, singlet). Infrared absorption spectrum $v_{max}$cm$^{-1}$ (KBr): 2975, 2923, 1645, 1607, 1582, 1047. Mass spectrometric analysis (FAB) m/z: 655 (M+H)$^+$; Elemental analysis; Calculated for C$_{35}$H$_{40}$N$_2$O$_4$SCl$_2$.1/2H$_2$O: C: 63.25%; H: 6.22%; N: 4.21%; S: 4.82%; Cl: 10.67%; Found: C: 62.96%; H: 6.38%; N: 4.08%; S: 4.71%; Cl: 10.41%.

EXAMPLE 78

1-{2-[(2R)-(3,4-Dichlorophenyl)-4-(3,4,5-trimethoxybenzoyl)hexahydro-1,4-oxazepin-2-yl]ethyl}spiro[benzo[c]thiophene-1(3H),4'-piperidine]-(2S)-oxide (Compound No. 3-74)

78(a) 4-(t-Butyldimethylsilyloxy)-(2R)-(3,4-dichlorophenyl)-1-[N-(t-butoxycarbonyl)-N-(3-hydroxypropyl)amino]-2-butanol Following a procedure similar to that described in Example 76(a), but using 5.00 g (13.7 mmole) of 4-t-butyldimethylsilyloxy-(2R)-(3,4-dichlorophenyl)butane-1,2-diol [prepared as described in Example 1(c)] and 5.15 g (68.6 mmole) of 3-amino-1-propanol as the starting materials, 6.00 g of the title compound were obtained.

$[\alpha]_D^{24}$ −1.31 (c=1.22, methanol). Nuclear Magnetic Resonance Spectrum (400 MHz, CDCl$_3$) δ ppm: 7.20–7.70 (3H, multiplet); 5.04 & 5.32 (total 1H, each singlet); 3.15–3.85 (9H, multiplet); 1.95–2.30 (2H, multiplet); 1.65–1.85 (2H, multiplet); 1.45 (9H, singlet); 0.86 (9H, singlet); −0.08 & −0.01 (total 6H, each singlet). Infrared absorption spectrum $v_{max}$cm$^{-1}$ (CHCl$_3$): 3432, 2957, 2885, 2861, 1675. Mass spectrometric analysis (FAB) m/z: 522 (M+H)$^+$;

78(b) 2-[4-t-Butoxycarbonyl-(2R)-(3,4-dichlorophenyl)hexahydro-1,4-oxazepin-2-yl]ethanol t-Butyldimethylsilyl Ether 300 mg (0.57 mmole) of 4-(t-butyldimethylsilyloxy)-(2R)-(3,4-dichlorophenyl)-1-[N-(t-butoxycarbonyl)-N-(3-hydroxypropyl)amino]-2-butanol [prepared as described in step (a) above] were dissolved in 2 ml of pyridine, and 196 mg (1.03 mmole) of p-toluenesulfonyl chloride were added to the resulting solution. The mixture was then stirred at room temperature for 16 hours under a nitrogen atmosphere. At the end of this time, the reaction mixture was poured into water and extracted with ethyl acetate. The organic extract was washed with water and with a saturated aqueous solution of sodium chloride, in that order, after which it was dried over anhydrous sodium sulfate. The solvent was removed by distillation under reduced pressure, and the resulting residue was dissolved in 3 ml of 2-methyl-2-propanol, and 67 mg (0.58 mmole) of potassium t-butoxide were added to the resulting solution. The mixture was then heated at 80° C. for 8 hours under a nitrogen atmosphere. At the end of this time, the reaction mixture was cooled to room temperature, poured into water, and then extracted with ethyl acetate. The organic extract was washed with a saturated aqueous solution of sodium chloride and then dried over anhydrous sodium sulfate. The solvent was removed by distillation under reduced pressure, and the resulting residue was purified by silica gel column chromatography, using a gradient elution method, with mixtures of hexane and ethyl acetate ranging from 47:3 to 23:2 by volume as the eluent, to give 56 mg of the title compound.

$[\alpha]_D^{24}$ +14.19 (c=0.74, methanol). Nuclear Magnetic Resonance Spectrum (270 MHz, CDCl$_3$) δ ppm: 7.17–7.65 (3H, multiplet); 3.10–4.10 (8H, multiplet); 1.75–2.30 (4H, multiplet); 1.37 & 1.44 (total 9H, each singlet); 0.82 (9H, singlet); −0.07 & −0.05 (total 6H, each singlet). Mass spectrometric analysis (FAB) m/z: 504 (M+H)$^+$.

78(c) 2-[(2R)-(3,4-Dichlorophenyl)-4-(3,4,5-trimethoxybenzoyl)hexahydro-1,4-oxazepin-2-yl]ethanol Methanesulfonate Following a procedure similar to that described in Examples 76(c), 76(d) and 70(e), but using 2-[4-t-butoxycarbonyl-(2R)-(3,4-dichlorophenyl)hexahydro-1,4-oxazepin-2-yl]ethanol t-butyldimethylsilyl ether [prepared as described in step (b) above], the title compound was obtained in a 65% yield.

$[\alpha]_D^{24}$ +19.41 (c=0.45, methanol). Nuclear Magnetic Resonance Spectrum (400 MHz, CDCl$_3$) δ ppm: 7.20–7.65 (3H, multiplet); 6.62 (2H, singlet); 0.75–4.90 (12H, multiplet); 3.87 & 3.89 (total 9H, each singlet); 2.86 (3H, singlet). Infrared absorption spectrum $v_{max}$cm$^{-1}$ (KBr): 2935, 1637, 1585. Mass spectrometric analysis (FAB) m/z: 562 (M+H)$^+$.

78(d) 1-{2-[(2R)-(3,4-Dichlorophenyl)-4-(3,4,5-trimethoxybenzoyl)hexahydro-1,4-oxazepin-2-yl]ethyl}spiro[benzo[c]thiophene-1(3H),4'-piperidine]-(2S)-oxide Following a procedure similar to that described in Example 76(f), but using 2-[(2R)-(3,4-dichlorophenyl)-4-(3,4,5-trimethoxybenzoyl)hexahydro-1,4-oxazepin-2-yl]ethanol methanesulfonate [prepared as described in step (c) above], the title compound was obtained in a 59% yield.

$[\alpha]_D^{24}$ +19.33 (c=0.1, methanol). HPLC analysis; Column: YMC-Pack ODS-A (250×4.6 mmφ); Eluent: CH$_3$CN:H$_2$O=40:60, 0.1% AcONH$_4$; Flow rate: 1.0 ml/min;

Retention time: 17.7 min; Nuclear Magnetic Resonance Spectrum (400 MHz, CDCl$_3$) δ ppm: 7.15–7.75 (7H, multiplet); 6.62 (2H, broad singlet); 0.75–4.80 (29H, multiplet); 4.29 (1H, doublet, J=17 Hz); 3.97 (1H, doublet, J=17 Hz). Infrared absorption spectrum $v_{max}$cm$^{-1}$ (KBr): 2928, 2855, 2836, 1637, 1584. Mass spectrometric analysis (FAB) m/z: 687 (M+H)$^+$.

EXAMPLE 79

1-{3-[(2R)-(3,4-Dichlorophenyl)-4-(3,4,5-trimethoxybenzoyl)morpholin-2-yl]propyl}spiro [benzo[c]thiophene-1(3H),4'-piperidine]-(2S)-oxide (Compound No. 3-42)

79(a) Methyl 4-(3,4-dichlorophenyl)-4-oxobutanoate 8.50 g (84.9 mmole) of succinic anhydride and 24.8 g (93.0 mmole) of aluminum bromide were added, in that order, to 150 ml of 1,2-dichlorobenzene, and the mixture was stirred at room temperature for 5 hours. At the end of this time, the reaction mixture was poured into ice-cold water and extracted with methylene chloride. The organic extract was washed with a saturated aqueous solution of sodium chloride and then dried over anhydrous sodium sulfate. The solvent was removed by distillation under reduced pressure, and the resulting residue was dissolved in 100 ml of methanol. 1.0 ml sulfuric acid was added to the resulting solution, and the mixture was heated under reflux for 4 hours. At the end of this time, the reaction mixture was cooled to room temperature, poured into water, and then extracted with ethyl acetate. The organic extract was washed with a saturated aqueous solution of sodium hydrogencarbonate and with a saturated aqueous solution of sodium chloride, in that order, after which it was dried over anhydrous sodium sulfate. The solvent was removed by distillation under reduced pressure, and the resulting residue was purified by silica gel column chromatography, using a gradient elution method, with mixtures of hexane and diethyl ether ranging from 17:3 to 7:3 by volume as the eluent, to give 9.10 g of the title compound as pale orange crystals.

Nuclear Magnetic Resonance Spectrum (400 MHz, CDCl$_3$) δ ppm: 8.07 (1H, doublet, J=2 Hz); 7.81 (1H, doublet of doublets, J=2 & 8 Hz); 7.56 (1H, doublet, J=8 Hz); 3.71 (3H, singlet); 3.27 (2H, triplet, J=7 Hz); 2.78 (2H, triplet, J=7 Hz). Infrared absorption spectrum $v_{max}$cm$^{-1}$ (KBr): 3093, 3061, 2954, 1746, 1678, 1583. Mass spectrometric analysis (EI) m/z: 260 (M$^+$).

79(b) Methyl 4-(3,4-dichlorophenyl)-4-pentenoate 1.75 g (49.0 mmole) of methyltriphenylphosphonium bromide and 5.50 g (49.0 mmole) of potassium t-butoxide were suspended in 200 ml of dried benzene, and the mixture was stirred at room temperature for 6 hours under a nitrogen atmosphere. At the end of this time, 8.50 g of methyl 4-(3,4-dichlorophenyl)-4-oxobutanoate [prepared as described in step (a) above] were dissolved in 40 ml of benzene, and the resulting solution was added to the reaction mixture. The mixture was then stirred for 1 hour. The reaction mixture was then poured into water and extracted with ethyl acetate. The organic extract was dried over anhydrous sodium sulfate, and the solvent was removed by distillation under reduced pressure. The resulting residue was purified by silica gel column chromatography, using a gradient elution method, with mixtures of hexane and diethyl ether ranging from 19:1 to 23:2 by volume as the eluent, to give 4.20 g of the title compound as a pale orange oil.

Nuclear Magnetic Resonance Spectrum (400 MHz, CDCl$_3$) δ ppm: 7.48 (1H, doublet, J=2 Hz); 7.40 (1H, doublet, J=8 Hz); 7.23 (1H, doublet of doublets, J=2 & 8 Hz); 5.32 (1H, singlet); 5.14 (1H, singlet); 3.67 (3H, singlet); 2.79 (2H, triplet, J=8 Hz); 2.48 (2H, triplet, J=8 Hz). Infrared absorption spectrum $v_{max}$cm$^{-1}$ (film): 2952, 1740, 1630, 1550. Mass spectrometric analysis (EI) m/z: 258 (M$^+$).

79(c) 4-(3,4-Dichlorophenyl)-4-penten-1-ol t-Butyldimethylsilyl Ether

Following a procedure similar to that described in Example 1(b), but using methyl 4-(3,4-dichlorophenyl)-4-pentenoate [prepared as described in step (b) above], the title compound was obtained in a 93% yield.

Nuclear Magnetic Resonance Spectrum (400 MHz, CDCl$_3$) δ ppm: 7.49 (1H, doublet, J=2 Hz); 7.38 (1H, doublet, J=9 Hz); 7.24 (1H, doublet of doublets, J=2 & 9 Hz); 5.30 (1H, singlet); 5.13 (1H, doublet, J=1 Hz); 3.62 (2H, triplet, J=6 Hz); 2.52 (2H, triplet, J=8 Hz); 1.60–1.68 (2H, multiplet); 0.90 (9H, singlet); 0.04 (6H, singlet). Infrared absorption spectrum $v_{max}$cm$^{-1}$ (film): 2954, 2929, 2887, 2858, 1627, 1550. Mass spectrometric analysis (FAB) m/z: 345 (M+H)$^+$.

79(d) (2R)-5-t-Butyldimethylsilyloxy-2-(3,4-dichlorophenyl)pentane-1,2-diol

Following a procedure similar to that described in Example 1(c), but using 4-(3,4-dichlorophenyl)-4-penten-1-ol t-butyldimethylsilyl ether [prepared as described in step (c) above], the title compound was obtained in a 94% yield.

Optical purity: 98% ee; $[\alpha]_D^{24}$-2.08 (c=0.48, methanol). Nuclear Magnetic Resonance Spectrum (400 MHz, CDCl$_3$) δ ppm: 7.56 (1H, doublet, J=2 Hz); 7.41 (1H, doublet, J=8 Hz); 7.23 (1H, doublet of doublets, J=2 & 8 Hz); 4.96 (1H, singlet); 3.53–3.70 (4H, multiplet); 1.98–2.14 (3H, multiplet); 1.35–1.57 (2H, multiplet); 0.91 (9H, singlet); 0.082 (3H, singlet); 0.078 (3H, singlet). Infrared absorption spectrum $v_{max}$cm$^{-1}$ (CHCl$_3$): 3584, 3311, 2956, 2932, 2861. Mass spectrometric analysis (FAB) m/z: 379 (M$^+$).

79(e) (2R)-5-(t-Butyldimethylsilyloxy)-2-(3,4-dichorophenyl)-1-[N-(t-butoxycarbonyl)-N-(2-hydroxyethyl)amino]-2-pentanol Following a procedure similar to that described in Example 76(a), but using (2R)-5-t-butyldimethylsilyloxy-2-(3,4-dichlorophenyl)pentane-1,2-diol [prepared as described in step (d) above], the title compound was obtained in a 95% yield.

$[\alpha]_D^{24}$-14.75 (c=0.61, methanol). Nuclear Magnetic Resonance Spectrum (400 MHz, CDCl$_3$) δ ppm: 7.15–7.65 (3H, multiplet); 5.30 & 5.79 (total 1H, each singlet); 2.50–3.95 (9H, multiplet); 1.85–2.25 (2H, multiplet); 1.30–1.60 (2H, multiplet); 1.43 (9H, singlet); 0.89 (9H, singlet); 0.04 & 0.05 (total 6H, each singlet). Infrared absorption spectrum $v_{max}$cm$^{-1}$ (KBr): 3355, 2955, 2931, 2894, 2858, 1668. Mass spectrometric analysis (FAB) m/z: 522 (M+H)$^+$.

79(f) (2R)-3-[4-t-Butoxycarbonyl-2-(3,4-dichlorophenyl)morpholin-2-yl]-1-propanol t-Butyldimethylsilyl Ether Following a procedure similar to that described in Example 76(b), but using (2R)-5-(t-butyldimethylsilyloxy)-2-(3,4-dichorophenyl)-1-[N-(t-butoxycarbonyl)-N-(2-hydroxyethyl)amino]-2-pentanol [prepared as described in step (e) above], the title compound was obtained in a 92% yield.

$[\alpha]_D^{24}$+58.15 (c=0.54, methanol). Nuclear Magnetic Resonance Spectrum (400 MHz, CDCl$_3$) δ ppm: 7.40–7.65 (3H, multiplet); 4.14 (1H, doublet, J=14 Hz); 3.42–3.75 (5H, multiplet); 3.23 (2H, doublet, J=14 Hz); 1.15–2.00 (4H, multiplet); 1.44 & 1.52 (total 9H, each broad singlet); 0.85 (9H, singlet); 0.00 & 0.01 (total 6H, each singlet). Infrared absorption spectrum $v_{max}$cm$^{-1}$ (CHCl$_3$): 2957, 2931, 2860, 1668. Mass spectrometric analysis (FAB) m/z: 504 (M+H)$^+$.

79(g) 3-[(2R)-(3,4-Dichlorophenyl-4-(3,4,5-trimethoxybenzoyl)morpholin-2-yl]-1-propanol 3.43 g (6.80 mmole) of (2R)-3-[4-t-butoxycarbonyl-2-(3,4-dichlorophenyl)morpholin-2-yl]-1-propanol t-butyldimethylsilyl ether [prepared as described in step (f) above] were dissolved in 60 ml of methylene chloride, and 2.98 g (15.0 mmole) of B-bromocatecholborane were added to the resulting solution. The mixture was then stirred at room temperature for 2 hours under a nitrogen atmosphere. At the end of this time, 60 ml of water were poured into the reaction mixture, which was then stirred for a further 2 hours. The mixture was then made basic by the addition of a 1 N aqueous solution of sodium hydroxide and then extracted with methylene chloride. The organic extract was washed with a saturated aqueous solution of sodium chloride and dried over anhydrous sodium sulfate. The solvent was removed by distillation under reduced pressure. The resulting residue was dissolved in 40 ml of methylene chloride, and 1.23 ml (8.87 mmole) of triethylamine, 1.65 g (7.15 mmole) of 3,4,5-trimethoxybenzoyl chloride and 10 mg of 4-dimethylaminopyridine were added to the resulting solution. The mixture was then stirred at room temperature for 12 hours. At the methylene chloride. The organic extract was washed with a saturated aqueous solution of sodium chloride and dried over anhydrous sodium sulfate, and the solvent was removed by distillation under reduced pressure. The resulting residue was purified by silica gel column chromatography using a 7:3 by volume mixture of methylene chloride and acetone as the eluent, to give 2.13 g of the title compound.

$[\alpha]_D^{24}$+30.78 (c=methanol). Nuclear Magnetic Resonance Spectrum (400 MHz, CDCl$_3$) δ ppm: 6.80–7.80 (multiplet); 6.48 (2H, broad singlet); 3.30–4.80 (8H, multiplet); 3.84 & 3.86 (total 9H, each singlet); 1.10–2.35 (4H, multiplet). Infrared absorption spectrum $\nu_{max}$cm$^{-1}$ (KBr): 3426, 2942, 2872, 1632, 1584. Mass spectrometric analysis m/z: 484 (M+H)$^+$.

79(h) 3-[(2R)-(3,4-Dichlorophenyl-4-(3,4,5-trimethoxybenzoyl)morpholin-2-yl]-1-propanol Methanesulfonate Following a procedure similar to that described in Example 70(e), but using 3-[(2R)-(3,4-dichlorophenyl)-4-(3,4,5-trimethoxybenzoyl)morpholin-2-yl]-1-propanol [prepared as described in step (g) above], the title compound was obtained in a 84% yield.

$[\alpha]_D^{24}$+27.87 (c=0.54, methanol). Nuclear Magnetic Resonance Spectrum (400 MHz, CDCl$_3$) δ ppm: 6.80–7.80 (3H, multiplet); 6.50 (2H, singlet); 3.20–4.50 (8H, multiplet); 3.85 & 3.86 (total 9H, each singlet); 2.97 (3H, singlet); 1.35–2.35 (4H, multiplet). Infrared absorption spectrum $\nu_{max}$cm$^{-1}$ (KBr): 3001, 2939, 2875, 2839, 1634, 1585. Mass spectrometric analysis (FAB) m/z: 562 (M+H)$^+$.

79(i) 1-{3-[(2R)-(3,4-Dichlorophenyl)-4-(3,4,5-trimethoxybenzoyl)morpholin-2-yl]propyl}spiro[benzo[c]thiophene-1(3H),4'-piperidine]-(2S)-oxide Following a procedure similar to that described in Example 76(g), but using 3-[(2R)-(3,4-dichlorophenyl)-4-(3,4,5-trimethoxybenzoyl)morpholin-2-yl]-1-propanol methanesulfonate [prepared as described in step (h) above], the title compound was obtained in a 68% yield.

$[\alpha]_D^{24}$+26.97 (c=0.55, methanol). HPLC analysis; Column: YMC-Pack ODS-A (250×4.6 mmφ); Eluent: CH$_3$CN:H$_2$O=40:60, 0.1% AcONH$_4$; Flow rate: 1.0 ml/min; Retention time: 23.4 min; Nuclear Magnetic Resonance Spectrum (400 MHz, CDCl$_3$) δ ppm: 6.80–7.80 (7H, multiplet); 6.48 (2H, broad singlet); 0.80–4.70 (20H, multiplet); 4.32 (1H, doublet, J=17 Hz); 4.00 (1H, doublet, J=17 Hz); 3.84 & 3.86 (total 9H, each singlet). Infrared absorption spectrum $\nu_{max}$cm$^{-1}$ (KBr): 2940, 2872, 2834, 2771, 1636, 1584. Mass spectrometric analysis (FAB) m/z: 687 (M+H)$^+$.

EXAMPLE 80

1-{2-[(5R)-(3,4-Dichlorophenyl)-3-(3,4-dimethoxybenzenesulfonyl)oxazolidin-5-yl]ethyl}spiro[benzo[c]thiophene-1(3H),4'-piperidine]-(2S)-oxide (Compound No. 3-2055)

80(a) 2-[(5R)-(3,4-Dichlorophenyl)-3-(3,4-dimethoxybenzenesulfonyl)oxazolidin-5-yl]ethanol t-Butyldimethylsilyl Ether 1.00 g (2.72 mmole) of 2-[(5R)-(3,4-dichlorophenyl)oxazolidin-5-yl]ethanol t-butyldimethylsilyl ether [prepared as described in the first part of Example 1(f)] was dissolved in 10 ml of pyridine, and 773 mg (3.27 mmole) of 3,4-dimethoxybenzenesulfonyl chloride were added to the resulting solution, whilst ice-cooling. The mixture was then stirred for 2 hours under a nitrogen atmosphere. At the end of this time, the reaction mixture was poured into 100 ml of ice-cooled 10% w/v aqueous hydrochloric acid, and then extracted with ethyl acetate. The organic extract was washed with a saturated aqueous solution of sodium chloride and then dried over anhydrous magnesium sulfate. The solvent was removed by distillation under reduced pressure, and the resulting residue was purified by silica gel column chromatography, using a gradient elution method, with mixtures of hexane and ethyl acetate ranging from 10:1 to 2:1 by volume as the eluent, to give 1.27 g of the title compound as white crystals.

$[\alpha]_D^{24}$−5.74 (c=1.29, methanol). Infrared absorption spectrum $\nu_{max}$cm$^{-1}$ (KBr): 1588, 1510, 1468, 1264, 1155, 1140.

80(b) 2-[(5R)-(3,4-Dichlorophenyl)-3-(3,4-dimethoxybenzenesulfonyl)oxazolidin-5-yl]ethanol Methanesulfonate 1.19 g (2.06 mmole) of 2-[(5R)-(3,4-dichlorophenyl)-3-(3,4-dimethoxybenzenesulfonyl)oxazolidin-5-yl]ethanol t-butyldimethylsilyl ether [prepared as described in step (a) above] were dissolved in 20 ml of a 3:3:1 by volume mixture of acetic acid, tetrahydrofuran and water, and the resulting mixture was then heated at 80° C. for 2 hours under a nitrogen atmosphere. At the end of this time, the reaction mixture was then neutralised with a saturated aqueous solution of sodium hydrogencarbonate and extracted with ethyl acetate. The organic extract was dried over anhydrous magnesium sulfate. The solvent was removed by distillation under reduced pressure, and the resulting residue was dissolved in 10 ml of pyridine. 23 mg (0.19 mmole) of 4-dimethylaminopyridine and 0.22 ml (2.84 mmole) of methanesulfonyl chloride were then added to the resulting solution, whilst ice-cooling. The mixture was then stirred for 2 hours at 0° C. under a nitrogen atmosphere. At the end of this time, the reaction mixture was poured into 200 ml of ice-cooled 10% w/v aqueous hydrochloric acid, and then extracted with ethyl acetate, The organic extract was washed with a saturated aqueous solution of sodium chloride and then dried over anhydrous magnesium sulfate. The solvent was removed by distillation under reduced pressure, and the resulting residue was purified by silica gel column chromatography, using a gradient elution method, with mixtures of hexane and ethyl acetate ranging from 2:1 to 1:2 by volume as the eluent, to give 992 mg of the title compound as white crystals.

$[\alpha]_D^{24}$−3.80 (c=0.5, methanol). Nuclear Magnetic Resonance Spectrum (400 MHz, CDCl$_3$) δ ppm: 7.33 (1H, doublet, J=8.6 Hz); 7.30 (1H, doublet of doublets, J=8.6 & 2.1 Hz); 7.14 (1H, doublet, J=2.2 Hz); 7.11 (1H, doublet, J=2.1 Hz); 6.92 (1H, doublet of doublets, J=8.7 & 2.2 Hz); 6.80 (1H, doublet, J=8.7 Hz); 5.08 (1H, doublet, J=5.7 Hz); 4.98 (1H, doublet, J=5.7 Hz); 4.11 (1H, multiplet); 3.94 (3H, singlet); 3.86 (3H, singlet); 3.82 (1H, multiplet); 3.70 (2H, AB-quartet, J=11.3 Hz, Δδ=0.08 ppm); 2.88 (3H, singlet); 2.16 (2H, multiplet). Mass spectrometric analysis (FAB) m/z: 540 (M+H)$^+$.

80(c) 1-{2-[(5R)-(3,4-Dichlorophenyl-3-(3,4-dimethoxybenzenesulfonyl)-oxazolidin-5-yl]ethyl}spiro[benzo[c]thiophene-1(3H),4'-piperidine]-(2S)-oxide 105 mg (0.19 mmole) of 2-[(5R)-(3,4-dichlorophenyl)-3-(3,4-dimethoxybenzenesulfonyl)oxazolidin-5-yl]ethanol methanesulfonate [prepared as described in step (b) above], 55 mg (0.21 mmole) of spiro[benzo[c]thiophene-1(3H),4'-piperidine]-(2S)-oxide hydrochloride (prepared as described in Preparation 6), 49 mg (0.58 mmole) of sodium hydrogencarbonate, and 48 mg (0.29 mmole) of potassium iodide were suspended in 2 ml of anhydrous dimethylformamide. The resulting mixture was then heated at 80° C. for 8 hours under a nitrogen atmosphere. At the end of this time, the reaction mixture was poured into 10 ml of a saturated aqueous solution of sodium chloride and extracted with ethyl acetate. The organic extract was dried over anhydrous magnesium sulfate, and the solvent was removed by distillation under reduced pressure. The resulting residue was purified by silica gel column chromatography, using a gradient elution method, with mixtures of methylene chloride and methanol ranging from 40:1 to 20:1 by volume as the eluent, and then crystallized from diisopropyl ether, to give 82 mg of the title compound as white crystals.

$[\alpha]_D^{24}$+2.5 (c=0.52, methanol). HPLC analysis Column: YMC-Pack ODS-A (250×4.6 mmφ) Eluent: CH$_3$CN:H$_2$O= 40:60, 0.1% AcONH$_4$ Flow rate: 1.0 ml/min Retention time: 21.4 min Infrared absorption spectrum $v_{max}$ cm$^{-1}$ (KBr): 1674, 1587, 1509, 1469, 1350, 1264, 1155, 1140, 1039. Mass spectrometric analysis (FAB) m/z: 665 (M+H)$^+$.

EXAMPLE 81

1-{2-[(2R)-(3,4-Dichlorophenyl)-4-(3,4,5-trimethoxybenzoyl)morpholin-2-yl]ethyl}-1-methylspiro[benzo[c]thiophene-1(3H),4'-piperidine]-(2S)-oxide iodide (the methyl iodide salt of Compound No. 3-42)

300 mg (0.45 mmole) of 1-{2-[(2R)-(3,4-dichlorophenyl)-4-(3,4,5-trimethoxybenzoyl)morpholin-2-yl]ethyl}spiro[benzo[c]thiophene-1(3H),4'-piperidine]-(2S)-oxide (prepared as described in Example 76) were dissolved in 3 ml of acetonitrile, and 30 μl (0.48 mmole) of methyl iodide were added to the resulting solution. The mixture was then stirred overnight at room temperature under a nitrogen atmosphere. At the end of this time, the solvent was removed by distillation under reduced pressure. The resulting residue was crystallized from diisopropyl ether, to give 312 mg of the title compound as pale-yellow crystals.

$[\alpha]_D^{24}$+42.0 (c=1.0, methanol). HPLC analysis Column: YMC-Pack ODS-A (250×4.6 mmφ) Eluent: CH$_3$CN:H$_2$O= 40:60, 0.1% AcONH$_4$ Flow rate: 1.0 ml/min Retention time: 9.9 mm Infrared absorption spectrum $v_{max}$ cm$^{-1}$ (KBr): 3444, 1632, 1584, 1464, 1126. Mass spectrometric analysis (FAB) m/z: 687 (free form, M$^+$) Elemental analysis: Calculated for C$_{35}$H$_{41}$N$_2$O$_6$SCl$_2$I: C: 51.54%; H: 5.07%; N: 3.44%; S: 3.93%; Cl: 8.69%; I: 15.56%. Found: C: 51.14%; H: 5.39%; N: 3.42%; S: 4.01%; Cl: 8.50%; I: 15.96%.

We claim:
1. A method for the treatment of an inflammatory disease which comprises administering to an animal suffering from said inflammatory disease a pharmaceutically effective amount of a compound of the following formula (I):

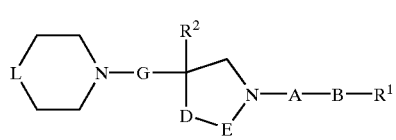

or a quaternary ammonium ion thereof of the following formula (Ia):

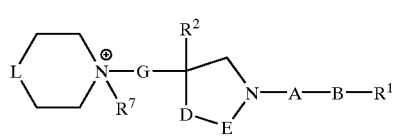

or a pharmaceutically acceptable salt or ester thereof, wherein:

R$^1$ and R$^2$ are the same as or different from each other, and each represents a carbocyclic aryl group, said aryl group being unsubstituted or being substituted by at least one substituent selected from the group consisting of substituents α, defined below;

A represents a methylene group, a carbonyl group or a sulfonyl group;

B represents a single bond between the groups represented by A and R$^1$, an alkylene group having from 1 to 4 carbon atoms or an alkenylene group having from 2 to 4 carbon atoms;

D represents an oxygen atom;

E represents an alkylene group having 2 carbon atoms;

G represents an alkylene group having from 1 to 4 carbon atoms or an alkenylene group having from 2 to 4 carbon atoms;

L represents a group of formula —C(R$^4$)(R$^5$)— wherein R$^4$ and R$^5$ together with the carbon atom to which they are attached represent a heterocyclic group having from 5 to 10 ring atoms which is unsubstituted or substituted by at least one substituent selected from the group consisting of substituents β defined below, said heterocyclic group having a single hetero-atom selected from the group consisting of a nitrogen atom, an oxygen and a sulfur atom, or R$^4$ and R$^5$ together with the carbon atom to which they are attached represent said heterocyclic group which is fused to a carbocyclic aryl group or an aromatic heterocyclic group, said aryl group and said aromatic heterocyclic group being unsubstituted or being substituted by at least one substituent selected from the group consisting of substituents a defined below;

R$^7$ represents a straight or branched alkyl group having from 1 to 6 carbon atoms; and said substituents α are selected from the group consisting of a halogen atom, an alkyl group having from 1 to 6 carbon atoms, a haloalkyl group having from 1 to 6 carbon atoms, an alkoxy group having from 1 to 6 carbon atoms, an aliphatic carboxylic acyl group having from 1 to 6 carbon atoms, an alkanesulfonyl group having from 1 to 6 carbon atoms, a haloalkanesulfonyl group having from 1 to 6 carbon atoms, a hydroxy group, a carboxy group, an alkoxycarbonyl group having from 1 to 6 carbon atoms in the alkoxy part, an acylamino group having from 1 to 6 carbon atoms, an alkanesulfonylamino group having from 1 to 6 carbon atoms, a haloalkanesulfonylamino group having from 1 to 6 carbon atoms, an amino group, a cyano group, and an alkylene group having from 1 to 8 carbon atoms to form a cycloalkyl group fused with the aryl or heterocyclic ring;

said substituents β are:
when substituting a carbon atom, an oxo group, or
when substituting a nitrogen atom, selected from the group consisting of an aliphatic acyl group, an alkanesulfonyl group having from 1 to 6 carbon atoms, an alkyl group having from 1 to 6 carbon atoms which is unsubstituted or is substituted by at least one substituent selected from the group consisting of substituents γ, defined below, a carbocyclic aryl group which is unsubstituted or is substituted by at least one substituent selected from the group consisting of said substituents α, and an aralkyl group in which an alkyl group having from 1 to 4 carbon atoms is substituted by from 1 to 3 carbocyclic aryl groups as defined above,
or when substituting a sulfur atom, one or two oxygen atoms form a sulfoxide or sulfone group; and said substituents γ are selected from the group consisting of a halogen atom, an alkoxy group having from 1 to 6 carbon atoms, an aliphatic carboxylic acyl group having from 1 to 6 carbon atoms, an alkanesulfonyl group having from 1 to 6 carbon atoms, a haloalkanesulfonyl group having from 1 to 6 carbon atoms, a hydroxy group, a carboxy group, an alkoxycarbonyl group having from 1 to 6 carbon atoms in the alkoxy part, an acylamino group having from 1 to 6 carbon atoms, an amino group and a cyano group.

2. The method of claim 1, wherein E is an ethylene group.

3. The method of claim 1, wherein $R^1$ and $R^2$ are the same or different and each represents a carbocyclic aryl group or a carbocyclic aryl group substituted with from 1 to 3 groups selected from the group consisting of said substituents α;

A is a carbonyl group;

B is a single bond; and

G is an alkylene group having from 1 to 4 carbon atoms.

4. The method of claim 2, wherein $R^1$ and $R^2$ are the same or different and each represents a carbocyclic aryl group, or a carbocyclic aryl group substituted with from 1 to 3 substituents selected from the group consisting of said substituents α;

A is a carbonyl group;

B is a single bond; and

G is an alkylene group having from 1 to 4 carbon atoms.

5. The method of claim 1, wherein $R^4$ and $R^5$ together with the carbon atom to which they are attached represent a group of formula:

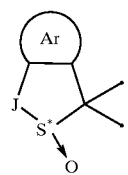

J represents an alkylene group having from 1 to 6 carbon atoms;

Ar represents a ring carbocyclic aryl group or aromatic heterocyclic group fused to the ring containing J and S, said aryl group and said aromatic heterocyclic group being unsubstituted or being substituted by at least one substituent selected from the group consisting of substituents α, defined above; and $S^* \rightarrow O$ represents a sulfoxide group in which the sulfur atom is in the S-configuration.

6. The method of claim 5, wherein $R^1$ represents a carbocyclic group substituted with from 1 to 3 substituents selected from the group consisting of said substituents α;

$R^2$ represents a carbocyclic aryl group or a carbocyclic aryl group substituted with from 1 to 3 substituents selected from the group consisting of said substituents α;

A represents a carbonyl group;

B represents a single bond;

G represents a $C_{1-4}$ alkylene group;

J represents a $C_{1-14}$ alkylene group; and the ring Ar represents an unsubstituted carbocyclic aryl group, a carbocyclic aryl group substituted with from 1 to 3 substituents selected from the group consisting of said substituents α or an aromatic heterocyclic group.

7. The method of claim 1, wherein the inflammatory disease is selected from the group consisting of rheumatism and arthrosis deformans.

8. The method of claim 1, wherein the method is for treatment of an inflammatory disease.

9. The method of claim 2, wherein the $R^1$ and $R^2$ are the same or different and each is an unsubstituted carbocyclic aryl group, or a carbocyclic aryl group substituted with from 1 to 3 substituents selected from the group consisting of said substituents α.

10. The method of claim 2, wherein $R^2$ is an unsubstituted carbocyclic group or a carbocyclic aryl group substituted with from 1 to 3 substituents selected from the group consisting of said substituents α.

11. The method of claim 2, wherein A is a carbonyl group.

12. The method of claim 2, wherein B is a single bond.

13. The method of claim 2, wherein G is an alkylene group having from 1 to 4 carbon atoms.

14. The method of claim 2, wherein G is an alkylene group having from 2 or 3 carbon atoms.

15. The method of claim 9, wherein $R^2$ is an unsubstituted carbocyclic aryl group or a carbocyclic group substituted with from 1 to 3 substituents selected from the group consisting of said substituents α.

16. The method of claim 15, wherein A is a carbonyl group.

17. The method of claim 16, wherein B is a single bond.

18. The method of claim 17, wherein G is an alkylene group having 1 to 4 carbon atoms.

19. The method of claim 18, wherein G is an alkylene group having 2 or 3 carbon atoms.

20. The method of claim 5, wherein $R^1$ is an unsubstituted carbocyclic aryl group, or a carbocyclic aryl group substi- 21. The method of claim 5, wherein $R^1$ is an unsubstituted carbocyclic aryl group or a carbocyclic aryl group substituted with from 1 to 3 substituents selected from the group consisting of an alkyl group having from 1 to 6 carbon atoms, a haloalkyl group having from 1 to 6 carbon atoms, and an alkoxy group having from 1 to 6 carbon atoms.

22. The method of claim 5, wherein $R^1$ is an unsubstituted carbocyclic aryl group or a carbocyclic aryl group substituted with from 1 to 3 substituents selected from the group consisting of said substituents α.

23. The method of claim 5, wherein $R^2$ is an unsubstituted carbocyclic aryl group or a carbocyclic aryl group substituted with from 1 to 3 halogen atoms.

24. The method of claim 5, wherein A is a carbocyclic group.

25. The method of claim 5, wherein B is a single bond.

26. The method of claim 5, wherein E is an ethylene group.

27. The method of claim 5, wherein G is a $C_{1-4}$ alkylene group.

28. The method of claim 5, wherein G is a $C_{2-3}$ alkylene group.

29. The method of claim 5, wherein J is a $C_{1-4}$ alkylene group.

30. The method of claim 5, wherein J is a methylene or ethylene group.

31. The method of claim 5, wherein the ring Ar is an aryl group, an aryl group substituted with from 1 to 3 substituents selected from the group consisting of substituents α or an aromatic heterocyclic group.

32. The method of claim 5, wherein the ring Ar is a carbocyclic aryl group or a carbocyclic aryl group substituted with from 1 to 3 substituents selected from the group consisting of substituents α.

33. The method of claim 5, wherein $R^1$ is an unsubstituted carbocyclic aryl group or a carbocyclic aryl group substituted with from 1 to 3 substituents selected from the group consisting of an alkyl group having from 1 to 6 carbon atoms, a haloalkyl group having from 1 to 6 carbon atoms and an alkoxy group having from 1 to 6 carbon atoms;

$R^2$ is an unsubstituted carbocyclic aryl group or a carbocyclic aryl group substituted with from 1 to 3 halogen atoms;

A is a carbonyl group;

B is a single bond;

E is an ethylene group;

G is a $C_{2-3}$ alkylene group;

J is a methylene or ethylene group; and the ring Ar is an unsubstituted carbocyclic aryl group or a carbocyclic aryl group substituted with from 1 to 3 groups selected from the group consisting of said substituents α.

34. The method of claim 1, wherein the compound is 1-{2-[2(3,4-dichlorophenyl)-4-(3,4,5-trimethoxybenzoyl)morpholin-2-yl]ethyl}spiro[isobenzofuran-1(3H), 4'-piperidine] or a pharmaceutically acceptable salt or ester thereof.

35. The method of claim 1, wherein the compound is 1-{2-[2(3,4-dichlorophenyl)-4-(3,4,5-trimethoxybenzoyl)morpholin-2-yl]ethyl}spiro[benzo[c]thiophene-1(3H), 4'-piperdine] or a pharmaceutically acceptable salt or ester thereof.

36. The method of claim 1, wherein the compound is 1-{2-[2(3,4-dichlorophenyl)-4-(3,4,5-trimethoxybenzoyl)morpholin-2-yl]ethyl}spiro[benzo[c]thiophene-1(3H), 4'-piperidine]-2-oxide or a pharmaceutically acceptable salt or ester thereof.

37. The method of claim 1, wherein the compound is 1-{2-[2(3,4-dichlorophenyl)-4-(3,4,5-trimethoxybenzoyl)morpholin-2-yl]ethyl}spiro[isoquinoline-1(2H), 4'-piperidine]-3(4H)-one or a pharmaceutically acceptable salt or ester thereof.

38. The method of claim 1, wherein the compound is 1-{2-[2(3,4-dichlorophenyl)-4-(3-methoxybenzoyl)morpholin-2-yl]ethyl}spiro[isobenzofuran-1(3H), 4'-piperidine] or a pharmaceutically acceptable salt or ester thereof.

39. The method of claim 1 wherein the compound is 1-{2-[2(3,4-dichlorophenyl)-4-(3-methoxybenzoyl)morpholin- 2-yl]ethyl}spiro[isobenzo[c]thiophene-1(3H), 4'-piperidine] or a pharmaceutically acceptable salt or ester thereof.

40. The method of claim 1, wherein the compound is 1-{2-[2(3,4-dichlorophenyl)-4-(3-methoxybenzoyl)morpholin-2-yl]ethyl}spiro[benzo[c]thiophene-1(3H), 4'-piperidine]-2-oxide or a pharmaceutically acceptable salt or ester thereof.

41. The method of claim 1, wherein the compound is 1-{2-[2(3,4-dichlorophenyl)-4-(3-methoxybenzoyl)morpholin-2-yl]ethyl}spiro[isoquinoline-1(2H), 4'-piperidine]-3(4H)-one or a pharmaceutically acceptable salt or ester thereof.

42. The method of claim 1, wherein the compound is 1-{2-[(2R)-(3,4-dichlorophenyl)-4-(3,4,5-trimethoxybenzoyl)morpholin-2-yl]ethyl}spiro[benzo[c]thiophene-1(3H), 4'-piperidine]-(2S)-oxide or a pharmaceutically acceptable salt or ester thereof.

43. The method of claim 1, wherein the compound is 1-{2-[(2R)-(4-chlorophenyl)-4-(3,4,5-trimethoxybenzoyl)morpholin-2-yl]ethyl}spiro[benzo[c]thiophene-1(3H), 4'-piperidine]-2S)-oxide or a pharmaceutically acceptable salt or ester thereof.

44. The method of claim 1, wherein the compound is 1-{2-[(2R)-(4-fluorophenyl)-4-(3,4,5-trimethoxybenzoyl)morpholin-2-yl]ethyl}spiro[benzo[c]thiophene-1(3H), 4'-piperidine]-2(S)-oxide or a pharmaceutically acceptable salt or ester thereof.

45. The method of claim 1, wherein the compound is 1-{2-[(2R)-(3,4-dichlorophenyl)-4-(3-isopropoxyphenylacetyl)morpholin-2-yl]ethyl}spiro[benzo[c]thiophene-1(3H), 4'-piperidine]-2S-oxide or a pharmaceutically acceptable salt or ester thereof.

46. The method of claim 1, wherein the compound is 1-(2-[(2R)-(4-chlorophenyl)-4-(3-isopropoxyphenylacetyl)morpholin-2-yl]ethyl}spiro[benzo[c]thiophene-1(3H), 4'-piperidine]-(2S)-oxide or a pharmaceutically acceptable salt or ester thereof.

47. The method of claim 1, wherein the compound is 1-{2-[(2R)-(4-fluorophenyl)-4(3-isopropoxyphenylacetyl)morpholin-2-yl]ethyl}spiro[benzo[c]thiophene-1(3H), 4'-piperidine](2S)-oxide or a pharmaceutically acceptable salt or ester thereof.

48. The method of claim 1, wherein $R^4$ and $R^5$, together with the carbon atom to which they are attached, represent a heterocyclic group which is fused to an aromatic heterocyclic group selected from the group consisting of furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl and pyrazinyl.

49. The method of claim 1, wherein the administering is orally.

50. The method of claim 1, wherein the administering is parenterally.

51. The method of claim 49, wherein the administering is to a patient in a dose of 0.01 mg/kg body weight to 100 mg/kg body weight.

* * * * *